United States Patent
Connolly et al.

(10) Patent No.: US 9,562,035 B2
(45) Date of Patent: Feb. 7, 2017

(54) BENZAMIDE DERIVATIVE USEFUL AS FASN INHIBITORS FOR THE TREATMENT OF CANCER

(71) Applicant: Janssen Pharmaceutica NV

(72) Inventors: Peter J Connolly, New Providence, NJ (US); Tianbao Lu, Churchville, PA (US)

(73) Assignee: Janssen Pharmaceutica NV (BE)

( * ) Notice: Subject to any disclaimer, the term of this patent is extended or adjusted under 35 U.S.C. 154(b) by 0 days.

(21) Appl. No.: 14/550,349

(22) Filed: Nov. 21, 2014

(65) Prior Publication Data

US 2016/0009688 A1    Jan. 14, 2016

Related U.S. Application Data

(60) Provisional application No. 61/911,016, filed on Dec. 3, 2013.

(51) Int. Cl.

| | | |
|---|---|---|
| *C07D 401/14* | (2006.01) | |
| *C07D 487/04* | (2006.01) | |
| *C07D 417/14* | (2006.01) | |
| *C07D 413/14* | (2006.01) | |
| *C07D 401/10* | (2006.01) | |
| *C07D 409/14* | (2006.01) | |
| *C07D 405/14* | (2006.01) | |
| *A61K 31/5377* | (2006.01) | |
| *A61K 31/4725* | (2006.01) | |
| *A61K 31/496* | (2006.01) | |
| *A61K 31/506* | (2006.01) | |
| *A61K 31/4709* | (2006.01) | |
| *C07D 401/12* | (2006.01) | |
| *C07D 403/10* | (2006.01) | |
| *C07D 471/04* | (2006.01) | |
| *A61K 31/437* | (2006.01) | |
| *A61K 31/454* | (2006.01) | |
| *A61K 31/4545* | (2006.01) | |

(52) U.S. Cl.
CPC ............ *C07D 401/14* (2013.01); *A61K 31/437* (2013.01); *A61K 31/454* (2013.01); *A61K 31/4545* (2013.01); *A61K 31/4709* (2013.01); *A61K 31/4725* (2013.01); *A61K 31/496* (2013.01); *A61K 31/506* (2013.01); *A61K 31/5377* (2013.01); *C07D 401/10* (2013.01); *C07D 401/12* (2013.01); *C07D 403/10* (2013.01); *C07D 405/14* (2013.01); *C07D 409/14* (2013.01); *C07D 413/14* (2013.01); *C07D 417/14* (2013.01); *C07D 471/04* (2013.01); *C07D 487/04* (2013.01)

(58) Field of Classification Search
CPC ... C07D 401/14; C07D 487/04; C07D 417/14; C07D 413/14; C07D 401/10; C07D 409/14; C07D 405/14; A61K 31/4725; A61K 31/5377; A61K 31/496; A61K 31/506; A61K 31/4709; A61K 31/454

See application file for complete search history.

(56) References Cited

FOREIGN PATENT DOCUMENTS

WO    2008059214 A1    5/2008

OTHER PUBLICATIONS

Bandyopadhyay, S., et al., "FAS expression inversely correlates with PTEN level in prostate cancer and a PI-3 kinase inhibitor synergizes with FAS siRNA to induce apoptosis", Oncogene, 2005, pp. 5389-5395, vol. 24.
Flavin, R., et al., "Fatty acid synthase as a potential therapeutic target in cancer", Future Oncology, Future Medicine Ltd., 2010, pp. 551-562, vol. 6, No. 4.
Kuhaja, F. P., "Fatty-acid synthase and human cancer: new perspectives on its role in tumor biology", Nutrition, 2000, pp. 202-208, vol. 16.
Maier, T., et al., "Architecture of mammalian fatty acid synthase at 4.5 Å resolution", Science, 2006, pp. 1258-1262, vol. 311.
Menendez, J.A., et al.,"Inhibition of fatty acid synthase (FAS) suppresses HER2/neu (erbB-2) oncogene overexpression in cancer cells", Proc. Natl Acad. Sci.USA, 2004, pp. 10715-10720, vol. 101.
Migita, et a., "Fatty Acid Synthase: A Metabolic Enzyme and Candidate Oncogene in Prostate Cancer", J Natl. Cancer Inst., 2009, pp. 519-532, vol. 101.
Portsmann, T., et al., "PKB/AKT induces transcription of enzymes involved in cholesterol and fatty acid biosynthesis via activation of SREBP", Oncogene, 2005, pp. 6465-6481, vol. 24.

(Continued)

*Primary Examiner* — Kahsay Habte

(57) ABSTRACT

The present invention is directed to benzamide derivatives, pharmaceutical compositions containing them, and their use as FASN inhibitors, in for example, the treatment of cancer, obesity related disorders, liver related disorders and viral infections. Such compounds are represented by formula (I) as follows:

Formula (I)

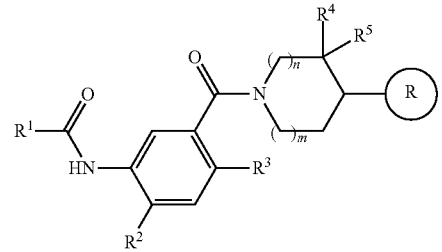

wherein $R^1$, $R^2$, $R^3$, $R^4$, $R^5$, m, n,

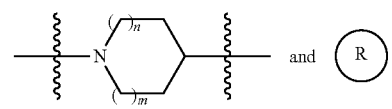

are defined herein.

23 Claims, No Drawings

(56) References Cited

Swinnen, J.V., et al., "Fatty acid synthase drives the synthesis of phospholipids partitioning into detergent resistant membrane microdomains", Biochem. Biophys.Res. Commun., 2000, pp. 898-903, vol. 302.

Swinnen, J.V., et al., "Stimulation of tumor-associated fatty acid synthase expression by growth factor activation of the sterol regulatory element-binding protein pathway". Oncogene, 2000, pp. 5173-5181, vol. 19.

Van De Dande, T., et al., "Role of the phosphatidylinositol 3'-kinase/PTEN/Akt kinase pathway in the overexpression of fatty acid synthase in LNCaP prostate cancer cells", Cancer Res., 2002, pp. 642-646, vol. 62.

BENZAMIDE DERIVATIVE USEFUL AS FASN INHIBITORS FOR THE TREATMENT OF CANCER

FIELD OF THE INVENTION

The present invention is directed to benzamide derivatives, pharmaceutical compositions containing them, and their use as FASN inhibitors, in for example, the treatment of cancer, obesity related disorders, liver related disorders and viral infections.

BACKGROUND OF THE INVENTION

Fatty acid synthase (FASN) is a key enzyme for the synthesis of long-chain fatty acids from acetyl-coenzyme A (CoA) and malonyl-CoA that uses reduced nicotinamide adenine dinucleotidephosphate as a cofactor. The final step in the de novo synthesis of fatty acids in mammalians is carried out by FASN, a 250 kDa protein containing 7 functional domains. Through an iterative enzymatic reaction, FASN produces palmitate starting from the substrates acetylCoA and malonylCo, using NADPH as a cofactor (See, MAIER, T., et al., "Architecture of mammalian fatty acid synthase at 4.5 Å resolution", *Science,* 2006, pp 1258-1262, Vol. 311).

FASN is minimally expressed in most normal human tissues except the liver and adipose tissue, where it is expressed at high levels. Except for these lipogenic tissues (such as liver, lactating breast, fetal lung, and adipose tissue), FASN has a low expression in normal cells which use fatty acids from the diet, while tumor cells largely depend on de novo fatty acid synthesis. FASN expression is highly up-regulated in various tumors, e.g. prostate, breast, colon, and lung cancer (See, SWINNEN, J. V., et al., "Stimulation of tumor-associated fatty acid synthase expression by growth factor activation of the sterol regulatory element-binding protein pathway". *Oncogene,* 2000, pp 5173-5181, Vol 19; KUHAJA, F. P., "Fatty-acid synthase and human cancer: new perspectives on its role in tumor biology", *Nutrition,* 2000, pp 202-208, Vol. 16).

FASN overexpression leads to growth and survival advantage to the tumors achieved through multiple mechanisms. Firstly, it provides lipids for membrane synthesis. Moreover, the more saturated lipid composition of the membranes increases resistance to chemotherapy. FASN also contributes to improved growth factor receptor expression in lipid rafts (See, SWINNEN, J. V., et al., "Fatty acid synthase drives the synthesis of phospholipids partitioning into detergent resistant membrane microdomains", *Biochem. Biophys. Res. Commun.,* 2000, pp 898-903, Vol. 302; MENENDEZ, J. A., et al., "Inhibition of fatty acid synthase (FAS) suppresses HER2/neu (erbB-2) oncogene overexpression in cancer cells", *Proc. Natl Acad. Sci. USA,* 2004, pp 10715-10720, Vol. 101), and improved cell signalling. Lastly, the NADPH consumption during palmitate synthesis in tumor cells keeps the redox balance in check.

In tumor cells, but not in normal cells, siRNA knock down or pharmacological inhibition of FASN results in apoptosis in vitro, and in a delayed tumor growth in vivo. The role of FASN as a potential oncogene has been further established in mouse models. Transgenic mouse models with FASN over expression in the prostate develop invasive prostate cancer in the presence of AR (See, MIGITA, et al, "Fatty Acid Synthase: A Metabolic Enzyme and Candidate Oncogene in Prostate Cancer", *J Natl. Cancer Inst.,* 2009, pp 519-532, Vol. 101). It has been proposed that FASN exerts its oncogenic effect by inhibiting the intrinsic pathway of apoptosis. Androgens and epidermal growth factor (EGF) up-regulate FASN expression and activity. In addition, FASN is also over expressed in androgen-independent prostate cancers most likely through activation of the PI3K/Akt pathway (See, BANDYOPADHYAY, S., et al., "FAS expression inversely correlates with PTEN level in prostate cancer and a PI-3 kinase inhibitor synergizes with FAS siRNA to induce apoptosis", *Oncogene,* 2005, pp 5389-5395, Vol. 24; VAN DE DANDE, T., et al., "Role of the phosphatidylinositol 3'-kinase/PTEN/Akt kinase pathway in the overexpression of fatty acid synthase in LNCaP prostate cancer cells", *Cancer Res.,* 2002, pp 642-646, Vol. 62; PORTSMANN, T., et al., "PKB/AKT induces transcription of enzymes involved in cholesterol and fatty acid biosynthesis via activation of SREBP", *Oncogene,* 2005, pp 6465-6481, Vol. 24). Thus, FASN is emerging as an important target for cancer therapy.

Since FASN expression is markedly increased in several human cancers compared with the corresponding normal tissue, and FASN over-expression in tumors has been associated with a poor prognosis, FASN inhibitors are viewed as potential therapeutics for the treatment of cancer. There remains a need for pharmaceutical agents for the treatment of a variety of cancers, including breast, prostate, head, neck, skin, lung, ovary, endometrium, thyroid, colon, rectum, esophagus, stomach, kidney, liver, bladder, pancreas, brain, blood, bone, and others.

FASN inhibitors have also shown promise in the treatment of other FASN-mediated diseases, disorders or conditions, such as obesity lack of appetite control and inflammatory conditions. Additionally, FASN has been implicated in diabetes and/or regulation of the general wellness of the liver, and therefore has potential in the treatment of obesity, Type II diabetes mellitus, Syndrome X and disorders of the liver; for the treatment of which there remains a need for pharmaceutical agents.

There remains a need for FASN inhibitors for the treatment of FASN-mediated disorders including, but not limited to, (a) cancer, as herein defined, (b) obesity and related disorders, (c) liver related disorders, and/or (d) viral infections such as respiratory infections (such as RSV), HBV and HCV.

SUMMARY OF THE INVENTION

The present invention is directed to compounds of formula (I)

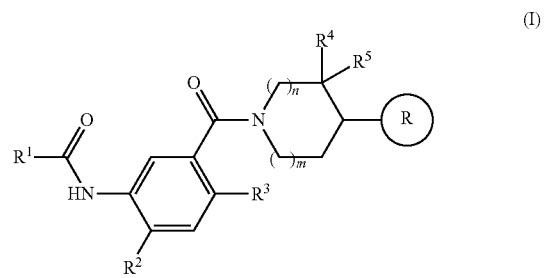

wherein $R^1$ is selected from the group consisting of $C_{1-6}$alkyl, fluorinated $C_{1-3}$alkyl, $C_{3-6}$cycloalkyl, —($C_{1-2}$alkyl)-$C_{3-6}$cycloalkyl, aryl, 5 to 6 membered heteroaryl, 9 to 10 membered heteroaryl, 4 to 6 membered saturated heterocyclyl and 9 to 10 membered saturated, partially unsaturated or benzo-fused heterocyclyl;

wherein the $C_{3-6}$cycloalkyl, aryl, 5 to 6 membered heteroaryl, 9 to 10 membered heteroaryl, 4 to 6 membered saturated heterocyclyl, or 9 to 10 membered saturated, partially unsaturated or benzo-fused heterocyclyl is optionally substituted with one to three $R^O$ substituents;

wherein each $R^O$ is independently selected from the group consisting of halogen, hydroxy, cyano, $C_{1-6}$alkyl, fluorinated $C_{1-2}$alkyl, $C_{1-4}$alkoxy, —$NR^AR^B$, —C(O)—($C_{1-4}$alkyl), —S—($C_{1-4}$alkyl), —SO—($C_{1-4}$alkyl), —$SO_2$—($C_{1-4}$alkyl), —$C_{3-6}$cycloalkyl, —($C_{1-2}$alkyl)-$C_{3-6}$cycloalkyl, —C(O)—$C_{3-6}$cycloalkyl, —($C_{1-2}$alkyl)-phenyl and 5 to 6 membered saturated heterocyclyl;

wherein the $C_{3-6}$cycloalkyl or 5 to 6 membered saturated heterocyclyl is optionally substituted with one to two substituents independently selected from the group consisting of $C_{1-4}$alkyl and hydroxy substituted $C_{1-2}$alkyl;

wherein $R^A$ is selected from the group consisting of hydrogen and $C_{1-4}$alkyl; and wherein $R^B$ is selected from the group consisting of hydrogen, formyl, $C_{1-6}$alkyl, $C_{3-6}$cycloalkyl and 5 to 6 membered saturated heterocyclyl; wherein the $R^B$ 5 to 6 membered saturated heterocyclyl is optionally substituted with $C_{1-4}$alkyl;

$R^2$ is selected from the group consisting of halogen, hydroxy, cyano, $C_{1-4}$alkyl, fluorinated $C_{1-3}$alkyl, $C_{1-4}$alkoxy, benzyloxy and —$NR^XR^Y$;

wherein $R^X$ is selected from the group consisting of hydrogen, $C_{1-4}$alkyl and —($C_{2-4}$alkyl)-O—($C_{1-2}$alkyl); and wherein $R^Y$ is selected from the group consisting of hydrogen, $C_{1-4}$alkyl, —($C_{2-4}$alkyl)-O—($C_{1-2}$alkyl), $C_{3-6}$cycloalkyl and —C(O)—$C_{3-6}$cycloalkyl;

$R^3$ is selected from the group consisting of hydrogen, halogen, methyl and trifluoromethyl;

n is an integer from 0 to 2; and m is an integer from 0 to 1; such that

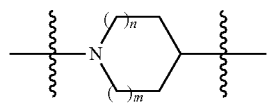

is selected from the group consisting of azetidin-1,3-diyl, pyrrolidin-1,3-diyl, piperidin-1,3-diyl and piperidin-1,4-diyl;

$R^4$ is selected from the group consisting of hydrogen and $C_{1-3}$alkyl;

$R^5$ is selected from the group consisting of hydrogen, hydroxy and $C_{1-3}$alkyl;

provided that when n is 0 and m is 0, such that

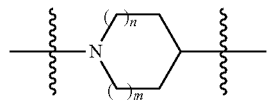

is azetidin-1,3-diyl, then $R^5$ is selected from the group consisting of hydrogen and $C_{1-3}$alkyl;

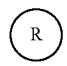

is selected from the group consisting of,

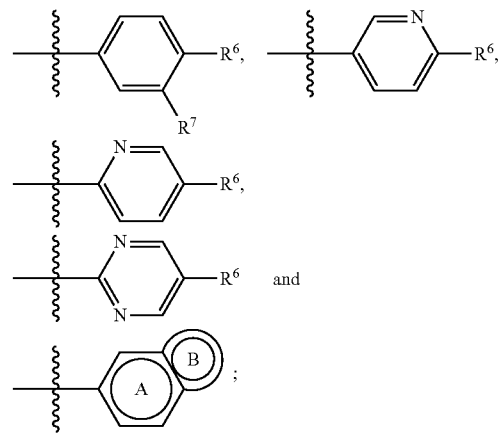

wherein $R^6$ is selected from the group consisting of aryl, 5 to 6 membered heteroaryl and 9 to 10 membered heteroaryl;

wherein the aryl, 5 to 6 membered heteroaryl or 9 to 10 membered heteroaryl is optionally substituted with one to three substituents independently selected from the group consisting of halogen, cyano, $C_{1-4}$alkyl, trifluoromethyl, hydroxy substituted $C_{1-3}$alkyl, $C_{1-4}$alkoxy, $NR^PR^Q$, —($C_{1-2}$alkyl)-$NR^PR^Q$, $C_{3-6}$cycloalkyl, —($C_{1-2}$alkyl)-$C_{3-6}$cycloalkyl, 5 to 6 membered saturated heterocyclyl and 5 to 6 membered hereroaryl; wherein $R^P$ and $R^Q$ are each independently selected from the group consisting of hydrogen and $C_{1-4}$alkyl;

wherein $R^7$ is selected from the group consisting of hydrogen, halogen, cyano, $C_{1-4}$alkyl and trifluoromethyl; wherein

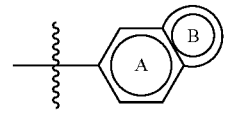

represents a 9 to 10 membered bicyclic, partially unsaturated or aromatic heterocyclyl; and wherein the

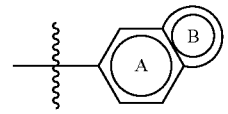

is optionally substituted with one to three substituents independently selected from the group consisting of halogen, oxo, cyano, $C_{1-4}$alkyl, trifluoromethyl, $C_{1-4}$alkoxy, $NR^SR^T$ and cyclopropyl; wherein $R^S$ and $R^T$ are each independently selected from the group consisting of hydrogen and $C_{1-4}$alkyl;

and stereoisomers, tautomers and pharmaceutically acceptable salts thereof.

The present invention is further directed to processes for the preparation of the compounds of formula (I), as described in more detail in the general synthesis schemes and examples, which follow herein. The present invention is further directed to a product prepared according to any of the processes as described in the general synthesis schemes and examples, which follow herein.

The present invention is further directed compounds of formula (VII)

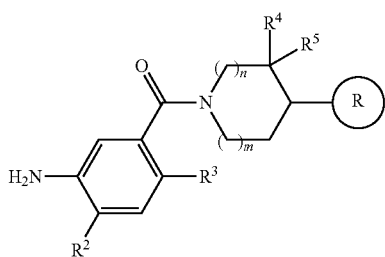

wherein $R^2$, $R^3$, $R^4$, $R^5$, m, n,

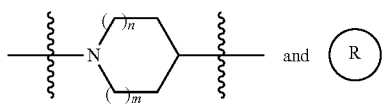

are as described in more detail herein, useful as intermediates in the synthesis of the compounds of formula (I). The present invention is further directed compounds of formula (XI)

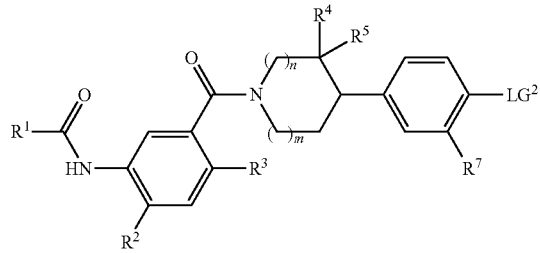

wherein $R^1$, $R^2$, $R^3$, $R^4$, $R^5$, $R^7$, $LG^1$, m, n and

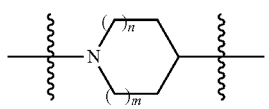

are as described in more detail herein, useful as intermediates in the synthesis of the compounds of formula (I).

Illustrative of the invention is a pharmaceutical composition comprising, consisting of and/or consisting essentially of a pharmaceutically acceptable carrier and the product prepared according to the process described herein. An illustration of the invention is a pharmaceutical composition made by mixing the product prepared according to the process described herein and a pharmaceutically acceptable carrier. Illustrating the invention is a process for making a pharmaceutical composition comprising mixing the product prepared according to the process described herein and a pharmaceutically acceptable carrier.

Exemplifying the invention are methods of treating a disorder mediated by inhibition of fatty acid synthase (FASN) enzyme (selected from the group consisting of cancer, obesity and related disorders and liver related disorders, as herein defined) comprising administering to a subject in need thereof a therapeutically effective amount of any of the compounds or pharmaceutical compositions described above. Exemplifying the invention are methods of treating a viral infection selected from the group consisting of respiratory viruses such as RSV (respiratory syncytial virus) infection, HBV (hepatitis B virus) infection and HCV (hepatitis C virus) infection, comprising administering to a subject in need thereof a therapeutically effective amount of any of the compounds or pharmaceutical compositions described above.

In an embodiment, the present invention is directed to a compound of formula (I) for use as a medicament. In another embodiment, the present invention is directed to a compound of formula (I) for use in the treatment of a disorder mediated by inhibition of fatty acid synthase (FASN) enzyme (selected from the group consisting of cancer, obesity and related disorders, liver related disorders, and viral infection (including respiratory viruses (such as RSV), HBV and HCV), as herein defined). In another embodiment, the present invention is directed to a composition comprising a compound of formula (I) for the treatment of a disorder mediated by inhibition of fatty acid synthase (FASN) enzyme (selected from the group consisting of cancer, obesity and related disorders, liver related disorders, and viral infection (including respiratory viruses (such as RSV), HBV and HCV), as herein defined).

Another example of the invention is the use of any of the compounds of formula (I) described herein in the preparation of a medicament for treating: (a) cancer, as herein defined, (b) obesity or related disorder, (c) liver related disorder, (d) viral infections selected from the group consisting of respiratory viruses (such as RSV), HBV and HCV, in a subject in need thereof.

In another example, the present invention is directed to a compound of formula (I) as described herein for use in a methods for treating a disorder selected from the group consisting of cancer, obesity and related disorders, liver related disorders, and viral infection (including respiratory viruses (such as RSV), HBV and HCV), as herein defined, in a subject in need thereof.

DETAILED DESCRIPTION OF THE INVENTION

The present invention is directed to compounds of formula (I)

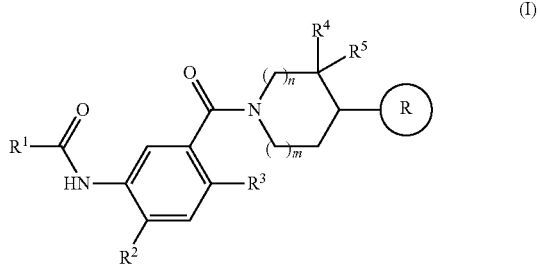

wherein $R^1$, $R^2$, $R^3$, $R^4$, $R^5$, m, n,

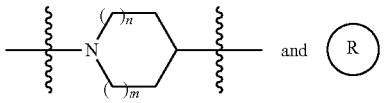

are as herein defined. The compounds of the present invention are FASN inhibitors useful in the treatment of, for example, cancer. More particularly, the compounds of formula (I) of the present invention are useful in the treatment of FASN-mediated disorders including, but not limited to, (a) cancer, as herein defined, (b) obesity and related disorders and (c) liver related disorders, as herein defined.

In an embodiment, the present invention is directed to methods for the treatment of cancer comprising administering to a subjected in need thereof, a therapeutically effective amount of a compound of formula (I); wherein the cancer is selected from the group consisting of cancer of the breast, prostate, head, neck, skin, lung, ovary, endometrium, thyroid, colon, rectum, esophagus, stomach, kidney, liver, bladder, pancreas, brain, spinal cord, blood and bone. Preferably, the cancer is selected from the group consisting of breast, prostate, colon, lung, brain, spinal cord, ovary, endometrium, thyroid, kidney and stomach.

In another embodiment, the aforementioned cancer is selected from the group consisting of glioma, glioblastoma, leukemia, Bannayan-Zonana syndrome, Cowden disease, Lhermitte-Duclos disease, breast cancer, inflammatory breast cancer, Wilm's tumor, Ewing's sarcoma, Rhabdomyosarcoma, ependymoma, medulloblastoma, sarcoma, osteosarcoma, melanoma, giant cell tumor of bone and giant cell tumor of thyroid.

In another embodiment, the present invention is directed to methods for the treatment of obesity or a related disorder comprising administering to a subjected in need thereof, a therapeutically effective amount of a compound of formula (I); wherein the obesity or related disorder is selected from the group consisting of obesity, overweight, weight gain, Type II diabetes mellitus, Syndrome X, and/appetite and/or satiety modulation. Preferably, the obesity or related disorders is selected from the group consisting of obesity, Type II diabetes mellitus, Syndrome X, and appetite and/or satiety modulation, more preferably obesity or Type II diabetes mellitus.

In another embodiment, the present invention is directed to methods for the treatment of an liver related disorder comprising administering to a subjected in need thereof, a therapeutically effective amount of a compound of formula (I); wherein the liver related disorder is selected from the group consisting of dyslipidemia, elevated cholesterol levels, elevated LDL, decreased HDL, elevated triglicerides, fatty libver, non-alcoholic steatohepatitis (NASH), fatty liver or non-alcoholic fatty liver disease (NAFLD). Preferably, the liver related disorder is selected from the group consisting of dylipidemia and elevated cholesterol levels.

In another embodiment, the present invention is directed to methods for the treatment of viral infection comprising administering to a subject in need thereof, a therapeutically effective amount of a compound of formula (I); wherein the viral infection is preferably selected from the group consisting of respiratory viruses (such as RSV (respiratory syncytial virus)), HBV (hepatitis B virus) and HCV (hepatitis C virus).

In an embodiment, the present invention is directed to a pharmaceutical composition comprising, consisting of and/or consisting essentially of a pharmaceutically acceptable carrier and a compound of formula (I). In another embodiment, the present invention is directed to a pharmaceutical composition made by mixing a compound of formula (I) and a pharmaceutically acceptable carrier. In another embodiment, the present invention is directed to a process for making a pharmaceutical composition comprising mixing a compound of formula (I) and a pharmaceutically acceptable carrier.

In an embodiment, the present invention is directed to a method of treating a disorder mediated by inhibition of fatty acid synthase (FASN) enzyme, comprising administering to a subject in need thereof a therapeutically effective amount of the compound of formula (I).

In another embodiment, the aforementioned disorder mediated by inhibition of fatty acid synthase (FASN) enzyme is cancer of the breast, prostate, head, neck, skin, lung, ovary, endometrium, thyroid, colon, rectum, esophagus, stomach, kidney, liver, bladder, pancreas, brain, spinal cord, blood or bone.

In another embodiment, the aforementioned disorder mediated by inhibition of fatty acid synthase (FASN) enzyme is selected from the group consisting of obesity, overweight, weight gain, Type II diabetes mellitus, Syndrome X, and appetite or satiety modulation.

In another embodiment, the aforementioned disorder mediated by inhibition of fatty acid synthase (FASN) enzyme, is selected from the group consisting of dyslipidemia, elevated cholesterol levels, elevated LDL, decreased HDL, elevated triglicerides, fatty liver, non-alcoholic steatohepatitis (NASH), fatty liver and non-alcoholic fatty liver disease (NAFLD).

In another embodiment, the aforementioned disorder mediated by inhibition of fatty acid synthase (FASN) enzyme, is a viral infection selected from the group consisting of respiratory viruses (such as RSV), HBV and HCV.

In an embodiment, the present invention is directed to a method of treating (a) cancer of the breast, prostate, head, neck, skin, lung, ovary, endometrium, thyroid, colon, rectum, esophagus, stomach, kidney, liver, bladder, pancreas, brain, spinal cord, blood or bone; (b) obesity or a related disorder selected from the group consisting of obesity, overweight, weight gain, Type II diabetes mellitus, Syndrome X, and appetite or satiety modulation; (c) a liver related disorders selected from the group consisting of dyslipidemia, elevated cholesterol levels, elevated LDL, decreased HDL, elevated triglicerides, fatty liver, non-alcoholic steatohepatitis (NASH), fatty liver and non-alcoholic fatty liver disease (NAFLD); or (d) a viral infection selected from the group consisting of respiratory viruses (such as RSV), HBV and HCV; comprising administering to a subject in need thereof, a therapeutically effective amount of the compound of formula (I).

In another embodiment, the present invention is directed to a method of treating (a) cancer of the breast, prostate, head, neck, skin, lung, ovary, endometrium, thyroid, colon, rectum, esophagus, stomach, kidney, liver, bladder, pancreas, brain, spinal cord, blood or bone; (b) obesity or a related disorder selected from the group consisting of obesity, overweight, weight gain, Type II diabetes mellitus, Syndrome X, and appetite or satiety modulation; (c) a liver related disorders selected from the group consisting of dyslipidemia, elevated cholesterol levels, elevated LDL, decreased HDL, elevated triglicerides, fatty liver, non-alcoholic steatohepatitis (NASH), fatty liver and non-alcoholic fatty liver disease (NAFLD); or (d) a viral infection selected from the group consisting of respiratory viruses (such as RSV), HBV and HCV; comprising administering to a subject in need thereof a therapeutically effective amount of a pharmaceutical composition comprising a compound of formula (I).

In an embodiment, the present invention is directed to the use of a compound formula (I) for the preparation of a medicament for treating: (a) cancer of the breast, prostate, head, neck, skin, lung, ovary, endometrium, thyroid, colon, rectum, esophagus, stomach, kidney, liver, bladder, pancreas, brain, spinal cord, blood or bone; (b) obesity or a related disorder selected from the group consisting of obesity, overweight, weight gain, Type II diabetes mellitus, Syndrome X, and appetite or satiety modulation; (c) a liver related disorders selected from the group consisting of dyslipidemia, elevated cholesterol levels, elevated LDL, decreased HDL, elevated triglicerides, fatty liver, non-alcoholic steatohepatitis (NASH), fatty liver and non-alcoholic fatty liver disease (NAFLD); or (d) a viral infection selected from the group consisting of respiratory viruses (such as RSV), HBV and HCV; in a subject in need thereof.

In another embodiment, the present invention is directed to the use of a compound of formula (I), for use in a method for treating a disorder selected from the group consisting of (a) cancer of the breast, prostate, head, neck, skin, lung, ovary, endometrium, thyroid, colon, rectum, esophagus, stomach, kidney, liver, bladder, pancreas, brain, spinal cord, blood or bone; (b) obesity or a related disorder selected from the group consisting of obesity, overweight, weight gain, Type II diabetes mellitus, Syndrome X, and appetite or satiety modulation; (c) a liver related disorders selected from the group consisting of dyslipidemia, elevated cholesterol levels, elevated LDL, decreased HDL, elevated triglycerides, fatty liver, non-alcoholic steatohepatitis (NASH), fatty liver and non-alcoholic fatty liver disease (NAFLD); or (d) a viral infection selected from the group consisting of respiratory viruses (such as RSV), HBV and HCV; in a subject in need thereof.

In another embodiment, the present invention is directed to a compound of formula (I) for use as a medicament. In another embodiment, the present invention is directed to a compound of formula (I) (as in, for example, claim 1) for use in the treatment of a disorder mediated by inhibition of fatty acid synthase (FASN) enzyme. In another embodiment, the present invention is directed to a compound of formula (I), for use in the treatment of a disorder mediated by inhibition of fatty acid synthase (FASN) enzyme, selected from the group consisting of cancer of the breast, prostate, head, neck, skin, lung, ovary, endometrium, thyroid, colon, rectum, esophagus, stomach, kidney, liver, bladder, pancreas, brain, spinal cord, blood or bone. In another embodiment, the present invention is directed to a compound of formula (I), for use in the treatment of a disorder mediated by inhibition of fatty acid synthase (FASN) enzyme, selected from the group consisting of (a) obesity and related disorders and (b) liver related disorders. In another embodiment, the present invention is directed to a compound of formula (I), for use in the treatment of a viral infection selected from the group consisting of respiratory viruses (such as RSV), HBV and HCV.

In an embodiment, the present invention is directed to a composition comprising compound of formula (I), for use in the treatment of a disorder mediated by inhibition of fatty acid synthase (FASN) enzyme.

In another embodiment, the present invention is directed to a composition comprising, consisting of, and/or consisting essentially of compound of formula (I) for use in the treatment of a disorder mediated by inhibition of fatty acid synthase (FASN) enzyme selected from the group consisting of (a) cancer of the breast, prostate, head, neck, skin, lung, ovary, endometrium, thyroid, colon, rectum, esophagus, stomach, kidney, liver, bladder, pancreas, brain, spinal cord, blood or bone; (b) obesity or a related disorder selected from the group consisting of obesity, overweight, weight gain, Type II diabetes mellitus, Syndrome X, and appetite or satiety modulation; (c) a liver related disorders selected from the group consisting of dyslipidemia, elevated cholesterol levels, elevated LDL, decreased HDL, elevated triglicerides, fatty liver, non-alcoholic steatohepatitis (NASH), fatty liver and non-alcoholic fatty liver disease (NAFLD); and viral infections selected from the group consisting of respiratory viruses (such as RSV), HBV and HCV.

In an embodiment, the present invention is directed to compounds of formula (I) wherein
$R^1$ is selected from the group consisting of $C_{1-6}$alkyl, fluorinated $C_{1-3}$alkyl, $C_{3-6}$cycloalkyl, aryl, 5 to 6 membered heteroaryl, 9 to 10 membered heteroaryl, 4 to 6 membered saturated heterocyclyl and 9 to 10 membered benzo-fused heterocyclyl; wherein the $C_{3-6}$cycloalkyl, aryl, 5 to 6 membered heteroaryl, 9 to 10 membered heteroaryl, 4 to 6 membered saturated heterocyclyl or 9 to 10 membered benzo-fused heterocyclyl is optionally substituted with one to three $R^0$ substituents; wherein each $R^0$ is independently selected from the group consisting of halogen, hydroxy, cyano, $C_{1-6}$alkyl, fluorinated $C_{1-2}$alkyl, $C_{1-4}$alkoxy, —$NR^A R^B$, —C(O)—($C_{1-4}$alkyl), —S—($C_{1-4}$alkyl), —SO$_2$—($C_{1-4}$alkyl), —$C_{3-6}$cycloalkyl, —($C_{1-2}$alkyl)-$C_{3-6}$cycloalkyl, —C(O)—$C_{3-6}$cycloalkyl, —($C_{1-2}$alkyl)-phenyl and 5 to 6 membered saturated heterocyclyl; wherein the $C_{3-6}$cycloalkyl or 5 to 6 membered saturated heterocyclyl is optionally substituted with one to two substituents independently selected from the group consisting of $C_{1-4}$alkyl and hydroxy substituted $C_{1-2}$alkyl; wherein $R^A$ is selected from the group consisting of hydrogen and $C_{1-4}$alkyl; and wherein $R^B$ is selected from the group consisting of hydrogen, formyl, $C_{1-6}$alkyl, $C_{3-6}$cycloalkyl and 5 to 6 membered saturated, nitrogen containing heterocyclyl; wherein the $R^B$ 5 to 6 membered saturated, nitrogen containing heterocyclyl is optionally substituted with $C_{1-4}$alkyl;

$R^2$ is selected from the group consisting of halogen, hydroxy, cyano, $C_{1-4}$alkyl, fluorinated $C_{1-2}$alkyl, $C_{1-4}$alkoxy, benzyloxy and —$NR^X R^Y$; wherein $R^X$ is selected from the group consisting of hydrogen, $C_{1-4}$alkyl and —($C_{2-4}$alkyl)-O—($C_{1-2}$alkyl); and wherein $R^Y$ is selected from the group consisting of hydrogen, $C_{1-4}$alkyl, —($C_{2-4}$alkyl)-O—($C_{1-2}$alkyl), $C_{3-6}$cycloalkyl and —C(O)—$C_{3-6}$cycloalkyl;

$R^3$ is selected from the group consisting of hydrogen, fluoro, chloro, bromo, methyl and trifluoromethyl;

n is an integer from 0 to 1; and m is an integer from 0 to 1; such that

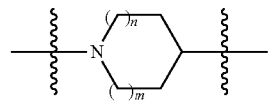

is selected from the group consisting of azetidin-1,3-diyl, pyrrolidin-1,3-diyl and piperidin-1,4-diyl;

$R^4$ is selected from the group consisting of hydrogen and $C_{1-3}$alkyl;

$R^5$ is selected from the group consisting of hydrogen, hydroxy and $C_{1-3}$alkyl;

provided that when n is 0 and m is 0, such that

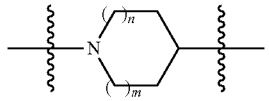

is azetidin-1,3-diyl, then $R^5$ is selected from the group consisting of hydrogen and $C_{1-3}$alkyl;

is selected from the group consisting of,

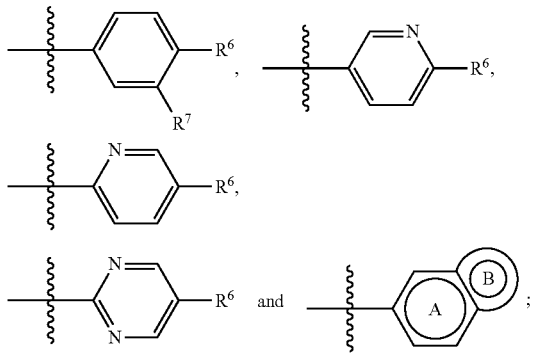

wherein $R^6$ is selected from the group consisting of aryl, 5 to 6 membered heteroaryl and 9 to 10 membered heteroaryl; wherein the aryl, 5 to 6 membered heteroaryl or 9 to 10 membered heteroaryl is optionally substituted with one to two substituents independently selected from the group consisting of halogen, $C_{1-4}$alkyl, trifluoromethyl, hydroxy substituted $C_{1-4}$alkyl, $C_{1-4}$alkoxy, $NR^PR^Q$, —($C_{1-2}$alkyl)-$NR^PR^Q$, $C_{3-6}$cycloalkyl, —($C_{1-2}$alkyl)-$C_{3-6}$cycloalkyl, 5 to 6 membered saturated, nitrogen containing heterocyclyl and 5 to 6 membered nitrogen containing hereroaryl; wherein $R^P$ and $R^Q$ are each independently selected from the group consisting of hydrogen and $C_{1-4}$alkyl;

wherein $R^7$ is selected from the group consisting of hydrogen, fluoro, chloro, bromo, $C_{1-4}$alkyl and trifluoromethyl;

wherein

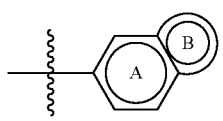

represents a 9 to 10 membered bicyclic, partially unsaturated or aromatic heterocyclyl; and wherein the

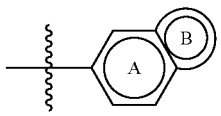

is optionally substituted with one to two substituents independently selected from the group consisting of halogen, oxo, cyano, $C_{1-4}$alkyl, trifluoromethyl, $C_{1-4}$alkoxy, $NR^SR^T$ and cyclopropyl; wherein $R^S$ and $R^T$ are each independently selected from the group consisting of hydrogen and $C_{1-4}$alkyl;

and stereoisomers, tautomers and pharmaceutically acceptable salts thereof.

In another embodiment, the present invention is directed to compounds of formula (I) wherein $R^1$ is selected from the group consisting of $C_{2-6}$alkyl, fluorinated $C_{1-2}$alkyl, $C_{3-6}$cycloalkyl, phenyl, 4 to 6 membered saturated heterocyclyl, 5 to 6 membered heteroaryl, 9 to 10 membered heteroaryl and 1,3-benzodioxolyl; wherein the $C_{3-6}$cycloalkyl, phenyl, 4 to 6 membered saturated heterocyclyl, 5 to 6 membered heteroaryl or 9 to 10 membered heteroaryl is optionally substituted with one to three $R^0$ substituents; wherein each $R^0$ is independently selected from the group consisting of halogen, hydroxy, cyano, $C_{1-6}$alkyl, fluorinated $C_{1-2}$alkyl, $C_{1-2}$alkoxy, $NR^AR^B$, —C(O)—($C_{1-2}$alkyl), —S—($C_{1-2}$alkyl), $C_{5-6}$cycloalkyl, —C(O)—$C_3$cycloalkyl, —($C_{1-2}$alkyl)-phenyl and 5 to 6 membered, saturated, nitrogen containing heterocyclyl; wherein the $C_{5-6}$cycloalkyl or 5 to 6 membered saturated, nitrogen containing heterocyclyl is optionally substituted with a substituent selected from the group consisting of $C_{1-2}$alkyl and —($C_{1-2}$alkyl)-OH; wherein $R^A$ is selected from the group consisting of hydrogen and $C_{1-2}$alkyl; and wherein $R^B$ is selected from the group consisting of hydrogen, formyl, $C_{1-4}$alkyl, $C_{3-4}$cycloalkyl and 6 membered, saturated, nitrogen containing heterocyclyl; wherein the $R^B$ 6 membered saturated, nitrogen containing heterocyclyl is optionally substituted with $C_{1-2}$alkyl;

$R^2$ is selected from the group consisting of halogen, hydroxy, $C_{1-2}$alkyl, $C_{1-2}$alkoxy, benzyloxy and $NR^XR^Y$; wherein $R^X$ is selected from the group consisting of hydrogen, $C_{1-3}$alkyl and —($C_2$alkyl)-O—($C_{1-2}$alkyl); and wherein $R^Y$ is selected from the group consisting of hydrogen, $C_{1-3}$alkyl, —($C_2$alkyl)-O—($C_{1-2}$alkyl), $C_3$cycloalkyl and C(O)—$C_3$cycloalkyl;

$R^3$ is hydrogen;

n is an integer from 0 to 1; and m is an integer from 0 to 1; such that

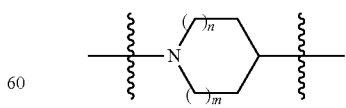

is selected from the group consisting of azetidin-1,3-diyl, pyrrolidin-1,3-diyl and piperidin-1,4-diyl;

$R^4$ is selected from the group consisting of hydrogen and $C_{1-2}$alkyl;

$R^5$ is selected from the group consisting of hydrogen, hydroxy and $C_{1-2}$alkyl;

provided that when n is 0 and m is 0, such that

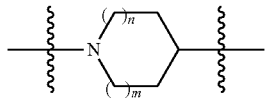

is azetidin-1,3-diyl, then $R^5$ is selected from the group consisting of hydrogen and $C_{1-3}$alkyl;

is selected from the group consisting of

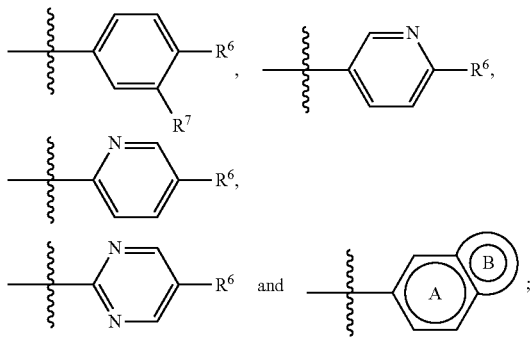

wherein $R^6$ is selected from the group consisting of phenyl, 5 to 6 membered heteroaryl and 9 to 10 membered, nitrogen containing heteroaryl; wherein the phenyl, 5 to 6 membered heteroaryl or 9 to 10 membered, nitrogen containing heteroaryl is optionally substituted with a substituent selected from the group consisting of halogen, $C_{1-4}$alkyl, —($C_{1-2}$alkyl)-OH, $C_{1-2}$alkoxy, $NR^P R^Q$, —($C_{1-2}$alkyl)-$NR^P R^Q$, $C_{3-4}$cycloalkyl, —($C_{1-2}$alkyl)-$C_{3-4}$cycloalkyl, 6 membered saturated, nitrogen containing heterocyclyl and 6 membered, nitrogen containing heteroaryl; wherein $R^P$ and $R^Q$ are each independently selected from the group consisting of hydrogen and $C_{1-2}$alkyl;

$R^7$ is hydrogen;

and wherein

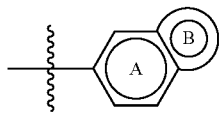

represents a 9 to 10 membered, bicyclic, partially unsaturated or aromatic, nitrogen containing heterocyclyl; wherein the

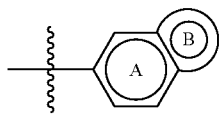

optionally substituted with one to two substituents independently selected from the group consisting of oxo and $C_{1-2}$alkyl;

and stereoisomers, tautomers and pharmaceutically acceptable salts thereof.

In another embodiment, the present invention is directed to compounds of formula (I) wherein $R^1$ is selected from the group consisting of t-butyl, n-pent-3-yl, isopropyl, 1-fluoro-ethyl, cyclopropyl, cyclobutyl, cyclopentyl, 4S-ethylcarbonyl-cyclopent-1S-yl, cyclohexyl, tetrahydropyran-4-yl, piperidin-4-yl, 1-methyl-piperidin-4-yl, 1-ethyl-piperidin-4-yl, 1-isopropyl-piperidin-4-yl, 1-(n-butyl)-piperidin-4-yl, 1-(1-methyl-n-pentyl)-piperidin-4-yl, 1-(n-pentyl)-piperidin-4-yl, 1-(2,2-dimethyl-propyl)-piperidin-4-yl, 1-isobutyl-piperidin-4-yl, 1-propyl-piperidin-4-yl, 1-isopentyl-piperidin-4-yl, 1-(n-hexyl)-piperidin-4-yl, 1-cyclobutyl-piperidin-4-yl, 1-cyclopentyl-piperidin-4-yl, 1-cyclohexyl-piperidin-4-yl, 1-(3-methyl-cyclopentyl)-piperidin-4-yl, 1-benzyl-piperidin-4-yl, tetrahydrofuran-2-yl, pyrrolidin-3-yl, pyrrolidin-2S-yl, pyrrolidin-2R-yl, 1-methyl-pyrrolidin-3R-yl, 1-methyl-pyrrolidin-3S-yl, 1-ethyl-pyrrolidin-3-yl, 1-propyl-pyrrolidin-3-yl, 1-isobutyl-pyrrolidin-3-yl, 1-(2,2-dimethyl-propyl)-pyrrolidin-3-yl, 1-isopropyl-pyrrolidin-3-yl, 1-(n-butyl)-pyrrolidin-3-yl, 1-(n-pentyl)-pyrrolidin-3-yl, 1-isopentyl-pyrrolidin-3-yl, 1-(1-methyl-n-pentyl)-pyrrolidin-3-yl, 1-(n-hexyl)-pyrrolidin-3-yl, 1-cyclobutyl-pyrrolidin-3-yl, 1-cyclopentyl-pyrrolidin-3-yl, 1-(3-methyl-cyclopentyl)-pyrrolidin-3-yl, 1-cyclohexyl-pyrrolidin-3-yl, 1-(cyclopropyl-carbonyl)-pyrrolidin-3-yl, azetidin-3-yl, 1-methyl-azetidin-3-yl, 1-ethyl-azetidin-3-yl, 1-isopropyl-azetidin-3-yl, 1-(n-propyl)-azetidin-3-yl, 1-(n-butyl)-azetidin-3-yl, 1-isobutyl-azetidin-3-yl, 1-isopentyl-azetidin-3-yl, 1-(n-pentyl)-azetidin-3-yl, 1-(2,2-dimethyl-propyl)-azetidin-3-yl, 1-(1-methyl-n-pentyl)-azetidin-3-yl, 1-(n-hexyl)-azetidin-3-yl, 1-cyclobutyl-azetidin-3-yl, 1-(3-methyl-cyclopentyl)-azetidin-3-yl, 1-cyclopentyl-azetidin-3-yl, 1-cyclohexyl-azetidin-3-yl, 1-(cyclopropyl-carbonyl)-azetidin-3-yl, phenyl, 2-chloro-phenyl, 3-chloro-phenyl, 4-chloro-phenyl, 2-fluoro-phenyl, 4-dichloro-phenyl, 2,4-dichloro-phenyl, 2,6-dichloro-phenyl, 3,4-dichloro-phenyl, 2,3,4-trifluoro-phenyl, 2,4-difluoro-phenyl, 2-fluoro-5-methyl-phenyl, 3-chloro-5-methoxy-phenyl, 2-fluoro-4-cyano-phenyl, 2-chloro-4-fluoro-phenyl, 4-isopropyl-phenyl, 2-methoxy-phenyl, 3-methoxy-phenyl, 2-methyl-4-fluoro-phenyl, 2-methyl-5-fluoro-phenyl, 3-hydroxy-4-methoxy-phenyl, 3-chloro-4-methoxy-phenyl, 4-methoxy-phenyl, 4-methyl-thio-phenyl, 2-trifluoromethyl-phenyl, 4-trifluoromethyl-phenyl, 4-cyano-phenyl, thiophen-2-yl, 3-chloro-thiophen-2-yl, 3-methyl-thiophen-2-yl, 5-methyl-thiophen-3-yl, thiazol-2-yl, thiazol-5-yl, 2-bromo-thiazol-2-yl, 4-t-butyl-thiazol-2-yl, pyridin-2-yl, pyridin-4-yl, 2-chloro-pyridin-3-yl, 4-chloro-pyridin-3-yl, 6-chloro-pyridin-3-yl, 3-fluoro-pyridin-4-yl, 5-bromo-pyridin-3-yl, 2-chloro-6-methoxy-pyridin-4-yl, 6-methyl-pyridin-4-yl, 6-trifluoromethyl-pyridin-2-yl, 6-methoxy-pyridin-3-yl, 5-(dimethylamino)-pyridin-2-yl, 6-(isopropyl-amino)-pyridin-3-yl, 6-(cyclobutyl-amino)-pyridin-3-yl, 6-(piperidin-1-yl)-pyridin-3-yl, 6-(morpholin-4-yl)-pyridin-3-yl, 6-(4-methyl-piperazin-1-yl)-pyridin-3-yl, 6-(N-methyl-N-(1-methyl-piperidin-4-yl)-amino-)-pyridin-3-yl, 6-(N-methyl-N-isopropyl-amino)-pyridin-3-yl, 6-(pyrrolidin-1-yl)-pyridin-3-yl, 6-(3S-hydroxymethyl-piperazin-1-yl)-pyridin-3-yl, 6-(3R-hydroxymethyl-piperazin-4-yl)-pyridin-3-yl, 6-(N-isopropyl-N-formyl)-pyridin-3-yl, 6-(dimethylamino)-pyridin-3-yl, 2-chloro-pyrimidin-5-yl, 2-(isopropyl-amino)-pyrimidin-5-yl, 2-(N-methyl-N-isopropyl-amino)-pyrimidin-5-yl, 2-(morpholin-4-yl)-pyrimidin-5-yl, 6-(morpholin-4-yl)-pyrimidin-5-yl, 2-(cyclobutyl-amino)-pyrimidin-5-yl, 1-methyl-imidazol-2-yl, quinolin-2-yl, indol-5-yl and 1,3-benzodioxol-5-yl;

R² is selected from the group consisting of chloro, hydroxy, methyl, ethyl, methoxy, amino, methyl-amino, isopropyl-amino, (methoxyethyl)-amino, cyclopropyl-amino, (cyclopropylcarbonyl)-amino, N,N-dimethylamino, N-methyl-N-isopropyl-amino, N-methyl-N-(methoxyethyl)-amino, N-methyl-N-cyclopropyl-amino, N-(methoxyethyl)-N-(cyclopropylcarbonyl)-amino and benzyloxy;

R³ is hydrogen;

n is an integer from 0 to 1; and m is an integer from 0 to 1; such that

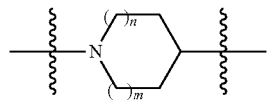

is selected from the group consisting of azetidin-1,3-diyl, pyrrolidin-1,3-diyl and piperidin-1,4-diyl;

R⁴ is selected from the group consisting of hydrogen and methyl;

R⁵ is selected from the group consisting of hydrogen, hydroxy, trans-hydroxy, methyl, trans-methyl and cis-methyl;

provided that when n is 0 and m is 0, such that

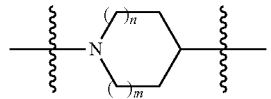

is azetidin-1,3-diyl, then R⁵ is selected from the group consisting of hydrogen, methyl, trans-methyl and cis-methyl;

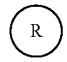

is selected from the group consisting of

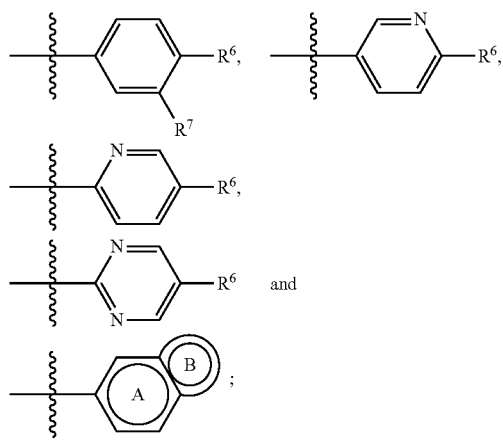

wherein R⁶ is selected from the group consisting of phenyl, 2-fluoro-phenyl, 3-fluoro-phenyl, 4-fluoro-phenyl, 2-methyl-phenyl, 3-methyl-phenyl, 4-methyl-phenyl, 2-methoxy-phenyl, 3-methoxy-phenyl, 4-methoxy-phenyl, thiophen-2-yl, thiophen-3-yl, furan-2-yl, furan-3-yl, isoxazol-4-yl, pyridin-3-yl, pyridin-4-yl, 2-amino-pyridin-3-yl, 3-amino-pyridin-4-yl, pyrazol-4-yl, 1-methyl-pyrazol-4-yl, 1-methyl-pyrazol-5-yl, 1-(tetrahydropyran-4-yl)-pyrazol-4-yl, 1-(cyclobutyl-methyl)-pyrazol-4-yl, 1,3-dimethyl-pyrazol-4-yl, 1-isopropyl-pyrazol-4-yl, 1-(2-hydroxyethyl)-pyrazol-4-yl, 1-cyclobutyl-pyrazol-4-yl, 1-(cyclopropyl)-pyrazol-4-yl, 1-(cyclopropyl-methyl)-pyrazol-4-yl, 1-(dimethylamino-ethyl)-pyrazol-4-yl, 1-(pyridin-3-yl)-pyrazol-4-yl, 1-(pyridin-4-yl)-pyrazol-4-yl, 1-methyl-indazol-6-yl, imidazol-1-yl, quinolin-4-yl, quinolin-5-yl and isoquinolin-6-yl;

R⁷ is hydrogen;

and wherein

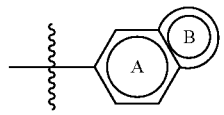

is selected from the group consisting of benzothiazol-6-yl, 2-oxo-benzothiazol-6-yl, 2-oxo-2,3,4-trihydro-quinolin-7-yl, isoquinolin-6-y, isoquinolin-7-yl, 2-oxo-indolin-5-yl, 1-methyl-2-oxo-isoindol-5-yl, 1,7-dimethyl-isoindol-5-yl, 1-methyl-indazol-6-yl, imidazo[1,2-a]pyridine-6-yl and [1,2,4]triazolo[4,3-a]pyridine-6-yl;

and stereoisomers, tautomers and pharmaceutically acceptable salts thereof.

In another embodiment, the present invention is directed to compounds of formula (I) wherein R¹ is selected from the group consisting of n-pent-3-yl, cyclopropyl, cyclobutyl, cyclopentyl, 4S-ethylcarbonyl-cyclopent-1S-yl, cyclohexyl, tetrahydropyran-4-yl, piperidin-4-yl, 1-methyl-piperidin-4-yl, 1-ethyl-piperidin-4-yl, 1-isopropyl-piperidin-4-yl, 1-(1-methyl-n-pentyl)piperidin-4-yl, 1-(n-pentyl)-piperidin-4-yl, 1-(2,2-dimethyl-propyl)piperidin-4-yl, 1-isobutyl-piperidin-4-yl, 1-propyl-piperidin-4-yl, 1-isopentyl-piperidin-4-yl, 1-(n-hexyl)piperidin-4-yl, 1-cyclobutyl-piperidin-4-yl, 1-cyclopentyl-piperidin-4-yl, 1-cyclohexyl-piperidin-4-yl, 1-benzyl-piperidin-4-yl, pyrrolidin-3-yl, 1-propyl-pyrrolidin-3-yl, 1-isobutyl-pyrrolidin-3-yl, 1-isopentyl-pyrrolidin-3-yl, 1-(3-methyl-cyclopentyl)-pyrrolidin-3-yl, 1-(cyclopropyl-carbonyl)-pyrrolidin-3-yl, 1-methyl-azetidin-3-yl, 1-(n-butyl)-azetidin-3-yl, 1-isobutyl-azetidin-3-yl, 1-isopentyl-azetidin-3-yl, 1-(2,2-dimethyl-propyl)-azetidin-3-yl, 1-cyclobutyl-azetidin-3-yl, 1-cyclohexyl-azetidin-3-yl, 1-(cyclopropyl-carbonyl)-azetidin-3-yl, phenyl, 2-chloro-phenyl, 3-chloro-phenyl, 4-chloro-phenyl, 2-fluoro-phenyl, 4-dichloro-phenyl, 2,4-dichloro-phenyl, 3,4-dichloro-phenyl, 2,3,4-trifluoro-phenyl, 2,4-difluoro-phenyl, 2-fluoro-4-cyano-phenyl, 2-chloro-4-fluoro-phenyl, 4-isopropyl-phenyl, 3-methoxy-phenyl, 2-methyl-5-fluoro-phenyl, 3-hydroxy-4-methoxy-phenyl, 3-chloro-4-methoxy-phenyl, 4-methoxy-phenyl, 4-methylthio-phenyl, 4-trifluoromethyl-phenyl, 4-cyano-phenyl, thiophen-2-yl, 3-chloro-thiophen-2-yl, 3-methyl-thiophen-2-yl, 5-methyl-thiophen-3-yl, thiazol-5-yl, 2-bromo-thiazol-2-yl, pyridin-2-yl, pyridin-4-yl, 2-chloro-pyridin-3-yl, 6-chloro-pyridin-3-yl, 3-fluoro-pyridin-4-yl, 2-chloro-6-methoxy-pyridin-4-yl, 6-methyl-pyridin-3-yl, 6-methoxy-pyridin-3-yl, 5-(dimethylamino)-pyridin-2-yl, 6-(isopropyl-amino)-pyridin-3-yl, 6-(cyclobutyl-amino)-pyridin-3-yl, 6-(piperidin-1-yl)-pyridin-3-yl, 6-(morpholin-4-yl)-pyridin-3-yl, 6-(4-methyl-piperazin-1-yl)-pyridin-3-yl, 6-(N-methyl-N-(1-methyl-piperidin-4-yl)-amino)-pyridin-3-yl, 6-(N-methyl-N-isopropyl-amino)-pyridin-3-yl, 6-(pyrrolidin-1-yl)-pyridin-3-yl, 6-(3S-hydroxymethyl-piperazin-1-yl)-pyridin-3-yl, 6-(3R-hydroxymethyl-piperazin-4-yl)-pyridin-3-yl, 2-chloro-pyrimidin-5-yl, 2-(isopropyl-amino)-pyrimidin-5-yl, 2-(N-methyl-N-isopropyl-amino)-pyrimidin-5-yl, 2-(morpholin-4-yl)-pyrimidin-5-yl, 6-(morpholin-4-yl)-pyrimidin-5-yl, 2-(cyclobutyl-amino)-pyrimidin-5-yl, quinolin-2-yl, indol-5-yl and 1,3-benzodioxol-5-yl;

$R^2$ is selected from the group consisting of chloro, hydroxy, methyl, ethyl, methoxy, benzyloxy, methylamino, (methoxyethyl)amino, dimethylamino and N-methyl-N-cyclopropyl-amino;

$R^3$ is hydrogen;

n is 0; and m is an 0; such that

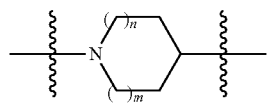

is azetidin-1,3-diyl;
alternatively, n is 1; and m is an 1; such that

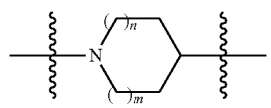

is piperidin-1,4-diyl;

$R^4$ is selected from the group consisting of hydrogen and methyl;

$R^5$ is selected from the group consisting of hydrogen, methyl and trans-methyl;

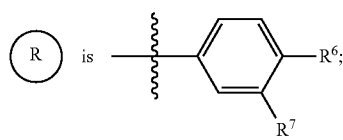

$R^6$ is selected from the group consisting of furan-3-yl, thiophen-3-yl, pyridin-3-yl, pyridin-4-yl, 2-amino-pyridin-3-yl, 3-amino-pyridin-4-yl, imidazol-1-yl, isoxazol-4-yl, pyrazol-4-yl, 1-methyl-pyrazol-4-yl, 1-isopropyl-pyrazol-4-yl, 1-(2-hydroxyethyl)-pyrazol-4-yl, 1-cyclopropyl-pyrazol-4-yl, 1-cyclobutyl-pyrazol-4-yl, 1-(cyclopropyl-methyl)-pyrazol-4-yl, 1,3-dimethyl-pyrazol-4-yl, 1-(pyridin-3-yl)-pyrazol-4-yl, 1-(pyridin-4-yl)-pyrazol-4-yl, 1-methyl-pyrazol-5-yl, quinolin-4-yl, quinolin-5-yl, isoquinolin-6-yl and 1-methyl-indazol-6-yl;

and $R^7$ is hydrogen;
and stereoisomers, tautomers and pharmaceutically acceptable salts thereof.

In another embodiment, the present invention is directed to compounds of formula (I) wherein $R^1$ is selected from the group consisting of n-pent-3-yl, cyclopropyl, cyclohexyl, 1-isopropyl-piperidin-4-yl, 1-isobutyl-piperidin-4-yl, 1-cyclopentyl-piperidin-4-yl, 1-cyclohexyl-piperidin-4-yl, 1-methyl-azetidin-3-yl, phenyl, 3-chloro-phenyl, 4-chloro-phenyl, 2-fluoro-phenyl, 2,4-dichloro-phenyl, 2-fluoro-4-cyano-phenyl, 3-methoxy-phenyl, 2-methyl-5-fluoro-phenyl, 3-hydroxy-4-methoxy-phenyl, 4-methoxy-phenyl, 4-methylthio-phenyl, 4-trifluoromethyl-phenyl, 3-chloro-thiophen-2-yl, pyridin-4-yl, 6-chloro-pyridin-3-yl, 3-fluoro-pyridin-4-yl, 6-methyl-pyridin-4-yl, 6-methoxy-pyridin-3-yl, 6-(isopropyl-amino)-pyridin-3-yl, 6-(cyclobutyl-amino)-pyridin-3-yl, 6-(piperidin-1-yl)-pyridin-3-yl, 6-(morpholin-4-yl)-pyridin-3-yl, 6-(4-methyl-piperazin-1-yl)-pyridin-3-yl, 6-(N-methyl-N-(1-methyl-piperidin-4-yl)-amino)-pyridin-3-yl, 6-(N-methyl-N-isopropyl-amino)-pyridin-3-yl, 6-(pyrrolidin-1-yl)-pyridin-3-yl, 6-(3S-hydroxymethyl-piperazin-1-yl)-pyridin-3-yl, 6-(3R-hydroxymethyl-piperazin-4-yl)-pyridin-3-yl, 2-chloro-pyrimidin-5-yl, 2-(isopropyl-amino)-pyrimidin-5-yl, 2-(N-methyl-N-isopropyl-amino)-pyrimidin-5-yl, 2-(morpholin-4-yl)-pyrimidin-5-yl, 6-(morpholin-4-yl)-pyrimidin-5-yl and 2-(cyclobutyl-amino)-pyrimidin-5-yl;

$R^2$ is selected from the group consisting of chloro, methyl, ethyl and methoxy;

$R^3$ is hydrogen;

n is 0; and m is an 0; such that

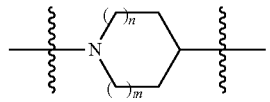

is azetidin-1,3-diyl;
alternatively, n is 1; and m is an 1; such that

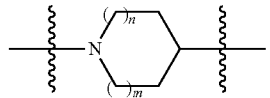

is piperidin-1,4-diyl;

$R^4$ is hydrogen;

$R^5$ is selected from the group consisting of hydrogen and trans-methyl;

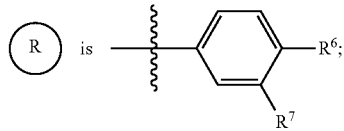

$R^6$ is selected from the group consisting of pyridin-4-yl, 2-amino-pyridin-3-yl, 3-amino-pyridin-4-yl, imidazol-1-yl, isoxazol-4-yl, pyrazol-4-yl, 1-methyl-pyrazol-4-yl, 1-(pyridin-4-yl)-pyrazol-4-yl, 1-methyl-pyrazol-5-yl and quinolin-4-yl;

and $R^7$ is hydrogen;
and stereoisomers, tautomers and pharmaceutically acceptable salts thereof.

In another embodiment, the present invention is directed to compounds of formula (I) wherein $R^1$ is selected from the group consisting of 1-methyl-azetidin-3-yl, 1-(n-butyl)-piperidin-4-yl, 1-(2,2-dimethyl-propyl)piperidin-4-yl, 1-isopentyl-piperidin-4-yl, 1-cyclobutyl-piperidin-4-yl, 1-cyclopentyl-piperidin-4-yl, 1-cyclohexyl-piperidin-4-yl, 4-methylthio-phenyl, 2-fluoro-4-cyano-phenyl, 3-fluoro-pyridin-4-yl, 6-(3S-hydroxymethyl-piperidin-1-yl)-pyridin-3-yl, 6-(isopropyl-amino)-pyridin-3-yl, 6-(cyclobutyl-amino)-pyridin-3-yl, 6-(N-methyl-N-isopropyl-amino)-pyridin-3-yl, 6-(N-methyl-N-(1-methyl-piperidin-4-yl)amino)-pyridin-3-yl, 6-(morpholin-4-yl)-pyridin-3-yl, 6-(4-methyl-piperazin-1-yl)-pyridin-3-yl, 2-(isopropyl-amino)-pyrimidin-5-yl, 2-(morpholin-4-yl)-pyrimidin-5-yl, 2-(cyclobutyl-amino)-pyrimidin-5-yl and indol-5-yl;

$R^2$ is methyl;

$R^3$ is hydrogen;

n is 0; and m is an 0; such that

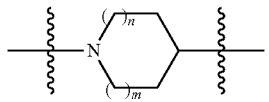

is azetidin-1,3-diyl;

alternatively, n is 1; and m is an 1; such that

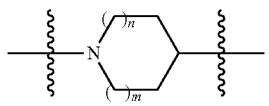

is piperidin-1,4-diyl;

$R^4$ is hydrogen;

$R^5$ is hydrogen;

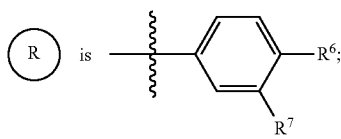

$R^6$ is selected from the group consisting of pyridin-4-yl, 3-amino-pyridin-4-yl, 1-methyl-pyrazol-4-yl, 1-(2-hydroxyethyl)-pyrazol-4-yl, 1-cyclopropyl-pyrazol-4-yl, 1-methyl-pyrazol-5-yl and quinolin-4-yl;

and $R^7$ is hydrogen;

and stereoisomers, tautomers and pharmaceutically acceptable salts thereof.

In another embodiment, the present invention is directed to compounds of formula (I) wherein $R^1$ is selected from the group consisting of cyclopropyl, 6-chloro-pyridin-3-yl, 6-(isopropyl-amino)-pyridin-3-yl, 6-(N-methyl-N-isopropyl-amino)-pyridin-3-yl and 6-(morpholin-4-yl)-pyridin-3-yl;

$R^2$ is selected from the group consisting of methyl, amino, methylamino, isopropylamino, (methoxyethyl)amino, cyclopropylamino, dimethylamino and N-methyl-N-cycloprpoyl-amino;

$R^3$ is hydrogen;

n is 0; and m is an 0; such that

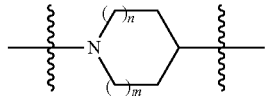

is azetidin-1,3-diyl;

alternatively, n is 1; and m is an 1; such that

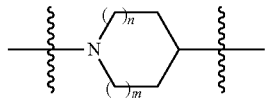

is piperidin-1,4-diyl;

$R^4$ is hydrogen;

$R^5$ is hydrogen;

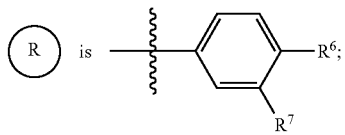

$R^6$ is 1-methyl-pyrazol-4-yl;

and $R^7$ is hydrogen;

and stereoisomers, tautomers and pharmaceutically acceptable salts thereof.

In another embodiment, the present invention is directed to compounds of formula (I) wherein $R^1$ is selected from the group consisting of t-butyl, n-pent-3-yl, isopropyl, 1-fluoro-ethyl, cyclopropyl, cyclobutyl, cyclopentyl, 4S-ethylcarbonyl-cyclopent-1S-yl, cyclohexyl, tetrahydropyran-4-yl, piperidin-4-yl, 1-methyl-piperidin-4-yl, 1-ethyl-piperidin-4-yl, 1-isopropyl-piperidin-4-yl, 1-(n-butyl)-piperidin-4-yl, 1-(1-methyl-n-pentyl)-piperidin-4-yl, 1-(n-pentyl)-piperidin-4-yl, 1-(2,2-dimethyl-propyl)-piperidin-4-yl, 1-isobutyl-piperidin-4-yl, 1-propyl-piperidin-4-yl, 1-isopentyl-piperidin-4-yl, 1-(n-hexyl)piperidin-4-yl, 1-cyclobutyl-piperidin-4-yl, 1-cyclopentyl-piperidin-4-yl, 1-cyclohexyl-piperidin-4-yl, 1-(3-methyl-cyclopentyl)-piperidin-4-yl, 1-benzyl-piperidin-4-yl, tetrahydrofuran-2-yl, pyrrolidin-3-yl, pyrrolidin-2S-yl, pyrrolidin-2R-yl, 1-methyl-pyrrolidin-3R-yl, 1-methyl-pyrrolidin-3S-yl, 1-ethyl-pyrrolidin-3-yl, 1-propyl-pyrrolidin-3-yl, 1-isobutyl-pyrrolidin-3-yl, 1-(2,2-dimethyl-propyl)-pyrrolidin-3-yl, 1-isopropyl-pyrrolidin-3-yl, 1-(n-butyl)-pyrrolidin-3-yl, 1-(n-pentyl)-pyrrolidin-3-yl, 1-isopentyl-pyrrolidin-3-yl, 1-(1-methyl-n-pentyl)-pyrrolidin-3-yl, 1-(n-hexyl)-pyrrolidin-3-yl, 1-cyclobutyl-pyrrolidin-3-yl, 1-cyclopentyl-pyrrolidin-3-yl, 1-(3-methyl-cyclopentyl)-pyrrolidin-3-yl, 1-cyclohexyl-pyrrolidin-3-yl, 1-(cyclopropyl-carbonyl)-pyrrolidin-3-yl, azetidin-3-yl, 1-methyl-azetidin-3-yl, 1-ethyl-azetidin-3-yl, 1-isopropyl-azetidin-3-yl, 1-(n-propyl)-azetidin-3-yl, 1-(n-butyl)-azetidin-3-yl, 1-isobutyl-azetidin-3-yl, 1-isopentyl-azetidin-3-yl, 1-(n-pentyl)-azetidin-3-yl, 1-(2,2-dimethyl-propyl)-azetidin-3-yl, 1-(1-methyl-n-pentyl)-azetidin-3-yl, 1-(n-hexyl)-azetidin-3-yl, 1-cyclobutyl-azetidin-3-yl, 1-(3-methyl-cyclopentyl)-azetidin-3-yl, 1-cyclopentyl-azetidin-3-yl, 1-cyclohexyl-azetidin-3-yl, 1-(cyclopropyl-carbonyl)-azetidin-3-yl, phenyl, 2-chloro-phenyl, 3-chloro-phenyl, 4-chloro-phenyl, 2-fluoro-phenyl, 4-dichloro-phenyl, 2,4-dichloro-phenyl, 2,6-dichloro-phenyl, 3,4-dichloro-phenyl, 2,3,4-trifluoro-phenyl, 2,4-difluoro-phenyl, 2-fluoro-5-methyl-phenyl, 3-chloro-5-methoxy-phenyl, 2-fluoro-4-cyano-phenyl, 2-chloro-4-fluoro-phenyl, 4-isopropyl-phenyl, 2-methoxy-phenyl, 3-methoxy-phenyl, 2-methyl-4-fluoro-phenyl, 2-methyl-5-fluoro-phenyl, 3-hydroxy-4-methoxy-phenyl, 3-chloro-4-methoxy-phenyl, 4-methoxy-phenyl, 4-methyl-thio-phenyl, 2-trifluoromethyl-phenyl, 4-trifluoromethyl-phenyl, 4-cyano-phenyl, thiophen-2-yl, 3-chloro-thiophen-2-yl, 3-methyl-thiophen-2-yl, 5-methyl-thiophen-3-yl, thiazol-2-yl, thiazol-5-yl, 2-bromo-thiazol-2-yl, 4-t-butyl-thiazol-2-yl, pyridin-2-yl, pyridin-4-yl, 2-chloro-pyridin-3-yl, 4-chloro-pyridin-3-yl, 6-chloro-pyridin-3-yl, 3-fluoro-pyridin-4-yl, 5-bromo-pyridin-3-yl, 2-chloro-6-methoxy-pyridin-4-yl, 6-methyl-pyridin-4-yl, 6-trifluoromethyl-pyridin-2-yl, 6-methoxy-pyridin-3-yl, 5-(dimethylamino)-pyridin-2-yl, 6-(isopropylamino)-pyridin-3-yl, 6-(cyclobutyl-amino)-pyridin-3-yl, 6-(piperidin-1-yl)-pyridin-3-yl, 6-(morpholin-4-yl)-pyridin-3-yl, 6-(4-methyl-piperazin-1-yl)-pyridin-3-yl, 6-(N-methyl-N-(1-methyl-piperidin-4-yl)-amino-)-pyridin-3-yl, 6-(N-methyl-N-isopropyl-amino)-pyridin-3-yl, 6-(pyrrolidin-1-yl)-pyridin-3-yl, 6-(3S-hydroxymethyl-piperazin-1-yl)-pyridin-3-yl, 6-(3R-hydroxymethyl-piperazin-4-yl)-pyridin-3-yl, 6-(N-isopropyl-N-formyl)-pyridin-3-yl, 6-(dimethylamino)-pyridin-3-yl, 2-chloro-pyrimidin-5-yl, 2-(isopropyl-amino)-pyrimidin-5-yl, 2-(N-methyl-N-isopropyl-amino)-pyrimidin-5-yl, 2-(morpholin-4-yl)-pyrimidin-5-yl, 6-(morpholin-4-yl)-pyrimidin-5-yl, 2-(cyclobutyl-amino)-pyrimidin-5-yl, 1-methyl-imidazol-2-yl, quinolin-2-yl, indol-5-yl and 1,3-benzodioxol-5-yl;

$R^2$ is selected from the group consisting of chloro, hydroxy, methyl, ethyl, methoxy, amino, methyl-amino, isopropyl-amino, (methoxyethyl)-amino, cyclopropyl-amino, (cyclopropylcarbonyl)-amino, N,N-dimethylamino, N-methyl-N-isopropyl-amino, N-methyl-N-(methoxyethyl)-amino, N-methyl-N-cyclopropyl-amino, N-(methoxyethyl)-N-(cyclopropylcarbonyl)-amino and benzyloxy;

$R^3$ is hydrogen;

n is an integer from 0 to 1; and m is an integer from 0 to 1; such that

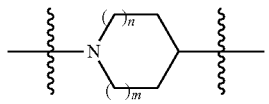

is selected from the group consisting of azetidin-1,3-diyl, pyrrolidin-1,3-diyl and piperidin-1,4-diyl;

$R^4$ is selected from the group consisting of hydrogen and methyl;

$R^5$ is selected from the group consisting of hydrogen, hydroxy, methyl, trans-methyl and cis-methyl;

provided that when n is 0 and m is 0, such that

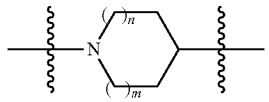

is azetidin-1,3-diyl, then $R^5$ is selected from the group consisting of hydrogen, methyl, trans-methyl and cis-methyl;

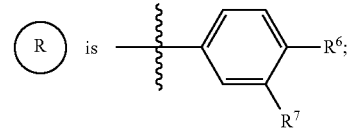

$R^6$ is selected from the group consisting of phenyl, 2-fluoro-phenyl, 3-fluoro-phenyl, 4-fluoro-phenyl, 2-methyl-phenyl, 3-methyl-phenyl, 4-methyl-phenyl, 2-methoxy-phenyl, 3-methoxy-phenyl, 4-methoxy-phenyl, thiophen-2-yl, thiophen-3-yl, furan-2-yl, furan-3-yl, isoxazol-4-yl, pyridin-3-yl, pyridin-4-yl, 2-amino-pyridin-3-yl, 3-amino-pyridin-4-yl, pyrazol-4-yl, 1-methyl-pyrazol-4-yl, 1-methyl-pyrazol-5-yl, 1-(tetrahydropyran-4-yl)-pyrazol-4-yl, 1-(cyclobutyl-methyl)-pyrazol-4-yl, 1,3-dimethyl-pyrazol-4-yl, 1-isopropyl-pyrazol-4-yl, 1-(2-hydroxyethyl)-pyrazol-4-yl, 1-cyclobutyl-pyrazol-4-yl, 1-(cyclopropyl)-pyrazol-4-yl, 1-(cyclopropyl-methyl)-pyrazol-4-yl, 1-(dimethylamino-ethyl)-pyrazol-4-yl, 1-(pyridin-3-yl)-pyrazol-4-yl, 1-(pyridin-4-yl)-pyrazol-4-yl, 1-methyl-indazol-6-yl, imidazol-1-yl, quinolin-4-yl, quinolin-5-yl and isoquinolin-6-yl;

and $R^7$ is hydrogen;

and stereoisomers, tautomers and pharmaceutically acceptable salts thereof.

In another embodiment, the present invention is directed to compounds of formula (I) wherein $R^1$ is selected from the group consisting of 6-chloro-pyridin-3-yl and 6-(isopropylamino)-pyridin-3-yl; $R^2$ is methyl; $R^3$ is hydrogen; n is 1; and m is 1; such that

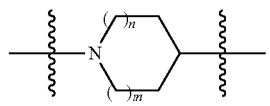

is piperidin-1,4-diyl; $R^4$ is hydrogen; $R^5$ is hydrogen;

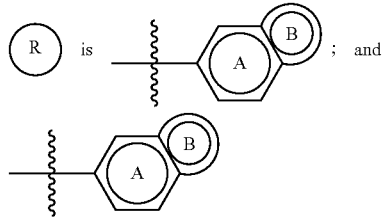

is selected from the group consisting of benzothiazol-6-yl, 2-oxo-benzothiazol-6-yl, 2-oxo-2,3,4-trihydro-quinolin-7-yl, isoquinolin-6-y, isoquinolin-7-yl, 2-oxo-indolin-5-yl, 1-methyl-2-oxo-isoindol-5-yl, 1,7-dimethyl-isoindol-5-yl, 1-methyl-indazol-6-yl, imidazo[1,2-a]pyridine-6-yl and [1,2,4]triazolo[4,3-a]pyridine-6-yl; and stereoisomers, tautomers and pharmaceutically acceptable salts thereof.

In another embodiment, the present invention is directed to compounds of formula (I) wherein $R^1$ is selected from the group consisting of 6-chloro-pyridin-3-yl and 6-(isopropylamino)-pyridin-3-yl; $R^2$ is methyl; $R^3$ is hydrogen; n is 1; and m is 1; such that

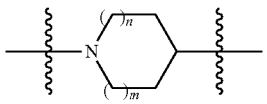

is piperidin-1,4-diyl; $R^4$ is hydrogen; $R^5$ is hydrogen;

is selected from the group consisting of

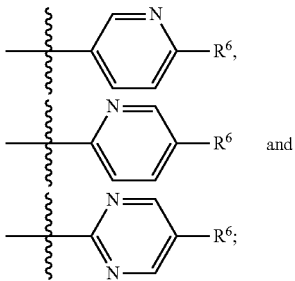

and $R^6$ is 1-methyl-pyrazol-4-yl; and stereoisomers, tautomers and pharmaceutically acceptable salts thereof.

In an embodiment, the present invention is directed to compounds of formula (I) wherein $R^1$ is selected from the group consisting of $C_{1-6}$alkyl, fluorinated $C_{1-3}$alkyl, $C_{3-6}$cycloalkyl, aryl, 5 to 6 membered heteroaryl, 9 to 10 membered heteroaryl, 4 to 6 membered saturated heterocyclyl and 9 to 10 membered benzo-fused heterocyclyl; wherein the $C_{3-6}$cycloalkyl aryl, 5 to 6 membered heteroaryl, 9 to 10 membered heteroaryl, 4 to 6 membered saturated heterocyclyl or 9 to 10 membered benzo-fused heterocyclyl is optionally substituted with one to three $R^0$ substituents; wherein each $R^0$ is independently selected from the group consisting of halogen, hydroxy, cyano, $C_{1-6}$alkyl, fluorinated $C_{1-2}$alkyl, $C_{1-4}$alkoxy, $-NR^AR^B$, $-C(O)-(C_{1-4}$alkyl), $-S-(C_{1-4}$alkyl), $-SO_2-(C_{1-4}$alkyl), $-C_{3-6}$cycloalkyl, $-(C_{1-2}$alkyl)$-C_{3-6}$cycloalkyl, $-C(O)-C_{3-6}$cycloalkyl, $-(C_{1-2}$alkyl)-phenyl and 5 to 6 membered saturated heterocyclyl; wherein the $C_{3-6}$cycloalkyl or 5 to 6 membered saturated heterocyclyl is optionally substituted with one to two substituents independently selected from the group consisting of $C_{1-4}$alkyl and hydroxy substituted $C_{1-2}$alkyl; wherein $R^A$ is selected from the group consisting of hydrogen and $C_{1-4}$alkyl; and wherein $R^B$ is selected from the group consisting of hydrogen, formyl, $C_{1-6}$alkyl, $C_{3-6}$cycloalkyl and 5 to 6 membered saturated, nitrogen containing heterocyclyl; wherein the $R^B$ 5 to 6 membered saturated, nitrogen containing heterocyclyl is optionally substituted with $C_{1-4}$alkyl.

In another embodiment, the present invention is directed to compounds of formula (I) wherein $R^1$ is selected from the group consisting of $C_{2-5}$alkyl, fluorinated $C_{1-2}$alkyl, $C_{3-6}$cycloalkyl, phenyl, 4 to 6 membered saturated heterocyclyl, 5 to 6 membered heteroaryl, 9 to 10 membered heteroaryl and 1,3-benzodioxolyl; wherein the $C_{3-6}$cycloalkyl, phenyl, 4 to 6 membered saturated heterocyclyl, 5 to 6 membered heteroaryl or 9 to 10 membered heteroaryl is optionally substituted with one to three $R^0$ substituents; wherein each $R^0$ is independently selected from the group consisting of halogen, hydroxy, cyano, $C_{1-6}$alkyl, fluorinated $C_{1-2}$alkyl, $C_{1-2}$alkoxy, $NR^AR^B$, $-C(O)-(C_{1-2}$alkyl), $-S-(C_{1-2}$alkyl), $C_{5-6}$cycloalkyl, $-C(O)-C_3$cycloalkyl, $-(C_{1-2}$alkyl)-phenyl and 5 to 6 membered, saturated, nitrogen containing heterocyclyl; wherein the $C_{5-6}$cycloalkyl or 5 to 6 membered saturated, nitrogen containing heterocyclyl is optionally substituted with a substituent selected from the group consisting of $C_{1-2}$alkyl and $-(C_{1-2}$alkyl)-OH; wherein $R^A$ is selected from the group consisting of hydrogen and $C_{1-2}$alkyl; and wherein $R^B$ is selected from the group consisting of hydrogen, formyl, $C_{1-4}$alkyl, $C_{3-4}$cycloalkyl and 6 membered, saturated, nitrogen containing heterocyclyl; wherein the $R^B$ 6 membered saturated, nitrogen containing heterocyclyl is optionally substituted with $C_{1-2}$alkyl.

In another embodiment, the present invention is directed to compounds of formula (I) wherein $R^1$ is selected from the group consisting of t-butyl, n-pent-3-yl, isopropyl, 1-fluoroethyl, cyclopropyl, cyclobutyl, cyclopentyl, 4S-ethylcarbonyl-cyclopent-1S-yl, cyclohexyl, tetrahydropyran-4-yl, piperidin-4-yl, 1-methyl-piperidin-4-yl, 1-ethyl-piperidin-4-yl, 1-isopropyl-piperidin-4-yl, 1-(n-butyl)-piperidin-4-yl, 1-(1-methyl-n-pentyl)-piperidin-4-yl, 1-(n-pentyl)-piperidin-4-yl, 1-(2,2-dimethyl-propyl)piperidin-4-yl, 1-isobutyl-piperidin-4-yl, 1-propyl-piperidin-4-yl, 1-isopentyl-piperidin-4-yl, 1-(n-hexyl)piperidin-4-yl, 1-cyclobutyl-piperidin-4-yl, 1-cyclopentyl-piperidin-4-yl, 1-cyclohexyl-piperidin-4-yl, 1-(3-methyl-cyclopentyl)-piperidin-4-yl, 1-benzyl-piperidin-4-yl, tetrahydrofuran-2-yl, pyrrolidin-3-yl, pyrrolidin-2S-yl, pyrrolidin-2R-yl, 1-methyl-pyrrolidin-3R-yl, 1-methyl-pyrrolidin-3S-yl, 1-ethyl-pyrrolidin-3-yl, 1-propyl-pyrrolidin-3-yl, 1-isobutyl-pyrrolidin-3-yl, 1-(2,2-dimethyl-propyl)-pyrrolidin-3-yl, 1-isopropyl-pyrrolidin-3-yl, 1-(n-butyl)-pyrrolidin-3-yl, 1-(n-pentyl)-pyrrolidin-3-yl, 1-isopentyl-pyrrolidin-3-yl, 1-(1-methyl-n-pentyl)-pyrrolidin-3-yl, 1-(n-hexyl)-pyrrolidin-3-yl, 1-cyclobutyl-pyrrolidin-3-yl, 1-cyclopentyl-pyrrolidin-3-yl, 1-(3-methyl-cyclopentyl)-pyrrolidin-3-yl, 1-cyclohexyl-pyrrolidin-3-yl, 1-(cyclopropyl-carbonyl)-pyrrolidin-3-yl, azetidin-3-yl, 1-methyl-azetidin-3-yl, 1-ethyl-azetidin-3-yl, 1-isopropyl-azetidin-3-yl, 1-(n-propyl)-azetidin-3-yl, 1-(n-butyl)-azetidin-3-yl, 1-isobutyl-azetidin-3-yl, 1-isopentyl-azetidin-3-yl, 1-(n-pentyl)-azetidin-3-yl, 1-(2,2-dimethyl-propyl)-azetidin-3-yl, 1-(1-methyl-n-pentyl)-azetidin-3-yl, 1-(n-hexyl) azetidin-3-yl, 1-cyclobutyl-azetidin-3-yl, 1-(3-methyl-cyclopentyl)-azetidin-3-yl, 1-cyclopentyl-azetidin-3-yl, 1-cyclohexyl-azetidin-3-yl, 1-(cyclopropyl-carbonyl)-azetidin-3-yl, phenyl, 2-chloro-phenyl, 3-chloro-phenyl, 4-chloro-phenyl, 2-fluoro-phenyl, 4-dichloro-phenyl, 2,4-dichloro-phenyl, 2,6-dichloro-phenyl, 3,4-dichloro-phenyl, 2,3,4-trifluoro-phenyl, 2,4-difluoro-phenyl, 2-fluoro-5-methyl-phenyl, 3-chloro-5-methoxy-phenyl, 2-fluoro-4-cyano-phenyl, 2-chloro-4-fluoro-phenyl, 4-isopropyl-phenyl, 2-methoxy-phenyl, 3-methoxy-phenyl, 2-methyl-4-fluoro-phenyl, 2-methyl-5-fluoro-phenyl, 3-hydroxy-4-methoxy-phenyl, 3-chloro-4-methoxy-phenyl, 4-methoxy-phenyl, 4-methylthio-phenyl, 2-trifluoromethyl-phenyl, 4-trifluoromethyl-phenyl, 4-cyano-phenyl, thiophen-2-yl, 3-chloro-thiophen-2-yl, 3-methyl-thiophen-2-yl, 5-methyl-thiophen-3-yl, thiazol-2-yl, thiazol-5-yl, 2-bromo-thiazol-2-yl, 4-t-butyl-thiazol-2-yl, pyridin-2-yl, pyridin-4-yl, 2-chloro-pyridin-3-yl, 4-chloro-pyridin-3-yl, 6-chloro-pyridin-3-yl, 3-fluoro-pyridin-4-yl, 5-bromo-pyridin-3-yl, 2-chloro-6-methoxy-pyridin-4-yl, 6-methyl-pyridin-4-yl, 6-trifluoromethyl-pyridin-2-yl, 6-methoxy-pyridin-3-yl, 5-(dimethylamino)-pyridin-2-yl, 6-(isopropyl-amino)-pyridin-3-yl, 6-(cyclobutyl-amino)-pyridin-3-yl, 6-(piperidin-1-yl)-pyridin-3-yl, 6-(morpholin-4-yl)-pyridin-3-yl, 6-(4-methyl-piperazin-1-yl)-pyridin-3-yl, 6-(N-methyl-N-(1-methyl-piperidin-4-yl)-amino-)-pyridin-3-yl, 6-(N-methyl-N-isopropyl-amino)-pyridin-3-yl, 6-(pyrrolidin-1-yl)-pyridin-3-yl, 6-(3S-hydroxymethyl-piperazin-1-yl)-pyridin-3-yl, 6-(3R-hydroxymethyl-piperazin-4-yl)-pyridin-3-yl, 6-(N-isopropyl-N-formyl)-pyridin-3-yl, 6-(dimethylamino)-pyridin-3-yl, 2-chloro-pyrimidin-5-yl, 2-(isopropyl-amino)-pyrimidin-5-yl, 2-(N-methyl-N-isopropyl-amino)-pyrimidin-5-yl, 2-(morpholin-4-yl)-pyrimidin-5-yl, 6-(morpholin-4-yl)-pyrimidin-5-yl, 2-(cyclobutyl-amino)-pyrimidin-5-yl, 1-methyl-imidazol-2-yl, quinolin-2-yl, indol-5-yl and 1,3-benzodioxol-5-yl.

In another embodiment, the present invention is directed to compounds of formula (I) wherein $R^1$ is selected from the group consisting of n-pent-3-yl, cyclopropyl, cyclobutyl, cyclopentyl, 4S-ethylcarbonyl-cyclopent-1S-yl, cyclohexyl, tetrahydropyran-4-yl, piperidin-4-yl, 1-methyl-piperidin-4-yl, 1-ethyl-piperidin-4-yl, 1-isopropyl-piperidin-4-yl, 1-(1-methyl-n-pentyl)piperidin-4-yl, 1-(n-pentyl)-piperidin-4-yl, 1-(2,2-dimethyl-propyl)piperidin-4-yl, 1-isobutyl-piperidin-4-yl, 1-propyl-piperidin-4-yl, 1-isopentyl-piperidin-4-yl, 1-(n-hexyl)-piperidin-4-yl, 1-cyclobutyl-piperidin-4-yl, 1-cyclopentyl-piperidin-4-yl, 1-cyclohexyl-piperidin-4-yl, 1-benzyl-piperidin-4-yl, pyrrolidin-3-yl, 1-propyl-pyrrolidin-3-yl, 1-isobutyl-pyrrolidin-3-yl, 1-isopentyl-pyrrolidin-3-yl, 1-(3-methyl-cyclopentyl)-pyrrolidin-3-yl, 1-(cyclopropyl-carbonyl)-pyrrolidin-3-yl, 1-methyl-azetidin-3-yl, 1-(n-butyl)azetidin-3-yl, 1-isobutyl-azetidin-3-yl, 1-isopentyl-azetidin-3-yl, 1-(2,2-dimethyl-propyl)azetidin-3-yl, 1-cyclobutyl-azetidin-3-yl, 1-cyclohexyl-azetidin-3-yl, 1-(cyclopropyl-carbonyl)azetidin-3-yl, phenyl, 2-chloro-phenyl, 3-chloro-phenyl, 4-chloro-phenyl, 2-fluoro-phenyl, 4-dichloro-phenyl, 2,4-dichloro-phenyl, 3,4-dichloro-phenyl, 2,3,4-trifluoro-phenyl, 2,4-difluoro-phenyl, 2-fluoro-4-cyano-phenyl, 2-chloro-4-fluoro-phenyl, 4-isopropyl-phenyl, 3-methoxy-phenyl, 2-methyl-5-fluoro-phenyl, 3-hydroxy-4-methoxy-phenyl, 3-chloro-4-methoxy-phenyl, 4-methoxy-phenyl, 4-methylthio-phenyl, 4-trifluoromethyl-phenyl, 4-cyano-phenyl, thiophen-2-yl, 3-chloro-thiophen-2-yl, 3-methyl-thiophen-2-yl, 5-methyl-thiophen-3-yl, thiazol-5-yl, 2-bromo-thiazol-2-yl, pyridin-2-yl, pyridin-4-yl, 2-chloro-pyridin-3-yl, 6-chloro-pyridin-3-yl, 3-fluoro-pyridin-4-yl, 2-chloro-6-methoxy-pyridin-4-yl, 6-methyl-pyridin-4-yl, 6-methoxy-pyridin-3-yl, 5-(dimethylamino)-pyridin-2-yl, 6-(isopropyl-amino)-pyridin-3-yl, 6-(cyclobutyl-amino)-pyridin-3-yl, 6-(piperidin-1-yl)-pyridin-3-yl, 6-(morpholin-4-yl)-pyridin-3-yl, 6-(4-methyl-piperazin-1-yl)-pyridin-3-yl, 6-(N-methyl-N-(1-methyl-piperidin-4-yl)-amino)-pyridin-3-yl, 6-(N-methyl-N-isopropyl-amino)-pyridin-3-yl, 6-(pyrrolidin-1-yl)-pyridin-3-yl, 6-(3S-hydroxymethyl-piperazin-1-yl)-pyridin-3-yl, 6-(3R-hydroxymethyl-piperazin-4-yl)-pyridin-3-yl, 2-chloro-pyrimidin-5-yl, 2-(isopropyl-amino)-pyrimidin-5-yl, 2-(N-methyl-N-isopropyl-amino)-pyrimidin-5-yl, 2-(morpholin-4-yl)-pyrimidin-5-yl, 6-(morpholin-4-yl)-pyrimidin-5-yl, 2-(cyclobutyl-amino)-pyrimidin-5-yl, quinolin-2-yl, indol-5-yl and 1,3-benzodioxol-5-yl.

In another embodiment, the present invention is directed to compounds of formula (I) wherein $R^1$ is selected from the group consisting of n-pent-3-yl, cyclopropyl, cyclohexyl, 1-isopropyl-piperidin-4-yl, 1-isobutyl-piperidin-4-yl, 1-cyclopentyl-piperidin-4-yl, 1-cyclohexyl-piperidin-4-yl, 1-methyl-azetidin-3-yl, phenyl, 3-chloro-phenyl, 4-chloro-phenyl, 2-fluoro-phenyl, 2,4-dichloro-phenyl, 2-fluoro-4-cyano-phenyl, 3-methoxy-phenyl, 2-methyl-5-fluoro-phenyl, 3-hydroxy-4-methoxy-phenyl, 4-methoxy-phenyl, 4-methylthio-phenyl, 4-trifluoromethyl-phenyl, 3-chloro-thiophen-2-yl, pyridin-4-yl, 6-chloro-pyridin-3-yl, 3-fluoro-pyridin-4-yl, 6-methyl-pyridin-4-yl, 6-methoxy-pyridin-3-yl, 6-(isopropyl-amino)-pyridin-3-yl, 6-(cyclobutyl-amino)-pyridin-3-yl, 6-(piperidin-1-yl)-pyridin-3-yl, 6-(morpholin-4-yl)-pyridin-3-yl, 6-(4-methyl-piperazin-1-yl)-pyridin-3-yl, 6-(N-methyl-N-(1-methyl-piperidin-4-yl)-amino)-pyridin-3-yl, 6-(N-methyl-N-isopropyl-amino)-pyridin-3-yl, 6-(pyrrolidin-1-yl)-pyridin-3-yl, 6-(3S-hydroxymethyl-piperazin-1-yl)-pyridin-3-yl, 6-(3R-hydroxymethyl-piperazin-4-yl)-pyridin-3-yl, 2-chloro-pyrimidin-5-yl, 2-(isopropyl-amino)-pyrimidin-5-yl, 2-(N-methyl-N-isopropyl-amino)-pyrimidin-5-yl, 2-(morpholin-4-yl)-pyrimidin-5-yl, 6-(morpholin-4-yl)-pyrimidin-5-yl and 2-(cyclobutyl-amino)-pyrimidin-5-yl.

In another embodiment, the present invention is directed to compounds of formula (I) wherein $R^1$ is selected from the group consisting of 1-methyl-azetidin-3-yl, 1-(n-butyl)-piperidin-4-yl, 1-(2,2-dimethyl-propyl)piperidin-4-yl, 1-isopentyl-piperidin-4-yl, 1-cyclobutyl-piperidin-4-yl, 1-cyclopentyl-piperidin-4-yl, 1-cyclohexyl-piperidin-4-yl, 4-methylthio-phenyl, 2-fluoro-4-cyano-phenyl, 3-fluoro-pyridin-4-yl, 6-(3S-hydroxymethyl-piperidin-1-yl)-pyridin-3-yl, 6-(isopropyl-amino)-pyridin-3-yl, 6-(cyclobutyl-amino)-pyridin-3-yl, 6-(N-methyl-N-isopropyl-amino)-pyridin-3-yl, 6-(N-methyl-N-(1-methyl-piperidin-4-yl)-amino)-pyridin-3-yl, 6-(morpholin-4-yl)-pyridin-3-yl, 6-(4-methyl-piperazin-1-yl)-pyridin-3-yl, 2-(isopropyl-amino)-pyrimidin-5-yl, 2-(morpholin-4-yl)-pyrimidin-5-yl, 2-(cyclobutyl-amino)-pyrimidin-5-yl and indol-5-yl.

In another embodiment, the present invention is directed to compounds of formula (I) wherein $R^1$ is selected from the group consisting of cyclopropyl, 6-chloro-pyridin-3-yl, 6-(isopropyl-amino)-pyridin-3-yl, 6-(N-methyl-N-isopropyl-amino)-pyridin-3-yl and 6-(morpholin-4-yl)-pyridin-3-yl.

In another embodiment, the present invention is directed to compounds of formula (I) wherein $R^1$ is selected from the group consisting of 6-chloro-pyridin-3-yl and 6-(isopropylamino)-pyridin-3-yl.

In an embodiment, the present invention is directed to compounds of formula (I) wherein $R^1$ is other than $C_{1-6}$alkyl or fluorinated $C_{1-3}$alkyl. In another embodiment, the present invention is directed to compounds of formula (I) wherein $R^1$ is other than $C_{1-6}$alkyl.

In an embodiment, the present invention is directed to compounds of formula (I) wherein $R^2$ is selected from the group consisting of halogen, hydroxy, cyano, $C_{1-4}$alkyl, fluorinated $C_{1-2}$alkyl, $C_{1-4}$alkoxy, benzyloxy and —$NR^XR^Y$; wherein $R^X$ is selected from the group consisting of hydrogen, $C_{1-4}$alkyl and —$(C_{2-4}$alkyl)-O—$(C_{1-2}$alkyl); and wherein $R^Y$ is selected from the group consisting of hydrogen, $C_{1-4}$alkyl, —$(C_{2-4}$alkyl)-O—$(C_{1-2}$alkyl), $C_{3-6}$cycloalkyl and —C(O)—$C_{3-6}$cycloalkyl.

In another embodiment, the present invention is directed to compounds of formula (I) wherein $R^2$ is selected from the group consisting of halogen, hydroxy, $C_{1-2}$alkyl, $C_{1-2}$alkoxy, benzyloxy and —$NR^XR^Y$; wherein $R^X$ is selected from the group consisting of hydrogen, $C_{1-3}$alkyl and —$(C_2$alkyl)-O—$(C_{1-2}$alkyl); and wherein $R^Y$ is selected from the group consisting of hydrogen, $C_{1-3}$alkyl, —$(C_2$alkyl)-O—$(C_{1-2}$alkyl), $C_3$cycloalkyl and —C(O)—$C_3$cycloalkyl.

In another embodiment, the present invention is directed to compounds of formula (I) wherein $R^2$ is selected from the group consisting of chloro, hydroxy, methyl, ethyl, methoxy, amino, methyl-amino, isopropyl-amino, (methoxyethyl)- amino, cyclopropyl-amino, (cyclopropylcarbonyl)-amino, N,N-dimethylamino, N-methyl-N-isopropyl-amino, N-methyl-N-(methoxyethyl)-amino, N-methyl-N-cyclopropyl-amino, N-(methoxyethyl)-N-(cyclopropylcarbonyl)-amino and benzyloxy.

In another embodiment, the present invention is directed to compounds of formula (I) wherein $R^2$ is selected from the group consisting of chloro, hydroxy, methyl, ethyl, methoxy, benzyloxy, methylamino, (methoxyethyl)amino, dimethylamino and N-methyl-N-cyclopropyl-amino.

In another embodiment, the present invention is directed to compounds of formula (I) wherein $R^2$ is selected from the group consisting of chloro, methyl, ethyl and methoxy. In another embodiment, the present invention is directed to compounds of formula (I) wherein $R^2$ is methyl.

In another embodiment, the present invention is directed to compounds of formula (I) wherein $R^2$ is selected from the group consisting of methyl, amino, methylamino, isopropylamino, (methoxyethyl)amino, cyclopropylamino, dimethylamino and N-methyl-N-cycloprpoyl-amino.

In an embodiment, the present invention is directed to compounds of formula (I) wherein $R^3$ is selected from the group consisting of hydrogen, fluoro, chloro, bromo, methyl and trifluoromethyl. In another embodiment, the present invention is directed to compounds of formula (I) wherein $R^3$ is selected from the group consisting of hydrogen, methyl and trifluoromethyl. In another embodiment, the present invention is directed to compounds of formula (I) wherein $R^3$ is hydrogen.

In an embodiment, the present invention is directed to compounds of formula (I) wherein m is 0. In another embodiment, the present invention is directed to compounds of formula (I) wherein m is 1. In an embodiment, the present invention is directed to compounds of formula (I) wherein n is 0. In another embodiment, the present invention is directed to compounds of formula (I) wherein n is 1.

In an embodiment, the present invention is directed to compounds of formula (I) wherein m is 0 and n is 0. In an embodiment, the present invention is directed to compounds of formula (I) wherein m is 1 and n is 1. In an embodiment, the present invention is directed to compounds of formula (I) wherein m is 1 and n is 0 or alternatively, m is 0 and n is 1.

In an embodiment, the present invention is directed to compounds of formula (I) wherein

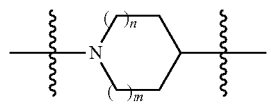

is selected from the group consisting of azetidin-1,3-diyl, pyrrolidin-1,3-diyl and piperidin-1,4-diyl. In another embodiment, the present invention is directed to compounds of formula (I) wherein

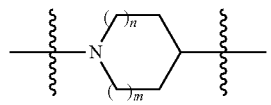

is selected from the group consisting of azetidin-1,3-diyl and piperidin-1,4-diyl. In another embodiment, the present invention is directed to compounds of formula (I) wherein

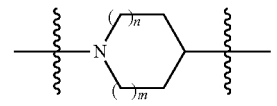

is azetidin-1,3-diyl. In another embodiment, the present invention is directed to compounds of formula (I) wherein

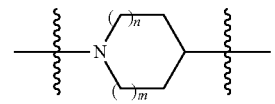

is piperidin-1,4-diyl.

In an embodiment, the present invention is directed to compounds of formula (I) wherein $R^4$ is selected from the group consisting of hydrogen and $C_{1-3}$alkyl. In another embodiment, the present invention is directed to compounds of formula (I) wherein $R^4$ is selected from the group consisting of hydrogen and $C_{1-2}$alkyl.

In another embodiment, the present invention is directed to compounds of formula (I) wherein $R^4$ is selected from the group consisting of hydrogen and methyl. In another embodiment, the present invention is directed to compounds of formula (I) wherein $R^4$ is hydrogen.

In an embodiment, the present invention is directed to compounds of formula (I) wherein $R^5$ is selected from the group consisting of hydrogen, hydroxy and $C_{1-3}$alkyl. In another embodiment, the present invention is directed to compounds of formula (I) wherein $R^5$ is selected from the group consisting of hydrogen, hydroxy and $C_{1-2}$alkyl.

In another embodiment, the present invention is directed to compounds of formula (I) wherein $R^5$ is selected from the group consisting of hydrogen, hydroxy, trans-hydroxy, methyl, trans-methyl and cis-methyl. In another embodiment, the present invention is directed to compounds of formula (I) wherein $R^5$ is selected from the group consisting of hydrogen, methyl and trans-methyl. In another embodiment, the present invention is directed to compounds of formula (I) wherein $R^5$ is selected from the group consisting of hydrogen and trans-methyl. In another embodiment, the present invention is directed to compounds of formula (I) wherein $R^5$ is hydrogen.

In an embodiment, the present invention is directed to compounds of formula (I) wherein

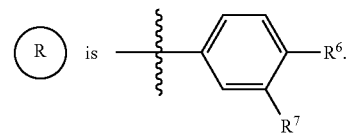

In another embodiment, the present invention is directed to compounds of formula (I) wherein

is selected from the group consisting of

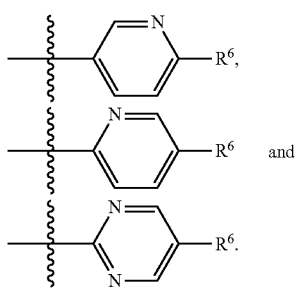

In an embodiment, the present invention is directed to compounds of formula (I) wherein

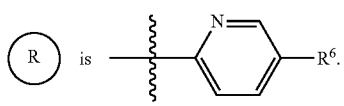

In an embodiment, the present invention is directed to compounds of formula (I) wherein

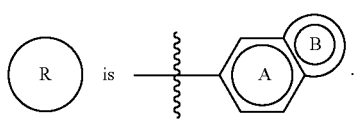

In an embodiment, the present invention is directed to compounds of formula (I) wherein $R^6$ is selected from the group consisting of aryl, 5 to 6 membered heteroaryl and 9 to 10 membered heteroaryl; wherein the aryl, 5 to 6 membered heteroaryl or 9 to 10 membered heteroaryl is optionally substituted with one to two substituents independently selected from the group consisting of halogen, $C_{1-4}$alkyl, trifluoromethyl, hydroxy substituted $C_{1-2}$alkyl, $C_{1-4}$alkoxy, $NR^PR^Q$, —($C_{1-2}$alkyl)-$NR^PR^Q$, $C_{3-6}$cycloalkyl, —($C_{1-2}$alkyl)-$C_{3-6}$cycloalkyl, 5 to 6 membered saturated, nitrogen containing heterocyclyl and 5 to 6 membered nitrogen containing heteroaryl; wherein $R^P$ and $R^Q$ are each independently selected from the group consisting of hydrogen and $C_{1-4}$alkyl;

In another embodiment, the present invention is directed to compounds of formula (I) wherein $R^6$ is selected from the group consisting of phenyl, 5 to 6 membered heteroaryl and 9 to 10 membered, nitrogen containing heteroaryl; wherein the phenyl, 5 to 6 membered heteroaryl or 9 to 10 membered, nitrogen containing heteroaryl is optionally substituted with a substituent selected from the group consisting of halogen, $C_{1-4}$alkyl, —($C_{1-2}$alkyl)-OH, $C_{1-2}$alkoxy, $NR^PR^Q$, —($C_{1-2}$alkyl)-$NR^PR^Q$, $C_{3-4}$cycloalkyl, —($C_{1-2}$alkyl)-$C_{3-4}$cycloalkyl, 6 membered saturated, nitrogen containing heterocyclyl and 6 membered, nitrogen containing heteroaryl; wherein $R^P$ and $R^Q$ are each independently selected from the group consisting of hydrogen and $C_{1-2}$alkyl.

In another embodiment, the present invention is directed to compounds of formula (I) wherein $R^6$ is selected from the group consisting of phenyl, 2-fluoro-phenyl, 3-fluoro-phenyl, 4-fluoro-phenyl, 2-methyl-phenyl, 3-methyl-phenyl, 4-methyl-phenyl, 2-methoxy-phenyl, 3-methoxy-phenyl, 4-methoxy-phenyl, thiophen-2-yl, thiophen-3-yl, furan-2-yl, furan-3-yl, isoxazol-4-yl, pyridin-3-yl, pyridin-4-yl, 2-amino-pyridin-3-yl, 3-amino-pyridin-4-yl, pyrazol-4-yl, 1-methyl-pyrazol-4-yl, 1-methyl-pyrazol-5-yl, 1-(tetrahydropyran-4-yl)-pyrazol-4-yl, 1-(cyclobutyl-methyl)-pyrazol-4-yl, 1,3-dimethyl-pyrazol-4-yl, 1-isopropyl-pyrazol-4-yl, 1-(2-hydroxyethyl)-pyrazol-4-yl, 1-cyclobutyl-pyrazol-4-yl, 1-(cyclopropyl)-pyrazol-4-yl, 1-(cyclopropyl-methyl)-pyrazol-4-yl, 1-(dimethylamino-ethyl)-pyrazol-4-yl, 1-(pyridin-3-yl)-pyrazol-4-yl, 1-(pyridin-4-yl)-pyrazol-4-yl, 1-methyl-indazol-6-yl, imidazol-1-yl, quinolin-4-yl, quinolin-5-yl and isoquinolin-6-yl.

In another embodiment, the present invention is directed to compounds of formula (I) wherein $R^6$ is selected from the group consisting of furan-3-yl, thiophen-3-yl, pyridin-3-yl, pyridin-4-yl, 2-amino-pyridin-3-yl, 3-amino-pyridin-4-yl, imidazol-1-yl, isoxazol-4-yl, pyrazol-4-yl, 1-methyl-pyrazol-4-yl, 1-isopropyl-pyrazol-4-yl, 1-(2-hydroxyethyl)-pyrazol-4-yl, 1-cyclopropyl-pyrazol-4-yl, 1-cyclobutyl-pyrazol-4-yl, 1-(cyclopropyl-methyl)-pyrazol-4-yl, 1,3-dimethyl-pyrazol-4-yl, 1-(pyridin-3-yl)-pyrazol-4-yl, 1-(pyridin-4-yl)-pyrazol-4-yl, 1-methyl-pyrazol-5-yl, quinolin-4-yl, quinolin-5-yl, isoquinolin-6-yl and 1-methyl-indazol-6-yl.

In another embodiment, the present invention is directed to compounds of formula (I) wherein $R^6$ is selected from the group consisting of pyridin-4-yl, 2-amino-pyridin-3-yl, 3-amino-pyridin-4-yl, imidazol-1-yl, isoxazol-4-yl, pyrazol-4-yl, 1-methyl-pyrazol-4-yl, 1-(pyridin-4-yl)-pyrazol-4-yl, 1-methyl-pyrazol-5-yl and quinolin-4-yl.

In another embodiment, the present invention is directed to compounds of formula (I) wherein $R^6$ is selected from the group consisting of pyridin-4-yl, 3-amino-pyridin-4-yl, 1-methyl-pyrazol-4-yl, 1-(2-hydroxyethyl)-pyrazol-4-yl, 1-cyclopropyl-pyrazol-4-yl, 1-methyl-pyrazol-5-yl and quinolin-4-yl. In another embodiment, the present invention is directed to compounds of formula (I) wherein $R^6$ is 1-methyl-pyrazol-4-yl.

In an embodiment, the present invention is directed to compounds of formula (I) wherein $R^7$ is selected from the group consisting of hydrogen, fluoro, chloro, bromo, $C_{1-4}$alkyl and trifluoromethyl. In another embodiment, the present invention is directed to compounds of formula (I) wherein $R^7$ is selected from the group consisting of hydrogen, halogen, $C_{1-2}$alkyl and trifluoromethyl. In another embodiment, the present invention is directed to compounds of formula (I) wherein $R^7$ is selected from the group consisting of hydrogen, methyl and trifluoromethyl. In another embodiment, the present invention is directed to compounds of formula (I) wherein $R^7$ is hydrogen.

In an embodiment, the present invention is directed to compounds of formula (I) wherein

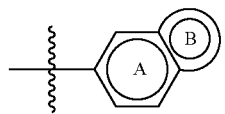

represents a 9 to 10 membered bicyclic, partially unsaturated or aromatic heterocyclyl; and wherein the

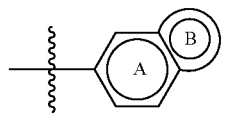

is optionally substituted with one to two substituents independently selected from the group consisting of halogen, oxo, cyano, $C_{1-4}$alkyl, trifluoromethyl, $C_{1-4}$alkoxy, $NR^SR^T$ and cyclopropyl; wherein $R^S$ and $R^T$ are each independently selected from the group consisting of hydrogen and $C_{1-4}$alkyl.

In another embodiment, the present invention is directed to compounds of formula (I) wherein

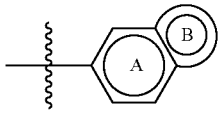

represents a 9 to 10 membered, bicyclic, partially unsaturated or aromatic, nitrogen containing heterocyclyl; wherein the

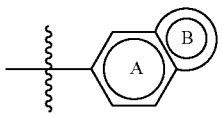

optionally substituted with one to two substituents independently selected from the group consisting of oxo and $C_{1-2}$alkyl.

In another embodiment, the present invention is directed to compounds of formula (I) wherein

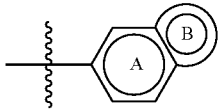

is selected from the group consisting of benzothiazol-6-yl, 2-oxo-benzothiazol-6-yl, 2-oxo-2,3,4-trihydro-quinolin-7-yl, isoquinolin-6-y, isoquinolin-7-yl, 2-oxo-indolin-5-yl, 1-methyl-2-oxo-isoindol-5-yl, 1,7-dimethyl-isoindol-5-yl, 1-methyl-indazol-6-yl, imidazo[1,2-a]pyridine-6-yl and [1,2,4]triazolo[4,3-a]pyridine-6-yl.

In an embodiment, the present invention is directed to a compound of formula (I) selected from the group consisting of 6-(isopropylamino)-N-(2-methyl-5-(4-(4-(1-methyl-1H-pyrazol-4-yl)phenyl)piperidine-1-carbonyl)phenyl)nicotinamide; (Compound #32) N-(2-methyl-5-(3-(4-(1-methyl-1H-pyrazol-4-yl)phenyl)azetidine-1-carbonyl)phenyl)-6-morpholinonicotinamide; (Compound #66) N-(2-chloro-5-(3-(4-(pyridin-3-yl)phenyl)azetidine-1-carbonyl)phenyl)-6-(isopropylamino)nicotinamide; (Compound #73) N-(2-chloro-5-(3-(4-(pyridin-4-yl)phenyl)azetidine-1-carbonyl)phenyl)-6-(isopropylamino)nicotinamide; (Compound #74) 6-(isopropyl(methyl)amino)-N-(2-methyl-5-(3-(4-(1-methyl-1H-pyrazol-4-yl)phenyl)azetidine-1-carbonyl)phenyl)nicotinamide; (Compound #78) 4-methoxy-N-(2-methyl-5-(3-(4-(1-methyl-1H-pyrazol-4-yl)phenyl)azetidine-1-carbonyl)phenyl)benzamide; (Compound #83) N-(2-methyl-5-(4-(4-(1-methyl-1H-pyrazol-4-yl)phenyl)piperidine-1-carbonyl)phenyl)-6-morpholinonicotinamide; (Compound #91) 4-chloro-N-(2-methyl-5-(4-(4-(1-methyl-1H-pyrazol-4-yl)phenyl)piperidine-1-carbonyl)phenyl)benzamide; (Compound #100) N-(2-Methyl-5-(4-(4-(1-methyl-1H-pyrazol-4-yl)phenyl)piperidine-1-carbonyl)phenyl)-6-(4-methylpiperazin-1-yl)nicotinamide; (Compound #112) 6-(isopropylamino)-N-(2-methoxy-5-(4-(4-(1-methyl-1H-pyrazol-4-yl)phenyl)piperidine-1-carbonyl)phenyl)nicotinamide; (Compound #251) N-(2-ethyl-5-(4-(4-(1-methyl-1H-pyrazol-4-yl)phenyl)piperidine-1-carbonyl)phenyl)-6-(isopropylamino)nicotinamide; (Compound #256) 6-(isopropylamino)-N-(5-(4-(4-(1-methyl-1H-pyrazol-4-yl)phenyl)piperidine-1-carbonyl)-2-(methylamino)phenyl) nicotinamide; (Compound #279) and stereoisomers, tautomers and pharmaceutically acceptable salts thereof.

In another embodiment, the present invention is directed to a compound of formula (I) selected from the group consisting of 6-(isopropylamino)-N-(2-methyl-5-(4-(4-(1-methyl-1H-pyrazol-4-yl)phenyl)piperidine-1-carbonyl)phenyl)nicotinamide; (Compound #32) N-(2-methyl-5-(3-(4-(1-methyl-1H-pyrazol-4-yl)phenyl)azetidine-1-carbonyl)phenyl)-6-morpholinonicotinamide; (Compound #66) 6-(isopropyl(methyl)amino)-N-(2-methyl-5-(3-(4-(1-methyl-1H-pyrazol-4-yl)phenyl)azetidine-1-carbonyl)phenyl)nicotinamide; (Compound #78) N-(2-methyl-5-(4-(4-(1-methyl-1H-pyrazol-4-yl)phenyl)piperidine-1-carbonyl)phenyl)-6-morpholinonicotinamide; (Compound #91) N-(2-ethyl-5-(4-(4-(1-methyl-1H-pyrazol-4-yl)phenyl)piperidine-1-carbonyl)phenyl)-6-(isopropylamino) nicotinamide; (Compound #256) and stereoisomers, tautomers and pharmaceutically acceptable salts thereof.

In an embodiment, the present invention is directed to compounds of formula (I) wherein when n is 0 and m is 0, such that

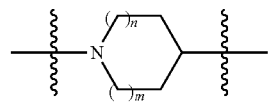

is azetidin-1,3-diyl, then $R^4$ is hydrogen and $R^5$ is hydrogen.

In another embodiment, the present invention is directed to compounds of formula (I) wherein when n is 1 and m is 0, or n is 0 and m is 1, such that

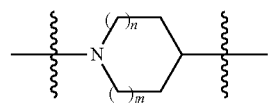

is pyrrolidin-1,3-diyl, then $R^4$ is hydrogen and $R^5$ is hydrogen.

In an embodiment, the present invention is directed to compounds of formula (I) wherein $R^1$ is other than $C_{1-2}$alkyl. In another embodiment, the present invention is directed to compounds of formula (I) wherein $R^1$ is other than $C_{1-4}$alkyl.

In an embodiment, the present invention is directed to compounds of formula (I) wherein

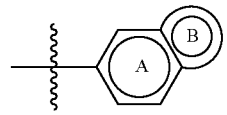

is other than an optionally substituted pyrazolo[1,5-a]pyrimidinyl.

In an embodiment, the present invention is directed to compounds of formula (I) wherein

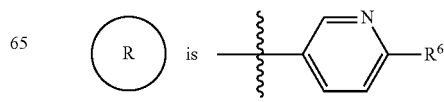

and R⁶ is other than optionally substituted aryl. In another embodiment, the present invention is directed to compounds of formula (I) wherein

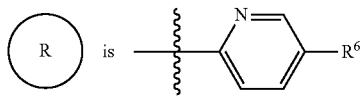

and R⁶ is other than optionally substituted aryl. In another embodiment, the present invention is directed to compounds of formula (I) wherein

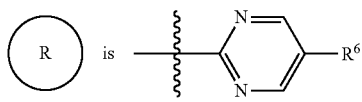

and R⁶ is other than optionally substituted aryl.

Additional embodiments of the present invention, include those wherein the substituents selected for one or more of the variables defined herein (e.g. $R^1$, $R^2$, $R^3$, $R^4$, $R^5$, m, n,

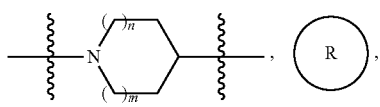

etc.) are independently selected to be any individual substituent or any subset of substituents selected from the complete list as defined herein. Additional embodiments of the present invention, include those wherein the substituents selected for one or more of the variables defined herein (e.g. $R^1$, $R^2$, $R^3$, $R^4$, $R^5$, m, n,

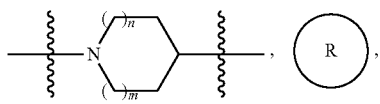

etc.) are independently selected to be any individual substituent or any subset of substituents selected from those exemplified in Tables 1-3, which follow herein.

In additional embodiments, the present invention is directed to any single compound or subset of compounds, selected from the representative compounds listed in Tables 1-3, below.

In an embodiment, the present invention is directed to compounds of formula (I) which, when tested according to the procedure as described in Biological Example 1, which follows herein, exhibit a $pIC_{50}$ of greater than about 5.0, preferably greater than about 6.0, more preferably greater than about 6.5, more preferably greater than about 7.0, more preferably greater than about 7.5. In another embodiment, the present invention is directed to compounds of formula (I) which, when tested according to the procedure as described in Biological Example 2, which follows herein, exhibit a $pIC_{50}$ of greater than about 5.0, preferably greater than about 6.0, more preferably greater than about 6.5, more preferably greater than about 7.0, more preferably greater than about 7.5. In an embodiment, the present invention is directed to compounds of formula (I) which, when tested according to the procedure as described in Biological Example 3, without palmitate, which follows herein, exhibit a $pIC_{50}$ of greater than about 5.0, preferably greater than about 6.0, more preferably greater than about 6.5, more preferably greater than about 7.0, more preferably greater than about 7.5, more preferably greater than about 8.0. In an embodiment, the present invention is directed to compounds of formula (I) which, when tested according to the procedure as described in Biological Example 4, which follows herein, exhibit a $pIC_{50}$ of greater than about 5.0, preferably greater than about 6.0, more preferably greater than about 6.5, more preferably greater than about 7.0, more preferably greater than about 7.5.

Representative compounds of formula (I) of the present invention are as listed in Tables 1-3, below. Unless otherwise noted, wherein a stereogenic center is present in the listed compound, the compound was prepared as a mixture of stereo-configurations. Where a stereogenic center is present, the S- and R-designations are intended to indicate that the exact stereo-configuration of the center was been determined.

TABLE 1

Representative Compounds of Formula (I)

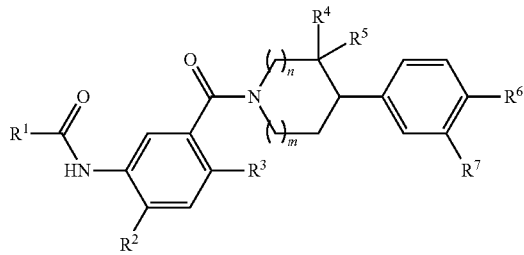

| ID No. | R¹ | R² | R³ | N-Ring | R⁴ | R⁵ | R⁷ | R⁶ |
|---|---|---|---|---|---|---|---|---|
| 3 | 6-chloro-pyridin-3-yl | methyl | H | azetidin-1,3-diyl | H | H | H | pyridin-4-yl |
| 4 | 6-chloro-pyridin-3-yl | methyl | H | azetidin-1,3-diyl | H | H | H | 1-methyl-pyrazol-4-yl |

TABLE 1-continued

Representative Compounds of Formula (I)

| ID No. | R¹ | R² | R³ | N-Ring | R⁴ | R⁵ | R⁷ | R⁶ |
|---|---|---|---|---|---|---|---|---|
| 6 | 6-chloro-pyridin-3-yl | methyl | H | piperidin-1,4-diyl | methyl | methyl | H | imidazol-1-yl |
| 10 | 6-(isopropyl-amino)-pyridin-3-yl | methyl | H | azetidin-1,3-diyl | H | H | H | pyridin-3-yl |
| 11 | 6-chloro-pyridin-3-yl | methyl | H | piperidin-1,4-diyl | H | H | H | imidazol-1-yl |
| 12 | 6-(isopropyl-amino)-pyridin-3-yl | methyl | H | azetidin-1,3-diyl | H | H | H | quinolin-5-yl |
| 13 | 4S-ethylcarbonyl-cyclopent-1S-yl | methyl | H | piperidin-1,4-diyl | H | H | H | 1-methyl-pyrazol-5-yl |
| 15 | 6-(isopropyl-amino)-pyridin-3-yl | methyl | H | piperidin-1,4-diyl | H | H | H | imidazol-1-yl |
| 16 | 6-(isopropyl-amino)-pyridin-3-yl | methyl | H | azetidin-1,3-diyl | H | H | H | 1-methyl-indazol-6-yl |
| 24 | 6-(isopropyl-amino)-pyridin-3-yl | methyl | H | azetidin-1,3-diyl | H | H | H | 1-methyl-pyrazol-4-yl |
| 25 | 6-(isopropyl-amino)-pyridin-3-yl | methyl | H | azetidin-1,3-diyl | H | H | H | 1-methyl-pyrazol-5-yl |
| 26 | 6-(isopropyl-amino)-pyridin-3-yl | methyl | H | azetidin-1,3-diyl | H | H | H | thiophen-3-yl |
| 31 | 6-(isopropyl-amino)-pyridin-3-yl | methyl | H | azetidin-1,3-diyl | H | H | H | pyridin-4-yl |
| 32 | 6-(isopropyl-amino)-pyridin-3-yl | methyl | H | piperidin-1,4-diyl | H | H | H | 1-methyl-pyrazol-4-yl |
| 39 | 6-(isopropyl-amino)-pyridin-3-yl | methyl | H | azetidin-1,3-diyl | H | H | H | quinolin-4-yl |
| 42 | 6-(isopropyl-amino)-pyridin-3-yl | methyl | H | piperidin-1,4-diyl | H | H | H | pyrazol-4-yl |
| 43 | 6-(isopropyl-amino)-pyridin-3-yl | methyl | H | piperidin-1,4-diyl | methyl | methyl | H | imidazol-1-yl |
| 44 | 6-(isopropyl-amino)-pyridin-3-yl | methyl | H | piperidin-1,4-diyl | H | H | H | 1-methyl-pyrazol-5-yl |
| 51 | 6-(isopropyl-amino)-pyridin-3-yl | methyl | H | piperidin-1,4-diyl | H | H | H | isoxazol-4-yl |
| 53 | 6-chloro-pyridin-3-yl | methyl | H | piperidin-1,4-diyl | H | cis-methyl | H | imidazol-1-yl |
| 54 | 6-chloro-pyridin-3-yl | methyl | H | piperidin-1,4-diyl | H | trans-methyl | H | imidazol-1-yl |
| 55 | quinolin-2-yl | methyl | H | azetidin-1,3-diyl | H | H | H | 1-methyl-pyrazol-5-yl |
| 56 | 5-bromo-pyridin-3-yl | methyl | H | azetidin-1,3-diyl | H | H | H | 1-methyl-pyrazol-5-yl |
| 57 | 6-(piperidin-1-yl)-pyridin-3-yl | methyl | H | azetidin-1,3-diyl | H | H | H | 1-methyl-pyrazol-5-yl |
| 58 | 6-(morpholin-4-yl)-pyridin-3-yl | methyl | H | azetidin-1,3-diyl | H | H | H | 1-methyl-pyrazol-5-yl |

TABLE 1-continued

Representative Compounds of Formula (I)

| ID No. | R¹ | R² | R³ | N-Ring | R⁴ | R⁵ | R⁷ | R⁶ |
|---|---|---|---|---|---|---|---|---|
| 59 | 6-(4-methyl-piperazin-4-yl)-pyridin-3-yl | methyl | H | azetidin-1,3-diyl | H | H | H | 1-methyl-pyrazol-5-yl |
| 60 | 6-(isopropyl-amino)-pyridin-3-yl | methyl | H | azetidin-1,3-diyl | H | H | H | 1-methyl-pyrazol-5-yl |
| 61 | 6-(N-methyl-N-(1-methyl-piperidin-4-yl)-amino)-pyridin-3-yl | methyl | H | azetidin-1,3-diyl | H | H | H | 1-methyl-pyrazol-5-yl |
| 62 | 6-(cyclobutyl-amino)-pyridin-3-yl | methyl | H | azetidin-1,3-diyl | H | H | H | 1-methyl-pyrazol-5-yl |
| 63 | 6-(isopropyl-amino)-pyridin-3-yl | chloro | H | azetidin-1,3-diyl | H | H | H | quinolin-4-yl |
| 64 | 4S-ethylcarbonyl-cyclopent-1S-yl | methyl | H | azetidin-1,3-diyl | H | H | H | 1-methyl-pyrazol-5-yl |
| 65 | 6-(isopropyl-amino)-pyridin-3-yl | chloro | H | azetidin-1,3-diyl | H | H | H | 1-methyl-pyrazol-4-yl |
| 66 | 6-(morpholin-4-yl)-pyridin-3-yl | methyl | H | azetidin-1,3-diyl | H | H | H | 1-methyl-pyrazol-4-yl |
| 67 | 6-(isopropyl-amino)-pyridin-3-yl | chloro | H | piperidin-1,4-diyl | H | H | H | isoquinolin-6-yl |
| 68 | 6-(isopropyl-amino)-pyridin-3-yl | chloro | H | piperidin-1,4-diyl | H | H | H | quinolin-4-yl |
| 69 | 6-(isopropyl-amino)-pyridin-3-yl | chloro | H | piperidin-1,4-diyl | H | H | H | 1-methyl-pyrazol-4-yl |
| 70 | 6-(isopropyl-amino)-pyridin-3-yl | chloro | H | piperidin-1,4-diyl | H | H | H | 1-methyl-pyrazol-5-yl |
| 71 | 6-(isopropyl-amino)-pyridin-3-yl | chloro | H | piperidin-1,4-diyl | H | H | H | pyridin-3-yl |
| 72 | 6-(isopropyl-amino)-pyridin-3-yl | chloro | H | piperidin-1,4-diyl | H | H | H | pyridin-4-yl |
| 73 | 6-(isopropyl-amino)-pyridin-3-yl | chloro | H | azetidin-1,3-diyl | H | H | H | pyridin-3-yl |
| 74 | 6-(isopropyl-amino)-pyridin-3-yl | chloro | H | azetidin-1,3-diyl | H | H | H | pyridin-4-yl |
| 75 | 6-(isopropyl-amino)-pyridin-3-yl | chloro | H | azetidin-1,3-diyl | H | H | H | isoquinolin-6-yl |
| 76 | 6-(isopropyl-amino)-pyridin-3-yl | methyl | H | piperidin-1,4-diyl | H | cis-methyl | H | 1-methyl-pyrazol-5-yl |
| 77 | 6-(isopropyl-amino)-pyridin-3-yl | chloro | H | piperidin-1,4-diyl | H | trans-hydroxy | H | 1-methyl-pyrazol-5-yl |
| 78 | 6-(N-methyl-N-isopropyl-amino)-pyridin-3-yl | methyl | H | azetidin-1,3-diyl | H | H | H | 1-methyl-pyrazol-4-yl |

TABLE 1-continued

Representative Compounds of Formula (I)

| ID No. | R¹ | R² | R³ | N-Ring | R⁴ | R⁵ | R⁷ | R⁶ |
|---|---|---|---|---|---|---|---|---|
| 79 | quinolin-2-yl | methyl | H | azetidin-1,3-diyl | H | H | H | 1-methyl-pyrazol-4-yl |
| 80 | pyridin-2-yl | methyl | H | azetidin-1,3-diyl | H | H | H | 1-methyl-pyrazol-4-yl |
| 81 | 6-(isopropyl-amino)-pyridin-3-yl | methyl | H | piperidin-1,4-diyl | H | trans-methyl | H | 1-methyl-pyrazol-5-yl |
| 82 | 2-fluoro-phenyl | methyl | H | azetidin-1,3-diyl | H | H | H | 1-methyl-pyrazol-4-yl |
| 83 | 4-methoxy-phenyl | methyl | H | azetidin-1,3-diyl | H | H | H | 1-methyl-pyrazol-4-yl |
| 84 | thiophen-2-yl | methyl | H | azetidin-1,3-diyl | H | H | H | 1-methyl-pyrazol-4-yl |
| 85 | 2-chloro-pyridin-3-yl | methyl | H | azetidin-1,3-diyl | H | H | H | 1-methyl-pyrazol-4-yl |
| 86 | cyclohexyl | methyl | H | piperidin-1,4-diyl | H | H | H | 1-methyl-pyrazol-4-yl |
| 87 | t-butyl | methyl | H | piperidin-1,4-diyl | H | H | H | 1-methyl-pyrazol-4-yl |
| 88 | cyclopentyl | methyl | H | piperidin-1,4-diyl | H | H | H | 1-methyl-pyrazol-4-yl |
| 89 | cyclopropyl | methyl | H | piperidin-1,4-diyl | H | H | H | 1-methyl-pyrazol-4-yl |
| 91 | 6-(morpholin-4-yl)-pyridin-3-yl | methyl | H | piperidin-1,4-diyl | H | H | H | 1-methyl-pyrazol-4-yl |
| 92 | 6-(N-methyl-N-isopropyl-amino)-pyridin-3-yl | methyl | H | piperidin-1,4-diyl | H | H | H | 1-methyl-pyrazol-4-yl |
| 93 | 4-methoxy-phenyl | methyl | H | piperidin-1,4-diyl | H | H | H | 1-methyl-pyrazol-4-yl |
| 94 | 3-methoxy-phenyl | methyl | H | piperidin-1,4-diyl | H | H | H | 1-methyl-pyrazol-4-yl |
| 95 | 3-chloro-phenyl | methyl | H | piperidin-1,4-diyl | H | H | H | 1-methyl-pyrazol-4-yl |
| 96 | 2-chloro-phenyl | methyl | H | piperidin-1,4-diyl | H | H | H | 1-methyl-pyrazol-4-yl |
| 97 | 6-trifluoromethyl-pyridin-2-yl | methyl | H | azetidin-1,3-diyl | H | H | H | 1-methyl-pyrazol-4-yl |
| 98 | 6-methyl-pyridin-4-yl | methyl | H | piperidin-1,4-diyl | H | H | H | 1-methyl-pyrazol-4-yl |
| 99 | 3-chloro-thiophen-2-yl | methyl | H | piperidin-1,4-diyl | H | H | H | 1-methyl-pyrazol-4-yl |
| 100 | 4-chloro-phenyl | methyl | H | piperidin-1,4-diyl | H | H | H | 1-methyl-pyrazol-4-yl |
| 101 | 2-chloro-pyridin-3-yl | methyl | H | piperidin-1,4-diyl | H | H | H | 1-methyl-pyrazol-4-yl |
| 102 | 6-chloro-pyridin-3-yl | methyl | H | piperidin-1,4-diyl | H | H | H | 1-methyl-pyrazol-4-yl |
| 103 | 2-chloro-6-methoxy-pyridin-4-yl | methyl | H | piperidin-1,4-diyl | H | H | H | 1-methyl-pyrazol-4-yl |
| 104 | tetrahydropyran-4-yl | methyl | H | piperidin-1,4-diyl | H | H | H | 1-methyl-pyrazol-4-yl |
| 105 | 2-methoxy-phenyl | methyl | H | piperidin-1,4-diyl | H | H | H | 1-methyl-pyrazol-4-yl |
| 106 | 6-(pyrrolidin-1-yl)-pyridin-3-yl | methyl | H | azetidin-1,3-diyl | H | H | H | 1-methyl-pyrazol-4-yl |
| 107 | 6-chloro-pyridin-3-yl | methyl | H | azetidin-1,3-diyl | H | hydroxy | H | 1-methyl-pyrazol-5-yl |

TABLE 1-continued

Representative Compounds of Formula (I)

| ID No. | R¹ | R² | R³ | N-Ring | R⁴ | R⁵ | R⁷ | R⁶ |
|---|---|---|---|---|---|---|---|---|
| 108 | 6-(isopropyl-amino)-pyridin-3-yl | chloro | H | azetidin-1,3-diyl | H | H | H | 1-methyl-pyrazol-5-yl |
| 109 | 6-(cyclobutyl-amino)-pyridin-3-yl | methyl | H | azetidin-1,3-diyl | H | H | H | 1-methyl-pyrazol-4-yl |
| 110 | 6-chloro-pyridin-3-yl | methyl | H | piperidin-1,4-diyl | H | trans-methyl | H | 1-methyl-pyrazol-5-yl |
| 111 | 6-chloro-pyridin-3-yl | methyl | H | piperidin-1,4-diyl | H | cis-methyl | H | 1-methyl-pyrazol-5-yl |
| 112 | 6-(4-methyl-piperazin-1-yl)-pyridin-3-yl | methyl | H | piperidin-1,4-diyl | H | H | H | 1-methyl-pyrazol-4-yl |
| 113 | 6-methoxy-pyridin-3-yl | methyl | H | piperidin-1,4-diyl | H | H | H | 1-methyl-pyrazol-4-yl |
| 114 | 4-chloro-pyridin-3-yl | methyl | H | piperidin-1,4-diyl | H | H | H | 1-methyl-pyrazol-4-yl |
| 115 | phenyl | methyl | H | piperidin-1,4-diyl | H | H | H | 1-methyl-pyrazol-4-yl |
| 116 | 4-fluoro-phenyl | methyl | H | piperidin-1,4-diyl | H | H | H | 1-methyl-pyrazol-4-yl |
| 117 | 2-fluoro-phenyl | methyl | H | piperidin-1,4-diyl | H | H | H | 1-methyl-pyrazol-4-yl |
| 118 | 2-methoxy-pyridin-3-yl | methyl | H | piperidin-1,4-diyl | H | H | H | 1-methyl-pyrazol-4-yl |
| 119 | 5-(dimethyl-amino)-pyridin-2-yl | methyl | H | piperidin-1,4-diyl | H | H | H | 1-methyl-pyrazol-4-yl |
| 120 | 2,3,4-trifluoro-phenyl | methyl | H | piperidin-1,4-diyl | H | H | H | 1-methyl-pyrazol-4-yl |
| 121 | 2,6-dichloro-phenyl | methyl | H | piperidin-1,4-diyl | H | H | H | 1-methyl-pyrazol-4-yl |
| 122 | 2,4-dichloro-phenyl | methyl | H | piperidin-1,4-diyl | H | H | H | 1-methyl-pyrazol-4-yl |
| 123 | 3,4-dichloro-phenyl | methyl | H | piperidin-1,4-diyl | H | H | H | 1-methyl-pyrazol-4-yl |
| 124 | 1-benzyl-piperidin-4-yl | methyl | H | piperidin-1,4-diyl | H | H | H | 1-methyl-pyrazol-4-yl |
| 125 | cyclohexyl | methyl | H | azetidin-1,3-diyl | H | H | H | 1-methyl-pyrazol-4-yl |
| 126 | 4-methylthio-phenyl | methyl | H | piperidin-1,4-diyl | H | H | H | 1-methyl-pyrazol-4-yl |
| 127 | 2-fluoro-5-methyl-phenyl | methyl | H | piperidin-1,4-diyl | H | H | H | 1-methyl-pyrazol-4-yl |
| 128 | 3-chloro-5-methoxy-phenyl | methyl | H | piperidin-1,4-diyl | H | H | H | 1-methyl-pyrazol-4-yl |
| 129 | 2-fluoro-4-cyano-phenyl | methyl | H | piperidin-1,4-diyl | H | H | H | 1-methyl-pyrazol-4-yl |
| 130 | thiophen-2-yl | methyl | H | piperidin-1,4-diyl | H | H | H | 1-methyl-pyrazol-4-yl |
| 131 | 2,4-difluoro-phenyl | methyl | H | piperidin-1,4-diyl | H | H | H | 1-methyl-pyrazol-4-yl |
| 132 | 2-trifluoromethyl-phenyl | methyl | H | piperidin-1,4-diyl | H | H | H | 1-methyl-pyrazol-4-yl |
| 133 | 1,3-benzodioxol-5-yl | methyl | H | piperidin-1,4-diyl | H | H | H | 1-methyl-pyrazol-4-yl |
| 134 | 6-(cyclobutyl-amino)-pyridin-3-yl | methyl | H | piperidin-1,4-diyl | H | H | H | 1-methyl-pyrazol-4-yl |

TABLE 1-continued

Representative Compounds of Formula (I)

| ID No. | R¹ | R² | R³ | N-Ring | R⁴ | R⁵ | R⁷ | R⁶ |
|---|---|---|---|---|---|---|---|---|
| 135 | 3-hydroxy-4-methoxy-phenyl | methyl | H | piperidin-1,4-diyl | H | H | H | 1-methyl-pyrazol-4-yl |
| 136 | 2-chloro-pyrimidin-5-yl | methyl | H | piperidin-1,4-diyl | H | H | H | 1-methyl-pyrazol-4-yl |
| 137 | 2-methyl-5-fluoro-phenyl | methyl | H | piperidin-1,4-diyl | H | H | H | 1-methyl-pyrazol-4-yl |
| 138 | 4-cyano-phenyl | methyl | H | piperidin-1,4-diyl | H | H | H | 1-methyl-pyrazol-4-yl |
| 139 | pyridin-4-yl | methyl | H | azetidin-1,3-diyl | H | H | H | 1-methyl-pyrazol-4-yl |
| 140 | 6-(N-methyl-N-(1-methyl-piperidin-4-yl)-amino)-pyridin-3-yl | methyl | H | azetidin-1,3-diyl | H | H | H | 1-methyl-pyrazol-4-yl |
| 141 | 6-(4-methyl-piperazin-1-yl)-pyridin-3-yl | methyl | H | azetidin-1,3-diyl | H | H | H | 1-methyl-pyrazol-4-yl |
| 142 | cyclopropyl | methyl | H | azetidin-1,3-diyl | H | H | H | 1-methyl-pyrazol-4-yl |
| 143 | cyclobutyl | methyl | H | azetidin-1,3-diyl | H | H | H | 1-methyl-pyrazol-4-yl |
| 144 | 2-(N-methyl-N-isopropyl-amino)-pyrimidin-5-yl | methyl | H | piperidin-1,4-diyl | H | H | H | 1-methyl-pyrazol-4-yl |
| 145 | 4-trifluoromethyl-phenyl | methyl | H | piperidin-1,4-diyl | H | H | H | 1-methyl-pyrazol-4-yl |
| 146 | 2-(isopropyl-amino)-pyrimidin-5-yl | methyl | H | piperidin-1,4-diyl | H | H | H | 1-methyl-pyrazol-4-yl |
| 147 | 2-chloro-4-fluoro-phenyl | methyl | H | piperidin-1,4-diyl | H | H | H | 1-methyl-pyrazol-4-yl |
| 148 | 4-isopropyl-phenyl | methyl | H | piperidin-1,4-diyl | H | H | H | 1-methyl-pyrazol-4-yl |
| 149 | 3-methyl-thiophen-2-yl | methyl | H | piperidin-1,4-diyl | H | H | H | 1-methyl-pyrazol-4-yl |
| 150 | piperidin-4-yl | methyl | H | piperidin-1,4-diyl | H | H | H | 1-methyl-pyrazol-4-yl |
| 151 | tetrahydrofuran-2-yl | methyl | H | piperidin-1,4-diyl | H | H | H | 1-methyl-pyrazol-4-yl |
| 152 | 2-(morpholin-4-yl)-pyrimidin-5-yl | methyl | H | piperidin-1,4-diyl | H | H | H | 1-methyl-pyrazol-4-yl |
| 153 | n-pent-3-yl | methyl | H | azetidin-1,3-diyl | H | H | H | 1-methyl-pyrazol-4-yl |
| 154 | 2-chloro-pyrimidin-5-yl | methyl | H | azetidin-1,3-diyl | H | H | H | 1-methyl-pyrazol-4-yl |
| 155 | 3-chloro-4-methoxy-phenyl | methyl | H | piperidin-1,4-diyl | H | H | H | 1-methyl-pyrazol-4-yl |
| 156 | isopropyl | methyl | H | piperidin-1,4-diyl | H | H | H | 1-methyl-pyrazol-4-yl |
| 157 | 5-methyl-thiophen-2-yl | methyl | H | piperidin-1,4-diyl | H | H | H | 1-methyl-pyrazol-4-yl |
| 158 | 2-(isopropyl-amino)-pyrimidin-5-yl | methyl | H | azetidin-1,3-diyl | H | H | H | 1-methyl-pyrazol-4-yl |

TABLE 1-continued

Representative Compounds of Formula (I)

| ID No. | R¹ | R² | R³ | N-Ring | R⁴ | R⁵ | R⁷ | R⁶ |
|---|---|---|---|---|---|---|---|---|
| 159 | 6-(morpholin-4-yl)-pyrimidin-5-yl | methyl | H | azetidin-1,3-diyl | H | H | H | 1-methyl-pyrazol-4-yl |
| 160 | indol-5-yl | methyl | H | piperidin-1,4-diyl | H | H | H | 1-methyl-pyrazol-4-yl |
| 161 | 3-fluoro-pyridin-4-yl | methyl | H | piperidin-1,4-diyl | H | H | H | 1-methyl-pyrazol-4-yl |
| 162 | 2-(cyclobutyl-amino)-pyrimidin-5-yl | methyl | H | piperidin-1,4-diyl | H | H | H | 1-methyl-pyrazol-4-yl |
| 163 | 6-(3S-hydroxymethyl-piperazin-1-yl)-pyridin-3-yl | methyl | H | piperidin-1,4-diyl | H | H | H | 1-methyl-pyrazol-4-yl |
| 164 | 6-(3R-hydroxymethyl-piperazin-1-yl)-pyridin-3-yl | methyl | H | piperidin-1,4-diyl | H | H | H | 1-methyl-pyrazol-4-yl |
| 167 | 1-isopentyl-piperidin-4-yl | methyl | H | piperidin-1,4-diyl | H | H | H | 1-methyl-pyrazol-4-yl |
| 168 | 1-ethyl-piperidin-4-yl | methyl | H | piperidin-1,4-diyl | H | H | H | 1-methyl-pyrazol-4-yl |
| 169 | 1-methyl-piperidin-4-yl | methyl | H | piperidin-1,4-diyl | H | H | H | 1-methyl-pyrazol-4-yl |
| 170 | pyrrolidin-3-yl | methyl | H | piperidin-1,4-diyl | H | H | H | 1-methyl-pyrazol-4-yl |
| 171 | pyrrolidin-2R-yl | methyl | H | piperidin-1,4-diyl | H | H | H | 1-methyl-pyrazol-4-yl |
| 172 | pyrrolidin-2S-yl | methyl | H | piperidin-1,4-diyl | H | H | H | 1-methyl-pyrazol-4-yl |
| 173 | 1-fluoro-ethyl | methyl | H | piperidin-1,4-diyl | H | H | H | 1-methyl-pyrazol-4-yl |
| 174 | thiazol-5-yl | methyl | H | piperidin-1,4-diyl | H | H | H | 1-methyl-pyrazol-4-yl |
| 175 | 1-(1-methyl-n-pentyl)-piperidin-4-yl | methyl | H | piperidin-1,4-diyl | H | H | H | 1-methyl-pyrazol-4-yl |
| 176 | 1-(n-pentyl)-piperidin-4-yl | methyl | H | piperidin-1,4-diyl | H | H | H | 1-methyl-pyrazol-4-yl |
| 177 | 1-cyclohexyl-piperidin-4-yl | methyl | H | piperidin-1,4-diyl | H | H | H | 1-methyl-pyrazol-4-yl |
| 178 | 1-(2,2,-dimethyl-propyl)-piperidin-4-yl | methyl | H | piperidin-1,4-diyl | H | H | H | 1-methyl-pyrazol-4-yl |
| 179 | 1-isobutyl-piperidin-4-yl | methyl | H | piperidin-1,4-diyl | H | H | H | 1-methyl-pyrazol-4-yl |
| 180 | 1-cyclopentyl-piperidin-4-yl | methyl | H | piperidin-1,4-diyl | H | H | H | 1-methyl-pyrazol-4-yl |
| 181 | 1-propyl-piperidin-4-yl | methyl | H | piperidin-1,4-diyl | H | H | H | 1-methyl-pyrazol-4-yl |
| 182 | 1-isopropyl-piperidin-4-yl | methyl | H | piperidin-1,4-diyl | H | H | H | 1-methyl-pyrazol-4-yl |
| 183 | 6-chloro-pyridin-3-yl | methoxy | H | azetidin-1,3-diyl | H | H | H | 1-methyl-pyrazol-4-yl |
| 184 | 6-(morpholin-4-yl)-pyridin-3-yl | methoxy | H | azetidin-1,3-diyl | H | H | H | 1-methyl-pyrazol-4-yl |
| 185 | 1-ethyl-pyrrolidin-3-yl | methyl | H | piperidin-1,4-diyl | H | H | H | 1-methyl-pyrazol-4-yl |
| 186 | 1-propyl-pyrrolidin-3-yl | methyl | H | piperidin-1,4-diyl | H | H | H | 1-methyl-pyrazol-4-yl |

TABLE 1-continued

Representative Compounds of Formula (I)

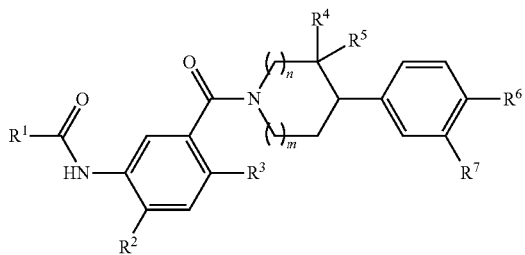

| ID No. | R¹ | R² | R³ | N-Ring | R⁴ | R⁵ | R⁷ | R⁶ |
|---|---|---|---|---|---|---|---|---|
| 187 | 1-cyclopentyl-azetidin-3-yl | methyl | H | piperidin-1,4-diyl | H | H | H | 1-methyl-pyrazol-4-yl |
| 188 | 1-isobutyl-pyrrolidin-3-yl | methyl | H | piperidin-1,4-diyl | H | H | H | 1-methyl-pyrazol-4-yl |
| 189 | 1-cyclopentyl-pyrrolidin-3-yl | methyl | H | piperidin-1,4-diyl | H | H | H | 1-methyl-pyrazol-4-yl |
| 190 | 1-(2,2-dimethyl-propyl)-azetidin-3-yl | methyl | H | piperidin-1,4-diyl | H | H | H | 1-methyl-pyrazol-4-yl |
| 191 | 1-cyclohexyl-azetidin-3-yl | methyl | H | piperidin-1,4-diyl | H | H | H | 1-methyl-pyrazol-4-yl |
| 192 | 1-(2,2-dimethyl-propyl)-pyrrolidin-3-yl | methyl | H | piperidin-1,4-diyl | H | H | H | 1-methyl-pyrazol-4-yl |
| 193 | 1-(3-methyl-cyclopentyl)-azetidin-3-yl | methyl | H | piperidin-1,4-diyl | H | H | H | 1-methyl-pyrazol-4-yl |
| 194 | 1-(3-methyl-cyclopentyl)-pyrrolidin-3-yl | methyl | H | piperidin-1,4-diyl | H | H | H | 1-methyl-pyrazol-4-yl |
| 195 | 1-isopentyl-pyrrolidin-3-yl | methyl | H | piperidin-1,4-diyl | H | H | H | 1-methyl-pyrazol-4-yl |
| 196 | 1-(1-methyl-n-pentyl)-azetidin-3-yl | methyl | H | piperidin-1,4-diyl | H | H | H | 1-methyl-pyrazol-4-yl |
| 197 | 1-(1-methyl-n-pentyl)-pyrrolidin-3-yl | methyl | H | piperidin-1,4-diyl | H | H | H | 1-methyl-pyrazol-4-yl |
| 198 | thiazol-2-yl | methyl | H | piperidin-1,4-diyl | H | H | H | 1-methyl-pyrazol-4-yl |
| 199 | 6-(isopropyl-amino)-pyridin-3-yl | methyl | H | piperidin-1,4-diyl | H | H | H | 4-methoxy-phenyl |
| 200 | 6-(isopropyl-amino)-pyridin-3-yl | methyl | H | piperidin-1,4-diyl | H | H | H | 2-methoxy-phenyl |
| 201 | 6-(isopropyl-amino)-pyridin-3-yl | methyl | H | piperidin-1,4-diyl | H | H | H | 3-methoxy-phenyl |
| 202 | 6-(isopropyl-amino)-pyridin-3-yl | methoxy | H | azetidin-1,3-diyl | H | H | H | 1-methyl-pyrazol-4-yl |
| 203 | 6-chloro-pyridin-3-yl | methyl | H | pyrrolidin-1,3-diyl | H | H | H | 1-methyl-pyrazol-4-yl |
| 204 | 6-(morpholin-4-yl)-pyridin-3-yl | methyl | H | pyrrolidin-1,3-diyl | H | H | H | 1-methyl-pyrazol-4-yl |
| 205 | 1-ethyl-azetidin-3-yl | methyl | H | piperidin-1,4-diyl | H | H | H | 1-methyl-pyrazol-4-yl |
| 206 | 1-isopropyl-azetidin-3-yl | methyl | H | piperidin-1,4-diyl | H | H | H | 1-methyl-pyrazol-4-yl |
| 207 | 1-isopropyl-pyrrolidin-3-yl | methyl | H | piperidin-1,4-diyl | H | H | H | 1-methyl-pyrazol-4-yl |
| 208 | 1-n-propyl-azetidin-3-yl | methyl | H | piperidin-1,4-diyl | H | H | H | 1-methyl-pyrazol-4-yl |
| 209 | 1-cyclobutyl-piperidin-4-yl | methyl | H | piperidin-1,4-diyl | H | H | H | 1-methyl-pyrazol-4-yl |
| 210 | 1-isobutyl-azetidin-3-yl | methyl | H | piperidin-1,4-diyl | H | H | H | 1-methyl-pyrazol-4-yl |
| 211 | 1-n-butyl-piperidin-4-yl | methyl | H | piperidin-1,4-diyl | H | H | H | 1-methyl-pyrazol-4-yl |

TABLE 1-continued

Representative Compounds of Formula (I)

| ID No. | R¹ | R² | R³ | N-Ring | R⁴ | R⁵ | R⁷ | R⁶ |
|---|---|---|---|---|---|---|---|---|
| 212 | 1-n-butyl-pyrrolidin-3-yl | methyl | H | piperidin-1,4-diyl | H | H | H | 1-methyl-pyrazol-4-yl |
| 213 | 1-isopentyl-azetidin-3-yl | methyl | H | piperidin-1,4-diyl | H | H | H | 1-methyl-pyrazol-4-yl |
| 214 | 1-n-pentyl-azetidin-3-yl | methyl | H | piperidin-1,4-diyl | H | H | H | 1-methyl-pyrazol-4-yl |
| 215 | 1-n-pentyl-pyrrolidin-3-yl | methyl | H | piperidin-1,4-diyl | H | H | H | 1-methyl-pyrazol-4-yl |
| 216 | 1-n-hexyl-piperidin-4-yl | methyl | H | piperidin-1,4-diyl | H | H | H | 1-methyl-pyrazol-4-yl |
| 217 | 6-(isopropyl-amino)-pyridin-3-yl | methyl | H | piperidin-1,4-diyl | H | H | H | 1-(tetrahydro-pyran-4-yl)-pyrazol-4-yl |
| 218 | 1-n-hexyl-pyrrolidin-3-yl | methyl | H | piperidin-1,4-diyl | H | H | H | 1-methyl-pyrazol-4-yl |
| 219 | 1-(cyclopropyl-carbonyl)-azetidin-3-yl | methyl | H | piperidin-1,4-diyl | H | H | H | 1-methyl-pyrazol-4-yl |
| 220 | 1-(cyclopropyl-carbonyl)-pyrrolidin-3-yl | methyl | H | piperidin-1,4-diyl | H | H | H | 1-methyl-pyrazol-4-yl |
| 221 | 6-(isopropyl-amino)-pyridin-3-yl | methyl | H | piperidin-1,4-diyl | H | H | H | 1-(cyclobutyl-methyl)-pyrazol-4-yl |
| 222 | 1-methyl-azetidin-3-yl | methyl | H | piperidin-1,4-diyl | H | H | H | 1-methyl-pyrazol-4-yl |
| 223 | 6-(isopropyl-amino)-pyridin-3-yl | methyl | H | piperidin-1,4-diyl | H | H | H | thiophen-3-yl |
| 224 | 6-(isopropyl-amino)-pyridin-3-yl | methyl | H | piperidin-1,4-diyl | H | H | H | 2-fluoro-phenyl |
| 225 | 6-(isopropyl-amino)-pyridin-3-yl | methyl | H | piperidin-1,4-diyl | H | H | H | phenyl |
| 226 | cyclopentyl | methyl | H | azetidin-1,3-diyl | H | H | H | 1-methyl-pyrazol-4-yl |
| 227 | 1-methyl-imidazol-2-yl | methyl | H | piperidin-1,4-diyl | H | H | H | 1-methyl-pyrazol-4-yl |
| 229 | 4-t-butyl-thiazol-2-yl | methyl | H | piperidin-1,4-diyl | H | H | H | 1-methyl-pyrazol-4-yl |
| 230 | 6-(isopropyl-amino)-pyridin-3-yl | methyl | H | piperidin-1,4-diyl | H | H | H | 3-fluoro-phenyl |
| 231 | 6-chloro-pyridin-3-yl | methoxy | H | piperidin-1,4-diyl | H | H | H | 1-methyl-pyrazol-4-yl |
| 232 | 6-(isopropyl-amino)-pyridin-3-yl | methyl | H | piperidin-1,4-diyl | H | H | H | 2-methyl-phenyl |
| 233 | 6-(isopropyl-amino)-pyridin-3-yl | methyl | H | piperidin-1,4-diyl | H | H | H | 3-methy-phenyl |
| 234 | 6-(isopropyl-amino)-pyridin-3-yl | methyl | H | piperidin-1,4-diyl | H | H | H | 4-methyl-phenyl |
| 235 | 6-(isopropyl-amino)-pyridin-3-yl | methyl | H | piperidin-1,4-diyl | H | H | H | furan-3-yl |
| 236 | 6-(isopropyl-amino)-pyridin-3-yl | methyl | H | piperidin-1,4-diyl | H | H | H | thiophen-2-yl |

TABLE 1-continued

Representative Compounds of Formula (I)

| ID No. | R¹ | R² | R³ | N-Ring | R⁴ | R⁵ | R⁷ | R⁶ |
|---|---|---|---|---|---|---|---|---|
| 237 | 6-(isopropyl-amino)-pyridin-3-yl | methyl | H | pyrrolidin-1,3-diyl | H | H | H | 1-methyl-pyrazol-4-yl |
| 238 | 1-methyl-pyrrolidin-3R-yl | methyl | H | piperidin-1,4-diyl | H | H | H | 1-methyl-pyrazol-4-yl |
| 239 | 1-methyl-pyrrolidin-3S-yl | methyl | H | piperidin-1,4-diyl | H | H | H | 1-methyl-pyrazol-4-yl |
| 240 | 1-cyclobutyl-azetidin-3-yl | methyl | H | piperidin-1,4-diyl | H | H | H | 1-methyl-pyrazol-4-yl |
| 241 | 1-cyclobutyl-pyrrolidin-3-yl | methyl | H | piperidin-1,4-diyl | H | H | H | 1-methyl-pyrazol-4-yl |
| 242 | 1-n-butyl-azetidin-3-yl | methyl | H | piperidin-1,4-diyl | H | H | H | 1-methyl-pyrazol-4-yl |
| 243 | 1-n-hexyl-azetidin-3-yl | methyl | H | piperidin-1,4-diyl | H | H | H | 1-methyl-pyrazol-4-yl |
| 244 | 4-bromo-thiazol-2-yl | methyl | H | piperidin-1,4-diyl | H | H | H | 1-methyl-pyrazol-4-yl |
| 245 | 6-(isopropyl-amino)-pyridin-3-yl | methyl | H | piperidin-1,4-diyl | H | H | H | 1,3-dimethyl-pyrazol-4-yl |
| 246 | 6-(isopropyl-amino)-pyridin-3-yl | methyl | H | piperidin-1,4-diyl | H | H | H | 1,3-dimethyl-pyrazol-4-yl |
| 247 | 6-(isopropyl-amino)-pyridin-3-yl | methyl | H | piperidin-1,4-diyl | H | H | H | 1-isopropyl-pyrazol-4-yl |
| 248 | 6-(isopropyl-amino)-pyridin-3-yl | methyl | H | piperidin-1,4-diyl | H | H | H | 1-cyclobutyl-pyrazol-4-yl |
| 249 | 6-(isopropyl-amino)-pyridin-3-yl | methyl | H | piperidin-1,4-diyl | H | H | H | 1-(cyclopropyl-methyl)-pyrazol-4-yl |
| 250 | 6-(isopropyl-amino)-pyridin-3-yl | methyl | H | piperidin-1,4-diyl | H | H | H | 4-fluoro-phenyl |
| 251 | 6-(isopropyl-amino)-pyridin-3-yl | methoxy | H | piperidin-1,4-diyl | H | H | H | 1-methyl-pyrazol-4-yl |
| 252 | 6-(isopropyl-amino)-pyridin-3-yl | methyl | H | piperidin-1,4-diyl | H | H | H | furan-2-yl |
| 253 | 6-(isopropyl-amino)-pyridin-3-yl | methyl | H | piperidin-1,4-diyl | H | H | H | 1-(dimethyl-amino-ethyl)-pyrazol-4-yl |
| 254 | 6-(isopropyl-amino)-pyridin-3-yl | methyl | H | piperidin-1,4-diyl | H | H | H | 1-cyclopropyl-pyrazol-4-yl |
| 255 | 6-chloro-pyridin-3-yl | ethyl | H | piperidin-1,4-diyl | H | H | H | 1-methyl-pyrazol-4-yl |
| 256 | 6-(isopropyl-amino)-pyridin-3-yl | ethyl | H | piperidin-1,4-diyl | H | H | H | 1-methyl-pyrazol-4-yl |
| 259 | 6-chloro-pyridin-3-yl | methyl | H | azetidin-1,3-diyl | H | H | H | 2-amino-pyridin-3-yl |
| 260 | 6-(morpholin-4-yl)-pyridin-3-yl | methyl | H | azetidin-1,3-diyl | H | H | H | 2-amino-pyridin-3-yl |
| 261 | 6-(isopropyl-amino)-pyridin-3-yl | methyl | H | piperidin-1,4-diyl | H | H | H | 1-(pyridin-3-yl)-pyrazol-4-yl |
| 262 | 6-chloro-pyridin-3-yl | benzyloxy | H | piperidin-1,4-diyl | H | H | H | 1-methyl-pyrazol-4-yl |

TABLE 1-continued

Representative Compounds of Formula (I)

| ID No. | R¹ | R² | R³ | N-Ring | R⁴ | R⁵ | R⁷ | R⁶ |
|---|---|---|---|---|---|---|---|---|
| 265 | 6-(morpholin-4-yl)-pyridin-3-yl | methyl | H | azetidin-1,3-diyl | H | H | H | 3-amino-pyridin-4-yl |
| 266 | 6-chloro-pyridin-3-yl | methyl | H | azetidin-1,3-diyl | H | H | H | 3-amino-pyridin-4-yl |
| 267 | 6-(isopropyl-amino)-pyridin-3-yl | methyl | H | piperidin-1,4-diyl | H | H | H | 1-(2-hydroxyethyl)-pyrazol-4-yl |
| 269 | 6-(isopropyl-amino)-pyridin-3-yl | hydroxy | H | piperidin-1,4-diyl | H | H | H | 1-methyl-pyrazol-4-yl |
| 271 | 6-(isopropyl-amino)-pyridin-3-yl | benzyloxy | H | piperidin-1,4-diyl | H | H | H | 1-methyl-pyrazol-4-yl |
| 272 | 6-(isopropyl-amino)-pyridin-3-yl | methyl | H | piperidin-1,4-diyl | H | H | H | 1-(pyridin-4-yl)-pyrazol-4-yl |
| 273 | cyclopropyl | dimethyl-amino | H | piperidin-1,4-diyl | H | H | H | 1-methyl-pyrazol-4-yl |
| 274 | 6-chloro-pyridin-3-yl | N-methyl-N-isopropyl-amino | H | piperidin-1,4-diyl | H | H | H | 1-methyl-pyrazol-4-yl |
| 275 | 6-chloro-pyridin-3-yl | dimethyl-amino | H | piperidin-1,4-diyl | H | H | H | 1-methyl-pyrazol-4-yl |
| 276 | 6-(isopropyl-amino)-pyridin-3-yl | N-methyl-N-isopropyl-amino | H | piperidin-1,4-diyl | H | H | H | 1-methyl-pyrazol-4-yl |
| 277 | cyclopropyl | cyclopropyl-carbonyl-amino- | H | piperidin-1,4-diyl | H | H | H | 1-methyl-pyrazol-4-yl |
| 278 | cyclopropyl | N-methyl-N-(methoxy-ethyl)-amino- | H | piperidin-1,4-diyl | H | H | H | 1-methyl-pyrazol-4-yl |
| 279 | 6-(isopropyl-amino)-pyridin-3-yl | methyl-amino- | H | piperidin-1,4-diyl | H | H | H | 1-methyl-pyrazol-4-yl |
| 280 | 6-(isopropyl-amino)-pyridin-3-yl | dimethyl-amino | H | piperidin-1,4-diyl | H | H | H | 1-methyl-pyrazol-4-yl |
| 281 | 6-(isopropyl-amino)-pyridin-3-yl | N-methyl-N-(methoxy-ethyl)-amino- | H | piperidin-1,4-diyl | H | H | H | 1-methyl-pyrazol-4-yl |
| 282 | 6-(isopropyl-amino)-pyridin-3-yl | (methoxy-ethyl)-amino- | H | piperidin-1,4-diyl | H | H | H | 1-methyl-pyrazol-4-yl |
| 283 | 6-(isopropyl-amino)-pyridin-3-yl | cyclopropyl-amino- | H | piperidin-1,4-diyl | H | H | H | 1-methyl-pyrazol-4-yl |
| 284 | 6-(isopropyl-amino)-pyridin-3-yl | isopropyl-amino- | H | piperidin-1,4-diyl | H | H | H | 1-methyl-pyrazol-4-yl |
| 285 | 6-(isopropyl-amino)-pyridin-3-yl | amino | H | piperidin-1,4-diyl | H | H | H | 1-methyl-pyrazol-4-yl |
| 286 | cyclopropyl | (methoxy-ethyl)-amino- | H | piperidin-1,4-diyl | H | H | H | 1-methyl-pyrazol-4-yl |
| 287 | 6-(isopropyl-amino)-pyridin-3-yl | N-methyl-N-cyclopropyl-amino- | H | piperidin-1,4-diyl | H | H | H | 1-methyl-pyrazol-4-yl |

TABLE 1-continued

Representative Compounds of Formula (I)

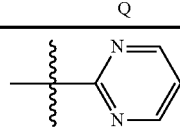

| ID No. | R¹ | R² | R³ | N-Ring | R⁴ | R⁵ | R⁷ | R⁶ |
|---|---|---|---|---|---|---|---|---|
| 288 | cyclopropyl | N-methyl-N-cyclopropyl-amino- | H | piperidin-1,4-diyl | H | H | H | 1-methyl-pyrazol-4-yl |
| 291 | cyclopropyl | N-(2-methoxy-ethyl)-N-(cyclopropyl-carbonyl)-amino | H | piperidin-1,4-diyl | H | H | H | 1-methyl-pyrazol-4-yl |
| 292 | cyclopropyl | N-methyl-N-isopropyl-amino | H | piperidin-1,4-diyl | H | H | H | 1-methyl-pyrazol-4-yl |
| 293 | 1-cyclohexyl-pyrrolidin-3-yl | methyl | H | piperidin-1,4-diyl | H | H | H | 1-methyl-pyrazol-4-yl |
| 294 | azetidin-3-yl | methyl | H | piperidin-1,4-diyl | H | H | H | 1-methyl-pyrazol-4-yl |
| 295 | 1-(3-methyl-cyclopentyl)-piperidin-4-yl | methyl | H | piperidin-1,4-diyl | H | H | H | 1-methyl-pyrazol-4-yl |
| 296 | 2-methyl-4-fluoro-phenyl | methyl | H | piperidin-1,4-diyl | H | H | H | 1-methyl-pyrazol-4-yl |
| 297 | 6-dimethyl-amino-pyridin-3-yl | methyl | H | piperidin-1,4-diyl | H | H | H | 1-methyl-pyrazol-4-yl |

TABLE 2

Representative Compounds of Formula (I)

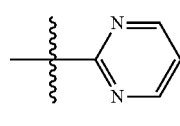

| ID No. | R¹ | R² | N-Ring | Q | R⁶ |
|---|---|---|---|---|---|
| 257 | 6-chloro-pyridin-3-yl | methyl | piperidin-1,4-diyl | pyrimidin-2-yl (5-R⁶) | 1-methyl-pyrazol-4-yl |
| 258 | 6-(isopropyl-amino)-pyridin-3-yl | methyl | piperidin-1,4-diyl | pyrimidin-2-yl (5-R⁶) | 1-methyl-pyrazol-4-yl |

TABLE 2-continued

Representative Compounds of Formula (I)

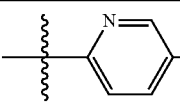

| ID No. | R¹ | R² | 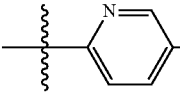 | Q | R⁶ |
|---|---|---|---|---|---|
| 263 | 6-chloro-pyridin-3-yl | methyl | piperidin-1,4-diyl | | 1-methyl-pyrazol-4-yl |
| 264 | 6-(isopropyl-amino)-pyridin-3-yl | methyl | piperidin-1,4-diyl | | 1-methyl-pyrazol-4-yl |
| 268 | 6-(isopropyl-amino)-pyridin-3-yl | methyl | piperidin-1,4-diyl | | 1-methyl-pyrazol-4-yl |
| 270 | 6-chloro-pyridin-3-yl | methyl | piperidin-1,4-diyl | | 1-methyl-pyrazol-4-yl |

TABLE 3

Representative Compounds of Formula (I)

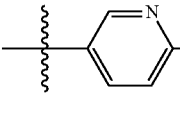

| ID No. | R¹ | R² | 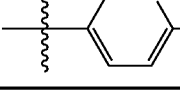 | Q (R6 + R7 bicycle) |
|---|---|---|---|---|
| 14 | 6-chloro-pyridin-3-yl | methyl | piperidin-1,4-diyl | imidazo[1,2-a]pyridin-6-yl |
| 17 | 6-(isopropyl-amino)-pyridin-3-yl | methyl | piperidin-1,4-diyl | imidazo[1,2-a]pyridin-6-yl |
| 18 | 6-chloro-pyridin-3-yl | methyl | piperidin-1,4-diyl | [1,2,4]triazolo[4,3-a]pyridin-6-yl |
| 19 | 6-(isopropyl-amino)-pyridin-3-yl | methyl | piperidin-1,4-diyl | 1-methyl-2-oxo-isoindol-5-yl |
| 20 | 6-(isopropyl-amino)-pyridin-3-yl | methyl | piperidin-1,4-diyl | [1,2,4]triazolo[4,3-a]pyridin-6-yl |
| 21 | 6-chloro-pyridin-3-yl | methyl | piperidin-1,4-diyl | 1,7-dimethyl-2-oxo-isoindol-5-yl |
| 22 | 6-(isopropyl-amino)-pyridin-3-yl | methyl | piperidin-1,4-diyl | 1,7-dimethyl-2-oxo-isoindol-5-yl |
| 23 | 6-chloro-pyridin-3-yl | methyl | piperidin-1,4-diyl | 2-oxo-2,3,4-trihydro-quinolin-7-yl |

TABLE 3-continued

Representative Compounds of Formula (I)

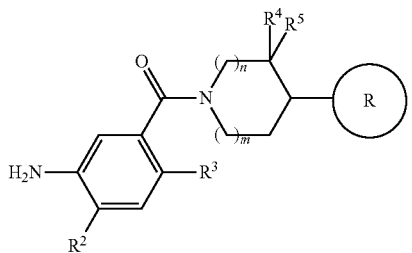

| ID No. | R¹ | R² | 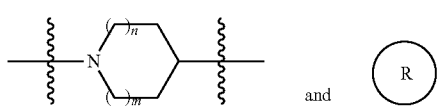 | Q (R6 + R7 bicycle) |
|---|---|---|---|---|
| 28 | 6-(isopropyl-amino)-pyridin-3-yl | methyl | piperidin-1,4-diyl | isoquinolin-7-yl |
| 29 | 6-(isopropyl-amino)-pyridin-3-yl | methyl | piperidin-1,4-diyl | isoquinolin-6-yl |
| 35 | 6-(isopropyl-amino)-pyridin-3-yl | methyl | piperidin-1,4-diyl | 2-oxo-2,3,4-trihydro-quinolin-7-yl |
| 36 | 6-(isopropyl-amino)-pyridin-3-yl | methyl | piperidin-1,4-diyl | 1-methyl-indazol-6-yl |
| 37 | 6-chloro-pyridin-3-yl | methyl | piperidin-1,4-diyl | isoquinolin-7-yl |
| 46 | 6-(isopropyl-amino)-pyridin-3-yl | methyl | piperidin-1,4-diyl | benzothiazol-6-yl |
| 47 | 6-chloro-pyridin-3-yl | methyl | piperidin-1,4-diyl | benzothiazol-6-yl |
| 48 | 6-chloro-pyridin-3-yl | methyl | piperidin-1,4-diyl | 2-oxo-benzothiazol-6-yl |
| 49 | 6-(isopropyl-amino)-pyridin-3-yl | methyl | piperidin-1,4-diyl | 2-oxo-benzothiazol-6-yl |
| 50 | 6-chloro-pyridin-3-yl | methyl | piperidin-1,4-diyl | 2-oxo-indolin-5-yl |

The present invention is further directed to intermediates in the synthesis of the compounds of formula (I), as described in more detail herein. In an embodiment, the present invention is directed to compound of formula (VII)

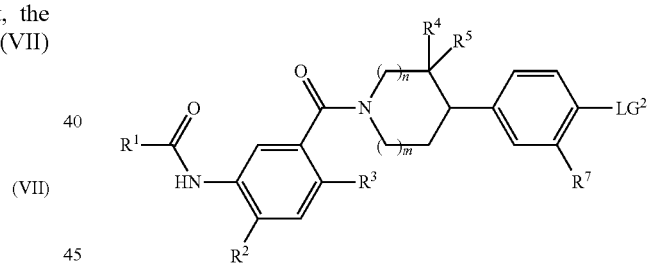

(VII)

wherein $R^2$, $R^3$, $R^4$, $R^5$, m, n,

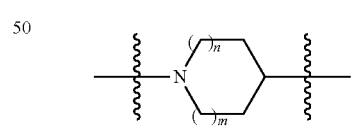

and are as herein defined. In another embodiment, the present invention is directed to compounds of formula (XI)

(XI)

wherein $R^1$, $R^2$, $R^3$, $R^4$, $R^5$, $R^7$, $LG^1$, m, n and are as herein defined.

DEFINITIONS

As used herein, unless otherwise noted, the term "halogen" means chloro, bromo, fluoro and iodo. Preferably, the halogen is bromo, chloro or fluoro.

As used herein, unless otherwise noted, the term "oxo" when used to define a substituent group means an oxygen atom which is bound to a chain or ring carbon atom through a double bond (i.e. =O).

As used herein, the term "$C_{X-Y}$alkyl" whether used alone or as part of a substituent group, means any straight and branched carbon chain composition of between X and Y carbon atoms. For example, "$C_{1-6}$alkyl" means any straight or branched carbon chain composition of between 1 and 6 carbon atoms, including, but not limited to methyl, ethyl, propyl, isopropyl, butyl, isobutyl, sec-butyl, t-butyl, n-pentyl, n-hexyl, and the like.

One skilled in the art will recognize that the term "—($C_{X-Y}$alkyl)-" means any $C_{X-Y}$alkyl carbon chain as herein defined, wherein said $C_{X-Y}$alkyl chain is divalent and is bound through two points of attachment, preferably through two terminal carbon atoms. For example, "—($C_{1-4}$alkyl)-" includes, but is not limited to —$CH_2$—, —$CH_2CH_2$—, —$CH(CH_3)$—, —$CH_2CH_2CH_2$—, —$CH_2CH(CH_3)$—, —$CH_2CH_2CH_2CH_2$—, $CH_2CH(CH_3)CH_2$—, and the like.

As used herein, unless otherwise noted, the term "fluorinated $C_{X-Y}$alkyl" means any $C_{X-Y}$alkyl group as defined above substituted with at least one fluoro atom. For example, the term "fluorinated $C_{1-4}$alkyl" includes, but is not limited to —$CF_3$, —$CH_2F$, —$CH_2$—$CF_3$, —$CH_2$—$CH_2F$, —$CHF$—$CH_3$, —$CF_2$—$CF_2$—$CF_2$—$CF_3$, and the like.

As used herein, unless otherwise noted, the term "hydroxy substituted $C_{X-Y}$alkyl" means $C_{X-Y}$alkyl group as defined above substituted with at least one hydroxy group. Preferably, the $C_{X-Y}$alkyl group is substituted with one hydroxy group. Preferably, the $C_{X-Y}$alkyl group is substituted with a hydroxy group at the terminal carbon. For example, the term "hydroxy substituted $C_{1-4}$alkyl" includes, but is not limited to, $CH_2(OH)$, —$CH_2$—$CH_2(OH)$, —$CH_2$—$CH(OH)$—$CH_2$, and the like.

As used herein, unless otherwise noted, "$C_{X-Y}$alkoxy" wherein X and Y are integers, means an oxygen ether radical of the above described straight or branched chain $C_{X-Y}$alkyl groups. For example, the term "$C_{1-4}$alkoxy" includes, but is not limited to methoxy, ethoxy, n-propoxy, sec-butoxy, t-butoxy, n-hexyloxy and the like.

As used herein, unless otherwise noted, the term "$C_{X-Y}$cycloalkyl" wherein X and Y are integers means any stable saturated ring system comprising between X and Y carbon ring atoms. For example, the term "$C_{1-8}$cycloalkyl" means any stable 3 to 8 membered saturated ring structure, including cyclopropyl, cyclobutyl, cyclopentyl, cyclohexyl, cycloheptyl and cyclooctyl.

As used herein, unless otherwise noted, "aryl" means any carbocylic aromatic ring structure as phenyl, naphthyl, and the like. Preferably, the aryl is phenyl or naphthyl, more preferably phenyl.

As used herein, unless otherwise noted, "heteroaryl" means any five or six membered monocyclic aromatic ring structure containing at least one heteroatom selected from the group consisting of O, N and S, optionally containing one to three additional heteroatoms independently selected from the group consisting of O, N and S; or any nine or ten membered bicyclic aromatic ring structure containing at least one heteroatom selected from the group consisting of O, N and S, optionally containing one to four additional heteroatoms independently selected from the group consisting of O, N and S; and wherein the heteroaryl contains one of more S heteroatom(s), said S heteroatom(s) are each independently optionally substituted with one to two oxo groups. The heteroaryl group may be attached at any heteroatom or carbon atom of the ring such that the result is a stable structure. Examples of suitable heteroaryl groups include, but are not limited to, pyrrolyl, furyl, thienyl, oxazolyl, imidazolyl, purazolyl, isoxazolyl, isothiazolyl, triazolyl, thiadiazolyl, tetrazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, and the like.

As used herein, unless otherwise noted, the term "5 to 6 membered heteroaryl" means any five or six membered monocyclic aromatic ring structure containing at least one heteroatom selected from the group consisting of O, N and S, optionally containing one to three additional heteroatoms independently selected from the group consisting of O, N and S; wherein the 5 to 6 membered heteroaryl contains one of more S heteroatom(s), said S heteroatom(s) are each independently optionally substituted with one to two oxo groups. The 5 to 6 membered heteroaryl may be attached at any heteroatom or carbon atom of the ring such that the result is a stable structure. Suitable examples include, but are not limited to, pyrrolyl, furyl, thienyl, oxazolyl, thiazolyl, imidazolyl, purazolyl, isoxazolyl, isothiazolyl, triazolyl, thiadiazolyl, tetrazolyl, pyridyl, pyridazinyl, pyrimidinyl, pyrazinyl, pyranyl, furazanyl, and the like. Preferred 5 to 6 membered heteroaryl include one or more selected from the group consisting of pyrrolyl, furanyl, thienyl, oxazolyl, thiazolyl, imidazolyl, pyrazolyl, triazolyl, tetrazolyl, pyridyl, pyrimidinyl, pyrazonyl, and pyranyl.

As used herein, unless otherwise noted the term "9 to 10 membered heteroaryl" means any nine or ten membered bicyclic aromatic ring structure containing at least one heteroatom selected from the group consisting of O, N and S, optionally containing one to four additional heteroatoms independently selected from the group consisting of O, N and S; and wherein the heteroaryl contains one of more S heteroatom(s), said S heteroatom(s) are each independently optionally substituted with one to two oxo groups. The bicyclic heteroaryl group may be attached at any heteroatom or carbon atom of the ring such that the result is a stable structure. Examples of suitable bicyclic heteroaryl groups include, but are not limited to, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, and the like.

As used herein, the term "heterocyclyl" means any four to eight membered monocyclic, saturated or partially unsaturated ring structure containing at least one heteroatom selected from the group consisting of O, N and S, optionally containing one to three additional heteroatoms independently selected from the group consisting of O, N and S; or a nine to ten membered saturated, partially unsaturated or partially aromatic (e.g. benzo-fused) bicyclic ring system containing at least one heteroatom selected from the group consisting of O, N and S, optionally containing one to four additional heteroatoms independently selected from the group consisting of O, N and S; and wherein the heterocyclcyl contains one of more S heteroatom(s), said S heteroatom(s) are each independently optionally substituted with one to two oxo groups. The heterocyclyl group may be attached at any heteroatom or carbon atom of the ring such that the result is a stable structure. Suitably examples include, but are not limited to, azetidinyl, pyrrolinyl, pyrrolidinyl, dioxalanyl, imidazolinyl, imidazolidinyl, pyrazolinyl, pyrazolidinyl, piperidinyl, 1,4-dioxanyl, morpholinyl, 1,4-dithianyl, thiomorpholinyl, piperazinyl, trithianyl, azepanyl, 1,4-diazepanyl, 1,4-oxazepnayl, indolinyl, isoindolinyl, chromenyl, 3,4-methylenedioxyphenyl, 2,3-dihydrobenzofuranyl, tetrahydrofuranyl, and the like. Preferred heterocycloalkyl groups include one or more selected from the group consisting of azetidinyl, pyrrolidinyl, dioxaklanyl, imidazolidinyl, pyrazolinyl, pyrazolidinyl, piperidinyl, morpholinyl, piperazinyl, azepanyl, 1,4-diazepanyl, 1,4-oxazepanyl, indolinyl, 1,3-benzodioxolyl, 2,3-dihydrofuranyl and tetrahydrofuranyl.

As used herein, unless otherwise noted, the term "4 to 6 membered saturated heterocyclyl" means any 4 to 6 membered monocyclic, saturated ring structure containing at least one heteroatom selected from the group consisting of O, S and N, optionally containing one to three additional heteroatoms independently selected from the group consisting of O, S and N; and wherein the 4 to 6 membered saturated heterocyclyl contains one or more S heteroatom(s), said S heteroatom(s) are each independently, optionally substituted with one to two oxo groups. The 4 to 6 membered saturated heterocyclyl group may be attached at any heteroatom or carbon atom of the ring such that the result is a stable structure. Suitable examples include, but are not limited to azetidinyl, pyrrolidinyl, dioxolanyl, imidazolidinyl, pyrazolidinyl, piperidinyl, 1,4-dioxanyl, morpholinyl, 1,4-dithianyl, thiomorpholinyl, piperazinyl, azepanyl, 1,4-diazepanyl, 1,4-oxazapanyl, and the like. Preferably, the 4 to 6 membered saturated heterocyclyl include one or more selected from the group consisting of azetidinyl, pyrrolidinyl, dioxolanyl, piperidinyl, 1,4-dioxanyl, morpholinyl, piperazinyl, azepanyl, 1,4-diazepanyl and 1,4-oxazapanyl.

As used herein, unless otherwise noted, the term "5 to 6 membered saturated heterocyclyl" means any 5 to 6 membered monocyclic, saturated ring structure containing at least one heteroatom selected from the group consisting of O, S and N, optionally containing one to three additional heteroatoms independently selected from the group consisting of O, S and N; and wherein the 5 to 6 membered saturated heterocyclyl contains one or more S heteroatom(s), said S heteroatom(s) are each independently, optionally substituted with one to two oxo groups. The 5 to 6 membered saturated heterocyclyl group may be attached at any heteroatom or carbon atom of the ring such that the result is a stable structure. Suitable examples include, but are not limited to Suitably examples include, but are not limited to, pyrrolidinyl, dioxolanyl, imidazolidinyl, pyrazolidinyl, piperidinyl, 1,4-dioxanyl, morpholinyl, 1,4-dithianyl, thiomorpholinyl, piperazinyl, azepanyl, 1,4-diazepanyl, 1,4-oxazapanyl, and the like. Preferably, the 5 to 6 membered saturated heterocyclyl include one or more selected from the group consisting of pyrrolidinyl, dioxolanyl, piperidinyl, 1,4-dioxanyl, morpholinyl, piperazinyl, azepanyl, 1,4-diazepanyl and 1,4-oxazapanyl.

As used herein, the term "9 to 10 membered, saturated, partially unsaturated or benzo-fused heterocyclyl" means any nine to ten membered saturated, partially unsaturated or partially aromatic (e.g. benzo-fused) bicyclic ring system containing at least one heteroatom selected from the group consisting of O, N and S, optionally containing one to four additional heteroatoms independently selected from the group consisting of O, N and S; and wherein the heterocyclcyl contains one of more S heteratom(s), said S heteroatom(s) are each independently optionally substituted with one to two oxo groups. The heterocyclyl group may be attached at any heteroatom or carbon atom of the ring such that the result is a stable structure. Suitably examples include, but are not limited to 3H-indolyl, indolinyl, isoindolinyl, chromenyl, 3,4-methylenedioxyphenyl, 1,3-benzodioxolyl, and the like.

As used herein, unless otherwise noted, the term "9 to 10 membered bicyclic, partially unsaturated or aromatic heterocyclyl" means any nine to ten membered bicyclic ring structure containing at least one heteroatom selected from the group consisting of O, N and S, optionally containing one to four additional heteroatoms independently selected from the group consisting of O, N and S, and wherein the heterocyclyl contains one or come S heteroatom(s), said S heteroatom(s) are each independently optionally substituted with one to two oxo groups; and wherein the bicyclic ring structure contains at least one unsaturated (double) bond, optionally one or more unsaturated (double) bonds, preferably one to five unsaturated double bonds; and wherein the bicyclic ring structure may, in certain embodiments, be benzo-fused or aromatic. The heterocyclyl group may be attached at any heteroatom or carbon atom of the ring such that the result is a stable structure. Suitably examples include, but are not limited to, indolyl, isoindolyl, indolinyl, indolizine, benzofuryl, benzothiophenyl, indazolyl, benzimidazolyl, benzthiazolyl, purinyl, quinolinyl, 2,3,4-trihydroquinolinyl, isoquinolinyl, quinolizinyl, cinnolinyl, phthalazinyl, quinazolinyl, quinoxaolinyl, naphthyridinyl, pteridinyl, quinoclidinyl, imidazo[1,2-a]pyridinyl, [1,2,4]triazolo[4,3-a]pyridinyl, and the like. Preferred 9 to 10 membered bicyclic, partially unsaturated or aromatic heterocyclyl include one or more selected from the group consisting of indolyl, isoindolyl, indolinyl, benzofuryl, benzothiophenyl, indazolyl, benzimidazolyl, benzthiazolyl, quinolinyl, 2,3,4-trihydroquinolinyl, isoquinolinyl, quinolizinyl, quinazolinyl, imidazo[1,2-a]pyridinyl and [1,2,4]triazolo[4,3-a]pyridinyl.

As used herein, unless otherwise noted, the term "nitrogen containing" when used in describing a heteroaryl or heterocyclyl ring structure means that said referenced heteroaryl or heterocyclyl ring structure contains at least one N heteroatom as part of the ring structure.

When a particular group is "substituted" (e.g., $C_{X-Y}$alkyl, $C_{X-Y}$cycloalkyl, aryl, heteroaryl, heterocyclyl, etc.), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

As used herein, the notation "*" means the presence of a stereogenic center.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

Furthermore, it is intended that within the scope of the present invention, any element, in particular when mentioned in relation to a compound of formula (I), shall comprise all isotopes and isotopic mixtures of said element, either naturally occurring or synthetically produced, either with natural abundance or in an isotopically enriched form. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$. The isotopes may be radioactive or non-radioactive. Radiolabelled compounds of formula (I) may comprise a radioactive isotope selected from the group of $^3H$, $^{11}C$, $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^3H$, $^{11}C$ and $^{18}F$.

Unless otherwise denoted through use of a "-" symbol, under standard nomenclature used throughout this disclosure, the terminal portion of the designated side chain is described first, followed by the adjacent functionality toward the point of attachment. Thus, for example, a "phenylC$_1$-C$_6$alkylaminocarbonylC$_1$-C$_6$alkyl" substituent refers to a group of the formula

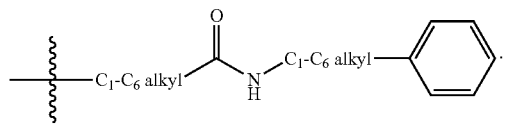

Abbreviations used in the specification, particularly the Schemes and Examples, are as follows:
ATP=Adenosine Triphosphate
BOC or Boc=tert-Butoxycarbonyl
BSA=Bovine Serum Albumin
n-BuLi=n-Butyl Lithium
CDI=Carbonyldiimidazole
CoA=Acetyl Coenzyme A
DCE=Dichloroethane
DCM=Dichloromethane
DIPEA or DIEA=Diisopropylethylamine
DMA=Dimethylamine
DMAP=4-N,N-Dimethylaminopyridine
DME=Dimethyl Ether
DMF=N,N-Dimethylformamide
DMSO=Dimethylsulfoxide
DTT=Dithiothreitol
EDAC or EDCI=1-Ethyl-3-(3-dimethylaminopropyl) carbodiimide
EDTA=Ethylenediaminetetraacetic acid
EGF=Epidermal Growth Factor
Et$_3$N or TEA=Triethylamine
FASN=Fatty Acid Synthase
FBS Fetal Bovine Serum
FCS=Fetal Calf Serum
GFP (gene)=Green Fluorescent Protein
HATU=o-(7-Azabenzotriazol-1-yl)-N,N,N',N'-tetramethyluronium hexafluorophosphate
HBTU=2-(1H-Benzotriazole-1-yl)-1,1,3,3-Tetramethyluronium hexafluorophosphate
HBV=Hepatitis B Virus
HCV=Hepatitis C Virus
HEPES=N-2-Hydroxyethylpiperazine-N'-2-Ethanesulfonic Acid (Buffer)
hFASN=Human fatty Acid Synthase
HDL=High Density Lipoprotein
HPLC=High Performance Liquid Chromatography
K-R (FASN)=Keto-reductase domain (of FASN)
LDL=Low Density Lipoprotein
LRS=Lipid-Reduced Serum
MaCoA=Malonyl Coenzyme A
MEM=Eagle's minimum essential medium
MeOH=Methanol
Mesylate=Methanesulfonate
MOM=Methoxymethyl
MTT=Methyl Thiazolyl Tetrazolium
NADPH=Nicotinamide adenine dinucleotide phosphate
NAFLD=Non-alcoholic Fatty Liver Disease
NASH=Non-alcoholic Steatohepatitis
NMP=1-Methyl-2-pyrrolidinone
NMR=Nuclear Magnetic Resonance
PBS=Phosphate-buffered Saline
PCR=Polymerase Chain Reaction
Pd/C=Palladium on Carbon Catalyst
PdCl$_2$(dppf)=[1,1'-Bis(diphenylphosphino) ferrocene]dichloropalladium(II)
PdCl$_2$(PPh$_3$)$_2$=Bis(triphenylphosphine)palladium(II) dichloride
Pd$_2$(OAc)$_2$=Palladium(II)acetate
Pd$_2$(dba)$_3$=Tris(dibenzylideneacetone)dipalladium(0)
Pd(dppf)=Palladium diphenylphosphinoferrocene
Pd(PPh$_3$)$_4$=Tetrakistriphenylphosphine palladium (0)
PPh$_3$=Triphenylphosphine
RSV=Respiratory Syncytial Virus
±SEM=±Standard Error of Measurement
SPA=Scintillation Proximity Assay
SPE=Solid-phase Extraction
TEA=Triethylamine
TES=Triethylsilane
TFA=Trifluoroacetic Acid
THF=Tetrahydrofuran
THP Tetrahydropyranyl
TIS=Triisopropylsilane
TMS=Trimethylsilyl
Tosylate=p-Toluenesulfonate
Tosyl=p-Toluenesulfonyl
Triflate or OTf=Trifluoromethanesulfonate As used herein, unless otherwise noted, the term "isolated form" means that the compound is present in a form which is separate from any solid mixture with another compound(s), solvent system or biological environment. In an embodiment of the present invention, the compound of formula (I) is present in an isolated form.

As used herein, unless otherwise noted, the term "substantially pure form" means that the mole percent of impurities in the isolated compound is less than about 5 mole percent, preferably less than about 2 mole percent, more preferably, less than about 0.5 mole percent, most preferably, less than about 0.1 mole percent. In an embodiment of the present invention, the compound of formula (I) is present as a substantially pure form.

As used herein, unless otherwise noted, the term "substantially free of a corresponding salt form(s)" when used to described the compound of formula (I) means that mole percent of the corresponding salt form(s) in the isolated base of formula (I) is less than about 5 mole percent, preferably less than about 2 mole percent, more preferably, less than about 0.5 mole percent, most preferably less than about 0.1 mole percent. In an embodiment of the present invention, the compound of formula (I) is present in a form which is substantially free of corresponding salt form(s).

As used herein, unless otherwise noted, the terms "treating", "treatment" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of additional symptoms; (d) delay or avoidance of the development of the disorder or condition; and/or the delay or avoidance of the progression of the disorder or condition.

One skilled in the art will recognize that wherein the present invention is directed to methods of prevention, a subject in need of thereof (i.e. a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (co-morbid) disorders or conditions, genetic testing, and the like.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named.

One skilled in the art will recognize that, where not otherwise specified, the reaction step(s) is performed under suitable conditions, according to known methods, to provide the desired product. One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same of different from each other. For example wherein two steps of a process recite an organic or inorganic base as a reagent, the organic or inorganic base selected for the first step may be the same or different than the organic or inorganic base of the second step. Further, one skilled in the art will recognize that wherein a reaction step of the present invention may be carried out in a variety of solvents or solvent systems, said reaction step may also be carried out in a mixture of the suitable solvents or solvent systems.

To provide a more concise description, some of the quantitative expressions yields herein are not qualified with the term "about". It is understood that whether the term "about" is used explicitly or not, every quantity yield herein is meant to refer to the actual yield value, and it is also meant to refer to the approximation to such yield value that would reasonably be inferred based on the ordinary skill in the art, including approximations due to the experimental and/or measurement conditions for such yield value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

Examples of suitable solvents, bases, reaction temperatures, and other reaction parameters and components are provided in the detailed descriptions which follow herein. One skilled in the art will recognize that the listing of said examples is not intended, and should not be construed, as limiting in any way the invention set forth in the claims which follow thereafter. One skilled in the art will further recognize that wherein a reaction step of the present invention may be carried out in a variety of solvents or solvent systems, said reaction step may also be carried out in a mixture of the suitable solvents or solvent systems.

As used herein, unless otherwise noted, the term "leaving group" means a charged or uncharged atom or group which departs during a substitution or displacement reaction. Suitable examples include, but are not limited to, Br, Cl, I, mesylate, tosylate, triflate, and the like.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

As used herein, unless otherwise noted, the term "nitrogen protecting group" means a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2=CH-CH_2-$, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

As used herein, unless otherwise noted, the term "oxygen protecting group" means a group which may be attached to a oxygen atom to protect said oxygen atom from participating in a reaction and which may be readily removed following the reaction. Suitable oxygen protecting groups include, but are not limited to, acetyl, benzoyl, t-butyl-dimethylsilyl, trimethylsilyl (TMS), methoxymethyl (MOM), tetrahydropyranyl (THP), and the like. Other suitable oxygen protecting groups may be found in texts such as T. W. Greene & P. G. M. Wuts, *Protective Groups in Organic Synthesis*, John Wiley & Sons, 1991.

Where the processes for the preparation of the compounds according to the invention yield rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Additionally, chiral HPLC against a standard may be used to determine percent enantiomeric excess (% ee). The enantiomeric excess may be calculated as follows $$[(Rmoles-Smoles)/(Rmoles+Smoles)] \times 100\%$$

where Rmoles and Smoles are the R and S mole fractions in the mixture such that Rmoles+Smoles=1. The enantiomeric excess may alternatively be calculated from the specific rotations of the desired enantiomer and the prepared mixture as follows:

$$ee=([\alpha\text{-}obs]/[\alpha\text{-max}]) \times 100.$$

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in *Design of Prodrugs*, ed. H. Bundgaard, Elsevier, 1985.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid.

Representative bases which may be used in the preparation of pharmaceutically acceptable salts include, but are not limited to, the following: bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

GENERAL SYNTHETIC SCHEMES

Compounds of formula (I) may be prepared according to the process as described in Scheme 1, below.

Scheme 1

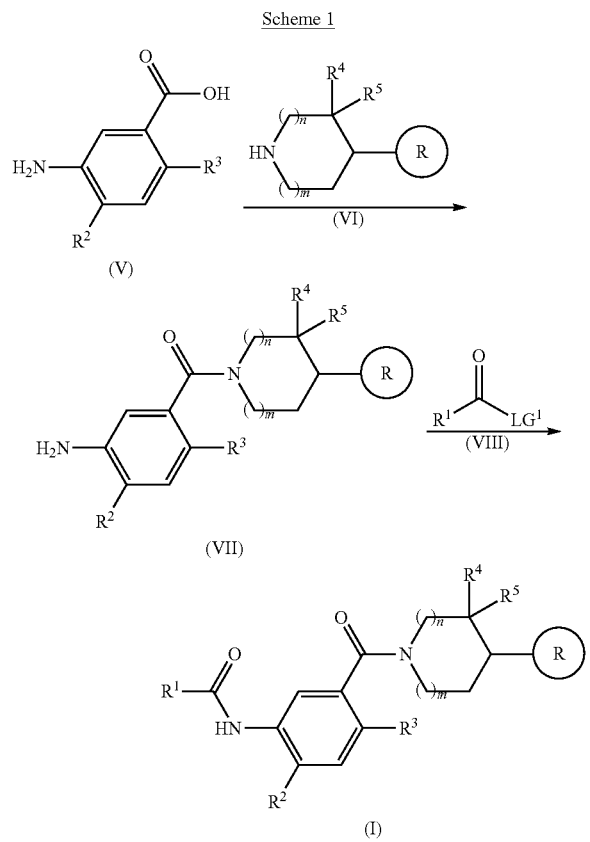

Accordingly, a suitably substituted compound of formula (V), a known compound or compound prepared by known methods, is reacted with a suitably substituted compound of formula (VI), a known compound or compound prepared by known methods; in the presence of a suitably selected coupling reagent such as HATU, HBTU, CDI, EDAC, and the like, in the presence of a suitably selected organic base such as pyridine, TEA, DIPEA, and the like; in a suitably selected organic solvent such as NMP, DMF, DCM, DCE, and the like; to yield the corresponding compound of formula (VII).

The compound of formula (VII) is reacted with a suitably substituted compound of formula (VIII), wherein $LG^1$ is a suitably selected leaving group such as chloro, bromo, and the like, a known compound or compound prepared by known methods; in the presence of a suitably selected organic base such as pyridine, TEA, DIPEA, and the like; optionally in the presence of DMAP, and the like; in a suitably selected solvent such as DCM, DCE, THF, and the like; to yield the corresponding compound of formula (I).

Compounds of formula (I) wherein

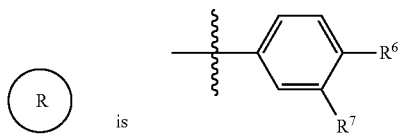

may alternatively be prepared according to the process as described in Scheme 2, below.

Scheme 2

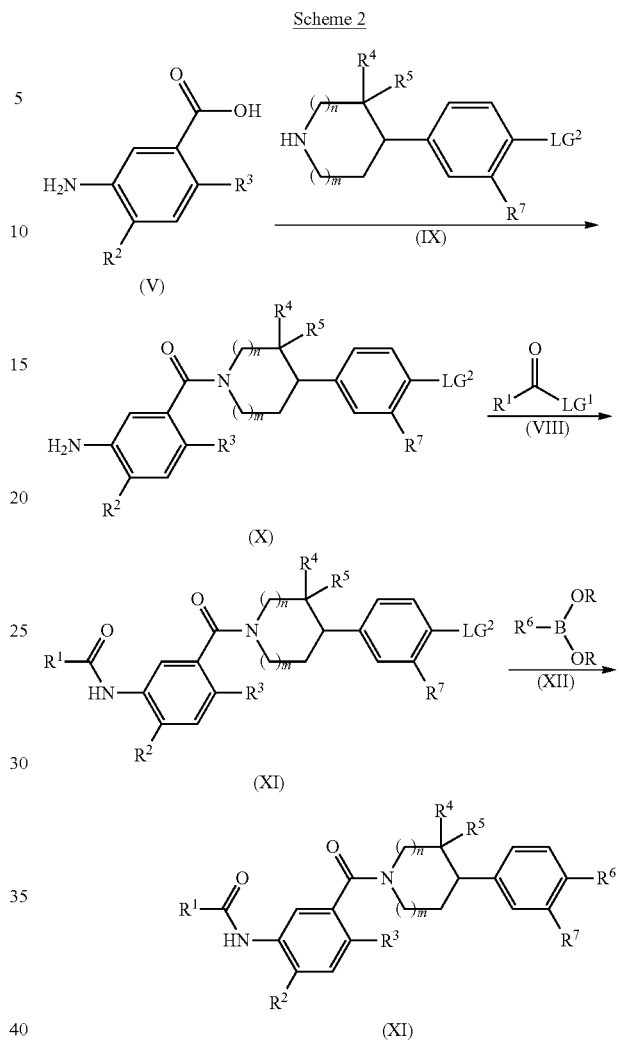

Accordingly, a suitably substituted compound of formula (V), a known compound or compound prepared by known methods, is reacted with a suitably substituted compound of formula (IX), wherein $LG^2$ is a suitably selected leaving group such as bromo, iodo, triflate, and the like, a known compound or compound prepared by known methods; in the presence of a suitably selected coupling reagent such as HATU, HBTU, CDI, EDAC, and the like, in the presence of a suitably selected organic base such as pyridine, TEA, DIPEA, and the like; in a suitably selected organic solvent such as NMP, DMF, DCM, DCE, and the like; to yield the corresponding compound of formula (X).

The compound of formula (X) is reacted with a suitably substituted compound of formula (VIII), wherein $LG^1$ is a suitably selected leaving group such as chloro, bromo, and the like, a known compound or compound prepared by known methods; in the presence of a suitably selected organic base such as pyridine, TEA, DIPEA, and the like; optionally in the presence of DMAP, and the like; in a suitably selected solvent such as DCM, DCE, THF, and the like; to yield the corresponding compound of formula (XI).

The compound of formula (XI) is reacted with a suitably substituted boronic acid, a compound of formula (XII), wherein the two R groups are each H, are each the same $C_{1-2}$alkyl or are taken together as —$C(CH_3)_2$—$C(CH_3)_2$— to form a ring (i.e. to form the

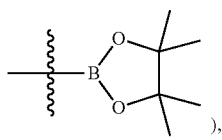 [SMILES: *B1OC(C)(C)C(C)(C)O1]

a known compound or compound prepared by known methods, under Suzuki coupling conditions, more particularly, in the presence of a suitably selected catalysts or catalyst system, such as Pd(PPh$_3$)$_4$, Pd$_2$(dba)$_3$, Pd(dppf), a mixture of Pd(OAc)$_2$ and PPh$_3$, and the like; in the presence of a suitably selected inorganic base such as K$_2$CO$_3$, Cs$_2$CO$_3$, Na$_2$CO$_3$, and the like; in a suitably selected solvent such as DME, 1,4-dioxane, and the like, preferably mixed with water; to yield the corresponding compound of formula (I).

Compounds of formula (I)

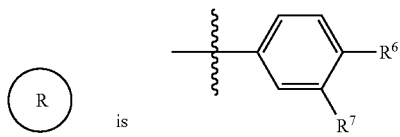

may alternatively be prepared according to the process as described in Scheme 3, below.

Scheme 3

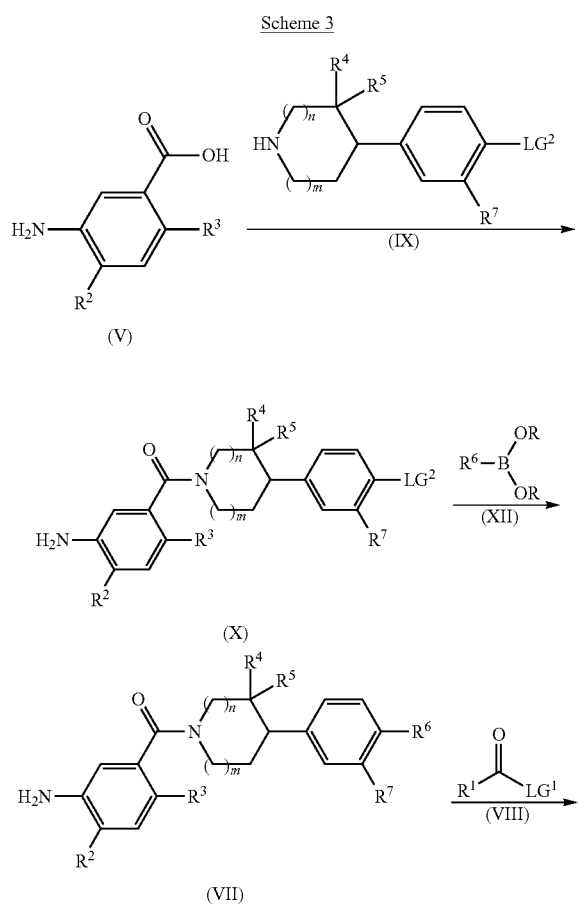

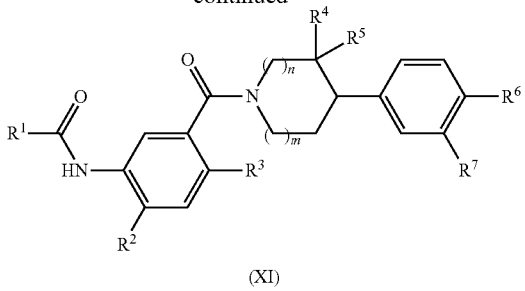

Accordingly, a suitably substituted compound of formula (V), a known compound or compound prepared by known methods, is reacted with a suitably substituted compound of formula (IX), wherein LG$^2$ is a suitably selected leaving group such as bromo, iodo, triflate, and the like, a known compound or compound prepared by known methods; in the presence of a suitably selected coupling reagent such as HATU, HBTU, CDI, EDAC, and the like, in the presence of a suitably selected organic base such as pyridine, TEA, DIPEA, and the like; in a suitably selected organic solvent such as NMP, DMF, DCM, DCE, and the like; to yield the corresponding compound of formula (X).

The compound of formula (X) is reacted with a suitably substituted boronic acid, a compound of formula (XII), wherein the two R groups are each H, are each the same C$_{1-2}$alkyl or are taken together as —C(CH$_3$)$_2$—C(CH$_3$)$_2$— to form a ring (i.e. to form the

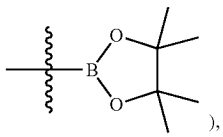

a known compound or compound prepared by known methods, under Suzuki coupling conditions, more particularly, in the presence of a suitably selected catalysts or catalyst system, such as Pd(PPh$_3$)$_4$, Pd$_2$(dba)$_3$, Pd(dppf), a mixture of Pd(OAc)$_2$ and PPh$_3$, and the like; in the presence of a suitably selected inorganic base such as K$_2$CO$_3$, Cs$_2$CO$_3$, Na$_2$CO$_3$, and the like; in a suitably selected solvent such as DME, 1,4-dioxane, and the like, preferably mixed with water; to yield the corresponding compound of formula (VII).

The compound of formula (VII)) is reacted with a suitably substituted compound of formula (VIII), wherein LG$^1$ is a suitably selected leaving group such as chloro, bromo, and the like, a known compound or compound prepared by known methods; in the presence of a suitably selected organic base such as pyridine, TEA, DIPEA, and the like; optionally in the presence of DMAP, and the like; in a suitably selected solvent such as DCM, DCE, THF, and the like; to yield the corresponding compound of formula (I).

One skilled in the art will recognize that compounds of formula (I) wherein

is selected from the group consisting of

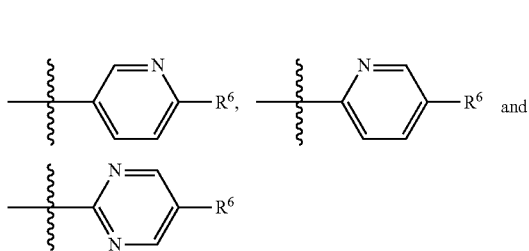

may be similarly prepared according to the procedures as described in Scheme 2 and Scheme 3 above, by selecting and substituting a suitably substituted compound of formula (A1), (A2) or (A3), respectively, (A1)
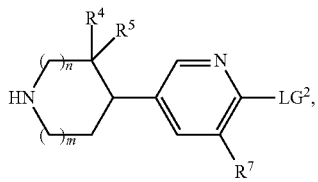

(A2)
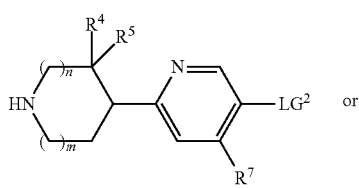
or (A3)
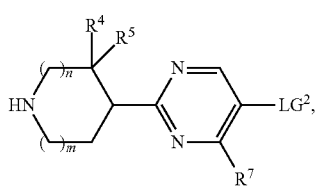

for the compound of formula (IX), and reacting as described in the procedures detailed above.

Compounds of formula (VI)

is of,

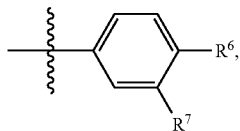

and wherein m is 1 and n is 1 (i.e. wherein

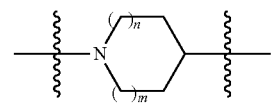

is piperidin-1,4-diyl) may be prepared according to the process as outlined in Scheme 4, below.

Scheme 4

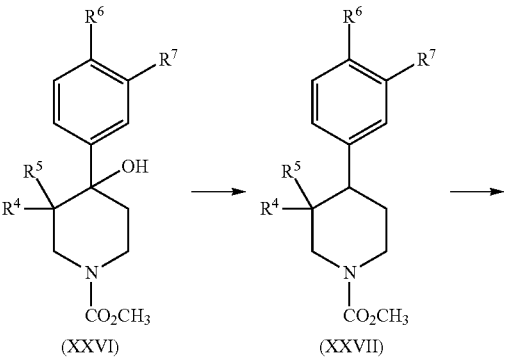

-continued

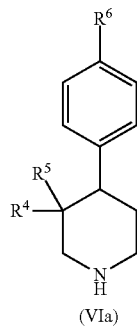

(VIa)

Accordingly, a suitably substituted compound of formula (XX), wherein $PG^1$ is a suitably selected nitrogen protecting group such as benzyl, t-butoxycarbonyl (BOC), and the like, a known compound or compound prepared by known methods, is reacted with a suitably substituted compound of formula (XXI), wherein $LG^3$ is a suitably selected leaving group such as bromo, iodo, $CH_3S(O)_2O$, and the like, a known compound or compound prepared by known methods; in the presence of a suitably selected base such as potassium t-butoxide, sodium t-butoxide, and the like; in a suitably selected organic solvent such as THF, DME, and the like; to yield the corresponding compound of formula (XXII).

The compound of formula (XXII) is reacted with a suitably substituted compound of formula (XXIII), wherein $LG^4$ is a suitably selected leaving group such as bromo, iodo, and the like, a known compound or compound prepared by known methods; in the presence of a suitably selected organometallic reagent, such as n-butyl lithium, t-butyl lithium, and the like; in a suitably selected organic solvent such as THF, DME, diethyl ether, and the like; to yield the corresponding compound of formula (XXIV).

The compound of formula (XXIV) is reacted with a suitably selected de-protecting agent such as 1-chloroethyl-chloroformate, and the like; in the presence of a suitably selected base such as potassium bicarbonate, sodium bicarbonate, and the like; in a suitably selected organic solvent such as DCM, DCE, $CCl_4$, and the like; to yield the corresponding compound of formula (XXV).

The compound of formula (XXV) is reacted with a suitably selected protecting reagent such as methyl chloroformate, ethyl chloroformate, and the like; in the presence of a suitably selected base such as pyridine, triethylamine, and the like; in a suitably selected organic solvent such as DCM, DCE, THF, and the like; to yield the corresponding compound of formula (XXVI).

The compound of formula (XXVI) is reacted with a suitably selected de-protecting agent, such as a mixture of TES and TFA, and the like; at a temperature in the range of from about 60° C. to about 90° C. for example, at about 65° C.; to yield the corresponding compound of formula (XXVII).

The compound of formula (XXVII) is reacted with a suitably selected acid or mixture, such as a mixture of concentrated sulphuric acid and concentrated aqueous HCl, and the like; to yield the corresponding compound of formula (VIb).

One skilled in the art will recognize that compounds of formula (VI) wherein n is 0 and m is 1 or n is 1 and m is 0, such that

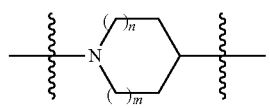

is pyrrolidin-1,3-diyl, may be similarly prepared according to the procedure as outlined in Scheme 2, above by selecting and substituting, a suitably substituted compound of formula (A4)

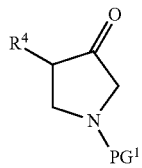

(A4)

for the compound of formula (XX) and reacting as described above.

One skilled in the art will recognize that compounds of formula (VIb)

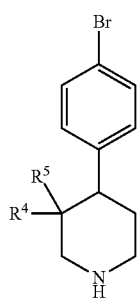

(VIb)

(compounds of formula (VI) wherein

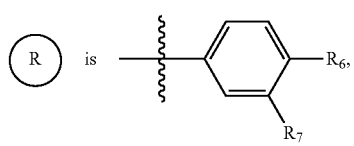

wherein m is 1 and n is 1 (i.e. wherein

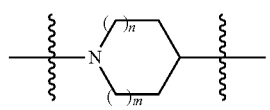

is piperidin-1,3-diyl), wherein $R^7$ is hydrogen and wherein $R^6$ is bromo may be similarly prepared according to the procedure as described in Scheme 4 above, by substituting a compound of formula (XXVIII)

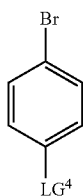

(XXVIII)

for the compound of formula (XXIII) and reacting as described therein.

Compounds of formula (VIa) may alternatively be prepared according to the process as outlined in Scheme 5, below

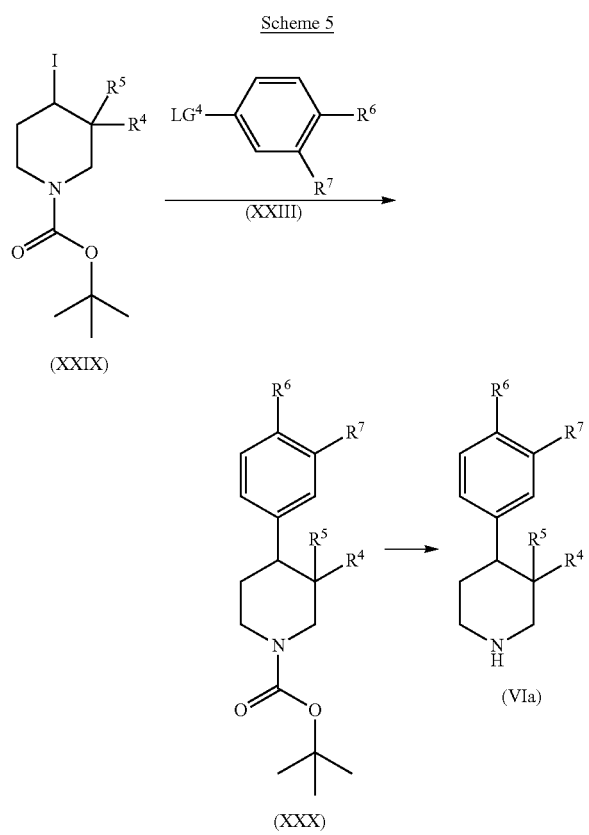

Accordingly, a suitably substituted compound of formula (XXIX), a known compound or compound prepared by known methods, is reacted with a suitably substituted compound of formula (XXIII), wherein LG4 is a suitably selected leaving group such as bromo, iodo, and the like, a known compound or compound prepared by known methods; in the presence of activated zinc (prepared for example by suspending zinc dust in DMA, under a nitrogen atmosphere, and reacted with 1,2-dibromomethane; with heating to a temperature of 60-70° C.; followed by cooling to room temperature); under coupling conditions, more particularly, in the presence of a suitably selected catalysts or catalyst system, such as copper(I) iodide and Pd(dppf)Cl$_2$.CH$_2$Cl$_2$; in a suitably selected organic solvent such as DME, DMF, DMA, and the like; to yield the corresponding compound of formula (XXX).

The compound of formula (XXX) is reacted with a suitably selected de-protecting agent such as TFA, HCl, and the like; in a suitably selected organic solvent such as DCM, DCE, and the like; to yield the corresponding compound of formula (VIa).

PHARMACEUTICAL COMPOSITIONS

The present invention further comprises pharmaceutical compositions containing one or more compounds of formula (I) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 mg to about 1000 mg or any amount or range therein, and may be yieldn at a dosage of from about 0.01 mg/kg/day to about 300 mg/kg/day, or any amount or range therein, preferably from about 0.1 mg/kg/day to about 100 mg/kg/day, or any amount or range therein, preferably from about 0.50 mg/kg/day to about 50 mg/kg/day, or any amount or range therein, preferably from about 0.75 mg/kg/day to about 15 mg/kg/day, or any amount or range therein, preferably from about 1.0 mg/kg/day to about 7.5 mg/kg/day, or any amount or range therein, preferably from about 1.5 mg/kg/day to about 5.0 mg/kg/day, or any amount or range therein. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.01 mg to about 1,000 mg, or any amount or range therein, of the active ingredient of the present invention. The tablets or pills of the novel composition can be coated or otherwise compounded to provide a dosage form yielding the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating disorders described in the present invention may also be carried out using a pharmaceutical composition comprising any of the compounds as defined herein and a pharmaceutically acceptable carrier. The pharmaceutical composition may contain between about 0.01 mg and about 1000 mg of the compound, or any amount or range therein; preferably from about 1.0 mg to about 500 mg of the compound, or any amount or range therein, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methylcellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications, including *Pharmaceutical Dosage Forms: Tablets, Second Edition,*

Revised and Expanded, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of this invention may be administered in any of the foregoing compositions and according to dosage regimens established in the art whenever treatment of disorders mediated by inhibition of fatty acid synthase (FASN) enzyme, as described herein, is required.

The daily dosage of the products may be varied over a wide range from about 0.01 mg to about 1,000 mg per adult human per day, or any amount or range therein. For oral administration, the compositions are preferably provided in the form of tablets containing about 0.01, 0.05, 0.1, 0.5, 1.0, 2.5, 5.0, 10.0, 15.0, 25.0, 50.0, 100, 150, 200, 250, 500 and 1000 milligrams of the active ingredient for the symptomatic adjustment of the dosage to the patient to be treated. An effective amount of the drug is ordinarily supplied at a dosage level of from about 0.01 mg/kg to about 300 mg/kg of body weight per day, or any amount or range therein. Preferably, the range is from about 0.5 to about 50.0 mg/kg of body weight per day, or any amount or range therein. More preferably, from about 0.75 to about 15.0 mg/kg of body weight per day, or any amount or range therein. More preferably, from about 1.0 to about 7.5 mg/kg of body weight per day, or any amount or range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Example 1

Compound #11

N-(5-(4-(4-(1H-imidazol-1-yl)phenyl)piperidine-1-carbonyl)-2-methylphenyl)-6-chloronicotinamide

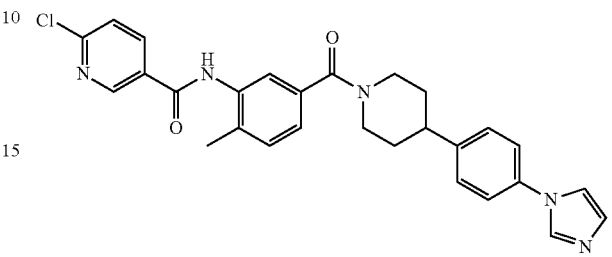

Step A: 4-Iodo-piperidine-1-carboxylic acid tert-butyl ester

A 2-necks round-bottom flask equipped with a stirring bar, addition funnel and a nitrogen inlet, was charged with 4-hydroxy-piperidine-1-carboxylic acid tert-butyl ester (25 g, 124 mmol), triphenylphosphine (39.1 g, 149 mmol) and imidazole (10.2 g, 149 mmol) in dry THF (150 ml) and cooled in ice bath under light nitrogen steam. A solution of iodine (37.8 g, 149 mmol) in dry THF (75 ml) was added dropwise from the addition funnel over 30 minutes. The mixture was then allowed to warm up to room temperature overnight with stirring. The mixture was then cooled again in ice bath and diluted with water (100 ml) and 10% $NaHSO_3$ (30 ml) was added. The organics were extracted with heptane (300 ml). The organic layer was dried over $MgSO_4$, then filtered. Most of the THF was removed to induce crystallization of triphenylphosphine oxide, which was removed by filtration. The filtrate was further concentrated to an oil. Filtration over a short column of silica gel eluting with 10% ethyl acetate in heptane yielded a clear oil that crystallized upon standing. $^1$H NMR (300 MHz, $CDCl_3$) δ ppm 1.46 (s, 9H), 2.03 (q, J=5.8 Hz, 4H), 3.24-3.33 (m, 2H), 3.56-3.64 (m, 2H), 4.45 (quint, J=6.0 Hz, 1H). MS m/z 312 $(M+H)^+$ Step B: 4-(4-Imidazol-1-yl-phenyl)-piperidine-1-carboxylic acid tert-butyl ester Zn dust (5.30 g, 81.3 mmol) was suspended in DMA (35 ml) under nitrogen atmosphere and then treated with 1,2-dibromoethane (0.67 ml, 7.8 mmol). The mixture was briefly heated to 60-70° C. and allowed to cool to room temperature (3 times). Chlorotrimethylsilane (0.66 ml, 5.2 mmol) was then added dropwise and the resulting mixture aged for 30 minutes. A solution of 4-iodo-piperidine-1-carboxylic acid tert-butyl ester (20.2 g, 65 mmol) in DMA (35 ml) was then added slowly added at a rate to maintain a temperature <65° C. The exothermic zinc insertion was allowed to cool to room temperature and stirring maintained for 1 hour, to yield a 0.92 M solution of (1-tert-butoxycarbonylpiperidin-4-yl)(iodo)zinc.

A freshly prepared solution of 1-(4-bromophenyl)-1H-imidazole (4.0 g, 17.9 mmol), copper(I) iodide (0.204 g, 1.07 mmol) and $Pd(dppf)Cl_2CH_2Cl_2$ (0.441 g, 0.54 mmol) was then treated with 19 ml of the above solution (17.9 mmol) and mixture heated to 80° C. overnight. The reaction mixture was allowed to cool to room temperature, diluted with ethyl acetate (100 ml) saturated aqueous NH₄Cl, (100 ml), water (50 ml) and stirred for 20 minutes. The mixture was filtered through a pad of CELITE that was further washed with ethyl acetate (2×25 ml). The phases were separated, and aqueous layer extracted once more with ethyl acetate (50 ml). The combined organic layer were washed with brine (2×100 ml), dried over MgSO₄, filtered and concentrated to yield a residue. Purification of the residue over silica gel eluting with a gradient of MeOH in DCM from 0 to 5% yielded 4-(4-imidazol-1-yl-phenyl)-piperidine-1-carboxylic acid tert-butyl ester as beige solid. ¹H NMR (300 MHz, CDCl₃) δ ppm 1.50 (s, 9H), 1.56-1.71 (m, 2H), 1.81-1.91 (m, 2H), 2.67-2.89 (m, 3H), 4.20-4.36 (m, 2H), 7.31 (d, J=8.7 Hz, 1H), 7.34 (br s, 4H), 7.65 (d, J=8.7 Hz, 1H). MS m/z 328 (M+H)⁺

Step C: 4-(4-Imidazol-1-yl-phenyl)-piperidine 4-(4-Imidazol-1-yl-phenyl)-piperidine-1-carboxylic acid tert-butyl ester (4.76 g, 14.5 mmol) was taken up in a stock solution of DCM/TFA/TIS (0.9/0.9/0.2, v/v/v) (35 ml) and stirred at room temperature of 3 hours. The mixture was concentrated under reduced pressure. Residual TFA was removed by co-evaporation with toluene (2×50 ml). The resulting residue was then taken up in DCM (50 ml) and 1M NaOH (250 ml) was added. The organic layer was separated and aqueous phase extracted once more with DCM (50 ml). The combined organic layers were dried over MgSO₄, filtered and concentrated. The resulting residue was purified by column chromatography (silica gel, gradient DCM/MeOH/NH₄OH from 100/0/0 to 90/9/1) to yield 4-(4-imidazol-1-yl-phenyl)-piperidine. ¹H NMR (300 MHz, DMSO-d₆) δ ppm 1.60-1.74 (m, 2H), 1.82-1.92 (m, 2H), 2.63-2.81 (m, 3H), 3.17-3.28 (m, 2H), 7.19 (br s, 1H), 7.26 (br s, 1H), 7.33 (s, 4H), 7.83 (br s, 1H). MS m/z 228 (M+H)⁺

Step D: (3-Amino-4-methyl-phenyl)-[4-(4-imidazol-1-yl-phenyl)-piperidin-1-yl]-methanone A round-bottom flask was charged with 4-(4-imidazol-1-yl-phenyl)-piperidine (1.86 g, 8.18 mmol) and 3-amino-4-methylbenzoic acid (1.24 g, 8.18 mmol). DCM (25 ml) and N,N-diisopropylethylamine (2.78 ml, 16.4 mmol) were added with stirring. Once an homogeneous solution was obtained, O-(benzotriazol-1-yl)-N,N,N'—N'-tetramethyl-uronium hexafluorophosphate (HBTU), (3.72 g, 9.82 mmol) was added. The reaction was stirred overnight at room temperature and then concentrated under reduced pressure. The residue was partitioned between ethyl acetate (75 ml) and 1M Na₂CO₃ (100 ml). The aqueous layer was extracted once more with DCM (75 ml). The combined organic layers were dried over MgSO₄, filtered and solvent removed in vacuo. The resulting residue was purified by column chromatography over silica gel eluting with a gradient of MeOH in DCM from 0 to 5% to yield the product as an amorphous solid. ¹H NMR (300 MHz, DMSO-d₆) δ ppm 1.55-2.09 (m, 4H), 2.18 (s, 3H), 2.78-3.78 (m, 3H), 4.03 (br s, 1H), 4.86 (br s, 1H), 6.72-6.77 (m, 2H), 7.07 (d, J=7.8 Hz, 1H), 7.20 (s, 1H), 7.26 (s, 1H), 7.30-7.37 (m, 4H), 7.84 (s, 1H). MS m/z 361 (M+H)⁺

Step E: N-(5-(4-(4-(1H-imidazol-1-yl)phenyl)piperidine-1-carbonyl)-2-methylphenyl)-6-chloronicotinamide (3-Amino-4-methyl-phenyl)-[4-(4-imidazol-1-yl-phenyl)-piperidin-1-yl]-methanone (0.32 g 0.888 mmol) was dissolved in DCM (5 ml). Pyridine (0.144 ml, 1.77 mmol) was added, followed by 6-chloronicotinoyl chloride (0.172 g, 0.977 mmol). The mixture was stirred overnight and then diluted with DCM (100 ml) and 1M NaOH (50 ml). The organic layer was separated, dried over MgSO₄, filtered and concentrated to dryness. The residue was triturated with acetonitrile to yield the title compound as a white solid.

¹H NMR (300 MHz, DMSO-d₆) δ ppm 1.55-1.74 (m, 2H), 1.82 (br. s., 2H), 2.29 (s, 3H), 2.76-3.02 (m, 2H), 3.06-3.27 (m, 1H), 3.80 (br. s., 1H), 4.64 (br. s., 1H), 7.09 (s, 1H), 7.24-7.32 (m, 1H), 7.33-7.51 (m, 5H), 7.57 (d, J=8.4 Hz, 2H), 7.65-7.78 (m, 2H), 8.21 (s, 1H), 8.36 (dd, J=8.2, 2.1 Hz, 1H), 8.97 (s, 1H), 10.22 (s, 1H). MS m/z 501 (M+H)⁺

Example 2

Compound #15

N-(5-(4-(4-(1H-imidazol-1-yl)phenyl)piperidine-1-carbonyl)-2-methylphenyl)-6-(isopropylamino)nicotinamide

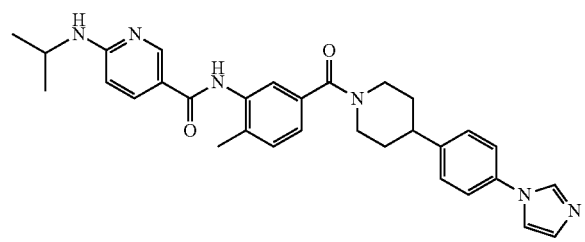 [SMILES: Cc1ccc(C(=O)N2CCC(c3ccc(-n4ccnc4)cc3)CC2)cc1NC(=O)c1ccc(NC(C)C)nc1]

N-(5-(4-(4-(1H-imidazol-1-yl)phenyl)piperidine-1-carbonyl)-2-methylphenyl)-6-chloronicotinamide (0.150 g, 0.300 mmol) and isopropylamine (1.5 ml, 17.51 mmol) were combined in 1,4-dioxane (2.5 ml) in a sealed tube. The mixture was heated to 150° C. for 16 hours and then allowed to cool to room temperature. The reaction mixture was diluted with DCM (100 ml) and washed with 1M NaOH (50 ml). The organic layer was dried over MgSO₄, filtered and concentrated to dryness. The resulting residue was purified by column chromatography over silica gel eluting with a gradient of MeOH in DCM from 0 to 5% to yield the title compound, which was then recrystallized from acetonitrile.

¹H NMR (300 MHz, CHLOROFORM-d) δ ppm 1.21 (d, J=6.5 Hz, 6H), 1.67 (br. s., 1H), 1.75-2.01 (m, 2H), 2.27 (s, 3H), 2.63-2.93 (m, 2H), 3.11 (br. s., 1H), 3.84-4.14 (m, 2H), 4.76 (d, J=7.8 Hz, 2H), 6.34 (d, J=8.8 Hz, 1H), 7.07-7.16 (m, 2H), 7.16-7.22 (m, 3H), 7.27 (s, 4H), 7.70 (s, 1H), 7.76 (s, 1H), 7.85-7.96 (m, 2H), 8.59 (d, J=2.2 Hz, 1H). MS m/z 523 (M+H)⁺

Example 3

Compound #111

(±)-6-chloro-N-(2-methyl-5-((3S,4S)-3-methyl-4-(4-(1-methyl-1H-pyrazol-5-yl)phenyl)piperidine-1-carbonyl)phenyl)nicotinamide

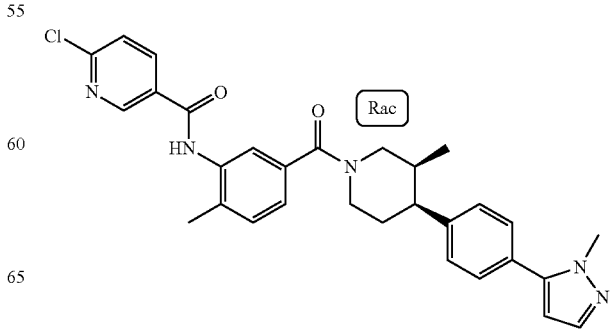

Step A: 1-Benzyl-4-(4-bromo-phenyl)-3-methyl-piperidin-4-ol 1,4-Dibromobenzene (22.3 g, 94.4 mmol) was dissolved in dry THF (450 ml) in a two necks round-bottom flask equipped with a stirring bar, a septum, and an addition funnel with nitrogen inlet. The solution was cooled to −78° C., and n-BuLi (1.6 M, 55.3 ml, 94.4 mmol) was added dropwise via syringe. The resulting milky suspension was stirred for 1 hour at the same temperature, before a solution of 1-benzyl-3-methyl-4-piperidinone (16 g, 78.7 mmol) in THF (200 ml) was slowly added from the addition funnel. The clear solution was then stirred for 3 hours allowing the temperature to rise to ambient. The reaction was quenched with saturated $NH_4Cl$ (400 ml) and water (120 ml). The organics were extracted with ethyl acetate (2×600 ml). The combined organic layers were washed with brine (300 ml), dried over $MgSO_4$, filtered and concentrated to yield a viscous oil. The oil was purified over silica gel eluting with a gradient of ethyl acetate in heptane from 0 to 40% to yield the title compound as a colorless viscous oil. $^1H$ NMR (300 MHz, $CDCl_3$) δ ppm 0.60 (d, J=6.5 Hz, 3H), 1.64-1.74 (m, 1H), 2.05-2.35 (m, 3H), 2.36-3.51 (m, 1H), 2.72-2.90 (m, 2H), 3.62 (s, 2H), 7.28-7.43 (m, 7H), (d, J=8.6 Hz, 2H). MS m/z 360 $(M+H)^+$

Step B: 4-(4-Bromo-phenyl)-3-methyl-piperidin-4-ol hydrochloride

1-Chloroethyl-chloroformate (16.1 ml, 149.8 mmol) was added to a mixture of 1-benzyl-4-(4-bromo-phenyl)-3-methyl-piperidin-4-ol (27 g, 74.9 mmol) and potassium bicarbonate (75 g, 749 mmol) in DCM (400 ml) at 0° C. The reaction was stirred for 15 minutes with ice cooling, and then allowed to come to room temperature and finally refluxed for 1 hour. The mixture was then allowed to cool to room temperature and insolubles filtered off. The filtrate was concentrated under reduced pressure and residue refluxed in MeOH (400 ml) for 30 minutes. The solution was concentrated to dryness. The residue was triturated in diethyl ether (200 ml) to yield a powdered solid. The hydrochloride salt was filtered and washed with diethyl ether (3×50 ml) and dried under vacuum. MS m/z 270 $(M+H)^+$

Step C: 4-(4-Bromo-phenyl)-4-hydroxy-3-methyl-piperidine-1-carboxylic acid methyl ester 4-(4-Bromo-phenyl)-3-methyl-piperidin-4-ol hydrochloride (20.7 g, 67.5 mmol) and pyridine (70 ml) were combined in DCM (210 ml) and cooled in ice bath under nitrogen steam. Methyl chloroformate (5.4 ml, 70 mmol) was added dropwise via syringe and then mixture stirred overnight allowing the temperature come to ambient. The reaction was then concentrated onto the rotary evaporator. The residue was partitioned between ethyl acetate (600 ml) and 1M HCl (300 ml). The aqueous layer was extracted once more with ethyl acetate (300 ml). The combined organic layers were washed with water (250 ml), dried over $MgSO_4$, filtered and concentrated to dryness. The residue was purified by column chromatography over silica gel eluting with a gradient of ethyl acetate in heptane from 0 to 75% yielding product. MS m/z 328 $(M+H)^+$

Step D: 4-(4-Bromo-phenyl)-3-methyl-piperidine-1-carboxylic acid methyl ester 4-(4-Bromo-phenyl)-4-hydroxy-3-methyl-piperidine-1-carboxylic acid methyl ester (18.6 g, 56.7 mmol) was added to a mixture of triethylsilane (22.9 ml, 141.7 mmol) in TFA (170 ml). The solution was heated at 60° C. for 3 hours and then concentrated under reduced pressure. The residue was taken twice in toluene (200 ml) and again concentrated to remove residual TFA. The residue was purified by column chromatography over silica gel eluting with a gradient of ethyl acetate in heptane from 0 to 35% to yield a yellow oil. MS m/z 312 $(M+H)^+$

Step E: 4-(4-Bromo-phenyl)-3-methyl-piperidine

The carbamate 4-(4-bromo-phenyl)-3-methyl-piperidine-1-carboxylic acid methyl ester (17.6 g, 56.4 mmol) was taken up in a mixture of concentrated sulphuric acid (150 ml) and 6M HCl (150 ml) and heated at 120° C. for 48 hours. The mixture was allowed to cool to room temperature and poured in ice water (400 g). Solid NaOH was added with ice cooling till pH 8. The aqueous solution was extracted with ethyl acetate (2×500 ml). The combined organic layers were dried over $MgSO_4$, filtered and concentrated to yield the product as a semi solid. MS m/z 254 $(M+H)^+$

Step F: (±)-1-Benzyl-(3S,4S)-4-(4-bromo-phenyl)-3-methyl-piperidine and (±)-1-Benzyl-(3R,4S)-4-(4-bromo-phenyl)-3-methyl-piperidine 4-(4-Bromo-phenyl)-3-methyl-piperidine (13.2 g, 51.9 mmol) and benzaldehyde (5.25 ml, 51.9 mmol) were mixed in DCE (300 ml) with stirring. After 15 minutes, sodium triacetoxyborohydride (16.5 g, 78 mmol) was introduced portion-wise over 30 minutes. The reaction was then continued overnight and then quenched with 1M NaOH (200 ml). The aqueous phase was extracted with DCM (3×300 ml). The organic extracts were combined, dried over $MgSO_4$, filtered and concentrated to an oily residue. Column chromatography over silica gel eluting with a gradient of ethyl acetate in heptane from 0 to 15%, allowed the separation of (±)-1-benzyl-(3S,4S)-4-(4-bromo-phenyl)-3-methyl-piperidine as white solid from its isomer (±)-1-benzyl-(3R,4S)-4-(4-bromo-phenyl)-3-methyl-piperidine.

(±)-1-Benzyl-(3S,4S)-4-(4-bromo-phenyl)-3-methyl-piperidine: $^1H$ NMR (300 MHz, $CDCl_3$) δ ppm 0.70 (d, J=7.0 Hz, 3H), 1.49-1.60 (m, 1H), 1.93-2.12 (m, 3H), 2.17-2.29 (m, 1H), 2.66-2.83 (m, 1H), 2.88-3.04 (m, 2H), 3.40 (d, J=13.8 Hz, 1H), 3.53, (d, J=13.4 Hz, 1H), 7.15 (d, J=8.4 Hz, 2H), 7.22-7.26 (m, 1H), 7.29-7.35 (m, 4H), 7.47 (d, J=8.4 Hz, 2H). MS m/z 344 $(M+H)^+$ (±)-1-Benzyl-(3R,4S)-4-(4-bromo-phenyl)-3-methyl-piperidine: $^1H$ NMR (300 MHz, $CDCl_3$) δ ppm 0.55 (d, J=6.2 Hz, 3H), 1.59-1.83 (m, 4H), 1.95-2.12 (m, 2H), 2.83-2.95 (m, 2H), 3.49 (s, 2H), 7.18 (d, J=8.4 Hz, 2H), 7.22-7.29 (m, 1H), 7.31-7.37 (m, 4H), 7.46 (d, J=8.4 Hz, 2H). MS m/z 344 $(M+H)^+$

Step G: (±)-(3S,4S)-4-(4-Bromo-phenyl)-3-methyl-piperidine hydrochloride

1-Chloroethyl-chloroformate (11.1 ml, 102.8 mmol) was added to a mixture of 1-benzyl-cis-4-(4-bromo-phenyl)-3-methyl-piperidine (11.8 g, 34.3 mmol) and potassium bicarbonate (41.2 g, 411 mmol) in DCM (140 ml) at room temperature. The mixture was refluxed for 1 hour and then allowed to cool to room temperature. The insolubles were filtered off. The filtrate was concentrated under reduced pressure and residue refluxed in MeOH (140 ml) for 30 minutes. The solution was again concentrated to dryness.

The residue was triturated in diethyl ether (100 ml) to yield (after filtration and diethyl ether washes), the hydrochloride salt as a powder. $^1$H NMR (300 MHz, DMSO-$d_6$) δ ppm 0.73 (d, J=7.3 Hz, 3H), 1.71-1.85 (m, 1H), 2.02-2.16 (m, 1H), 2.20-2.32 (m, 1H), 2.89-3.03 (m, 1H), 3.06-3.16 (m, 1H), 3.19 (br s, 2H), 3.27-3.34 (m, 1H), 7.17 (d, J=8.4 Hz, 2H), 7.53 (d, J=8.4 Hz, 2H), 8.84 (br s, 2H). MS m/z 254 (M+H)$^+$ Step I: (±)-(3-Amino-4-methyl-phenyl)-[(3S,4S)-4-(4-bromo-phenyl)-3-methyl-piperidin-1-yl]-methanone A round-bottom flask was charged with (±)-(3S,4S)-4-(4-bromo-phenyl)-3-methyl-piperidine hydrochloride (0.8 g, 2.75 mmol) and 3-amino-4-methylbenzoic acid (0.416 g, 2.75 mmol). DCM (20 ml) and N,N-diisopropylethylamine (1.44 ml, 8.25 mmol) were added with stirring. Once an homogenous solution was obtained, O-(benzotriazol-1-yl)-N,N,N',N'-tetramethyluronium hexafluorophosphate (HBTU), (1.25 g, 2.75 mmol) was added. The reaction was stirred for 1 hour at room temperature. The mixture was diluted with ethyl acetate (110 ml) and washed successively with 1M Na$_2$CO$_3$ (80 ml), water (80 ml) and brine (60 ml). The organic layer was dried over MgSO$_4$, filtered and solvent removed in vacuo. The residue was purified by column chromatography over silica gel eluting with a gradient of MeOH in DCM from 0 to 5%. The product was then recrystallized from acetonitrile to yield a white solid. MS m/z 387 (M+H)$^+$ Step J: (±)-(3-Amino-4-methyl-phenyl)-{(3S,4S)-3-methyl-4-[4-(2-methyl-2H-pyrazol-3-yl)-phenyl]-piperidin-1-yl}-methanone (±)-(3-Amino-4-methyl-phenyl)-[(3S,4S)-4-(4-bromo-phenyl)-3-methyl-piperidin-1-yl]-methanone (0.883 g, 2.28 mmol), was dissolved in 1,4-dioxane (15 ml) and solution bubbled with nitrogen. While maintaining the nitrogen bubbling, 1M Na$_2$CO$_3$ (4.56 ml, 4.56 mmol) was added followed by 1-methyl-1H-pyrazole-5-boronic acid pinacol ester (0.948 g, 4.56.mmol) and PdCl$_2$(PPh$_3$)$_2$ (0.08 g, 0.11 mmol). The reaction mixture was then refluxed under nitrogen atmosphere for 2 hours and then allowed to cool to room temperature. Water (70 ml) was added, and organics extracted with ethyl acetate (120 ml). The organic layer was dried over MgSO$_4$ and concentrated to a brown oily residue. The product, (±)-(3-amino-4-methyl-phenyl)-{(3S,4S)-3-methyl-4-[4-(2-methyl-2H-pyrazol-3-yl)-phenyl]-piperidin-1-yl}-methanone was obtained by column chromatography over silica gel eluting with a gradient of MeOH in DCM from 0 to 4%. $^1$H NMR (300 MHz, DMSO-$d_6$) δ ppm 0.60 (br s, 3H), 1.51-1.73 (m, 1H), 1.97-2.16 (m, 2H), 2.08 (s, 3H), 2.76-3.20 (m, 3H), 3.54-3.96 (m, 1H), 3.84 (s, 3H), 4.36-4.77 (m, 1H), 5.02 (s, 2H), 6.38 (d, J=1.8 Hz, 1H), 6.48 (br s, 1H), 6.64 (br s, 1H), 6.97 (d, J=8.0 Hz, 1H), 7.33 (d, J=7.9 Hz, 2H), 7.45 (d, J=1.8 Hz, 1H), 7.48 (d, J=8.0 Hz, 2H). MS m/z 389 (M+H)$^+$ Step L: (±)-6-chloro-N-(2-methyl-5-((3S,4S)-3-methyl-4-(4-(1-methyl-1H-pyrazol-5-yl)phenyl)piperidine-1-carbonyl)phenyl)nicotinamide (±)-(3-Amino-4-methyl-phenyl)-{(3S,4S)-3-methyl-4-[4-(2-methyl-2H-pyrazol-3-yl)-phenyl]-piperidin-1-yl}-methanone (0.25 g 0.64 mmol) was dissolved in DCM (5 ml). Pyridine (0.077 ml, 0.96 mmol) was added, followed by 6-chloronicotinoyl chloride (0.113 g, 0.64 mmol). The mixture was stirred for 2 hours and then diluted with DCM (50 ml) and 1M Na$_2$CO$_3$ (30 ml). The organic layer was separated, washed with water (30 ml), brine (30 ml), dried over MgSO$_4$, filtered and concentrated to dryness. The residue was crystallized in acetonitrile to yield the title compound as a white solid.

$^1$H NMR (300 MHz, DMSO-$d_6$) δ ppm 0.55-0.69 (m, 3H), 1.65 (br. s., 1H), 2.04-2.20 (m, 2H), 2.30 (s, 3H), 2.90 (br. s., 1H), 3.16 (d, J=12.5 Hz, 2H), 3.61 (br. s., 1H), 3.75 (s, 3H), 4.51-4.70 (m, 1H), 6.38 (d, J=1.8 Hz, 1H), 7.25 (br. s., 1H), 7.30-7.41 (m, 3H), 7.42-7.53 (m, 4H), 7.73 (d, J=8.2 Hz, 1H), 8.38 (d, J=7.3 Hz, 1H), 8.99 (br. s., 1H), 10.23 (s, 1H). MS m/z 528 (M+H)$^+$ Example 4

Compound #76

(±)-6-(Isopropylamino)-N-(2-methyl-5-((3S,4S)-3-methyl-4-(4-(1-methyl-1H-pyrazol-5-yl)phenyl)piperidine-1-carbonyl)phenyl)nicotinamide

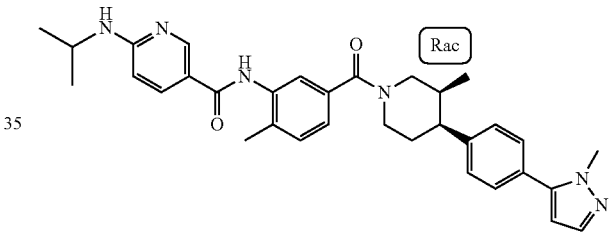

(±)-6-chloro-N-(2-methyl-5-((3S,4S)-3-methyl-4-(4-(1-methyl-1H-pyrazol-5-yl)phenyl)piperidine-1-carbonyl)phenyl)nicotinamide (0.130 g, 0.24 mmol) and isopropylamine (0.21 ml, 2.4 mmol) were combined in 1,4-dioxane (2 ml) in a sealed tube. The mixture was heated to 150° C. for 16 hours and then allowed to cool to room temperature. The reaction mixture was diluted with ethyl acetate (80 ml) and washed with 1M Na$_2$CO$_3$ (50 ml). The organic layer was washed with water (40 ml), brine (40 ml), dried over MgSO$_4$, filtered and concentrated to dryness. The residue was purified by column chromatography over silica gel eluting with a gradient of MeOH in DCM from 0 to 5%. The product was then recrystallized from acetonitrile.

$^1$H NMR (300 MHz, DMSO-$d_6$) δ ppm 0.56-0.68 (m, 3H), 1.17 (d, J=6.5 Hz, 6H), 1.64 (br. s., 1H), 1.96-2.19 (m, 2H), 2.27 (s, 3H), 3.04-3.26 (m, 2H), 3.61 (br. s., 1H), 3.84 (s, 3H), 4.01-4.21 (m, 1H), 4.69 (br. s., 1H), 6.38 (d, J=1.9 Hz, 1H), 6.49 (d, J=8.9 Hz, 1H), 7.06 (d, J=7.6 Hz, 1H), 7.19 (br. s., 1H), 7.33 (d, J=7.8 Hz, 3H), 7.39-7.53 (m, 4H), 7.85-7.97 (m, 1H), 8.61-8.73 (m, 1H), 9.59 (br. s., 1H). MS m/z 551 (M+H)$^+$

Example 5

Compound #110

(±)-6-Chloro-N-(2-methyl-5-((3R,4S)-3-methyl-4-(4-(1-methyl-1H-pyrazol-5-yl)phenyl)piperidine-1-carbonyl)phenyl)nicotinamide

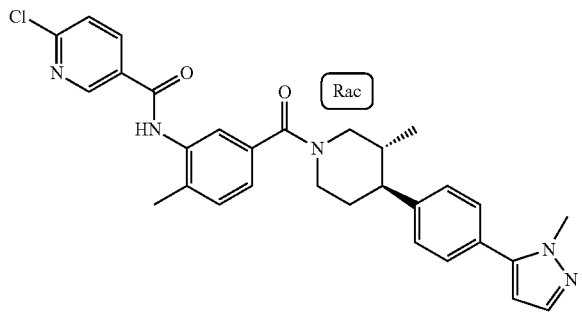 [SMILES: Cc1ccc(C(=O)N2CC[C@H](c3ccc(-c4ccnn4C)cc3)[C@@H](C)C2)cc1NC(=O)c1ccc(Cl)nc1]

Step A: (±)-(3R,4S)-4-(4-bromo-phenyl)-3-methyl-piperidine hydrochloride

1-Chloroethyl-chloroformate (2.07 ml, 19.2 mmol) was added to a mixture of (±)-1-benzyl-(3R,4S)-4-(4-bromo-phenyl)-3-methyl-piperidine (2.2 g, 6.38 mmol) and potassium bicarbonate (7.66 g, 76.5 mmol) in DCM (30 ml) at room temperature. The mixture was refluxed for 1 hour and then allowed to cool to room temperature. The insolubles were filtered off. The filtrate was concentrated under reduced pressure and residue refluxed in MeOH (30 ml) for 30 minutes. The solution was again concentrated to dryness. The residue was triturated in diethyl ether (30 ml) to yield (after filtration and washes with diethyl ether), the hydrochloride salt as a powder. $^1$H NMR (300 MHz, DMSO-$d_6$) δ ppm 0.63 (d, J=6.5 Hz, 3H), 1.72-1.99 (m, 2H), 2.01-2.15 (m, 1H), 2.44 (dt, J=11.4, 3.9 Hz, 1H), 2.56-2.72 (m, 1H), 2.84-3.00 (m, 1H), 7.15 (d, J=8.4 Hz, 2H), 7.54 (d, J=8.4 Hz, 2H), 9.08 (br s, 2H). MS m/z 254 (M+H)$^+$

Step B: (±)-(3-Amino-4-methyl-phenyl)-[(3R,4S)-4-(4-bromo-phenyl)-3-methyl-piperidin-1-yl]-methanone A round-bottom flask was charged with (±)-(3R,4S)-4-(4-bromo-phenyl)-3-methyl-piperidine hydrochloride (0.5 g, 1.72 mmol) and 3-amino-4-methylbenzoic acid (0.26 g, 1.72 mmol). DCM (15 ml) and N,N-diisopropylethylamine (0.9 ml, 5.29 mmol) were added with stirring. Once an homogenous solution was obtained, O-(benzotriazol-1-yl)-N,N,N'—N'-tetramethyluronium hexafluorophosphate (HBTU), (0.848 g, 2.23 mmol) was added. The reaction was stirred for 1 hour at room temperature. The mixture was diluted with ethyl acetate (80 ml) and washed successively with 1M Na$_2$CO$_3$ (50 ml), water (50 ml) and brine (40 ml). The organic layer was dried over MgSO$_4$, filtered and solvent removed in vacuo. The residue was purified by column chromatography over silica gel eluting with a gradient of MeOH in DCM from 0 to 5% to yield the title product. MS m/z 387 (M+H)$^+$

Step C: (±)-(3-Amino-4-methyl-phenyl)-{(3R,4S)-3-methyl-4-[4-(2-methyl-2H-pyrazol-3-yl)-phenyl]-piperidin-1-yl}-methanone (±)-(3-Amino-4-methyl-phenyl)-[(3R,4S)-4-(4-bromo-phenyl)-3-methyl-piperidin-1-yl]-methanone (0.527 g, 1.36 mmol), was dissolved in 1,4-dioxane (10 ml) and solution bubbled with nitrogen. While maintaining the nitrogen bubbling, 1M Na$_2$CO$_3$ (2.72 ml, 2.72 mmol) was added followed by 1-methyl-1H-pyrazole-5-boronic acid pinacol ester (0.566 g, 2.72.mmol) and PdCl$_2$(PPh$_3$)$_2$ (0.065 g, 0.09 mmol). The reaction mixture was then refluxed under nitrogen atmosphere for 2 hours and then allowed to cool to room temperature. Water (60 ml) was added, and organics extracted with ethyl acetate (100 ml). The organic layer was dried over MgSO$_4$, filtered and concentrated to a brown oily residue. (±)-(3-Amino-4-methyl-phenyl)-{(3R,4S)-3-methyl-4-[4-(2-methyl-2H-pyrazol-3-yl)-phenyl]-piperidin-1-yl}-methanone was obtained by column chromatography over silica gel eluting with a gradient of MeOH in DCM from 0 to 4%. $^1$H NMR (300 MHz, DMSO-$d_6$) δ ppm 0.65 (br s, 3H), 1.53-1.89 (m, 3H), 2.06 (s, 3H), 2.45 (dt, J=11.0, 3.9 Hz, 1H), 2.60-3.25 (m, 2H), 3.65-3.91 (m, 1H), 3.84 (s, 3H), 4.33-4.80 (m, 1H), 5.01 (s, 2H), 6.38 (d, J=1.8 Hz, 1H), 6.52 (dd, J=7.5, 1.3 Hz, 1H), 6.66 (d, J=1.3 Hz, 1H), 6.96 (d, J=7.5 Hz, 1H), 7.36 (d, J=8.4 Hz, 2H), 7.44-7.48 (m, 3H). MS m/z 389 (M+H)$^+$

Step D: (±)-6-chloro-N-(2-methyl-5-((3R,4S)-3-methyl-4-(4-(1-methyl-1H-pyrazol-5-yl)phenyl)piperidine-1-carbonyl)phenyl)nicotinamide (±)-(3-Amino-4-methyl-phenyl)-{(3R,4S)-3-methyl-4-[4-(2-methyl-2H-pyrazol-3-yl)-phenyl]-piperidin-1-yl}-methanone (0.16 g 0.41 mmol) was dissolved in DCM (3 ml). Pyridine (0.06 ml, 0.61 mmol) was added, followed by 6-chloronicotinoyl chloride (0.072 g, 0.41 mmol). The mixture was stirred for 2 hours and then diluted with DCM (50 ml) and 1M Na$_2$CO$_3$ (30 ml). The organic layer was separated, washed with water (30 ml), brine (30 ml), dried over MgSO$_4$, filtered and concentrated to dryness. The residue was crystallized in acetonitrile to yield the title compound as a white solid.

$^1$H NMR (300 MHz, DMSO-$d_6$) δ ppm 0.52-0.65 (m, 3H), 1.65 (br. s., 2H), 1.82 (br. s. 2H), 2.24 (s, 3H), 2.80 (br. s., 1H), 3.11 (d, J=5.4 Hz, 1H), 3.70 (br. s., 1H), 3.79 (s, 3H), 4.56 (br. s., 1H), 6.33 (d, J=1.8 Hz, 1H), 7.17-7.28 (m, 1H), 7.33 (d, J=8.4 Hz, 4H), 7.36-7.41 (m, 3H), 7.43 (d, J=2.6 Hz, 2H), 7.67 (d, J=8.2 Hz, 1H), 8.31 (dd, J=8.3, 2.4 Hz, 1H), 8.92 (d, J=2.2 Hz, 1H), 10.16 (s, 1H). MS m/z 528 (M+H)$^+$

Example 6

Compound #81

(±)-6-(isopropylamino)-N-(2-methyl-5-((3R,4S)-3-methyl-4-(4-(1-methyl-1H-pyrazol-5-yl)phenyl)piperidine-1-carbonyl)phenyl)nicotinamide

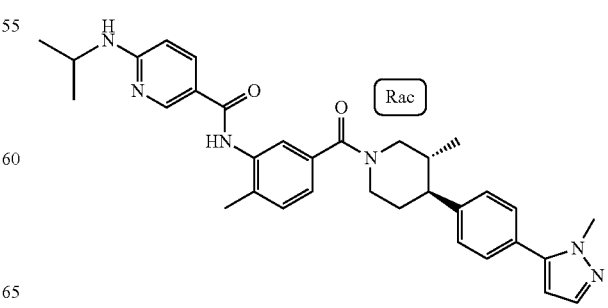

(±)-6-chloro-N-(2-methyl-5-((3R,4S)-3-methyl-4-(4-(1-methyl-1H-pyrazol-5-yl)phenyl)piperidine-1-carbonyl)phenyl)nicotinamide (0.080 g, 0.15 mmol) and isopropylamine (0.129 ml, 1.51 mmol) were combined in 1,4-dioxane (2 ml) in a sealed tube. The mixture was heated to 150° C. for 16 hours and then allowed to cool to room temperature. The reaction mixture was diluted with ethyl acetate (80 ml) and washed with 1M Na$_2$CO$_3$ (50 ml). The organic layer was washed with water (40 ml), brine (40 ml), dried over MgSO$_4$, filtered and concentrated to dryness. The residue was purified by column chromatography over silica gel eluting with a gradient of MeOH in DCM from 0 to 5%. The product was then recrystallized from acetonitrile.

$^1$H NMR (300 MHz, DMSO-d$_6$) δ ppm 0.45-0.83 (m, 3H), 1.17 (d, J=6.5 Hz, 6H), 1.71 (br. s., 2H), 1.87 (d, J=10.9 Hz, 1H), 2.27 (s, 3H), 2.85 (br. s., 1H), 3.14 (d, J=15.3 Hz, 1H), 3.66-3.83 (m, 1H), 3.85 (s, 3H), 4.03-4.19 (m, 1H), 4.61 (br. s., 1H), 6.39 (d, J=1.9 Hz, 1H), 6.49 (d, J=8.9 Hz, 1H), 7.05 (d, J=7.6 Hz, 1H), 7.19-7.29 (m, 1H), 7.30-7.42 (m, 3H), 7.43-7.51 (m, 4H), 7.89 (dd, J=8.8, 2.3 Hz, 1H), 8.66 (d, J=2.1 Hz, 1H), 9.58 (s, 1H). MS m/z 551 (M+H)$^+$ Example 7

Compound #7

6-(Isopropylamino)-N-(2-methyl-5-(4-(4-(pyrimidin-2-ylcarbamoyl)phenyl)piperidine-1-carbonyl)phenyl)nicotinamide

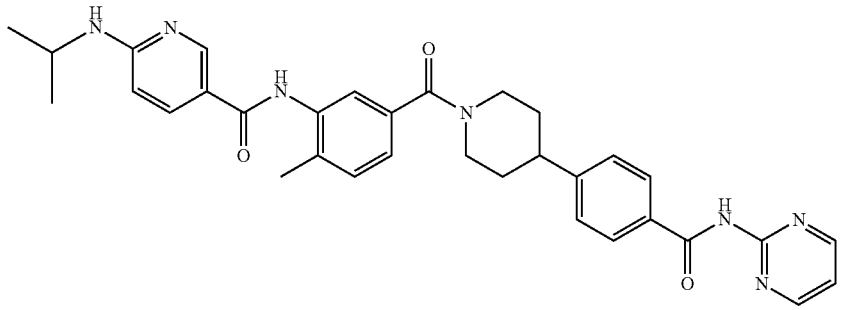 [SMILES: Cc1ccc(C(=O)N2CCC(c3ccc(C(=O)Nc4ncccn4)cc3)CC2)cc1NC(=O)c1ccc(NC(C)C)nc1]

Step A: 4-(4-Methoxycarbonyl-phenyl)-piperidine-1-carboxylic acid tert-butyl ester Zn dust (3.34 g, 51.04 mmol) was suspended in DMA (25 ml) under nitrogen atmosphere and then treated with 1,2-dibromo-ethane (0.43 ml, 4.90 mmol). The mixture was briefly heated to 60-70° C. and allowed to cool to room temperature (3 times). Chlorotrimethylsilane (0.43 ml, 3.27 mmol) was then added dropwise and resulting mixture aged for 30 minutes. Then a solution of 4-iodo-piperidine-1-carboxylic acid tert-butyl ester (7.62 g, 24.5 mmol) in DMA (25 ml) was added slowly added at such a rate to maintain a temperature <65° C. The exothermic zinc insertion was allowed to cool to room temperature and stirring maintained for 1 hour, to yield a ~0.5 M solution of (1-tert-butoxycarbonylpiperidin-4-yl)(iodo)zinc.

A freshly prepared solution of 4-bromo-benzoic acid methyl ester (5.26 g, 24.5 mmol), copper(I) iodide (0.280 g, 1.47 mmol) and Pd(dppf)Cl$_2$CH$_2$Cl$_2$ (0.600 g, 0.735 mmol) was then treated with the above solution and mixture heated to 120° C. overnight. The reaction mixture was allowed to cool to room temperature, diluted with ethyl acetate (100 ml). The mixture was filtered through a pad of CELITE that was further washed with ethyl acetate (2×50 ml). The filtrate was washed with 1M Na$_2$CO$_3$ (500 ml), dried over MgSO$_4$, filtered and concentrated to dryness. Purification of the resulting residue over silica gel eluting with a gradient of ethyl acetate in heptane from 0 to 25% yielded 4-(4-methoxycarbonyl-phenyl)-piperidine-1-carboxylic acid tert-butyl ester. MS m/z 320 (M+H)$^+$ Step B:
4-(4-Carboxy-phenyl)-piperidine-1-carboxylic acid tert-butyl ester 4-(4-Methoxycarbonyl-phenyl)-piperidine-1-carboxylic acid tert-butyl ester (4.5 g, 14.1 mmol) was dissolved in MeOH (31 ml). 1M NaOH (56 ml, 56 mmol) was added and resulting mixture was stirred at room temperature for 1 hour and then at 40° C. during 4 hours. The mixture was cooled in ice bath and 1M HCl was slowly added to pH 3-4. The product was extracted with DCM (2×150 ml), dried over MgSO$_4$, filtered and concentrated to a solid. MS m/z 306 (M+H)$^+$ Step C: 4-[4-(Pyrimidin-2-ylcarbamoyl)-phenyl]-piperidine-1-carboxylic acid tert-butyl ester In a first round bottom flask, 4-(4-carboxy-phenyl)-piperidine-1-carboxylic acid tert-butyl ester (1.0 g, 3.27 mmol) in THF (15 ml) was treated with 1-chloro-N,N,2-trimethyl-propenylamine (0.65 ml, 4.91 mmol) and stirred for 1 hour. In a second flask, 2-aminopyrimidine was dissolved in 15 ml of THF and cooled to 0° C. under nitrogen atmosphere. 1M lithium bis-(trimethylsilyl)amide (10 ml, 10 mmol) was added dropwise and the cold solution was stirred for 30 minutes before the content of the first flask was introduced via cannula. The mixture was then stirred for 2 hours. The reaction was quenched with water (50 ml) and organics extracted with ethyl acetate (100 ml). The organic layer was dried over MgSO$_4$, filtered and concentrated to dryness. The residue was purified by column chromatography over silica gel eluting with gradient of MeOH in DCM from 0 to 2%. The product fractions were collected and concentrated to yield 4-[4-(pyrimidin-2-ylcarbamoyl)-phenyl]-piperidine-1-carboxylic acid tert-butyl ester. MS m/z 383 (M+H)$^+$ Step D:
4-Piperidin-4-yl-N-pyrimidin-2-yl-benzamide. hydrochloride To a solution of 4-[4-(pyrimidin-2-ylcarbamoyl)-phenyl]-piperidine-1-carboxylic acid tert-butyl ester (1.07 g, 2.79 mmol) in 1,4-dioxane (15 ml) was added 4N HCl in 1,4-dioxane (7 ml, 28 mmol). The mixture was stirred at room temperature for 2 hours. The mixture was concentrated to dryness to yield the hydrochloride salt as a solid. MS m/z 283 (M+H)⁺

Step E: 4-[1-(3-Amino-4-methyl-benzoyl)-piperidin-4-yl]-N-pyrimidin-2-yl-benzamide A flask was charged with 4-piperidin-4-yl-N-pyrimidin-2-yl-benzamide hydrochloride (0.79 g, 2.79 mmol) and 3-amino-4-methylbenzoic acid (0.422 g, 2.79 mmol). DCM (20 ml) and N,N-diisopropylethylamine (1.27 ml, 7.44 mmol) were added with stirring. Once an homogenous solution was obtained, 0-(benzotriazol-1-yl)-N,N,N'—N'-tetramethyluronium hexafluorophosphate (HBTU), (1.27 g, 3.35 mmol) was added. The reaction was stirred for 1 hour at room temperature. After 1 hour, the precipitate that formed was filtered and washed with DCM (2×10 ml) to yield 4-[1-(3-amino-4-methyl-benzoyl)-piperidin-4-yl]-N-pyrimidin-2-yl-benzamide as a white solid. MS m/z 416 (M+H)⁺

Step F: Isopropylammonium 6-isopropylamino-nicotinate

A solution of 6-chloronicotinic acid (5.0 g, 31.74 mmol) was heated at 150° C. for 4 days, with isopropylamine (20 ml, 233 mmol) in 1,4-dioxane (60 ml) in a closed pressure reaction vessel. The reaction mixture was allowed to cool to room temperature with gentle stirring inducing crystallization of desired product. The solid was filtered, washed with 1,4-dioxane (2×20 ml) and under high vacuum. ¹H NMR (300 MHz, DMSO-d₆) δ ppm 1.11 (d, J=6.7 Hz, 6H), 1.14 (d, J=6.7 Hz, 6H), 3.17 (sept, J=6.6 Hz, 1H), 4.03 (sept, J=6.7 Hz, 1H), 6.34 (d, J=8.7 Hz, 1H), 6.65 (d, J=7.6 Hz, 1H), 7.75 (dd, J=8.8, 2.2 Hz, 1H), 8.47 (d, J=2.0 Hz, 1H). MS m/z 181 (M+H)⁺

Step G: 6-Isopropylamino-N-(2-methyl-5-{4-[4-(pyrimidin-2-ylcarbamoyl)-phenyl]-piperidine-1-carbonyl}-phenyl)-nicotinamide Isopropylammonium 6-Isopropylamino-nicotinate (0.181 g, 0.756 mmol) was taken in DCM (5 ml) and DMF (1 ml). Thionyl chloride (0.15 ml, 2 mmol) was added and mixture refluxed for 3 hours. The solution was concentrated and briefly dried under high vacuum. The residue was dissolved in DCM (10 ml) and added to a solution of 4-[1-(3-amino-4-methyl-benzoyl)-piperidin-4-yl]-N-pyrimidin-2-yl-benzamide (0.20 g, 0.48 mmol) and pyridine (0.12 ml, 1.44 mmol) in DCM (15 ml). The resulting mixture was stirred at room temperature for 2 hours and then quenched with 1M Na₂CO₃ (20 ml). The organics were extracted with DCM (2×30 ml), dried over MgSO₄, filtered a concentrated to dryness. The residue was purified by column chromatography over silica gel eluting with a gradient of MeOH in DCM from 0 to 4%. 6-Isopropylamino-N-(2-methyl-5-{4-[4-(pyrimidin-2-ylcarbamoyl)-phenyl]-piperidine-1-carbonyl}-phenyl)-nicotinamide was yield the title compound as a solid.
¹H NMR (300 MHz, DMSO-d₆) δ ppm 1.18 (d, J=6.5 Hz, 6H), 1.55-1.76 (m, 3H), 1.83 (br. s., 2H), 2.27 (s, 3H), 2.93 (t, J=11.5 Hz, 2H), 3.19 (br. s., 1H), 3.84 (br. s., 1H), 4.02-4.21 (m, 1H), 4.62 (br. s., 1H), 6.49 (d, J=8.8 Hz, 1H), 7.02 (d, J=7.6 Hz, 1H), 7.18-7.30 (m, 2H), 7.30-7.38 (m, 1H), 7.38-7.51 (m, 3H), 7.83-7.98 (m, 3H), 8.66 (d, J=2.2 Hz, 1H), 8.73 (d, J=4.8 Hz, 2H), 9.57 (s, 1H), 10.89 (s, 1H). MS m/z 578 (M+H)⁺

Example 8

Compound #6

N-(5-(4-(4-(1H-imidazol-1-yl)phenyl)-3,3-dimethyl-piperidine-1-carbonyl)-2-methylphenyl)-6-chloronicotinamide

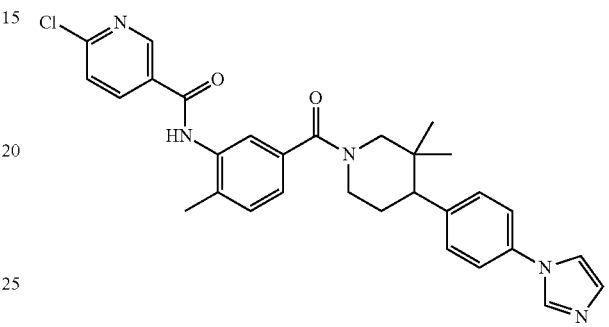

Step A: 1-Benzyl-3,3-dimethyl-piperidin-4-one

1-Benzyl-3-methyl-piperidin-4-one (12.0 g, 59.0 mmol) was dissolved in THF (60 ml). Potassium tert-Butoxide (7.28 g, g64.9 mmol) was added and reaction vessel capped with a septum. Methyl iodide (3.67 ml, 59.0 mmol) was introduced via syringe and mixture stirred at room temperature for 72 hours. Brine (250 ml) was added and organics extracted with ethyl acetate (2×100 ml). The combined organic layers were dried over MgSO₄, filtered and concentrated to dryness. The residue was purified by column chromatography over silica gel eluting with a gradient of ethyl acetate in heptane from 0 to 40% to yield 1-benzyl-3,3-dimethyl-piperidin-4-one. ¹H NMR (300 MHz, CDCl₃) δ ppm 1.13 (s, 6H), 2.40 (s, 2H), 2.51 (t, J=6.2 Hz, 2H), 2.72 (t, J=6.2 Hz, 2H), 3.56 (s, 2H), 7.24-7.39 (m, 5H). MS m/z 218 (M+H)⁺

Step B: 1-Benzyl-4-(4-bromo-phenyl)-3,3-dimethyl-piperidin-4-ol 1,4-Dibromobenzene (9.31 g, 39.5 mmol) was dissolved in dry THF (50 ml) in a two necks round-bottom flask equipped with a stirring bar, a septum, and an addition funnel with nitrogen inlet. The solution was cooled to −78° C., and n-BuLi (1.6 M, 24.7 ml, 39.5 mmol) was added dropwise via syringe. The resulting milky suspension was stirred for 1 hour at the same temperature, before a solution of 1-benzyl-3,3-dimethyl-piperidin-4-one (7.15 g, 32.9 mmol) in THF (50 ml) was slowly added from the addition funnel. The clear solution was then stirred for 3 hours allowing the temperature to rise to ambient. The reaction was quenched with saturated NH₄Cl (50 ml) and water (100 ml). The organics were extracted with ethyl acetate (100 ml). The organic layer was washed with brine (50 ml), dried over MgSO₄, filtered and concentrated to a viscous oil. Purification of the oil over silica gel eluting with a gradient of MeOH in DCM from 0 to 6% yielded the desired product.

¹H NMR (300 MHz, CDCl₃) δ ppm 0.72 (s, 3H), 0.94 (s, 3H), 1.41-1.55 (m, 2H), 2.29 (d, J=11.2 Hz, 1H), 2.38 (d, J=11.2 Hz, 1H), 2.48 (m, 1H), 2.74-2.86 (m, 2H), 3.47 (d, J=13.4 Hz, 1H), 3.59 (d, J=13.4 Hz, 1H), 7.22-7.39 (m, 7H), 7.44 (d, J=8.7 Hz, 2H). MS m/z 374 (M+H)⁺

Step C: 1-Benzyl-4-(4-bromo-phenyl)-3,3-dimethyl-1,2,3,6-tetrahydro-pyridine

1-Benzyl-4-(4-bromo-phenyl)-3,3-dimethyl-piperidin-4-ol (2.44 g, 7.07 mmol) was refluxed in TFA overnight. The solution was allowed to cool to room temperature and concentrated to dryness. The solid was taken in toluene and again concentrated (2×50 ml) to remove residual TFA. The residue was taken in 1M Na₂CO₃ (50 ml) and then product extracted with DCM (2×100 ml). The combined organic layers were washed with brine (50 ml), dried over MgSO₄, filtered and concentrated in vacuo and dried under high vacuum to yield a white solid. ¹H NMR (300 MHz, CDCl₃) δ ppm 1.02 (s, 6H), 2.33 (s, 2H), 3.06 (d, J=3.3 Hz, 2H), 3.60 (s, 2H), 5.42 (t, J=3.3 Hz, 1H), 7.04 (d, J=8.4 Hz, 2H), 7.23-7.42 (m, 7H). MS m/z 356 (M+H)⁺

Step D: 1-Benzyl-4-(4-imidazol-1-yl-phenyl)-3,3-dimethyl-1,2,3,6-tetrahydro-pyridine 1-Benzyl-4-(4-bromo-phenyl)-3,3-dimethyl-1,2,3,6-tetrahydro-pyridinium trifluroacetate (1.37 g, 3.84 mmol), imidazole (0.317 g, 4.61 mmol), copper(I) iodide (0.073 g, 0.385 mmol) and Cs₂CO₃ (8.06 mmol) were placed in DMF (8 ml) in a sealed tube. Nitrogen was bubbled into the mixture for 10 minutes before trans-1,2-Bis(methylamino)cyclohexane (0.125 ml, 0.77 mmol) was added. The reaction was sealed tight and heated at 110° C. with magnetic stirring for 64 hours. The mixture was allowed to cool to room temperature and poured into water (20 ml). The organics were extracted with ethyl acetate (2×25 ml). The combined organic layers were dried over MgSO₄, filtered and concentrated in vacuo. The residue was purified by column chromatography over silica gel washing out first the residual starting material with a gradient of ethyl acetate in heptane from 50 to 100%. The product was eluted with a gradient of MeOH in DCM from 0 to 5%. The product fractions were collected and concentrated to dryness to yield a foam. MS m/z 344 (M+H)⁺

Step E: 4-(4-Imidazol-1-yl-phenyl)-3,3-dimethylpiperidine

1-Benzyl-4-(4-imidazol-1-yl-phenyl)-3,3-dimethyl-1,2,3,6-tetrahydro-pyridine (0.833 g, 2.43 mmol) was hydrogenated overnight over 10% Pd/C (0.25 g) in MeOH (10 ml) at atmospheric pressure of hydrogen. The catalyst was filtered off through CELITE. The filtrate was concentrated to an oil. MS m/z 256 (M+H)⁺

Step F: (3-Amino-4-methyl-phenyl)-[4-(4-imidazol-1-yl-phenyl)-3,3-dimethyl-piperidin-1-yl]-methanone A flask was charged with 4-(4-imidazol-1-yl-phenyl)-3,3-dimethylpiperidine (0.619 g, 2.42 mmol) and 3-amino-4-methylbenzoic acid (0.370 g, 2.42 mmol). DCM (15 ml) and N,N-diisopropylethylamine (1.26 ml, 7.41 mmol) were added with stirring. Once an homogenous solution was obtained, 0-(benzotriazol-1-yl)-N,N,N'—N'-tetramethyluronium hexafluorophosphate (HBTU), (1.10 g, 2.90 mmol) was added. The reaction was stirred for 1 hour at room temperature before 1M Na₂CO₃ (20 ml) was added. The organics were extracted with DCM (2×30 ml). The combined organic layers were dried over MgSO₄, filtered and concentrated to a residue mixture. The residue mixture was purified over silica gel eluting with a gradient of MeOH in DCM from 0 to 4% and then recrystallization from acetonitrile to yield (3-amino-4-methyl-phenyl)-[4-(4-imidazol-1-yl-phenyl)-3,3-dimethyl-piperidin-1-yl]-methanone as a white solid. ¹H NMR (300 MHz, DMSO-d₆) δ ppm 0.81 (br s, 6H), 1.39-1.62 (m, 1H), 2.07 (s, 3H), 2.09-2.28 (m, 1H), 2.55-3.12 (m, 2H), 3.37-3.99 (br m, 1H), 4.14-4.78 (br m, 1H), 5.00 (br s, 2H), 6.50 (br s, 1H), 6.66 (br s, 1H), 6.96 (d, J=7.5 Hz, 1H), 7.09 (s, 1H), 7.32 (d, J=8.2 Hz, 1H), 7.56 (d, J=8.4 Hz, 2H), 7.72 (s, 1H), 8.22 (s, 1H). MS m/z 389 (M+H)⁺

Step G: N-(5-(4-(4-(1H-imidazol-1-yl)phenyl)-3,3-dimethylpiperidine-1-carbonyl)-2-methylphenyl)-6-chloronicotinamide 6-Chloronicotinoyl chloride (0.113 g, 0.62 mmol) was added to a solution of (3-amino-4-methyl-phenyl)-[4-(4-imidazol-1-yl-phenyl)-3,3-dimethyl-piperidin-1-yl]-methanone (0.20 g 0.514 mmol) and pyridine (0.125 ml, 1.54 mmol) in DCM (10 ml). The mixture was stirred for 4 hours and then diluted with DCM (50 ml) and 1M NaOH (50 ml). The organic layer was separated, dried over MgSO₄, filtered and concentrated to dryness. The residue purified by column chromatography over silica gel with a gradient of MeOH in DCM from 0 to 4%. The product fractions were collected and concentrated to a foam. The foam was recrystallized from acetonitrile (5 ml) to yield N-(5-(4-(4-(1H-imidazol-1-yl)phenyl)-3,3-dimethylpiperidine-1-carbonyl)-2-methylphenyl)-6-chloronicotinamide as a white solid.

¹H NMR (300 MHz, DMSO-d₆) δ ppm 0.47 (br. s., 3H), 0.51-0.71 (m, 3H), 1.31 (br. s., 1H), 2.00 (d, J=14.4 Hz, 1H), 2.24-2.30 (m, 3H), 2.53 (d, J=10.2 Hz, 2H), 2.90 (br. s., 1H), 3.21-3.60 (m, 1H), 4.11-4.45 (m, 1H), 6.88 (s, 1H), 6.98-7.20 (m, 4H), 7.35 (d, J=8.5 Hz, 2H), 7.46-7.57 (m, 2H), 8.01 (s, 1H), 8.16 (dd, J=8.2, 2.2 Hz, 1H), 8.71-8.84 (m, 1H), 10.00 (s, 1H). MS m/z 528 (M+H)⁺

Example 9

Compound #43

N-(5-(4-(4-(1H-imidazol-1-yl)phenyl)-3,3-dimethyl-piperidine-1-carbonyl)-2-methylphenyl)-6-(isopropylamino)nicotinamide

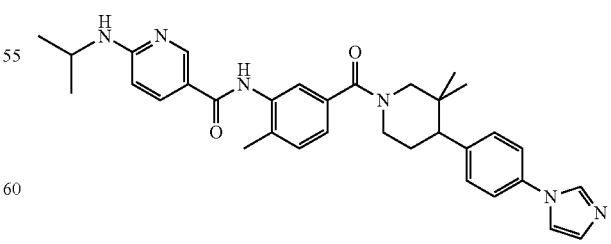

A solution of N-(5-(4-(4-(1H-imidazol-1-yl)phenyl)-3,3-dimethylpiperidine-1-carbonyl)-2-methylphenyl)-6-chloronicotinamide (0.161 g, 0.30 mmol) and Isopropylamine (1 ml, 11.6 mmol) in 1,4-dioxane (5 ml) was heated at 150° C.

in a sealed tube for 16 hours. The reaction mixture was allowed to cool to room temperature, and poured into 1M Na$_2$CO$_3$ (20 ml). The product was extracted with ethyl acetate (50 ml) and washed with water (20 ml) and brine (20 ml). The ethyl acetate solution was dried over MgSO$_4$, filtered and concentrated to an amorphous solid. Recrystallization of the solid from acetonitrile yielded N-(5-(4-(4-(1H-imidazol-1-yl)phenyl)-3,3-dimethylpiperidine-1-carbonyl)-2-methylphenyl)-6-(isopropylamino)nicotinamide as a white solid.

$^1$H NMR (300 MHz, DMSO-d$_6$) δ ppm 0.58 (br. s., 6H), 0.94 (d, J=6.5 Hz, 6H), 1.28 (br. s., 1H), 1.90-1.98 (m, 1H), 2.24-2.29 (m, 3H), 2.37-2.56 (m, 2H), 2.88 (br. s., 1H), 3.20-3.69 (m, 1H), 3.77-3.96 (m, 1H), 4.08-4.44 (m, 1H), 6.26 (d, J=8.8 Hz, 1H), 6.80 (d, J=7.7 Hz, 1H), 6.86 (s, 1H), 6.97 (br. s., 1H), 7.10 (d, J=7.7 Hz, 3H), 7.21 (br. s., 1H), 7.33 (d, J=8.5 Hz, 2H), 7.49 (s, 1H), 7.66 (dd, J=8.8, 2.2 Hz, 1H), 7.99 (s, 1H), 8.43 (d, J=2.1 Hz, 1H), 9.34 (s, 1H). MS m/z 551 (M+H)$^+$ Example 10

Compound #75

N-(2-chloro-5-(3-(4-(isoquinolin-6-yl)phenyl)azetidine-1-carbonyl)phenyl)-6-(isopropylamino)nicotinamide

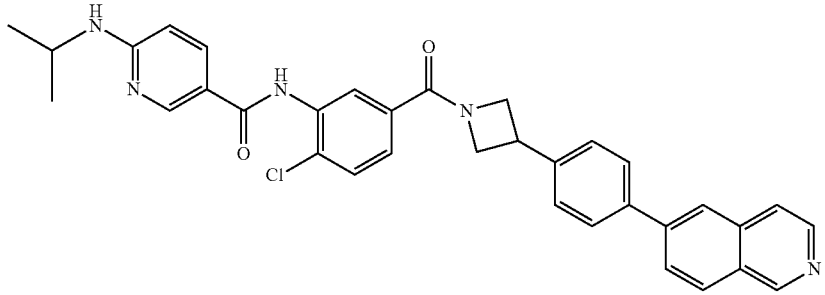 [SMILES: CC(C)Nc1ccc(C(=O)Nc2cc(C(=O)N3CC(c4ccc(-c5ccc6cnccc6c5)cc4)C3)ccc2Cl)cn1]

Step A: 3-Amino-4-chloro-benzoic acid methyl ester

Thionyl chloride (2.76 ml, 37.8 mmol) was added dropwise to an ice cold solution of 3-amino-4-chloro-benzoic acid (5 g, 29.14 mmol) in MeOH under nitrogen atmosphere. Once the addition complete, the mixture was allowed to come to room temperature and finally refluxed for 3 hours. The solution was allowed to cool to room temperature and concentrated in vacuo. The residue was partitioned between DCM (200 ml) and 1M Na$_2$CO$_3$ (100 ml). The organic layer was dried over MgSO$_4$, filtered and concentrated to yield the product as a solid. $^1$H NMR (300 MHz, DMSO-d$_6$) δ ppm 3.81 (s, 3H), 5.67 (s, 2H), 7.10 (dd, J=8.2, 2.1 Hz, 1H), 7.32 (d, J=8.2 Hz, 1H), 7.43 (d, J=2.1 Hz, 1H). MS m/z 185 (M+H)$^+$ Step B: 4-Chloro-3-[(6-isopropylamino-pyridine-3-carbonyl)-amino]-benzoic acid methyl ester To a solution of Isopropylammonium 6-isopropylamino-nicotinate (3.38 g, 18.8 mmol) in DCM (50 ml) was added thionyl chloride (2.75 ml, 37.6 mmol). The mixture was refluxed for 3 hours. The solution was concentrated and briefly dried under high vacuum. The residue was dissolved in DCM (50 ml) and added to a solution of 3-amino-4-chloro-benzoic acid methyl ester (3.36 g, 18.1 mmol) and pyridine (4.40 ml, 54.3 mmol) in DCM (90 ml). The resulting mixture was stirred at room temperature overnight. The white solid that crystallized was filtered off and washed with DCM (2×30 ml). Drying under high vacuum yielded 4-chloro-3-[(6-isopropylamino-pyridine-3-carbonyl)-amino]-benzoic acid methyl ester as a white solid. $^1$H NMR (300 MHz, DMSO-d$_6$) δ ppm 1.18 (d, J=6.4 Hz, 6H), 3.88 (s, 3H), 4.11 (sept, J=6.4 Hz, 1H), 6.50 (d, J=8.9 Hz, 1H), 7.13 (d, J=7.6 Hz, 1H), 7.70 (d, J=8.4 Hz, 1H), 7.80 (dd, J=8.0, 2.0 Hz, 1H), 7.90 (dd, J=8.9, 2.3 Hz, 1H), 8.23 (d, J=2.0 Hz, 1H), 8.67 (d, J=2.3 Hz, 1H), 9.80 (s, 1H). MS m/z 348 (M+H)$^+$ Step C: 4-Chloro-3[(6-isopropylamino-pyridine-3-carbonyl)-amino]-benzoic acid A 25 ml methanol solution of 4-chloro-3-[(6-isopropylamino-pyridine-3-carbonyl)-amino]-benzoic acid methyl ester (3.58 g, 10.3 mmol) was diluted with 1M NaOH (100 ml, 100 mmol) and mixture heated to 40° C. for 4 hours. After cooling in ice bath, 1M HCl was added to a pH in the range of pH 3-4. The product was extracted with DCM (2×200 ml), dried over MgSO$_4$, filtered and concentrated to a solid. The solid was recrystallized from acetonitrile (30 ml) to yield 4-chloro-3-[(6-isopropylamino-pyridine-3-carbonyl)-amino]-benzoic acid a beige solid. $^1$H NMR (300 MHz, DMSO-d$_6$) δ ppm 1.18 (d, J=6.4 Hz, 6H), 4.11 (sept, J=6.4 Hz, 1H), 6.53 (d, J=8.9 Hz, 1H), 7.23 (br s, 1H), 7.67 (d, J=8.4 Hz, 1H), 7.79 (dd, J=8.0, 2.0 Hz, 1H), 7.92 (dd, J=8.9, 2.3 Hz, 1H), 8.17 (d, J=2.0 Hz, 1H), 8.66 (d, J=2.3 Hz, 1H), 9.82 (s, 1H), 13.23 (s, 1H). MS m/z 334 (M+H)$^+$ Step D: N-{5-[3-(4-Bromo-phenyl)-azetidine-1-carbonyl]-2-chloro-phenyl}-6-isopropylamino-nicotinamide O-(Benzotriazol-1-yl)-N,N,N'—N'-tetramethyluronium hexafluorophosphate (HBTU), (2.05 g, 5.40 mmol) was added to mixture of 4-chloro-3-[(6-isopropylamino-pyridine-3-carbonyl)-amino]-benzoic acid (1.5 g, 4.50 mmol), 3-(4-bromophenyl)-azetidine hydrochloride (1.35 g, 4.95 mmol) and N,N-diisopropylethylamine (2.35 ml, 13.8 mmol) in DCM (25 ml). The reaction was stirred for 1 hour at room temperature before 1M Na$_2$CO$_3$ (50 ml) was added. The organics were extracted with DCM (2×50 ml). The combined organic layers were dried over MgSO$_4$, filtered and concentrated to a residue mixture. The residue was recrystallized from acetonitrile to yield N-{5-[3-(4-bromophenyl)-azetidine-1-carbonyl]-2-chloro-phenyl}-6-isopropylamino-nicotinamide as a white solid. $^1$H NMR (300 MHz, DMSO-d$_6$) δ ppm 1.18 (d, J=6.4 Hz, 6H), 3.89-4.15 (m, 3H), 4.37, (t, J=7.0 Hz, 1H), 4.48, (t, J=8.9 Hz, 1H), 4.70, (t, J=8.4 Hz, 1H), 6.49 (d, J=8.9 Hz, 1H), 7.11 (d, J=7.6 Hz, 1H), 7.40 (d, J=8.4 Hz, 2H), 7.52-7.58 (m, 3H), 7.89 (dd, J=8.9, 2.4 Hz, 1H), 7.95 (d, J=2.0 Hz, 1H), 8.66 (d, J=2.3 Hz, 1H), 9.74 (s, 1H). MS m/z 528× (M+H)$^+$ Step E: N-(2-chloro-5-(3-(4-(isoquinolin-6-yl)phenyl)azetidine-1-carbonyl)phenyl)-6-(isopropylamino)nicotinamide N-{5-[3-(4-Bromo-phenyl)-azetidine-1-carbonyl]-2-chloro-phenyl}-6-isopropylamino-nicotinamide (0.30 g, 0.57 mmol), was dissolved in 1,4-dioxane (10 ml) and solution bubbled with nitrogen. While maintaining the nitrogen bubbling, 1M Na$_2$CO$_3$ (1.20 ml, 1.20 mmol) was added followed by isoquinoline-6-boronic acid (0.197 g, 1.14.mmol) and PdCl$_2$(PPh$_3$)$_2$ (0.02 g, 0.029 mmol). The reaction mixture was then refluxed under nitrogen atmosphere for 3 hours and then allowed to cool to room temperature. Water (70 ml) was added, and the organics extracted with ethyl acetate (120 ml). The organic layer was dried over MgSO$_4$, filtered and concentrated to a brown oily residue. The residue was purified by column chromatography over silica gel eluting with a gradient of MeOH in DCM from 0 to 3%. The product fractions were combined and concentrated under reduced pressure. The resulting residue was recrystallized from acetonitrile to yield N-{2-chloro-5-[3-(4-isoquinolin-6-yl-phenyl)-azetidine-1-carbonyl]-phenyl}-6-isopropylamino-nicotinamide as white solid.

$^1$H NMR (300 MHz, DMSO-d$_6$) δ ppm 1.17 (d, J=6.5 Hz, 6H), 3.98-4.19 (m, 3H), 4.45 (d, J=14.0 Hz, 1H), 4.50-4.61 (m, 1H), 4.77 (t, J=8.4 Hz, 1H), 6.50 (d, J=8.8 Hz, 1H), 7.12 (d, J=7.6 Hz, 1H), 7.53-7.69 (m, 4H), 7.84-7.94 (m, 4H), 7.98 (d, J=1.8 Hz, 1H), 8.04 (dd, J=8.6, 1.4 Hz, 1H), 8.22 (d, J=8.7 Hz, 1H), 8.28 (s, 1H), 8.53 (d, J=5.6 Hz, 1H), 8.67 (d, J=2.2 Hz, 1H), 9.34 (s, 1H), 9.76 (s, 1H). MS m/z 576 (M+H)$^+$ Example 11

Compound #77

(±)-N-(2-chloro-5-((3R,4R)-3-hydroxy-4-(4-(1-methyl-1H-pyrazol-5-yl)phenyl)piperidine-1-carbonyl)phenyl)-6-(isopropylamino)nicotinamide

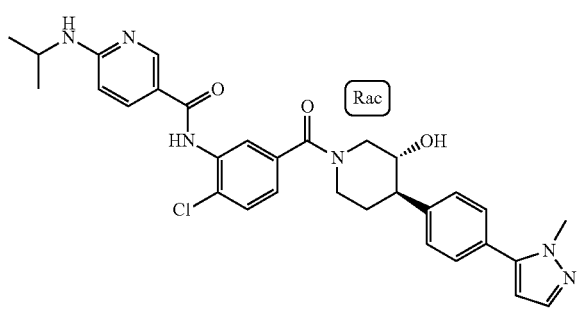 [SMILES: CC(C)Nc1ccc(C(=O)Nc2cc(C(=O)N3CC[C@H](c4ccc(-c5ccnn5C)cc4)[C@@H](O)C3)ccc2Cl)cn1]

Step A:
4-(4-Bromo-phenyl)-1,2,3,6-tetrahydro-pyridinium trifluoroacetate 4-(4-Bromo-phenyl)-piperidin-4-ol (25 g, 97.6 mmol) was heated at 90° ° C. in TFA (350 ml) for 6 hours. The solution was allowed to cool to room temperature and concentrated in vacuo. The residue was taken in toluene (2×300 ml) and again concentrated to remove residual TFA. The resulting solid was further dried under high vacuum. MS m/z 238 (M+H)$^+$ Step b: 4-(4-Bromo-phenyl)-3,6-dihydro-2H-pyridine-1-carboxylic acid tert-butyl ester 4-(4-Bromo-phenyl)-1,2,3,6-tetrahydro-pyridinium trifluoroacetate (34.4 g, 96.6 mmol) was taken in DCM (200 ml) and treated with 1M Na$_2$CO$_3$ (195 ml, 195 mmol) with stirring. After 15 minutes, di-tert-butyl dicarbonate (23.4 g, 107.3 mmol) was added dropwise and resulting mixture further stirred for 1 hour. The organic layer was separated and aqueous layer extracted with DCM (2×150 ml). The combined organic layers were dried over MgSO$_4$, filtered and concentrated to an oil. The oil was flash chromatographed over silica gel eluting with a gradient of ethyl acetate in heptane from 0 to 50% to yield 4-(4-bromo-phenyl)-3,6-dihydro-2H-pyridine-1-carboxylic acid tert-butyl ester as a viscous oil. MS m/z 338 (M+H)$^+$ Step C: (±)-(3R,4R)-4-(4-Bromo-phenyl)-3-hydroxy-piperidine-1-carboxylic acid tert-butyl ester A solution of 4-(4-bromo-phenyl)-3,6-dihydro-2H-pyridine-1-carboxylic acid tert-butyl ester (33.0 g, 97.6 mmol) in dry THF (300 ml) was treated with 1M borane (488 ml, 488 mmol) at room temperature. The mixture was stirred overnight before 4M NaOH (610 ml, 2440 mmol) was slowly added, followed by 30% hydrogen peroxide (16.7 ml, 197.1 mmol). The temperature was then raised to 65° C. for 2 hours. After cooling to room temperature, the organics were extracted with ethyl acetate (2×1500 ml). The combined organic layers were washed with brine (500 ml), dried over MgSO$_4$, filtered and concentrated to an oil. The oil was taken in heptane (400 ml) and gently stirred for 48 hours to yield a precipitate. The solid was filtered off, washed with heptane and dried under high vacuum to yield (±)-(3R,4R)-4-(4-bromo-phenyl)-3-hydroxy-piperidine-1-carboxylic acid tert-butyl ester as a white crystalline solid. $^1$H NMR (300 MHz, CDCl$_3$) δ ppm 1.48 (s, 9H), 1.61-1.85 (m, 2H), 2.51 (dt, J=10.3 4.1 Hz, 1H), 2.62 (t, J=11.6 Hz, 1H), 2.75 (t, J=12.4 Hz, 1H), 3.60-3.72 (m, 1H), 4.18 (br s, 1H), 4.40 (br s, 1H), 7.14 (d, J=8.4 Hz, 2H), 7.48 (d, J=8.4 Hz, 2H). MS m/z 356 (M+H)$^+$ Step D: (±)-(3R,4R)-4-(4-Bromo-phenyl)-piperidin-3-ol hydrochloride To a solution of (±)-(3R,4R)-4-(4-bromo-phenyl)-3-hydroxy-piperidine-1-carboxylic acid tert-butyl ester (2.5 g, 7.02 mmol) in 1,4-dioxane (6 ml) was added 4N HCl in 1,4-dioxane (18 ml, 72 mmol). The mixture was stirred at room temperature for 2 hours. Diethyl ether (40 ml) was added to complete the precipitation of the hydrochloride salt product, which was recovered by filtration. $^1$H NMR (300 MHz, DMSO-d$_6$) δ ppm 1.80-2.00 (m, 2H), 2.59-2.75 (m, 2H), 2.81-3.00 (m, 2H), 3.21-3.5 (m, 3H), 3.89 (dt, J=10.4, 4.5 Hz, 1H), 5.26 (br s, 1H), 7.18 (d, J=8.4 Hz, 1H), 7.52 (d, J=8.4 Hz, 1H), 8.66 (d, J=2.2 Hz, 1H), 9.07-9.40 (m, 1H). MS m/z 256 (M+H)$^+$ Step E: e). (±)-N-{5-[((3R,4R)-4-(4-Bromo-phenyl)-3-hydroxy-piperidine-1-carbonyl]-2-chlorophenyl}-6-isopropylamino-nicotinamide O-(benzotriazol-1-yl)-N,N,N',N'-tetramethyluronium hexafluorophosphate (HBTU), (0.135 g, 0.36 mmol) was added to mixture of 4-chloro-3-[(6-isopropylamino-pyridine-3-carbonyl)-amino]-benzoic acid (0.10 g, 0.30 mmol), (±)-(3R,4R)-4-(4-bromo-phenyl)-piperidin-3-ol hydrochloride (0.088 g, 0.30 mmol) and N,N-diisopropylethylamine (0.157 ml, 0.90 mmol) in DCM (10 ml). The reaction was stirred for 1 hour at room temperature before 1M $Na_2CO_3$ (20 ml) was added. The organics were extracted with DCM (2×30 ml). The combined organic layers were dried over $MgSO_4$, filtered and concentrated. The residue was purified by column chromatography over silica gel with a gradient of MeOH in DCM from 0 to 4%. The product was recrystallized from acetonitrile to yield (±)-N-{5-[(3R,4R)-4-(4-bromo-phenyl)-3-hydroxy-piperidine-1-carbonyl]-2-chloro-phenyl}-6-isopropylamino-nicotinamide as a white solid. $^1$H NMR (300 MHz, DMSO-$d_6$) δ ppm 1.17 (d, J=6.5 Hz, 6H), 1.57-1.85 (m, 2H), 2.55-2.68 (m, 1H), 2.71-3.00 (m, 2H), 3.03-3.22 (m, 0.5H), 3.48-3.68 (m, 1.5H), 3.69-3.85 (m, 0.5H), 4.10 (sept, J=6.5 Hz, 1H), 4.42-4.75 (m, 1H), 4.80-5.08 (m, 1H), 6.50 (d, J=8.8 Hz, 1H), 7.12 (d, J=7.6 Hz, 1H), 7.27 (d, J=8.4 Hz, 2H), 7.33 (dd, J=8.2, 1.3 Hz, 1H), 7.47 (d, J=8.4 Hz, 2H), 7.62 (d, J=8.2 Hz, 1H), 7.70 (d, J=1.8 Hz, 1H), 7.89 (dd, J=6.8, 2.2, 1 H), 8.66 (d, J=2.2 Hz, 1H), 9.76 (s, 1H). MS m/z 528× (M+H)$^+$ Step F: (±)-N-(2-chloro-5-((3R,4R)-3-hydroxy-4-(4-(1-methyl-1H-pyrazol-5-yl)phenyl)piperidine-1-carbonyl)phenyl)-6-(isopropylamino)nicotinamide (±)-N-{5-[(3R,4R)-4-(4-bromo-phenyl)-3-hydroxy-piperidine-1-carbonyl]-2-chloro-phenyl}-6-isopropylamino-nicotinamide (0.128 g, 0.224 mmol), was dissolved in 1,4-dioxane (5 ml) and solution bubbled with nitrogen. While maintaining the nitrogen bubbling, 1M $Na_2CO_3$ (1.0 ml, 1.00 mmol) was added followed by 1-methyl-1H-pyrazole-5-boronic acid pinacol ester (0.096 g, 0.450 mmol) and $PdCl_2(PPh_3)_2$ (0.010 g, 0.011 mmol). The reaction mixture was then refluxed under nitrogen atmosphere for 3 hours and then allowed to cool to room temperature. Water (20 ml) was added, and organics extracted with ethyl acetate (50 ml). The organic layer was dried over $MgSO_4$, filtered and concentrated to a brown residue. The residue was purified by column chromatography over silica gel eluting with a gradient of MeOH in DCM from 0 to 3%. The product fractions were combined and concentrated under reduced pressure. The resulting residue was recrystallized from acetonitrile to yield (±)-N-(2-chloro-5-{(3R,4R)-3-hydroxy-4-[4-(2-methyl-2H-pyrazol-3-yl)-phenyl]-piperidine-1-carbonyl}-phenyl)-6-isopropylamino-nicotinamide as white solid.

$^1$H NMR (300 MHz, DMSO-$d_6$) δ ppm 1.17 (d, J=6.5 Hz, 6H), 1.61-1.94 (m, 2H), 2.69 (dd, J=16.2, 9.9 Hz, 1.5H), 2.83 (br. s., 0.5H), 2.96 (br. s., 0.5H), 3.17 (br. s., 0.5H), 3.43-3.80 (m, 2H), 3.85 (s, 3H), 4.10 (dq, J=13.2, 6.6 Hz, 1H), 4.52 (br. s., 0.5H), 4.68 (br. s., 0.5H), 4.90 (br. s., 0.5H), 5.03 (br. s., 0.5H), 6.37 (d, J=1.8 Hz, 1H), 6.50 (d, J=8.9 Hz, 1H), 7.12 (d, J=7.7 Hz, 1H), 7.26-7.38 (m, 1H), 7.38-7.53 (m, 5H), 7.63 (d, J=8.1 Hz, 1H), 7.72 (d, J=1.8 Hz, 1H), 7.90 (dd, J=8.8, 2.2 Hz, 1H), 8.67 (d, J=2.2 Hz, 1H), 9.76 (s, 1H). MS m/z 573 (M+H)$^+$ Example 12

Compound #89

N-(2-methyl-5-(4-(4-(1-methyl-1H-pyrazol-4-yl) phenyl)piperidine-1-carbonyl)phenyl)cyclopropanecarboxamide

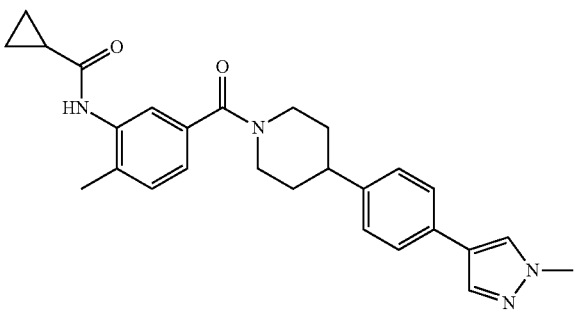 [SMILES: Cc1ccc(C(=O)N2CCC(c3ccc(-c4cnn(C)c4)cc3)CC2)cc1NC(=O)C1CC1]

Step A: 4-(4-Bromo-phenyl)-4-hydroxy-piperidine-1-carboxylic acid methyl ester

A solution of methyl chloroformate (1 ml, 11.7 mmol) in DCM (10 ml) was added dropwise to an ice cold solution of 4-(4-bromo-phenyl)-piperidin-4-ol (3.0 g, 11.7 mmol) and TEA (1.95 ml, 14.0 mmol) in DCM (30 ml) under nitrogen atmosphere. The mixture was stirred for 4 hours allowing the temperature to come to ambient. The reaction solution was then concentrated and residue partitioned between 1M HCl (50 ml) and ethyl acetate (50 ml). The organic layer was washed with brine, dried over $MgSO_4$, filtered and concentrated to dryness. The residue was purified by column chromatography over silica gel with a gradient of MeOH in DCM from 0 to 5%, to yield 4-(4-bromo-phenyl)-4-hydroxy-piperidine-1-carboxylic acid methyl ester. $^1$H NMR (300 MHz, DMSO-$d_6$) δ ppm 1.57 (d, J=12.7 Hz, 2H), 1.81 (dt, J=12.7, 4.7, 2 H), 3.08-3.29 (m, 2H), 3.61 (s, 3H), 3.83-3.96 (m, 2H), 5.20 (s, 1H), 7.44 (d, J=8.7 Hz, 2H), 7.51 (d, J=8.7 Hz, 2H). MS m/z 314 (M+H)$^+$ Step B: 4-(4-Bromo-phenyl)-piperidine-1-carboxylic acid methyl ester Triethylsilane (4.5 ml, 27.7 mmol) was added to a solution of 4-(4-bromo-phenyl)-4-hydroxy-piperidine-1-carboxylic acid methyl ester (3.48 g, 11.5 mmol) in TFA (40 ml). The solution was stirred at 60° C. for 16 hours. The reaction mixture was then concentrated to dryness. Residual TFA was co-evaporated with toluene (3×80 ml). The residue was purified by column chromatography over silica gel with a gradient of ethyl acetate in heptane from 0 to 100% to yield 4-(4-bromo-phenyl)-piperidine-1-carboxylic acid methyl ester. MS m/z 298 (M+H)$^+$ Step C: 4-(4-Bromo-phenyl)-piperidinium hydroiodide Trimethylsilyl iodide (4.9 ml, 33.2 mmol) was added to a solution of 4-(4-bromo-phenyl)-piperidine-1-carboxylic acid methyl ester (3.30 g, 11.1 mmol) in DCM (60 ml). The mixture was refluxed overnight and then allowed to cool to room temperature. Diethyl ether (100 ml) was added to ensure complete precipitation of the resulting salt. Solid 4-(4-Bromo-phenyl)-piperidinium hydroiodide was recovered by filtration. MS m/z 240 (M+H)+

Step D: (3-Amino-4-methyl-phenyl)-[4-(4-bromo-phenyl)-piperidin-1-yl]-methanone

A flask was charged with 4-(4-bromo-phenyl)-piperidinium hydroiodide (2.12 g, 5.76 mmol) and 3-amino-4-methylbenzoic acid (0.871 g, 5.76 mmol). DCM (30 ml) and N,N-diisopropylethylamine (4.0 ml, 23.5 mmol) were added with stirring. Once an homogenous solution was obtained, O-(benzotriazol-1-yl)-N,N,N'—N'-tetramethyluronium hexafluorophosphate (H BTU), (2.62 g, 6.92 mmol) was added. The reaction was stirred for 1 hour at room temperature before 1M $Na_2CO_3$ (50 ml) was added. The organics were extracted with DCM (2×50 ml). The combined organic layers were dried over $MgSO_4$, filtered and concentrated to a residue mixture. Purification of the residue mixture over silica gel with a gradient of MeOH in DCM from 0 to 4% and then triturating in diethyl ether yielded (3-amino-4-methyl-phenyl)-[4-(4-bromo-phenyl)-piperidin-1-yl]-methanone as an off white solid. $^1$H NMR (300 MHz, DMSO-$d_6$) δ ppm 1.46-1.61 (m, 2H), 1.67-1.90 (m, 2H), 2.07 (s, 3H), 2.74-3.16 (m, 3H), 3.85 (br s, 1H), 4.54 (br s, 1H), 4.98 (s, 2H), 6.49 (dd, J=7.5, 1.5 Hz, 1H), 6.64 (d, J=1.5 Hz, 1H), 6.96 (d, J=7.5 Hz, 1H), 7.25 (d, J=8.4 Hz, 2H), 7.49 (d, J=8.4 Hz, 2H). MS m/z 373 (M+H)+

Step E: (3-Amino-4-methyl-phenyl)-{4-[4-(1-methyl-1H-pyrazol-4-yl)-phenyl]-piperidin-1-yl}-methanone To a solution of (3-amino-4-methyl-phenyl)-[4-(4-bromo-phenyl)-piperidin-1-yl]-methanone (0.602 g, 1.613 mmol), in dioxane (10 ml) were added sequentially while bubbling nitrogen, 1M $Na_2CO_3$ (3.0 ml, 3.00 mmol), 1-methyl-1H-pyrazole-4-boronic acid pinacol ester (0.685 g, 3.22 mmol) and $PdCl_2(PPh_3)_2$ (0.057 g, 0.081 mmol). The reaction mixture was then refluxed under nitrogen atmosphere for 3 hours and then allowed to cool to room temperature. Water (50 ml) was added, and organics extracted with ethyl acetate (2×50 ml). The organic layer was dried over $MgSO_4$, filtered and concentrated to a brown residue. The residue was purified by column chromatography over silica gel with a gradient of MeOH in DCM from 0 to 4%. The product fractions were combined and concentrated under reduced pressure to yield (3-amino-4-methyl-phenyl)-{4-[4-(1-methyl-1H-pyrazol-4-yl)-phenyl]-piperidin-1-yl}-methanone as foam. $^1$H NMR (300 MHz, DMSO-$d_6$) δ ppm 1.49-1.63 (m, 2H), 1.70-1.91 (m, 2H), 2.06 (s, 3H), 2.71-3.16 (m, 3H), 3.85 (s, 3H), 3.90 (br s, 1H), 4.58 (br s, 1H), 5.00 (s, 2H), 6.50 (dd, J=7.5, 1.5 Hz, 1H), 6.65 (d, J=1.5 Hz, 1H), 6.96 (d, J=7.5 Hz, 1H), 7.24 (d, J=8.4 Hz, 2H), 7.48 (d, J=8.4 Hz, 2H), 7.81 (s, 1H), 8.08 (s, 1H). MS m/z 375 (M+H)+

Step F: N-(2-methyl-5-(4-(4-(1-methyl-1H-pyrazol-4-yl)phenyl)piperidine-1-carbonyl)phenyl)cyclopropanecarboxamide To an ice cold solution of (3-amino-4-methyl-phenyl)-{4-[4-(1-methyl-1H-pyrazol-4-yl)phenyl]-piperidin-1-yl}-methanone (0.089 g, 024 mmol) and triethylamine (0.1 ml, 0.72 mmol) in DCM (3 ml) was added cyclopropanecarbonyl chloride (0.025 ml, 0.24 mmol) under nitrogen atmosphere. The reaction was allowed to warm up to room temperature and stirring maintained for 2 hours. The mixture was then concentrated to dryness and product crystallized from acetonitrile (2 ml). N-(2-methyl-5-(4-(4-(1-methyl-1H-pyrazol-4-yl)phenyl)piperidine-1-carbonyl)phenyl)cyclopropanecarboxamide was isolated as a white solid.
$^1$H NMR (300 MHz, DMSO-$d_6$) δ ppm 0.63-0.80 (m, 4H), 1.39-1.61 (m, 2H), 1.71 (br. s., 2H), 2.19 (s, 3H), 2.72 (t, J=12.0 Hz, 2H), 3.03 (br. s., 2H), 3.68 (br. s., 1H), 3.78 (s, 3H), 4.51 (br. s., 1H), 6.99-7.10 (m, 1H), 7.12-7.26 (m, 3H), 7.41 (d, J=8.1 Hz, 2H), 7.74 (s, 1H), 8.01 (s, 1H), 9.51 (s, 1H). MS m/z 443 (M+H)+

Example 13

Compound #32

6-(isopropylamino)-N-(2-methyl-5-(4-(4-(1-methyl-1H-pyrazol-4-yl)phenyl)piperidine-1-carbonyl)phenyl)nicotinamide

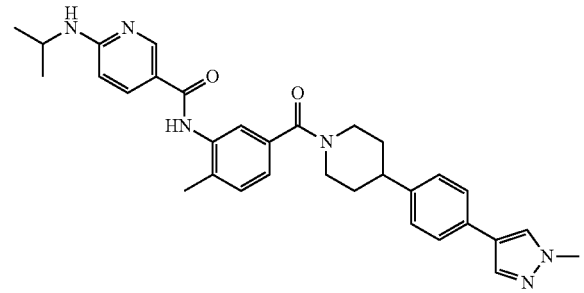 [SMILES: Cc1ccc(C(=O)N2CCC(c3ccc(-c4cnn(C)c4)cc3)CC2)cc1NC(=O)c1ccc(NC(C)C)nc1]

Step A: 4-(4-Bromo-phenyl)-1,2,3,6-tetrahydro-pyridinium Trifluoroacetate

A solution of 4-(4-bromophenyl)-piperidin-4-ol (19.2 g, 75 mmol) in TFA (200 ml) was refluxed for 3 hours. The mixture was allowed to cool to room temperature and concentrated in vacuo. The residue was taken in toluene and again concentrated (2×100 ml) to remove residual TFA, to yield a white solid. MS m/z 238 (M+H)+

Step B: 4-[4-(1-Methyl-1H-pyrazol-4-yl)-phenyl]-1,2,3,6-tetrahydro-pyridine

To a solution of 4-(4-bromo-phenyl)-1,2,3,6-tetrahydropyridinium trifluoroacetate (10 g, 28.4 mmol) in dioxane (115 ml) were added successively 1M $Na_2CO_3$ (57 ml, 57 mmol), 1-methyl-1H-pyrazole-4-boronic acid pinacol ester (7.682 g, 36.9 mmol) and $PdCl_2(PPh_3)_2$ (0.997 g, 1.42 mmol). The mixture was degassed by bubbling nitrogen for 15-20 minutes, and then heated at 100° C. under nitrogen atmosphere for 3 hours. The reaction was allowed to cool to room temperature and diluted with water (50 ml). The organics were extracted with ethyl acetate (2×150 ml), dried over $MgSO_4$, filtered and concentrated. The residue was purified over silica gel column with a gradient of MeOH in DCM from 0 to 8% to yield the product as a white solid. $^1$H NMR (300 MHz, DMSO-$d_6$) δ ppm 2.53-2.61 (m, 2H), 3.15-3.22 (m, 2H), 3.59-3.66 (m, 2H), 3.87 (s, 3H), 6.21 (br s, 1H), 7.44 (d, J=8.3 Hz, 2H), 7.55 (d, J=8.3 Hz, 2H), 7.80 (s, 1H), 7.86 (s, 1H), 8.14 (s, 1H). MS m/z 240 (M+H)+

Step C: 4-[4-(1-Methyl-1H-pyrazol-4-yl)-phenyl]-piperidine

A solution of 4-[4-(1-methyl-1H-pyrazol-4-yl)-phenyl]-1,2,3,6-tetrahydro-pyridine (4.5 g, 18.8 mmol) in MeOH (75 ml) was hydrogenated at atmospheric pressure over 10% Pd/C (0.45 g) overnight. The catalyst was filtered off through a pad of CELITE. The filtrate was concentrated in vacuo to yield an oil. $^1$H NMR (300 MHz, DMSO-$d_6$) δ ppm 1.73 (dt, J=13.3, 3.8 Hz, 2H), 1.81-1.92 (m, 2H), 2.75 (tt, J=7.4, 3.4 Hz, 1H), 2.89 (dt, J=12.4, 2.4 Hz, 1H), 3.22-3.33 (m, 2H), 3.85 (s, 3H), 7.20 (d, J=8.1 Hz, 2H), 7.49 (d, J=8.1 Hz, 2H), 7.80 (s, 1H), 7.80 (s, 1H), 8.07 (s, 1H). MS m/z 242 (M+H)$^+$

Step D: (3-Amino-4-methyl-phenyl)-{4-[4-(1-methyl-1H-pyrazol-4-yl)-phenyl]-piperidin-1-yl}methanone To a solution of 3-amino-4-methylbenzoic acid (3.33 g, 22.0 mmol), 4-[4-(1-methyl-1H-pyrazol-4-yl)-phenyl]-piperidine (5.29 g, 21.9 mmol) and N,N-diisopropylethylamine (7.7 ml, 44.0 mmol) in DCM (60 ml) was added O-(benzotriazol-1-yl)-N,N,N'—N'-tetramethyluronium hexafluorophosphate (HBTU), (10 g, 26.4 mmol). The reaction was stirred for 2 hours at room temperature before 1M Na$_2$CO$_3$ (150 ml) was added. The organics were extracted with DCM (2×150 ml). The combined organic layers were dried over MgSO$_4$, filtered and concentrated to a residue mixture. Purification of the residue mixture over silica gel with a gradient of MeOH in DCM from 0 to 4% yielded an amorphous solid, which was recrystallized from acetonitrile (20 ml) to yield (3-amino-4-methyl-phenyl)-{4-[4-(1-methyl-1H-pyrazol-4-yl)-phenyl]-piperidin-1-yl}-methanone as a white solid. $^1$H NMR (300 MHz, DMSO-$d_6$) δ ppm 1.46-1.65 (m, 2H), 1.67-1.91 (m, 2H), 2.69-2.89 (m, 2H), 2.89-3.14 (m, 1H), 3.68-4.00 (m, 1H), 3.85 (s, 3H), 4.36-4.78 (m, 1H), 5.00 (s, 2H), 6.50 (dd, J=7.4, 1.3 Hz, 1H), 6.65 (d, J=1.3 Hz, 1H), 6.96 (d, J=8.1 Hz, 1H), 7.24 (d, J=8.1 Hz, 2H), 7.48 (d, J=8.1 Hz, 2H), 7.78 (s, 1H), 8.08 (s, 1H). MS m/z 375 (M+H)$^+$

Step E: 6-Chloro-N-(2-methyl-5-{4-[4-(1-methyl-1H-pyrazol-4-yl)-phenyl]-piperidine-1-carbonyl}-phenyl)-nicotinamide (3-Amino-4-methyl-phenyl)-{4-[4-(1-methyl-1H-pyrazol-4-yl)-phenyl]-piperidin-1-yl}-methanone (7.0 g 18.8 mmol) was dissolved in DCM (70 ml). Pyridine (3 ml, 37.6 mmol) was added and mixture cooled in ice/water bath under nitrogen atmosphere. A solution of 6-chloronicotinoyl chloride (3.97 g, 22.6 mmol) in DCM (30 ml) was then added dropwise. The mixture was stirred 2 hours allowing the mixture to warm up to room temperature. The mixture was then diluted with DCM (100 ml) and 1M Na$_2$CO$_3$ (250 ml). The organic layer was separated, dried over MgSO$_4$, filtered and concentrated to dryness. The residue was flash chromatographed over silica gel with a gradient of MeOH in DCM from 0 to 5%, and recrystallized from acetonitrile to yield a white solid. $^1$H NMR (300 MHz, DMSO-$d_6$) δ ppm 1.52-1.71 (m, 2H), 1.71-1.95 (m, 2H), 2.29 (s, 3H), 2.69-2.97 (m, 2H), 3.00-3.29 (m, 1H), 3.67-3.94 (m, 1H), 3.85 (s, 3H), 4.43-4.84 (m, 1H), 7.21-7.31 (m, 3H), 7.37 (d, J=7.8 Hz, 1H), 7.45-7.51 (m, 3H), 7.72 (d, J=8.3 Hz, 1H), 7.89 (s, 1H), 8.07 (s, 1H), 8.37 (dd, J=8.3, 2.3 Hz, 1H), 8.98 (d, J=2.0 Hz, 1H), 10.23 (s, 1H). MS m/z 514 (M+H)$^+$

Step F: 6-(isopropylamino)-N-(2-methyl-5-(4-(4-(1-methyl-1H-pyrazol-4-yl)phenyl)piperidine-1-carbonyl)phenyl)nicotinamide A sealed reaction vessel was charged with 6-chloro-N-(2-methyl-5-{4-[4-(1-methyl-1H-pyrazol-4-yl)-phenyl]-piperidine-1-carbonyl}-phenyl)-nicotinamide (7.25 g, 14.1 mmol) and isopropylamine (9 ml, 105.0 mmol) in 1,4-dioxane (30 ml). The mixture was heated to 150° C. for 16 hours and then allowed to cool to room temperature. The reaction mixture was concentrated to dryness. The residue was crystallized from acenotrile to yield 6-(isopropylamino)-N-(2-methyl-5-(4-(4-(1-methyl-1H-pyrazol-4-yl)phenyl)piperidine-1-carbonyl)phenyl)nicotinamide.

$^1$H NMR (300 MHz, DMSO-$d_6$) δ ppm 1.14-1.22 (m, 6H), 1.53-1.70 (m, 2H), 1.80 (br. s., 2H), 2.27 (s, 3H), 2.80 (t, J=11.5 Hz, 2H), 3.13 (br. s., 1H), 3.79 (br. s., 1H), 3.85 (s, 3H), 4.02-4.22 (m, 1H), 4.63 (br. s., 1H), 6.49 (d, J=8.8 Hz, 1H), 7.04 (d, J=7.6 Hz, 1H), 7.17-7.30 (m, 3H), 7.33 (d, J=8.0 Hz, 1H), 7.40-7.52 (m, 3H), 7.81 (s, 1H), 7.89 (dd, J=8.8, 2.3 Hz, 1H), 8.08 (s, 1H), 8.66 (d, J=2.1 Hz, 1H), 9.57 (s, 1H). MS m/z 537 (M+H)$^+$

Example 14

Compound #182

1-isopropyl-N-(2-methyl-5-(4-(4-(1-methyl-1H-pyrazol-4-yl)phenyl)piperidine-1-carbonyl)phenyl)piperidine-4-carboxamide

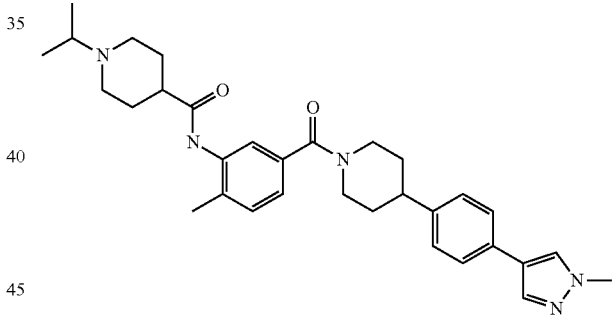

Step A: 4-(2-Methyl-5-{4-[4-(1-methyl-1H-pyrazol-4-yl)-phenyl]-piperidine-1-carbonyl}-phenylcarbamoyl)-piperidine-1-carboxylic acid tert-butyl ester N-t-Butoxycarbonyl-piperidine-4-carboxylic acid (0.628 g, 2.74 mmol) was treated with 1-chloro-N,N,2-trimethylpropenylamine (0.542 ml, 4.10 mmol) in DCM (10 ml) at room temperature. The mixture was concentrated to dryness after 1 hour. The resulting acid chloride was re-dissolved in DCM (10 ml) and added to an ice cold solution of (3-amino-4-methyl-phenyl)-{4-[4-(1-methyl-1H-pyrazol-4-yl)-phenyl]-piperidin-1-yl}-methanone (0.788 g, 2.10 mmol) and pyridine (0.51 ml, 6.30 mmol) in DCM (10 ml). The reaction was continued for 2 hours at room temperature and then quenched with 1M Na$_2$CO$_3$ (30 ml). The residue was extracted with DCM (2×50 ml), dried over MgSO$_4$, filtered and concentrated to dryness. Flash column chromatography of the residue over silica gel with a gradient of MeOH in DCM from 0 to 5%, and subsequent crystallization from acetonitrile yielded the product as a white solid. $^1$H NMR (300 MHz, DMSO-$d_6$) δ ppm 1.41 (s, 9H), 1.44-1.68 (m, 4H), 1.71-1.93 (m, 4H), 2.22 (s, 3H), 2.56-2.68 (m, 1H), 2.70-2.94 (m, 4H), 3.00-3.33 (m, 1H), 3.64-3.91 (m, 1H), 3.85 (s, 3H), 3.94-4.07 (m, 2H), 4.41-4.78 (m, 1H), 7.15 (d, J=7.7 Hz, 1H), 7.22-7.30 (m, 3H), 7.43-7.52 (m, 3H), 7.81 (s, 1H), 8.08 (s, 1H). MS m/z 486 (M+H)$^+$ Step B: Piperidine-4-carboxylic acid (2-methyl-5-{4-[4-(1-methyl-1H-pyrazol-4-yl)-phenyl]-piperidine-1-carbonyl}-phenyl)-amide To a solution of 4-(2-methyl-5-{4-[4-(1-methyl-1H-pyrazol-4-yl)-phenyl]-piperidine-1-carbonyl}-phenylcarbamoyl)-piperidine-1-carboxylic acid tert-butyl ester (1.07 g, 1.83 mmol) in 1,4-dioxane (10 ml) was added dry 4N HCl in dioxane (4.55 ml, 18.20 mmol). The mixture was stirred 2 hours at room temperature and then concentrated under reduced pressure. The residue was partitioned between 1M NaOH (15 ml) and DCM (30 ml). The organic layer was separated, dried over MgSO$_4$, filtered and concentrated to a solid residue that was recrystallized from acetonitrile to yield the product as a white solid. $^1$H NMR (300 MHz, DMSO-$d_6$) δ ppm 1.46-1.88 (m, 8H), 2.22 (s, 3H), 2.48-2.60 (m, 1H), 2.69-3.30 (m, 8H), 3.68-3.91 (m, 1H), 3.85 (s, 3H), 4.46-4.77 (m, 1H), 7.14 (d, J=7.7 Hz, 1H), 7.22-7.30 (m, 3H), 7.44-7.52 (m, 3H), 7.81 (s, 1H), 8.08 (s, 1H). MS m/z 486 (M+H)$^+$ Step C: 1-isopropyl-N-(2-methyl-5-(4-(4-(1-methyl-1H-pyrazol-4-yl)phenyl)piperidine-1-carbonyl)phenyl)piperidine-4-carboxamide Acetone (0.023 ml, 0.309 mmol) was added to a solution of piperidine-4-carboxylic acid (2-methyl-5-{4-[4-(1-methyl-1H-pyrazol-4-yl)-phenyl]-piperidine-1-carbonyl}-phenyl)-amide (0.10 g, 0.206 mmol) in DCE (5 ml) at room temperature. Sodium triacetoxyborohydride (0.087 g, 0.412 mmol) was then added and reaction stirred overnight. 1M NaOH (10 ml) was added with stirring and organics extracted with DCM (2×50 ml). The extracts were dried over MgSO$_4$, filtered and concentrated to an oil which was purified over silica gel with a gradient of MeOH in DCM from 0 to 20%. The product fractions were collected and concentrated to a semi-solid. Triturating with diethyl ether yielded the title compound as a powder.
$^1$H NMR (300 MHz, DMSO-$d_6$) δ ppm 1.01 (d, J=5.9 Hz, 6H), 1.52-1.78 (m, 5H), 1.82 (br. s., 3H), 2.23 (s, 3H), 2.43 (br. s., 1H), 2.73-2.97 (m, 4H), 3.36 (br. s., 4H), 3.72 (br. s., 1H), 3.86 (s, 3H), 4.39-4.79 (m, 1H), 7.15 (d, J=7.4 Hz, 1H), 7.26 (t, J=7.6 Hz, 3H), 7.38-7.60 (m, 3H), 7.81 (s, 1H), 8.08 (s, 1H), 9.31 (br. s., 1H). MS m/z 528 (M+H)$^+$ Example 15

Compound #255

6-chloro-N-(2-ethyl-5-(4-(4-(1-methyl-1H-pyrazol-4-yl)phenyl)piperidine-1-carbonyl)phenyl)nicotinamide

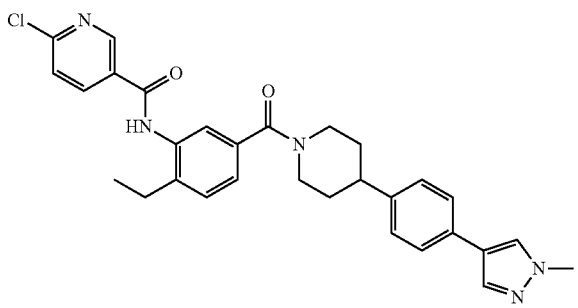

Step A: 4-Ethyl-3-nitro-benzoic acid

A mixture of 4-ethylbenzoic acid (0.60 g, 4.00 mmol) in 97% H$_2$SO$_4$ (7 ml) was cooled in ice bath. A solution of nitric acid (0.334 ml, 4.80 mmol) in 97% H$_2$SO$_4$ (2 ml) was added dropwise. The reaction was continued overnight at room temperature and then poured onto iced water (100 g). The precipitate was filtered off and washed with water. The solid was taken up in ethyl acetate, dried over MgSO$_4$, filtered and concentrated to a white solid. $^1$H NMR (300 MHz, CDCl$_3$) δ ppm 1.35 (t, J=7.4 Hz, 3H), 3.02 (q, J=7.4 Hz, 2H), 7.54 (d, J=8.1 Hz, 1H), 8.26 (dd, J=8.1 Hz, 1.7 Hz, 1H), 8.62 (d, J=1.7 Hz, 1H), 11.90 (s, 1H). MS m/z 196 (M+H)$^+$ Step B: 3-Amino-4-ethyl-benzoic acid A solution of 4-ethyl-3-nitro-benzoic acid (0.78 g, 4.00 mmol) in MeOH (15 ml) was hydrogenated overnight at atmospheric pressure, over 10% Pd/C (0.10 g). The catalyst was filtered off and filtrate concentrated in vacuo to yield 3-amino-4-ethyl-benzoic acid as a light beige solid. MS m/z 166 (M+H)$^+$ Step C: (3-Amino-4-ethyl-phenyl)-{4-[4-(1-methyl-1H-pyrazol-4-yl)-phenyl]-piperidin-1-yl}-methanone To a solution of 3-amino-4-ethyl-benzoic acid (0.40 g, 2.42 mmol), 4-[4-(1-methyl-1H-pyrazol-4-yl)-phenyl]-piperidine (0.58 g, 2.42 mmol) and N,N-diisopropylethylamine (0.85 ml, 4.84 mmol) in DCM (15 ml) was added 0-(benzotriazol-1-yl)-N,N,N'—N'-tetramethyluronium hexafluorophosphate (HBTU), (1.10 g, 2.90 mmol). The reaction was stirred for 2 hours at room temperature before 1M Na$_2$CO$_3$ (50 ml) was added. The organics were extracted with DCM (2×50 ml). The combined organic layers were dried over MgSO$_4$, filtered and concentrated to a residue mixture. Purification over silica gel with a gradient of MeOH in DCM from 0 to 4% and then, recrystallization from acetonitrile (5 ml), yielded (3-amino-4-ethyl-phenyl)-{4-[4-(1-methyl-1H-pyrazol-4-yl)-phenyl]-piperidin-1-yl}-methanone as a white solid. $^1$H NMR (300 MHz, DMSO-$d_6$) δ ppm 1.13 (t, J=7.4 Hz, 3H), 1.45-1.56 (m, 2H), 1.68-1.91 (m, 2H), 2.44 (q, J=7.4 Hz, 2H), 2.70-3.05 (m, 3H), 3.72-3.98 (m, 1H), 3.84 (s, 3H), 4.37-4.76 (m, 1H), 5.00 (s, 2H), 6.53 (d, J=7.5 Hz, 1H), 6.65 (s, 1H), 6.96 (d, J=7.6 Hz, 1H), 7.23 (d, J=8.1 Hz, 2H), 7.48 (d, J=8.1 Hz, 2H), 7.80 (s, 1H), 8.07 (s, 1H). MS m/z 389 (M+H)$^+$ Step D: 6-chloro-N-(2-ethyl-5-(4-(4-(1-methyl-1H-pyrazol-4-yl)phenyl)piperidine-1-carbonyl)phenyl)nicotinamide Solid 6-chloronicotinoyl chloride (0.164 g, 0.93 mmol) was added to an ice cold solution of (3-Amino-4-ethyl-phenyl)-{4-[4-(1-methyl-1H-pyrazol-4-yl)-phenyl]-piperidin-1-yl}-methanone (0.30 g 0.77 mmol) and pyridine (0.116 ml, 1.44 mmol) in DCM (5 ml) under nitrogen atmosphere. The mixture was stirred 2 hours allowing the mixture to warm up to room temperature. The solution was then diluted with DCM (20 ml) and washed with 1M Na$_2$CO$_3$ (20 ml). The organic layer dried over MgSO$_4$, filtered and concentrated to dryness. The residue flash chromatographed over silica gel with a gradient of MeOH in DCM from 0 to 4%, and recrystallized from acetonitrile to yield the title compound as a white solid.

$^1$H NMR (300 MHz, DMSO-d$_6$) δ ppm 1.17 (t, J=7.5 Hz, 3H), 1.53-1.72 (m, 2H), 1.72-1.98 (m, 2H), 2.67 (q, J=7.4 Hz, 2H), 2.81 (t, J=11.8 Hz, 2H), 3.18 (br. s., 1H), 3.77 (br. s., 1H), 3.86 (s, 3H), 4.63 (br. s., 1H), 7.26 (d, J=8.1 Hz, 2H), 7.30-7.55 (m, 4H), 7.72 (d, J=8.2 Hz, 1H), 7.67 (d, J=8.4 Hz, 1H), 7.81 (s, 1H), 8.08 (s, 1H), 8.25-8.42 (m, 1H), 8.93-9.06 (m, 1H), 10.21 (s, 1H). MS m/z 528 (M+H)$^+$ Example 16

Compound #256

N-(2-ethyl-5-(4-(4-(1-methyl-1H-pyrazol-4-yl)phenyl)piperidine-1-carbonyl)phenyl)-6-(isopropylamino)nicotinamide

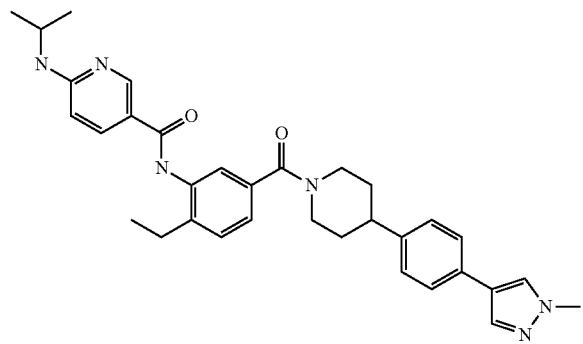 [SMILES: CCc1ccc(C(=O)N2CCC(c3ccc(-c4cnn(C)c4)cc3)CC2)cc1NC(=O)c1ccc(NC(C)C)nc1]

A sealed reaction vessel was charged with 6-chloro-N-(2-ethyl-5-(4-(4-(1-methyl-1H-pyrazol-4-yl)phenyl)piperidine-1-carbonyl)phenyl)nicotinamide (0.132 g, 0.25 mmol) and isopropylamine (1.5 ml, 17.5 mmol) in 1,4-dioxane (5 ml). The mixture was heated to 150° C. for 16 hours and then allowed to cool to room temperature. The reaction mixture was concentrated to dryness. The residue was crystallized from acetonitrile to yield the title compound.

$^1$H NMR (300 MHz, DMSO-d$_6$) δ ppm 1.00-1.11 (m, 9H), 1.42-1.60 (m, 2H), 1.69 (br. s., 2H), 2.55 (q, J=7.4 Hz, 2H), 2.61-2.89 (m, 2H), 3.04 (br. s., 1H), 3.67 (br. s., 1H), 3.75 (s, 3H), 3.89-4.11 (m, 1H), 4.51 (br. s., 1H), 6.38 (d, J=8.8 Hz, 1H), 6.91 (d, J=7.6 Hz, 1H), 7.09-7.22 (m, 3H), 7.22-7.32 (m, 2H), 7.37 (d, J=8.1 Hz, 2H), 7.70 (s, 1H), 7.78 (dd, J=8.8, 2.2 Hz, 1H), 7.97 (s, 1H), 8.55 (d, J=1.9 Hz, 1H), 9.47 (s, 1H). MS m/z 551 (M+H)$^+$ Example 17

Compound #273

N-(2-(dimethylamino)-5-(4-(4-(1-methyl-1H-pyrazol-4-yl)phenyl)piperidine-1-carbonyl)phenyl)cyclopropanecarboxamide

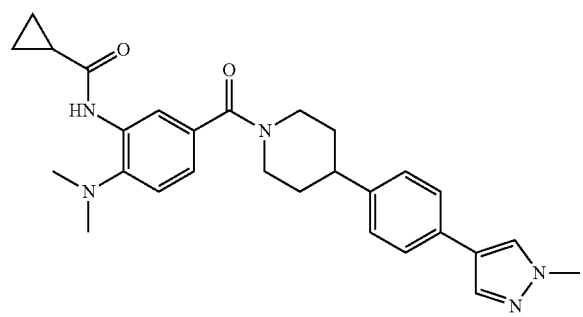 [SMILES: CN(C)c1ccc(C(=O)N2CCC(c3ccc(-c4cnn(C)c4)cc3)CC2)cc1NC(=O)C1CC1]

Step A: (4-Fluoro-3-nitro-phenyl)-{4-[4-(1-methyl-1H-pyrazol-4-yl)-phenyl]-piperidin-1-yl}-methanone To a solution of 4-fluoro-3-nitro-benzoic acid (0.102 g, 0.54 mmol), 4-[4-(1-Methyl-1H-pyrazol-4-yl)-phenyl]-piperidine (0.143 g, 0.594 mmol) and N,N-diisopropylethylamine (0.188 ml, 1.08 mmol) in DCM (5 ml) was added 0-(benzotriazol-1-yl)-N,N,N'—N'-tetramethyluronium hexafluorophosphate (HBTU), (0.246 g, 0.648 mmol). The reaction was stirred for 1 hour at room temperature before 1M Na$_2$CO$_3$ (20 ml) was added. The organics were extracted with DCM (2×20 ml). The combined organic layers were dried over MgSO$_4$, filtered and concentrated to a residue mixture. The residue was purified by column chromatography over silica gel with a gradient of ethyl acetate in heptane from 50 to 100% to yield a solid. $^1$H NMR (300 MHz, DMSO-d$_6$) δ ppm 1.58-1.94 (m, 4H), 2.74-3.00 (m, 2H), 3.12-3.29 (m, 1H), 3.55-3.75 (m, 1H), 3.85 (s, 3H), 4.51-4.74 (m, 1H), 7.27 (d, J=8.1 Hz, 2H), 7.49 (d, J=8.1 Hz, 2H), 7.68 (dd, J=11.2, 8.6 Hz, 1H), 7.48 (d, J=8.1 Hz, 2H), 7.81 (s, 1H), 7.89-7.94 (m, 1H), 8.08 (s, 1H), 8.22 (dd, J=7.2, 2.0 Hz, 1H). MS m/z 409 (M+H)$^+$ Step B: (4-Dimethylamino-3-nitro-phenyl)-{4-[4-(1-methyl-1H-pyrazol-4-yl)-phenyl]-piperidin-1-yl}-methanone A 40% solution of dimethylamine in water (0.187 ml, 1.47 mmol) was added to (4-fluoro-3-nitro-phenyl)-{4-[4-(1-methyl-1H-pyrazol-4-yl)-phenyl]-piperidin-1-yl}-methanone (0.15 g, 0.367 mmol) in MeOH (10 ml). The reaction was stirred for 2 hours at room temperature and concentrated to dryness. The residue was subjected to column chromatography over silica gel with gradient of MeOH in DCM from 0 to 10%. Solid (4-dimethylamino-3-nitro-phenyl)-{4-[4-(1-methyl-1H-pyrazol-4-yl)-phenyl]-piperidin-1-yl}-methanone was recovered by solvent removal. $^1$H NMR (300 MHz, DMSO-d$_6$) δ ppm 1.64 (dq, J=12.2, 2.4 Hz, 2H), 1.74-1.88 (m, 2H), 2.71-2.93 (m, 2H), 2.89 (s, 6H), 2.94-3.14 (m, 1H), 3.75-3.96 (m, 1H), 3.85 (s, 3H), 4.04-4.42 (m, 1H), 7.20 (d, J=8.7 Hz, 1H), 7.26 (d, J=8.1 Hz, 2H), 7.48 (d, J=8.1 Hz, 2H), 7.59 (dd, J=8.7, 1.9 Hz, 1H), 7.81 (s, 1H), 7.86 (d, J=1.8 Hz, 1H), 8.08 (s, 1H). MS m/z 434 (M+H)$^+$ Step C: (3-Amino-4-dimethylamino-phenyl)-M-{4-(1-methyl-1H-pyrazol-4-yl)-phenyl-piperidin-1-yl}-methanone A solution of (4-dimethylamino-3-nitro-phenyl)-{4-[4-(1-methyl-1H-pyrazol-4-yl)-phenyl]-piperidin-1-yl}-methanone (0.63 g, 1.46 mmol) in MeOH (15 ml) was hydrogenated overnight at atmospheric pressure, over 10% Pd/C (0.20 g). The catalyst was filtered off and filtrate concentrated in vacuo to yield an oil. $^1$H NMR (300 MHz, DMSO-d$_6$) δ ppm 1.56 (dq, J=12.4, 3.7 Hz, 2H), 1.71-1.88 (m, 2H), 2.60 (s, 6H), 2.72-3.10 (m, 3H), 3.75-3.96 (m, 1H), 3.85 (s, 3H), 4.04-4.72 (m, 1H), 4.89 (s, 2H), 6.61 (dd, J=7.9, 1.6 Hz, 1H), 6.73 (d, J=1.6 Hz, 1H), 6.92 (d, J=7.9 Hz, 1H), 7.25 (d, J=8.1 Hz, 2H), 7.48 (d, J=8.1 Hz, 2H), 7.81 (s, 1H), 8.08 (s, 1H). MS m/z 404 (M+H)$^+$ Step D: N-(2-(dimethylamino)-5-(4-(4-(1-methyl-1H-pyrazol-4-yl)phenyl)piperidine-1-carbonyl)phenyl)cyclopropanecarboxamide A solution of (3-amino-4-dimethylamino-phenyl)-{4-[4-(1-methyl-1H-pyrazol-4-yl)-phenyl]-piperidin-1-yl}-methanone (0.130 g, 0.322 mmol) and triethylamine (0.090 ml, 0.644 mmol) in DCM (10 ml) was cooled to 0° C. under nitrogen atmosphere. Cyclopropanecarbonyl chloride (0.033 ml, 0.354 mmol) was added and resulting mixture stirred for 2 hours allowing the temperature come to ambient. The reaction was quenched by addition of 1M Na$_2$CO$_3$ (10 ml). The residue was extracted with DCM (2×20 ml), dried over MgSO$_4$, filtered and concentrated. The residue was purified by column chromatography over silica gel with a gradient of MeOH in DCM form 0 to 4% to yield a sticky solid that was triturated with diethyl ether to yield the title compound a powdered solid.

$^1$H NMR (300 MHz, DMSO-d$_6$) δ ppm 0.49-0.64 (m, 4H), 1.35 (d, J=10.6 Hz, 2H), 1.55 (br. s., 2H), 2.28 (br. s., 3H), 2.60 (br. s., 2H), 2.74 (br. s., 2H), 3.10 (s, 6H), 3.63 (s, 4H), 4.30 (br. s., 1H), 6.92 (s, 2H), 7.02 (m, J=8.1 Hz, 2H), 7.25 (m, J=8.0 Hz, 2H), 7.58 (s, 1H), 7.69 (s, 1H), 7.85 (s, 1H), 9.18 (s, 1H). MS m/z 472 (M+H)$^+$ Example 18

Compound #279

6-(isopropylamino)-N-(5-(4-(4-(1-methyl-1H-pyrazol-4-yl)phenyl)piperidine-1-carbonyl)-2-(methylamino)phenyl)nicotinamide

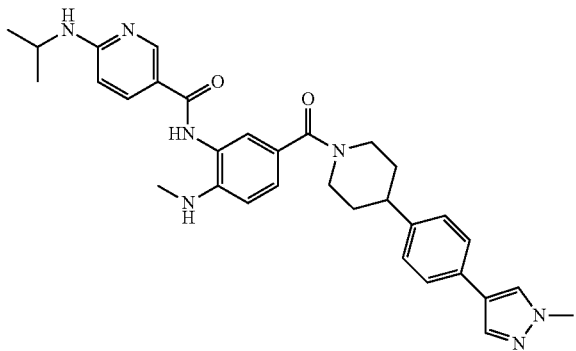 [SMILES: CNc1ccc(C(=O)N2CCC(c3ccc(-c4cnn(C)c4)cc3)CC2)cc1NC(=O)c1ccc(NC(C)C)nc1]

Step A: 4-Methylamino-3-nitro-benzoic acid

A 2M solution of methylamine in THF (6.88 ml, 13.76 mmol) was added to (4-fluoro-3-nitro-benzoic acid (0.51 g, 2.70 mmol) in MeOH (3 ml). The reaction was stirred for 2 hours at room temperature and then concentrated to dryness. The residue was subjected to column chromatography over silica gel with gradient of MeOH in DCM from 0 to 10% to yield 4-methylamino-3-nitro-benzoic acid. $^1$H NMR (300 MHz, DMSO-d$_6$) δ ppm 2.99 (d, J=5.0 Hz, 3H), 6.95 (d, J=8.9 Hz, 1H), 8.01 (d, J=8.9 Hz, 1H), 8.32 (q, J=5.0 Hz, 1H), 8.59 (s, 1H). MS m/z 197 (M+H)$^+$ Step B: (4-Methylamino-3-nitro-phenyl)-{4-[4-(1-methyl-1H-pyrazol-4-yl)-phenyl]-piperidin-1-yl}-methanone To a solution of 4-methylamino-3-nitro-benzoic acid (0.25 g, 1.274 mmol), 4-[4-(1-methyl-1H-pyrazol-4-yl)-phenyl]-piperidine (0.338 g, 1.40 mmol) and N,N-diisopropylethylamine (0.428 ml, 2.46 mmol) in DCM (10 ml) was added O-(benzotriazol-1-yl)-N,N,N'—N'-tetramethyluronium hexafluorophosphate (HBTU), (0.58 g, 1.53 mmol). The reaction was stirred for 1 hour at room temperature before 1M Na$_2$CO$_3$ (20 ml) was added. The organics were extracted with DCM (2×20 ml). The combined organic layers were dried over MgSO$_4$, filtered and concentrated to a residue mixture. The residue was purified by column chromatography over silica gel with a gradient of ethyl acetate in heptane from 50 to 100% to yield a solid. $^1$H NMR (300 MHz, DMSO-d$_6$) δ ppm 1.64 (dq, J=12.6, 3.5 Hz, 2H), 1.75-1.87 (m, 2H), 2.74-2.87 (m, 1H), 2.95-3.15 (m, 3H), 3.00 (d, J=4.9 Hz, 3H), 3.85 (s, 3H), 4.00-4.51 (m, 1H), 7.05 (d, J=8.9 Hz, 1H), 7.26 (d, J=8.0 Hz, 2H), 7.49 (d, J=8.0 Hz, 2H), 7.66 (d, J=8.9 Hz, 1H), 7.81 (s, 1H), 8.08 (s, 1H), 8.16 (s, 1H), 8.37 (q, J=4.9 Hz, 1H). MS m/z 420 (M+H)$^+$ Step C: (3-Amino-4-methylamino-phenyl)-{4-[4-(1-methyl-1H-pyrazol-4-yl)-phenyl]-piperidin-1-yl}-methanone A solution of (4-methylamino-3-nitro-phenyl)-{4-[4-(1-methyl-1H-pyrazol-4-yl)-phenyl]-piperidin-1-yl}-methanone (0.46 g, 1.10 mmol) in MeOH (15 ml) was hydrogenated overnight at atmospheric pressure, over 10% Pd/C (0.15 g). The catalyst was filtered off and filtrate concentrated in vacuo to yield an oil. $^1$H NMR (300 MHz, DMSO-d$_6$) δ ppm 1.57 (dq, J=12.2, 3.4 Hz, 2H), 1.74-1.85 (m, 2H), 2.71-2.85 (m, 1H), 2.74 (br s, 3H), 2.86-3.02 (m, 2H), 3.85 (s, 3H), 4.15-4.30 (m, 2H), 4.63 (br s, 2H), 4.90-5.11 (m, 1H) 6.38 (d, J=8.7 Hz, 1H), 7.65-7.70 (m, 2H), 7.24 (d, J=8.1 Hz, 2H), 7.48 (d, J=8.1 Hz, 2H), 7.81 (s, 1H), 8.08 (s, 1H). MS m/z 390 (M+H)$^+$ Step D: 6-(isopropylamino)-N-(5-(4-(4-(1-methyl-1H-pyrazol-4-yl)phenyl)piperidine-1-carbonyl)-2-(methylamino)phenyl)nicotinamide Isopropylammonium 6-isopropylamino-nicotinate (0.068 g, 0.284 mmol) was taken in DCM (5 ml). Thionyl chloride (0.27 ml, 3.72 mmol) was added and mixture refluxed for 3 hours. The solution was concentrated and briefly dried under high vacuum. The residue was dissolved in DCM (5 ml) and added to an ice cold solution of (3-amino-4-methylamino-phenyl)-{4-[4-(1-methyl-1H-pyrazol-4-yl)-phenyl]-piperidin-1-yl}-methanone (0.145 g, 0.372 mmol) and pyridine (0.09 ml, 0.378 mmol) in DCM (10 ml). The resulting mixture was stirred at room temperature for 2 hours and then quenched with 1M Na$_2$CO$_3$ (20 ml). The organics were extracted with DCM (2×30 ml), dried over MgSO$_4$, filtered a concentrated to dryness. The residue was filtered through a short column chromatography over silica gel eluting with a gradient of MeOH in DCM from 0 to 4%. Final purification was performed by preparative reverse phase chromatography to yield 6-(isopropylamino)-N-(5-(4-(4-(1-methyl-1H-pyrazol-4-yl)phenyl)piperidine-1-carbonyl)-2-(methylamino)phenyl)nicotinamide, which was triturated in diethyl ether to yield the title compound as a white powder.

$^1$H NMR (300 MHz, DMSO-d$_6$) δ ppm 1.18 (d, J=6.5 Hz, 6H), 1.49-1.71 (m, 2H), 1.81 (d, J=10.9 Hz, 2H), 2.68-2.87 (m, 4H), 3.00 (t, J=11.3 Hz, 2H), 3.86 (s, 3H), 4.00-4.19 (m, 1H), 4.28 (br. s., 2H), 5.55 (d, J=4.5 Hz, 1H), 6.47 (d, J=8.9 Hz, 1H), 6.64 (d, J=8.4 Hz, 1H), 6.98 (d, J=7.6 Hz, 1H), 7.19-7.33 (m, 4H), 7.48 (d, J=8.0 Hz, 2H), 7.81 (s, 1H), 7.91 (br. s., 1H), 8.08 (s, 1H), 8.67 (s, 1H), 9.29 (s, 1H). MS m/z 552 (M+H)$^+$

Example 19

Compound #36

6-(isopropylamino)-N-(2-methyl-5-(3-(4-(1-methyl-1H-indazol-6-yl)phenyl)azetidine-1-carbonyl)phenyl)nicotinamide

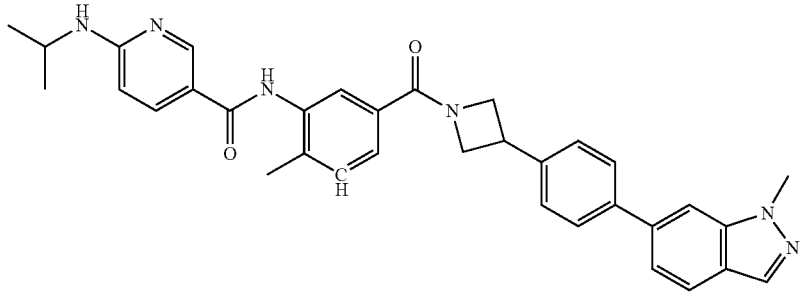 [SMILES: Cc1ccc(C(=O)N2CC(c3ccc(-c4ccc5cnn(C)c5c4)cc3)C2)cc1NC(=O)c1ccc(NC(C)C)nc1]

Step A: Methyl 3-(6-chloronicotinamido)-4-methylbenzoate

To a solution of methyl 3-amino-4-methylbenzoate (826 mg, 5.0 mmol) and DIEA (1.3 mL, 7.5 mmol) in $CH_2Cl_2$ was added 6-chloronicotinoyl chloride (880 mg, 5.0 mmol) at 0° C. The mixture was warmed to room temperature and stirred for 3 h. Additional $CH_2Cl_2$ was added, washed with 10% citric acid (2×), sat.$NaHCO_3$ (2×) and water (2×), dried over $Na_2SO_4$, concentrated and dried to yield an off white solid. $^1H$ NMR (400 MHz, CHLOROFORM-d) δ ppm 2.38 (s, 3H), 3.91 (s, 3H), 7.34 (d, J=8.1 Hz, 1H), 7.49 (d, J=8.1 Hz, 1H), 7.69 (br. s., 1H), 7.86 (d, J=9.6 Hz, 1H), 8.20 (dd, J=8.6, 2.5 Hz, 1H), 8.43 (s, 1H), 8.89 (d, J=2.0 Hz, 1H). MS m/z 305.0 $(M+H)^+$

Step B: 3-(6-Chloronicotinamido)-4-methylbenzoic acid

The mixture of methyl 3-(6-chloronicotinamido)-4-methylbenzoate (1.5 g, 4.9 mmol) and NaOH (1N, 9.8 mL, 9.8 mmol) in THF (20 mL) was stirred at room temperature overnight, acidified with 1NHCl to pH 5-6, extracted with ethyl acetate (2×). The organic phase was washed with water (2×), dried over $Na_2SO_4$, concentrated and dried under high vacuum to yield an off white solid. $^1H$ NMR (400 MHz, DMSO-$d_6$) δ ppm 2.32 (s, 3H), 7.42 (d, J=7.8 Hz, 1H), 7.75 (t, J=9.4 Hz, 2H), 7.97 (s, 1H), 8.37 (d, J=8.3 Hz, 1H), 8.98 (s, 1H), 10.27 (s, 1H), 12.96 (br. s., 1H). MS m/z 290.9 $(M+H)^+$

Step B: N-(5-(3-(4-bromophenyl)azetidine-1-carbonyl)-2-methylphenyl)-6-chloronicotinamide To a solution of 3-(6-chloronicotinamido)-4-methylbenzoic acid (290 mg, 1.0 mmol) in DMF (10 mL) was added HBTU (454 mg, 1.2 mmol), 3-(4-bromophenyl)azetidine hydrochloride (273 mg, 1.1 mmol) and DIPEA (0.86 mL, 10 mmol). The mixture was stirred at room temperature for 3 h, ethyl acetate was added, washed with water (2×), dried over $Na_2SO_4$, concentrated. The residue was purified by chromatograph (50-100% ethyl acetate in heptane) followed by recrystallized from ethyl acetate/heptane to yield a white solid. $^1H$ NMR (400 MHz, DMSO-$d_6$) δ ppm 2.30 (s, 3H), 3.89-3.97 (m, 1H), 3.97-4.01 (m, 1H), 4.34 (t, J=6.8 Hz, 1H), 4.47 (t, J=9.9 Hz, 1H), 4.70 (t, J=8.6 Hz, 1H), 7.33-7.42 (m, 3H), 7.47-7.53 (m, 1H), 7.56 (d, J=8.6 Hz, 2H), 7.72 (d, J=8.1 Hz, 2H), 8.36 (dd, J=8.6, 2.5 Hz, 1H), 8.97 (d, J=2.0 Hz, 1H), 10.21 (s, 1H). MS m/z 483.8 $(M+H)^+$

Step D: N-(5-(3-(4-bromophenyl)azetidine-1-carbonyl)-2-methylphenyl)-6-(isopropylamino)nicotinamide The mixture of N-(5-(3-(4-bromophenyl)azetidine-1-carbonyl)-2-methylphenyl)-6-chloronicotinamide (200 mg, 0.41 mmol) and isopropylamine (487 mg, 8.2 mmol) in a pressure reactor was heated to 140° C. for 2 days. The mixture was cooled to room temperature, ethyl acetate was added, washed with water, dried over $Na_2SO_4$, and concentrated. The residue was washed with ethyl acetate:heptane (1:4) and dried to yield the product as a white solid. $^1H$ NMR (400 MHz, DMSO-$d_6$) δ ppm 1.16 (d, J=6.1 Hz, 6H), 2.27 (s, 3H), 3.88-3.97 (m, 1H), 3.97-4.05 (m, 1H), 4.09 (dd, J=13.1, 6.6 Hz, 1H), 4.32 (t, J=6.6 Hz, 1H), 4.46 (t, J=9.1 Hz, 1H), 4.69 (t, J=8.6 Hz, 1H), 6.48 (d, J=9.1 Hz, 1H), 7.05 (d, J=7.6 Hz, 1H), 7.33 (d, J=8.1 Hz, 1H), 7.38 (d, J=8.6 Hz, 2H), 7.42-7.47 (m, 1H), 7.55 (d, J=8.6 Hz, 2H), 7.69 (s, 1H), 7.88 (dd, J=8.8, 2.3 Hz, 1H), 8.65 (d, J=2.5 Hz, 1H), 9.58 (s, 1H). MS m/z 506.8 $(M+H)^+$

Step E: 6-(isopropylamino)-N-(2-methyl-5-(3-(4-(1-methyl-1H-indazol-6-yl)phenyl)azetidine-1-carbonyl)phenyl)nicotinamide To a mixture of N-(5-(3-(4-bromophenyl)azetidine-1-carbonyl)-2-methylphenyl)-6-(isopropylamino)nicotinamide (90 mg, 0.18 mmol), $PdCl_2(dppf)$ (13, 0.02 mmol), $K_2CO_3$ (49 mg, 0.36 mmol) in 1,4-dioxane (5 mL) and water (1 mL) was added (1-methyl-1H-indazol-6-yl)boronic acid (47 mg, 0.27 mmoL). The mixture was heated to 70° C. and stirred overnight. The heat was removed and the reaction mixture was cooled to room temperature, diluted with ethyl acetate (30 mL), washed with water. The organic layer was dried over $Na_2SO_4$, filtered and concentrated. The residue was purified by Gilson and converted to free base by washing with $NaHCO_3$ to yield a white solid.

$^1H$ NMR (400 MHz, DMSO-$d_6$) δ ppm 1.16 (d, J=6.6 Hz, 6H), 2.28 (s, 3H), 3.96-4.06 (m, 1H), 4.06-4.15 (m, 5H), 4.40 (t, J=6.8 Hz, 1H), 4.52 (t, J=9.3 Hz, 1H), 4.75 (t, J=8.3 Hz, 1H), 6.49 (d, J=9.1 Hz, 1H), 7.06 (d, J=7.6 Hz, 1H), 7.35 (d, J=8.1 Hz, 1H), 7.47 (t, J=8.6 Hz, 2H), 7.54 (d, J=8.1

2H), 7.73 (s, 1H), 7.77-7.85 (m, 3H), 7.85-7.93 (m, 2H), 8.06 (s, 1H), 8.66 (d, J=2.5 Hz, 1H), 9.60 (s, 1H). MS m/z 559.0 (M+H)$^+$

Example 20

Compound #79

N-(2-methyl-5-(3-(4-(1-methyl-1H-pyrazol-4-yl)phenyl)azetidine-1-carbonyl)phenyl)quinoline-2-carboxamide

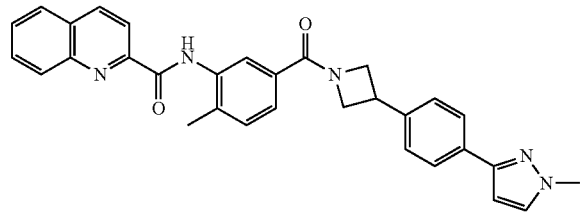 [SMILES: Cc1ccc(C(=O)N2CC(c3ccc(-c4ccn(C)n4)cc3)C2)cc1NC(=O)c1ccc2ccccc2n1]

Step A: (3-amino-4-methylphenyl)(3-(4-bromophenyl)azetidin-1-yl)methanone

To a solution of 3-amino-4-methylbenzoic acid (1.2 g, 8.0 mmol) in DMF (40 mL) was added HBTU (3.6 g, 9.6 mmol), 3-(4-bromophenyl)azetidine hydrochloride (2.0 g, 8.0 mmol) and DIEA (4.3 mL, 30 mmol). The mixture was stirred at room temperature for 3 h, ethyl acetate was added, washed with water (2×), dried over Na$_2$SO$_4$, concentrated. The residue was purified by chromatograph (50-100% ethyl acetate in heptane) followed by recrystallized from ethyl acetate/heptane to yield a slightly yellow solid. $^1$H NMR (400 MHz, CHLOROFORM-d) δ ppm 2.19 (s, 3H), 3.60-3.77 (m, 2H), 3.77-3.87 (m, 1H), 4.16-4.32 (m, 2H), 4.59 (t, J=9.3 Hz, 1H), 4.63-4.73 (m, 1H), 6.93 (d, J=7.6 Hz, 1H), 7.03 (s, 1H), 7.06 (d, J=8.1 Hz, 1H), 7.21 (d, J=8.6 Hz, 2H), 7.48 (d, J=8.6 Hz, 2H). MS m/z 347.0 (M+H)$^+$ Step B: (3-amino-4-methylphenyl)(3-(4-(1-methyl-1H-pyrazol-4-yl)phenyl)azetidin-1-yl)methanone To a mixture of (3-amino-4-methylphenyl)(3-(4-bromophenyl)azetidin-1-yl)methanone (1.2 g, 3.5 mmol), PdCl$_2$(dppf) (254 mg, 0.35 mmol), K$_2$CO$_3$ (960 mg, 6.9 mmol) in dioxane (30 mL) and water (3 mL) was added 1-methyl-4-(4,4,5,5-tetramethyl-1,3,2-dioxaborolan-2-yl)-1H-pyrazole (1.1 g, 5.2 mmoL). The mixture was heated to 70° C. and stirred overnight. The heat was removed and the reaction mixture was cooled to room temperature, diluted with ethyl acetate (80 mL), washed with water. The organic layer was dried over Na$_2$SO$_4$, filtered and concentrated. The residue was directly used for next step. $^1$H NMR (400 MHz, CHLOROFORM-d) δ ppm 2.19 (s, 3H), 3.70 (br. s., 2H), 3.81-3.90 (m, 1H), 3.95 (s, 3H), 4.21-4.28 (m, 1H), 4.28-4.35 (m, 1H), 4.60 (t, J=9.3 Hz, 1H), 4.64-4.73 (m, 1H), 6.96 (d, J=7.6 Hz, 1H), 7.02-7.09 (m, 2H), 7.32 (d, J=8.6 Hz, 2H), 7.46 (d, J=8.1 Hz, 2H), 7.61 (s, 1H), 7.75 (s, 1H). MS m/z 347.2 (M+H)$^+$ Step C: N-(2-methyl-5-(3-(4-(1-methyl-1H-pyrazol-4-yl)phenyl)azetidine-1-carbonyl)phenyl)quinoline-2-carboxamide To a solution of (3-amino-4-methylphenyl)(3-(4-(1-methyl-1H-pyrazol-4-yl)phenyl)azetidin-1-yl)methanone (140 mg, 0.34 mmol) and DIPEA (0.12 mL, 0.69 mmol) in CH$_2$Cl$_2$ (15 mL) was added quinoline-2-carbonyl chloride (79 mg, 0.41 mmol) at 0° C. The mixture was warmed to room temperature and stirred for 3 h. Additional CH$_2$Cl$_2$ was added, washed with 10% citric acid (2×), sat.NaHCO$_3$ (2×) and water (2×), dried over Na$_2$SO$_4$, filtered and concentrated. The residue was purified by Gilson and converted into free base by washing with NaHCO$_3$. The final compound was isolated an off white solid.

$^1$H NMR (400 MHz, CHLOROFORM-d) δ ppm 2.54 (s, 3H), 3.86-3.93 (m, 1H), 3.93-3.97 (m, 3H), 4.32 (dd, J=9.6, 6.6 Hz, 1H), 4.49 (t, J=7.3 Hz, 1H), 4.57-4.70 (m, 1H), 4.85-4.98 (m, 1H), 7.35 (d, J=8.1 Hz, 3H), 7.43-7.50 (m, 2H), 7.54-7.62 (m, 2H), 7.66 (t, J=7.3 Hz, 1H), 7.75 (s, 1H), 7.81 (t, J=7.6 Hz, 1H), 7.92 (d, J=8.1 Hz, 1H), 8.16 (d, J=8.1 Hz, 1H), 8.31-8.41 (m, 2H), 8.71 (s, 1H), 10.44 (s, 1H). MS m/z 502.3 (M+H)$^+$ Example 21

Compound #183

6-chloro-N-(2-methoxy-5-(3-(4-(1-methyl-1H-pyrazol-4-yl)phenyl)azetidine-1-carbonyl)phenyl)nicotinamide

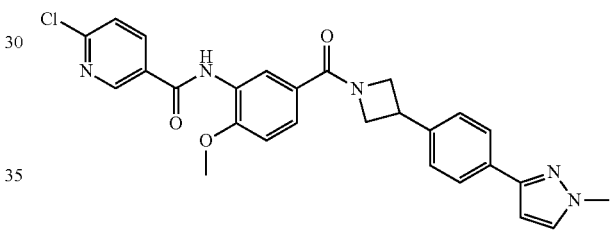

Step A: (3-amino-4-methoxyphenyl)(3-(4-bromophenyl)azetidin-1-yl)methanone

To a solution of 3-amino-4-methoxybenzoic acid (500 mg, 3.0 mmol) in DMF (20 mL) was added HBTU (1.4 g, 3.6 mmol), 3-(4-bromophenyl)azetidine hydrochloride (746 mg, 3.0 mmol) and DIPEA (2.1 mL, 12 mmol). The mixture was stirred at room temperature for 3 h, ethyl acetate was added, washed with water (2×), dried over Na$_2$SO$_4$, concentrated. The residue was purified by chromatograph (50-100% ethyl acetate in heptane) to yield a slightly yellow gum. $^1$H NMR (400 MHz, CHLOROFORM-d) δ ppm 3.77-3.84 (m, 1H), 3.88 (s, 3H), 3.92 (br. s., 2H), 4.21 (br. s., 1H), 4.26 (br. s., 1H), 4.58 (br. s., 1H), 4.68 (br. s., 1H), 6.76 (d, J=8.1 Hz, 1H), 7.04 (dd, J=8.1, 2.0 Hz, 1H), 7.09 (d, J=2.0 Hz, 1H), 7.21 (d, J=8.6 Hz, 2H), 7.48 (d, J=8.6 Hz, 2H), 8.01 (s, 1H). MS m/z 361.1 (M+H)$^+$ Step B: (3-amino-4-methoxyphenyl)(3-(4-(1-methyl-1H-pyrazol-4-yl)phenyl)azetidin-1-yl)methanone To a mixture of (3-amino-4-methoxyphenyl)(3-(4-bromophenyl)azetidin-1-yl)methanone (900 mg, 2.5 mmol), PdCl$_2$(dppf) (182, 0.25 mmol), K$_2$CO$_3$ (689 mg, 4.9 mmol) in 1,4-dioxane (25 mL) and water (3 mL) was added 1-methyl-4-(4,4,5,5-tetramethyl-1,3,2-dioxaborolan-2-yl)-1H-pyrazole (778 mg, 3.7 mmoL). The mixture was heated to 70° C. and stirred overnight. The heat was removed and the reaction mixture was cooled to room temperature, diluted with ethyl acetate (80 mL), washed with water. The organic layer was dried over Na$_2$SO$_4$, filtered and concentrated. The residue was directly used for next step. $^1$H NMR (400 MHz, CHLOROFORM-d) δ ppm 3.80-3.92 (m, 5H), 3.93-3.98 (m, 3H), 4.26 (br. s., 1H), 4.32 (br. s., 1H), 4.60 (br. s., 1H), 4.70 (br. s., 1H), 6.77 (d, J=8.6 Hz, 1H), 7.06 (d, J=8.6 Hz, 1H), 7.11 (d, J=2.0 Hz, 1H), 7.32 (d, J=8.1 Hz, 2H), 7.46 (d, J=8.6 Hz, 2H), 7.61 (s, 1H), 7.75 (s, 1H). MS m/z 363.3 (M+H)$^+$ Step C: 6-chloro-N-(2-methoxy-5-(3-(4-(1-methyl-1H-pyrazol-4-yl)phenyl)azetidine-1-carbonyl)phenyl)nicotinamide To a solution of (3-amino-4-methoxyphenyl)(3-(4-(1-methyl-1H-pyrazol-4-yl)phenyl)azetidin-1-yl)methanone (550 mg, 1.4 mmol) and DIPEA (0.47 mL, 2.7 mmol) in CH$_2$Cl$_2$ (30 mL) was added 6-chloronicotinoyl chloride (288 mg, 1.6 mmol) at 0° C. The mixture was warmed to room temperature and stirred for 3 h. Additional CH$_2$Cl$_2$ was added, washed with 10% citric acid (2×), sat.NaHCO$_3$ (2×) and water (2×), dried over Na$_2$SO$_4$, filtered and concentrated. The residue was purified by chromatography (ethyl acetate) to yield the title compound as a white solid.
$^1$H NMR (400 MHz, CHLOROFORM-d) δ ppm 3.88-3.94 (m, 1H), 3.95 (s, 3H), 3.99 (s, 3H), 4.26-4.37 (m, 1H), 4.47 (t, J=7.1 Hz, 1H), 4.62 (t, J=9.3 Hz, 1H), 4.89 (t, J=8.3 Hz, 1H), 7.02 (d, J=8.6 Hz, 1H), 7.34 (d, J=8.1 Hz, 2H), 7.42-7.51 (m, 3H), 7.61 (s, 1H), 7.70 (dd, J=8.6, 2.0 Hz, 1H), 7.75 (s, 1H), 8.16 (dd, J=8.1, 2.5 Hz, 1H), 8.47 (s, 1H), 8.82 (s, 1H), 8.88 (d, J=2.5 Hz, 1H). MS m/z 502.1 (M+H)$^+$ Example 22

Compound #202

6-(isopropylamino)-N-(2-methoxy-5-(3-(4-(1-methyl-1H-pyrazol-4-yl)phenyl)azetidine-1-carbonyl)phenyl)nicotinamide

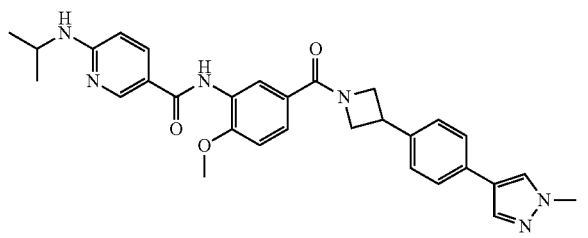 [SMILES: COc1ccc(C(=O)N2CC(c3ccc(-c4cnn(C)c4)cc3)C2)cc1NC(=O)c1ccc(NC(C)C)nc1]

A mixture of 6-chloro-N-(2-methoxy-5-(3-(4-(1-methyl-1H-pyrazol-4-yl)phenyl)azetidine-1-carbonyl)phenyl)nicotinamide (140 mg, 0.28 mmol) and isopropylamine (82 mg, 1.4 mmol) in a pressure reactor was heated to 140° C. for 2 days. The mixture was cooled to room temperature, ethyl acetate was added, washed with water, dried over Na$_2$SO$_4$, and concentrated. The residue was purified by Gilson and converted into free base by washing with NaHCO$_3$ to yield the title compound as a white solid.
$^1$H NMR (400 MHz, CHLOROFORM-d) δ ppm 1.27 (d, J=6.6 Hz, 6H), 3.85-3.93 (m, 1H), 3.94 (s, 3H), 3.97 (s, 3H), 3.98-4.04 (m, 1H), 4.24-4.37 (m, 1H), 4.48 (t, J=7.1 Hz, 1H), 4.60 (t, J=9.3 Hz, 1H), 4.85-4.96 (m, 2H), 6.40 (d, J=8.6 Hz, 1H), 6.98 (d, J=8.6 Hz, 1H), 7.33 (d, J=8.1 Hz, 2H), 7.45 (d, J=8.1 Hz, 2H), 7.60 (s, 1H), 7.65 (dd, J=8.6, 2.0 Hz, 1H), 7.75 (s, 1H), 7.93 (dd, J=9.1, 2.5 Hz, 1H), 8.38 (s, 1H), 8.63 (d, J=2.0 Hz, 1H), 8.85 (d, J=2.0 Hz, 1H). MS m/z 525.3 (M+H)$^+$ The following additional representative compounds of formula (I) of the present invention with prepared according to the procedures as described in the Schemes and Examples, selecting and substituting suitably substituted reagents as would be readily recognized by those skilled in the art.

Example 23

Compound #23

6-chloro-N-(2-methyl-5-(4-(2-oxo-1,2,3,4-tetrahydroquinolin-7-yl)piperidine-1-carbonyl)phenyl)nicotinamide

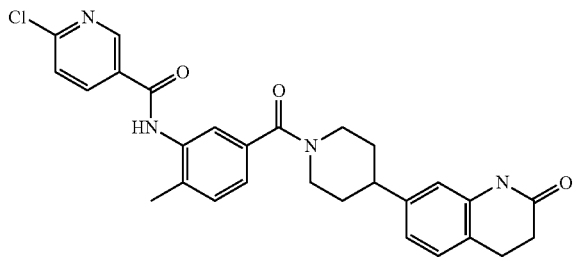 [SMILES: Cc1ccc(C(=O)N2CCC(c3ccc4c(c3)NC(=O)CC4)CC2)cc1NC(=O)c1ccc(Cl)nc1]

$^1$H NMR (300 MHz, DMSO-d$_6$) δ ppm 1.53 (d, J=10.9 Hz, 2H), 1.77 (br. s., 2H), 2.42 (t, J=7.5 Hz, 2H), 2.51 (s, 5H), 2.67-2.87 (m, 3H), 3.78 (br. s., 1H), 4.58 (br. s., 1H), 6.73 (s, 1H), 6.84 (s, 1H), 7.09 (d, J=7.7 Hz, 1H), 7.25 (d, J=7.8 Hz, 1H), 7.37 (d, J=7.8 Hz, 1H), 7.46 (s, 1H), 7.72 (d, J=8.2 Hz, 1H), 8.36 (dd, J=8.2, 2.2 Hz, 1H), 8.88-9.09 (m, 1H), 9.98 (s, 1H), 10.20 (br. s., 1H). MS m/z 504 (M+H)$^+$ Example 24

Compound #35

6-(isopropylamino)-N-(2-methyl-5-(4-(2-oxo-1,2,3,4-tetrahydroquinolin-7-yl)piperidine-1-carbonyl)phenyl)nicotinamide

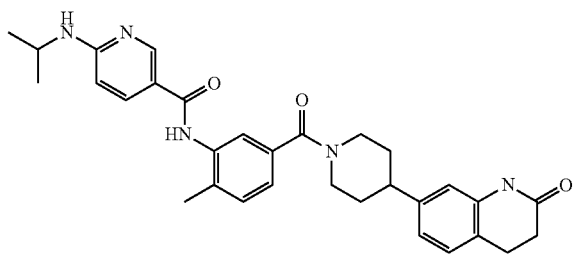 [SMILES: Cc1ccc(C(=O)N2CCC(c3ccc4c(c3)NC(=O)CC4)CC2)cc1NC(=O)c1ccc(NC(C)C)nc1]

$^1$H NMR (300 MHz, DMSO-d$_6$) δ ppm 1.18 (d, J=6.3 Hz, 6H), 1.52 (d, J=10.7 Hz, 2H), 1.77 (br. s., 2H), 2.27 (s, 3H), 2.35-2.45 (m, 2H), 2.81 (d, J=7.7 Hz, 4H), 3.81 (br. s., 1H), 4.10 (d, J=6.6 Hz, 1H), 4.60 (br. s., 1H), 6.49 (d, J=8.8 Hz, 1H), 6.74 (s, 1H), 6.84 (br. s., 1H), 7.09 (d, J=7.6 Hz, 1H), 7.03 (d, J=7.4 Hz, 1H), 7.20 (br. s., 1H), 7.33 (d, J=7.6 Hz, 1H), 7.43 (s, 1H), 7.88 (br. s., 1H), 8.58-8.73 (m, 1H), 9.57 (s, 1H), 9.97 (s, 1H). MS m/z 526 (M+H)$^+$ Example 25

Compound #19

6-(isopropylamino)-N-(2-methyl-5-(4-(2-methyl-1-oxoisoindolin-5-yl)piperidine-1-carbonyl)phenyl)nicotinamide

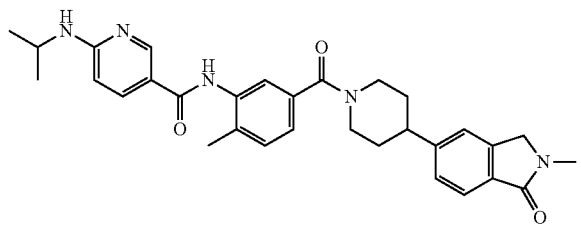 [SMILES: Cc1ccc(C(=O)N2CCC(c3ccc4c(c3)CN(C)C4=O)CC2)cc1NC(=O)c1ccc(NC(C)C)nc1]

$^1$H NMR (300 MHz, CHLOROFORM-d) δ ppm 1.17-1.25 (m, 6H), 1.63-1.98 (m, 3H), 2.27 (s, 3H), 2.67-2.94 (m, 2H), 3.12 (s, 4H), 3.83-4.12 (m, 2H), 4.28 (s, 2H), 4.76 (d, J=7.8 Hz, 2H), 6.34 (d, J=8.8 Hz, 1H), 7.08-7.15 (m, 1H), 7.15-7.21 (m, 2H), 7.21-7.29 (m, 2H), 7.60-7.74 (m, 2H), 7.89 (dd, J=8.8, 2.5 Hz, 1H), 7.92-7.97 (m, 1H), 8.58 (d, J=2.3 Hz, 1H). MS m/z 526 (M+H)$^+$ Example 26

Compound #22

N-(5-(4-(2,3-dimethyl-1-oxoisoindolin-5-yl)piperidine-1-carbonyl)-2-methylphenyl)-6-(isopropylamino)nicotinamide

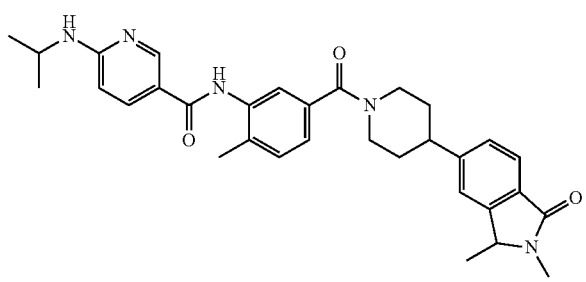 [SMILES: Cc1ccc(C(=O)N2CCC(c3ccc4c(c3)C(C)N(C)C4=O)CC2)cc1NC(=O)c1ccc(NC(C)C)nc1]

$^1$H NMR (300 MHz, CHLOROFORM-d) δ ppm 1.16-1.20 (m, 6H), 1.21 (s, 3H), 1.56 (br. s., 1H), 1.86 (br. s., 2H), 2.27 (s, 3H), 2.69-2.92 (m, 2H), 3.04 (s, 3H), 3.12 (br. s., 1H), 3.94 (dt, J=13.7, 6.6 Hz, 2H), 4.33 (q, J=6.7 Hz, 1H), 4.79 (br. s., 2H), 6.34 (d, J=8.9 Hz, 1H), 7.07-7.16 (m, 1H), 7.16-7.21 (m, 3H), 7.23 (d, J=8.0 Hz, 1H), 7.63 (s, 1H), 7.68 (d, J=7.8 Hz, 1H), 7.89 (dd, J=8.8, 2.3 Hz, 1H), 7.92-7.99 (m, 1H), 8.57 (d, J=2.2 Hz, 1H). MS m/z 540 (M+H)$^+$ Example 27

Compound #50

6-chloro-N-(2-methyl-5-(4-(2-oxoindolin-5-yl)piperidine-1-carbonyl)phenyl)nicotinamide

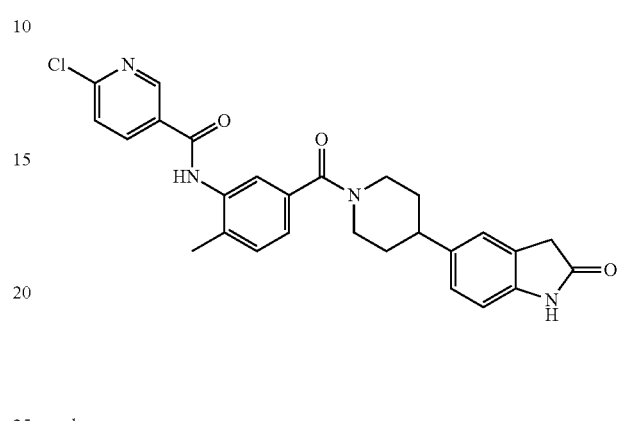

$^1$H NMR (300 MHz, DMSO-d$_6$) δ ppm 1.21-1.43 (m, 2H), 1.52 (br. s., 2H), 2.05 (s, 3H), 2.51 (br. s., 1H), 2.65 (br. s., 1H), 2.86 (br. s., 1H), 3.06 (s, 2H), 3.54 (br. s., 1H), 4.34 (br. s., 1H), 6.50 (d, J=7.8 Hz, 1H), 6.90 (s, 1H), 7.04 (s, 1H), 7.07-7.17 (m, 1H), 7.22 (s, 1H), 7.48 (d, J=8.2 Hz, 1H), 8.12 (dd, J=8.4, 2.1 Hz, 1H), 8.73 (s, 1H), 9.95 (s, 1H), 10.01 (s, 1H). MS m/z 489 (M+H)$^+$ Example 28

Compound #54

(±)-N-(5-(4-((3R,4S)-4-(1H-imidazol-1-yl)phenyl)-3-methylpiperidine-1-carbonyl)-2-methylphenyl)-6-chloronicotinamide

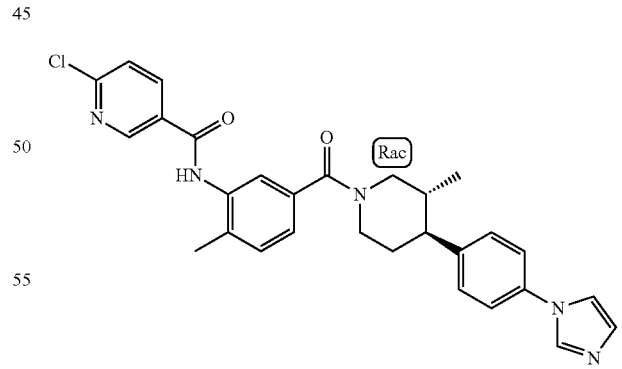

$^1$H NMR (300 MHz, DMSO-d$_6$) δ ppm 0.68 (br. s., 2H), 1.72 (br. s., 2H), 1.80-1.97 (m, 1H), 2.30 (s, 3H), 2.84 (br. s., 1H), 3.78 (br. s., 1H), 4.61 (br. s., 1H), 7.11 (s, 1H), 7.25-7.35 (m, 1H), 7.35-7.46 (m, 3H), 7.50 (s, 1H), 7.58 (d, J=8.5 Hz, 2H), 7.70-7.77 (m, 2H), 8.24 (s, 1H), 8.33-8.41 (m, 1H), 8.98 (d, J=2.2 Hz, 1H), 10.22 (s, 1H). MS m/z 515 (M+H)$^+$

Example 29

Compound #53

(±)-N-(5-((3S,4S)-4-(4-(1H-imidazol-1-yl)phenyl)-3-methylpiperidine-1-carbonyl)-2-methylphenyl)-6-chloronicotinamide

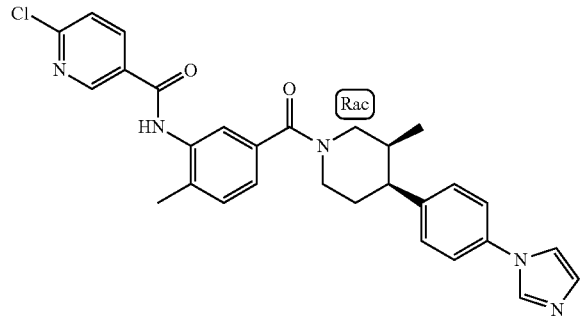 [SMILES: Cc1ccc(C(=O)N2CC[C@H](c3ccc(-n4ccnc4)cc3)[C@H](C)C2)cc1NC(=O)c1ccc(Cl)nc1]

$^1$H NMR (300 MHz, DMSO-d$_6$) δ ppm 0.40-0.76 (m, 2H), 1.63 (br. s., 2H), 2.08 (br. s., 2H), 2.30 (s, 3H), 3.55-3.85 (m, 1H), 4.45-4.75 (m, 1H), 7.10 (s, 1H), 7.31-7.41 (m, 3H), 7.45 (br. s., 1H), 7.59 (d, J=8.5 Hz, 2H), 7.68-7.78 (m, 2H), 8.22 (s, 1H), 8.37 (d, J=6.5 Hz, 1H), 8.98 (br. s., 1H), 10.22 (s, 1H). MS m/z 515 (M+H)$^+$

Example 30

Compound #44

6-(Isopropylamino)-N-(2-methyl-5-(4-(4-(1-methyl-1H-pyrazol-5-yl)phenyl)piperidine-1-carbonyl)phenyl)nicotinamide

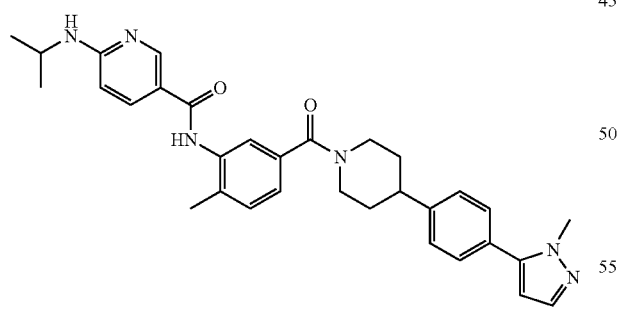

$^1$H NMR (300 MHz, DMSO-d$_6$) δ ppm 1.17 (d, J=6.5 Hz, 6H), 1.68 (br. s., 2H), 1.84 (br. s., 2H), 2.27 (s, 3H), 2.90 (br. s., 2H), 3.17 (br. s., 1H), 3.85 (s, 3H), 4.01-4.21 (m, 1H), 4.64 (br. s., 1H), 6.37 (d, J=1.8 Hz, 1H), 6.49 (d, J=8.9 Hz, 1H), 7.02 (d, J=7.7 Hz, 1H), 7.16-7.27 (m, 1H), 7.33 (d, J=8.0 Hz, 1H), 7.37-7.53 (m, 6H), 7.89 (dd, J=8.8, 2.3 Hz, 1H), 8.66 (d, J=2.3 Hz, 1H), 9.56 (s, 1H). MS m/z 537 (M+H)$^+$

Example 31

Compound #42

N-(5-(4-(4-(1H-pyrazol-4-yl)phenyl)piperidine-1-carbonyl)-2-methylphenyl)-6-(isopropylamino)nicotinamide

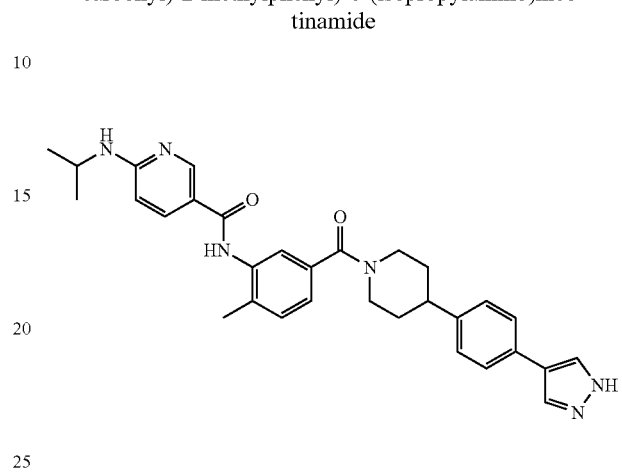

$^1$H NMR (300 MHz, DMSO-d$_6$) δ ppm 1.22 (d, J=6.5 Hz, 6H), 1.67 (br. s., 2H), 1.89 (br. s., 2H), 2.26-2.36 (m, 3H), 2.84 (d, J=4.7 Hz, 2H), 3.85 (br. s., 1H), 4.15 (s, 1H), 4.66 (br. s., 1H), 6.53 (d, J=8.9 Hz, 1H), 7.07 (d, J=7.6 Hz, 1H), 7.19-7.42 (m, 4H), 7.49 (s, 1H), 7.57 (d, J=8.1 Hz, 3H), 7.93 (dd, J=8.8, 2.5 Hz, 2H), 8.17 (br. s., 1H), 8.70 (d, J=2.2 Hz, 1H), 9.61 (s, 1H), 12.92 (br. s., 1H). MS m/z 523 (M+H)$^+$

Example 32

Compound #37

6-chloro-N-(5-(4-(isoquinolin-7-yl)piperidine-1-carbonyl)-2-methylphenyl)nicotinamide

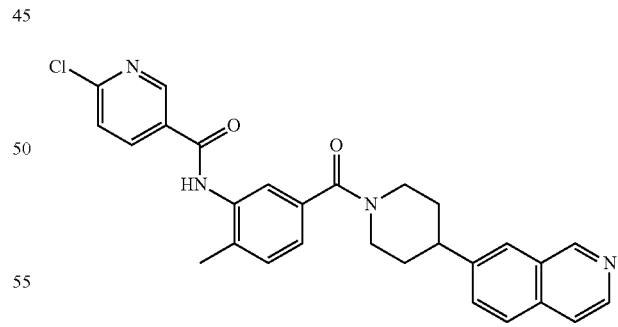

$^1$H NMR (300 MHz, DMSO-d$_6$) δ ppm 1.75 (d, J=8.8 Hz, 2H), 1.84-2.05 (m, 2H), 2.30 (s, 3H), 2.76-3.14 (m, 3H), 3.85 (br. s., 1H), 4.66 (br. s., 1H), 7.25-7.34 (m, 1H), 7.34-7.42 (m, 1H), 7.50 (s, 1H), 7.63-7.75 (m, 2H), 7.77 (d, J=5.8 Hz, 1H), 7.84 (s, 1H), 8.07 (d, J=8.5 Hz, 1H), 8.37 (dd, J=8.2, 2.2 Hz, 1H), 8.47 (d, J=5.8 Hz, 1H), 8.98 (d, J=1.9 Hz, 1H), 9.26 (s, 1H), 10.21 (s, 1H). MS m/z 485 (M+H)$^+$

Example 33

Compound #28

6-(isopropylamino)-N-(5-(4-(isoquinolin-7-yl)piperidine-1-carbonyl)-2-methylphenyl)nicotinamide

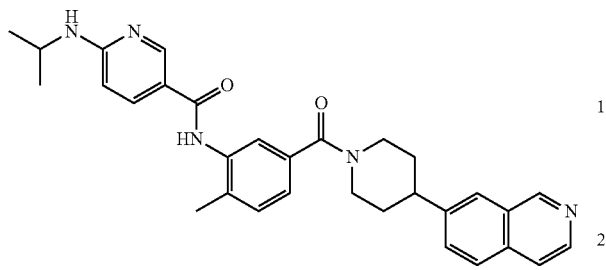

$^1$H NMR (300 MHz, DMSO-$d_6$) δ ppm 1.17 (d, J=6.5 Hz, 6H), 1.76 (br. s., 2H), 1.83-2.05 (m, 2H), 2.27 (s, 3H), 2.98-3.14 (m, 3H), 3.87 (br. s., 1H), 3.99-4.24 (m, 1H), 4.65 (br. s., 1H), 6.49 (d, J=8.8 Hz, 1H), 7.03 (d, J=7.6 Hz, 1H), 7.24 (d, J=7.7 Hz, 1H), 7.34 (d, J=7.7 Hz, 1H), 7.47 (s, 1H), 7.68 (d, J=8.4 Hz, 1H), 7.77 (d, J=5.8 Hz, 1H), 7.81-7.94 (m, 2H), 8.07 (d, J=8.4 Hz, 1H), 8.47 (d, J=5.6 Hz, 1H), 8.61-8.71 (m, 1H), 9.26 (s, 1H), 9.57 (s, 1H). MS m/z 508 (M+H)$^+$

Example 34

Compound #47

N-(5-(4-(benzo[d]thiazol-6-yl)piperidine-1-carbonyl)-2-methylphenyl)-6-chloronicotinamide

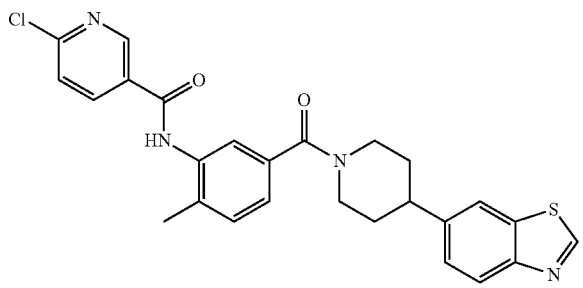 [SMILES: Cc1ccc(C(=O)N2CCC(c3ccc4ncsc4c3)CC2)cc1NC(=O)c1ccc(Cl)nc1]

$^1$H NMR (300 MHz, DMSO-$d_6$) δ ppm 1.73 (br. s., 2H), 1.87 (br. s., 2H), 2.30 (s, 3H), 3.01 (br. s., 2H), 3.18 (d, J=5.4 Hz, 1H), 3.83 (br. s., 1H), 4.65 (br. s., 1H), 7.23-7.33 (m, 1H), 7.38 (d, J=7.8 Hz, 1H), 7.43-7.55 (m, 2H), 7.72 (d, J=8.4 Hz, 1H), 8.02 (d, J=8.4 Hz, 1H), 8.06-8.14 (m, 1H), 8.37 (dd, J=8.3, 2.3 Hz, 1H), 8.98 (d, J=1.9 Hz, 1H), 9.33 (s, 1H), 10.21 (s, 1H). MS m/z 492 (M+H)$^+$

Example 35

Compound #46

N-(5-(4-(benzo[d]thiazol-6-yl)piperidine-1-carbonyl)-2-methylphenyl)-6-(isopropylamino)nicotinamide

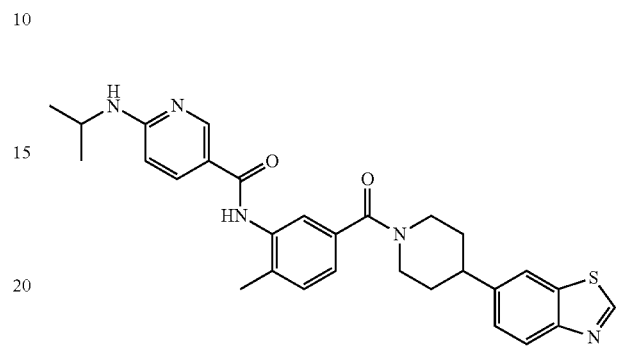

$^1$H NMR (300 MHz, DMSO-$d_6$) δ ppm 1.17 (d, J=6.3 Hz, 6H), 1.72 (br. s., 2H), 1.86 (br. s., 2H), 2.26 (s, 3H), 2.76-3.14 (m, 3H), 3.84 (br. s., 1H), 4.10 (br. s., 1H), 4.65 (br. s., 1H), 6.48 (d, J=8.8 Hz, 1H), 7.02 (d, J=7.6 Hz, 1H), 7.24 (s, 1H), 7.33 (d, J=7.7 Hz, 1H), 7.45 (s, 2H), 7.81-7.94 (m, 1H), 8.01 (d, J=8.4 Hz, 1H), 8.09 (s, 1H), 8.66 (s, 1H), 9.32 (s, 1H), 9.57 (s, 1H). MS m/z 514 (M+H)$^+$

Example 36

Compound #48

6-chloro-N-(2-methyl-5-(4-(2-oxo-2,3-dihydrobenzo[d]thiazol-6-yl)piperidine-1-carbonyl)phenyl)nicotinamide

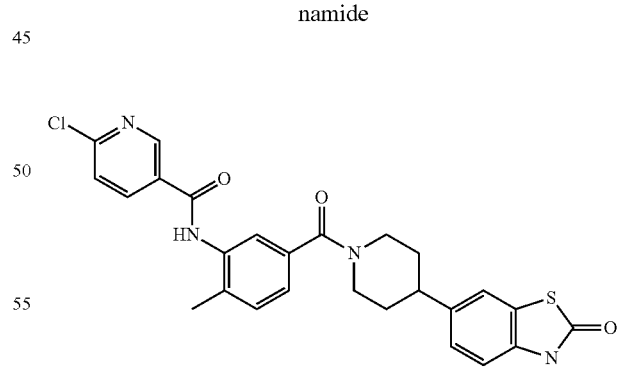

$^1$H NMR (300 MHz, DMSO-$d_6$) δ ppm 1.53-1.70 (m, 2H), 1.79 (br. s., 2H), 2.29 (s, 3H), 2.82 (br. s., 2H), 3.13 (br. s., 1H), 3.80 (br. s., 1H), 4.61 (br. s., 1H), 7.04 (d, J=8.2 Hz, 1H), 7.19 (d, J=7.7 Hz, 1H), 7.28 (s, 1H), 7.33-7.42 (m, 1H), 7.50 (s, 1H), 7.47 (s, 1H), 7.73 (d, J=8.2 Hz, 1H), 8.29-8.45 (m, 1H), 8.97 (s, 1H), 10.21 (s, 1H), 11.78 (br. s., 1H). MS m/z 508 (M+H)$^+$

Example 37

Compound #49

6-(isopropylamino)-N-(2-methyl-5-(4-(2-oxo-2,3-dihydrobenzo[d]thiazol-6-yl)piperidine-1-carbonyl)phenyl)nicotinamide

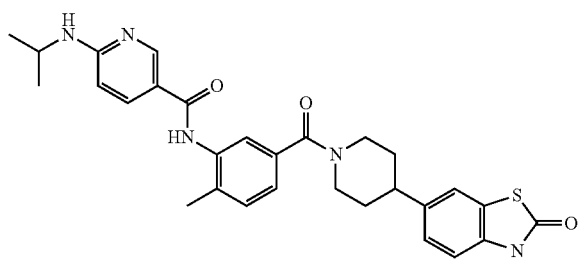 [SMILES: Cc1ccc(C(=O)N2CCC(c3ccc4[nH]c(=O)sc4c3)CC2)cc1NC(=O)c1ccc(NC(C)C)nc1]

$^1$H NMR (300 MHz, DMSO-d$_6$) δ ppm 1.18 (d, J=6.5 Hz, 6H), 1.52-1.70 (m, 2H), 1.70-1.90 (m, 2H), 2.27 (s, 3H), 2.65-3.02 (m, 3H), 3.82 (br. s., 1H), 4.00-4.20 (m, 1H), 4.61 (br. s., 1H), 6.49 (d, J=8.8 Hz, 1H), 6.94-7.12 (m, 2H), 7.12-7.27 (m, 2H), 7.33 (d, J=7.8 Hz, 1H), 7.43 (s, 1H), 7.89 (dd, J=8.7, 2.1 Hz, 1H), 8.65 (d, J=1.9 Hz, 1H), 9.57 (s, 1H), 11.67 (br. s., 1H). MS m/z 530 (M+H)$^+$

Example 38

Compound #299

6-(N-isopropylformamido)-N-(2-methyl-5-(4-(4-(pyrimidin-2-ylcarbamoyl)phenyl)piperidine-1-carbonyl)phenyl)nicotinamide

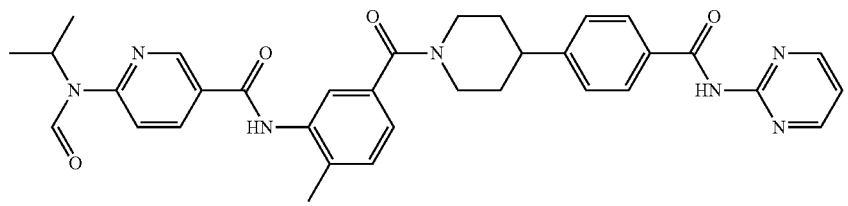 [SMILES: Cc1ccc(C(=O)N2CCC(c3ccc(C(=O)Nc4ncccn4)cc3)CC2)cc1NC(=O)c1ccc(N(C=O)C(C)C)nc1]

$^1$H NMR (300 MHz, DMSO-d$_6$) δ ppm 1.42 (d, J=6.9 Hz, 6H), 1.59-1.77 (m, 2H), 1.77-2.02 (m, 2H), 2.25-2.35 (m, 3H), 2.92 (d, J=11.5 Hz, 2H), 3.84 (br. s., 1H), 4.62 (br. s., 1H), 4.77 (dt, J=13.8, 6.9 Hz, 1H), 7.22-7.32 (m, 2H), 7.34-7.40 (m, 1H), 7.44 (m, J=8.2 Hz, 2H), 7.49 (s, 1H), 7.61 (br. s., 1H), 7.93 (m, J=8.2 Hz, 2H), 8.37 (dd, J=8.5, 2.3 Hz, 1H), 8.73 (d, J=4.8 Hz, 2H), 8.80 (s, 1H), 9.02 (d, J=2.1 Hz, 1H), 10.11 (br. s., 1H), 10.90 (br. s., 1H). MS m/z 606 (M+H)$^+$

Example 39

Compound #45

6-(isopropylamino)-N-(2-methyl-5-(4-(4-((4-methylpyrimidin-2-yl)carbamoyl)phenyl)piperidine-1-carbonyl)phenyl)nicotinamide

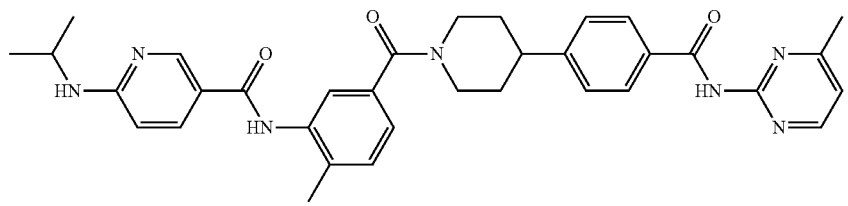 [SMILES: Cc1ccnc(NC(=O)c2ccc(C3CCN(C(=O)c4ccc(C)c(NC(=O)c5ccc(NC(C)C)nc5)c4)CC3)cc2)n1]

$^1$H NMR (300 MHz, DMSO-d$_6$) δ ppm 1.18 (d, J=6.5 Hz, 6H), 1.55-1.75 (m, 2H), 1.83 (br. s., 2H), 2.45 (s, 3H), 2.48-2.57 (m, 3H), 2.92 (t, J=11.7 Hz, 2H), 3.11 (br. s., 1H), 3.84 (br. s., 1H), 4.02-4.24 (m, 1H), 4.64 (br. s., 1H), 6.49 (d, J=8.8 Hz, 1H), 7.03 (d, J=7.6 Hz, 1H), 7.13 (d, J=5.1 Hz, 1H), 7.23 (dd, J=7.8, 1.4 Hz, 1H), 7.34 (d, J=8.0 Hz, 1H), 7.38-7.51 (m, 3H), 7.81-8.00 (m, 3H), 8.56 (d, J=5.1 Hz, 1H), 8.66 (d, J=2.2 Hz, 1H), 9.58 (s, 1H), 10.81 (s, 1H). MS m/z 592 (M+H)$^+$ Example 40

Compound #51

6-(isopropylamino)-N-(5-(4-(4-(isoxazol-4-yl)phenyl)piperidine-1-carbonyl)-2-methylphenyl)nicotinamide

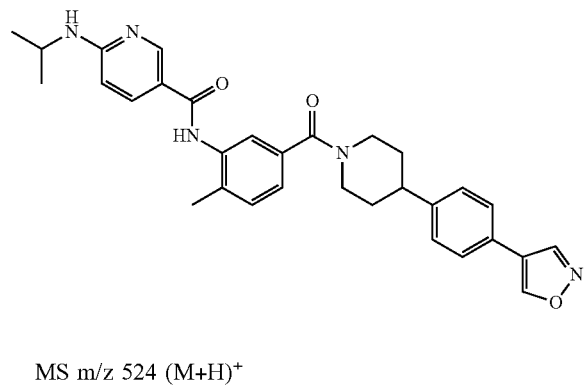

MS m/z 524 (M+H)$^+$

Example 41

Compound #91

N-(2-methyl-5-(4-(4-(1-methyl-1H-pyrazol-4-yl)phenyl)piperidine-1-carbonyl)phenyl)-6-morpholinonicotinamide

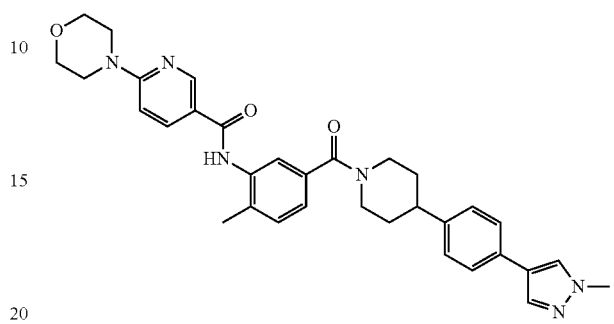

$^1$H NMR (300 MHz, DMSO-d$_6$) δ ppm 1.61 (d, J=13.3 Hz, 2H), 1.80 (br. s., 2H), 2.27 (s, 3H), 2.71-2.97 (m, 2H), 3.17 (d, J=5.2 Hz, 2H), 3.54-3.65 (m, 4H), 3.66-3.76 (m, 4H), 3.85 (s, 3H), 4.62 (br. s., 1H), 6.93 (d, J=9.1 Hz, 1H), 7.18-7.30 (m, 3H), 7.30-7.38 (m, 1H), 7.40-7.53 (m, 3H), 7.81 (s, 1H), 8.04-8.17 (m, 2H), 8.77 (d, J=2.3 Hz, 1H), 9.73 (s, 1H). MS m/z 565 (M+H)$^+$ Example 42

Compound #112

N-(2-Methyl-5-(4-(4-(1-methyl-1H-pyrazol-4-yl)phenyl)piperidine-1-carbonyl)phenyl)-6-(4-methylpiperazin-1-yl)nicotinamide

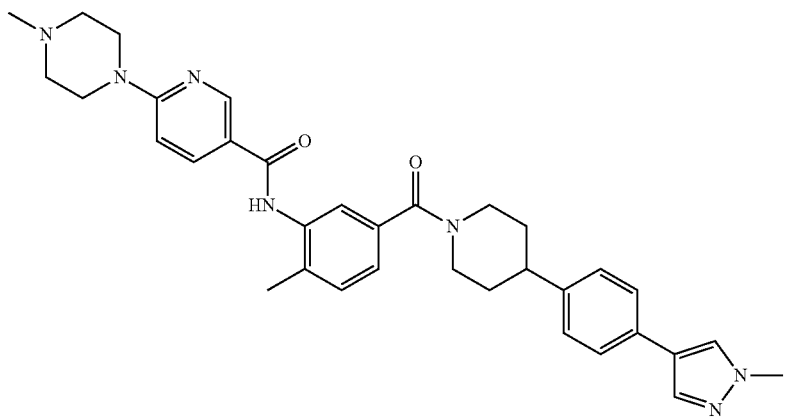

$^1$H NMR (300 MHz, DMSO-d$_6$) δ ppm 1.61 (d, J=11.1 Hz, 2H), 1.80 (br. s., 2H), 2.22 (s, 3H), 2.27 (s, 3H), 2.33-2.43 (m, 4H), 2.80 (t, J=11.5 Hz, 2H), 3.17 (d, J=5.1 Hz, 2H), 3.59-3.68 (m, 4H), 3.85 (s, 3H), 4.62 (br. s., 1H), 6.92 (d, J=9.1 Hz, 1H), 7.16-7.28 (m, 3H), 7.34 (d, J=7.8 Hz, 1H), 7.41-7.53 (m, 3H), 7.81 (s, 1H), 8.02-8.11 (m, 2H), 8.74 (d, J=2.3 Hz, 1H), 9.70 (s, 1H). MS m/z 578 (M+H)$^+$ Example 43

Compound #92

6-(Isopropyl(methyl)amino)-N-(2-methyl-5-(4-(4-(1-methyl-1H-pyrazol-4-yl)phenyl)piperidine-1-carbonyl)phenyl)nicotinamide

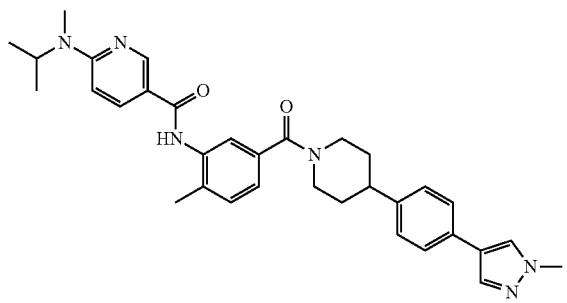 [SMILES: Cc1ccc(C(=O)N2CCC(c3ccc(-c4cnn(C)c4)cc3)CC2)cc1NC(=O)c1ccc(N(C)C(C)C)nc1]

$^1$H NMR (300 MHz, DMSO-d$_6$) δ ppm 1.11-1.20 (m, 6H), 1.63 (br. s., 2H), 1.80 (br. s., 2H), 2.27 (s, 3H), 2.71-2.86 (m, 2H), 2.88 (s, 3H), 3.11 (br. s., 1H), 3.85 (s, 3H), 4.63 (br. s., 1H), 4.96 (s, 1H), 6.70 (d, J=9.1 Hz, 1H), 7.17-7.30 (m, 3H), 7.34 (d, J=7.8 Hz, 1H), 7.40-7.52 (m, 3H), 7.81 (s, 1H), 8.04 (dd, J=9.0, 2.4 Hz, 1H), 8.08 (s, 1H), 8.73 (d, J=2.3 Hz, 1H), 9.64 (s, 1H). MS m/z 551 (M+H)$^+$ Example 44

Compound #93

4-methoxy-N-(2-methyl-5-(4-(4-(1-methyl-1H-pyrazol-4-yl)phenyl)piperidine-1-carbonyl)phenyl)benzamide

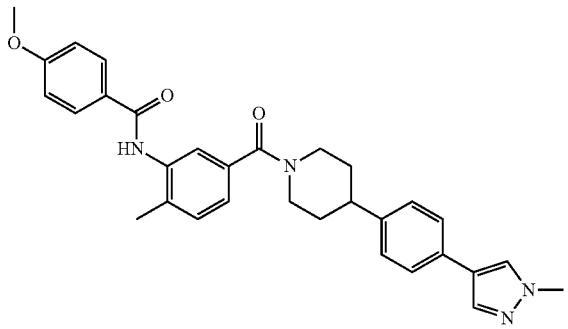 [SMILES: COc1ccc(C(=O)Nc2cc(C(=O)N3CCC(c4ccc(-c5cnn(C)c5)cc4)CC3)ccc2C)cc1]

$^1$H NMR (300 MHz, DMSO-d$_6$) δ ppm 1.53-1.71 (m, 2H), 1.80 (br. s., 2H), 2.27 (s, 3H), 2.80 (br. s., 2H), 2.98-3.29 (m, 2H), 3.85 (d, J=2.5 Hz, 6H), 4.62 (br. s., 1H), 7.07 (d, J=8.9 Hz, 2H), 7.19-7.30 (m, 3H), 7.30-7.39 (m, 1H), 7.39-7.52 (m, 3H), 7.81 (s, 1H), 7.98 (d, J=8.8 Hz, 2H), 8.08 (s, 1H), 9.80 (s, 1H). MS m/z 509 (M+H)$^+$ Example 45

Compound #105

2-methoxy-N-(2-methyl-5-(4-(4-(1-methyl-1H-pyrazol-4-yl)phenyl)piperidine-1-carbonyl)phenyl)benzamide

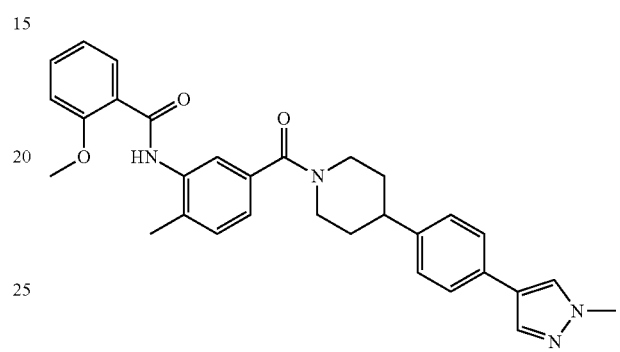

$^1$H NMR (300 MHz, DMSO-d$_6$) δ ppm 1.48 (d, J=11.0 Hz, 2H), 1.56-1.86 (m, 2H), 2.22 (s, 3H), 2.66 (t, J=11.9 Hz, 2H), 2.85-3.16 (m, 2H), 3.71 (s, 3H), 3.88 (s, 3H), 4.49 (br. s., 1H), 6.93-7.05 (m, 2H), 7.12 (d, J=8.1 Hz, 3H), 7.20 (d, J=7.8 Hz, 1H), 7.34 (d, J=8.2 Hz, 2H), 7.39-7.47 (m, 1H), 7.67 (s, 1H), 7.80 (dd, J=7.7, 1.5 Hz, 1H), 7.94 (s, 2H), 9.82 (s, 1H). MS m/z 509 (M+H)$^+$ Example 46

Compound #94

3-methoxy-N-(2-methyl-5-(4-(4-(1-methyl-1H-pyrazol-4-yl)phenyl)piperidine-1-carbonyl)phenyl)benzamide

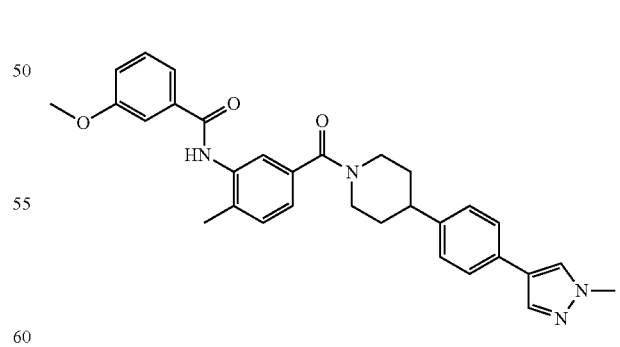

$^1$H NMR (300 MHz, DMSO-d$_6$) δ ppm 1.53-1.71 (m, 2H), 1.81 (br. s., 2H), 2.28 (s, 3H), 2.81 (t, J=11.6 Hz, 2H), 3.17 (br. s., 2H), 3.85 (s, 3H), 3.84 (s, 3H), 4.62 (br. s., 1H), 7.13-7.20 (m, 1H), 7.26 (d, J=8.0 Hz, 3H), 7.36 (d, J=7.8 Hz, 1H), 7.40-7.61 (m, 6H), 7.81 (s, 1H), 8.08 (s, 1H), 9.95 (s, 1H). MS m/z 509 (M+H)$^+$

Example 47

Compound #95

3-chloro-N-(2-methyl-5-(4-(4-(1-methyl-1H-pyrazol-4-yl)phenyl)piperidine-1-carbonyl)phenyl)benzamide

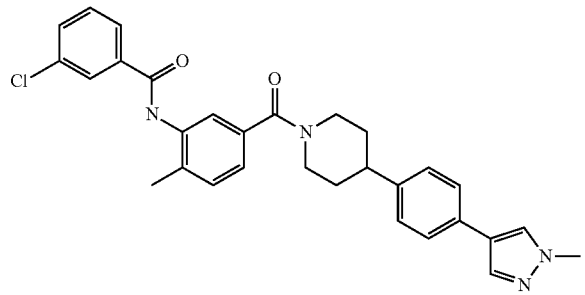 [SMILES: Cc1ccc(C(=O)N2CCC(c3ccc(-c4cnn(C)c4)cc3)CC2)cc1NC(=O)c1cccc(Cl)c1]

$^1$H NMR (300 MHz, DMSO-d$_6$) δ ppm 1.53-1.71 (m, 2H), 1.81 (br. s., 2H), 2.28 (s, 3H), 2.81 (t, J=11.7 Hz, 2H), 3.18 (br. s., 2H), 3.82-3.90 (m, 3H), 4.63 (br. s., 1H), 7.26 (d, J=8.2 Hz, 3H), 7.37 (d, J=7.8 Hz, 1H), 7.47 (t, J=8.4 Hz, 3H), 7.54-7.63 (m, 1H), 7.65-7.73 (m, 1H), 7.81 (s, 1H), 7.90-7.98 (m, 1H), 8.03 (s, 1H), 8.08 (s, 1H), 10.10 (s, 1H). MS m/z 513 (M+H)$^+$

Example 48

Compound #96

2-chloro-N-(2-methyl-5-(4-(4-(1-methyl-1H-pyrazol-4-yl)phenyl)piperidine-1-carbonyl)phenyl)benzamide

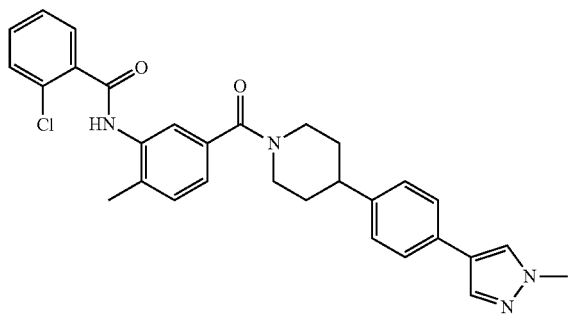 [SMILES: Cc1ccc(C(=O)N2CCC(c3ccc(-c4cnn(C)c4)cc3)CC2)cc1NC(=O)c1ccccc1Cl]

$^1$H NMR (300 MHz, DMSO-d$_6$) δ ppm 1.52-1.71 (m, 2H), 1.81 (br. s., 2H), 2.34 (s, 3H), 2.70-2.96 (m, 2H), 3.18 (br. s., 2H), 3.85 (s, 3H), 4.63 (br. s., 1H), 7.20-7.30 (m, 3H), 7.31-7.39 (m, 1H), 7.43-7.53 (m, 4H), 7.53-7.59 (m, 2H), 7.65 (dd, J=7.1, 2.0 Hz, 1H), 7.81 (s, 1H), 8.08 (s, 1H), 10.08 (s, 1H). MS m/z 513 (M+H)$^+$

Example 49

Compound #103

2-Chloro-6-methoxy-N-(2-methyl-5-(4-(4-(1-methyl-1H-pyrazol-4-yl)phenyl)piperidine-1-carbonyl)phenyl)isonicotinamide

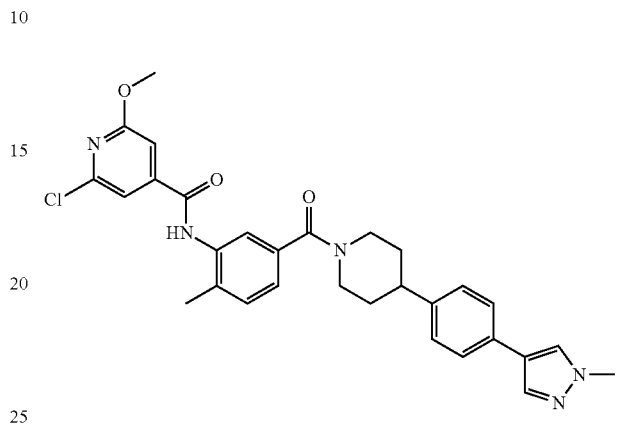

$^1$H NMR (300 MHz, DMSO-d$_6$) δ ppm 1.51-1.71 (m, 2H), 1.71-1.99 (m, 2H), 2.27 (s, 3H), 2.80 (br. s., 2H), 3.18 (br. s., 1H), 3.62-3.83 (m, 1H), 3.85 (s, 3H), 3.94 (s, 3H), 4.62 (br. s., 1H), 7.19-7.31 (m, 3H), 7.31-7.41 (m, 2H), 7.47 (t, J=7.8 Hz, 3H), 7.56 (s, 1H), 7.81 (s, 1H), 8.08 (s, 1H), 10.24 (s, 1H). MS m/z 544 (M+H)$^+$

Example 50

Compound #102

6-Chloro-N-(2-methyl-5-(4-(4-(1-methyl-1H-pyrazol-4-yl)phenyl)piperidine-1-carbonyl)phenyl)nicotinamide

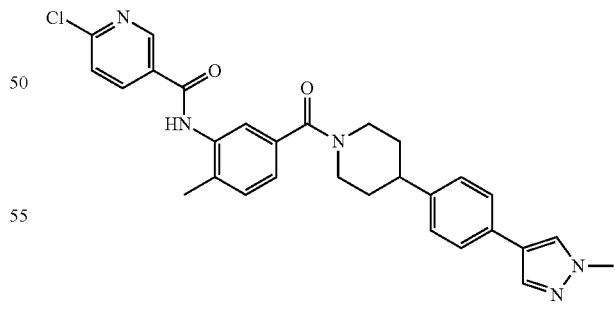

$^1$H NMR (300 MHz, DMSO-d$_6$) δ ppm 1.51-1.71 (m, 2H), 1.81 (br. s., 2H), 2.29 (s, 3H), 2.70-3.00 (m, 2H), 3.17 (br. s., 1H), 3.77 (br. s., 1H), 3.85 (s, 3H), 4.63 (br. s., 1H), 7.20-7.31 (m, 3H), 7.34-7.41 (m, 1H), 7.44-7.52 (m, 3H), 7.73 (d, J=8.4 Hz, 1H), 7.81 (s, 1H), 8.08 (s, 1H), 8.37 (dd, J=8.3, 2.4 Hz, 1H), 8.98 (d, J=2.1 Hz, 1H), 10.22 (s, 1H). MS m/z 514 (M+H)$^+$

Example 51

Compound #101

2-Chloro-N-(2-methyl-5-(4-(4-(1-methyl-1H-pyrazol-4-yl)phenyl)piperidine-1-carbonyl)phenyl)nicotinamide

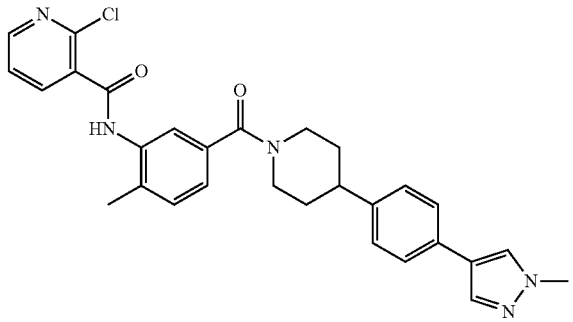

$^1$H NMR (300 MHz, DMSO-d$_6$) δ ppm 1.32-1.51 (m, 2H), 1.62 (br. s., 2H), 2.13 (s, 3H), 2.49-2.75 (m, 2H), 2.97 (s, 1H), 3.58 (br. s., 1H), 3.65 (s, 3H), 4.43 (br. s., 1H), 7.06 (d, J=8.1 Hz, 3H), 7.12-7.20 (m, 1H), 7.28 (d, J=8.2 Hz, 2H), 7.33-7.43 (m, 2H), 7.61 (s, 1H), 7.88 (s, 1H), 7.93 (dd, J=7.6, 1.9 Hz, 1H), 8.34 (dd, J=4.8, 1.9 Hz, 1H), 10.01 (s, 1H). MS m/z 514 (M+H)$^+$

Example 52

Compound #100

4-chloro-N-(2-methyl-5-(4-(4-(1-methyl-1H-pyrazol-4-yl)phenyl)piperidine-1-carbonyl)phenyl)benzamide

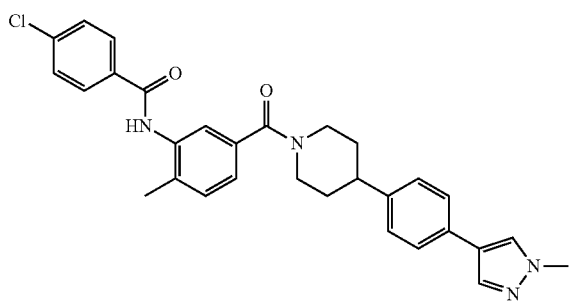 [SMILES: Cc1ccc(C(=O)N2CCC(c3ccc(-c4cnn(C)c4)cc3)CC2)cc1NC(=O)c1ccc(Cl)nc1]

$^1$H NMR (300 MHz, DMSO-d$_6$) δ ppm 1.52-1.71 (m, 2H), 1.81 (br. s., 2H), 2.28 (s, 3H), 2.80 (t, J=12.0 Hz, 2H), 3.18 (br. s., 1H), 3.76 (br. s., 1H), 3.85 (s, 3H), 4.62 (br. s., 1H), 7.26 (d, J=8.2 Hz, 3H), 7.36 (d, J=7.8 Hz, 1H), 7.48 (d, J=8.1 Hz, 3H), 7.62 (m, J=8.5 Hz, 2H), 7.81 (s, 1H), 8.01 (m, J=8.4 Hz, 2H), 8.08 (s, 1H), 10.05 (s, 1H). MS m/z 513 (M+H)$^+$

Example 53

Compound #98

2-methyl-N-(2-methyl-5-(4-(4-(1-methyl-1H-pyrazol-4-yl)phenyl)piperidine-1-carbonyl)phenyl)isonicotinamide

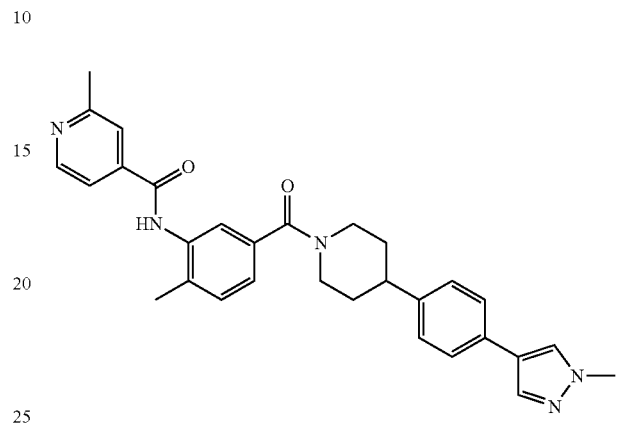

$^1$H NMR (300 MHz, DMSO-d$_6$) δ ppm 1.62 (d, J=8.8 Hz, 2H), 1.81 (br. s., 2H), 2.29 (s, 3H), 2.69 (s, 3H), 2.75-3.02 (m, 2H), 3.85 (s, 3H), 4.08 (br. s., 2H), 4.62 (br. s., 1H), 7.18-7.33 (m, 3H), 7.34-7.42 (m, 1H), 7.42-7.53 (m, 3H), 7.81 (s, 1H), 8.08 (s, 3H), 8.81 (d, J=5.5 Hz, 1H), 10.42 (s, 1H). MS m/z 494 (M+H)$^+$

Example 54

Compound #114

4-chloro-N-(2-methyl-5-(4-(4-(1-methyl-1H-pyrazol-4-yl)phenyl)piperidine-1-carbonyl)phenyl)nicotinamide

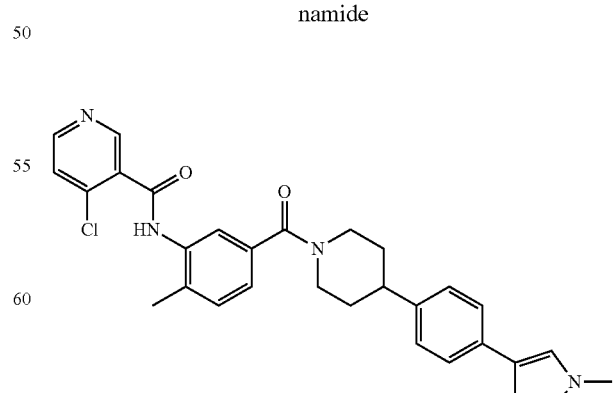

MS m/z 514 (M+H)$^+$

Example 55

Compound #113

6-methoxy-N-(2-methyl-5-(4-(4-(1-methyl-1H-pyrazol-4-yl)phenyl)piperidine-1-carbonyl)phenyl)nicotinamide

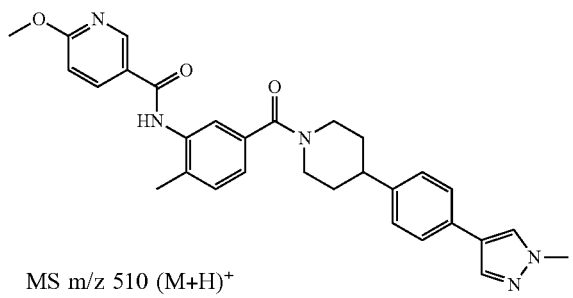

MS m/z 510 (M+H)⁺

Example 56

Compound #225

N-(5-(4-([1,1'-biphenyl]-4-yl)piperidine-1-carbonyl)-2-methylphenyl)-6-(isopropylamino)nicotinamide

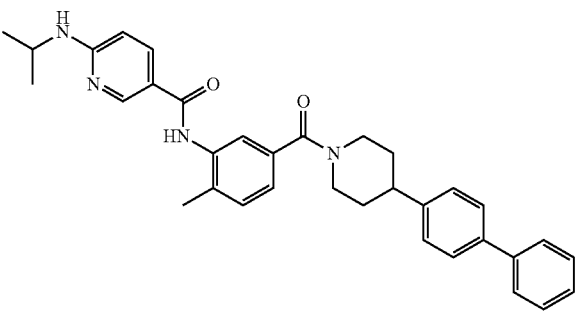 [SMILES: Cc1ccc(C(=O)N2CCC(c3ccc(-c4ccccc4)cc3)CC2)cc1NC(=O)c1ccc(NC(C)C)nc1]

$^1$H NMR (300 MHz, DMSO-d$_6$) δ ppm 1.17 (d, J=6.5 Hz, 6H), 1.56-1.74 (m, 2H), 1.83 (br. s., 2H), 2.27 (s, 3H), 2.88 (t, J=11.9 Hz, 2H), 3.16 (d, J=14.0 Hz, 1H), 3.83 (br. s., 1H), 3.99-4.21 (m, 1H), 4.64 (br. s., 1H), 6.49 (d, J=8.8 Hz, 1H), 7.03 (d, J=7.6 Hz, 1H), 7.22 (dd, J=7.7, 1.5 Hz, 1H), 7.38 (d, J=8.1 Hz, 2H), 7.34 (d, J=7.4 Hz, 2H), 7.41-7.51 (m, 3H), 7.64 (d, J=7.3 Hz, 2H), 7.60 (d, J=8.2 Hz, 2H), 7.89 (dd, J=8.9, 2.4 Hz, 1H), 8.66 (d, J=2.3 Hz, 1H), 9.57 (s, 1H). MS m/z 533 (M+H)⁺

Example 57

Compound #224

N-(5-(4-(2'-fluoro-[1,1'-biphenyl]-4-yl)piperidine-1-carbonyl)-2-methylphenyl)-6-(isopropylamino)nicotinamide

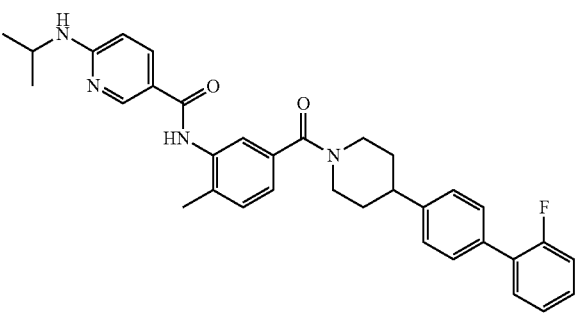 [SMILES: Cc1ccc(C(=O)N2CCC(c3ccc(-c4ccccc4C)cc3)CC2)cc1NC(=O)c1ccc(NC(C)C)nc1]

$^1$H NMR (300 MHz, DMSO-d$_6$) δ ppm 1.17 (d, J=6.5 Hz, 6H), 1.57-1.75 (m, 2H), 1.84 (br. s., 2H), 2.27 (s, 3H), 2.89 (t, J=11.8 Hz, 2H), 3.16 (br. s., 1H), 3.83 (br. s., 1H), 4.04-4.17 (m, 1H), 4.64 (br. s., 1H), 7.03 (d, J=7.6 Hz, 1H), 7.19-7.25 (m, 1H), 7.26-7.36 (m, 3H), 7.36-7.44 (m, 3H), 7.44-7.46 (m, 1H), 7.46-7.57 (m, 3H), 7.89 (dd, J=8.9, 2.4 Hz, 1H), 8.66 (d, J=2.3 Hz, 1H), 9.57 (s, 1H). MS m/z 551 (M+H)⁺

Example 58

Compound #230

N-(5-(4-(3'-fluoro-[1,1'-biphenyl]-4-yl)piperidine-1-carbonyl)-2-methylphenyl)-6-(isopropylamino)nicotinamide

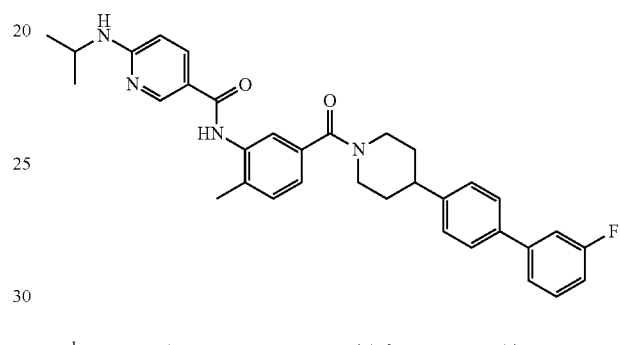

$^1$H NMR (300 MHz, DMSO-d$_6$) δ ppm 1.17 (d, J=6.5 Hz, 6H), 1.57-1.74 (m, 2H), 1.83 (br. s., 2H), 2.27 (s, 3H), 2.88 (t, J=11.6 Hz, 2H), 3.04-3.28 (m, 1H), 3.83 (br. s., 1H), 4.10 (dq, J=13.4, 6.6 Hz, 1H), 4.63 (br. s., 1H), 6.49 (d, J=8.8 Hz, 1H), 7.04 (d, J=7.6 Hz, 1H), 7.12-7.26 (m, 2H), 7.34 (d, J=7.8 Hz, 1H), 7.39 (m, J=8.2 Hz, 2H), 7.44-7.54 (m, 4H), 7.64 (m, J=8.2 Hz, 2H), 7.89 (dd, J=8.9, 2.4 Hz, 1H), 8.66 (d, J=2.2 Hz, 1H), 9.58 (s, 1H). MS m/z 551 (M+H)⁺

Example 59

Compound #232

6-(isopropylamino)-N-(2-methyl-5-(4-(2'-methyl-[1,1'-biphenyl]-4-yl)piperidine-1-carbonyl)phenyl)nicotinamide

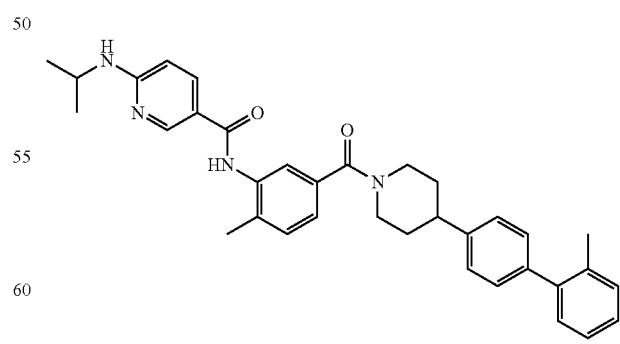

$^1$H NMR (300 MHz, DMSO-d$_6$) δ ppm 1.17 (d, J=6.5 Hz, 6H), 1.54-1.75 (m, 2H), 1.86 (br. s., 2H), 2.23 (s, 3H), 2.27 (s, 3H), 2.76-3.01 (m, 2H), 3.03-3.27 (m, 1H), 3.84 (br. s., 1H), 4.01-4.20 (m, 1H), 4.64 (br. s., 1H), 6.49 (d, J=8.8 Hz, 1H), 7.03 (d, J=7.6 Hz, 1H), 7.14-7.31 (m, 7H), 7.31-7.39 (m, 3H), 7.45 (s, 1H), 7.89 (dd, J=8.8, 2.3 Hz, 1H), 8.66 (d, J=2.2 Hz, 1H), 9.58 (s, 1H). MS m/z 547 (M+H)⁺

Example 60

Compound #233

6-(isopropylamino)-N-(2-methyl-5-(4-(3'-methyl-[1,1'-biphenyl]-4-yl)piperidine-1-carbonyl)phenyl)nicotinamide

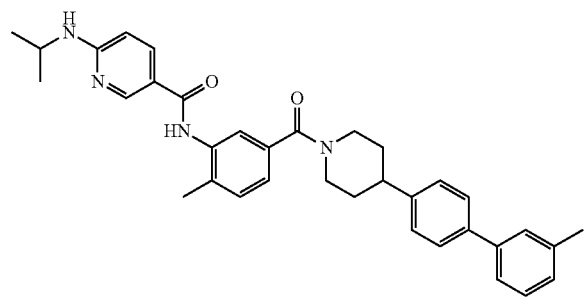 [SMILES: Cc1cccc(-c2ccc(C3CCN(C(=O)c4ccc(C)c(NC(=O)c5ccc(NC(C)C)nc5)c4)CC3)cc2)c1]

¹H NMR (300 MHz, DMSO-d₆) δ ppm 1.17 (d, J=6.5 Hz, 6H), 1.54-1.74 (m, 2H), 1.83 (br. s., 2H), 2.27 (s, 3H), 2.37 (s, 3H), 2.87 (t, J=12.0 Hz, 2H), 3.02-3.27 (m, 1H), 3.83 (br. s., 1H), 4.01-4.21 (m, 1H), 4.63 (br. s., 1H), 6.49 (d, J=8.8 Hz, 1H), 7.04 (d, J=7.6 Hz, 1H), 7.12-7.25 (m, 2H), 7.26-7.40 (m, 4H), 7.40-7.49 (m, 3H), 7.58 (d, J=8.2 Hz, 2H), 7.89 (dd, J=8.8, 2.3 Hz, 1H), 8.66 (d, J=2.2 Hz, 1H), 9.58 (s, 1H). MS m/z 547 (M+H)⁺

Example 61

Compound #234

6-(isopropylamino)-N-(2-methyl-5-(4-(4'-methyl-[1,1'-biphenyl]-4-yl)piperidine-1-carbonyl)phenyl)nicotinamide

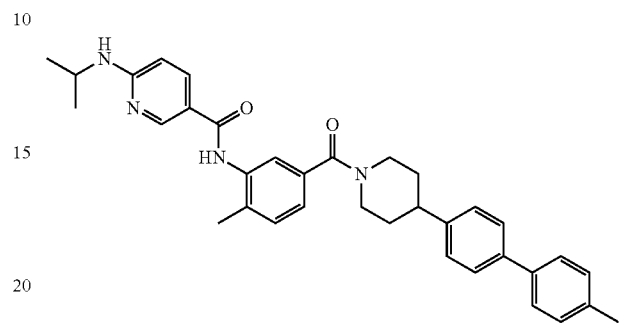

¹H NMR (300 MHz, DMSO-d₆) δ ppm 1.17 (d, J=6.5 Hz, 6H), 1.53-1.73 (m, 2H), 1.83 (br. s., 2H), 2.27 (s, 3H), 2.34 (s, 3H), 2.86 (t, J=11.8 Hz, 2H), 3.04-3.26 (m, 1H), 3.84 (br. s., 1H), 4.01-4.20 (m, 1H), 4.64 (br. s., 1H), 6.49 (d, J=8.9 Hz, 1H), 7.04 (d, J=7.6 Hz, 1H), 7.19-7.30 (m, 3H), 7.30-7.39 (m, 3H), 7.41-7.48 (m, 1H), 7.57 (d, J=8.2 Hz, 2H), 7.53 (d, J=8.2 Hz, 2H), 7.89 (dd, J=8.9, 2.3 Hz, 1H), 8.66 (d, J=2.2 Hz, 1H), 9.58 (s, 1H). MS m/z 547 (M+H)⁺

Example 62

Compound #221

N-(5-(4-(4-(1-(cyclobutylmethyl)-1H-pyrazol-4-yl)phenyl)piperidine-1-carbonyl)-2-methylphenyl)-6-(isopropylamino)nicotinamide

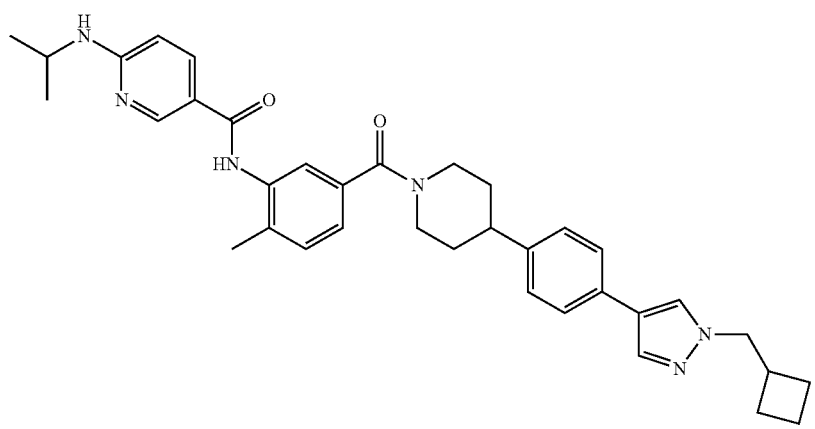 [SMILES: Cc1ccc(C(=O)N2CCC(c3ccc(-c4cnn(CC5CCC5)c4)cc3)CC2)cc1NC(=O)c1ccc(NC(C)C)nc1]

¹H NMR (300 MHz, DMSO-d₆) δ ppm 1.17 (d, J=6.5 Hz, 6H), 1.63 (br. s., 2H), 1.70-1.92 (m, 6H), 1.92-2.07 (m, 2H), 2.27 (s, 3H), 2.68-2.94 (m, 3H), 3.01-3.24 (m, 1H), 3.82 (br. s., 1H), 4.02-4.18 (m, 3H), 4.62 (br. s., 1H), 6.49 (d, J=8.8 Hz, 1H), 7.04 (d, J=7.7 Hz, 1H), 7.17-7.29 (m, 3H), 7.33 (d, J=7.8 Hz, 1H), 7.41-7.54 (m, 3H), 7.81 (s, 1H), 7.89 (dd, J=8.9, 2.4 Hz, 1H), 8.09 (s, 1H), 8.66 (d, J=2.2 Hz, 1H), 9.58 (s, 1H). MS m/z 591 (M+H)⁺

Example 63

Compound #272

6-(isopropylamino)-N-(2-methyl-5-(4-(4-(1-(pyridin-4-yl)-1H-pyrazol-4-yl)phenyl)piperidine-1-carbonyl)phenyl)nicotinamide

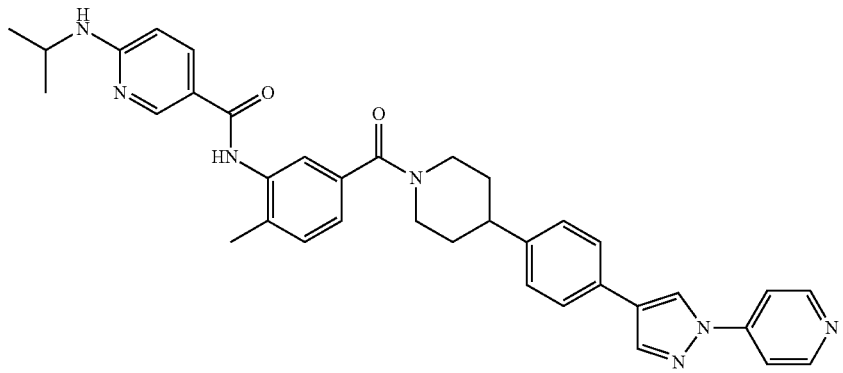 [SMILES: Cc1ccc(C(=O)N2CCC(c3ccc(-c4cnn(-c5ccncc5)c4)cc3)CC2)cc1NC(=O)c1ccc(NC(C)C)nc1]

¹H NMR (300 MHz, DMSO-d₆) δ ppm 1.18 (d, J=6.5 Hz, 6H), 1.54-1.74 (m, 2H), 1.82 (br. s., 2H), 2.27 (s, 3H), 2.75-2.96 (m, 2H), 3.05-3.26 (m, 1H), 3.84 (br. s., 1H), 4.00-4.21 (m, 1H), 4.63 (br. s., 1H), 6.49 (d, J=8.9 Hz, 1H), 7.04 (d, J=7.7 Hz, 1H), 7.22 (d, J=8.0 Hz, 1H), 7.34 (d, J=8.4 Hz, 3H), 7.45 (s, 1H), 7.58 (dd, J=8.3, 4.7 Hz, 1H), 7.66 (d, J=8.0 Hz, 2H), 7.90 (dd, J=8.9, 2.2 Hz, 1H), 8.23-8.33 (m, 2H), 8.54 (d, J=4.5 Hz, 1H), 8.66 (d, J=2.1 Hz, 1H), 9.06 (s, 1H), 9.16 (d, J=2.3 Hz, 1H), 9.58 (s, 1H). MS m/z 600 (M+H)⁺

Example 64

Compound #261

6-(isopropylamino)-N-(2-methyl-5-(4-(4-(1-(pyridin-3-yl)-1H-pyrazol-4-yl)phenyl)piperidine-1-carbonyl)phenyl)nicotinamide

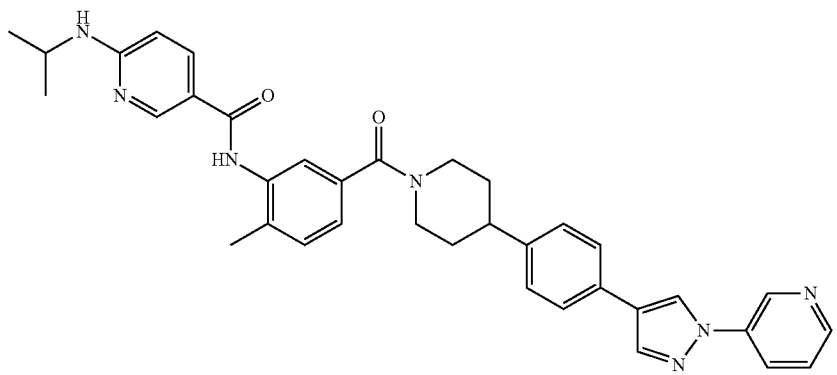 [SMILES: Cc1ccc(C(=O)N2CCC(c3ccc(-c4cnn(-c5cccnc5)c4)cc3)CC2)cc1NC(=O)c1ccc(NC(C)C)nc1]

¹H NMR (300 MHz, DMSO-d₆) δ ppm 1.18 (d, J=6.5 Hz, 6H), 1.57-1.74 (m, 2H), 1.83 (br. s., 2H), 2.28 (s, 3H), 2.76-2.99 (m, 2H), 3.17 (br. s., 1H), 3.86 (br. s., 1H), 4.09 (br. s., 1H), 4.64 (br. s., 1H), 6.49 (d, J=8.7 Hz, 1H), 7.02 (d, J=7.6 Hz, 1H), 7.23 (d, J=7.4 Hz, 1H), 7.29-7.40 (m, 3H), 7.46 (s, 1H), 7.68 (d, J=8.0 Hz, 2H), 7.90 (d, J=6.2 Hz, 3H), 8.33 (s, 1H), 8.61-8.73 (m, 3H), 9.16 (s, 1H), 9.57 (s, 1H). MS m/z 600 (M+H)⁺

Example 65

Compound #254

N-(5-(4-(4-(1-cyclopropyl-1H-pyrazol-4-yl)phenyl)piperidine-1-carbonyl)-2-methylphenyl)-6-(isopropylamino)nicotinamide

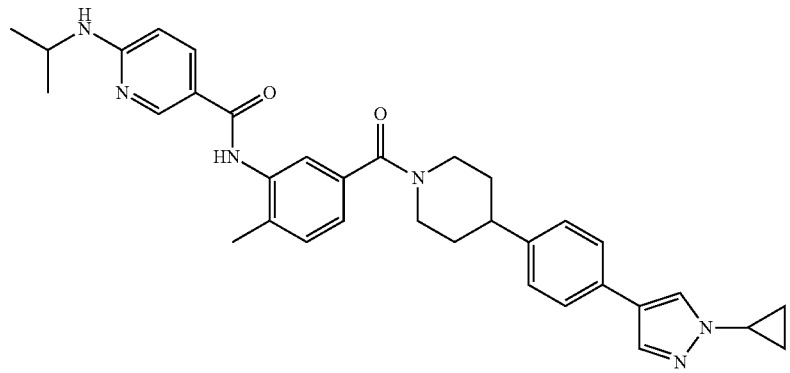 [SMILES: Cc1ccc(C(=O)N2CCC(c3ccc(-c4cnn(C5CC5)c4)cc3)CC2)cc1NC(=O)c1ccc(NC(C)C)nc1]

¹H NMR (300 MHz, DMSO-d₆) δ ppm 0.68-0.78 (m, 2H), 0.78-0.87 (m, 2H), 0.94 (d, J=6.5 Hz, 6H), 1.37 (d, J=9.6 Hz, 2H), 1.56 (br. s., 2H), 2.02 (s, 3H), 2.56 (br. s., 2H), 2.81 (br. s., 1H), 3.38-3.52 (m, 1H), 3.56 (br. s. 1H), 3.75-3.94 (m, 1H), 4.38 (br. s., 1H), 6.29 (d, J=8.8 Hz, 1H), 6.85-7.05 (m, 4H), 7.09 (d, J=7.8 Hz, 1H), 7.20 (s, 1H), 7.25 (d, J=8.1 Hz, 2H), 7.56 (s, 1H), 7.63-7.75 (m, 1H), 7.93 (s, 1H), 8.41 (d, J=1.9 Hz, 1H), 9.37 (s, 1H). MS m/z 563 (M+H)⁺

Example 66

Compound #253

N-(5-(4-(4-(1-(2-(dimethylamino)ethyl)-1H-pyrazol-4-yl)phenyl)piperidine-1-carbonyl)-2-methylphenyl)-6-(isopropylamino)nicotinamide

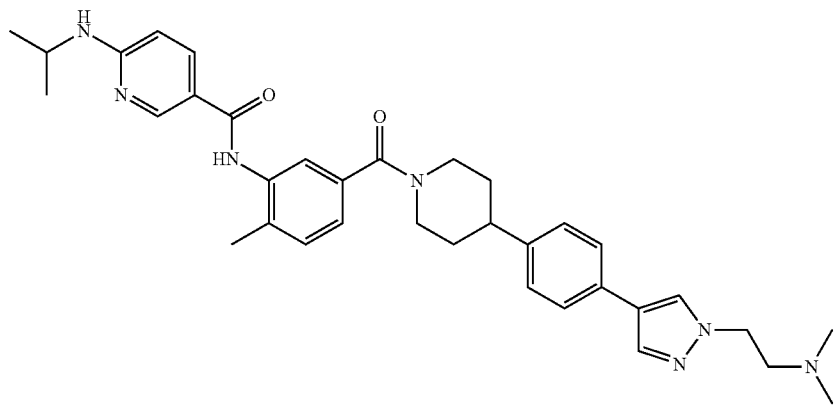 [SMILES: Cc1ccc(C(=O)N2CCC(c3ccc(-c4cnn(CCN(C)C)c4)cc3)CC2)cc1NC(=O)c1ccc(NC(C)C)nc1]

¹H NMR (300 MHz, DMSO-d₆) δ ppm 1.18 (d, J=6.5 Hz, 6H), 1.61 (d, J=12.2 Hz, 2H), 1.80 (br. s., 2H), 2.17 (s, 6H), 2.27 (s, 3H), 2.67 (t, J=6.5 Hz, 2H), 2.81 (br. s., 2H), 3.12 (br. s., 1H), 3.83 (br. s., 1H), 4.02-4.14 (m, 1H), 4.19 (t, J=6.5 Hz, 2H), 4.61 (br. s., 1H), 6.49 (d, J=8.8 Hz, 1H), 7.02 (d, J=7.6 Hz, 1H), 7.15-7.29 (m, 3H), 7.33 (d, J=8.0 Hz, 1H), 7.40-7.53 (m, 3H), 7.81 (s, 1H), 7.89 (dd, J=8.8, 2.3 Hz, 1H), 8.12 (s, 1H), 8.66 (d, J=2.3 Hz, 1H), 9.57 (s, 1H). MS m/z 594 (M+H)⁺

Example 67

Compound #247

N-(5-(4-(4-(1-isopropyl-1H-pyrazol-4-yl)phenyl)piperidine-1-carbonyl)-2-methylphenyl)-6-(isopropylamino)nicotinamide

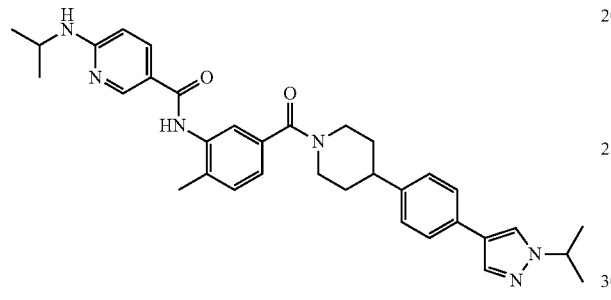

¹H NMR (300 MHz, DMSO-d₆) δ ppm 1.17 (d, J=6.5 Hz, 6H), 1.44 (d, J=6.6 Hz, 6H), 1.53-1.71 (m, 2H), 1.81 (br. s., 2H), 2.27 (s, 3H), 2.69-2.98 (m, 2H), 3.15 (br. s., 1H), 3.84 (br. s., 1H), 4.01-4.20 (m, 1H), 4.49 (dt, J=13.3, 6.7 Hz, 1H), 4.60 (br. s., 1H), 6.49 (d, J=8.8 Hz, 1H), 7.03 (d, J=7.6 Hz, 1H), 7.17-7.29 (m, 3H), 7.33 (d, J=7.8 Hz, 1H), 7.40-7.47 (m, 1H), 7.50 (d, J=8.1 Hz, 2H), 7.81 (s, 1H), 7.89 (dd, J=8.9, 2.4 Hz, 1H), 8.16 (s, 1H), 8.66 (d, J=2.2 Hz, 1H), 9.57 (s, 1H). MS m/z 565 (M+H)⁺

Example 68

Compound #245

N-(5-(4-(4-(1,3-dimethyl-1H-pyrazol-4-yl)phenyl)piperidine-1-carbonyl)-2-methylphenyl)-6-(isopropylamino)nicotinamide

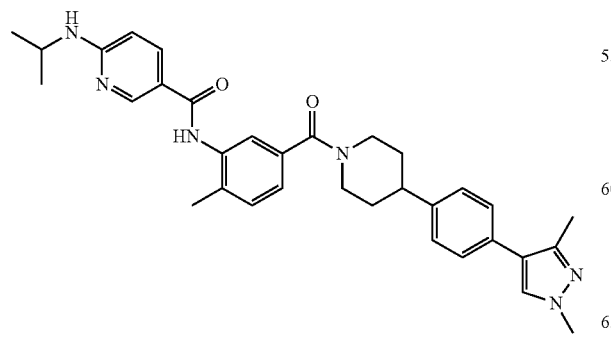

¹H NMR (300 MHz, DMSO-d₆) δ ppm 1.12-1.22 (m, 6H), 1.64 (br. s., 2H), 1.71-1.97 (m, 2H), 2.27 (s, 6H), 2.82 (br. s., 2H), 3.01-3.26 (m, 1H), 3.77 (s, 3H), 3.83 (br. s., 1H), 4.02-4.17 (m, 1H), 4.62 (br. s., 1H), 6.49 (d, J=8.8 Hz, 1H), 7.03 (d, J=7.6 Hz, 1H), 7.21 (dd, J=7.7, 1.4 Hz, 1H), 7.25-7.39 (m, 5H), 7.41-7.47 (m, 1H), 7.83 (s, 1H), 7.89 (dd, J=8.9, 2.4 Hz, 1H), 8.66 (d, J=2.3 Hz, 1H), 9.57 (s, 1H). MS m/z 551 (M+H)⁺

Example 69

Compound #246

N-(5-(4-(4-(1,5-dimethyl-1H-pyrazol-4-yl)phenyl)piperidine-1-carbonyl)-2-methylphenyl)-6-(isopropylamino)nicotinamide

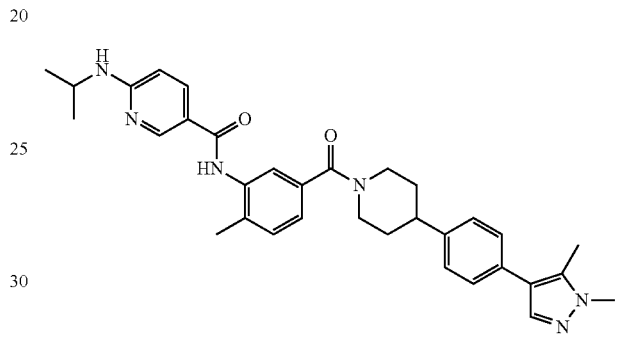

¹H NMR (300 MHz, DMSO-d₆) δ ppm 1.17 (d, J=6.5 Hz, 6H), 1.51-1.71 (m, 2H), 1.82 (br. s., 2H), 2.27 (s, 3H), 2.35 (s, 3H), 2.83 (t, J=12.1 Hz, 2H), 3.11 (br. s., 1H), 3.78 (s, 3H), 3.82 (br. s., 1H), 4.03-4.18 (m, 1H), 4.63 (br. s., 1H), 6.49 (d, J=8.8 Hz, 1H), 7.03 (d, J=7.6 Hz, 1H), 7.21 (dd, J=7.8, 1.4 Hz, 1H), 7.26-7.37 (m, 5H), 7.40-7.47 (m, 1H), 7.52 (s, 1H), 7.89 (dd, J=8.8, 2.5 Hz, 1H), 8.66 (d, J=2.3 Hz, 1H), 9.57 (s, 1H). MS m/z 551 (M+H)⁺

Example 70

Compound #250

N-(5-(4-(4'-fluoro-[1,1'-biphenyl]-4-yl)piperidine-1-carbonyl)-2-methylphenyl)-6-(isopropylamino)nicotinamide

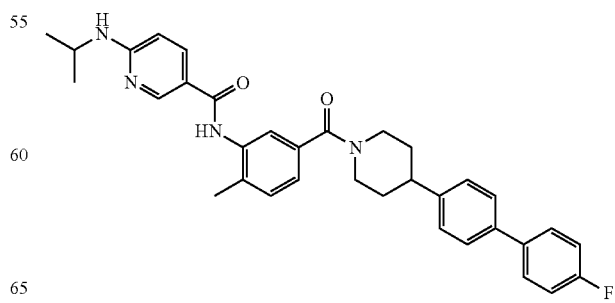

¹H NMR (300 MHz, DMSO-d₆) δ ppm 1.17 (d, J=6.5 Hz, 6H), 1.56-1.74 (m, 2H), 1.83 (br. s., 2H), 2.27 (s, 3H), 2.75-3.01 (m, 2H), 3.12-3.26 (m, 1H), 3.86 (br. s., 1H), 4.03-4.17 (m, 1H), 4.62 (br. s., 1H), 6.49 (d, J=8.8 Hz, 1H), 7.03 (d, J=7.6 Hz, 1H), 7.16-7.41 (m, 6H), 7.43-7.48 (m, 1H), 7.58 (d, J=8.1 Hz, 2H), 7.64-7.73 (m, 2H), 7.89 (dd, J=8.9, 2.4 Hz, 1H), 8.66 (d, J=2.2 Hz, 1H), 9.57 (s, 1H). MS m/z 551 (M+H)⁺

Example 71

Compound #223

6-(isopropylamino)-N-(2-methyl-5-(4-(4-(thiophen-3-yl)phenyl)piperidine-1-carbonyl)phenyl)nicotinamide

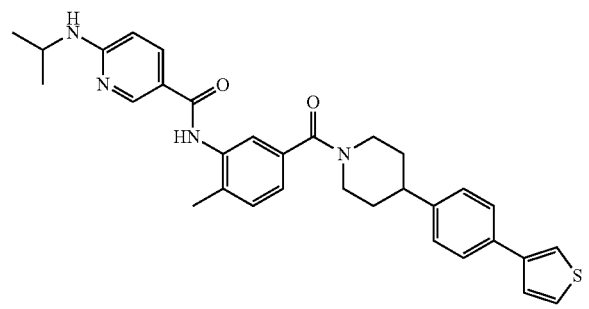 [SMILES: Cc1ccc(C(=O)N2CCC(c3ccc(-c4ccsc4)cc3)CC2)cc1NC(=O)c1ccc(NC(C)C)nc1]

¹H NMR (300 MHz, DMSO-d₆) δ ppm 1.17 (d, J=6.5 Hz, 6H), 1.53-1.72 (m, 2H), 1.82 (br. s., 2H), 2.27 (s, 3H), 2.79-2.99 (m, 2H), 3.13 (br. s., 1H), 3.84 (br. s., 1H), 4.03-4.17 (m, 1H), 4.62 (br. s., 1H), 6.49 (d, J=8.8 Hz, 1H), 7.04 (d, J=7.6 Hz, 1H), 7.22 (dd, J=7.7, 1.5 Hz, 1H), 7.28-7.37 (m, 3H), 7.41-7.48 (m, 1H), 7.53 (dd, J=5.0, 1.2 Hz, 1H), 7.57-7.70 (m, 3H), 7.81 (dd, J=2.9, 1.2 Hz, 1H), 7.89 (dd, J=8.9, 2.4 Hz, 1H), 8.66 (d, J=2.3 Hz, 1H), 9.58 (s, 1H). MS m/z 539 (M+H)⁺

Example 72

Compound #213

6-(isopropylamino)-N-(2-methyl-5-(4-(4-(1-(tetrahydro-2H-pyran-4-yl)-1H-pyrazol-4-yl)phenyl)piperidine-1-carbonyl)phenyl)nicotinamide

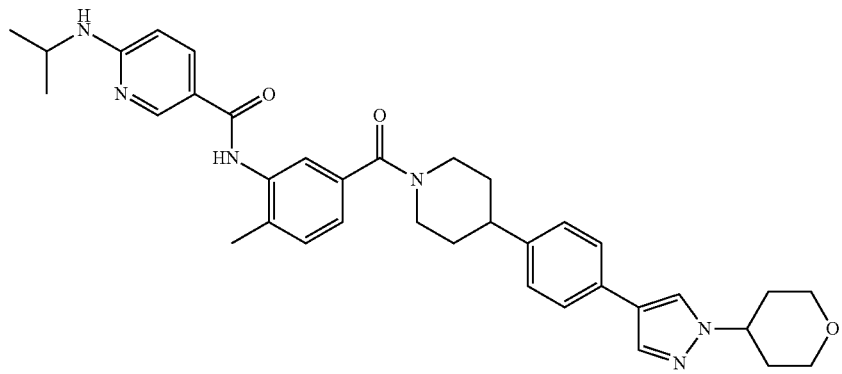 [SMILES: Cc1ccc(C(=O)N2CCC(c3ccc(-c4cnn(C5CCOCC5)c4)cc3)CC2)cc1NC(=O)c1ccc(NC(C)C)nc1]

$^1$H NMR (300 MHz, DMSO-d$_6$) δ ppm 1.11-1.23 (m, 6H), 1.49-1.71 (m, 2H), 1.80 (br. s., 2H), 1.91-2.06 (m, 4H), 2.27 (s, 3H), 2.71-2.97 (m, 2H), 3.01-3.24 (m, 1H), 3.41-3.54 (m, 2H), 3.81 (br. s., 1H), 3.92-4.03 (m, 2H), 4.03-4.17 (m, 1H), 4.31-4.47 (m, 1H), 4.62 (br. s., 1H), 6.49 (d, J=8.9 Hz, 1H), 7.04 (d, J=7.6 Hz, 1H), 7.16-7.30 (m, 3H), 7.33 (d, J=7.8 Hz, 1H), 7.38-7.47 (m, 1H), 7.47-7.55 (m, 2H), 7.85 (s, 1H), 7.89 (dd, J=8.9, 2.4 Hz, 1H), 8.21 (s, 1H), 8.66 (d, J=2.2 Hz, 1H), 9.58 (s, 1H). MS m/z 607 (M+H)$^+$ Example 73

Compound #248

N-(5-(4-(4-(1-cyclobutyl-1H-pyrazol-4-yl)phenyl)piperidine-1-carbonyl)-2-methylphenyl)-6-(isopropylamino)nicotinamide

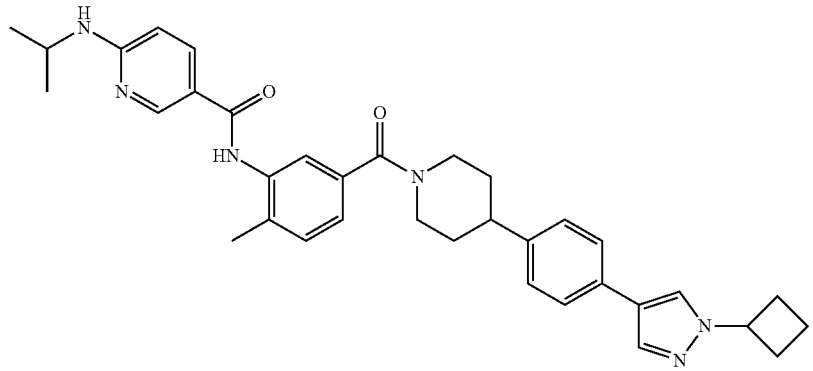 [SMILES: Cc1ccc(C(=O)N2CCC(c3ccc(-c4cnn(C5CCC5)c4)cc3)CC2)cc1NC(=O)c1ccc(NC(C)C)nc1]

$^1$H NMR (300 MHz, DMSO-d$_6$) δ ppm 1.17 (d, J=6.5 Hz, 6H), 1.63 (br. s., 2H), 1.71-1.91 (m, 4H), 2.27 (s, 3H), 2.33-2.45 (m, 2H), 2.69-2.97 (m, 2H), 3.34-3.45 (m, 2H), 3.83 (br. s., 1H), 4.02-4.19 (m, 1H), 4.62 (br. s., 1H), 4.81 (d, J=8.4 Hz, 1H), 6.49 (d, J=8.9 Hz, 1H), 7.03 (d, J=7.6 Hz, 1H), 7.17-7.30 (m, 3H), 7.33 (d, J=7.8 Hz, 1H), 7.41-7.46 (m, 1H), 7.51 (d, J=8.1 Hz, 2H), 7.80-7.86 (m, 1H), 7.89 (dd, J=8.8, 2.3 Hz, 1H), 8.22 (s, 1H), 8.66 (d, J=2.2 Hz, 1H), 9.57 (s, 1H). MS m/z 577 (M+H)$^+$ Example 74

Compound #249

N-(5-(4-(4-(1-(cyclopropylmethyl)-1H-pyrazol-4-yl)phenyl)piperidine-1-carbonyl)-2-methylphenyl)-6-(isopropylamino)nicotinamide

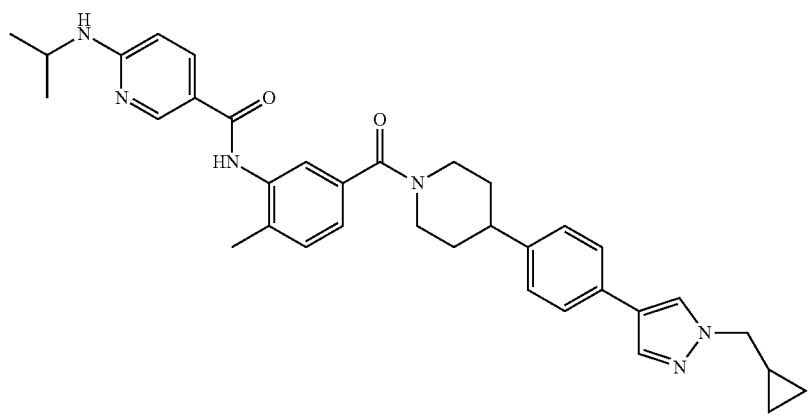 [SMILES: Cc1ccc(C(=O)N2CCC(c3ccc(-c4cnn(CC5CC5)c4)cc3)CC2)cc1NC(=O)c1ccc(NC(C)C)nc1]

¹H NMR (300 MHz, DMSO-d₆) δ ppm 0.32-0.44 (m, 2H), 0.55 (s, 2H), 1.17 (d, J=6.5 Hz, 6H), 1.47-1.70 (m, 2H), 1.79 (br. s., 2H), 2.27 (s, 3H), 2.72-3.00 (m, 3H), 3.67-3.92 (m, 1H), 3.97 (d, J=7.0 Hz, 2H), 4.03-4.17 (m, 2H), 4.60-4.68 (m, 1H), 6.49 (d, J=8.9 Hz, 1H), 7.04 (s, 1H), 7.11-7.40 (m, 4H), 7.40-7.55 (m, 3H), 7.82 (s, 1H), 7.87 (s, 1H), 8.15 (s, 1H), 8.66 (d, J=2.2 Hz, 1H), 9.57 (s, 1H). MS m/z 577 (M+H)⁺

Example 75

Compound #267

N-(5-(4-(4-(1-(2-hydroxyethyl)-1H-pyrazol-4-yl)phenyl)piperidine-1-carbonyl)-2-methylphenyl)-6-(isopropylamino)nicotinamide

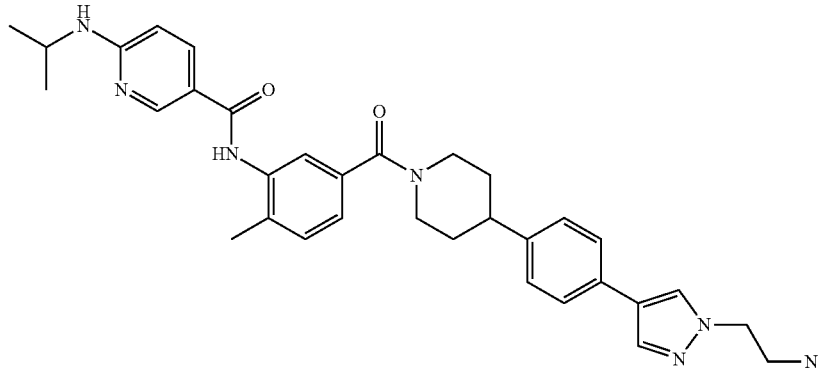 [SMILES: Cc1ccc(C(=O)N2CCC(c3ccc(-c4cnn(CCN)c4)cc3)CC2)cc1NC(=O)c1ccc(NC(C)C)nc1]

¹H NMR (300 MHz, DMSO-d₆) δ ppm 1.17 (d, J=6.5 Hz, 6H), 1.61 (d, J=9.8 Hz, 2H), 1.81 (br. s., 1H), 1.88 (br. s., 1H), 2.27 (s, 3H), 2.80 (t, J=11.8 Hz, 2H), 2.98-3.30 (m, 1H), 3.77 (q, J=5.5 Hz, 3H), 4.03-4.20 (m, 3H), 4.62 (br. s., 1H), 4.93 (t, J=5.3 Hz, 1H), 6.49 (d, J=8.8 Hz, 1H), 7.04 (d, J=7.6 Hz, 1H), 7.17-7.29 (m, 3H), 7.33 (d, J=8.0 Hz, 1H), 7.40-7.53 (m, 3H), 7.83 (s, 1H), 7.89 (dd, J=8.9, 2.4 Hz, 1H), 8.09 (s, 1H), 8.66 (d, J=2.3 Hz, 1H), 9.59 (s, 1H). MS m/z 567 (M+H)⁺

Example 76

Compound #118

2-methoxy-N-(2-methyl-5-(4-(4-(1-methyl-1H-pyrazol-4-yl)phenyl)piperidine-1-carbonyl)phenyl)nicotinamide

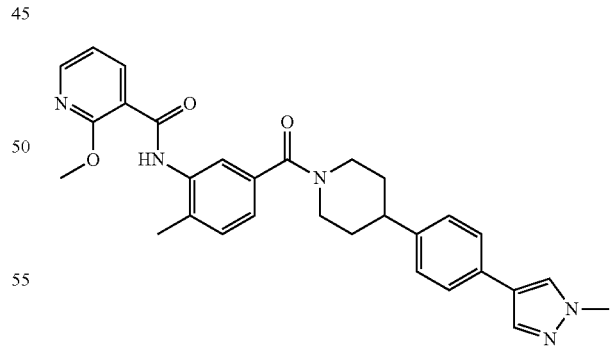

¹H NMR (300 MHz, DMSO-d₆) δ ppm 1.62 (d, J=11.7 Hz, 2H), 1.81 (br. s., 2H), 2.38 (s, 3H), 2.81 (br. s., 2H), 3.17 (br. s., 1H), 3.78 (br. s., 1H), 3.86 (s, 3H), 4.09 (s, 3H), 4.62 (br. s., 1H), 7.13-7.31 (m, 4H), 7.32-7.41 (m, 1H), 7.49 (d, J=8.1 Hz, 2H), 7.81 (s, 1H), 8.03 (s, 1H), 8.08 (s, 1H), 8.30 (dd, J=7.5, 1.9 Hz, 1H), 8.40 (dd, J=4.8, 1.9 Hz, 1H), 9.95 (s, 1H). MS m/z 510 (M+H)⁺

Example 77

Compound #164

(3S)-6-(3-(hydroxymethyl)piperazin-1-yl)-N-(2-methyl-5-(4-(4-(1-methyl-1H-pyrazol-4-yl)phenyl)piperidine-1-carbonyl)phenyl)nicotinamide

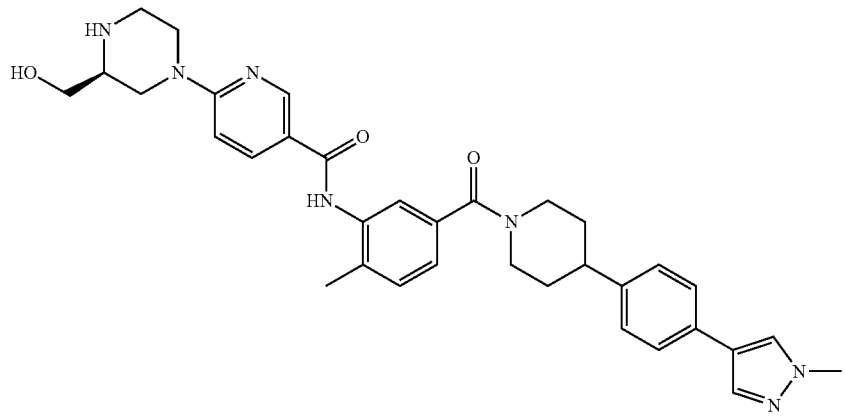 [SMILES: Cc1ccc(C(=O)N2CCC(c3ccc(-c4cnn(C)c4)cc3)CC2)cc1NC(=O)c1ccc(N2CCN[C@H](CO)C2)nc1]

$^1$H NMR (300 MHz, DMSO-d$_6$) δ ppm 1.49-1.71 (m, 2H), 1.80 (br. s., 2H), 2.27 (s, 3H), 2.35 (br. s., 1H), 2.61-2.74 (m, 2H), 2.74-3.06 (m, 4H), 3.16 (br. s., 1H), 3.36-3.45 (m, 2H), 3.78 (br. s., 1H), 3.85 (s, 3H), 4.21 (br. s., 1H), 4.33 (br. s., 1H), 4.62 (br. s., 1H), 4.69 (s, 1H), 6.87 (d, J=9.2 Hz, 1H), 7.17-7.30 (m, 3H), 7.34 (d, J=7.7 Hz, 1H), 7.48 (d, J=8.1 Hz, 3H), 7.81 (s, 1H), 7.98-8.13 (m, 2H), 8.74 (d, J=2.1 Hz, 1H), 9.68 (s, 1H). MS m/z 594 (M+H)$^+$

Example 78

Compound #163

(3R)-6-(3-(hydroxymethyl)piperazin-1-yl)-N-(2-methyl-5-(4-(4-(1-methyl-1H-Pyrazol-4-yl)phenyl)piperidine-1-carbonyl)phenyl)nicotinamide

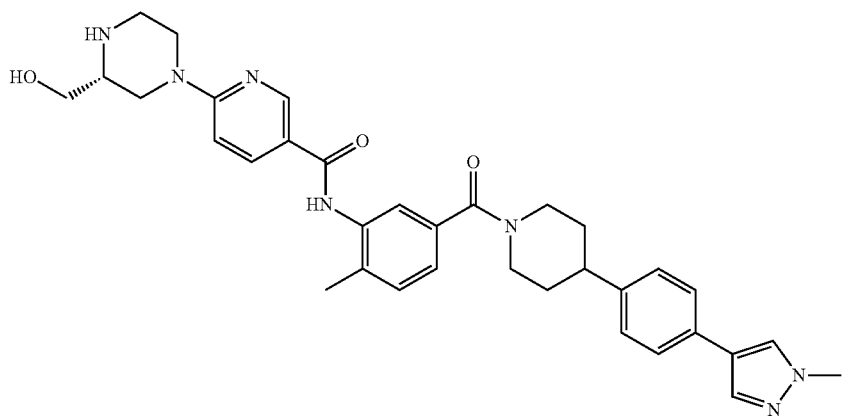 [SMILES: Cc1ccc(C(=O)N2CCC(c3ccc(-c4cnn(C)c4)cc3)CC2)cc1NC(=O)c1ccc(N2CCN[C@@H](CO)C2)nc1]

$^1$H NMR (300 MHz, DMSO-d$_6$) δ ppm 1.61 (d, J=12.1 Hz, 2H), 1.80 (br. s., 2H), 2.27 (s, 3H), 2.35 (br. s., 1H), 2.66 (br. s., 2H), 2.86 (d, J=11.3 Hz, 2H), 2.99 (d, J=11.4 Hz, 2H), 3.17 (br. s., 1H), 3.38 (t, J=5.5 Hz, 2H), 3.77 (br. s., 1H), 3.85 (s, 3H), 4.21 (br. s., 1H), 4.33 (br. s., 1H), 4.60 (br. s., 1H), 4.69 (t, J=5.4 Hz, 1H), 6.87 (d, J=9.1 Hz, 1H), 7.16-7.30 (m, 3H), 7.34 (d, J=8.0 Hz, 1H), 7.39-7.52 (m, 3H), 7.81 (s, 1H), 8.00-8.13 (m, 2H), 8.74 (d, J=2.3 Hz, 1H), 9.68 (s, 1H). MS m/z 594 (M+H)$^+$ $^1$H NMR (300 MHz, DMSO-d$_6$) δ ppm 1.19-1.29 (m, 6H), 1.51-1.70 (m, 2H), 1.83 (d, J=14.8 Hz, 2H), 2.23-2.32 (m, 3H), 2.64-2.93 (m, 2H), 2.98 (dt, J=13.8, 6.9 Hz, 1H), 3.17 (br. s., 1H), 3.75 (br. s., 1H), 3.85 (s, 3H), 4.62 (br. s., 1H), 7.20-7.30 (m, 3H), 7.35 (d, J=7.8 Hz, 1H), 7.39 (s, 1H), 7.42 (s, 1H), 7.43-7.48 (m, 2H), 7.49 (s, 1H), 7.81 (s, 1H), 7.92 (d, J=8.2 Hz, 2H), 8.08 (s, 1H), 9.87 (s, 1H). MS m/z 521 (M+H)$^+$ Example 79

Compound #148

4-isopropyl-N-(2-methyl-5-(4-(4-(1-methyl-1H-pyrazol-4-yl)phenyl)piperidine-1-carbonyl)phenyl)benzamide

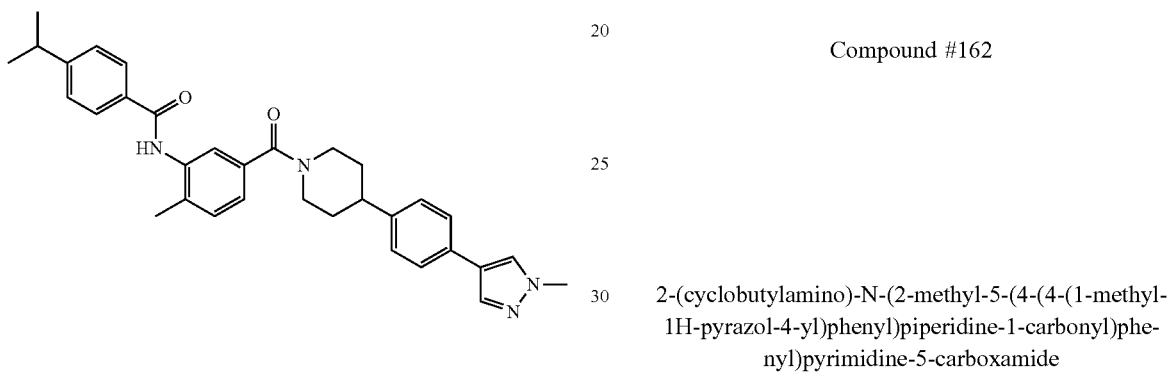

Example 80

Compound #162

2-(cyclobutylamino)-N-(2-methyl-5-(4-(4-(1-methyl-1H-pyrazol-4-yl)phenyl)piperidine-1-carbonyl)phenyl)pyrimidine-5-carboxamide

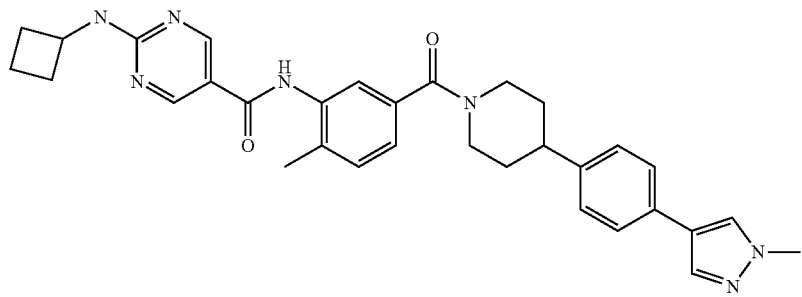 [SMILES: Cc1ccc(C(=O)N2CCC(c3ccc(-c4cnn(C)c4)cc3)CC2)cc1NC(=O)c1cnc(NC2CCC2)nc1]

¹H NMR (300 MHz, DMSO-d₆) δ ppm 1.55-1.75 (m, 5H), 1.79 (br. s., 1H), 1.93-2.10 (m, 2H), 2.27 (s, 5H), 2.70-2.97 (m, 2H), 3.01-3.26 (m, 1H), 3.78 (br. s., 1H), 3.85 (s, 3H), 4.45 (s, 1H), 4.63 (br. s., 1H), 7.17-7.29 (m, 3H), 7.34 (d, J=8.0 Hz, 1H), 7.48 (d, J=8.1 Hz, 3H), 7.81 (s, 1H), 8.08 (s, 1H), 8.18 (d, J=7.6 Hz, 1H), 8.83 (br. s., 2H), 9.73 (s, 1H). MS m/z 550 (M+H)⁺

Example 81

Compound #146

2-(isopropylamino)-N-(2-methyl-5-(4-(4-(1-methyl-1H-pyrazol-4-yl)phenyl)piperidine-1-carbonyl)phenyl)pyrimidine-5-carboxamide

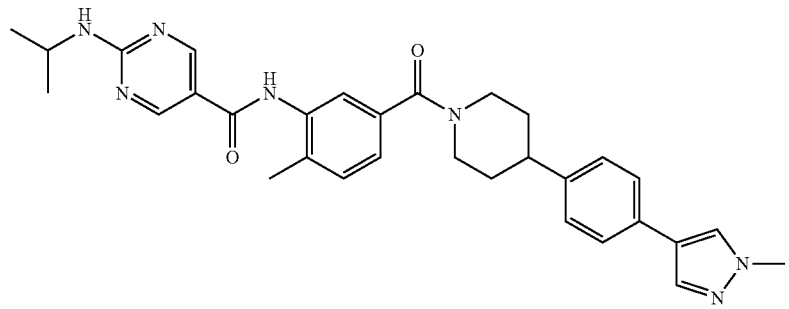 [SMILES: Cc1ccc(C(=O)N2CCC(c3ccc(-c4cnn(C)c4)cc3)CC2)cc1NC(=O)c1cnc(NC(C)C)nc1]

¹H NMR (300 MHz, DMSO-d₆) δ ppm 1.00 (d, J=6.5 Hz, 6H), 1.33-1.52 (m, 2H), 1.61 (br. s., 2H), 2.09 (s, 3H), 2.51-2.80 (m, 2H), 2.95 (br. s., 1H), 3.58 (br. s., 1H), 3.67 (s, 3H), 3.86-4.07 (m, 1H), 4.44 (br. s., 1H), 7.00-7.12 (m, 3H), 7.16 (d, J=8.0 Hz, 1H), 7.22-7.34 (m, 3H), 7.55-7.66 (m, 2H), 7.90 (s, 1H), 8.64 (br. s., 2H), 9.54 (s, 1H). MS m/z 538 (M+H)⁺

Example 82

Compound #155

3-chloro-4-methoxy-N-(2-methyl-5-(4-(4-(1-methyl-1H-pyrazol-4-yl)phenyl)piperidine-1-carbonyl)phenyl)benzamide

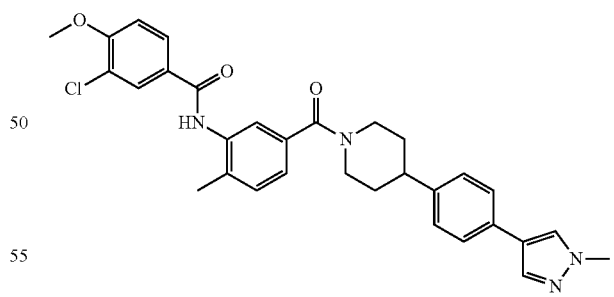

¹H NMR (300 MHz, DMSO-d₆) δ ppm 1.44-1.63 (m, 2H), 1.71 (br. s., 2H), 2.18 (s, 3H), 2.58-2.89 (m, 2H), 2.96-3.18 (m, 1H), 3.70 (br. s., 1H), 3.76 (s, 3H), 3.86 (s, 3H), 4.53 (br. s., 1H), 7.12-7.29 (m, 5H), 7.32 (s, 1H), 7.39 (d, J=8.1 Hz, 2H), 7.72 (s, 1H), 7.90 (dd, J=8.7, 1.8 Hz, 1H), 7.99 (s, 2H), 9.85 (s, 1H). MS m/z 543 (M+H)⁺

Example 83

Compound #145

N-(2-methyl-5-(4-(4-(1-methyl-1H-pyrazol-4-yl)phenyl)piperidine-1-carbonyl)phenyl)-4-(trifluoromethyl)benzamide

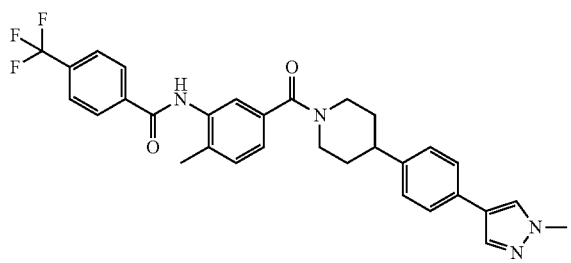 [SMILES: Cc1ccc(C(=O)N2CCC(c3ccc(-c4cnn(C)c4)cc3)CC2)cc1NC(=O)c1ccc(C(F)(F)F)cc1]

$^1$H NMR (300 MHz, DMSO-$d_6$) δ ppm 1.55-1.78 (m, 2H), 1.86 (br. s., 2H), 2.36 (s, 3H), 2.87 (t, J=11.7 Hz, 2H), 3.25 (br. s., 1H), 3.83 (br. s., 1H), 3.91 (s, 3H), 4.68 (br. s., 1H), 7.32 (d, J=8.0 Hz, 3H), 7.44 (d, J=7.8 Hz, 1H), 7.48-7.59 (m, 3H), 7.87 (s, 1H), 7.99 (m, J=8.1 Hz, 2H), 8.14 (s, 1H), 8.23 (m, 2H), 10.26 (s, 1H). MS m/z 547 (M+H)$^+$

Example 84

Compound #144

2-(isopropyl(methyl)amino)-N-(2-methyl-5-(4-(4-(1-methyl-1H-pyrazol-4-yl)phenyl)piperidine-1-carbonyl)phenyl)pyrimidine-5-carboxamide

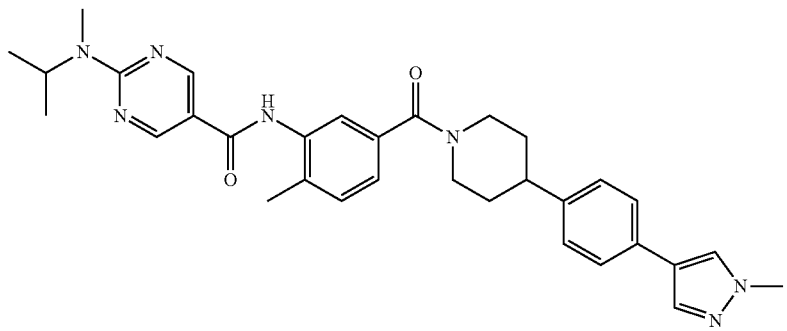 [SMILES: Cc1ccc(C(=O)N2CCC(c3ccc(-c4cnn(C)c4)cc3)CC2)cc1NC(=O)c1cnc(N(C)C(C)C)nc1]

$^1$H NMR (300 MHz, DMSO-$d_6$) δ ppm 1.18 (d, J=6.7 Hz, 6H), 1.51-1.70 (m, 2H), 1.80 (br. s., 2H), 2.28 (s, 3H), 2.80 (t, J=11.6 Hz, 2H), 3.02 (s, 3H), 3.17 (br. s., 1H), 3.77 (br. s., 1H), 3.85 (s, 3H), 4.62 (br. s., 1H), 5.10 (quin, J=6.7 Hz, 1H), 7.19-7.30 (m, 3H), 7.35 (d, J=7.8 Hz, 1H), 7.43-7.52 (m, 3H), 7.81 (s, 1H), 8.08 (s, 1H), 8.89 (s, 2H), 9.75 (s, 1H). MS m/z 552 (M+H)$^+$

Example 85

Compound #152

N-(2-methyl-5-(4-(4-(1-methyl-1H-pyrazol-4-yl)phenyl)piperidine-1-carbonyl)phenyl)-2-morpholinopyrimidine-5-carboxamide

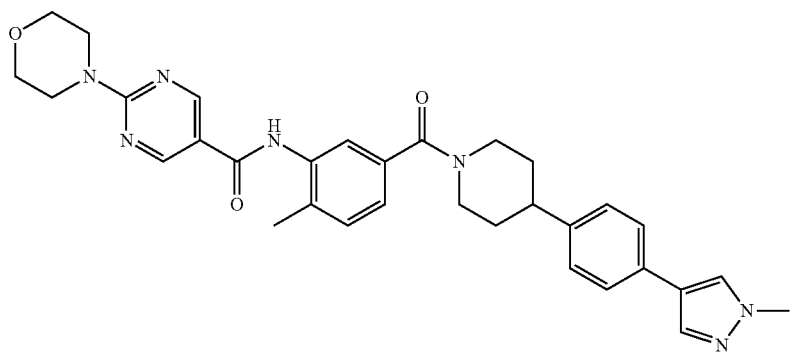 [SMILES: Cc1ccc(C(=O)N2CCC(c3ccc(-c4cnn(C)c4)cc3)CC2)cc1NC(=O)c1cnc(N2CCOCC2)nc1]

¹H NMR (300 MHz, DMSO-d₆) δ ppm 1.58-1.77 (m, 2H), 1.77-2.05 (m, 2H), 2.34 (s, 3H), 2.87 (t, J=11.9 Hz, 2H), 3.09-3.18 (m, 1H), 3.70-3.80 (m, 4H), 3.80-3.85 (m, 1H), 3.86-3.96 (m, 7H), 4.68 (br. s., 1H), 7.24-7.37 (m, 3H), 7.42 (d, J=7.8 Hz, 1H), 7.48-7.59 (m, 3H), 7.87 (s, 1H), 8.15 (s, 1H), 8.99 (s, 2H), 9.89 (s, 1H). MS m/z 566 (M+H)⁺

Example 86

Compound #147

2-chloro-4-fluoro-N-(2-methyl-5-(4-(4-(1-methyl-1H-pyrazol-4-yl)phenyl)piperidine-1-carbonyl)phenyl)benzamide

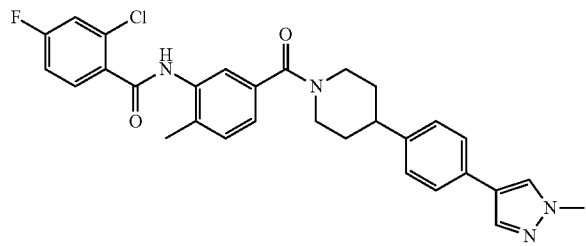

¹H NMR (300 MHz, DMSO-d₆) δ ppm 1.56-1.77 (m, 2H), 1.85 (br. s., 2H), 2.38 (s, 3H), 2.74-3.05 (m, 2H), 3.07-3.33 (m, 1H), 3.82 (br. s., 1H), 3.91 (s, 3H), 4.67 (br. s., 1H), 7.31 (d, J=8.0 Hz, 3H), 7.35-7.47 (m, 2H), 7.54 (d, J=8.1 Hz, 2H), 7.59-7.69 (m, 2H), 7.79 (dd, J=8.5, 6.3 Hz, 1H), 7.86 (s, 1H), 8.13 (s, 1H), 10.13 (s, 1H). MS m/z 531 (M+H)⁺

Example 87

Compound #136

2-chloro-N-(2-methyl-5-(4-(4-(1-methyl-1H-pyrazol-4-yl)phenyl)piperidine-1-carbonyl)phenyl)pyrimidine-5-carboxamide

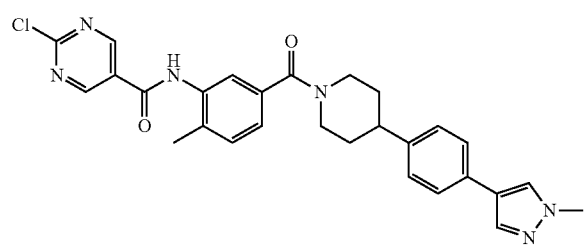 [SMILES: Cc1ccc(C(=O)N2CCC(c3ccc(-c4cnn(C)c4)cc3)CC2)cc1NC(=O)c1cnc(Cl)nc1]

¹H NMR (300 MHz, DMSO-d₆) δ ppm 1.37-1.57 (m, 2H), 1.66 (br. s., 2H), 2.17 (s, 3H), 2.56-2.84 (m, 2H), 3.01 (br. s., 1H), 3.64 (br. s., 1H), 3.71 (s, 3H), 4.47 (br. s., 1H), 7.05-7.19 (m, 3H), 7.20-7.27 (m, 1H), 7.34 (d, J=8.1 Hz, 3H), 7.67 (s, 1H), 7.94 (s, 1H), 9.11 (s, 2H), 10.18 (s, 1H). MS m/z 515 (M+H)⁺

Example 88

Compound #137

5-fluoro-2-methyl-N-(2-methyl-5-(4-(4-(1-methyl-1H-pyrazol-4-yl)phenyl)piperidine-1-carbonyl)phenyl)benzamide

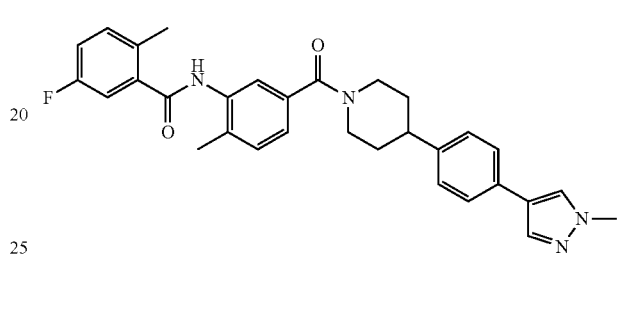

¹H NMR (300 MHz, DMSO-d₆) δ ppm 1.51-1.72 (m, 2H), 1.82 (br. s., 2H), 2.32 (s, 3H), 2.41 (s, 3H), 2.69-2.95 (m, 2H), 3.14 (br. s., 1H), 3.78 (br. s., 1H), 3.85 (s, 3H), 4.63 (br. s., 1H), 7.18-7.30 (m, 4H), 7.31-7.44 (m, 3H), 7.49 (d, J=8.1 Hz, 2H), 7.54 (s, 1H), 7.81 (s, 1H), 8.08 (s, 1H), 9.94 (s, 1H). MS m/z 511 (M+H)⁺

Example 89

Compound #126

N-(2-methyl-5-(4-(4-(1-methyl-1H-pyrazol-4-yl)phenyl)piperidine-1-carbonyl)phenyl)-4-(methylthio)benzamide

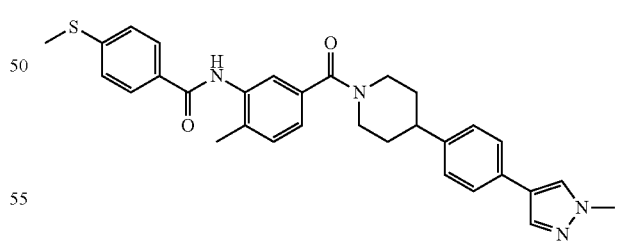

¹H NMR (300 MHz, DMSO-d₆) δ ppm 1.52-1.70 (m, 2H), 1.70-1.97 (m, 2H), 2.27 (s, 3H), 2.66-2.96 (m, 2H), 3.18 (br. s., 1H), 3.62-3.84 (m, 1H), 3.85 (s, 3H), 4.62 (br. s., 1H), 7.19-7.30 (m, 3H), 7.31-7.42 (m, 3H), 7.42-7.53 (m, 3H), 7.77-7.84 (m, 1H), 7.94 (d, J=8.5 Hz, 2H), 8.08 (s, 1H), 9.91 (s, 1H). MS m/z 525 (M+H)⁺

Example 90

Compound #135

3-hydroxy-4-methoxy-N-(2-methyl-5-(4-(4-(1-methyl-1H-pyrazol-4-yl)phenyl)piperidine-1-carbonyl)phenyl)benzamide

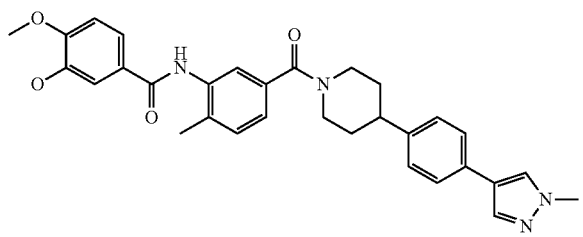

$^1$H NMR (300 MHz, DMSO-d$_6$) δ ppm 1.31-1.50 (m, 2H), 1.60 (br. s., 2H), 2.05 (s, 3H), 2.59 (t, J=11.6 Hz, 2H), 2.78-3.05 (m, 1H), 3.58 (br. s., 1H), 3.64 (d, J=1.5 Hz, 6H), 4.40 (br. s., 1H), 6.82 (d, J=8.5 Hz, 1H), 6.97-7.08 (m, 3H), 7.08-7.16 (m, 1H), 7.21 (d, J=1.8 Hz, 2H), 7.23-7.32 (m, 3H), 7.60 (s, 1H), 7.87 (s, 1H), 9.07 (s, 1H), 9.50 (s, 1H). MS m/z 525 (M+H)$^+$

Example 91

Compound #127

2-fluoro-5-methyl-N-(2-methyl-5-(4-(4-(1-methyl-1H-pyrazol-4-yl)phenyl)piperidine-1-carbonyl)phenyl)benzamide

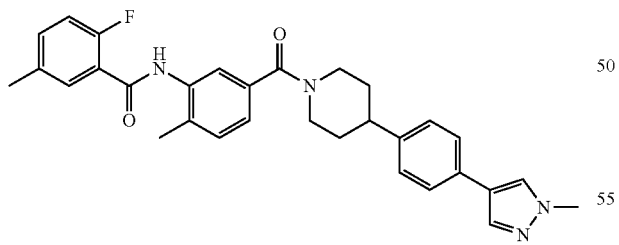

$^1$H NMR (300 MHz, DMSO-d$_6$) δ ppm 1.52-1.71 (m, 2H), 1.82 (br. s., 2H), 2.27-2.33 (m, 3H), 2.36 (s, 3H), 2.77-2.99 (m, 2H), 3.17 (t, J=10.8 Hz, 1H), 3.77 (br. s., 1H), 3.85 (s, 3H), 4.63 (br. s., 1H), 7.18-7.30 (m, 4H), 7.35 (d, J=8.0 Hz, 2H), 7.49 (d, J=8.1 Hz, 2H), 7.52-7.62 (m, 2H), 7.81 (s, 1H), 8.09 (s, 1H), 9.88 (s, 1H). MS m/z 511 (M+H)$^+$

Example 92

Compound #128

3-chloro-5-methoxy-N-(2-methyl-5-(4-(4-(1-methyl-1H-pyrazol-4-yl)phenyl)piperidine-1-carbonyl)phenyl)benzamide

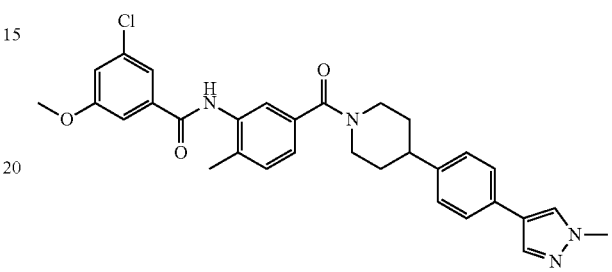

$^1$H NMR (300 MHz, DMSO-d$_6$) δ ppm 1.52-1.71 (m, 2H), 1.71-1.96 (m, 2H), 2.27 (s, 3H), 2.81 (t, J=11.8 Hz, 2H), 3.17 (br. s., 1H), 3.75 (br. s., 1H), 3.87 (s, 3H), 3.85 (s, 3H), 4.61 (br. s., 1H), 7.19-7.31 (m, 4H), 7.32-7.39 (m, 1H), 7.42 (s, 1H), 7.48 (d, J=8.1 Hz, 3H), 7.60 (s, 1H), 7.81 (s, 1H), 8.08 (s, 1H), 10.07 (s, 1H). MS m/z 543 (M+H)$^+$

Example 93

Compound #129

4-cyano-2-fluoro-N-(2-methyl-5-(4-(4-(1-methyl-1H-pyrazol-4-yl)phenyl)piperidine-1-carbonyl)phenyl)benzamide

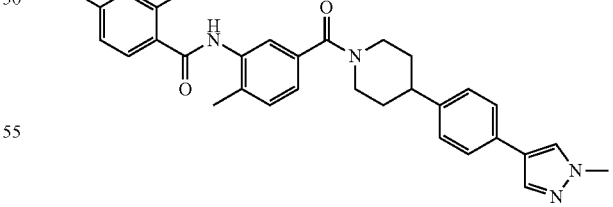

$^1$H NMR (300 MHz, DMSO-d$_6$) δ ppm 1.53-1.72 (m, 2H), 1.81 (br. s., 2H), 2.31 (s, 3H), 2.67-2.97 (m, 2H), 3.18 (br. s., 1H), 3.77 (br. s., 1H), 3.85 (s, 3H), 4.62 (br. s., 1H), 7.26 (d, J=8.1 Hz, 3H), 7.37 (d, J=7.8 Hz, 1H), 7.48 (d, J=8.1 Hz, 2H), 7.60 (s, 1H), 7.81 (s, 1H), 7.84-7.98 (m, 2H), 8.02-8.13 (m, 2H), 10.17 (s, 1H). MS m/z 522 (M+H)$^+$

Example 94

Compound #268

6-(isopropylamino)-N-(2-methyl-5-(4-(6-(1-methyl-1H-pyrazol-4-yl)pyridin-3-yl)piperidine-1-carbonyl)phenyl)nicotinamide

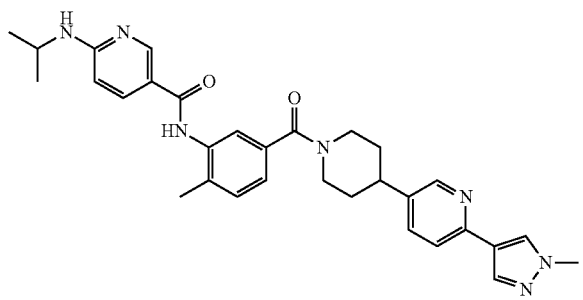 [SMILES: Cc1ccc(C(=O)N2CCC(c3ccc(-c4cnn(C)c4)nc3)CC2)cc1NC(=O)c1ccc(NC(C)C)nc1]

¹H NMR (300 MHz, DMSO-d₆) δ ppm 1.13-1.19 (m, 6H), 1.55-1.75 (m, 2H), 1.81 (br. s., 2H), 2.27 (s, 3H), 2.86 (t, J=11.6 Hz, 2H), 3.88 (s, 3H), 3.93 (br. S. 1H), 4.02-4.20 (m, 1H), 4.62 (br. s., 1H), 6.49 (d, J=8.9 Hz, 1H), 7.04 (d, J=7.6 Hz, 1H), 7.16-7.25 (m, 1H), 7.33 (d, J=7.8 Hz, 1H), 7.40-7.50 (m, 1H), 7.57 (d, J=8.1 Hz, 1H), 7.70 (dd, J=8.2, 2.1 Hz, 1H), 7.90 (dd, J=8.9, 2.3 Hz, 1H), 7.95 (s, 1H), 8.23 (s, 1H), 8.43 (d, J=1.6 Hz, 1H), 8.66 (d, J=2.1 Hz, 1H), 9.59 (s, 1H). MS m/z 538 (M+H)⁺

Example 95

Compound #270

6-chloro-N-(2-methyl-5-(4-(6-(1-methyl-1H-pyrazol-4-yl)pyridin-3-yl)piperidine-1-carbonyl)phenyl)nicotinamide

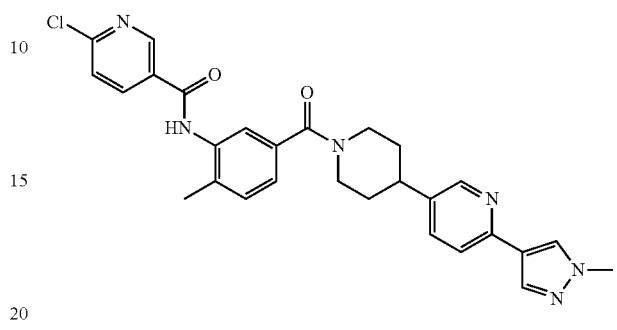

¹H NMR (300 MHz, DMSO-d₆) δ ppm 1.67-1.92 (m, 4H), 2.30 (s, 3H), 2.85-3.24 (m, 3H), 3.80 (br. s., 1H), 3.95 (s, 3H), 4.64 (br. s., 1H), 7.29 (d, J=7.7 Hz, 1H), 7.38 (d, J=7.8 Hz, 1H), 7.50 (s, 1H), 7.72 (d, J=8.4 Hz, 1H), 8.10 (d, J=8.5 Hz, 1H), 8.27-8.44 (m, 3H), 8.55 (s, 1H), 8.69 (s, 1H), 8.99 (s, 1H), 10.28 (s, 1H). MS m/z 515 (M+H)⁺

Example 96

Compound #264

6-(isopropylamino)-N-(2-methyl-5-(4-(5-(1-methyl-1H-pyrazol-4-yl)pyridin-2-yl)piperidine-1-carbonyl)phenyl)nicotinamide

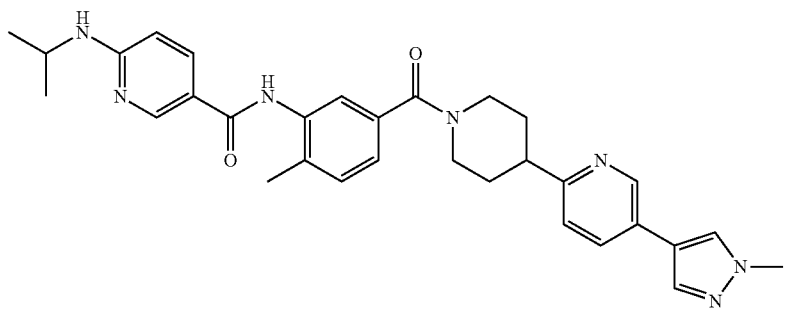 [SMILES: Cc1ccc(C(=O)N2CCC(c3ccc(-c4cnn(C)c4)cn3)CC2)cc1NC(=O)c1ccc(NC(C)C)nc1]

¹H NMR (300 MHz, DMSO-d₆) δ ppm 1.18 (d, J=3.3 Hz, 6H), 1.71 (br. s., 2H), 1.88 (br. s., 2H), 2.27 (s, 3H), 2.98 (t, J=11.4 Hz, 2H), 3.32 (br. s., 1H), 3.88 (s, 3H), 4.00-4.20 (m, 1H), 4.59 (br. s., 1H), 6.49 (d, J=8.9 Hz, 1H), 7.04 (d, J=7.6 Hz, 1H), 7.13-7.24 (m, 1H), 7.32 (t, J=7.8 Hz, 2H), 7.43 (s, 1H), 7.85-7.93 (m, 3H), 8.20 (s, 1H), 8.66 (d, J=2.2 Hz, 1H), 8.73 (d, J=2.1 Hz, 1H), 9.59 (s, 1H). MS m/z 538 (M+H)⁺

Example 97

Compound #263

6-chloro-N-(2-methyl-5-(4-(5-(1-methyl-1H-pyrazol-4-yl)pyridin-2-yl)piperidine-1-carbonyl)phenyl)nicotinamide

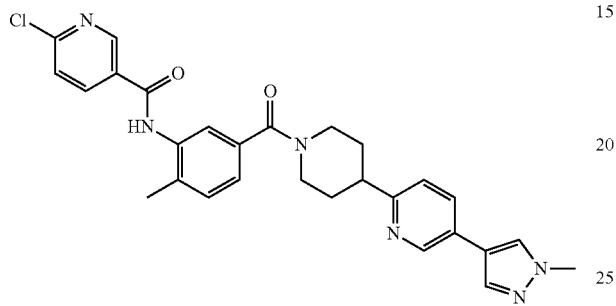

¹H NMR (300 MHz, DMSO-d₆) δ ppm 1.83 (d, J=12.2 Hz, 2H), 1.95 (br. s., 2H), 2.30 (s, 3H), 2.93 (br. s., 1H), 3.15 (br. s., 1H), 3.26-3.43 (m, 1H), 3.82 (br. s., 1H), 3.90 (s, 3H), 4.65 (br. s., 1H), 7.21-7.34 (m, 1H), 7.39 (d, J=8.0 Hz, 1H), 7.50 (s, 1H), 7.72 (d, J=8.2 Hz, 1H), 7.86 (d, J=8.2 Hz, 1H), 8.12 (s, 1H), 8.39 (dd, J=8.3, 2.3 Hz, 1H), 8.43 (s, 1H), 8.50 (d, J=7.7 Hz, 1H), 8.90-8.97 (m, 1H), 9.00 (d, J=1.9 Hz, 1H), 10.30 (s, 1H). MS m/z 515 (M+H)⁺

Example 98

Compound #258

6-(isopropylamino)-N-(2-methyl-5-(4-(5-(1-methyl-1H-pyrazol-4-yl)pyrimidin-2-yl)piperidine-1-carbonyl)phenyl)nicotinamide

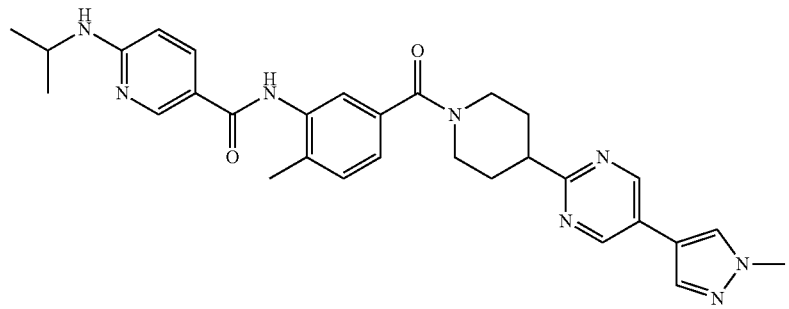 [SMILES: Cc1ccc(C(=O)N2CCC(c3ncc(-c4cnn(C)c4)cn3)CC2)cc1NC(=O)c1ccc(NC(C)C)nc1]

¹H NMR (300 MHz, DMSO-d₆) δ ppm 1.17 (d, J=6.5 Hz, 6H), 1.65-1.85 (m, 2H), 1.99 (br. s., 2H), 2.27 (s, 3H), 3.03-3.22 (m, 3H), 3.80 (br. s., 1H), 3.89 (s, 3H), 4.10 (dd, J=13.2, 6.6 Hz, 1H), 4.52 (br. s., 1H), 6.49 (d, J=8.8 Hz, 1H), 7.04 (d, J=7.6 Hz, 1H), 7.14-7.23 (m, 1H), 7.33 (d, J=7.8 Hz, 1H), 7.37-7.46 (m, 1H), 7.89 (dd, J=8.8, 2.3 Hz, 1H), 8.01 (s, 1H), 8.30 (s, 1H), 8.65 (d, J=2.2 Hz, 1H), 8.98 (s, 2H), 9.57 (s, 1H). MS m/z 539 (M+H)⁺

Example 99

Compound #257

6-chloro-N-(2-methyl-5-(4-(5-(1-methyl-1H-pyrazol-4-yl)pyrimidin-2-yl)piperidine-1-carbonyl)phenyl)nicotinamide

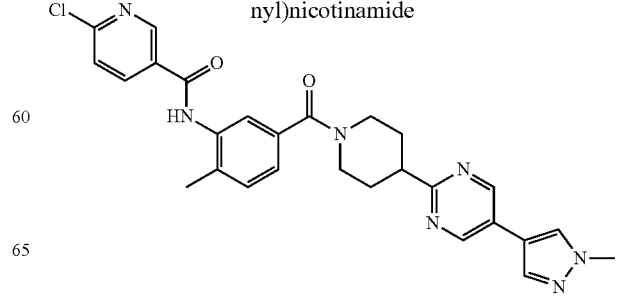

¹H NMR (300 MHz, DMSO-d₆) δ ppm 1.61-1.85 (m, 2H), 1.85-2.07 (m, 2H), 2.30 (s, 3H), 2.87-3.27 (m, 3H), 3.80 (br. s., 1H), 3.89 (s, 3H), 4.52 (br. s., 1H), 7.19-7.29 (m, 1H), 7.38 (d, J=7.8 Hz, 1H), 7.46 (s, 1H), 7.72 (d, J=8.2 Hz, 1H), 8.01 (s, 1H), 8.30 (s, 1H), 8.37 (dd, J=8.4, 2.3 Hz, 1H), 8.97 (s, 3H), 10.21 (s, 1H). MS m/z 516 (M+H)⁺

Example 100

Compound #131

2,4-difluoro-N-(2-methyl-5-(4-(4-(1-methyl-1H-pyrazol-4-yl)phenyl)piperidine-1-carbonyl)phenyl)benzamide

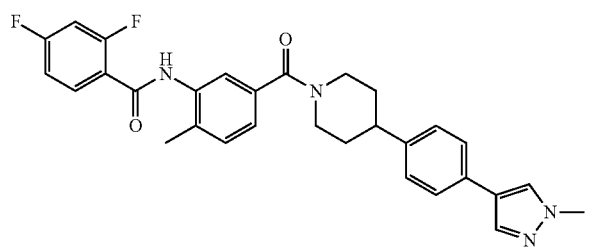

¹H NMR (300 MHz, DMSO-d₆) δ ppm 1.51-1.71 (m, 2H), 1.80 (br. s., 2H), 2.26-2.34 (m, 3H), 2.70-2.97 (m, 2H), 3.15 (br. s., 1H), 3.79 (br. s., 1H), 3.85 (s, 3H), 4.62 (br. s., 1H), 7.18-7.30 (m, 4H), 7.35 (d, J=7.8 Hz, 1H), 7.38-7.52 (m, 3H), 7.60 (s, 1H), 7.75-7.89 (m, 2H), 8.08 (s, 1H), 9.91 (s, 1H). MS m/z 515 (M+H)⁺

Example 101

Compound #132

N-(2-methyl-5-(4-(4-(1-methyl-1H-pyrazol-4-yl)phenyl)piperidine-1-carbonyl)phenyl)-2-(trifluoromethyl)benzamide

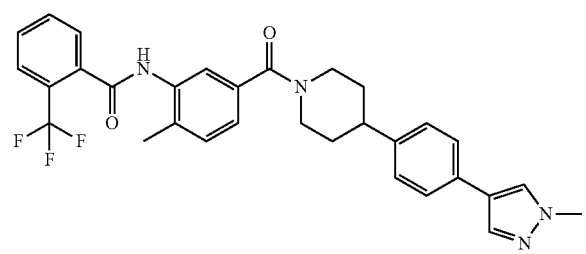 [SMILES: Cc1ccc(C(=O)N2CCC(c3ccc(-c4cnn(C)c4)cc3)CC2)cc1NC(=O)c1ccccc1C(F)(F)F]

¹H NMR (300 MHz, DMSO-d₆) δ ppm 1.62 (d, J=12.4 Hz, 2H), 1.83 (br. s., 2H), 2.23-2.34 (m, 3H), 2.81 (br. s., 2H), 3.19 (br. s., 1H), 3.58-3.80 (m, 1H), 3.80-3.89 (m, 3H), 4.62 (br. s., 1H), 7.20-7.39 (m, 3H), 7.45-7.56 (m, 2H), 7.81 (d, J=4.4 Hz, 2H), 8.00 (t, J=6.9 Hz, 1H), 8.09 (s, 1H), 8.51 (t, J=7.8 Hz, 1H), 8.90 (d, J=5.1 Hz, 2H), 10.15 (s, 1H). MS m/z 547 (M+H)⁺

Example 102

Compound #138

4-cyano-N-(2-methyl-5-(4-(4-(1-methyl-1H-pyrazol-4-yl)phenyl)piperidine-1-carbonyl)phenyl)benzamide

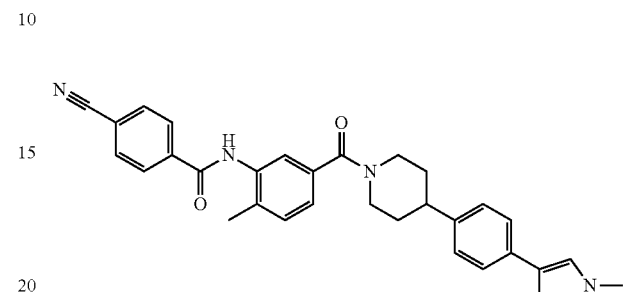

¹H NMR (300 MHz, DMSO-d₆) δ ppm 1.44-1.61 (m, 2H), 1.78 (br. s., 2H), 2.22 (s, 3H), 2.70-2.92 (m, 2H), 3.06 (s, 1H), 3.69 (br. s., 1H), 3.78 (s, 3H), 4.53 (br. s., 1H), 7.12-7.24 (m, 3H), 7.27-7.33 (m, 1H), 7.36-7.46 (m, 3H), 7.74 (s, 1H), 7.94-8.04 (m, 3H), 8.07 (d, J=8.4 Hz, 2H), 10.16 (s, 1H). MS m/z 504 (M+H)⁺

Example 103

Compound #122

2,4-dichloro-N-(2-methyl-5-(4-(4-(1-methyl-1H-pyrazol-4-yl)phenyl)piperidine-1-carbonyl)phenyl)benzamide

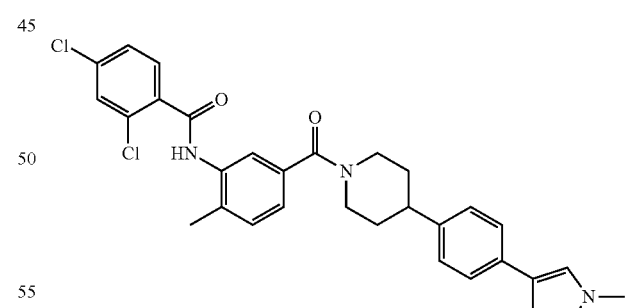

¹H NMR (300 MHz, DMSO-d₆) δ ppm 1.53-1.71 (m, 2H), 1.71-2.02 (m, 2H), 2.28 (s, 3H), 2.81 (t, J=11.8 Hz, 2H), 3.17 (br. s., 1H), 3.79 (br. s., 1H), 3.85 (s, 3H), 4.63 (br. s., 1H), 7.20-7.31 (m, 3H), 7.33-7.40 (m, 1H), 7.40-7.53 (m, 3H), 7.78-7.87 (m, 2H), 7.96 (dd, J=8.5, 1.7 Hz, 1H), 8.08 (s, 1H), 8.23 (d, J=1.8 Hz, 1H), 10.15 (s, 1H). MS m/z 547 (M+H)⁺

Example 104

Compound #133

N-(2-methyl-5-(4-(4-(1-methyl-1H-pyrazol-4-yl)phenyl)piperidine-1-carbonyl)phenyl)benzo[d][1,3]dioxole-5-carboxamide

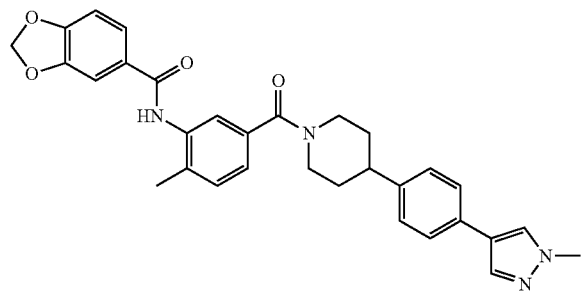 [SMILES: Cc1ccc(C(=O)N2CCC(c3ccc(-c4cnn(C)c4)cc3)CC2)cc1NC(=O)c1ccc2c(c1)OCO2]

$^1$H NMR (300 MHz, CHLOROFORM-d) δ ppm 1.67 (br. s., 2H), 1.76-1.96 (m, 2H), 2.28 (s, 3H), 2.62-2.89 (m, 2H), 3.11 (br. s., 1H), 3.87 (s, 3H), 3.96 (br. s., 1H), 4.82 (br. s., 1H), 6.00 (s, 2H), 6.83 (d, J=8.1 Hz, 1H), 7.15 (d, J=8.1 Hz, 3H), 7.17-7.24 (m, 4H), 7.30-7.40 (m, 4H), 7.51 (s, 1H), 7.63 (s, 1H), 7.67 (s, 1H), 7.92 (s, 1H). MS m/z 523 (M+H)$^+$

Example 105

Compound #120

2,3,4-trifluoro-N-(2-methyl-5-(4-(4-(1-methyl-1H-pyrazol-4-yl)phenyl)piperidine-1-carbonyl)phenyl)benzamide

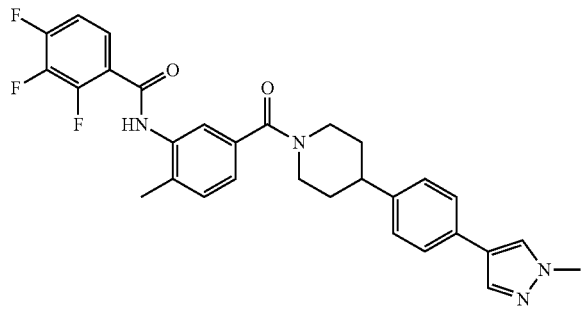 [SMILES: Cc1ccc(C(=O)N2CCC(c3ccc(-c4cnn(C)c4)cc3)CC2)cc1NC(=O)c1ccc(F)c(F)c1F]

$^1$H NMR (300 MHz, DMSO-d$_6$) δ ppm 1.53-1.71 (m, 2H), 1.81 (br. s., 2H), 2.31 (s, 3H), 2.70-2.97 (m, 2H), 3.17 (br. s., 1H), 3.75 (br. s., 1H), 3.85 (s, 3H), 4.62 (br. s., 1H), 7.26 (d, J=8.0 Hz, 3H), 7.37 (d, J=7.8 Hz, 1H), 7.48 (d, J=8.2 Hz, 3H), 7.59 (s, 1H), 7.64 (d, J=4.9 Hz, 1H), 7.81 (s, 1H), 8.08 (s, 1H), 10.06 (s, 1H). MS m/z 533 (M+H)$^+$

Example 106

Compound #121

2,6-dichloro-N-(2-methyl-5-(4-(4-(1-methyl-1H-pyrazol-4-yl)phenyl)piperidine-1-carbonyl)phenyl)benzamide

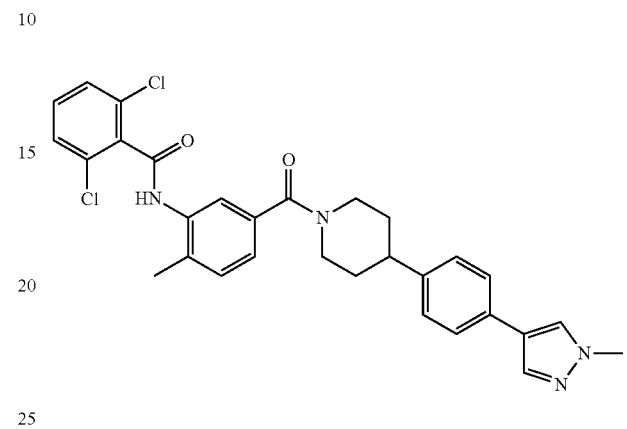

$^1$H NMR (300 MHz, DMSO-d$_6$) δ ppm 1.51-1.71 (m, 2H), 1.82 (br. s., 2H), 2.34 (s, 3H), 2.82 (t, J=11.2 Hz, 2H), 3.19 (br. s., 1H), 3.78 (br. s., 1H), 3.86 (s, 3H), 4.61 (br. s., 1H), 7.26 (d, J=8.2 Hz, 3H), 7.36 (d, J=7.8 Hz, 1H), 7.44-7.56 (m, 4H), 7.56-7.64 (m, 2H), 7.82 (s, 1H), 8.09 (s, 1H), 10.35 (s, 1H). MS m/z 547 (M+H)$^+$

Example 107

Compound #123

3,4-dichloro-N-(2-methyl-5-(4-(4-(1-methyl-1H-pyrazol-4-yl)phenyl)piperidine-1-carbonyl)phenyl)benzamide

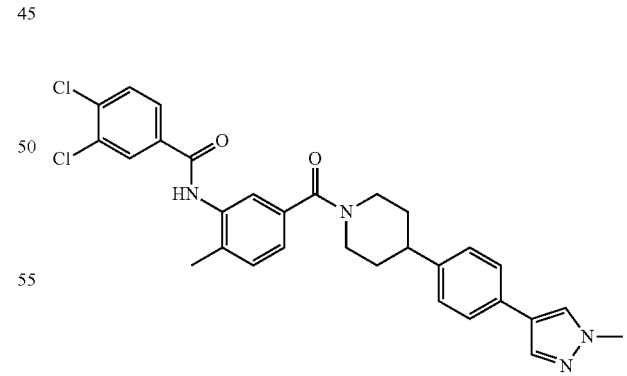

$^1$H NMR (300 MHz, DMSO-d$_6$) δ ppm 1.53-1.71 (m, 2H), 1.80 (br. s., 2H), 2.28 (s, 3H), 2.81 (t, J=11.8 Hz, 2H), 3.17 (br. s., 1H), 3.79 (br. s., 1H), 3.85 (s, 3H), 4.62 (br. s., 1H), 7.21-7.31 (m, 3H), 7.33-7.40 (m, 1H), 7.40-7.54 (m, 3H), 7.78-7.88 (m, 2H), 7.96 (dd, J=8.4, 1.6 Hz, 1H), 8.08 (s, 1H), 8.17-8.29 (m, 1H), 10.15 (s, 1H). MS m/z 547 (M+H)$^+$

Example 108

Compound #116

4-fluoro-N-(2-methyl-5-(4-(4-(1-methyl-1H-pyrazol-4-yl)phenyl)piperidine-1-carbonyl)phenyl)benzamide

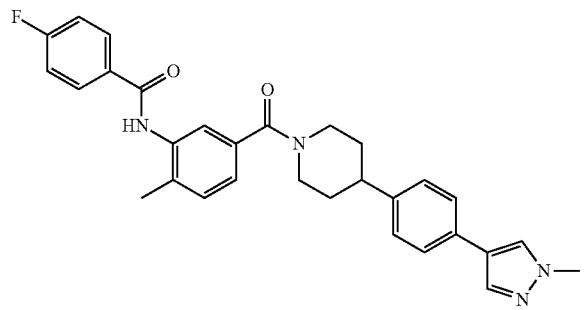 [SMILES: Cc1ccc(C(=O)N2CCC(c3ccc(-c4cnn(C)c4)cc3)CC2)cc1NC(=O)c1ccc(F)cc1]

$^1$H NMR (300 MHz, DMSO-d$_6$) δ ppm 1.52-1.71 (m, 2H), 1.81 (br. s., 2H), 2.28 (s, 3H), 2.72-2.99 (m, 2H), 3.18 (br. s., 1H), 3.46 (br. s., 1H), 3.87 (s, 3H), 4.63 (br. s., 1H), 7.26 (d, J=8.1 Hz, 3H), 7.32-7.42 (m, 3H), 7.42-7.52 (m, 3H), 7.81 (s, 1H), 8.01-8.13 (m, 3H), 9.99 (s, 1H). MS m/z 497 (M+H)$^+$

Example 109

Compound #117

2-fluoro-N-(2-methyl-5-(4-(4-(1-methyl-1H-pyrazol-4-yl)phenyl)piperidine-1-carbonyl)phenyl)benzamide

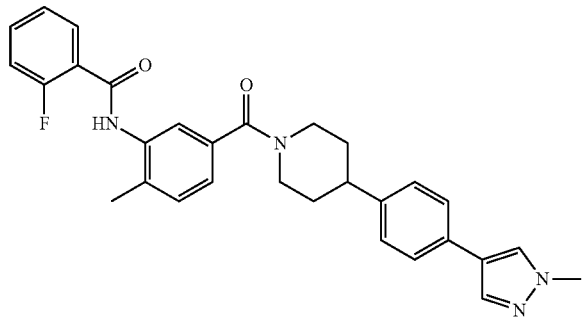 [SMILES: Cc1ccc(C(=O)N2CCC(c3ccc(-c4cnn(C)c4)cc3)CC2)cc1NC(=O)c1ccccc1F]

$^1$H NMR (300 MHz, DMSO-d$_6$) δ ppm 1.50-1.71 (m, 2H), 1.81 (br. s., 2H), 2.30 (s, 3H), 2.81 (t, J=12.0 Hz, 2H), 3.17 (br. s., 1H), 3.74 (br. s., 1H), 3.85 (s, 3H), 4.63 (br. s., 1H), 7.19-7.29 (m, 3H), 7.31-7.42 (m, 3H), 7.48 (d, J=8.1 Hz, 2H), 7.61 (br. s., 2H), 7.76 (t, J=7.0 Hz, 1H), 7.81 (s, 1H), 8.08 (s, 1H), 9.91 (s, 1H). MS m/z 497 (M+H)$^+$

Example 110

Compound #115

N-(2-methyl-5-(4-(4-(1-methyl-1H-pyrazol-4-yl)phenyl)piperidine-1-carbonyl)phenyl)benzamide

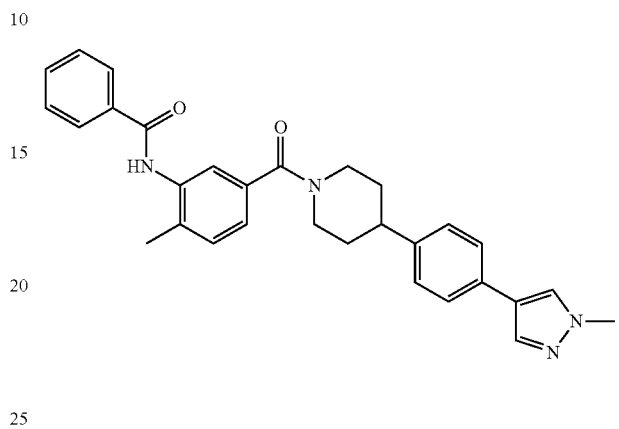

$^1$H NMR (300 MHz, DMSO-d$_6$) δ ppm 1.53-1.71 (m, 2H), 1.71-1.99 (m, 2H), 2.29 (s, 3H), 2.81 (t, J=12.0 Hz, 2H), 3.17 (br. s., 1H), 3.78 (br. s., 1H), 3.85 (s, 3H), 4.64 (br. s., 1H), 7.26 (d, J=8.1 Hz, 3H), 7.33-7.40 (m, 1H), 7.42-7.65 (m, 6H), 7.81 (s, 1H), 7.99 (d, J=6.9 Hz, 2H), 8.08 (s, 1H), 9.96 (s, 1H). MS m/z 479 (M+H)$^+$

Example 111

Compound #161

3-fluoro-N-(2-methyl-5-(4-(4-(1-methyl-1H-pyrazol-4-yl)phenyl)piperidine-1-carbonyl)phenyl)isonicotinamide

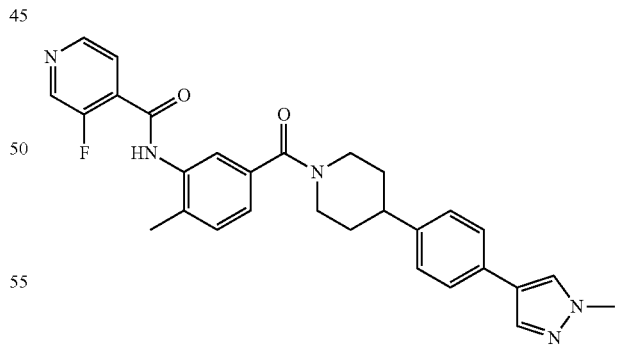

$^1$H NMR (300 MHz, DMSO-d$_6$) δ ppm 1.52-1.72 (m, 2H), 1.72-1.98 (m, 2H), 2.32 (s, 3H), 2.81 (t, J=11.7 Hz, 2H), 3.13 (br. s., 1H), 3.75 (br. s., 1H), 3.86 (s, 3H), 4.63 (br. s., 1H), 7.26 (d, J=8.2 Hz, 3H), 7.38 (d, J=8.0 Hz, 1H), 7.49 (d, J=8.2 Hz, 2H), 7.60 (s, 1H), 7.76 (t, J=5.4 Hz, 1H), 7.81 (s, 1H), 8.08 (s, 1H), 8.61 (d, J=4.8 Hz, 1H), 8.73-8.83 (m, 1H), 10.22 (s, 1H). MS m/z 498 (M+H)$^+$

Example 112

Compound #160

N-(2-methyl-5-(4-(4-(1-methyl-1H-pyrazol-4-yl)phenyl)piperidine-1-carbonyl)phenyl)-1H-indole-5-carboxamide

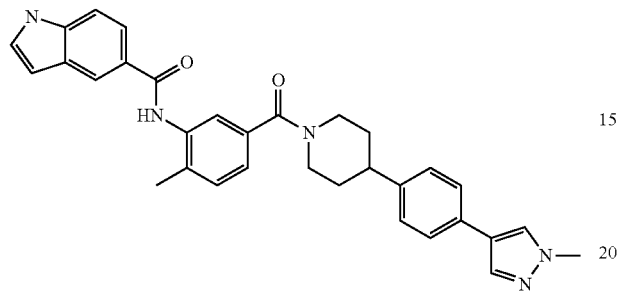

$^1$H NMR (300 MHz, DMSO-d$_6$) δ ppm 1.49-1.67 (m, 2H), 1.72 (br. s., 2H), 2.27 (s, 3H), 2.73-2.88 (m, 1H), 3.08 (br. s., 1H), 3.81 (s, 4H), 4.58 (br. s., 1H), 6.54 (br. s., 1H), 7.13-7.26 (m, 3H), 7.31 (d, J=8.0 Hz, 1H), 7.37-7.49 (m, 5H), 7.71 (dd, J=8.5, 1.5 Hz, 1H), 7.76 (s, 1H), 8.03 (s, 1H), 8.25 (s, 1H), 9.74 (s, 1H), 11.34 (br. s., 1H). MS m/z 518 (M+H)$^+$

Example 113

Compound #134

6-(cyclobutylamino)-N-(2-methyl-5-(4-(4-(1-methyl-1H-pyrazol-4-yl)phenyl)piperidine-1-carbonyl)phenyl)nicotinamide

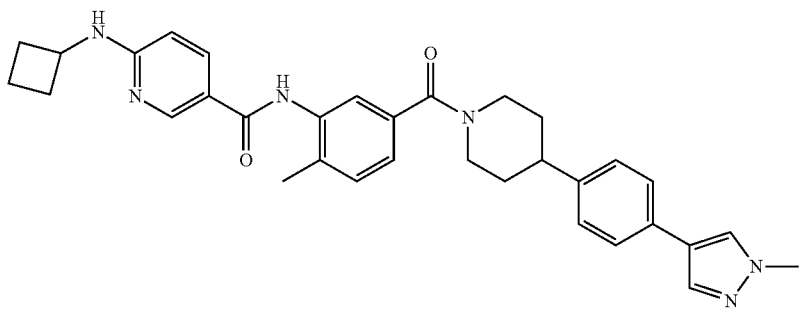 [SMILES: Cc1ccc(C(=O)N2CCC(c3ccc(-c4cnn(C)c4)cc3)CC2)cc1NC(=O)c1ccc(NC2CCC2)nc1]

$^1$H NMR (300 MHz, CHLOROFORM-d) δ ppm 1.64-1.97 (m, 8H), 2.26 (s, 3H), 2.34-2.46 (m, 2H), 2.64-2.89 (m, 2H), 3.11 (br. s., 1H), 3.87 (s, 3H), 3.98 (br. s., 1H), 4.14 (d, J=7.4 Hz, 1H), 4.82 (br. s., 1H), 6.31 (d, J=8.8 Hz, 1H), 7.12-7.18 (m, 3H), 7.19 (s, 2H), 7.35 (d, J=8.2 Hz, 2H), 7.51 (s, 1H), 7.67 (s, 2H), 7.86-7.97 (m, 2H), 8.57 (d, J=2.3 Hz, 1H). MS m/z 549 (M+H)$^+$

Example 114

Compound #252

N-(5-(4-(4-(furan-2-yl)phenyl)piperidine-1-carbonyl)-2-methylphenyl)-6-(isopropylamino)nicotinamide

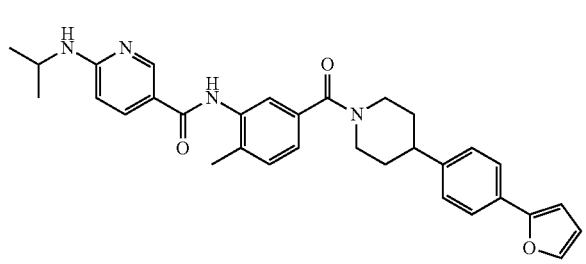

$^1$H NMR (300 MHz, DMSO-d$_6$) δ ppm 1.17 (d, J=6.5 Hz, 6H), 1.52-1.72 (m, 2H), 1.73-1.94 (m, 2H), 2.27 (s, 3H), 2.67-2.93 (m, 2H), 3.03-3.22 (m, 1H), 4.04-4.14 (m, 1H), 4.62 (br. s., 1H), 6.49 (d, J=8.8 Hz, 1H), 6.58 (dd, J=3.2, 1.8 Hz, 1H), 6.89 (d, J=3.3 Hz, 1H), 7.03 (d, J=7.6 Hz, 1H), 7.22 (d, J=7.6 Hz, 1H), 7.27-7.39 (m, 3H), 7.44 (s, 1H), 7.64 (d, J=8.1 Hz, 2H), 7.72 (s, 1H), 7.89 (dd, J=8.9, 2.4 Hz, 1H), 8.66 (d, J=2.2 Hz, 1H), 9.58 (s, 1H). MS m/z 523 (M+H)$^+$

Example 115
Compound #201
6-(isopropylamino)-N-(5-(4-(3'-methoxy-[1,1'-biphenyl]-4-yl)piperidine-1-carbonyl)-2-methylphenyl)nicotinamide
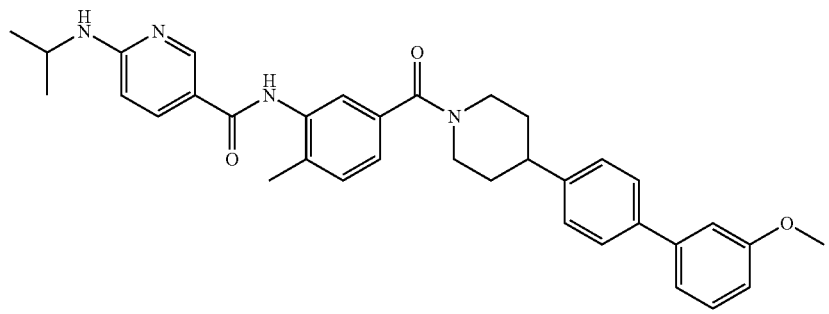 [SMILES: COc1cccc(-c2ccc(C3CCN(C(=O)c4ccc(C)c(NC(=O)c5ccc(NC(C)C)nc5)c4)CC3)cc2)c1]
$^1$H NMR (300 MHz, DMSO-$d_6$) δ ppm 1.17 (d, J=6.5 Hz, 6H), 1.54-1.74 (m, 2H), 1.83 (br. s., 2H), 2.27 (s, 3H), 2.87 (t, J=11.8 Hz, 2H), 3.15 (br. s., 2H), 3.82 (s, 3H), 4.02-4.17 (m, 1H), 4.64 (br. s., 1H), 6.49 (d, J=8.9 Hz, 1H), 6.92 (dd, J=8.2, 2.1 Hz, 1H), 7.04 (d, J=7.6 Hz, 1H), 7.11-7.26 (m, 3H), 7.29-7.41 (m, 4H), 7.45 (s, 1H), 7.60 (d, J=8.1 Hz, 2H), 7.90 (dd, J=8.9, 2.3 Hz, 1H), 8.66 (d, J=2.1 Hz, 1H), 9.59 (br. s., 1H). MS m/z 563 (M+H)$^+$
Example 116
Compound #199
6-(isopropylamino)-N-(5-(4-(4'-methoxy-[1,1'-biphenyl]-4-yl)piperidine-1-carbonyl)-2-methylphenyl)nicotinamide
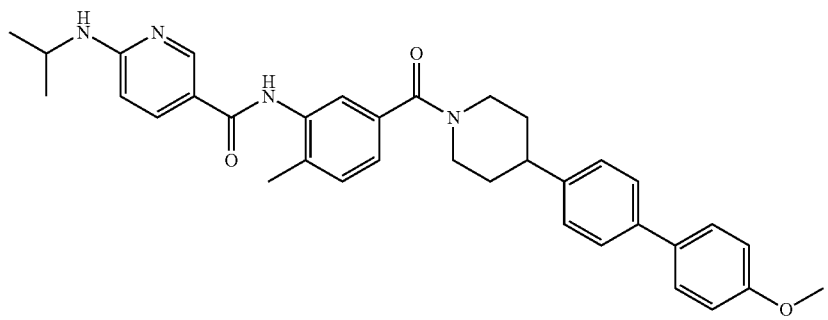 [SMILES: COc1ccc(-c2ccc(C3CCN(C(=O)c4ccc(C)c(NC(=O)c5ccc(NC(C)C)nc5)c4)CC3)cc2)cc1]

¹H NMR (300 MHz, DMSO-d₆) δ ppm 0.93 (d, J=6.5 Hz, 6H), 1.31-1.49 (m, 2H), 1.58 (br. s., 2H), 2.03 (s, 3H), 2.61 (t, J=11.0 Hz, 2H), 2.92 (br. s., 2H), 3.55 (s, 3H), 3.86 (d, J=6.9 Hz, 1H), 4.39 (br. s., 1H), 6.25 (d, J=8.8 Hz, 1H), 6.71-6.86 (m, 3H), 6.98 (d, J=7.7 Hz, 1H), 7.10 (d, J=8.1 Hz, 3H), 7.21 (s, 1H), 7.26-7.40 (m, 4H), 7.65 (dd, J=8.7, 1.9 Hz, 1H), 8.42 (s, 1H), 9.34 (s, 1H). MS m/z 563 (M+H)⁺

Example 117

Compound #236

6-(isopropylamino)-N-(2-methyl-5-(4-(4-(thiophen-2-yl)phenyl)piperidine-1-carbonyl)phenyl)nicotinamide

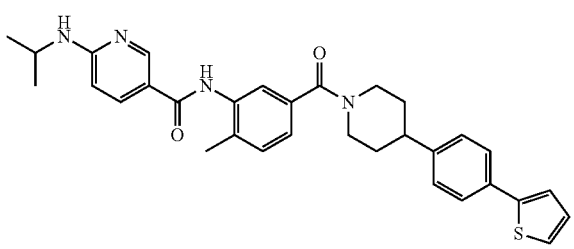 [SMILES: Cc1ccc(C(=O)N2CCC(c3ccc(-c4cccs4)cc3)CC2)cc1NC(=O)c1ccc(NC(C)C)nc1]

¹H NMR (300 MHz, DMSO-d₆) δ ppm 1.17 (d, J=6.5 Hz, 6H), 1.51-1.72 (m, 2H), 1.72-1.99 (m, 2H), 2.21-2.33 (m, 3H), 2.85 (t, J=11.4 Hz, 2H), 3.17 (br. s., 1H), 3.83 (br. s., 1H), 4.00-4.25 (m, 1H), 4.62 (br. s., 1H), 6.49 (d, J=8.8 Hz, 1H), 7.04 (d, J=7.7 Hz, 1H), 7.13 (dd, J=4.9, 3.8 Hz, 1H), 7.22 (d, J=7.7 Hz, 1H), 7.33 (d, J=7.8 Hz, 3H), 7.41-7.49 (m, 2H), 7.51 (d, J=5.1 Hz, 1H), 7.59 (d, J=8.1 Hz, 2H), 7.89 (dd, J=8.8, 2.2 Hz, 1H), 8.66 (d, J=1.9 Hz, 1H), 9.58 (s, 1H). MS m/z 539 (M+H)⁺

Example 118

Compound #235

N-(5-(4-(4-(furan-3-yl)phenyl)piperidine-1-carbonyl)-2-methylphenyl)-6-(isopropylamino)nicotinamide

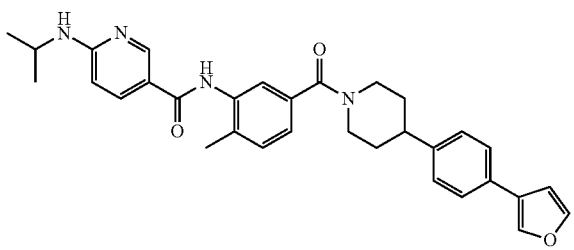 [SMILES: Cc1ccc(C(=O)N2CCC(c3ccc(-c4ccoc4)cc3)CC2)cc1NC(=O)c1ccc(NC(C)C)nc1]

¹H NMR (300 MHz, DMSO-d₆) δ ppm 1.19 (br. s., 6H), 1.66 (br. s., 2H), 1.82 (br. s., 2H), 2.28 (br. s., 3H), 2.84 (br. s., 1H), 3.19 (br. s., 1H), 3.81 (br. s., 1H), 4.11 (br. s., 2H), 4.64 (br. s., 1H), 6.50 (d, J=7.8 Hz, 1H), 6.94 (br. s., 1H), 7.06 (br. s., 1H), 7.24 (br. s., 1H), 7.32 (br. s., 3H), 7.45 (br. s., 1H), 7.54 (br. s., 2H), 7.73 (br. s., 1H), 7.91 (br. s., 1H), 8.14 (br. s., 1H), 8.67 (br. s., 1H), 9.60 (br. s., 1H). MS m/z 523 (M+H)⁺

Example 119

Compound #200

6-(isopropylamino)-N-(5-(4-(2'-methoxy-[1,1'-biphenyl]-4-yl)piperidine-1-carbonyl)-2-methylphenyl)nicotinamide

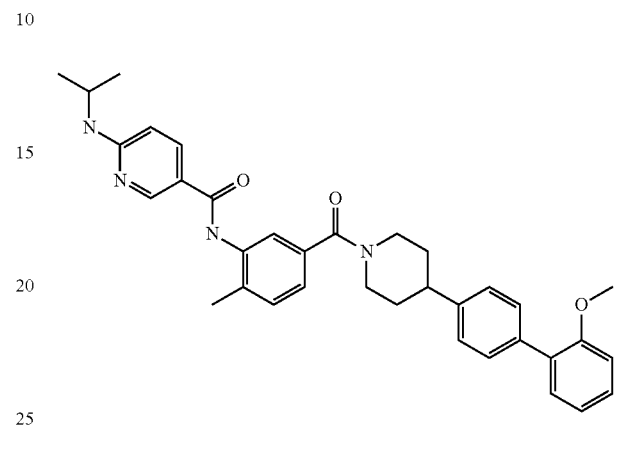

¹H NMR (300 MHz, DMSO-d₆) δ ppm 1.17 (d, J=6.3 Hz, 6H), 1.54-1.74 (m, 2H), 1.85 (br. s., 2H), 2.27 (s, 3H), 2.75-3.00 (m, 2H), 3.14 (br. s., 1H), 3.76 (s, 3H), 3.81 (br. s., 1H), 4.02-4.20 (m, 1H), 4.63 (br. s., 1H), 6.49 (d, J=8.8 Hz, 1H), 6.95-7.15 (m, 3H), 7.17-7.37 (m, 6H), 7.37-7.50 (m, 3H), 7.89 (dd, J=8.8, 1.9 Hz, 1H), 8.56-8.74 (m, 1H), 9.58 (s, 1H). MS m/z 563 (M+H)⁺

Example 120

Compound #266

N-(5-(3-(4-(3-aminopyridin-4-yl)phenyl)azetidine-1-carbonyl)-2-methylphenyl)-6-chloronicotinamide

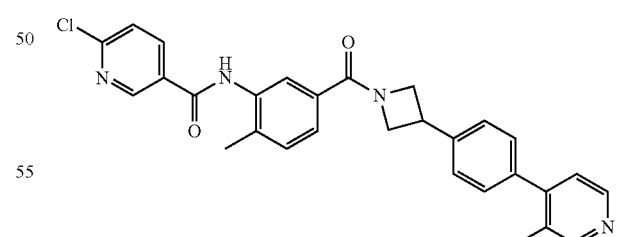

¹H NMR (400 MHz, CHLOROFORM-d) δ ppm 2.36 (s, 3H), 3.80 (br. s., 2H), 3.91-4.01 (m, 1H), 4.27-4.36 (m, 1H), 4.36-4.45 (m, 1H), 4.64 (t, J=9.6 Hz, 1H), 4.81 (t, J=8.8 Hz, 1H), 7.02 (d, J=5.1 Hz, 1H), 7.30 (d, J=8.1 Hz, 1H), 7.43-7.51 (m, 6H), 7.99 (s, 1H), 8.06 (d, J=5.1 Hz, 1H), 8.15 (s, 1H), 8.24 (dd, J=8.3, 2.3 Hz, 1H), 8.27 (s, 1H), 8.96 (d, J=2.0 Hz, 1H). MS m/z 498.3 (M+H)⁺

Example 121

Compound #260

N-(5-(3-(4-(2-aminopyridin-3-yl)phenyl)azetidine-1-carbonyl)-2-methylphenyl)-6-morpholinonicotinamide

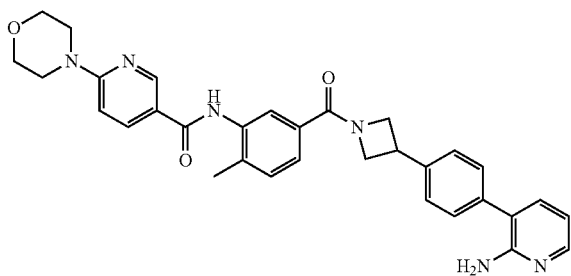 [SMILES: Cc1ccc(C(=O)N2CC(c3ccc(-c4cccnc4N)cc3)C2)cc1NC(=O)c1ccc(N2CCOCC2)nc1]

$^1$H NMR (400 MHz, CHLOROFORM-d) δ ppm 2.37 (s, 3H), 3.62-3.70 (m, 4H), 3.79-3.86 (m, 4H), 3.90-4.00 (m, 1H), 4.32 (dd, J=9.6, 6.6 Hz, 1H), 4.42-4.50 (m, 1H), 4.56 (br. s., 2H), 4.64 (t, J=9.6 Hz, 1H), 4.87 (t, J=8.8 Hz, 1H), 6.68 (d, J=8.6 Hz, 1H), 6.75 (dd, J=7.3, 4.8 Hz, 1H), 7.30 (d, J=7.6 Hz, 1H), 7.35 (dd, J=7.6, 2.0 Hz, 1H), 7.41-7.48 (m, 4H), 7.51-7.57 (m, 1H), 7.64 (s, 1H), 8.03 (dd, J=9.1, 2.5 Hz, 1H), 8.07 (d, J=5.1 Hz, 1H), 8.32 (s, 1H), 8.71 (d, J=2.5 Hz, 1H). MS m/z 550.4 (M+H)$^+$

Example 122

Compound #259

N-(5-(3-(4-(2-aminopyridin-3-yl)phenyl)azetidine-1-carbonyl)-2-methylphenyl)-6-chloronicotinamide

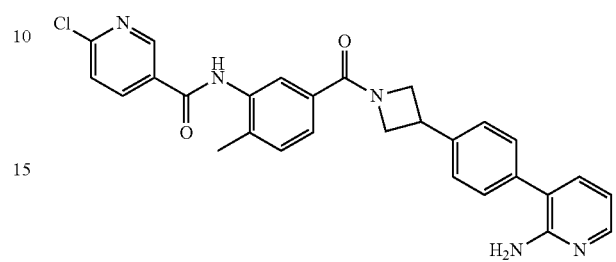

$^1$H NMR (400 MHz, CHLOROFORM-d) δ ppm 2.35 (s, 3H), 3.89-4.00 (m, 1H), 4.30 (dd, J=10.1, 6.6 Hz, 1H), 4.35-4.43 (m, 1H), 4.56 (s, 2H), 4.63 (t, J=9.9 Hz, 1H), 4.78 (t, J=8.8 Hz, 1H), 6.75 (dd, J=7.6, 5.1 Hz, 1H), 7.29 (s, 1H), 7.33-7.37 (m, 1H), 7.39-7.51 (m, 6H), 7.89 (s, 1H), 8.07 (dd, J=5.1, 2.0 Hz, 1H), 8.25 (dd, J=8.6, 2.5 Hz, 1H), 8.41 (s, 1H), 8.98 (d, J=2.5 Hz, 1H)

Example 123

Compound #237

6-(isopropylamino)-N-(2-methyl-5-(3-(4-(1-methyl-1H-pyrazol-4-yl)phenyl)pyrrolidine-1-carbonyl)phenyl)nicotinamide

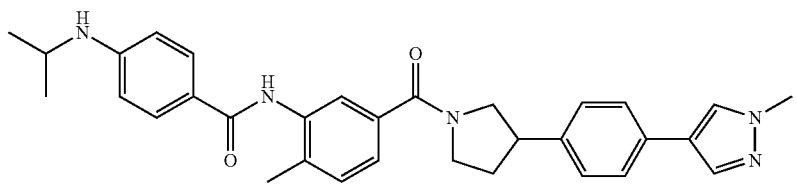 [SMILES: Cc1ccc(C(=O)N2CCC(c3ccc(-c4cnn(C)c4)cc3)C2)cc1NC(=O)c1ccc(NC(C)C)cc1]

¹H NMR (400 MHz, CHLOROFORM-d) δ ppm 1.24-1.30 (m, 6H), 1.96-2.18 (m, 1H), 2.32 (s, 1.5H), 2.34 (s, 1.5H), 3.32-3.42 (m, 0.5H), 3.42-3.50 (m, 0.5H), 3.54 (t, J=10.1 Hz, 0.5H), 3.59-3.79 (m, 2H), 3.94 (d, J=7.1 Hz, 1H), 3.97-4.06 (m, 1H), 4.12 (dd, J=12.1, 8.1 Hz, 0.5H), 4.84 (t, J=7.3 Hz, 1H), 6.36-6.45 (m, 1H), 7.16-7.24 (m, 2H), 7.26-7.32 (m, 3H), 7.39 (d, J=8.1 Hz, 1H), 7.44 (d, J=8.1 Hz, 1H), 7.57 (s, 0.5H), 7.61 (s, 0.5H), 7.71 (s, 0.5H), 7.75 (s, 0.5H), 7.78 (s, 0.5H), 7.86 (s, 0.5H), 7.93-8.02 (m, 1H), 8.05 (d, J=3.0 Hz, 1H), 8.65 (d, J=2.5 Hz, 0.5H), 8.68 (d, J=2.0 Hz, 0.5H). MS m/z 523.3 (M+H)⁺

Example 124

Compound #204

N-(2-methyl-5-(3-(4-(1-methyl-1H-pyrazol-4-yl)phenyl)pyrrolidine-1-carbonyl)phenyl)-6-morpholinonicotinamide

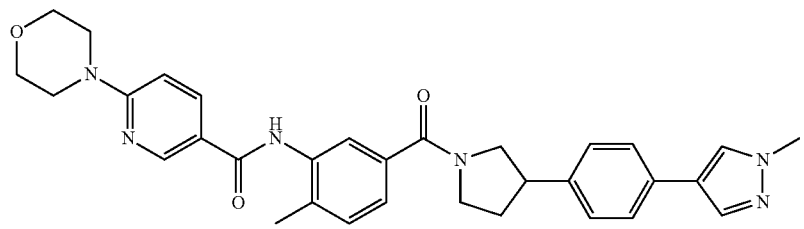 [SMILES: Cc1ccc(C(=O)N2CCC(c3ccc(-c4cnn(C)c4)cc3)C2)cc1NC(=O)c1ccc(N2CCOCC2)nc1]

¹H NMR (400 MHz, CHLOROFORM-d) δ ppm 1.96-2.20 (m, 1H), 2.33 (d, J=9.1 Hz, 3H), 2.35-2.44 (m, 0.5H), 3.33-3.42 (m, 0.5H), 3.42-3.50 (m, 0.5H), 3.50-3.58 (m, 1H), 3.62-3.68 (m, 4H), 3.68-3.79 (m, 1.5H), 3.79-3.85 (m, 4H), 3.85-3.92 (m, 1H), 3.94 (d, J=7.1 Hz, 3H), 4.13 (dd, J=11.9, 7.8 Hz, 1H), 6.68 (dd, J=9.1, 7.1 Hz, 1H), 7.14-7.25 (m, 2H), 7.26-7.34 (m, 2H), 7.39 (d, J=8.1 Hz, 1H), 7.45 (d, J=8.1 Hz, 1H), 7.61 (s, 0.5H), 7.57 (s, 0.5H), 7.76 (s, 0.5H), 7.72 (s, 0.5H), 7.79 (s, 0.5H), 7.90 (s, 0.5H), 8.02-8.11 (m, 2H), 8.77 (d, J=2.5 Hz, 1H), 8.73 (d, J=2.5 Hz, 1H). MS m/z 551.3 (M+H)⁺

Example 125

Compound #203

6-chloro-N-(2-methyl-5-(3-(4-(1-methyl-1H-pyrazol-4-yl)phenyl)pyrrolidine-1-carbonyl)phenyl)nicotinamide

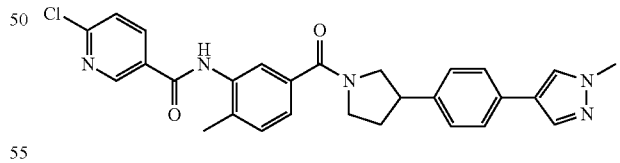

¹H NMR (400 MHz, CHLOROFORM-d) δ ppm 1.96-2.07 (m, 0.5H), 2.07-2.20 (m, 0.5H), 2.27 (d, J=8.6 Hz, 3H), 2.32 (br. s., 0.5H), 2.34-2.45 (m, 0.5H), 3.31-3.51 (m, 1.5H), 3.53-3.76 (m, 2H), 3.79-3.91 (m, 1H), 3.94 (d, J=9.1 Hz, 3H), 4.09 (dd, J=12.1, 8.1 Hz, 0.5H), 7.07-7.20 (m, 3H), 7.23-7.29 (m, 2H), 7.31 (s, 0.5H), 7.34-7.42 (m, 1.5H), 7.43-7.50 (m, 1H), 7.57 (s, 0.5H), 7.62 (s, 0.5H), 7.71 (s, 0.5H), 7.76 (s, 0.5H), 8.29-8.42 (m, 1H), 9.03-9.14 (m, 1H), 9.33 (br. s., 0.5H), 9.45 (br. s., 0.5H). MS m/z 501.2 (M+H)⁺

Example 126
Compound #159
N-(2-methyl-5-(3-(4-(1-methyl-1H-pyrazol-4-yl)phenyl)azetidine-1-carbonyl)phenyl)-2-morpholinopyrimidine-5-carboxamide
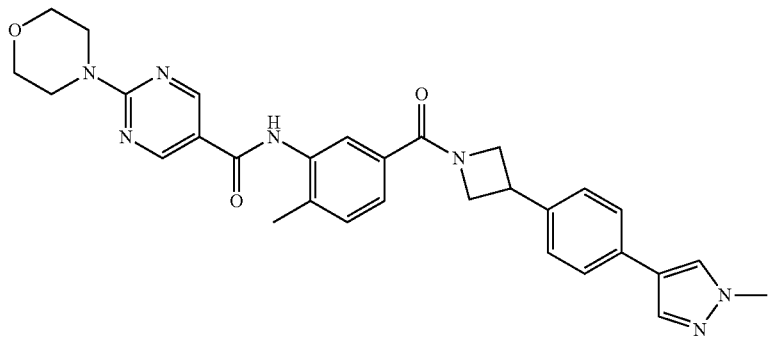 [SMILES: Cc1ccc(C(=O)N2CC(c3ccc(-c4cnn(C)c4)cc3)C2)cc1NC(=O)c1cnc(N2CCOCC2)nc1]
$^1$H NMR (400 MHz, CHLOROFORM-d) δ ppm 2.32 (s, 3H), 3.72-3.80 (m, 4H), 3.86-3.91 (m, 1H), 3.92 (d, J=5.6 Hz, 4H), 3.94 (s, 3H), 4.28 (dd, J=9.6, 6.6 Hz, 1H), 4.32-4.40 (m, 1H), 4.59 (t, J=9.6 Hz, 1H), 4.76 (t, J=8.8 Hz, 1H), 7.23-7.28 (m, 2H), 7.30 (d, J=8.1 Hz, 2H), 7.39-7.48 (m, 3H), 7.61 (s, 1H), 7.75 (s, 1H), 7.95 (s, 1H), 8.03 (s, 1H), 8.89 (s, 2H). MS m/z 538.3 (M+H)$^+$
Example 127
Compound #158
2-(isopropylamino)-N-(2-methyl-5-(3-(4-(1-methyl-1H-pyrazol-4-yl)phenyl)azetidine-1-carbonyl)phenyl)pyrimidine-5-carboxamide
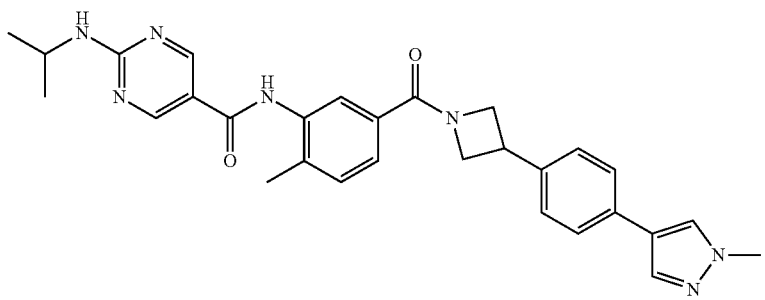 [SMILES: Cc1ccc(C(=O)N2CC(c3ccc(-c4cnn(C)c4)cc3)C2)cc1NC(=O)c1cnc(NC(C)C)nc1]

¹H NMR (400 MHz, CHLOROFORM-d) δ ppm 1.27 (d, J=6.6 Hz, 6H), 2.33 (s, 3H), 3.84-3.92 (m, 1H), 3.94 (s, 3H), 4.28 (dd, J=10.6, 6.6 Hz, 1H), 4.32-4.41 (m, 1H), 4.59 (t, J=9.6 Hz, 1H), 4.77 (t, J=8.8 Hz, 1H), 5.44 (d, J=8.1 Hz, 1H), 7.24-7.28 (m, 2H), 7.31 (d, J=8.1 Hz, 2H), 7.41-7.48 (m, 3H), 7.61 (s, 1H), 7.75 (s, 1H), 7.91 (s, 1H), 8.01 (s, 1H), 8.84 (br. s., 2H). MS m/z 510.2 (M+H)⁺

Example 128

Compound #154

2-chloro-N-(2-methyl-5-(3-(4-(1-methyl-1H-pyrazol-4-yl)phenyl)azetidine-1-carbonyl)phenyl)pyrimidine-5-carboxamide

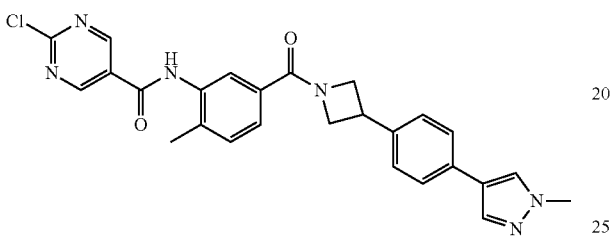

¹H NMR (400 MHz, CHLOROFORM-d) δ ppm 2.29 (s, 3H), 3.85-3.93 (m, 1H), 3.94 (s, 3H), 4.22-4.33 (m, 2H), 4.58 (t, J=9.6 Hz, 1H), 4.65 (t, J=9.1 Hz, 1H), 7.17-7.23 (m, 1H), 7.23-7.31 (m, 4H), 7.42 (s, 1H), 7.47 (d, J=8.1 Hz, 2H), 7.61 (s, 1H), 7.75 (s, 1H), 9.28 (s, 2H), 9.63 (br. s., 1H). MS m/z 487.1 (M+H)⁺

Example 129

Compound #141

N-(2-methyl-5-(3-(4-(1-methyl-1H-pyrazol-4-yl)phenyl)azetidine-1-carbonyl)phenyl)-6-(4-methylpiperazin-1-yl)nicotinamide

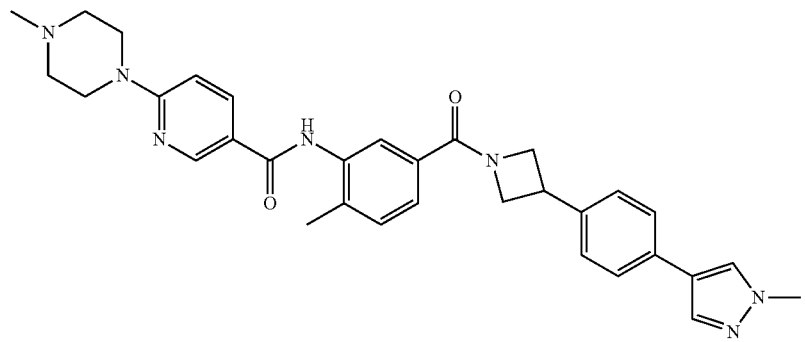

¹H NMR (400 MHz, CHLOROFORM-d) δ ppm 2.34 (d, J=4.5 Hz, 6H), 2.47-2.57 (m, 4H), 3.64-3.74 (m, 4H), 3.84-3.91 (m, 1H), 3.92-3.96 (m, 3H), 4.28 (dd, J=9.6, 6.6 Hz, 1H), 4.35-4.44 (m, 1H), 4.59 (t, J=9.6 Hz, 1H), 4.81 (t, J=8.8 Hz, 1H), 6.68 (d, J=8.6 Hz, 1H), 7.24-7.29 (m, 1H), 7.31 (d, J=8.1 Hz, 2H), 7.41-7.51 (m, 3H), 7.60 (s, 1H), 7.75 (s, 1H), 7.80 (s, 1H), 8.02 (dd, J=9.1, 2.5 Hz, 1H), 8.19 (s, 1H), 8.72 (d, J=2.0 Hz, 1H). MS m/z 550.5 (M+H)⁺

Example 130

Compound #140

6-(methyl(1-methylpiperidin-4-yl)amino)-N-(2-methyl-5-(3-(4-(1-methyl-1H-pyrazol-4-yl)phenyl)azetidine-1-carbonyl)phenyl)nicotinamide

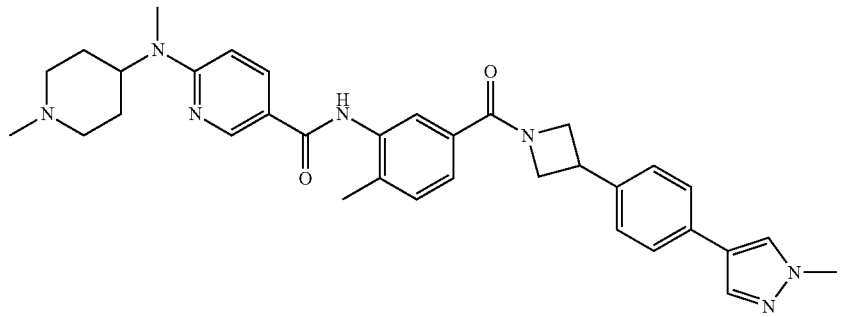

¹H NMR (400 MHz, CHLOROFORM-d) δ ppm 1.56-1.74 (m, 4H), 1.83-2.04 (m, 2H), 2.11-2.21 (m, 2H), 2.35 (s, 3H), 2.96 (s, 3H), 3.01-3.13 (m, 1H), 3.84-3.92 (m, 1H), 3.94 (s, 3H), 4.26-4.46 (m, 2H), 4.60 (t, J=9.6 Hz, 1H), 4.84 (t, J=8.8 Hz, 1H), 6.55 (d, J=9.1 Hz, 1H), 6.70 (d, J=9.1 Hz, 1H), 7.31-7.35 (m, 1H), 7.29 (d, J=8.1 Hz, 1H), 7.45 (d, J=8.1 Hz, 2H), 7.52 (d, J=8.1 Hz, 1H), 7.57-7.65 (m, 2H), 7.75 (s, 1H), 7.99 (dt, J=9.0, 3.3 Hz, 1H), 8.27-8.37 (m, 1H), 8.68 (s, 1H). MS m/z 578.4 (M+H)⁺

Example 131

Compound #139

N-(2-methyl-5-(3-(4-(1-methyl-1H-pyrazol-4-yl)phenyl)azetidine-1-carbonyl)phenyl)isonicotinamide

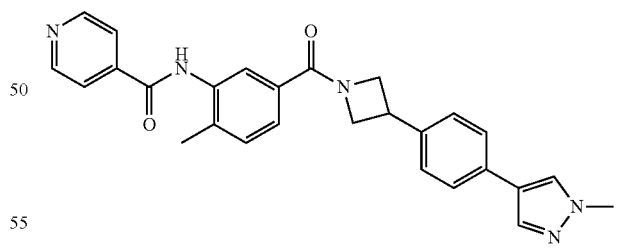

¹H NMR (400 MHz, CHLOROFORM-d) δ ppm 2.35 (s, 3H), 3.84-3.93 (m, 1H), 3.94 (s, 3H), 4.27 (dd, J=9.9, 6.3 Hz, 1H), 4.37 (t, J=7.3 Hz, 1H), 4.59 (t, J=9.6 Hz, 1H), 4.77 (t, J=8.8 Hz, 1H), 7.27-7.34 (m, 3H), 7.43-7.50 (m, 3H), 7.61 (s, 1H), 7.75 (s, 1H), 7.80 (d, J=5.6 Hz, 2H), 7.96 (s, 1H), 8.31 (br. s., 1H), 8.83 (d, J=5.6 Hz, 2H). MS m/z 452.4 (M+H)⁺

Example 132

Compound #85

2-chloro-N-(2-methyl-5-(3-(4-(1-methyl-1H-pyrazol-4-yl)phenyl)azetidine-1-carbonyl)phenyl)nicotinamide

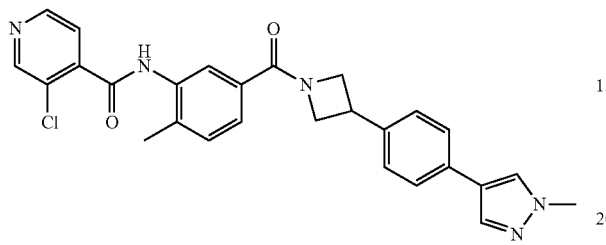

¹H NMR (400 MHz, CHLOROFORM-d) δ ppm 2.46 (s, 3H), 3.85-3.92 (m, 1H), 3.95 (s, 3H), 4.28 (br. s., 2H), 4.56-4.70 (m, 2H), 7.22-7.28 (m, 1H), 7.29-7.36 (m, 3H), 7.48 (d, J=8.6 Hz, 2H), 7.57-7.64 (m, 2H), 7.72 (s, 1H), 7.76 (s, 1H), 7.85 (d, J=6.1 Hz, 2H), 8.36 (d, J=3.5 Hz, 1H). MS m/z 486.8 (M+H)⁺

Example 133

Compound #83

4-methoxy-N-(2-methyl-5-(3-(4-(1-methyl-1H-pyrazol-4-yl)phenyl)azetidine-1-carbonyl)phenyl)benzamide

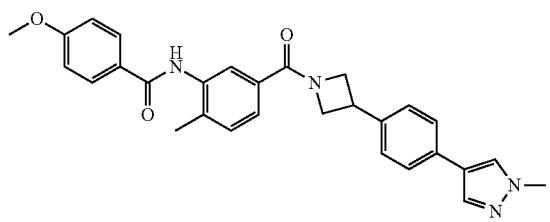

¹H NMR (400 MHz, CHLOROFORM-d) δ ppm 2.35 (s, 3H), 3.87 (s, 3H), 3.90 (br. s., 1H), 3.94 (s, 3H), 4.23-4.32 (m, 1H), 4.41 (t, J=7.6 Hz, 1H), 4.59 (t, J=9.6 Hz, 1H), 4.82 (t, J=8.8 Hz, 1H), 6.99 (d, J=8.6 Hz, 1H), 7.28-7.35 (m, 1H), 7.45 (d, J=8.1 Hz, 2H), 7.50 (d, J=8.1 Hz, 1H), 7.60 (s, 1H), 7.75 (s, 1H), 7.84-7.92 (m, 3H), 8.02 (d, J=8.6 Hz, 1H), 8.20 (s, 1H). MS m/z 481.3 (M+H)⁺

Example 134

Compound #82

2-fluoro-N-(2-methyl-5-(3-(4-(1-methyl-1H-pyrazol-4-yl)phenyl)azetidine-1-carbonyl)phenyl)benzamide

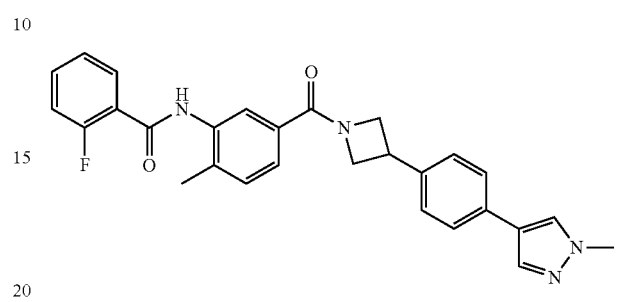

¹H NMR (400 MHz, CHLOROFORM-d) δ ppm 2.39 (s, 3H), 3.86-3.92 (m, 1H), 3.95 (s, 3H), 4.30 (dd, J=9.6, 6.1 Hz, 1H), 4.39-4.49 (m, 1H), 4.56-4.67 (m, 1H), 4.81-4.92 (m, 1H), 7.20-7.23 (m, 1H), 7.33 (t, J=8.3 Hz, 4H), 7.46 (d, J=8.1 Hz, 2H), 7.52-7.58 (m, 2H), 7.61 (s, 1H), 7.75 (s, 1H), 8.19 (t, J=7.8 Hz, 1H), 8.45-8.57 (m, 2H). MS m/z 469.3 (M+H)⁺

Example 135

Compound #106

N-(2-methyl-5-(3-(4-(1-methyl-1H-pyrazol-4-yl)phenyl)azetidine-1-carbonyl)phenyl)-6-(pyrrolidin-1-yl)nicotinamide

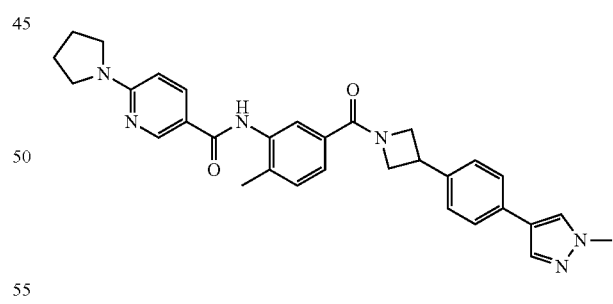

¹H NMR (400 MHz, CHLOROFORM-d) δ ppm 2.05 (t, J=6.6 Hz, 4H), 2.35 (s, 3H), 3.53 (br. s., 4H), 3.84-3.93 (m, 1H), 3.94 (s, 3H), 4.29 (dd, J=9.6, 6.6 Hz, 1H), 4.42 (t, J=7.3 Hz, 1H), 4.60 (t, J=9.6 Hz, 1H), 4.84 (t, J=8.8 Hz, 1H), 6.41 (d, J=9.1 Hz, 1H), 7.32 (d, J=8.1 Hz, 2H), 7.29 (d, J=8.1 Hz, 1H), 7.45 (d, J=8.1 Hz, 2H), 7.51 (d, J=8.1 Hz, 1H), 7.57-7.66 (m, 2H), 7.75 (s, 1H), 7.97 (dd, J=8.6, 2.5 Hz, 1H), 8.34 (s, 1H), 8.69 (d, J=2.0 Hz, 1H). MS m/z 521.3 (M+H)⁺

Example 136

Compound #78

6-(isopropyl(methyl)amino)-N-(2-methyl-5-(3-(4-(1-methyl-1H-pyrazol-4-yl)phenyl)azetidine-1-carbonyl)phenyl)nicotinamide

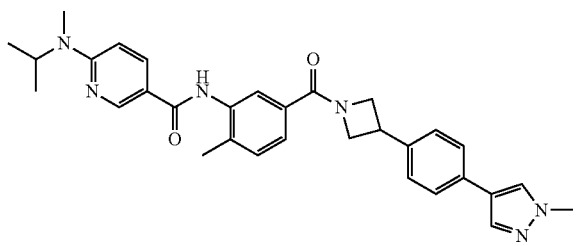 [SMILES: Cc1ccc(C(=O)N2CC(c3ccc(-c4cnn(C)c4)cc3)C2)cc1NC(=O)c1ccc(N(C)C(C)C)nc1]

$^1$H NMR (400 MHz, CHLOROFORM-d) δ ppm 1.21 (d, J=6.6 Hz, 6H), 2.35 (s, 3H), 2.92 (s, 3H), 3.83-3.92 (m, 1H), 3.94 (s, 3H), 4.28 (dd, J=9.6, 6.6 Hz, 1H), 4.42 (t, J=7.6 Hz, 1H), 4.60 (t, J=9.6 Hz, 1H), 4.84 (t, J=9.1 Hz, 1H), 4.90-5.02 (m, 1H), 6.55 (d, J=9.1 Hz, 1H), 7.27-7.35 (m, 3H), 7.45 (d, J=8.1 Hz, 2H), 7.50 (d, J=7.6 Hz, 1H), 7.60 (s, 1H), 7.67 (s, 1H), 7.75 (s, 1H), 7.98 (dd, J=9.1, 2.5 Hz, 1H), 8.31 (s, 1H), 8.69 (d, J=2.5 Hz, 1H). MS m/z 523.3 (M+H)$^+$

Example 137

Compound #109

6-(cyclobutylamino)-N-(2-methyl-5-(3-(4-(1-methyl-1H-pyrazol-4-yl)phenyl)azetidine-1-carbonyl)phenyl)nicotinamide

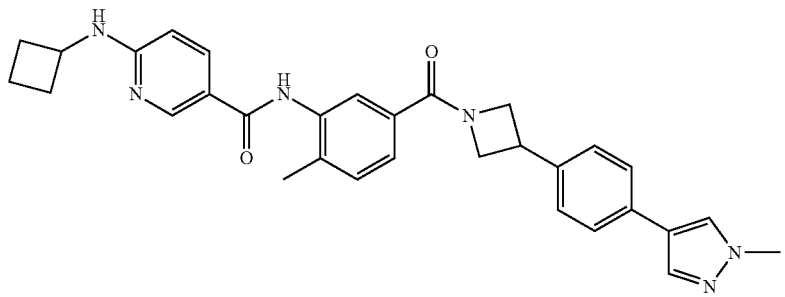 [SMILES: Cc1ccc(C(=O)N2CC(c3ccc(-c4cnn(C)c4)cc3)C2)cc1NC(=O)c1ccc(NC2CCC2)nc1]

$^1$H NMR (400 MHz, CHLOROFORM-d) δ ppm 1.75-1.85 (m, 2H), 1.85-1.98 (m, 2H), 2.34 (s, 3H), 2.41-2.51 (m, 2H), 3.85-3.92 (m, 1H), 3.94 (s, 3H), 4.14-4.33 (m, 2H), 4.40 (t, J=7.3 Hz, 1H), 4.59 (t, J=9.6 Hz, 1H), 4.82 (t, J=8.6 Hz, 1H), 5.21 (d, J=6.6 Hz, 1H), 6.36 (d, J=8.6 Hz, 1H), 7.27-7.35 (m, 3H), 7.45 (d, J=8.1 Hz, 2H), 7.50 (d, J=8.1 Hz, 1H), 7.60 (s, 1H), 7.70 (s, 1H), 7.75 (s, 1H), 7.96 (dd, J=8.6, 2.5 Hz, 1H), 8.22 (s, 1H), 8.63 (d, J=2.0 Hz, 1H). MS m/z 521.3 (M+H)$^+$

Example 138

Compound #66

N-(2-methyl-5-(3-(4-(1-methyl-1H-pyrazol-4-yl)phenyl)azetidine-1-carbonyl)phenyl)-6-morpholinonicotinamide

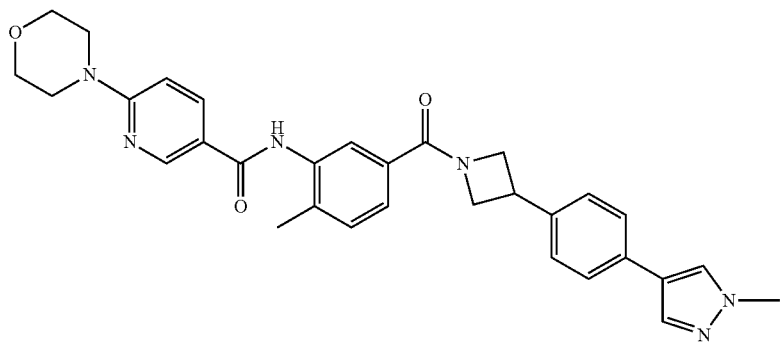 [SMILES: Cc1ccc(C(=O)N2CC(c3ccc(-c4cnn(C)c4)cc3)C2)cc1NC(=O)c1ccc(N2CCOCC2)nc1]

¹H NMR (400 MHz, CHLOROFORM-d) δ ppm 2.34 (s, 3H), 3.61-3.69 (m, 4H), 3.78-3.85 (m, 4H), 3.85-3.92 (m, 1H), 3.94 (s, 3H), 4.28 (dd, J=9.9, 6.3 Hz, 1H), 4.35-4.43 (m, 1H), 4.59 (t, J=9.6 Hz, 1H), 4.81 (t, J=9.1 Hz, 1H), 6.67 (d, J=9.1 Hz, 1H), 7.27-7.34 (m, 3H), 7.41-7.51 (m, 3H), 7.61 (s, 1H), 7.75 (s, 1H), 7.84 (s, 1H), 8.05 (dd, J=9.1, 2.5 Hz, 1H), 8.17 (s, 1H), 8.74 (d, J=2.0 Hz, 1H). MS m/z 537.4 (M+H)⁺

Example 139

Compound #62

6-(cyclobutylamino)-N-(2-methyl-5-(3-(4-(1-methyl-1H-pyrazol-5-yl)phenyl)azetidine-1-carbonyl)phenyl)nicotinamide

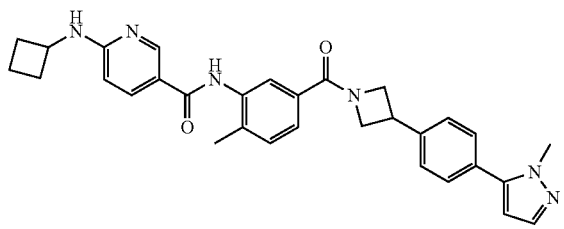 [SMILES: Cc1ccc(C(=O)N2CC(c3ccc(-c4ccnn4C)cc3)C2)cc1NC(=O)c1ccc(NC2CCC2)nc1]

¹H NMR (400 MHz, CHLOROFORM-d) δ ppm 1.78-1.87 (m, 2H), 1.87-1.99 (m, 2H), 2.35 (s, 3H), 2.42-2.52 (m, 2H), 3.89 (s, 3H), 3.92-4.00 (m, 1H), 4.16-4.28 (m, 1H), 4.32 (dd, J=10.1, 6.1 Hz, 1H), 4.41-4.50 (m, 1H), 4.64 (t, J=9.6 Hz, 1H), 4.87 (t, J=8.8 Hz, 1H), 5.23 (d, J=6.6 Hz, 1H), 6.30 (d, J=2.0 Hz, 1H), 6.37 (d, J=8.6 Hz, 1H), 7.29 (d, J=8.1 Hz, 1H), 7.38-7.46 (m, 4H), 7.49-7.56 (m, 2H), 7.69 (s, 1H), 7.96 (dd, J=8.8, 2.3 Hz, 1H), 8.25 (s, 1H), 8.63 (d, J=2.5 Hz, 1H). MS m/z 521.3 (M+H)⁺

Example 140

Compound #61

6-(methyl(1-methylpiperidin-4-yl)amino)-N-(2-methyl-5-(3-(4-(1-methyl-1H-pyrazol-5-yl)phenyl)azetidine-1-carbonyl)phenyl)nicotinamide

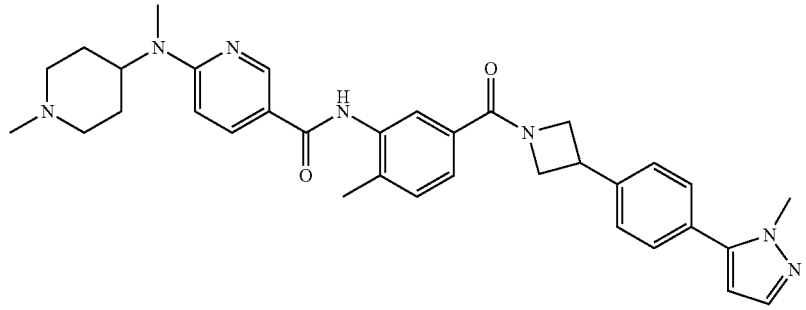 [SMILES: Cc1ccc(C(=O)N2CC(c3ccc(-c4ccnn4C)cc3)C2)cc1NC(=O)c1ccc(N(C)C2CCN(C)CC2)nc1]

¹H NMR (400 MHz, CHLOROFORM-d) δ ppm 1.31-1.42 (m, 1H), 1.70 (d, J=9.6 Hz, 3H), 1.84-2.05 (m, 2H), 2.11-2.21 (m, 1H), 2.33 (s, 1.5H), 2.36 (s, 3H), 2.48 (s, 1.5H), 2.97 (s, 3H), 3.03-3.12 (m, 1H), 3.89 (s, 3H), 3.92-4.00 (m, 1H), 4.28-4.41 (m, 2H), 4.42-4.49 (m, 1H), 4.64 (t, J=9.6 Hz, 1H), 4.88 (t, J=8.8 Hz, 1H), 6.30 (d, J=2.0 Hz, 1H), 6.55 (d, J=9.1 Hz, 0.5H), 6.70 (d, J=8.6 Hz, 0.5H), 7.29 (d, J=8.1 Hz, 1H), 7.39-7.45 (m, 4H), 7.49-7.54 (m, 2H), 7.69 (d, J=8.6 Hz, 1H), 7.99 (td, J=6.2, 3.3 Hz, 1H), 8.31 (d, J=7.6 Hz, 1H), 8.69 (s, 1H). MS m/z 564.4 (M+H)⁺

Example 141

Compound #60

6-(isopropyl(methyl)amino)-N-(2-methyl-5-(3-(4-(1-methyl-1H-pyrazol-5-yl)phenyl)azetidine-1-carbonyl)phenyl)nicotinamide

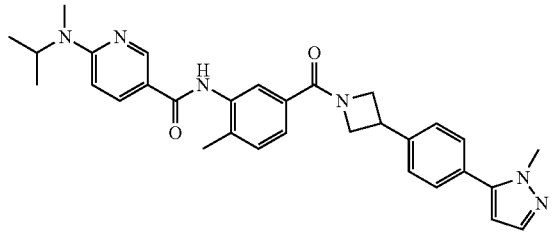 [SMILES: Cc1ccc(C(=O)N2CC(c3ccc(-c4ccnn4C)cc3)C2)cc1NC(=O)c1ccc(N(C)C(C)C)nc1]

¹H NMR (400 MHz, CHLOROFORM-d) δ ppm 1.22 (d, J=7.1 Hz, 6H), 2.33-2.40 (m, 3H), 2.93 (s, 3H), 3.89 (s, 3H), 3.92-4.00 (m, 1H), 4.32 (dd, J=9.9, 6.3 Hz, 1H), 4.42-4.50 (m, 1H), 4.64 (t, J=9.6 Hz, 1H), 4.89 (t, J=9.1 Hz, 1H), 4.92-5.01 (m, 1H), 6.30 (s, 1H), 6.55 (d, J=9.1 Hz, 1H), 7.30 (d, J=7.6 Hz, 1H), 7.38-7.46 (m, 4H), 7.49-7.55 (m, 2H), 7.67 (s, 1H), 7.98 (dd, J=9.1, 2.5 Hz, 1H), 8.34 (s, 1H), 8.69 (d, J=2.5 Hz, 1H). MS m/z 523.3 (M+H)⁺

Example 142

Compound #59

N-(2-methyl-5-(3-(4-(1-methyl-1H-pyrazol-5-yl)phenyl)azetidine-1-carbonyl)phenyl)-6-(4-methyl-piperazin-1-yl)nicotinamide

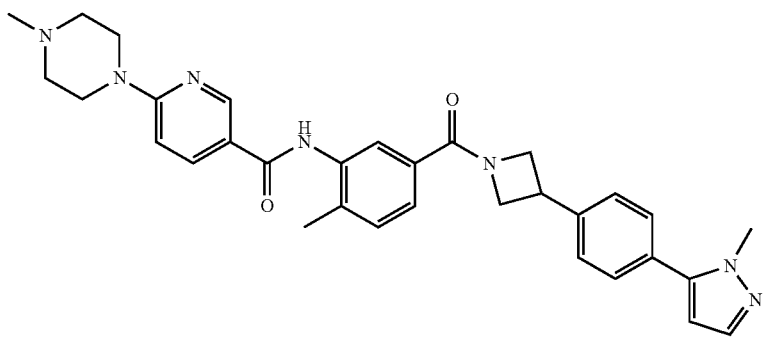 [SMILES: Cc1ccc(C(=O)N2CC(c3ccc(-c4ccnn4C)cc3)C2)cc1NC(=O)c1ccc(N2CCN(C)CC2)nc1]

¹H NMR (400 MHz, CHLOROFORM-d) δ ppm 2.35 (s, 3H), 3.62-3.69 (m, 4H), 3.79-3.85 (m, 4H), 3.89 (s, 3H), 3.91-3.99 (m, 1H), 4.31 (dd, J=9.9, 6.3 Hz, 1H), 4.39-4.49 (m, 1H), 4.63 (t, J=9.6 Hz, 1H), 4.85 (t, J=8.8 Hz, 1H), 6.30 (d, J=2.0 Hz, 1H), 6.68 (d, J=8.6 Hz, 1H), 7.29 (s, 1H), 7.39-7.45 (m, 4H), 7.47-7.53 (m, 2H), 7.84 (s, 1H), 8.05 (dd, J=9.1, 2.5 Hz, 1H), 8.20 (s, 1H), 8.74 (d, J=2.5 Hz, 1H). MS m/z 537.2 (M+H)⁺

¹H NMR (400 MHz, CHLOROFORM-d) δ ppm 2.36 (s, 6H), 2.49-2.56 (m, 4H), 3.68-3.74 (m, 4H), 3.89 (s, 3H), 3.92-4.00 (m, 1H), 4.32 (dd, J=9.9, 6.3 Hz, 1H), 4.41-4.50 (m, 1H), 4.64 (t, J=9.6 Hz, 1H), 4.87 (t, J=8.8 Hz, 1H), 6.30 (d, J=2.0 Hz, 1H), 6.69 (d, J=8.6 Hz, 1H), 7.29 (d, J=8.1 Hz, 1H), 7.38-7.46 (m, 4H), 7.49-7.55 (m, 2H), 7.70 (s, 1H), 8.01 (dd, J=9.1, 2.5 Hz, 1H), 8.29 (s, 1H), 8.70 (d, J=2.0 Hz, 1H). MS m/z 550.3 (M+H)⁺

Example 143

Compound #58

N-(2-methyl-5-(3-(4-(1-methyl-1H-pyrazol-5-yl)phenyl)azetidine-1-carbonyl)phenyl)-6-morpholinonicotinamide

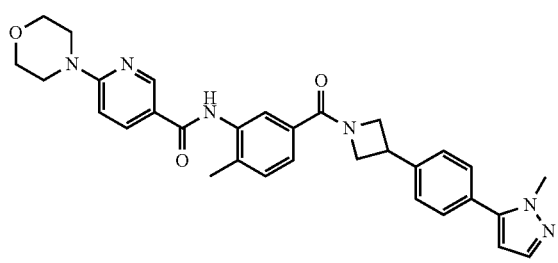 [SMILES: Cc1ccc(C(=O)N2CC(c3ccc(-c4ccnn4C)cc3)C2)cc1NC(=O)c1ccc(N2CCOCC2)nc1]

Example 144

Compound #56

5-bromo-N-(2-methyl-5-(3-(4-(1-methyl-1H-pyrazol-5-yl)phenyl)azetidine-1-carbonyl)phenyl)nicotinamide

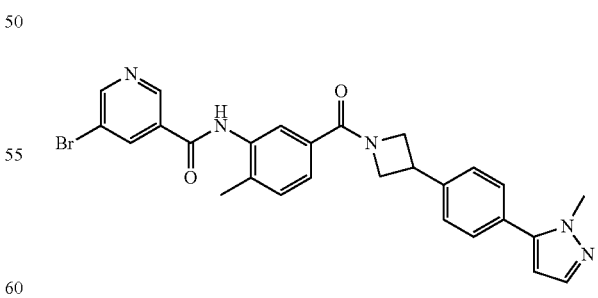

¹H NMR (400 MHz, CHLOROFORM-d) δ ppm 2.34 (s, 3H), 3.89 (s, 3H), 3.95 (t, J=6.3 Hz, 1H), 4.26-4.34 (m, 1H), 4.37 (d, J=8.6 Hz, 1H), 4.63 (t, J=9.6 Hz, 1H), 4.76 (t, J=8.8 Hz, 1H), 6.31 (s, 1H), 7.22-7.29 (m, 1H), 7.37-7.46 (m, 5H), 7.52 (s, 1H), 7.78 (s, 1H), 8.48 (s, 1H), 8.85 (s, 1H), 8.82 (s, 1H), 9.13 (s, 1H). MS m/z 532.1 (M+H)⁺

Example 145

Compound #57

N-(2-methyl-5-(3-(4-(1-methyl-1H-pyrazol-5-yl)phenyl)azetidine-1-carbonyl)phenyl)-6-(piperidin-1-yl)nicotinamide

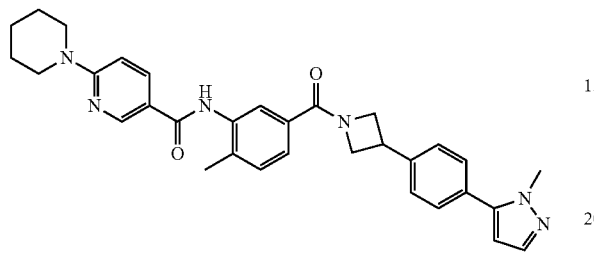

¹H NMR (400 MHz, CHLOROFORM-d) δ ppm 1.66-1.76 (m, 6H), 2.36 (s, 3H), 3.65-3.70 (m, 4H), 3.89 (s, 3H), 3.93-3.99 (m, 1H), 4.32 (dd, J=10.1, 6.6 Hz, 1H), 4.43-4.50 (m, 1H), 4.64 (t, J=9.6 Hz, 1H), 4.89 (t, J=9.1 Hz, 1H), 6.30 (s, 1H), 6.68 (d, J=9.1 Hz, 1H), 7.30 (d, J=7.6 Hz, 1H), 7.42 (d, J=3.5 Hz, 4H), 7.50-7.55 (m, 2H), 7.63 (s, 1H), 7.96 (dd, J=9.1, 2.5 Hz, 1H), 8.35 (s, 1H), 8.68 (d, J=2.5 Hz, 1H). MS m/z 535.2 (M+H)⁺

Example 146

Compound #39

6-(isopropylamino)-N-(2-methyl-5-(3-(4-(Quinolin-4-yl)phenyl)azetidine-1-carbonyl)phenyl)nicotinamide

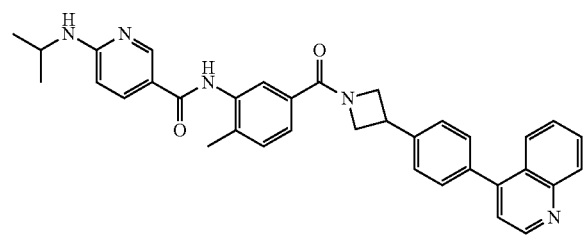 [SMILES: Cc1ccc(C(=O)N2CC(c3ccc(-c4ccnc5ccccc45)cc3)C2)cc1NC(=O)c1ccc(NC(C)C)nc1]

¹H NMR (400 MHz, CHLOROFORM-d) δ ppm 1.27 (d, J=6.1 Hz, 6H), 2.37 (s, 3H), 3.94-4.06 (m, 2H), 4.38 (dd, J=10.1, 6.6 Hz, 1H), 4.48-4.56 (m, 1H), 4.68 (t, J=9.6 Hz, 1H), 4.86-4.96 (m, 2H), 6.42 (d, J=9.1 Hz, 1H), 7.27 (s, 1H), 7.29-7.36 (m, 2H), 7.48-7.56 (m, 5H), 7.69-7.78 (m, 2H), 7.88-7.99 (m, 2H), 8.18 (d, J=8.1 Hz, 1H), 8.29 (s, 1H), 8.65 (d, J=2.0 Hz, 1H), 8.95 (d, J=4.5 Hz, 1H). MS m/z 556.2 (M+H)⁺

Example 147

Compound #26

6-(isopropylamino)-N-(2-methyl-5-(3-(4-(thiophen-3-yl)phenyl)azetidine-1-carbonyl)phenyl)nicotinamide

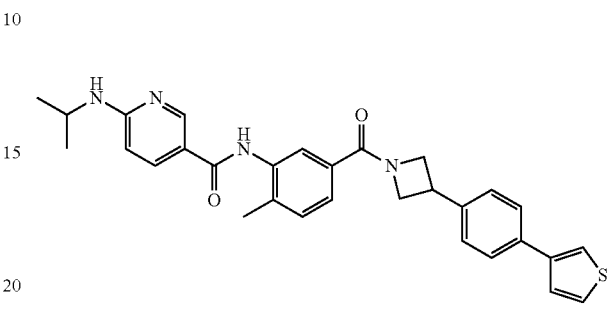

¹H NMR (400 MHz, CHLOROFORM-d) δ ppm 1.27 (d, J=6.6 Hz, 6H), 2.36 (s, 3H), 3.86-4.04 (m, 2H), 4.31 (dd, J=9.6, 6.6 Hz, 1H), 4.40-4.49 (m, 1H), 4.62 (t, J=9.6 Hz, 1H), 4.80-4.90 (m, 2H), 6.41 (d, J=9.1 Hz, 1H), 7.29 (d, J=8.1 Hz, 1H), 7.34-7.40 (m, 4H), 7.44 (d, J=2.0 Hz, 1H), 7.50-7.55 (m, 1H), 7.56-7.63 (m, 3H), 7.95 (dd, J=8.6, 2.5 Hz, 1H), 8.30 (s, 1H), 8.63 (d, J=2.0 Hz, 1H). MS m/z 511.2 (M+H)⁺

Example 148

Compound #29

6-(isopropylamino)-N-(5-(3-(4-(isoquinolin-6-yl)phenyl)azetidine-1-carbonyl)-2-methylphenyl)nicotinamide

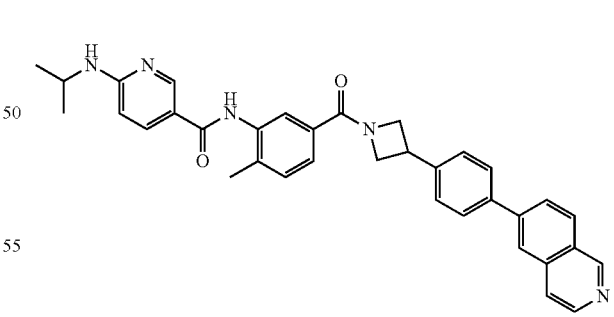

¹H NMR (400 MHz, CHLOROFORM-d) δ ppm 1.27 (d, J=6.6 Hz, 6H), 2.36 (s, 3H), 3.91-4.05 (m, 2H), 4.34 (dd, J=9.9, 6.3 Hz, 1H), 4.43-4.52 (m, 1H), 4.65 (t, J=9.9 Hz, 1H), 4.82-4.96 (m, 2H), 6.41 (d, J=9.1 Hz, 1H), 7.30 (d, J=8.1 Hz, 1H), 7.45-7.56 (m, 3H), 7.67-7.74 (m, 4H), 7.86 (d, J=8.6 Hz, 1H), 7.96 (dd, J=8.6, 2.5 Hz, 1H), 8.00 (s, 1H), 8.05 (d, J=8.6 Hz, 1H), 8.29 (s, 1H), 8.55 (d, J=5.6 Hz, 1H), 8.64 (d, J=2.0 Hz, 1H), 9.27 (s, 1H). MS m/z 556.0 (M+H)⁺

Example 149

Compound #12

6-(isopropylamino)-N-(2-methyl-5-(3-(4-(quinolin-5-yl)phenyl)azetidine-1-carbonyl)phenyl)nicotinamide

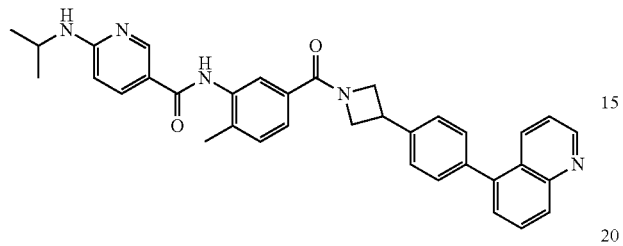

¹H NMR (400 MHz, CHLOROFORM-d) δ ppm 1.28 (d, J=6.6 Hz, 6H), 2.37 (s, 3H), 3.93-4.06 (m, 2H), 4.38 (dd, J=10.1, 6.6 Hz, 1H), 4.48-4.56 (m, 1H), 4.68 (t, J=9.6 Hz, 1H), 4.81-4.97 (m, 2H), 6.42 (d, J=9.1 Hz, 1H), 7.31 (d, J=8.1 Hz, 1H), 7.37 (dd, J=8.6, 4.0 Hz, 1H), 7.45-7.52 (m, 5H), 7.52-7.57 (m, 1H), 7.67 (s, 1H), 7.72-7.80 (m, 1H), 7.96 (dd, J=9.1, 2.5 Hz, 1H), 8.13 (d, J=8.6 Hz, 1H), 8.24 (d, J=8.6 Hz, 1H), 8.31 (s, 1H), 8.64 (d, J=2.5 Hz, 1H), 8.93 (d, J=2.5 Hz, 1H). MS m/z 556.0 (M+H)⁺

Example 150

Compound #10

6-(isopropylamino)-N-(2-methyl-5-(3-(4-(pyridin-3-yl)phenyl)azetidine-1-carbonyl)phenyl)nicotinamide

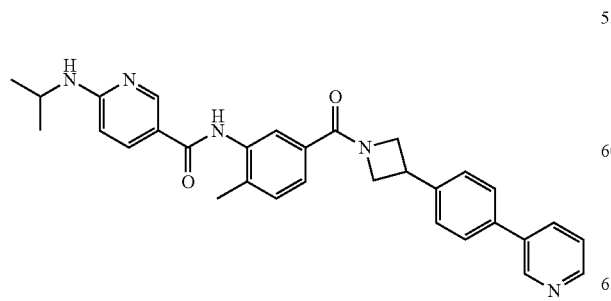

¹H NMR (400 MHz, CHLOROFORM-d) δ ppm 1.27 (d, J=6.1 Hz, 6H), 2.36 (s, 3H), 3.91-4.05 (m, 2H), 4.32 (dd, J=9.9, 6.3 Hz, 1H), 4.40-4.49 (m, 1H), 4.64 (t, J=9.6 Hz, 1H), 4.81-4.93 (m, 2H), 6.41 (d, J=9.1 Hz, 1H), 7.29 (d, J=8.1 Hz, 1H), 7.37 (dd, J=7.8, 4.8 Hz, 1H), 7.45 (d, J=8.1 Hz, 2H), 7.52 (d, J=6.1 Hz, 1H), 7.58 (d, J=8.1 Hz, 2H), 7.70 (s, 1H), 7.87 (d, J=8.6 Hz, 1H), 7.96 (dd, J=8.6, 2.5 Hz, 1H), 8.26 (s, 1H), 8.56-8.62 (m, 1H), 8.64 (d, J=2.5 Hz, 1H), 8.84 (d, J=2.0 Hz, 1H). MS m/z 506.1 (M+H)⁺

Example 151

Compound #16

6-(isopropylamino)-N-(2-methyl-5-(3-(4-(1-methyl-1H-indazol-5-yl)phenyl)azetidine-1-carbonyl)phenyl)nicotinamide

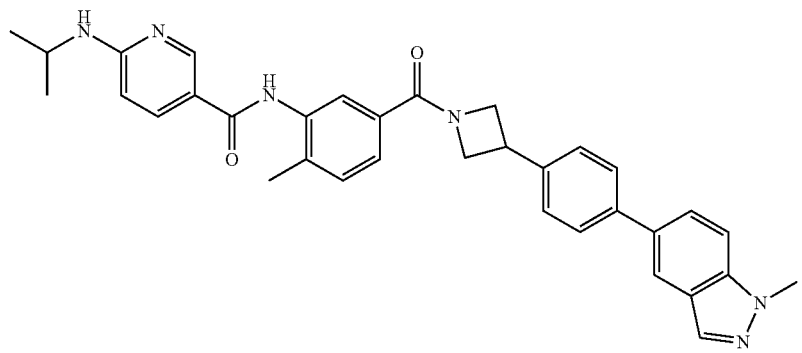 [SMILES: Cc1ccc(C(=O)N2CC(c3ccc(-c4ccc5c(cnn5C)c4)cc3)C2)cc1NC(=O)c1ccc(NC(C)C)nc1]

¹H NMR (400 MHz, DMSO-d₆) δ ppm 1.16 (d, J=6.6 Hz, 6H), 2.28 (s, 3H), 3.94-4.03 (m, 1H), 4.03-4.14 (m, 5H), 4.39 (br. s., 1H), 4.51 (t, J=9.3 Hz, 1H), 4.69-4.82 (m, 1H), 6.48 (d, J=9.1 Hz, 1H), 7.06 (d, J=7.1 Hz, 1H), 7.35 (d, J=8.1 Hz, 1H), 7.44-7.55 (m, 3H), 7.66-7.76 (m, 5H), 7.86-7.94 (m, 1H), 8.02 (s, 1H), 8.09 (s, 1H), 8.65 (d, J=2.0 Hz, 1H), 9.60 (s, 1H). MS m/z 559.0 (M+H)⁺

Example 152

Compound #25

6-(isopropylamino)-N-(2-methyl-5-(3-(4-(1-methyl-1H-pyrazol-5-yl)phenyl)azetidine-1-carbonyl)phenyl)nicotinamide

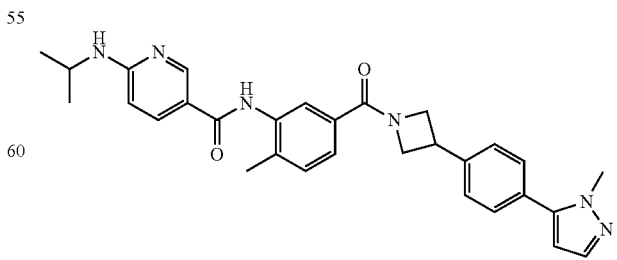

¹H NMR (400 MHz, CHLOROFORM-d) δ ppm 1.28 (d, J=6.1 Hz, 6H), 2.36 (s, 3H), 3.89 (s, 3H), 3.91-4.05 (m, 2H), 4.32 (dd, J=10.4, 6.3 Hz, 1H), 4.41-4.49 (m, 1H), 4.64 (t, J=9.3 Hz, 1H), 4.81-4.97 (m, 2H), 6.30 (d, J=2.0 Hz, 1H), 6.42 (d, J=9.1 Hz, 1H), 7.29 (d, J=8.1 Hz, 1H), 7.38-7.45 (m, 4H), 7.49-7.55 (m, 2H), 7.70 (s, 1H), 7.96 (dd, J=8.6, 2.5 Hz, 1H), 8.27 (s, 1H), 8.64 (d, J=2.5 Hz, 1H). MS m/z 509.0 (M+H)$^+$

Example 153

Compound #24

6-(isopropylamino)-N-(2-methyl-5-(3-(4-(1-methyl-1H-pyrazol-4-yl)phenyl)azetidine-1-carbonyl)phenyl)nicotinamide

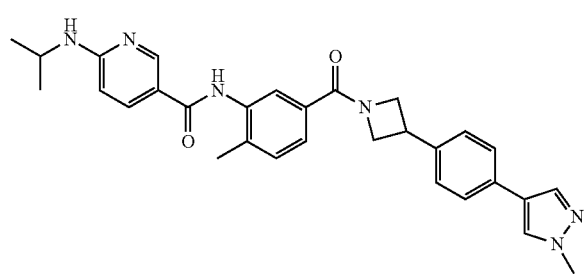 [SMILES: Cc1ccc(C(=O)N2CC(c3ccc(-c4cnn(C)c4)cc3)C2)cc1NC(=O)c1ccc(NC(C)C)nc1]

$^1$H NMR (400 MHz, DMSO-d$_6$) δ ppm 1.26 (d, J=6.1 Hz, 6H), 2.28 (s, 3H), 3.87 (s, 3H), 3.89-3.95 (m, 1H), 4.01-4.08 (m, 1H), 4.19 (br. s., 1H), 4.36 (t, J=6.8 Hz, 1H), 4.47 (t, J=9.3 Hz, 1H), 4.71 (t, J=8.6 Hz, 1H), 7.11 (d, J=9.1 Hz, 1H), 7.34-7.41 (m, 3H), 7.47-7.59 (m, 3H), 7.68 (s, 1H), 7.85 (s, 1H), 8.13 (s, 1H), 8.30 (d, J=8.6 Hz, 1H), 8.51-8.71 (m, 1H), 9.30 (br. s., 1H), 10.30 (br. s., 1H). MS m/z 509.0 (M+H)$^+$

Example 154

Compound #31

6-(isopropylamino)-N-(2-methyl-5-(3-(4-(pyridin-4-yl)phenyl)azetidine-1-carbonyl)phenyl)nicotinamide

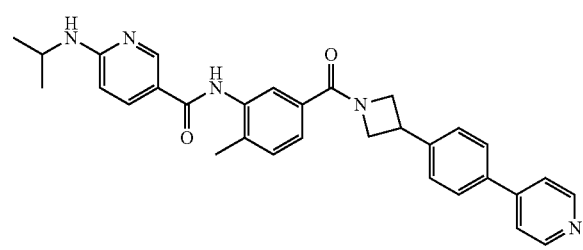 [SMILES: Cc1ccc(C(=O)N2CC(c3ccc(-c4ccncc4)cc3)C2)cc1NC(=O)c1ccc(NC(C)C)nc1]

$^1$H NMR (400 MHz, DMSO-d$_6$) δ ppm 1.24 (d, J=6.6 Hz, 6H), 2.28 (s, 3H), 3.75 (s, 3H), 4.08 (br. s., 2H), 4.14 (br. s., 1H), 4.43 (br. s., 1H), 4.53 (br. s., 1H), 4.77 (br. s., 1H), 6.94 (br. s., 1H), 7.37 (d, J=8.1 Hz, 1H), 7.51 (d, J=7.6 Hz, 1H), 7.61-7.78 (m, 3H), 8.02 (d, J=8.1 Hz, 2H), 8.20 (br. s., 1H), 8.28 (br. s., 2H), 8.60 (br. s., 1H), 8.89 (d, J=5.1 Hz, 2H), 10.08 (br. s., 1H). MS m/z 506.0 (M+H)$^+$

Example 155

Compound #4

6-chloro-N-(2-methyl-5-(3-(4-(1-methyl-1H-pyrazol-4-yl)phenyl)azetidine-1-carbonyl)phenyl)nicotinamide

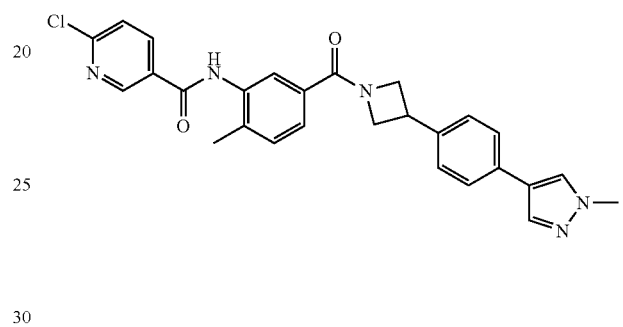

$^1$H NMR (400 MHz, DMSO-d$_6$) δ ppm 2.30 (s, 3H), 3.85 (s, 3H), 3.89-3.97 (m, 1H), 4.02-4.08 (m, 1H), 4.25 (br. s., 1H), 4.33-4.39 (m, 1H), 4.48 (t, J=9.1 Hz, 1H), 4.71 (t, J=8.6 Hz, 1H), 7.38 (d, J=8.1 Hz, 3H), 7.55 (d, J=8.1 Hz, 3H), 7.68-7.78 (m, 2H), 7.85 (s, 1H), 8.13 (s, 1H), 8.29-8.44 (m, 1H), 8.97 (s, 1H), 10.22 (s, 1H). MS m/z 485.9 (M+H)$^+$

Example 156

Compound #3

6-chloro-N-(2-methyl-5-(3-(4-(pyridin-4-yl)phenyl)azetidine-1-carbonyl)phenyl)nicotinamide

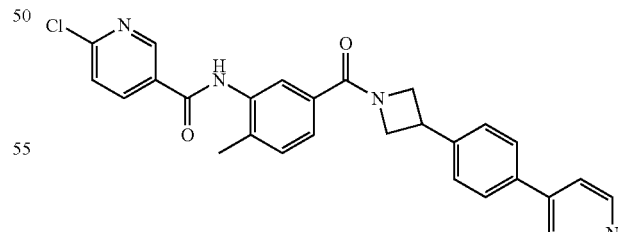

$^1$H NMR (400 MHz, DMSO-d$_6$) δ ppm 2.26-2.33 (m, 3H), 3.65 (br. s., 1H), 4.01-4.14 (m, 2H), 4.36-4.47 (m, 1H), 4.47-4.59 (m, 1H), 4.76 (t, J=8.3 Hz, 1H), 7.39 (d, J=7.6 Hz, 1H), 7.54 (d, J=8.1 Hz, 1H), 7.63 (d, J=8.1 Hz, 2H), 7.68-7.79 (m, 2H), 7.96 (d, J=8.1 Hz, 2H), 8.10 (d, J=5.1 Hz, 2H), 8.36 (dd, J=8.3, 2.3 Hz, 1H), 8.81 (d, J=6.1 Hz, 2H), 8.97 (s, 1H), 10.22 (s, 1H). MS m/z 482.9 (M+H)$^+$

Example 157

Compound #55

N-(2-methyl-5-(3-(4-(1-methyl-1H-pyrazol-5-yl)phenyl)azetidine-1-carbonyl)phenyl)quinoline-2-carboxamide

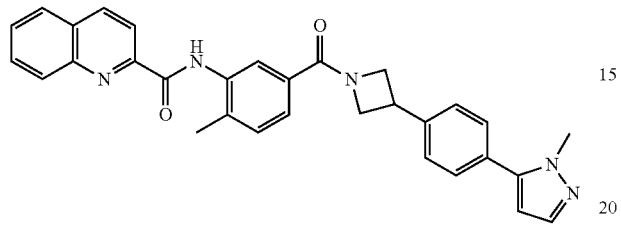

$^1$H NMR (400 MHz, CHLOROFORM-d) δ ppm 2.56 (s, 3H), 3.88-3.93 (m, 3H), 3.93-4.06 (m, 1H), 4.36 (dd, J=10.1, 6.6 Hz, 1H), 4.47-4.59 (m, 1H), 4.68 (t, J=9.6 Hz, 1H), 4.97 (t, J=8.8 Hz, 1H), 6.31 (s, 1H), 7.33-7.40 (m, 1H), 7.45 (q, J=8.4 Hz, 4H), 7.52 (d, J=2.0 Hz, 1H), 7.57-7.64 (m, 1H), 7.64-7.72 (m, 1H), 7.83 (t, J=7.6 Hz, 1H), 7.94 (d, J=8.1 Hz, 1H), 8.17 (d, J=8.6 Hz, 1H), 8.35-8.44 (m, 2H), 8.72 (s, 1H), 10.48 (s, 1H). MS m/z 502.2 (M+H)$^+$

Example 158

Compound #80

N-(2-methyl-5-(3-(4-(1-methyl-1H-pyrazol-4-yl)phenyl)azetidine-1-carbonyl)phenyl)picolinamide

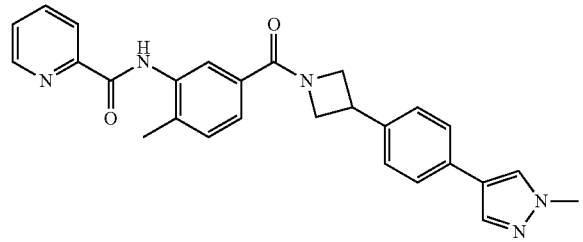 [SMILES: Cc1ccc(C(=O)N2CC(c3ccc(-c4cnn(C)c4)cc3)C2)cc1NC(=O)c1ccccn1]

$^1$H NMR (400 MHz, CHLOROFORM-d) δ ppm 2.46 (s, 3H), 3.86-3.93 (m, 1H), 3.94 (s, 3H), 4.31 (dd, J=9.9, 6.3 Hz, 1H), 4.41-4.52 (m, 1H), 4.62 (t, J=9.6 Hz, 1H), 4.90 (t, J=8.8 Hz, 1H), 7.29-7.38 (m, 3H), 7.42-7.49 (m, 2H), 7.50 (dd, J=7.1, 4.0 Hz, 1H), 7.56 (d, J=9.6 Hz, 1H), 7.61 (s, 1H), 7.75 (s, 1H), 7.92 (m, 1H), 8.28 (d, J=8.1 Hz, 1H), 8.64 (d, J=5.1 Hz, 1H), 8.67 (s, 1H), 10.19 (s, 1H). MS m/z 452.4 (M+H)$^+$

Example 159

Compound #84

N-(2-methyl-5-(3-(4-(1-methyl-1H-pyrazol-4-yl)phenyl)azetidine-1-carbonyl)phenyl)thiophene-2-carboxamide

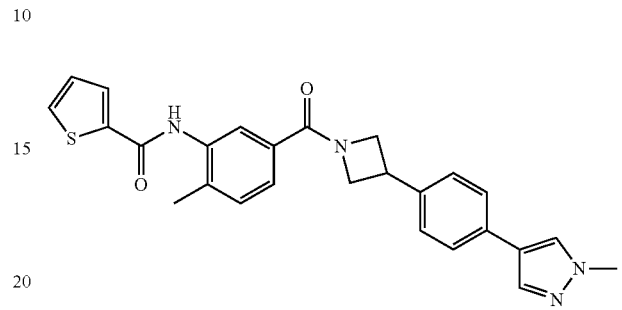

$^1$H NMR (400 MHz, CHLOROFORM-d) δ ppm 2.31 (s, 3H), 3.83-3.91 (m, 1H), 3.93 (s, 3H), 4.21-4.29 (m, 1H), 4.29-4.38 (m, 1H), 4.56 (t, J=9.6 Hz, 1H), 4.75 (t, J=9.1 Hz, 1H), 7.11-7.17 (m, 1H), 7.22 (d, J=7.6 Hz, 1H), 7.28 (d, J=8.6 Hz, 2H), 7.39-7.48 (m, 3H), 7.55 (d, J=5.1 Hz, 1H), 7.60 (s, 1H), 7.74 (s, 1H), 7.80-7.88 (m, 2H), 8.32 (d, J=8.6 Hz, 1H). MS m/z 457.1 (M+H)$^+$

Example 160

Compound #97

N-(2-methyl-5-(3-(4-(1-methyl-1H-pyrazol-4-yl)phenyl)azetidine-1-carbonyl)phenyl)-6-(trifluoromethyl)picolinamide

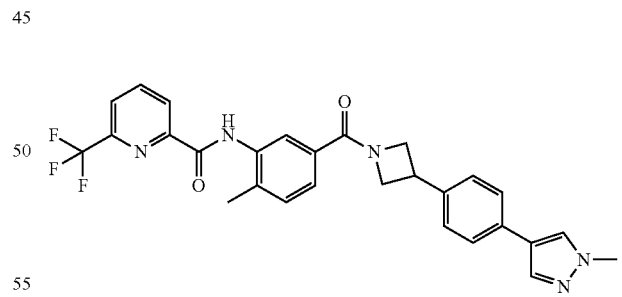

$^1$H NMR (400 MHz, CHLOROFORM-d) δ ppm 2.46 (s, 3H), 3.87-3.93 (m, 1H), 3.95 (s, 3H), 4.25-4.37 (m, 1H), 4.46 (t, J=7.3 Hz, 1H), 4.63 (t, J=9.6 Hz, 1H), 4.87 (t, J=8.6 Hz, 1H), 7.34 (dd, J=7.8, 4.3 Hz, 3H), 7.46 (d, J=8.1 Hz, 2H), 7.57 (d, J=8.1 Hz, 1H), 7.61 (s, 1H), 7.75 (s, 1H), 7.90 (d, J=7.6 Hz, 1H), 8.15 (t, J=7.8 Hz, 1H), 8.48 (d, J=7.6 Hz, 1H), 8.64 (s, 1H), 10.03 (br. s., 1H). MS m/z 520.3 (M+H)$^+$ Example 161

Compound #125

N-(2-methyl-5-(3-(4-(1-methyl-1H-pyrazol-4-yl)phenyl)azetidine-1-carbonyl)phenyl)cyclohexanecarboxamide

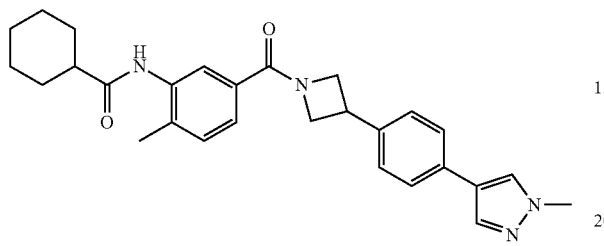

¹H NMR (400 MHz, CHLOROFORM-d) δ ppm 1.28-1.36 (m, 2H), 1.48-1.61 (m, 2H), 1.63-1.72 (m, 2H), 1.80-1.85 (m, 2H), 1.93-1.99 (m, 2H), 2.25-2.34 (m, 4H), 3.83-3.91 (m, 1H), 3.94 (s, 3H), 4.23-4.32 (m, 1H), 4.37 (t, J=7.3 Hz, 1H), 4.58 (t, J=9.3 Hz, 1H), 4.81 (t, J=8.8 Hz, 1H), 7.13 (br. s., 1H), 7.24 (d, J=8.1 Hz, 1H), 7.31 (d, J=8.1 Hz, 2H), 7.41-7.50 (m, 3H), 7.60 (s, 1H), 7.75 (s, 1H), 8.19 (s, 1H). MS m/z 457.3 (M+H)⁺

Example 162

Compound #142

N-(2-methyl-5-(3-(4-(1-methyl-1H-pyrazol-4-yl)phenyl)azetidine-1-carbonyl)phenyl)cyclopropanecarboxamide

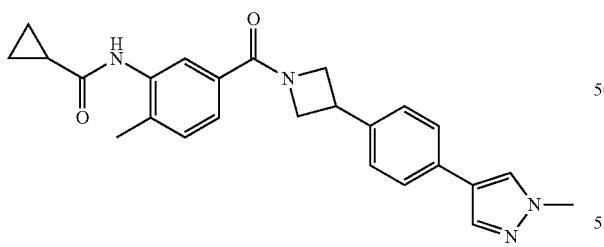

¹H NMR (400 MHz, CHLOROFORM-d) δ ppm 0.87 (d, J=5.1 Hz, 2H), 1.05-1.12 (m, 2H), 1.52-1.61 (m, 1H), 2.32 (s, 3H), 3.82-3.91 (m, 1H), 3.94 (s, 3H), 4.20-4.31 (m, 1H), 4.31-4.39 (m, 1H), 4.57 (t, J=9.3 Hz, 1H), 4.78 (t, J=8.6 Hz, 1H), 7.24 (s, 1H), 7.30 (d, J=8.1 Hz, 3H), 7.41-7.50 (m, 3H), 7.60 (s, 1H), 7.75 (s, 1H), 8.18 (br. s., 1H). MS m/z 415.3 (M+H)⁺

Example 163

Compound #143

N-(2-methyl-5-(3-(4-(1-methyl-1H-pyrazol-4-yl)phenyl)azetidine-1-carbonyl)phenyl)cyclobutanecarboxamide

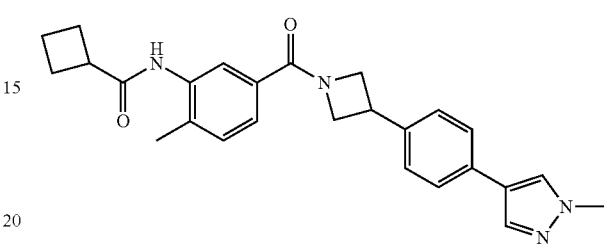

¹H NMR (400 MHz, CHLOROFORM-d) δ ppm 1.90-2.09 (m, 2H), 2.23-2.32 (m, 5H), 2.32-2.45 (m, 2H), 3.22 (t, J=8.6 Hz, 1H), 3.84-3.91 (m, 1H), 3.95 (s, 3H), 4.28 (dd, J=9.9, 6.3 Hz, 1H), 4.39 (t, J=7.3 Hz, 1H), 4.59 (t, J=9.6 Hz, 1H), 4.83 (t, J=8.8 Hz, 1H), 6.94 (br. s., 1H), 7.22-7.28 (m, 1H), 7.32 (d, J=8.1 Hz, 2H), 7.45 (d, J=8.1 Hz, 2H), 7.50 (d, J=7.6 Hz, 1H), 7.60 (s, 1H), 7.75 (s, 1H), 8.26 (s, 1H). MS m/z 429.2 (M+H)⁺

Example 164

Compound #153

2-ethyl-N-(2-methyl-5-(3-(4-(1-methyl-1H-pyrazol-4-yl)phenyl)azetidine-1-carbonyl)phenyl)butanamide

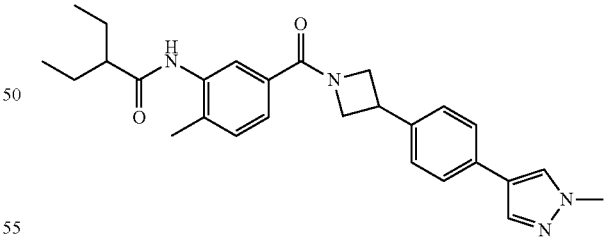

¹H NMR (400 MHz, CHLOROFORM-d) δ ppm 0.99 (t, J=7.1 Hz, 6H), 1.53-1.64 (m, 2H), 1.72 (d, J=5.1 Hz, 2H), 2.06-2.16 (m, 1H), 2.29 (s, 3H), 3.84-3.92 (m, 1H), 3.94 (s, 3H), 4.28 (dd, J=9.9, 6.3 Hz, 1H), 4.33-4.40 (m, 1H), 4.58 (t, J=9.6 Hz, 1H), 4.80 (t, J=8.8 Hz, 1H), 7.24 (d, J=8.1 Hz, 2H), 7.30 (d, J=8.1 Hz, 2H), 7.41-7.49 (m, 3H), 7.60 (s, 1H), 7.75 (s, 1H), 8.09 (s, 1H). MS m/z 445.3 (M+H)⁺

Example 165

Compound #184

N-(2-methoxy-5-(3-(4-(1-methyl-1H-pyrazol-4-yl)phenyl)azetidine-1-carbonyl)phenyl)-6-morpholinonicotinamide

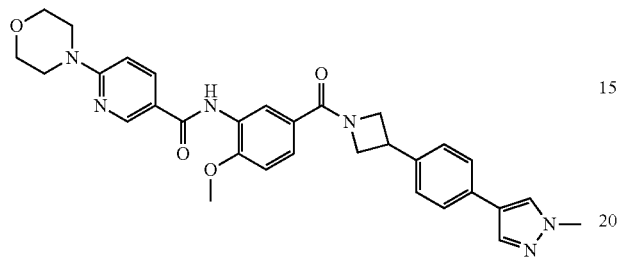

$^1$H NMR (400 MHz, CHLOROFORM-d) δ ppm 3.60-3.69 (m, 4H), 3.79-3.85 (m, 4H), 3.85-3.94 (m, 1H), 3.94 (s, 3H), 3.97 (s, 3H), 4.25-4.35 (m, 1H), 4.48 (t, J=7.1 Hz, 1H), 4.61 (t, J=9.6 Hz, 1H), 4.92 (t, J=8.8 Hz, 1H), 6.67 (d, J=9.1 Hz, 1H), 6.99 (d, J=8.6 Hz, 1H), 7.34 (d, J=8.1 Hz, 2H), 7.45 (d, J=8.1 Hz, 2H), 7.61 (s, 1H), 7.66 (dd, J=8.6, 2.0 Hz, 1H), 7.75 (s, 1H), 8.02 (dd, J=8.6, 2.5 Hz, 1H), 8.41 (s, 1H), 8.71 (d, J=2.5 Hz, 1H), 8.85 (d, J=2.0 Hz, 1H). MS m/z 553.3 (M+H)$^+$

Example 166

Compound #244

4-bromo-N-(2-methyl-5-(4-(4-(1-methyl-1H-pyrazol-4-yl)phenyl)piperidine-1-carbonyl)phenyl)thiazole-2-carboxamide

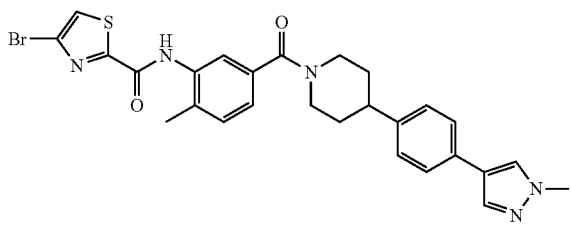 [SMILES: Cc1ccc(C(=O)N2CCC(c3ccc(-c4cnn(C)c4)cc3)CC2)cc1NC(=O)c1nc(Br)cs1]

$^1$H NMR (300 MHz, DMSO-d$_6$) δ ppm 1.50-1.71 (m, 2H), 1.81 (br. s., 2H), 2.34 (s, 3H), 2.77-2.99 (m, 2H), 3.14 (br. s., 1H), 3.77 (br. s., 1H), 3.86 (s, 3H), 4.63 (br. s., 1H), 7.26 (d, J=8.1 Hz, 3H), 7.37 (d, J=7.8 Hz, 1H), 7.48 (d, J=8.2 Hz, 2H), 7.58 (s, 1H), 7.81 (s, 1H), 8.08 (s, 1H), 9.28 (s, 1H), 10.05 (s, 1H). MS m/z 565 (M+H)$^+$

Example 167

Compound #229

4-(tert-butyl)-N-(2-methyl-5-(4-(4-(1-methyl-1H-pyrazol-4-yl)phenyl)piperidine-1-carbonyl)phenyl)thiazole-2-carboxamide

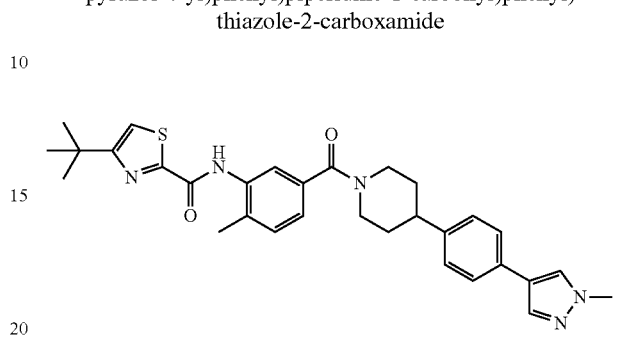

$^1$H NMR (300 MHz, DMSO-d$_6$) δ ppm 1.34-1.45 (m, 9H), 1.62 (d, J=13.1 Hz, 2H), 1.81 (br. s., 2H), 2.25-2.38 (m, 3H), 2.81 (br. s., 2H), 3.17 (br. s., 1H), 3.77 (br. s., 1H), 3.85 (s, 3H), 4.63 (br. s., 1H), 7.26 (d, J=8.0 Hz, 3H), 7.38 (d, J=7.8 Hz, 1H), 7.48 (d, J=8.1 Hz, 2H), 7.64-7.75 (m, 2H), 7.81 (s, 1H), 8.08 (s, 1H), 10.02 (s, 1H). MS m/z 542 (M+H)$^+$

Example 168

Compound #169

1-methyl-N-(2-methyl-5-(4-(4-(1-methyl-1H-pyrazol-4-yl)phenyl)piperidine-1-carbonyl)phenyl)piperidine-4-carboxamide

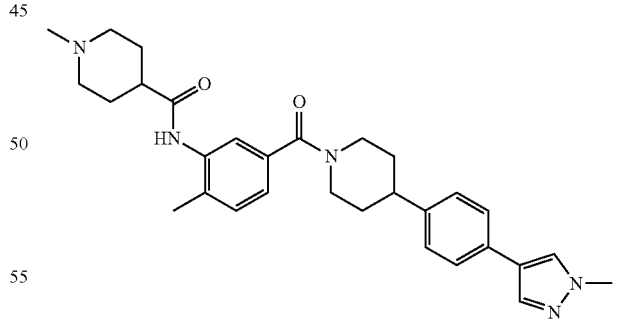

$^1$H NMR (300 MHz, DMSO-d$_6$) δ ppm 1.54-1.94 (m, 10H), 2.17 (s, 3H), 2.22 (s, 3H), 2.31-2.45 (m, 1H), 2.82 (d, J=11.3 Hz, 4H), 3.10 (br. s., 1H), 3.78 (br. s., 1H), 3.86 (s, 3H), 4.60 (br. s., 1H), 7.09-7.18 (m, 1H), 7.20-7.31 (m, 3H), 7.41-7.54 (m, 3H), 7.81 (s, 1H), 8.08 (s, 1H), 9.29 (s, 1H). MS m/z 500 (M+H)$^+$ Example 169

Compound #171

(S)—N-(2-methyl-5-(4-(4-(1-methyl-1H-pyrazol-4-yl)phenyl)piperidine-1-carbonyl)phenyl)pyrrolidine-2-carboxamide

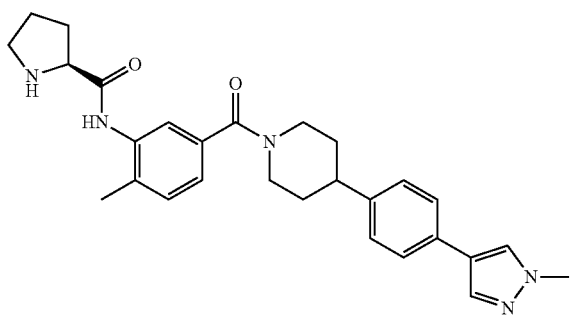 [SMILES: Cc1ccc(C(=O)N2CCC(c3ccc(-c4cnn(C)c4)cc3)CC2)cc1NC(=O)[C@@H]1CCCN1]

$^1$H NMR (300 MHz, DMSO-d$_6$) δ ppm 1.53-1.72 (m, 4H), 1.73-1.94 (m, 3H), 1.96-2.14 (m, 1H), 2.26 (s, 3H), 2.70-2.92 (m, 3H), 2.93-3.03 (m, 1H), 3.11 (br. s., 1H), 3.43 (br. s., 1H), 3.76 (dd, J=9.0, 5.2 Hz, 2H), 3.86 (s, 3H), 4.62 (br. s., 1H), 7.09 (dd, J=7.6, 1.4 Hz, 1H), 7.29 (d, J=8.0 Hz, 1H), 7.25 (d, J=8.2 Hz, 2H), 7.49 (d, J=8.1 Hz, 2H), 7.81 (s, 1H), 7.98-8.12 (m, 2H), 10.06 (s, 1H). MS m/z 472 (M+H)$^+$ Example 170

Compound #172

(R)—N-(2-methyl-5-(4-(4-(1-methyl-1H-pyrazol-4-yl)phenyl)piperidine-1-carbonyl)phenyl)pyrrolidine-2-carboxamide

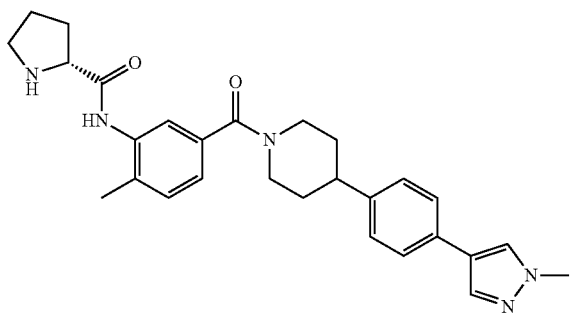

$^1$H NMR (300 MHz, DMSO-d$_6$) δ ppm 1.54-1.73 (m, 4H), 1.83 (td, J=12.3, 6.5 Hz, 3H), 1.98-2.15 (m, 1H), 2.26 (s, 3H), 2.70-2.93 (m, 3H), 2.93-3.04 (m, 1H), 3.12 (br. s., 1H), 3.46 (br. s., 1H), 3.77 (dd, J=9.0, 5.2 Hz, 2H), 3.86 (s, 3H), 4.62 (br. s., 1H), 7.09 (dd, J=7.7, 1.4 Hz, 1H), 7.20-7.33 (m, 3H), 7.48 (d, J=8.1 Hz, 2H), 7.81 (s, 1H), 8.04 (s, 1H), 8.08 (s, 1H), 10.06 (s, 1H). MS m/z 572 (M+H)$^+$ Example 171

Compound #168

1-ethyl-N-(2-methyl-5-(4-(4-(1-methyl-1H-pyrazol-4-yl)phenyl)piperidine-1-carbonyl)phenyl)piperidine-4-carboxamide

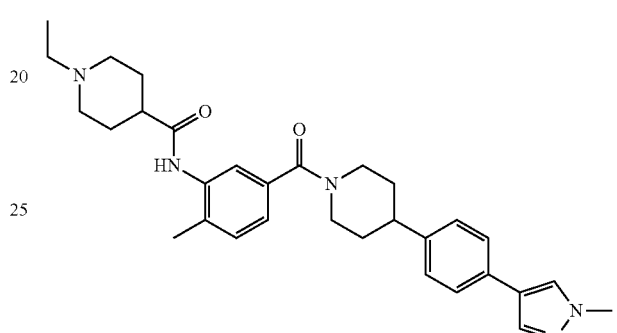

$^1$H NMR (300 MHz, DMSO-d$_6$) δ ppm 1.08 (dt, J=10.4, 7.0 Hz, 3H), 1.44-1.66 (m, 2H), 1.66-2.04 (m, 7H), 2.23 (s, 3H), 2.71-2.97 (m, 3H), 3.08 (br. s., 3H), 3.43 (br. s., 3H), 3.76 (br. s., 1H), 3.86 (s, 3H), 4.61 (br. s., 1H), 7.15 (d, J=7.3 Hz, 1H), 7.20-7.33 (m, 3H), 7.40-7.55 (m, 3H), 7.81 (s, 1H), 8.08 (s, 1H), 9.35 (br. s., 1H). MS m/z 514 (M+H)$^+$ Example 172

Compound #173

1-isopentyl-N-(2-methyl-5-(4-(4-(1-methyl-1H-pyrazol-4-yl)phenyl)piperidine-1-carbonyl)phenyl)piperidine-4-carboxamide

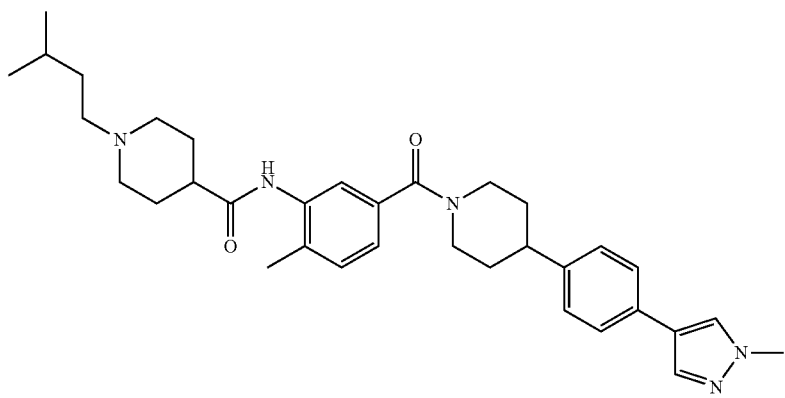 [SMILES: Cc1ccc(C(=O)N2CCC(c3ccc(-c4cnn(C)c4)cc3)CC2)cc1NC(=O)C1CCN(CCC(C)C)CC1]

$^1$H NMR (300 MHz, DMSO-d$_6$) δ ppm 0.89 (d, J=6.6 Hz, 6H), 1.39 (br. s., 2H), 1.48-1.67 (m, 4H), 1.67-1.95 (m, 6H), 2.23 (s, 4H), 2.42 (br. s., 2H), 2.68-2.93 (m, 3H), 3.02 (br. s., 3H), 3.76 (br. s., 1H), 3.86 (s, 3H), 4.60 (br. s., 1H), 7.16 (s, 1H), 7.20-7.34 (m, 3H), 7.42-7.56 (m, 3H), 7.81 (s, 1H), 8.08 (s, 1H), 9.34 (br. s., 1H). MS m/z 556 (M+H)$^+$ Example 173

Compound #176

N-(2-methyl-5-(4-(4-(1-methyl-1H-pyrazol-4-yl)phenyl)piperidine-1-carbonyl)phenyl)-1-pentylpiperidine-4-carboxamide

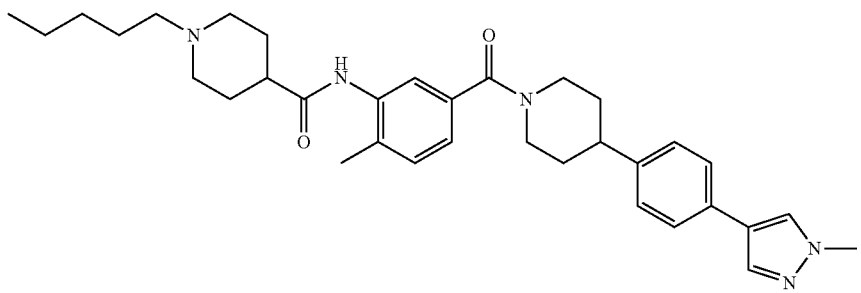 [SMILES: CCCCCN1CCC(C(=O)Nc2cc(C(=O)N3CCC(c4ccc(-c5cnn(C)c5)cc4)CC3)ccc2C)CC1]

$^1$H NMR (300 MHz, DMSO-d$_6$) δ ppm 0.82 (t, J=6.7 Hz, 3H), 1.22 (br. s., 4H), 1.44 (br. s., 2H), 1.53 (d, J=9.9 Hz, 2H), 1.62-1.97 (m, 6H), 2.17 (s, 3H), 2.65-2.85 (m, 2H), 2.94-3.04 (m, 3H), 3.34 (br. s., 3H), 3.70 (br. s., 1H), 3.80 (s, 3H), 4.55 (br. s., 1H), 7.04-7.10 (m, 1H), 7.15-7.31 (m, 3H), 7.37-7.51 (m, 3H), 7.75 (s, 1H), 8.02 (s, 1H), 9.29 (br. s., 1H). MS m/z 556 (M+H)$^+$ Example 174

Compound #181

N-(2-methyl-5-(4-(4-(1-methyl-1H-pyrazol-4-yl)phenyl)piperidine-1-carbonyl)phenyl)-1-propylpiperidine-4-carboxamide

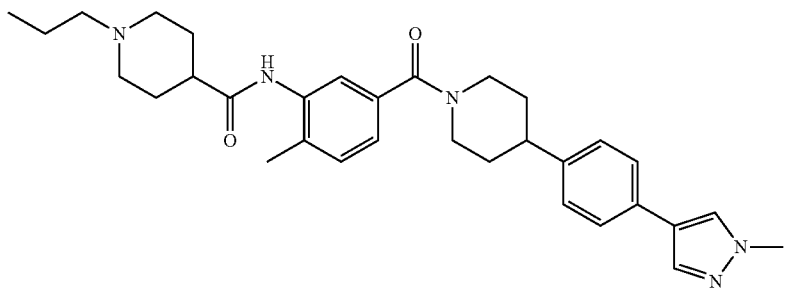 [SMILES: CCCN1CCC(C(=O)Nc2cc(C(=O)N3CCC(c4ccc(-c5cnn(C)c5)cc4)CC3)ccc2C)CC1]

$^1$H NMR (300 MHz, DMSO-d$_6$) δ ppm 0.87 (t, J=7.1 Hz, 3H), 1.42-1.57 (m, 3H), 1.61 (br. s., 2H), 1.66-1.78 (m, 2H), 1.82 (br. s., 3H), 2.08 (br. s., 2H), 2.23 (s, 3H), 2.36 (br. s., 1H), 2.80 (t, J=11.2 Hz, 2H), 3.00 (br. s., 2H), 3.36 (br. s., 3H), 3.78 (br. s., 1H), 3.86 (s, 3H), 4.61 (br. s., 1H), 7.15 (d, J=7.4 Hz, 1H), 7.20-7.34 (m, 3H), 7.39-7.57 (m, 3H), 7.81 (s, 1H), 8.09 (s, 1H), 9.37 (br. s., 1H). MS m/z 528 (M+H)$^+$ Example 175

Compound #180

1-cyclopentyl-N-(2-methyl-5-(4-(4-(1-methyl-1H-pyrazol-4-yl)phenyl)piperidine-1-carbonyl)phenyl)piperidine-4-carboxamide

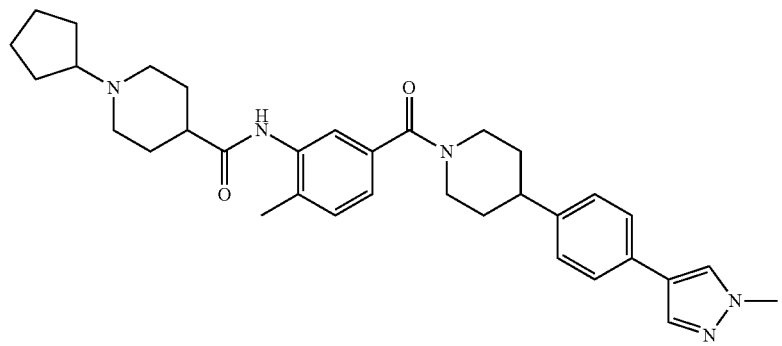 [SMILES: Cc1ccc(C(=O)N2CCC(c3ccc(-c4cnn(C)c4)cc3)CC2)cc1NC(=O)C1CCN(C2CCCC2)CC1]

$^1$H NMR (300 MHz, DMSO-d$_6$) δ ppm 1.41 (br. s., 4H), 1.45-1.62 (m, 6H), 1.62-1.89 (m, 8H), 2.16 (s, 4H), 2.64-2.82 (m, 2H), 3.06 (br. s., 4H), 3.66 (br. s., 1H), 3.78 (s, 3H), 4.53 (br. s., 1H), 7.08 (d, J=7.4 Hz, 1H), 7.13-7.27 (m, 3H), 7.30-7.49 (m, 3H), 7.74 (s, 1H), 8.01 (s, 1H), 9.29 (br. s., 1H). MS m/z 554 (M+H)$^+$ Example 176

Compound #177

1-cyclohexyl-N-(2-methyl-5-(4-(4-(1-methyl-1H-pyrazol-4-yl)phenyl)piperidine-1-carbonyl)phenyl)piperidine-4-carboxamide

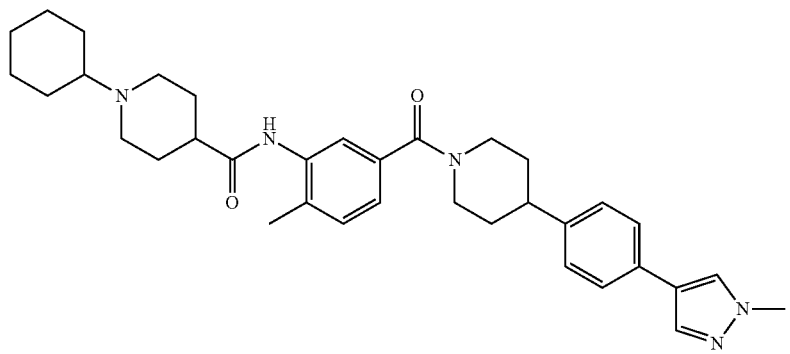 [SMILES: Cc1ccc(C(=O)N2CCC(c3ccc(-c4cnn(C)c4)cc3)CC2)cc1NC(=O)C1CCN(C2CCCCC2)CC1]

$^1$H NMR (300 MHz, DMSO-d$_6$) δ ppm 1.22 (br. s., 6H), 1.54-1.86 (m, 12H), 2.22 (s, 3H), 2.32 (br. s., 4H), 2.79 (br. s., 2H), 2.88-3.01 (m, 2H), 3.14 (br. s., 1H), 3.75 (br. s., 1H), 3.86 (s, 3H), 4.61 (br. s., 1H), 7.16 (s, 1H), 7.20-7.33 (m, 3H), 7.38-7.55 (m, 3H), 7.81 (s, 1H), 8.08 (s, 1H), 9.32 (br. s., 1H). MS m/z 568 (M+H)$^+$

Example 177

Compound #179

1-isobutyl-N-(2-methyl-5-(4-(4-(1-methyl-1H-pyrazol-4-yl)phenyl)piperidine-1-carbonyl)phenyl)piperidine-4-carboxamide

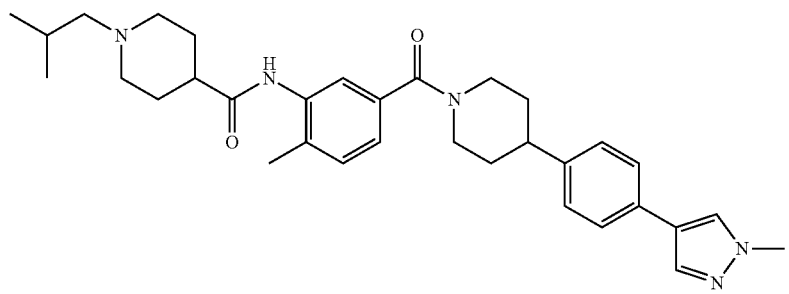 [SMILES: Cc1ccc(C(=O)N2CCC(c3ccc(-c4cnn(C)c4)cc3)CC2)cc1NC(=O)C1CCN(CC(C)C)CC1]

$^1$H NMR (300 MHz, DMSO-d$_6$) δ ppm 0.64 (br. s., 6H), 1.32-1.69 (m, 11H), 2.27 (br. s., 3H), 2.45-2.77 (m, 5H), 2.95 (br. s., 3H), 3.53 (br. s., 1H), 3.62 (s, 3H), 4.37 (br. s., 1H), 7.03 (br. s., 3H), 7.16-7.34 (m, 3H), 7.57 (s, 1H), 7.85 (s, 1H), 8.95-9.20 (m, 1H). MS m/z 542 (M+H)$^+$

Example 178

Compound #175

1-(hexan-2-yl)-N-(2-methyl-5-(4-(4-(1-methyl-1H-pyrazol-4-yl)phenyl)piperidine-1-carbonyl)phenyl)piperidine-4-carboxamide

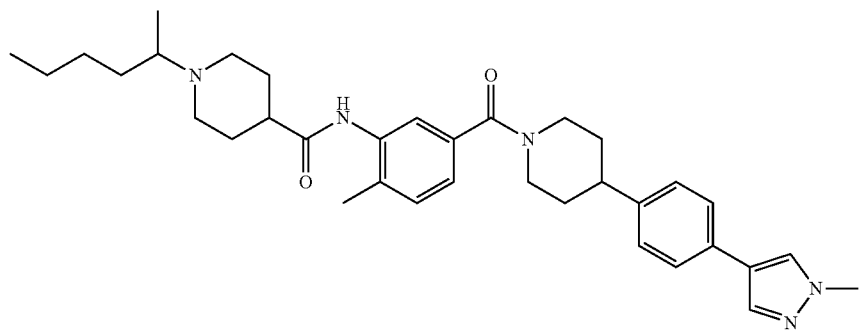 [SMILES: CCCCC(C)N1CCC(C(=O)Nc2cc(C(=O)N3CCC(c4ccc(-c5cnn(C)c5)cc4)CC3)ccc2C)CC1]

$^1$H NMR (300 MHz, DMSO-d$_6$) δ ppm 0.61-0.75 (m, 6H), 0.98-1.10 (m, 5H), 1.17-1.48 (m, 6H), 1.56 (br. s., 4H), 1.92 (br. s., 1H), 2.00 (s, 3H), 2.04-2.25 (m, 2H), 2.36 (br. s., 1H), 2.56 (d, J=7.8 Hz, 3H), 2.91 (br. s., 2H), 3.54 (br. s., 1H), 3.64 (s, 3H), 4.39 (br. s., 1H), 6.88-6.97 (m, 1H), 6.99-7.10 (m, 3H), 7.21-7.30 (m, 3H), 7.59 (s, 1H), 7.87 (s, 1H), 9.09 (s, 1H). MS m/z 570 (M+H)$^+$

Example 179

Compound #170

N-(2-methyl-5-(4-(4-(1-methyl-1H-pyrazol-4-yl)phenyl)piperidine-1-carbonyl)phenyl)pyrrolidine-3-carboxamide

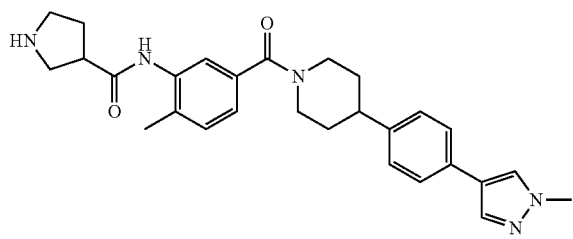 [SMILES: Cc1ccc(C(=O)N2CCC(c3ccc(-c4cnn(C)c4)cc3)CC2)cc1NC(=O)C1CCNC1]

$^1$H NMR (300 MHz, DMSO-d$_6$) δ ppm 1.59 (d, J=11.1 Hz, 2H), 1.89 (dd, J=13.7, 6.5 Hz, 4H), 2.23 (s, 3H), 2.73-3.07 (m, 8H), 3.29 (br. s., 1H), 3.76 (br. s., 1H), 3.86 (s, 3H), 4.61 (br. s., 1H), 7.10-7.18 (m, 1H), 7.22-7.32 (m, 3H), 7.43-7.55 (m, 3H), 7.81 (s, 1H), 8.08 (s, 1H), 9.44 (s, 1H). MS m/z 572 (M+H)$^+$

Example 180

Compound #173

2-fluoro-N-(2-methyl-5-(4-(4-(1-methyl-1H-pyrazol-4-yl)phenyl)piperidine-1-carbonyl)phenyl)propanamide

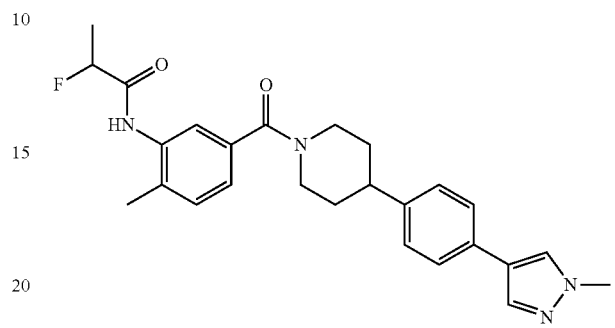

$^1$H NMR (300 MHz, DMSO-d$_6$) δ ppm 1.52 (d, J=6.5 Hz, 2H), 1.60 (d, J=6.3 Hz, 3H), 1.79 (br. s., 2H), 2.24 (s, 3H), 2.80 (t, J=10.0 Hz, 2H), 3.14 (br. s., 2H), 3.86 (s, 3H), 4.62 (br. s., 1H), 5.15-5.34 (m, 1H), 7.17-7.37 (m, 4H), 7.42 (br. s., 1H), 7.49 (d, J=7.7 Hz, 2H), 7.82 (s, 1H), 8.08 (s, 1H), 9.66 (br. s., 1H). MS m/z 499 (M+H)$^+$

Example 181

Compound #178

N-(2-methyl-5-(4-(4-(1-methyl-1H-pyrazol-4-yl)phenyl)piperidine-1-carbonyl)phenyl)-1-neopentylpiperidine-4-carboxamide

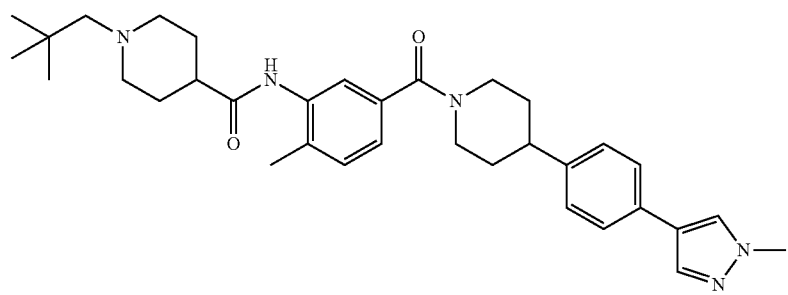 [SMILES: Cc1ccc(C(=O)N2CCC(c3ccc(-c4cnn(C)c4)cc3)CC2)cc1NC(=O)C1CCN(CC(C)(C)C)CC1]

¹H NMR (300 MHz, DMSO-d₆) δ ppm 0.64 (br. s., 9H), 1.50 (br. s., 8H), 1.83 (br. s., 2H), 2.00 (s, 5H), 2.60 (d, J=10.6 Hz, 4H), 2.90 (br. s., 1H), 3.54 (br. s., 1H), 3.64 (s, 3H), 4.39 (br. s., 1H), 6.93 (d, J=7.6 Hz, 1H), 7.05 (t, J=6.7 Hz, 3H), 7.20-7.35 (m, 3H), 7.60 (s, 1H), 7.87 (s, 1H), 9.08 (br. s., 1H). MS m/z 556 (M+H)⁺

Example 182

Compound #186

N-(2-methyl-5-(4-(4-(1-methyl-1H-pyrazol-4-yl)phenyl)piperidine-1-carbonyl)phenyl)-1-propylpyrrolidine-3-carboxamide

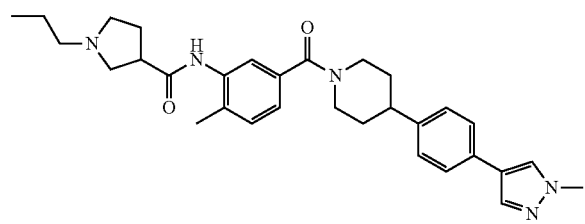 [SMILES: CCCN1CCC(C(=O)Nc2cc(C(=O)N3CCC(c4ccc(-c5cnn(C)c5)cc4)CC3)ccc2C)C1]

¹H NMR (300 MHz, DMSO-d₆) δ ppm 0.88 (t, J=7.4 Hz, 3H), 1.39-1.69 (m, 5H), 1.79 (br. s., 2H), 1.94-2.08 (m, 2H), 2.23 (s, 3H), 2.39 (t, J=7.4 Hz, 2H), 2.54-2.68 (m, 3H), 2.81 (t, J=8.2 Hz, 2H), 3.03-3.15 (m, 2H), 3.75 (br. s., 1H), 3.86 (s, 3H), 4.60 (br. s., 1H), 7.13 (d, J=7.4 Hz, 1H), 7.20-7.32 (m, 3H), 7.48 (d, J=8.0 Hz, 2H), 7.58 (s, 1H), 7.81 (s, 1H), 8.08 (s, 1H), 9.47 (s, 1H). MS m/z 514 (M+H)⁺

Example 183

Compound #192

N-(2-methyl-5-(4-(4-(1-methyl-1H-pyrazol-4-yl)phenyl)piperidine-1-carbonyl)phenyl)-1-neopentylpyrrolidine-3-carboxamide

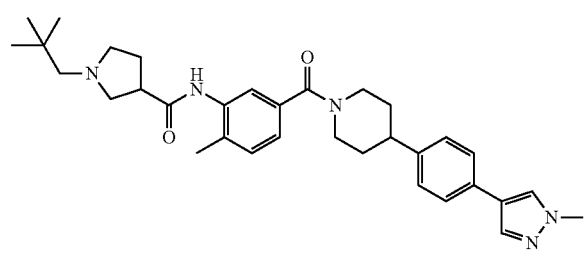 [SMILES: Cc1ccc(C(=O)N2CCC(c3ccc(-c4cnn(C)c4)cc3)CC2)cc1NC(=O)C1CCN(CC(C)(C)C)C1]

¹H NMR (300 MHz, DMSO-d₆) δ ppm 0.89 (br. s., 9H), 1.61 (br. s., 2H), 1.79 (br. s., 2H), 2.02 (br. s., 2H), 2.23 (s, 5H), 2.61 (br. s., 1H), 2.69-2.86 (m, 3H), 2.97 (br. s., 2H), 3.04-3.24 (m, 2H), 3.74 (br. s., 1H), 3.86 (s, 3H), 4.61 (br. s., 1H), 7.15 (d, J=7.6 Hz, 1H), 7.21-7.33 (m, 3H), 7.42-7.53 (m, 3H), 7.81 (s, 1H), 8.08 (s, 1H), 9.33 (br. s., 1H). MS m/z 542 (M+H)⁺

Example 184

Compound #197

1-(hexan-2-yl)-N-(2-methyl-5-(4-(4-(1-methyl-1H-pyrazol-4-yl)phenyl)piperidine-1-carbonyl)phenyl)pyrrolidine-3-carboxamide

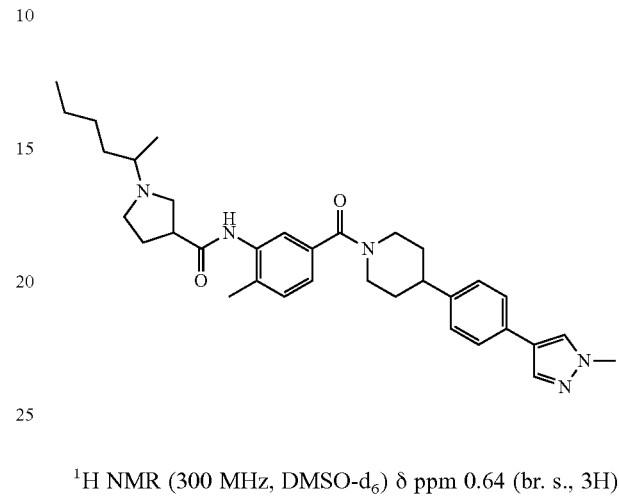

¹H NMR (300 MHz, DMSO-d₆) δ ppm 0.64 (br. s., 3H), 1.05 (br. s., 5H), 1.37 (br. s., 3H), 1.56 (br. s., 2H), 1.72-1.85 (m, 1H), 1.89 (br. s., 1H), 2.00 (s, 3H), 2.41-2.78 (m, 6H), 2.95 (br. s., 6H), 3.49 (br. s., 1H), 3.62 (s, 3H), 4.37 (br. s., 1H), 6.91 (d, J=7.6 Hz, 1H), 6.97-7.09 (m, 3H), 7.24 (d, J=8.0 Hz, 2H), 7.32 (s, 1H), 7.57 (s, 1H), 7.84 (s, 1H), 9.35 (br. s., 1H). MS m/z 556 (M+H)⁺

Example 185

Compound #185

1-ethyl-N-(2-methyl-5-(4-(4-(1-methyl-1H-pyrazol-4-yl)phenyl)piperidine-1-carbonyl)phenyl)pyrrolidine-3-carboxamide

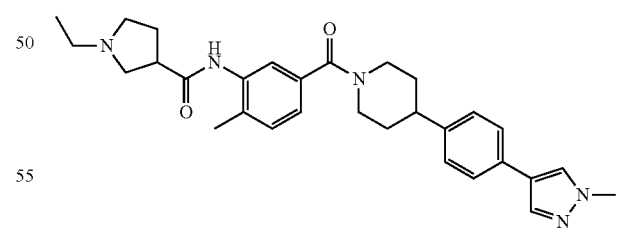

¹H NMR (300 MHz, DMSO-d₆) δ ppm 1.05-1.12 (m, 3H), 1.39-1.69 (m, 4H), 1.76 (br. s., 2H), 1.92-2.12 (m, 2H), 2.24 (s, 3H), 2.59 (t, J=6.9 Hz, 2H), 2.68 (dd, J=8.7, 6.4 Hz, 1H), 2.73-2.92 (m, 3H), 2.96-3.23 (m, 2H), 3.76 (br. s., 1H), 3.85 (s, 3H), 4.60 (br. s., 1H), 7.13 (d, J=7.4 Hz, 1H), 7.20-7.32 (m, 3H), 7.48 (d, J=8.0 Hz, 2H), 7.60 (s, 1H), 7.81 (s, 1H), 8.09 (s, 1H), 9.60 (s, 1H). MS m/z 500 (M+H)⁺

Example 186

Compound #189

1-cyclopentyl-N-(2-methyl-5-(4-(4-(1-methyl-1H-pyrazol-4-yl)phenyl)piperidine-1-carbonyl)phenyl)pyrrolidine-3-carboxamide

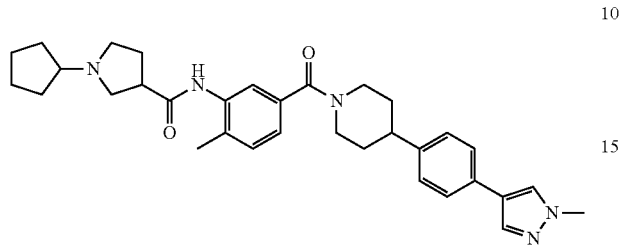

¹H NMR (300 MHz, DMSO-d₆) δ ppm 1.50 (br. s., 5H), 1.65 (br. s., 3H), 1.81 (br. s., 4H), 1.99-2.14 (m, 2H), 2.24 (s, 3H), 2.73 (br. s., 4H), 2.81 (br. s., 2H), 2.95 (br. s., 1H), 3.14 (br. s., 2H), 3.67 (br. s., 1H), 3.86 (s, 3H), 4.61 (br. s., 1H), 7.14 (d, J=7.3 Hz, 1H), 7.20-7.31 (m, 3H), 7.48 (d, J=7.7 Hz, 2H), 7.62 (br. s., 1H), 7.81 (s, 1H), 8.08 (s, 1H), 9.56 (br. s., 1H). MS m/z 540 (M+H)⁺

Example 187

Compound #194

N-(2-methyl-5-(4-(4-(1-methyl-1H-pyrazol-4-yl)phenyl)piperidine-1-carbonyl)phenyl)-1-(3-methylcyclopentyl)pyrrolidine-3-carboxamide

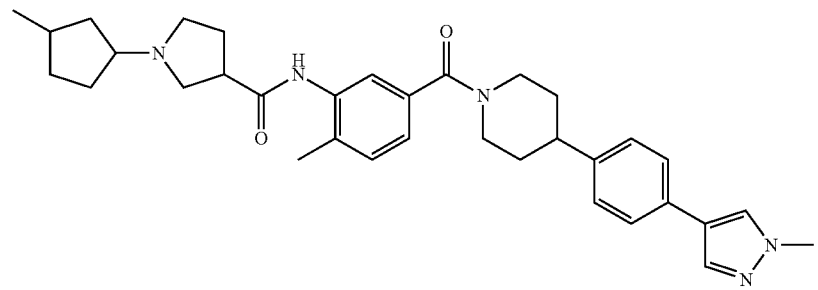

¹H NMR (300 MHz, DMSO-d₆) δ ppm 0.73-0.82 (m, 3H), 0.88-0.92 (m, 4H), 1.40 (d, J=11.3 Hz, 3H), 1.56 (br. s., 4H), 1.72-1.91 (m, 3H), 2.06 (s, 3H), 2.37 (br. s., 2H), 2.40-2.71 (m, 4H), 2.80-2.93 (m, 1H), 3.02 (dt, J=12.8, 6.2 Hz, 2H), 3.57 (br. s., 1H), 3.67 (s, 3H), 4.43 (br. s., 1H), 6.94 (d, J=7.4 Hz, 1H), 7.02-7.16 (m, 3H), 7.30 (d, J=8.0 Hz, 2H), 7.47 (br. s., 1H), 7.63 (s, 1H), 7.90 (s, 1H), 9.34 (br. s., 1H). MS m/z 554 (M+H)⁺

Example 188

Compound #195

1-isopentyl-N-(2-methyl-5-(4-(4-(1-methyl-1H-pyrazol-4-yl)phenyl)piperidine-1-carbonyl)phenyl)pyrrolidine-3-carboxamide

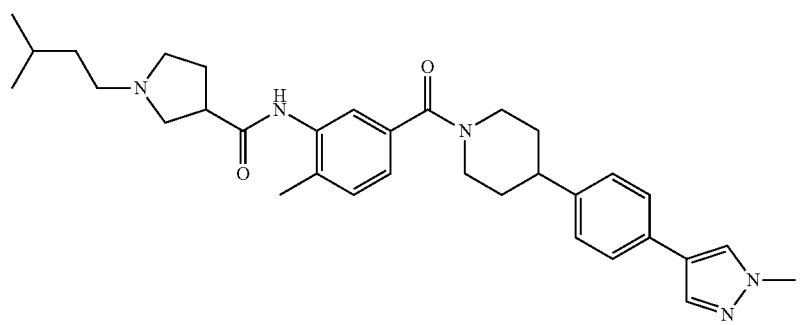 [SMILES: Cc1ccc(C(=O)N2CCC(c3ccc(-c4cnn(C)c4)cc3)CC2)cc1NC(=O)C1CCN(CCC(C)C)C1]

¹H NMR (300 MHz, DMSO-d₆) δ ppm 0.65 (d, J=6.6 Hz, 6H), 1.17 (br. s., 2H), 1.25-1.45 (m, 4H), 1.57 (br. s., 2H), 1.80 (d, J=6.6 Hz, 2H), 2.00 (s, 3H), 2.41 (br. s., 2H), 2.47-2.77 (m, 5H), 2.78-2.92 (m, 2H), 3.53 (br. s., 1H), 3.62 (s, 3H), 4.37 (br. s., 1H), 6.87-6.94 (m, 1H), 6.98-7.09 (m, 3H), 7.25 (d, J=8.1 Hz, 2H), 7.34 (s, 1H), 7.58 (s, 1H), 7.85 (s, 1H), 9.26 (br. s., 1H). MS m/z 542 (M+H)⁺

Example 189

Compound #188

1-isobutyl-N-(2-methyl-5-(4-(4-(1-methyl-1H-pyrazol-4-yl)phenyl)piperidine-1-carbonyl)phenyl)pyrrolidine-3-carboxamide

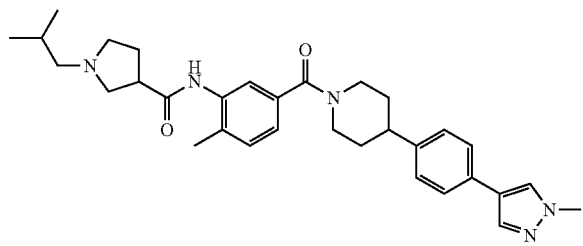 [SMILES: Cc1ccc(C(=O)N2CCC(c3ccc(-c4cnn(C)c4)cc3)CC2)cc1NC(=O)C1CCN(CC(C)C)C1]

¹H NMR (300 MHz, DMSO-d₆) δ ppm 0.84-1.04 (m, 6H), 1.22 (br. s., 2H), 1.62 (br. s., 2H), 1.79 (br. s., 2H), 2.06 (br. s., 2H), 2.24 (s, 3H), 2.61 (br. s., 3H), 2.80 (br. s., 4H), 3.17 (br. s., 2H), 3.75 (br. s., 1H), 3.86 (s, 3H), 4.63 (br. s., 1H), 7.17 (br. s., 1H), 7.22-7.41 (m, 3H), 7.43-7.59 (m, 3H), 7.81 (s, 1H), 8.09 (s, 1H), 9.44 (br. s., 1H). MS m/z 528 (M+H)⁺

Example 190

Compound #215

N-(2-methyl-5-(4-(4-(1-methyl-1H-pyrazol-4-yl)phenyl)piperidine-1-carbonyl)phenyl)-1-pentylpyrrolidine-3-carboxamide

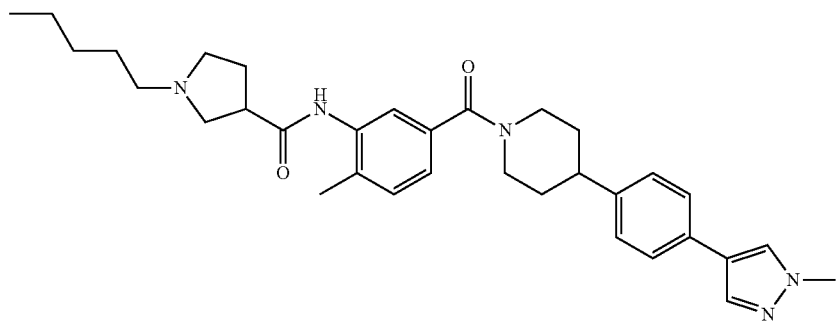 [SMILES: CCCCCN1CCC(C(=O)Nc2cc(C(=O)N3CCC(c4ccc(-c5cnn(C)c5)cc4)CC3)ccc2C)C1]

¹H NMR (300 MHz, DMSO-d₆) δ ppm 0.88 (br. s., 3H), 1.30 (br. s., 4H), 1.47 (br. s., 2H), 1.62 (br. s., 2H), 1.82 (br. s., 2H), 1.94-2.15 (m, 2H), 2.24 (br. s., 3H), 2.42 (br. s., 2H), 2.65 (br. s., 2H), 2.73-2.98 (m, 3H), 3.07 (br. s., 2H), 3.87 (br. s., 5H), 4.63 (br. s., 1H), 7.15 (br. s., 1H), 7.28 (br. s., 2H), 7.50 (br. s., 2H), 7.60 (br. s., 1H), 7.82 (br. s., 1H), 8.09 (br. s., 1H), 9.43 (br. s., 1H). MS m/z 542 (M+H)⁺

Example 191

Compound #216

N-(5-(4-(4-(1H-pyrazol-4-yl)phenyl)piperidine-1-carbonyl)-2-methylphenyl)-1-hexylpiperidine-4-carboxamide

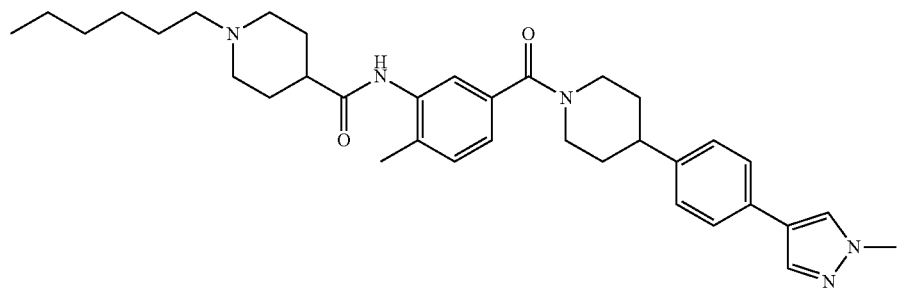 [SMILES: CCCCCCN1CCC(C(=O)Nc2cc(C(=O)N3CCC(c4ccc(-c5cnn(C)c5)cc4)CC3)ccc2C)CC1]

¹H NMR (300 MHz, DMSO-d₆) δ ppm 0.66 (t, J=6.5 Hz, 3H), 1.21 (br. s., 2H), 1.31-1.63 (m, 8H), 1.68-1.77 (m, 2H), 2.01 (s, 3H), 2.06 (t, J=7.1 Hz, 2H), 2.58 (br. s., 2H), 2.71 (d, J=10.9 Hz, 2H), 3.01-3.24 (m, 8H), 3.58 (br. s., 1H), 3.64 (s, 3H), 4.38 (br. s., 1H), 6.93 (d, J=7.6 Hz, 1H), 6.99-7.11 (m, 3H), 7.18-7.32 (m, 3H), 7.59 (s, 1H), 7.86 (s, 1H), 9.06 (s, 1H). MS m/z 570 (M+H)⁺

Example 192

Compound #191

1-cyclohexyl-N-(2-methyl-5-(4-(4-(1-methyl-1H-pyrazol-4-yl)phenyl)piperidine-1-carbonyl)phenyl)azetidine-3-carboxamide

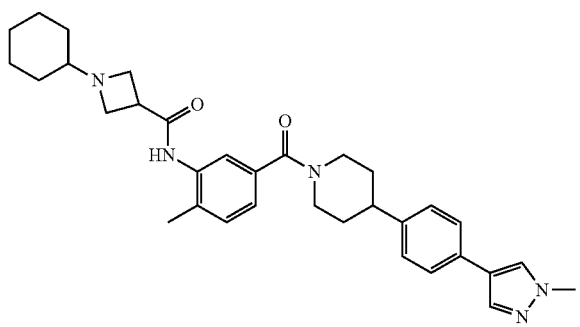 [SMILES: Cc1ccc(C(=O)N2CCC(c3ccc(-c4cnn(C)c4)cc3)CC2)cc1NC(=O)C1CN(C2CCCCC2)C1]

¹H NMR (300 MHz, DMSO-d₆) δ ppm 0.88-1.01 (m, 2H), 1.13-1.25 (m, 2H), 1.55 (br. s., 2H), 1.60-1.74 (m, 6H), 1.81 (br. s., 2H), 2.10 (br. s., 1H), 2.23 (s, 3H), 2.80 (t, J=11.6 Hz, 2H), 3.08-3.32 (m, 4H), 3.45-3.53 (m, 2H), 3.76 (br. s., 1H), 3.86 (s, 3H), 4.61 (br. s., 1H), 7.15 (d, J=7.3 Hz, 1H), 7.20-7.33 (m, 3H), 7.48 (d, J=8.0 Hz, 2H), 7.55 (s, 1H), 7.81 (s, 1H), 8.08 (s, 1H), 9.48 (s, 1H). MS m/z 540 (M+H)⁺

Example 193

Compound #208

N-(2-methyl-5-(4-(4-(1-methyl-1H-pyrazol-4-yl)phenyl)piperidine-1-carbonyl)phenyl)-1-propylazetidine-3-carboxamide

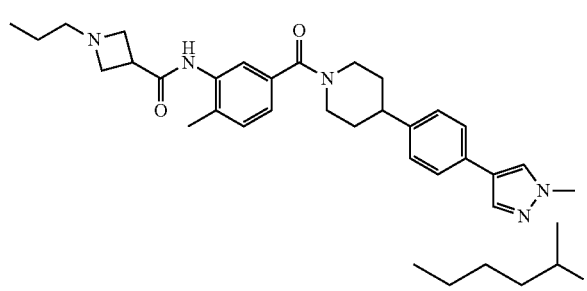

¹H NMR (300 MHz, CHLOROFORM-d) δ ppm 0.90 (t, J=7.4 Hz, 3H), 1.15-1.24 (m, 2H), 1.45-1.54 (m, 2H), 1.66 (br. s., 2H), 2.25 (s, 3H), 2.68-2.81 (m, 4H), 3.65 (d, J=10.3 Hz, 1H), 3.75 (d, J=6.9 Hz, 3H), 3.87 (s, 3H), 3.88-4.03 (m, 3H), 4.77 (br. s., 1H), 7.03-7.11 (m, 1H), 7.11-7.18 (m, 3H), 7.35 (d, J=8.1 Hz, 2H), 7.51 (s, 1H), 7.66 (s, 1H), 7.79 (s, 1H), 9.29 (br. s., 1H). MS m/z 500 (M+H)⁺

Example 194

Compound #190

N-(2-methyl-5-(4-(4-(1-methyl-1H-pyrazol-4-yl)phenyl)piperidine-1-carbonyl)phenyl)-1-neopentylazetidine-3-carboxamide

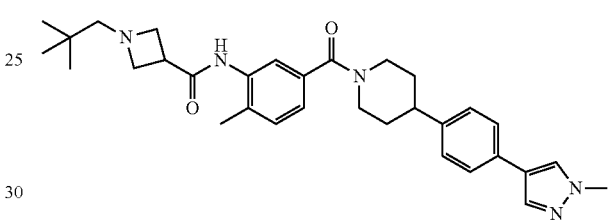

¹H NMR (300 MHz, DMSO-d₆) δ ppm 0.67 (br. s., 9H), 1.26-1.46 (m, 2H), 1.58 (br. s., 2H), 2.01 (s, 3H), 2.58 (t, J=12.0 Hz, 2H), 2.90 (br. s., 4H), 3.29 (br. s., 2H), 3.55 (br. s., 1H), 3.63 (s, 3H), 4.00 (br. s., 1H), 4.38 (br. s., 2H), 6.95 (d, J=7.4 Hz, 1H), 7.03 (d, J=8.0 Hz, 3H), 7.26 (d, J=7.8 Hz, 2H), 7.59 (s, 1H), 7.86 (s, 1H), 9.35 (br. s., 1H). MS m/z 528 (M+H)⁺

Example 195

Compound #196

1-(hexan-2-yl)-N-(2-methyl-5-(4-(4-(1-methyl-1H-pyrazol-4-yl)phenyl)piperidine-1-carbonyl)phenyl)azetidine-3-carboxamide

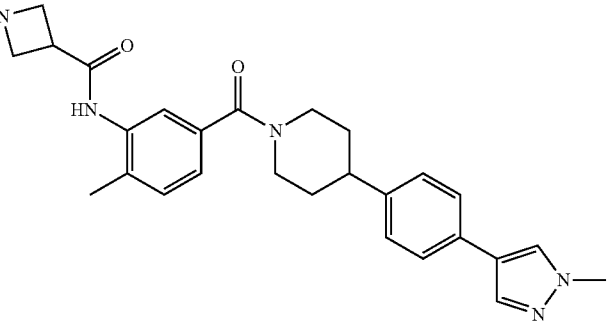

¹H NMR (300 MHz, DMSO-d₆) δ ppm 0.64 (t, J=6.3 Hz, 3H), 0.72 (d, J=5.9 Hz, 3H), 0.94 (br. s., 2H), 1.05 (br. s., 4H), 1.28-1.44 (m, 2H), 1.56 (br. s., 2H), 2.00 (s, 3H), 2.49-2.73 (m, 2H), 2.91 (br. s., 1H), 3.29 (d, J=6.9 Hz, 2H), 3.39 (br. s., 2H), 3.56 (br. s., 3H), 3.62 (s, 3H), 4.38 (br. s., 1H), 6.93 (d, J=7.6 Hz, 1H), 6.98-7.10 (m, 3H), 7.25 (d, J=8.0 Hz, 2H), 7.33 (s, 1H), 7.57 (s, 1H), 7.84 (s, 1H), 9.31 (br. s., 1H). MS m/z 542 (M+H)⁺

Example 196

Compound #205

1-ethyl-N-(2-methyl-5-(4-(4-(1-methyl-1H-pyrazol-4-yl)phenyl)piperidine-1-carbonyl)phenyl)azetidine-3-carboxamide

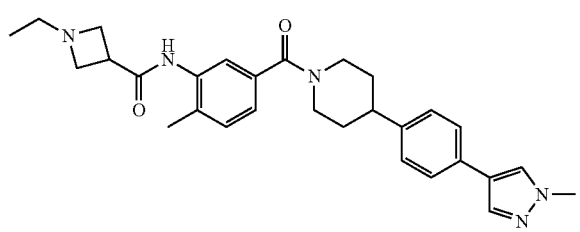 [SMILES: CCN1CC(C(=O)Nc2cc(C(=O)N3CCC(c4ccc(-c5cnn(C)c5)cc4)CC3)ccc2C)C1]

¹H NMR (300 MHz, DMSO-d₆) δ ppm 0.86 (t, J=6.9 Hz, 3H), 1.17 (br. s., 2H), 1.38 (br. s., 4H), 2.00 (s, 3H), 2.44-2.71 (m, 2H), 3.11-3.20 (m, 4H), 3.35 (br. s., 2H), 3.49 (br. s., 1H), 3.62 (s, 3H), 4.37 (br. s., 1H), 6.95 (br. s., 1H), 6.97-7.11 (m, 3H), 7.25 (d, J=7.7 Hz, 2H), 7.34 (br. s., 1H), 7.58 (s, 1H), 7.85 (s, 1H), 9.32 (br. s., 1H). MS m/z 486 (M+H)⁺

Example 197

Compound #187

1-cyclopentyl-N-(2-methyl-5-(4-(4-(1-methyl-1H-pyrazol-4-yl)phenyl)piperidine-1-carbonyl)phenyl)azetidine-3-carboxamide

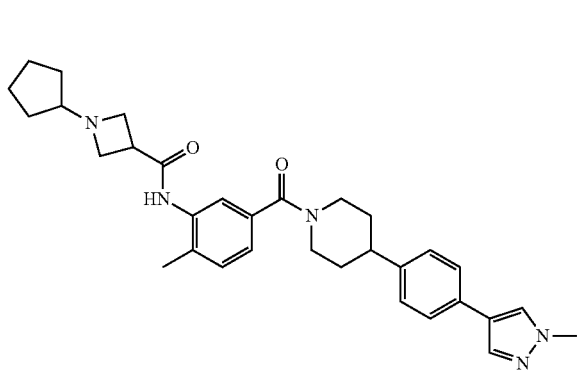 [SMILES: Cc1ccc(C(=O)N2CCC(c3ccc(-c4cnn(C)c4)cc3)CC2)cc1NC(=O)C1CN(C2CCCC2)C1]

¹H NMR (300 MHz, DMSO-d₆) δ ppm 0.97 (dd, J=15.1, 6.3 Hz, 3H), 1.26 (d, J=8.7 Hz, 1H), 1.51-1.66 (m, 2H), 1.66-1.89 (m, 4H), 1.98-2.16 (m, 1H), 2.24 (s, 3H), 2.81 (t, J=11.3 Hz, 2H), 3.18 (br. s., 4H), 3.61 (br. s., 2H), 3.68-3.82 (m, 2H), 3.86 (s, 4H), 4.62 (br. s., 1H), 7.19 (br. s., 1H), 7.22-7.36 (m, 3H), 7.49 (d, J=7.7 Hz, 2H), 7.58 (br. s., 1H), 7.81 (s, 1H), 8.09 (s, 1H), 9.56 (br. s., 1H). MS m/z 526 (M+H)⁺

Example 198

Compound #193

N-(2-methyl-5-(4-(4-(1-methyl-1H-pyrazol-4-yl)phenyl)piperidine-1-carbonyl)phenyl)-1-(3-methyl-cyclopentyl)azetidine-3-carboxamide

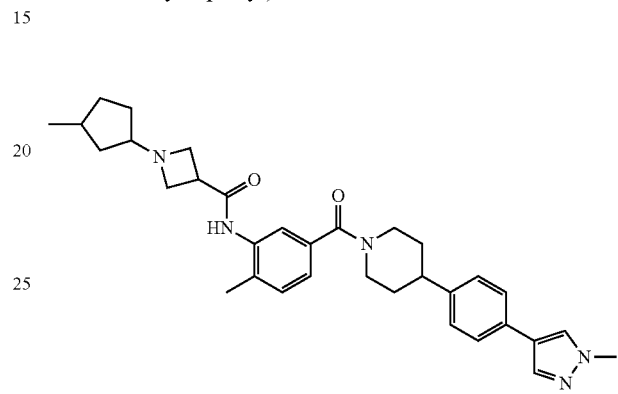

MS m/z 540 (M+H)⁺

Example 199

Compound #213

1-isopentyl-N-(2-methyl-5-(4-(4-(1-methyl-1H-pyrazol-4-yl)phenyl)piperidine-1-carbonyl)phenyl)azetidine-3-carboxamide

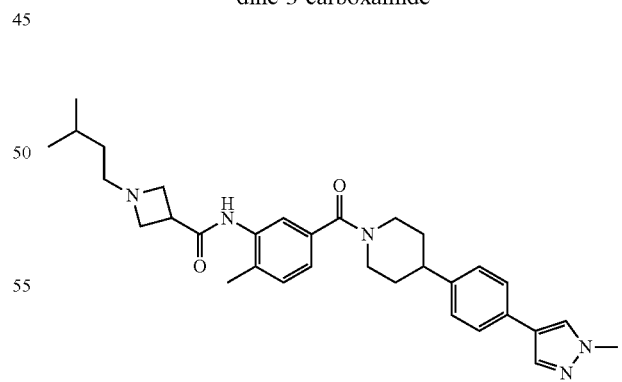

¹H NMR (300 MHz, DMSO-d₆) δ ppm 0.86 (d, J=6.5 Hz, 6H), 1.04-1.21 (m, 3H), 1.48-1.69 (m, 3H), 1.79 (br. s., 2H), 1.86 (br. s., 1H), 2.22 (s, 3H), 2.35 (t, J=7.3 Hz, 2H), 2.80 (t, J=12.6 Hz, 2H), 3.14 (br. s., 2H), 3.36-3.46 (m, 3H), 3.86 (s, 3H), 4.62 (br. s., 1H), 7.21-7.32 (m, 3H), 7.49 (d, J=7.7 Hz, 3H), 7.81 (s, 1H), 8.08 (s, 1H), 9.35 (br. s., 1H). MS m/z 528 (M+H)⁺

Example 200

Compound #210

1-isobutyl-N-(2-methyl-5-(4-(4-(1-methyl-1H-pyrazol-4-yl)phenyl)piperidine-1-carbonyl)phenyl)azetidine-3-carboxamide

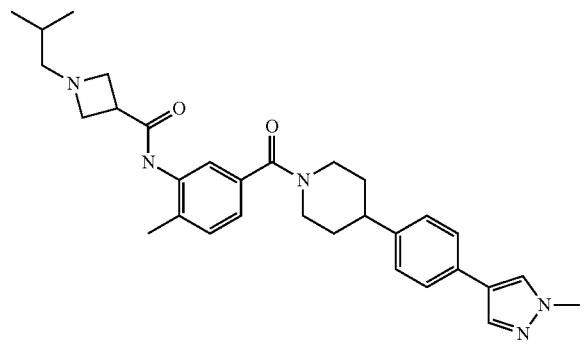 [SMILES: Cc1ccc(C(=O)N2CCC(c3ccc(-c4cnn(C)c4)cc3)CC2)cc1NC(=O)C1CN(CC(C)C)C1]

$^1$H NMR (300 MHz, DMSO-d$_6$) δ ppm 0.68 (d, J=6.3 Hz, 6H), 1.41 (br. s., 3H), 1.53 (br. s., 3H), 2.03 (s, 3H), 2.43 (br. s., 1H), 2.51-2.69 (m, 2H), 2.97 (br. s., 2H), 3.43 (br. s., 4H), 3.62-3.73 (m, 4H), 4.39 (br. s., 1H), 6.97 (d, J=7.3 Hz, 1H), 7.06 (br. s., 3H), 7.28 (d, J=7.7 Hz, 2H), 7.36 (br. s., 1H), 7.60 (s, 1H), 7.87 (s, 1H), 9.30 (br. s., 1H). MS m/z 514 (M+H)$^+$

Example 201

Compound #214

N-(2-methyl-5-(4-(4-(1-methyl-1H-pyrazol-4-yl)phenyl)piperidine-1-carbonyl)phenyl)-1-pentylazetidine-3-carboxamide

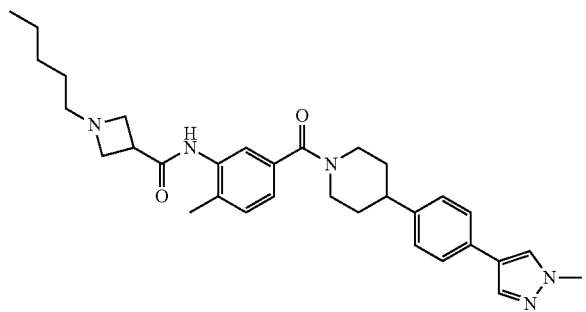 [SMILES: CCCCCN1CC(C(=O)Nc2cc(C(=O)N3CCC(c4ccc(-c5cnn(C)c5)cc4)CC3)ccc2C)C1]

$^1$H NMR (300 MHz, CHLOROFORM-d) δ ppm 0.79-0.85 (m, 3H), 1.27-1.34 (m, 2H), 1.51-1.77 (m, 4H), 1.77-2.03 (m, 4H), 2.24 (s, 3H), 2.34-2.47 (m, 2H), 2.62-2.87 (m, 2H), 2.95-3.17 (m, 2H), 3.30 (t, J=7.4 Hz, 2H), 3.38-3.49 (m, 2H), 3.87 (s, 3H), 3.92 (d, J=18.7 Hz, 1H), 4.68-4.90 (m, 1H), 7.03-7.11 (m, 1H), 7.12-7.17 (m, 3H), 7.30-7.34 (m, 1H), 7.35 (s, 1H), 7.51 (s, 1H), 7.66 (s, 1H), 8.03 (s, 1H), 9.33 (s, 1H). MS m/z 528 (M+H)$^+$

Example 202

Compound #207

1-isopropyl-N-(2-methyl-5-(4-(4-(1-methyl-1H-pyrazol-4-yl)phenyl)piperidine-1-carbonyl)phenyl)pyrrolidine-3-carboxamide

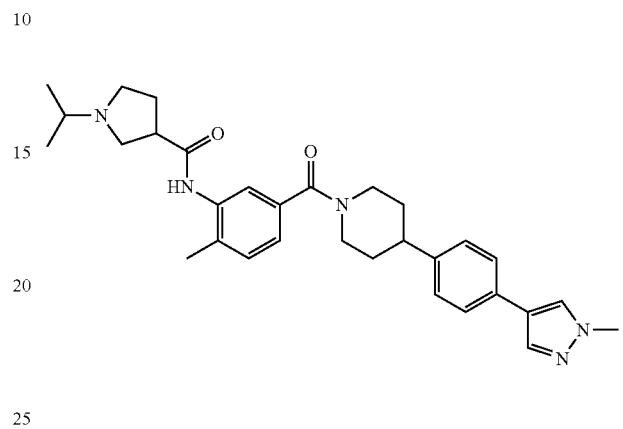

$^1$H NMR (300 MHz, DMSO-d$_6$) δ ppm 0.98 (d, J=6.0 Hz, 6H), 1.43 (d, J=11.0 Hz, 2H), 1.67 (br. s., 2H), 1.83-1.95 (m, 1H), 1.99 (br. s., 1H), 2.09 (s, 3H), 2.58-2.75 (m, 4H), 3.02 (br. s., 5H), 3.60 (br. s., 1H), 3.70 (s, 3H), 4.44 (br. s., 1H), 6.99 (d, J=7.6 Hz, 1H), 7.05-7.16 (m, 3H), 7.32 (d, J=8.1 Hz, 2H), 7.44 (s, 1H), 7.65 (s, 1H), 7.92 (s, 1H), 9.41 (br. s., 1H). MS m/z 514 (M+H)$^+$

Example 203

Compound #206

1-isopropyl-N-(2-methyl-5-(4-(4-(1-methyl-1H-pyrazol-4-yl)phenyl)piperidine-1-carbonyl)phenyl)azetidine-3-carboxamide

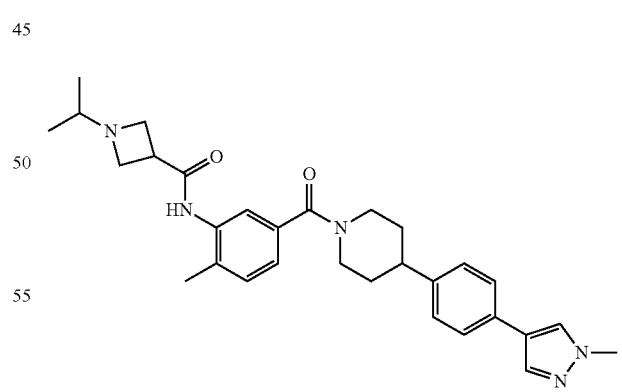

$^1$H NMR (300 MHz, DMSO-d$_6$) δ ppm 0.91 (d, J=5.1 Hz, 6H), 1.52-1.70 (m, 2H), 1.80 (br. s., 2H), 2.23 (s, 3H), 2.80 (t, J=10.9 Hz, 2H), 3.16 (br. s., 2H), 3.40-3.48 (m, 3H), 3.57 (br. s., 2H), 3.76 (br. s., 1H), 3.86 (s, 3H), 4.61 (br. s., 1H), 7.16 (d, J=8.2 Hz, 1H), 7.21-7.33 (m, 3H), 7.49 (d, J=8.0 Hz, 2H), 7.55 (s, 1H), 7.81 (s, 1H), 8.08 (s, 1H), 9.46 (br. s., 1H). MS m/z 500 (M+H)$^+$

Example 204

Compound #239

(R)-1-methyl-N-(2-methyl-5-(4-(4-(1-methyl-1H-pyrazol-4-yl)phenyl)piperidine-1-carbonyl)phenyl)pyrrolidine-2-carboxamide

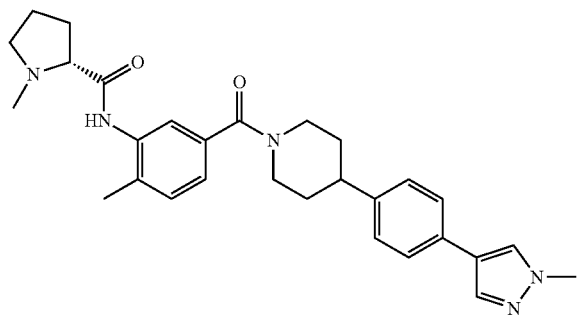 [SMILES: Cc1ccc(C(=O)N2CCC(c3ccc(-c4cnn(C)c4)cc3)CC2)cc1NC(=O)[C@H]1CCCN1C]

¹H NMR (300 MHz, CHLOROFORM-d) δ ppm 1.43-1.72 (m, 6H), 1.73-1.87 (m, 2H), 2.09 (s, 3H), 2.11-2.30 (m, 2H), 2.31 (s, 3H), 2.50-2.71 (m, 2H), 2.87 (dd, J=10.3, 4.8 Hz, 1H), 2.98-3.07 (m, 1H), 3.74 (s, 3H), 3.86 (br. s., 1H), 4.67 (br. s., 1H), 6.93-7.05 (m, 4H), 7.21 (d, J=8.1 Hz, 2H), 7.38 (s, 1H), 7.53 (s, 1H), 7.99 (s, 1H), 9.34 (br. s., 1H). MS m/z 486 (M+H)⁺

Example 205

Compound #238

(S)-1-methyl-N-(2-methyl-5-(4-(4-(1-methyl-1H-pyrazol-4-yl)phenyl)piperidine-1-carbonyl)phenyl)pyrrolidine-2-carboxamide

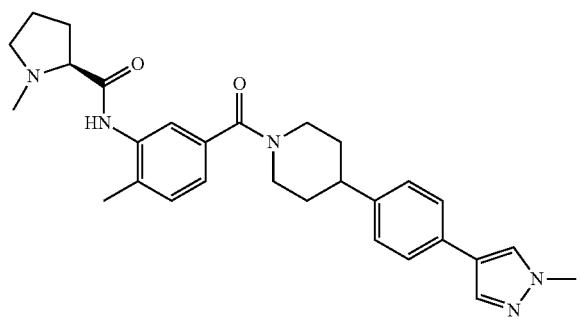 [SMILES: Cc1ccc(C(=O)N2CCC(c3ccc(-c4cnn(C)c4)cc3)CC2)cc1NC(=O)[C@@H]1CCCN1C]

¹H NMR (300 MHz, CHLOROFORM-d) δ ppm 1.58-1.83 (m, 6H), 1.85-1.99 (m, 2H), 2.22 (s, 3H), 2.23-2.42 (m, 2H), 2.45 (s, 3H), 2.63-2.78 (m, 2H), 3.02 (br. s., 1H), 3.12-3.20 (m, 1H), 3.87 (s, 3H), 3.98 (br. s., 1H), 4.79 (br. s., 1H), 7.06-7.18 (m, 4H), 7.34 (d, J=8.2 Hz, 2H), 7.51 (s, 1H), 7.66 (s, 1H), 8.11 (br. s., 1H), 9.47 (br. s., 1H). MS m/z 486 (M+H)⁺

Example 206

Compound #220

1-(cyclopropanecarbonyl)-N-(2-methyl-5-(4-(4-(1-methyl-1H-pyrazol-4-yl)phenyl)piperidine-1-carbonyl)phenyl)pyrrolidine-3-carboxamide

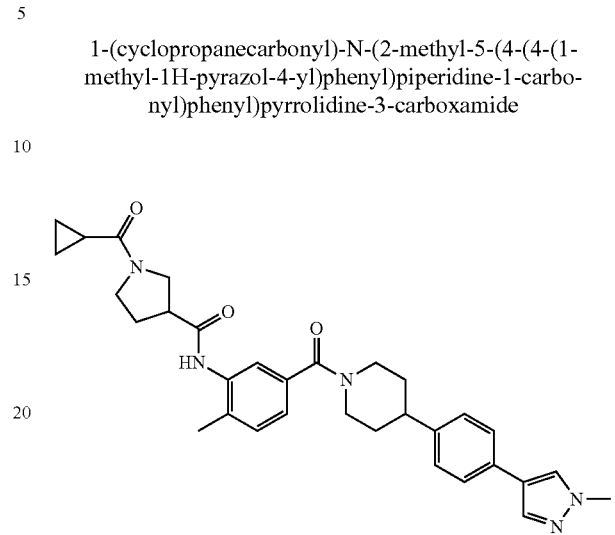

¹H NMR (300 MHz, DMSO-d₆) δ ppm 0.74 (br. s., 4H), 1.60 (d, J=10.4 Hz, 2H), 1.70-1.91 (m, 3H), 1.94-2.12 (m, 1H), 2.19 (br. s., 1H), 2.25 (d, J=3.6 Hz, 3H), 2.79 (t, J=10.0 Hz, 2H), 3.23 (br. s., 2H), 3.40 (br. s., 1H), 3.48 (d, J=6.6 Hz, 1H), 3.60-3.72 (m, 1H), 3.73-3.82 (m, 1H), 3.86 (s, 3H), 3.92 (d, J=8.5 Hz, 1H), 4.61 (br. s., 1H), 7.17 (d, J=7.4 Hz, 1H), 7.21-7.34 (m, 3H), 7.48 (d, J=7.7 Hz, 3H), 7.81 (s, 1H), 8.08 (s, 1H), 9.54 (d, J=7.8 Hz, 1H). MS m/z 540 (M+H)⁺

Example 207

Compound #222

1-methyl-N-(2-methyl-5-(4-(4-(1-methyl-1H-pyrazol-4-yl)phenyl)piperidine-1-carbonyl)phenyl)azetidine-3-carboxamide

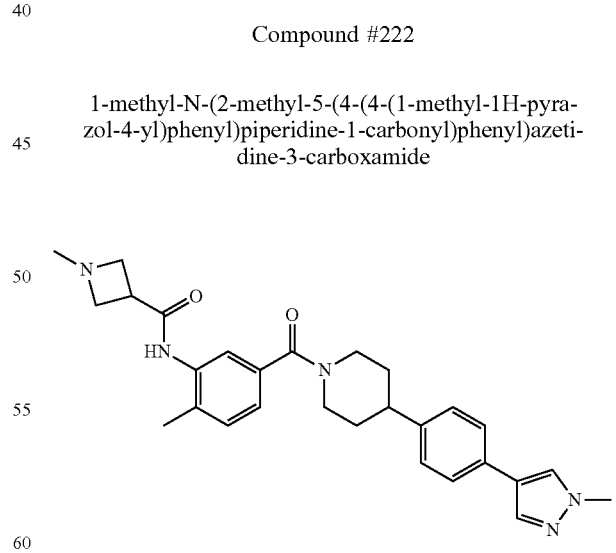

¹H NMR (300 MHz, DMSO-d₆) δ ppm 1.50-1.70 (m, 2H), 1.81 (br. s., 2H), 2.25 (br. s., 3H), 2.71-2.92 (m, 5H), 3.41 (br. s., 2H), 3.86 (br. s., 3H), 4.01 (br. s., 5H), 4.61 (br. s., 1H), 7.17 (d, J=7.0 Hz, 1H), 7.21-7.35 (m, 3H), 7.49 (d, J=7.6 Hz, 2H), 7.63 (br. s., 1H), 7.81 (s, 1H), 8.08 (s, 1H), 9.53 (br. s., 1H). MS m/z 472 (M+H)⁺

Example 208

Compound #219

1-(cyclopropanecarbonyl)-N-(2-methyl-5-(4-(4-(1-methyl-1H-pyrazol-4-yl)phenyl)piperidine-1-carbonyl)phenyl)azetidine-3-carboxamide

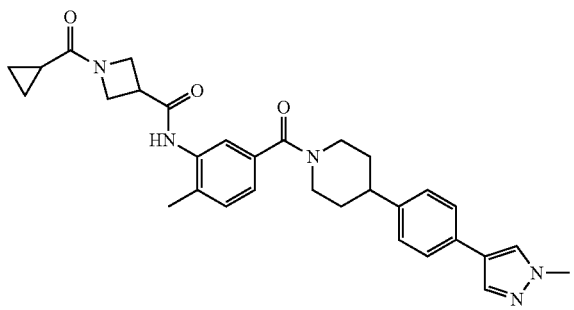 [SMILES: Cc1ccc(C(=O)N2CCC(c3ccc(-c4cnn(C)c4)cc3)CC2)cc1NC(=O)C1CN(C(=O)C2CC2)C1]

¹H NMR (300 MHz, DMSO-d₆) δ ppm 0.64-0.80 (m, 4H), 1.48-1.69 (m, 3H), 1.80 (br. s., 2H), 2.25 (s, 3H), 2.80 (t, J=11.6 Hz, 2H), 3.17 (br. s., 1H), 3.58-3.83 (m, 2H), 3.86 (s, 3H), 3.92-4.00 (m, 1H), 4.00-4.11 (m, 1H), 4.31-4.48 (m, 2H), 4.61 (br. s., 1H), 7.18 (d, J=7.4 Hz, 1H), 7.22-7.34 (m, 3H), 7.48 (d, J=8.0 Hz, 2H), 7.56 (s, 1H), 7.81 (s, 1H), 8.08 (s, 1H), 9.55 (s, 1H). MS m/z 526 (M+H)⁺

Example 209

Compound #218

1-hexyl-N-(2-methyl-5-(4-(4-(1-methyl-1H-pyrazol-4-yl)phenyl)piperidine-1-carbonyl)phenyl)pyrrolidine-3-carboxamide

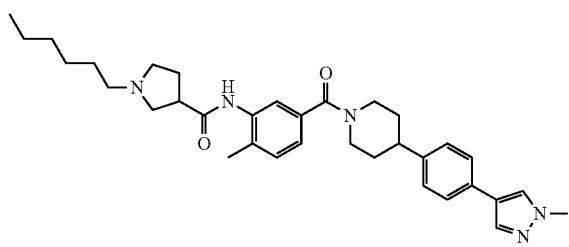 [SMILES: CCCCCCN1CCC(C(=O)Nc2cc(C(=O)N3CCC(c4ccc(-c5cnn(C)c5)cc4)CC3)ccc2C)C1]

MS m/z 556(M+H)⁺

Example 210

Compound #241

1-cyclobutyl-N-(2-methyl-5-(4-(4-(1-methyl-1H-pyrazol-4-yl)phenyl)piperidine-1-carbonyl)phenyl)pyrrolidine-3-carboxamide

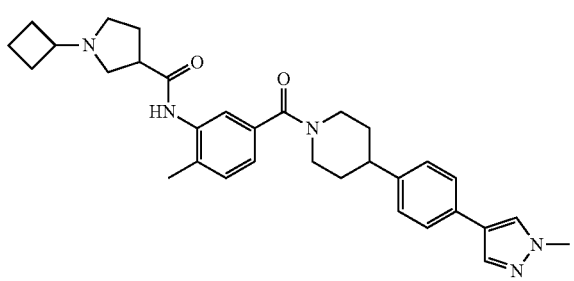 [SMILES: Cc1ccc(C(=O)N2CCC(c3ccc(-c4cnn(C)c4)cc3)CC2)cc1NC(=O)C1CCN(C2CCC2)C1]

¹H NMR (300 MHz, DMSO-d₆) δ ppm 1.51-1.78 (m, 5H), 1.95-2.14 (m, 5H), 2.25 (s, 3H), 2.61 (br. s., 2H), 2.73-2.89 (m, 3H), 3.11 (br. s., 3H), 3.23-3.56 (m, 3H), 3.78 (br. s., 1H), 3.86 (s, 3H), 4.61 (br. s., 1H), 7.14 (d, J=7.6 Hz, 1H), 7.20-7.34 (m, 3H), 7.48 (d, J=8.0 Hz, 2H), 7.61 (s, 1H), 7.81 (s, 1H), 8.08 (s, 1H), 9.52 (br. s., 1H). MS m/z 526 (M+H)⁺

Example 211

Compound #209

1-cyclobutyl-N-(2-methyl-5-(4-(4-(1-methyl-1H-pyrazol-4-yl)phenyl)piperidine-1-carbonyl)phenyl)piperidine-4-carboxamide

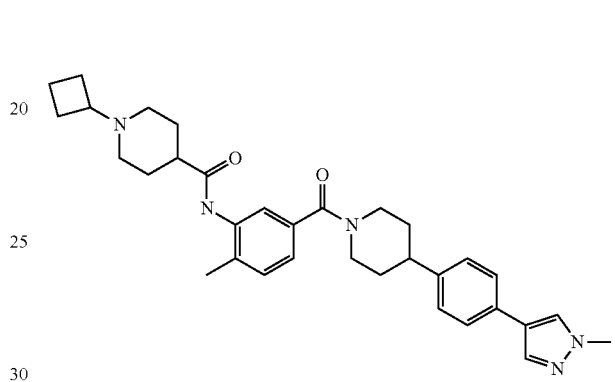

¹H NMR (300 MHz, DMSO-d₆) δ ppm 1.47-1.65 (m, 6H), 1.79 (br. s., 3H), 1.75 (br. s., 3H), 1.92 (br. s., 4H), 2.16 (s, 3H), 2.39 (br. s., 1H), 2.75 (d, J=11.3 Hz, 2H), 2.86 (d, J=10.3 Hz, 4H), 3.70 (br. s., 1H), 3.79 (s, 3H), 4.54 (br. s., 1H), 7.08 (d, J=7.6 Hz, 1H), 7.13-7.25 (m, 3H), 7.35-7.48 (m, 3H), 7.75 (s, 1H), 8.01 (s, 1H), 9.26 (s, 1H). MS m/z 540 (M+H)⁺

Example 212

Compound #211

1-butyl-N-(2-methyl-5-(4-(4-(1-methyl-1H-pyrazol-4-yl)phenyl)piperidine-1-carbonyl)phenyl)piperidine-4-carboxamide

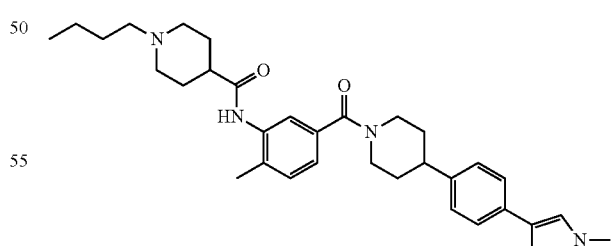

¹H NMR (300 MHz, DMSO-d₆) δ ppm 0.85-0.94 (m, 3H), 1.21-1.34 (m, 2H), 1.42 (br. s., 2H), 1.50-1.70 (m, 4H), 1.79 (d, J=10.2 Hz, 4H), 1.91 (br. s., 2H), 2.22 (s, 3H), 2.27 (d, J=6.9 Hz, 2H), 2.40 (br. s., 1H), 2.73-2.96 (m, 4H), 3.17 (br. s., 1H), 3.75 (br. s., 1H), 3.86 (s, 3H), 4.60 (br. s., 1H), 7.20-7.32 (m, 3H), 7.41-7.54 (m, 3H), 7.81 (s, 1H), 8.08 (s, 1H), 9.27 (s, 1H). MS m/z 542 (M+H)⁺

Example 213

Compound #212

1-butyl-N-(2-methyl-5-(4-(4-(1-methyl-1H-pyrazol-4-yl)phenyl)piperidine-1-carbonyl)phenyl)pyrrolidine-3-carboxamide

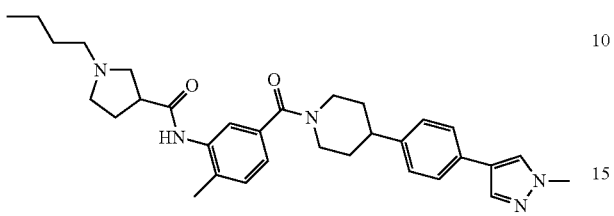

MS m/z 528 (M+H)$^+$

Example 214

Compound #240

1-cyclobutyl-N-(2-methyl-5-(4-(4-(1-methyl-1H-pyrazol-4-yl)phenyl)piperidine-1-carbonyl)phenyl)azetidine-3-carboxamide

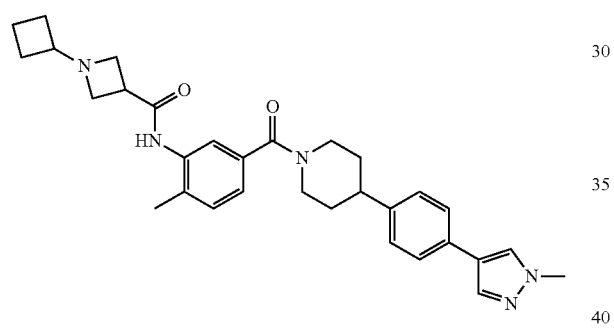

$^1$H NMR (300 MHz, DMSO-d$_6$) δ ppm 1.50-1.71 (m, 4H), 1.71-1.86 (m, 4H), 1.90 (br. s., 4H), 2.23 (s, 3H), 2.80 (t, J=11.9 Hz, 2H), 3.14 (br. s., 2H), 3.33 (d, J=15.9 Hz, 3H), 3.78 (br. s., 1H), 3.86 (s, 3H), 4.61 (br. s., 1H), 7.15 (d, J=7.6 Hz, 1H), 7.20-7.33 (m, 3H), 7.48 (d, J=7.8 Hz, 2H), 7.54 (br. s., 1H), 7.81 (s, 1H), 8.08 (s, 1H), 9.40 (br. s., 1H). MS m/z 512 (M+H)$^+$ Example 215

Compound #243

1-hexyl-N-(2-methyl-5-(4-(4-(1-methyl-1H-pyrazol-4-yl)phenyl)piperidine-1-carbonyl)phenyl)azetidine-3-carboxamide

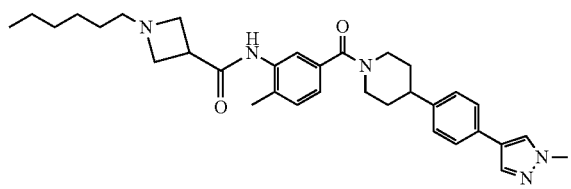 [SMILES: CCCCCCN1CC(C(=O)Nc2cc(C(=O)N3CCC(c4ccc(-c5cnn(C)c5)cc4)CC3)ccc2C)C1]

$^1$H NMR (300 MHz, DMSO-d$_6$) δ ppm 0.89 (t, J=6.5 Hz, 3H), 1.28 (br. s., 8H), 1.63 (d, J=10.9 Hz, 2H), 1.83 (br. s., 2H), 2.25 (s, 3H), 2.37 (br. s., 2H), 2.75-2.94 (m, 2H), 3.18 (br. s., 3H), 3.43 (br. s., 3H), 3.81 (br. s., 1H), 3.89 (s, 3H), 4.65 (br. s., 1H), 7.18 (d, J=7.7 Hz, 1H), 7.25-7.36 (m, 3H), 7.52 (d, J=8.2 Hz, 2H), 7.57 (s, 1H), 7.84 (s, 1H), 8.11 (s, 1H), 9.39 (s, 1H). MS m/z 542 (M+H)$^+$ Example 216

Compound #242

1-butyl-N-(2-methyl-5-(4-(4-(1-methyl-1H-pyrazol-4-yl)phenyl)piperidine-1-carbonyl)phenyl)azetidine-3-carboxamide

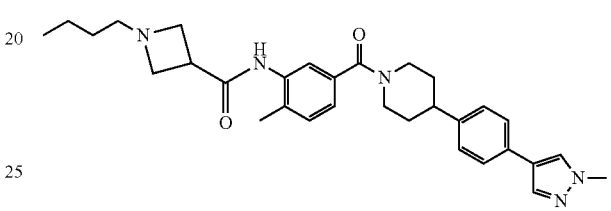

$^1$H NMR (300 MHz, DMSO-d$_6$) δ ppm 0.80 (t, J=6.7 Hz, 3H), 1.11-1.27 (m, 6H), 1.53 (d, J=10.4 Hz, 2H), 1.62-1.87 (m, 2H), 2.31 (br. s., 2H), 2.73 (t, J=11.8 Hz, 2H), 3.11 (br. s., 4H), 3.69 (br. s., 1H), 3.79 (s, 3H), 4.54 (br. s., 1H), 7.07 (s, 1H), 7.14-7.25 (m, 3H), 7.41 (d, J=8.0 Hz, 2H), 7.47 (s, 1H), 7.74 (s, 1H), 8.01 (s, 1H), 9.30 (s, 1H). MS m/z 514 (M+H)$^+$ Example 217

Compound #231

6-chloro-N-(2-methoxy-5-(4-(4-(1-methyl-1H-pyrazol-4-yl)phenyl)piperidine-1-carbonyl)phenyl)nicotinamide

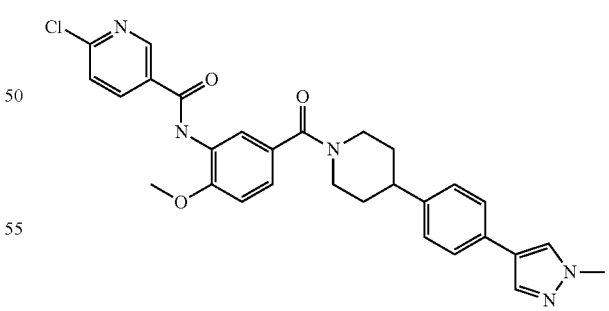

$^1$H NMR (300 MHz, DMSO-d$_6$) δ ppm 1.46-1.65 (m, 2H), 1.73 (br. s., 2H), 2.40-2.44 (m, 3H), 2.73 (t, J=11.8 Hz, 1H), 2.95 (br. s., 2H), 3.66 (br. s., 1H), 3.78 (s, 3H), 3.82 (s, 3H), 4.47 (br. s., 1H), 7.11 (d, J=8.5 Hz, 1H), 7.19 (m, J=8.2 Hz, 2H), 7.23-7.30 (m, 1H), 7.41 (m, J=8.2 Hz, 2H), 7.62 (d, J=8.4 Hz, 1H), 7.74 (s, 1H), 7.75-7.81 (m, 1H), 8.01 (s, 1H), 8.27 (dd, J=8.2, 2.5 Hz, 1H), 8.87 (d, J=2.2 Hz, 1H), 9.88 (s, 1H). MS m/z 530 (M+N)$^+$

Example 218

Compound #251

6-(isopropylamino)-N-(2-methoxy-5-(4-(4-(1-methyl-1H-pyrazol-4-yl)phenyl)piperidine-1-carbonyl)phenyl)nicotinamide

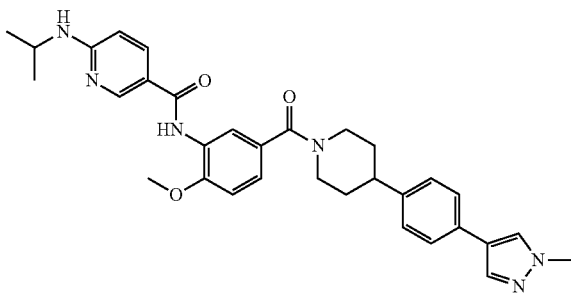 [SMILES: COc1ccc(C(=O)N2CCC(c3ccc(-c4cnn(C)c4)cc3)CC2)cc1NC(=O)c1ccc(NC(C)C)nc1]

$^1$H NMR (300 MHz, DMSO-d$_6$) δ ppm 1.17 (d, J=6.5 Hz, 6H), 1.49-1.72 (m, 2H), 1.80 (br. s., 2H), 2.08 (s, 1H), 2.51 (br. s., 5H), 2.81 (t, J=11.3 Hz, 1H), 3.00 (br. s., 2H), 3.86 (s, 3H), 3.90 (s, 3H), 4.01-4.17 (m, 1H), 4.53 (br. s., 1H), 6.49 (d, J=8.9 Hz, 1H), 7.14 (d, J=8.5 Hz, 1H), 7.08 (d, J=7.6 Hz, 1H), 7.26 (d, J=8.2 Hz, 3H), 7.49 (d, J=8.1 Hz, 2H), 7.81 (s, 1H), 7.88 (dd, J=8.8, 2.2 Hz, 1H), 7.92-7.99 (m, 1H), 8.08 (s, 1H), 8.63 (d, J=1.9 Hz, 1H), 9.16 (s, 1H). MS m/z 553 (M+H)$^+$

Example 219

Compound #130

N-(2-methyl-5-(4-(4-(1-methyl-1H-pyrazol-4-yl)phenyl)piperidine-1-carbonyl)phenyl)thiophene-2-carboxamide

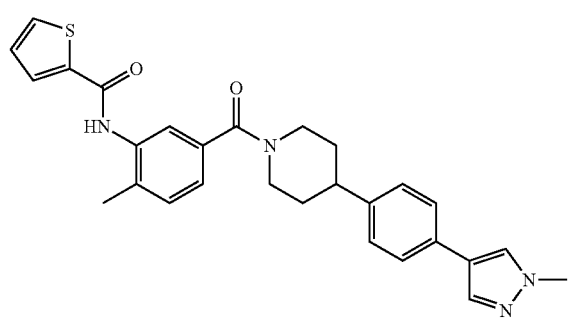 [SMILES: Cc1ccc(C(=O)N2CCC(c3ccc(-c4cnn(C)c4)cc3)CC2)cc1NC(=O)c1cccs1]

$^1$H NMR (300 MHz, DMSO-d$_6$) δ ppm 1.52-1.71 (m, 2H), 1.81 (br. s., 2H), 2.28 (s, 3H), 2.80 (t, J=11.8 Hz, 2H), 3.17 (br. s., 1H), 3.76 (br. s., 1H), 3.85 (s, 3H), 4.62 (br. s., 1H), 7.19-7.30 (m, 4H), 7.32-7.39 (m, 1H), 7.41 (s, 1H), 7.48 (d, J=8.2 Hz, 2H), 7.81 (s, 1H), 7.86 (d, J=4.3 Hz, 1H), 7.99 (d, J=3.2 Hz, 1H), 8.08 (s, 1H), 9.99 (s, 1H). MS m/z 485 (M+H)$^+$

Example 220

Compound #262

N-(2-(benzyloxy)-5-(4-(4-(1-methyl-1H-pyrazol-4-yl)phenyl)piperidine-1-carbonyl)phenyl)-6-chloronicotinamide

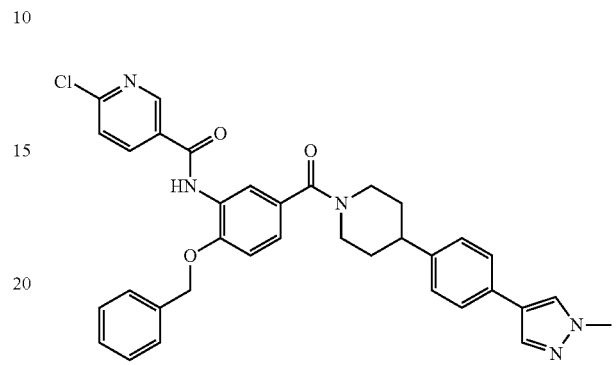

$^1$H NMR (300 MHz, DMSO-d$_6$) δ ppm 1.52-1.72 (m, 2H), 1.73-1.92 (m, 2H), 2.81 (t, J=11.6 Hz, 1H), 3.03 (br. s., 2H), 3.66 (br. s., 1H) 3.86 (s, 3H), 4.52 (br. s., 1H), 5.26 (s, 2H), 7.22-7.41 (m, 7H), 7.43-7.57 (m, 4H), 7.71 (d, J=8.2 Hz, 1H), 7.81 (s, 2H), 8.08 (s, 1H), 8.33 (dd, J=8.3, 2.4 Hz, 1H), 8.93 (d, J=2.2 Hz, 1H), 10.01 (s, 1H). MS m/z 606 (M+H)$^+$

Example 221

Compound #271

N-(2-(benzyloxy)-5-(4-(4-(1-methyl-1H-pyrazol-4-yl)phenyl)piperidine-1-carbonyl)phenyl)-6-(isopropylamino)nicotinamide

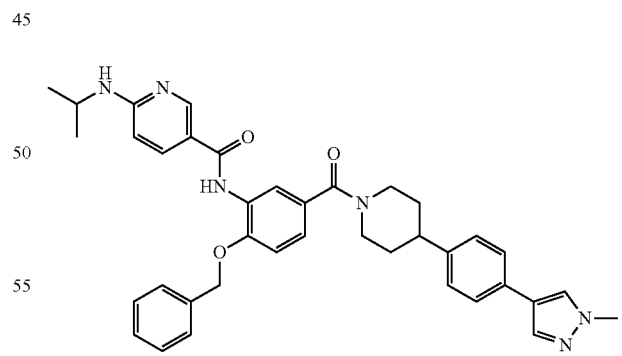

$^1$H NMR (300 MHz, DMSO-d$_6$) δ ppm 1.17 (d, J=6.5 Hz, 6H), 1.53-1.71 (m, 2H), 1.74-1.90 (m, 2H), 2.67-2.90 (m, 2H), 3.02 (br. s., 2H), 3.86 (s, 3H), 4.01-4.18 (m, 2H), 4.43 (br. s., 1H), 5.26 (s, 2H), 6.48 (d, J=8.9 Hz, 1H), 7.06 (d, J=7.6 Hz, 1H), 7.17-7.29 (m, 4H), 7.31-7.43 (m, 3H), 7.54 (d, J=7.1 Hz, 2H), 7.49 (d, J=8.1 Hz, 2H), 7.77-7.89 (m, 2H), 7.94 (s, 1H), 8.08 (s, 1H), 8.54-8.65 (m, 1H), 9.21 (s, 1H). MS m/z 629 (M+H)$^+$

Example 222

Compound #269

N-(2-hydroxy-5-(4-(4-(1-methyl-1H-pyrazol-4-yl)phenyl)piperidine-1-carbonyl)phenyl)-6-(isopropylamino)nicotinamide

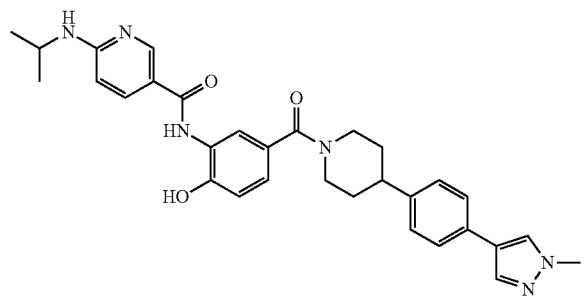 [SMILES: CC(C)Nc1ccc(C(=O)Nc2cc(C(=O)N3CCC(c4ccc(-c5cnn(C)c5)cc4)CC3)ccc2O)cn1]

$^{1}$H NMR (300 MHz, DMSO-d$_6$) δ ppm 1.17 (d, J=6.5 Hz, 6H), 1.54-1.69 (m, 2H), 1.82 (d, J=11.1 Hz, 2H), 2.09 (s, 3H), 2.80 (t, J=11.7 Hz, 1H), 3.01 (br. s., 2H), 3.86 (s, 3H), 4.03-4.16 (m, 1H), 4.25 (br. s., 1H), 6.49 (d, J=8.9 Hz, 1H), 6.94 (d, J=8.2 Hz, 1H), 7.05-7.16 (m, 2H), 7.26 (m, J=8.2 Hz, 2H), 7.49 (m, J=8.2 Hz, 2H), 7.81 (s, 1H), 7.84 (d, J=1.8 Hz, 1H), 7.89 (dd, J=8.9, 2.4 Hz, 1H), 8.08 (s, 1H), 8.64 (d, J=2.2 Hz, 1H), 9.34 (br. s., 1H). MS m/z 539 (M+H)$^+$

Example 223

Compound #150

N-(2-methyl-5-(4-(4-(1-methyl-1H-pyrazol-4-yl)phenyl)piperidine-1-carbonyl)phenyl)piperidine-4-carboxamide

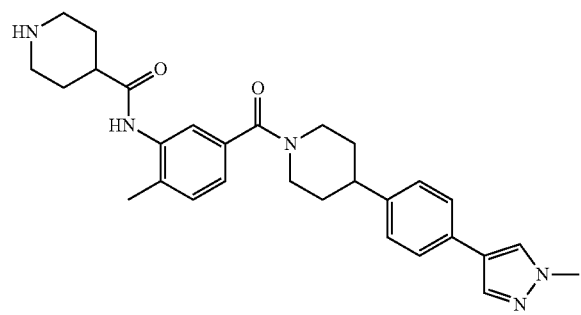 [SMILES: Cc1ccc(C(=O)N2CCC(c3ccc(-c4cnn(C)c4)cc3)CC2)cc1NC(=O)C1CCNCC1]

$^{1}$H NMR (300 MHz, DMSO-d$_6$) δ ppm 1.46-1.64 (m, 4H), 1.72 (br. s., 4H), 2.22 (s, 3H), 2.79 (br. s., 2H), 3.02 (d, J=12.0 Hz, 2H), 3.18 (br. s., 3H), 3.78 (br. s., 1H), 3.86 (s, 3H), 4.61 (br. s., 1H), 7.15 (d, J=7.7 Hz, 1H), 7.20-7.32 (m, 3H), 7.40-7.54 (m, 3H), 7.81 (s, 1H), 8.08 (s, 1H), 9.27 (s, 1H). MS m/z 486 (M+H)$^+$

Example 224

Compound #119

5-(dimethylamino)-N-(2-methyl-5-(4-(4-(1-methyl-1H-pyrazol-4-yl)phenyl)piperidine-1-carbonyl)phenyl)picolinamide

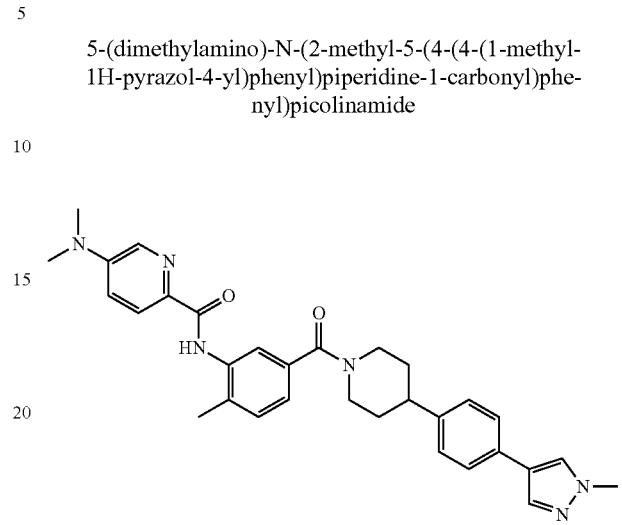

$^{1}$H NMR (300 MHz, DMSO-d$_6$) δ ppm 1.62 (d, J=11.4 Hz, 2H), 1.80 (br. s., 2H), 2.36 (s, 3H), 2.81 (br. s., 2H), 3.07 (s, 6H), 3.18 (br. s., 1H), 3.80 (br. s., 1H), 3.86 (s, 3H), 4.64 (br. s., 1H), 7.14 (dd, J=7.7, 1.5 Hz, 1H), 7.18-7.30 (m, 3H), 7.34 (d, J=8.0 Hz, 1H), 7.49 (d, J=8.1 Hz, 2H), 7.81 (s, 1H), 7.96 (d, J=8.8 Hz, 1H), 8.09 (s, 1H), 8.14 (d, J=1.4 Hz, 1H), 8.18 (d, J=2.9 Hz, 1H), 10.03 (s, 1H). MS m/z 523 (M+H)$^+$

Example 225

Compound #277

N-(2-(cyclopropanecarboxamido)-4-(4-(4-(1-methyl-1H-pyrazol-4-yl)phenyl)piperidine-1-carbonyl)phenyl)-N-methylcyclopropanecarboxamide

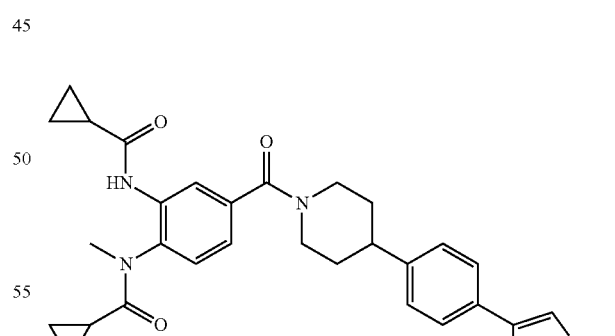

$^{1}$H NMR (300 MHz, DMSO-d$_6$) δ ppm 0.42-0.57 (m, 2H), 0.59-0.85 (m, 6H), 1.17 (br. s., 2H), 1.54 (d, J=12.5 Hz, 2H), 1.63-1.87 (m, 2H), 2.73 (t, J=11.4 Hz, 2H), 3.06 (s, 4H), 3.68 (br. s., 1H), 3.79 (s, 3H), 4.54 (br. s., 1H), 7.19 (d, J=7.8 Hz, 3H), 7.35 (d, J=8.0 Hz, 1H), 7.42 (d, J=7.8 Hz, 2H), 7.74 (s, 1H), 7.89 (s, 1H), 8.01 (s, 1H), 9.70 (s, 1H). MS m/z 526 (M+H)$^+$

Example 226

Compound #278

N-(2-((2-methoxyethyl)(methyl)amino)-5-(4-(4-(1-methyl-1H-pyrazol-4-yl)phenyl)piperidine-1-carbonyl)phenyl)cyclopropanecarboxamide

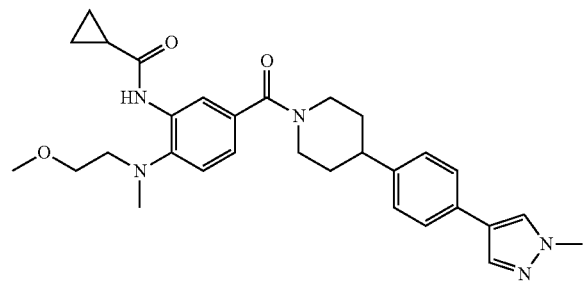

$^1$H NMR (300 MHz, DMSO-d$_6$) δ ppm 0.83 (d, J=6.0 Hz, 4H), 1.58 (d, J=10.3 Hz, 2H), 1.71-1.90 (m, 3H), 2.75 (s, 3H), 2.79 (br. s., 1H), 2.95 (t, J=4.7 Hz, 3H), 3.36 (s, 3H), 3.51-3.60 (m, 3H), 3.86 (s, 4H), 4.56 (br. s., 1H), 7.06-7.15 (m, 1H), 7.20-7.32 (m, 3H), 7.49 (d, J=8.0 Hz, 2H), 7.81 (s, 1H), 8.08 (s, 1H), 8.25 (s, 1H), 9.45 (s, 1H). MS m/z 516 (M+H)$^+$

Example 227

Compound #274

6-chloro-N-(2-(isopropyl(methyl)amino)-5-(4-(4-(1-methyl-1H-pyrazol-4-yl)phenyl)piperidine-1-carbonyl)phenyl)nicotinamide

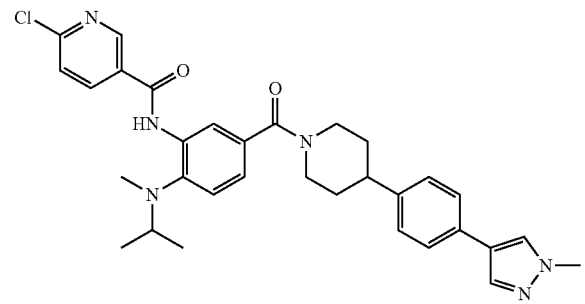 [SMILES: CC(C)N(C)c1ccc(C(=O)N2CCC(c3ccc(-c4cnn(C)c4)cc3)CC2)cc1NC(=O)c1ccc(Cl)nc1]

$^1$H NMR (300 MHz, DMSO-d$_6$) δ ppm 0.95-1.08 (m, 6H), 1.50-1.73 (m, 2H), 1.83 (d, J=11.0 Hz, 2H), 2.62 (s, 3H), 2.81 (t, J=11.7 Hz, 1H), 3.05 (br. s., 2H), 3.24-3.31 (m, 1H), 3.86 (br. s., 4H), 4.50 (br. s., 1H), 7.18-7.33 (m, 4H), 7.49 (d, J=8.0 Hz, 2H), 7.73 (d, J=8.4 Hz, 1H), 7.81 (s, 1H), 7.94 (s, 1H), 8.08 (s, 1H), 8.37 (dd, J=8.3, 2.1 Hz, 1H), 8.90-9.04 (m, 1H), 9.85 (s, 1H). MS m/z 571 (M+H)$^+$

Example 228

Compound #285

N-(2-amino-5-(4-(4-(1-methyl-1H-pyrazol-4-yl)phenyl)piperidine-1-carbonyl)phenyl)-6-(isopropylamino)nicotinamide

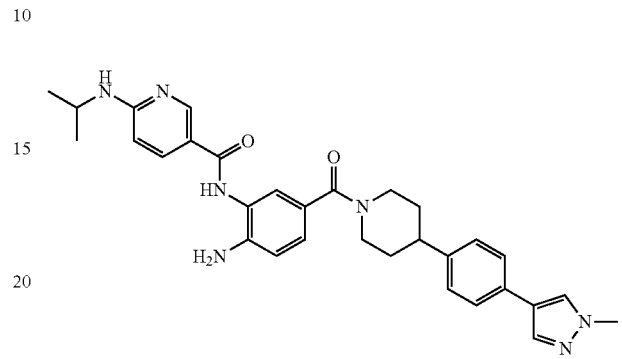

$^1$H NMR (300 MHz, DMSO-d$_6$) δ ppm 1.18 (d, J=6.3 Hz, 6H), 1.47-1.71 (m, 2H), 1.81 (d, J=12.1 Hz, 2H), 2.70-2.88 (m, 1H), 2.99 (t, J=12.9 Hz, 2H), 3.19 (br. s., 1H), 3.86 (s, 3H), 4.00-4.17 (m, 1H), 4.30 (br. s., 1H), 5.30 (br. s., 2H), 6.48 (d, J=8.9 Hz, 1H), 6.79 (d, J=8.2 Hz, 1H), 7.01 (br. s., 1H), 7.12 (s, 1H), 7.18-7.35 (m, 3H), 7.47 (br. s., 2H), 7.81 (s, 1H), 8.08 (s, 1H), 8.65 (s, 1H), 9.36 (s, 1H). MS m/z 538 (M+H)$^+$

Example 229

Compound #275

6-chloro-N-(2-(dimethylamino)-5-(4-(4-(1-methyl-1H-pyrazol-4-yl)phenyl)piperidine-1-carbonyl)phenyl)nicotinamide

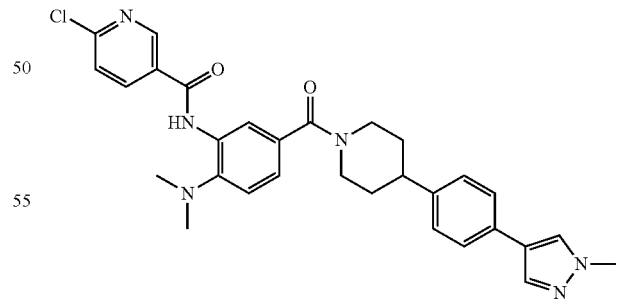

$^1$H NMR (300 MHz, DMSO-d$_6$) δ ppm 1.52-1.72 (m, 2H), 1.73-1.91 (m, 2H), 2.73 (s, 6H), 2.77 (br. s., 1H), 3.04 (br. s., 2H), 3.29 (br. s., 1H), 3.86 (s, 3H), 4.28 (br. s., 1H), 7.14-7.22 (m, 1H), 7.22-7.33 (m, 3H), 7.49 (d, J=8.0 Hz, 2H), 7.71 (d, J=8.4 Hz, 1H), 7.81 (s, 2H), 8.08 (s, 1H), 8.36 (dd, J=8.2, 2.3 Hz, 1H), 8.96 (d, J=2.1 Hz, 1H), 9.95 (s, 1H). MS m/z 543 (M+H)$^+$

Example 230

Compound #276

N-(2-(isopropyl(methyl)amino)-5-(4-(4-(1-methyl-1H-pyrazol-4-yl)phenyl)piperidine-1-carbonyl)phenyl)-6-(isopropylamino)nicotinamide

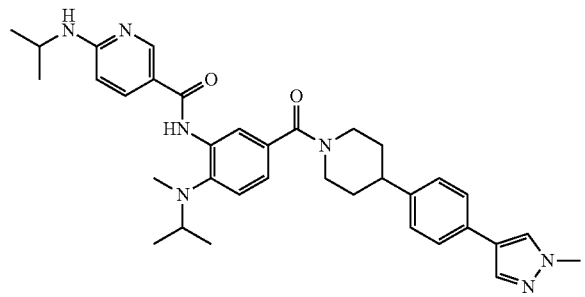 [SMILES: CC(C)Nc1ccc(C(=O)Nc2cc(C(=O)N3CCC(c4ccc(-c5cnn(C)c5)cc4)CC3)ccc2N(C)C(C)C)cn1]

$^1$H NMR (300 MHz, DMSO-d$_6$) δ ppm 1.06 (d, J=6.3 Hz, 6H), 1.18 (d, J=6.3 Hz, 6H), 1.50-1.72 (m, 2H), 1.72-1.95 (m, 2H), 2.63 (s, 3H), 2.71-2.86 (m, 1H), 3.00 (br. s., 2H), 3.23 (d, J=6.6 Hz, 1H), 3.81-3.93 (m, 3H), 3.98-4.20 (m, 2H), 4.61 (br. s., 1H), 6.52 (d, J=8.9 Hz, 1H), 7.08-7.22 (m, 2H), 7.22-7.34 (m, 3H), 7.49 (d, J=8.0 Hz, 2H), 7.76-7.92 (m, 2H), 8.08 (s, 1H), 8.54-8.69 (m, 1H), 9.34 (s, 1H). MS m/z 594 (M+H)$^+$

Example 231

Compound #283

N-(2-(cyclopropylamino)-5-(4-(4-(1-methyl-1H-pyrazol-4-yl)phenyl)piperidine-1-carbonyl)phenyl)-6-(isopropylamino)nicotinamide

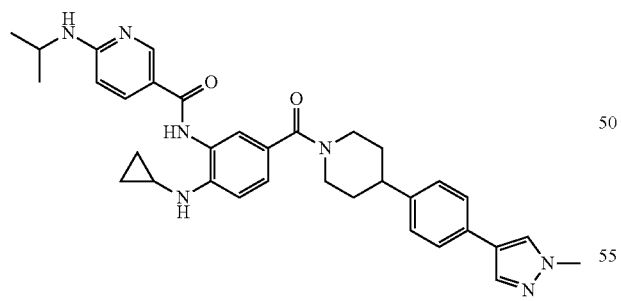

$^1$H NMR (300 MHz, DMSO-d$_6$) δ ppm 0.46 (br. s., 2H), 0.75 (d, J=5.4 Hz, 2H), 1.17 (d, J=6.3 Hz, 6H), 1.50-1.71 (m, 2H), 1.81 (d, J=12.9 Hz, 2H), 2.42 (br. s., 1H), 2.70-2.87 (m, 1H), 3.01 (br. s., 2H), 3.86 (s, 3H), 4.01-4.17 (m, 1H), 4.30 (br. s., 2H), 5.90 (s, 1H), 6.47 (d, J=8.9 Hz, 1H), 7.07 (d, J=8.4 Hz, 1H), 7.00 (d, J=7.6 Hz, 1H), 7.18-7.37 (m, 4H), 7.48 (d, J=7.8 Hz, 2H), 7.81 (s, 1H), 7.88 (d, J=9.6 Hz, 1H), 8.08 (s, 1H), 8.56-8.71 (m, 1H), 9.26 (s, 1H). MS m/z 578 (M+H)$^+$

Example 232

Compound #284

6-(isopropylamino)-N-(2-(isopropylamino)-5-(4-(4-(1-methyl-1H-pyrazol-4-yl)phenyl)piperidine-1-carbonyl)phenyl)nicotinamide

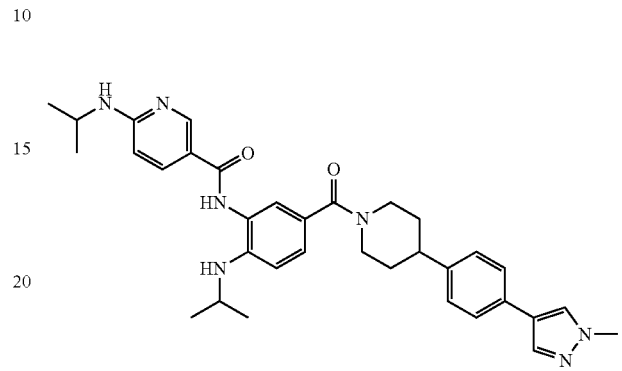

$^1$H NMR (300 MHz, DMSO-d$_6$) δ ppm 1.08-1.23 (m, 12H), 1.49-1.70 (m, 2H), 1.81 (d, J=11.3 Hz, 2H), 2.72-2.86 (m, 1H), 2.89-3.10 (m, 2H), 3.58-3.76 (m, 1H), 3.86 (s, 3H), 4.02-4.16 (m, 1H), 4.30 (br. s., 2H), 5.00 (d, J=7.3 Hz, 1H), 6.49 (d, J=8.9 Hz, 1H), 6.73 (d, J=8.5 Hz, 1H), 7.02 (d, J=7.7 Hz, 1H), 7.18-7.34 (m, 4H), 7.48 (d, J=8.0 Hz, 2H), 7.81 (s, 1H), 7.87 (br. s., 1H), 8.08 (s, 1H), 8.57-8.73 (m, 1H), 9.32 (br. s., 1H). MS m/z 580 (M+H)$^+$

Example 233

Compound #280

N-(2-(dimethylamino)-5-(4-(4-(1-methyl-1H-pyrazol-4-yl)phenyl)piperidine-1-carbonyl)phenyl)-6-(isopropylamino)nicotinamide

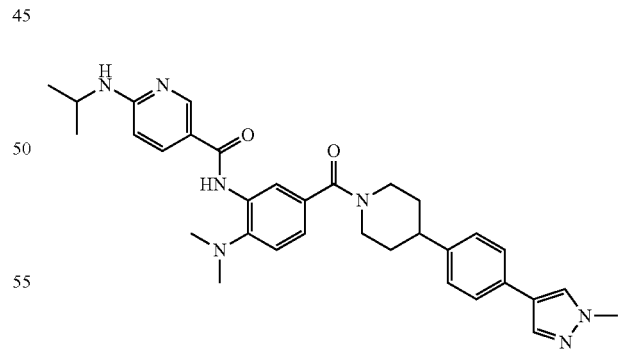

$^1$H NMR (300 MHz, DMSO-d$_6$) δ ppm 1.07 (d, J=6.5 Hz, 6H), 1.37-1.60 (m, 2H), 1.61-1.81 (m, 2H), 2.60 (s, 6H), 2.64-2.76 (m, 1H), 2.90 (br. s., 2H), 3.17 (br. s., 1H), 3.75 (s, 3H), 3.91-4.07 (m, 1H), 4.38 (br. s., 1H), 6.41 (d, J=8.8 Hz, 1H), 7.00 (d, J=7.7 Hz, 1H), 7.05-7.20 (m, 4H), 7.38 (d, J=8.1 Hz, 1H), 7.71 (s, 1H), 7.77 (dd, J=8.8, 2.2 Hz, 1H), 7.89 (s, 1H), 7.97 (s, 1H), 8.45-8.60 (m, 1H), 9.18 (s, 1H). MS m/z 566 (M+H)$^+$

Example 234

Compound #281

6-(isopropylamino)-N-(2((2-methoxyethyl)(methyl)amino)-5-(4-(4-(1-methyl-1H-pyrazol-4-yl)phenyl)piperidine-1-carbonyl)phenyl)nicotinamide

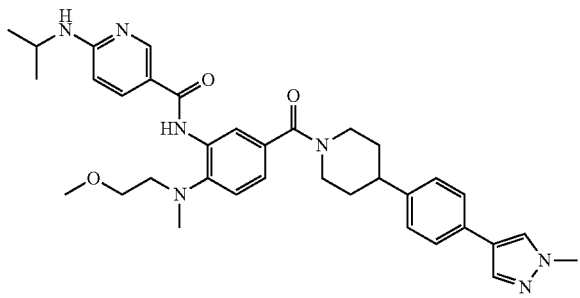 [SMILES: COCCN(C)c1ccc(C(=O)N2CCC(c3ccc(-c4cnn(C)c4)cc3)CC2)cc1NC(=O)c1ccc(NC(C)C)nc1]

¹H NMR (300 MHz, DMSO-d₆) δ ppm 1.18 (d, J=6.5 Hz, 6H), 1.50-1.71 (m, 2H), 1.82 (br. s., 2H), 2.74 (s, 3H), 2.81 (dd, J=12.7, 12.2 Hz, 1H), 2.96 (t, J=4.9 Hz, 3H), 3.16 (s, 4H), 3.43 (t, J=4.7 Hz, 2H), 3.86 (s, 4H), 4.02-4.18 (m, 1H), 4.60 (br. s., 1H), 6.52 (d, J=8.9 Hz, 1H), 7.06-7.19 (m, 2H), 7.26 (m, J=8.1 Hz, 2H), 7.36 (d, J=8.1 Hz, 1H), 7.49 (m, J=8.0 Hz, 2H), 7.74-7.90 (m, 2H), 8.08 (s, 1H), 8.30-8.41 (m, 1H), 8.60 (d, J=2.1 Hz, 1H), 9.58 (s, 1H). MS m/z 610 (M+H)⁺

Example 235

Compound #286

N-(2-((2-methoxyethyl)amino)-5-(4-(4-(1-methyl-1H-pyrazol-4-yl)phenyl)piperidine-1-carbonyl)phenyl)cyclopropanecarboxamide

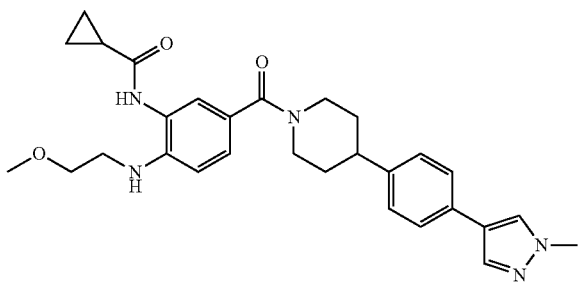

MS m/z 502 (M+H)⁺

Example 236

Compound #282

6-(isopropylamino)-N-(2-((2-methoxyethyl)amino)-5-(4-(4-(1-methyl-1H-Pyrazol-4-yl)phenyl)piperidine-1-carbonyl)phenyl)nicotinamide

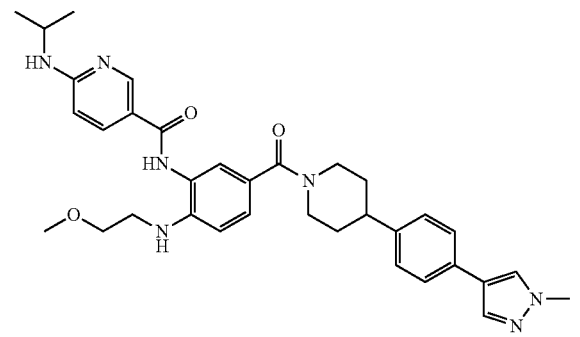 [SMILES: COCCNc1ccc(C(=O)N2CCC(c3ccc(-c4cnn(C)c4)cc3)CC2)cc1NC(=O)c1ccc(NC(C)C)nc1]

¹H NMR (300 MHz, DMSO-d₆) δ ppm 1.18 (d, J=6.5 Hz, 6H), 1.59 (q, J=12.1 Hz, 2H), 1.81 (d, J=11.0 Hz, 2H), 2.70-2.86 (m, 1H), 2.90-3.12 (m, 2H), 3.26-3.32 (m, 5H), 3.48-3.56 (m, 2H), 3.86 (s, 3H), 4.02-4.16 (m, 1H), 4.17-4.44 (m, 2H), 5.40 (t, J=5.6 Hz, 1H), 6.48 (d, J=8.8 Hz, 1H), 6.75 (d, J=8.4 Hz, 1H), 7.01 (d, J=7.6 Hz, 1H), 7.17-7.32 (m, 4H), 7.48 (d, J=8.1 Hz, 2H), 7.81 (s, 1H), 7.84-7.94 (m, 1H), 8.08 (s, 1H), 8.58-8.74 (m, 1H), 9.39 (s, 1H). MS m/z 596 (M+H)⁺

Example 237

Compound #288

N-(2-(cyclopropyl(methyl)amino)-5-(4-(4-(1-methyl-1H-pyrazol-4-yl)phenyl)piperidine-1-carbonyl)phenyl)cyclopropanecarboxamide

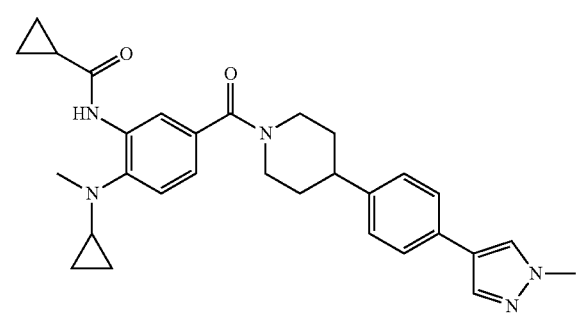 [SMILES: CN(c1ccc(C(=O)N2CCC(c3ccc(-c4cnn(C)c4)cc3)CC2)cc1NC(=O)C1CC1)C1CC1]

MS m/z 598 (M+H)⁺

Example 238

Compound #287

N-(2-(cyclopropyl(methyl)amino)-5-(4-(4-(1-methyl-1H-pyrazol-4-yl)phenyl)piperidine-1-carbonyl)phenyl)-6-(isopropylamino)nicotinamide

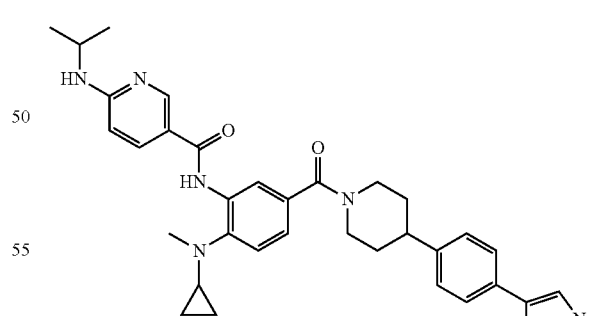

¹H NMR (300 MHz, DMSO-d₆) δ ppm 0.21 (br. s., 2H), 0.31-0.44 (m, 2H), 0.94 (d, J=6.5 Hz, 6H), 1.38 (q, J=12.7 Hz, 2H), 1.59 (d, J=12.8 Hz, 2H), 2.36 (br. s., 1H), 2.50 (s, 3H), 2.62 (br. s., 1H), 2.78 (br. s., 2H), 3.00 (br. s., 1H), 3.62 (s, 3H), 3.80-3.93 (m, 1H), 4.29 (br. s., 1H), 6.27 (d, J=8.8 Hz, 1H), 6.87 (d, J=7.7 Hz, 1H), 6.96 (dd, J=8.1, 1.6 Hz, 1H), 7.03 (m, J=8.1 Hz, 2H), 7.19 (d, J=8.2 Hz, 1H), 7.25

(m, J=8.0 Hz, 2H), 7.52-7.62 (m, 2H), 7.73-7.80 (m, 1H), 7.84 (s, 1H), 8.32 (d, J=2.1 Hz, 1H), 8.83 (s, 1H). MS m/z 592 (M+H)$^+$

Example 239

Compound #227

1-methyl-N-(2-methyl-5-(4-(4-(1-methyl-1H-pyrazol-4-yl)phenyl)piperidine-1-carbonyl)phenyl)-1H-imidazole-2-carboxamide

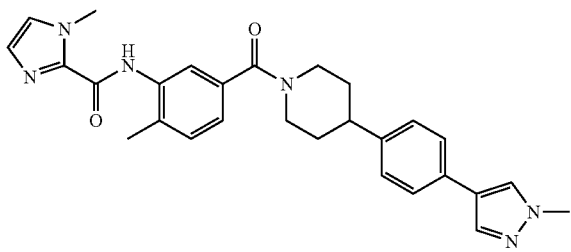 [SMILES: Cc1ccc(C(=O)N2CCC(c3ccc(-c4cnn(C)c4)cc3)CC2)cc1NC(=O)c1nccn1C]

$^1$H NMR (300 MHz, DMSO-d$_6$) δ ppm 1.53-1.71 (m, 2H), 1.71-1.93 (m, 2H), 2.32 (s, 3H), 2.97 (br. s., 1H), 3.18 (br. s., 2H), 3.69-3.84 (m, 1H), 3.86 (s, 3H), 4.00 (s, 3H), 4.62 (br. s., 1H), 7.10 (s, 1H), 7.16-7.22 (m, 1H), 7.26 (d, J=8.1 Hz, 2H), 7.34 (d, J=7.8 Hz, 1H), 7.42-7.51 (m, 3H), 7.72-7.78 (m, 1H), 7.81 (s, 1H), 8.08 (s, 1H), 9.85 (s, 1H). MS m/z 583 (M+H)$^+$

Example 240

Compound #151

N-(2-methyl-5-(4-(4-(1-methyl-1H-pyrazol-4-yl)phenyl)piperidine-1-carbonyl)phenyl)tetrahydrofuran-2-carboxamide

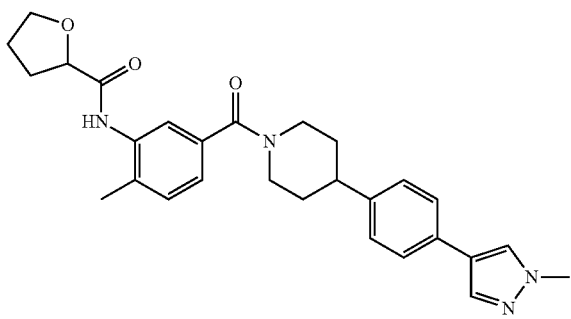 [SMILES: Cc1ccc(C(=O)N2CCC(c3ccc(-c4cnn(C)c4)cc3)CC2)cc1NC(=O)C1CCCO1]

$^1$H NMR (300 MHz, DMSO-d$_6$) δ ppm 1.32-1.51 (m, 2H), 1.70 (dt, J=13.7, 6.8 Hz, 4H), 1.76-1.94 (m, 2H), 1.96-2.13 (m, 4H), 2.50-2.78 (m, 2H), 2.79-3.08 (m, 1H), 3.60-3.73 (m, 4H), 3.77-3.90 (m, 1H), 4.26 (dd, J=8.2, 5.3 Hz, 1H), 4.42 (br. s., 1H), 6.99 (d, J=7.6 Hz, 1H), 7.12 (d, J=7.7 Hz, 1H), 7.07 (d, J=8.0 Hz, 2H), 7.30 (d, J=8.0 Hz, 2H), 7.38 (s, 1H), 7.63 (s, 1H), 7.90 (s, 1H), 9.05 (s, 1H). MS m/z 473 (M+H)$^+$

Example 241

Compound #149

3-methyl-N-(2-methyl-5-(4-(4-(1-methyl-1H-pyrazol-4-yl)phenyl)piperidine-1-carbonyl)phenyl)thiophene-2-carboxamide

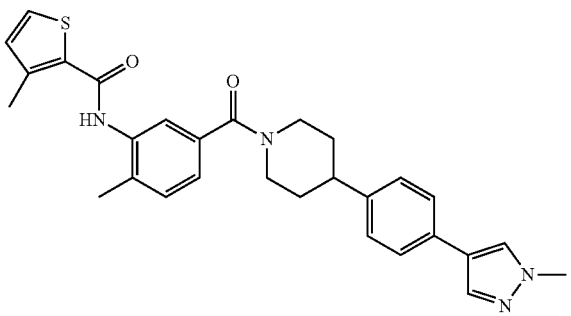 [SMILES: Cc1ccc(C(=O)N2CCC(c3ccc(-c4cnn(C)c4)cc3)CC2)cc1NC(=O)c1sccc1C]

$^1$H NMR (300 MHz, DMSO-d$_6$) δ ppm 1.52-1.71 (m, 2H), 1.81 (br. s., 2H), 2.28 (s, 3H), 2.71-2.98 (m, 2H), 3.17 (br. s., 1H), 3.33 (s, 3H), 3.79 (br. s., 1H), 3.85 (s, 3H), 4.62 (br. s., 1H), 7.04 (d, J=4.9 Hz, 1H), 7.20-7.29 (m, 3H), 7.29-7.39 (m, 1H), 7.48 (d, J=8.2 Hz, 3H), 7.68 (d, J=5.1 Hz, 1H), 7.81 (s, 1H), 8.08 (s, 1H), 9.53 (s, 1H). MS m/z 499 (M+H)$^+$

Example 242

Compound #124

1-benzyl-N-(2-methyl-5-(4-(4-(1-methyl-1H-pyrazol-4-yl)phenyl)piperidine-1-carbonyl)phenyl)piperidine-4-carboxamide

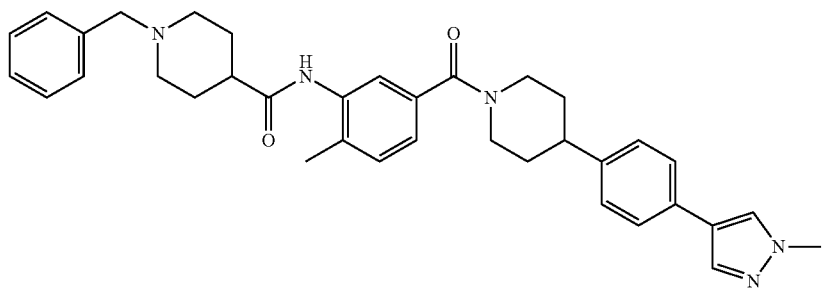 [SMILES: Cc1ccc(C(=O)N2CCC(c3ccc(-c4cnn(C)c4)cc3)CC2)cc1NC(=O)C1CCN(Cc2ccccc2)CC1]

$^1$H NMR (300 MHz, DMSO-d$_6$) δ ppm 1.50-1.68 (m, 2H), 1.82 (br. s., 2H), 1.90-2.08 (m, 4H), 2.23 (s, 3H), 2.71-2.86 (m, 2H), 2.89-3.03 (m, 2H), 3.20 (d, J=18.0 Hz, 2H), 3.40 (d, J=13.7 Hz, 2H), 3.74 (br. s., 1H), 3.85 (s, 3H), 4.31 (br. s., 2H), 4.61 (br. s., 1H), 7.16 (d, J=7.4 Hz, 1H), 7.22-7.31 (m, 2H), 7.41-7.50 (m, 6H), 7.60 (br. s., 2H), 7.81 (s, 1H), 8.08 (s, 1H), 9.45-9.64 (m, 1H), 10.31 (br. s., 1H). MS m/z 576 (M+H)$^+$ Example 243

Compound #156

N-(2-methyl-5-(4-(4-(1-methyl-1H-pyrazol-4-yl)phenyl)piperidine-1-carbonyl)phenyl)isobutyramide

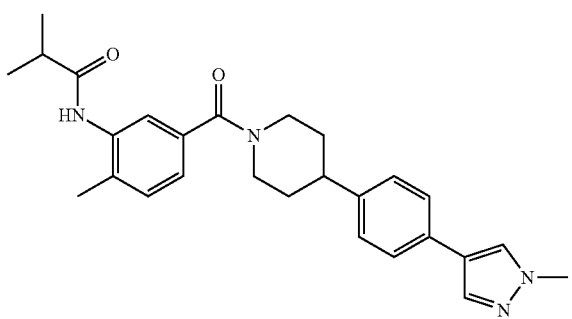 [SMILES: Cc1ccc(C(=O)N2CCC(c3ccc(-c4cnn(C)c4)cc3)CC2)cc1NC(=O)C(C)C]

$^1$H NMR (300 MHz, DMSO-d$_6$) δ ppm 0.89-0.98 (m, 6H), 1.40 (d, J=13.7 Hz, 2H), 1.60 (br. s., 2H), 2.04 (s, 3H), 2.54 (br. s., 1H), 2.57-2.78 (m, 1H), 2.93 (br. s., 1H), 3.54 (br. s., 2H), 3.66 (s, 3H), 4.41 (br. s., 1H), 6.90-6.99 (m, 1H), 7.03-7.12 (m, 3H), 7.24-7.33 (m, 3H), 7.62 (s, 1H), 7.89 (s, 1H), 9.08 (s, 1H). MS m/z 545 (M+H)$^+$ Example 244

Compound #157

5-methyl-N-(2-methyl-5-(4-(4-(1-methyl-1H-pyrazol-4-yl)phenyl)piperidine-1-carbonyl)phenyl)thiophene-2-carboxamide

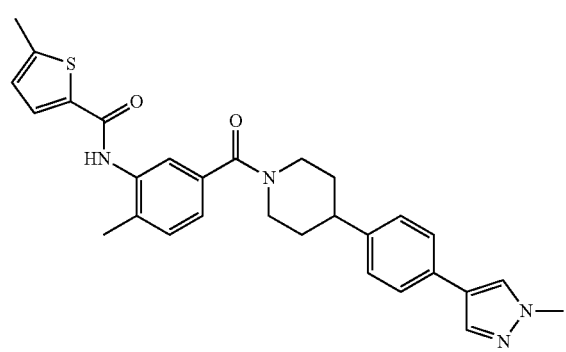 [SMILES: Cc1ccc(C(=O)Nc2cc(C(=O)N3CCC(c4ccc(-c5cnn(C)c5)cc4)CC3)ccc2C)s1]

$^1$H NMR (300 MHz, DMSO-d$_6$) δ ppm 1.52-1.70 (m, 2H), 1.80 (br. s., 2H), 2.27 (s, 3H), 2.53 (s, 3H), 2.80 (t, J=11.7 Hz, 2H), 3.17 (br. s., 1H), 3.80 (br. s., 1H), 3.85 (s, 3H), 4.62 (br. s., 1H), 6.93 (dd, J=3.6, 0.9 Hz, 1H), 7.19-7.29 (m, 3H), 7.31-7.38 (m, 1H), 7.38-7.42 (m, 1H), 7.48 (d, J=8.1 Hz, 2H), 7.74-7.84 (m, 2H), 8.08 (s, 1H), 9.84 (s, 1H). MS m/z 499 (M+H)$^+$ Example 245

Compound #99

3-chloro-N-(2-methyl-5-(4-(4-(1-methyl-1H-pyrazol-4-yl)phenyl)piperidine-1-carbonyl)phenyl)thiophene-2-carboxamide

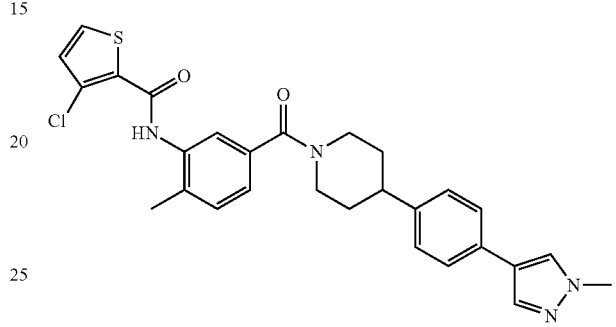

$^1$H NMR (300 MHz, CHLOROFORM-d) δ ppm 1.66 (br. s., 2H), 1.80 (br. s., 1H), 1.88 (br. s., 1H), 2.35 (s, 3H), 2.71 (br. s., 1H), 2.80 (br. s., 1H), 3.11 (d, J=8.1 Hz, 1H), 3.87 (s, 3H), 3.96 (br. s., 1H), 4.80 (br. s., 1H), 6.99 (d, J=5.4 Hz, 1H), 7.13-7.17 (m, 2H), 7.20-7.28 (m, 2H), 7.30-7.41 (m, 2H), 7.49 (d, J=5.4 Hz, 1H), 7.51 (s, 1H), 7.67 (s, 1H), 8.16-8.23 (m, 1H), 8.63 (s, 1H). MS m/z 519 (M+H)$^+$ Example 246

Compound #198

N-(2-methyl-5-(4-(4-(1-methyl-1H-pyrazol-4-yl)phenyl)piperidine-1-carbonyl)phenyl)thiazole-2-carboxamide

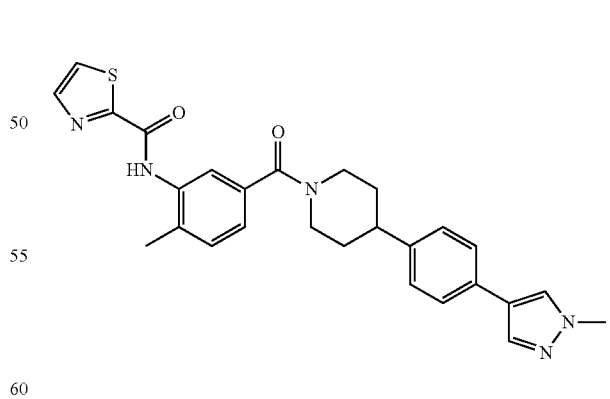

$^1$H NMR (300 MHz, CHLOROFORM-d) δ ppm 1.71 (br. s., 2H), 1.84-2.03 (m, 2H), 2.45 (s, 3H), 2.74-3.00 (m, 2H), 3.07-3.37 (m, 1H), 3.96 (s, 3H), 4.06 (d, J=11.4 Hz, 1H), 4.90 (br. s., 1H), 7.22-7.34 (m, 4H), 7.43 (s, 1H), 7.46 (s, 1H), 7.61 (s, 1H), 7.68 (d, J=3.0 Hz, 1H), 7.76 (s, 1H), 7.96 (d, J=3.2 Hz, 1H), 8.28-8.35 (m, 1H), 9.19 (s, 1H). MS m/z 486 (M+H)$^+$

Example 247

Compound #174

N-(2-methyl-5-(4-(4-(1-methyl-1H-pyrazol-4-yl)phenyl)piperidine-1-carbonyl)phenyl)thiazole-5-carboxamide

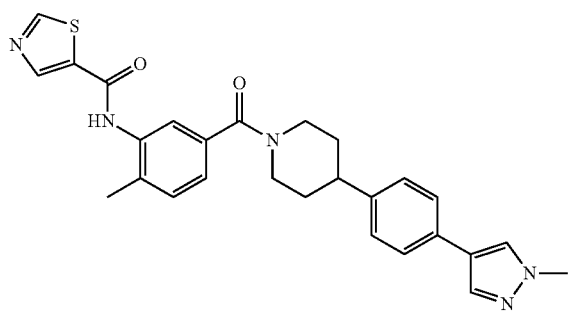 [SMILES: Cc1ccc(C(=O)N2CCC(c3ccc(-c4cnn(C)c4)cc3)CC2)cc1NC(=O)c1cncs1]

$^1$H NMR (300 MHz, DMSO-d$_6$) δ ppm 1.54-1.70 (m, 2H), 1.80 (br. s., 2H), 2.29 (s, 3H), 2.71-2.98 (m, 2H), 3.18 (br. s., 1H), 3.73-3.91 (m, 4H), 4.62 (br. s., 1H), 7.26 (d, J=8.0 Hz, 3H), 7.34-7.43 (m, 2H), 7.48 (d, J=8.0 Hz, 2H), 7.81 (s, 1H), 8.08 (s, 1H), 8.68 (s, 1H), 9.32 (s, 1H), 10.23 (s, 1H). MS m/z 486 (M+H)$^+$

Example 248

Compound #13

(1S,3R)—N-(2-methyl-5-(4-(4-(1-methyl-1H-pyrazol-5-yl)phenyl)piperidine-1-carbonyl)phenyl)-3-propionamidocyclopentanecarboxamide

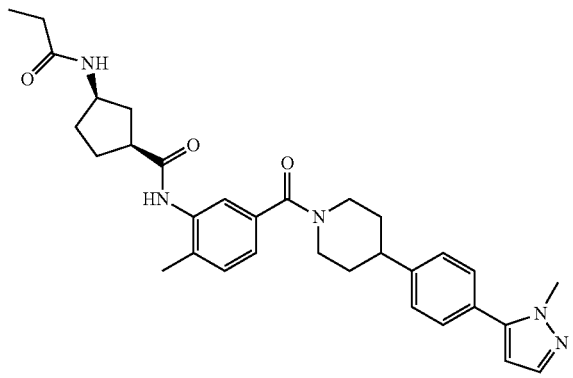 [SMILES: CCC(=O)N[C@@H]1CC[C@H](C(=O)Nc2cc(C(=O)N3CCC(c4ccc(-c5ccnn5C)cc4)CC3)ccc2C)C1]

$^1$H NMR (300 MHz, DMSO-d$_6$) δ ppm 0.97 (t, J=7.6 Hz, 3H), 1.43-1.72 (m, 4H), 1.74-1.96 (m, 5H), 2.04 (q, J=7.6 Hz, 2H), 2.11-2.20 (m, 1H), 2.23 (s, 3H), 2.78-3.02 (m, 3H), 3.03-3.27 (m, 1H), 3.79 (br. s., 1H), 3.85 (s, 3H), 4.00-4.16 (m, 1H), 4.63 (br. s., 1H), 6.37 (d, J=1.9 Hz, 1H), 7.16 (dd, J=7.8, 1.3 Hz, 1H), 7.29 (d, J=8.0 Hz, 1H), 7.36-7.43 (m, 2H), 7.43-7.52 (m, 4H), 7.82 (d, J=7.4 Hz, 1H), 9.36 (s, 1H). MS m/z 542 (M+H)$^+$

Example 249

Compound #63

N-(2-chloro-5-(3-(4-(quinolin-4-yl)phenyl)azetidine-1-carbonyl)phenyl)-6-(isopropylamino)nicotinamide

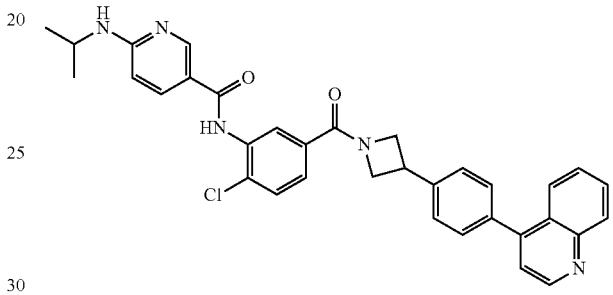

MS m/z 576 (M+H)$^+$

Example 250

Compound #65

N-(2-chloro-5-(3-(4-(1-methyl-1H-pyrazol-4-yl)phenyl)azetidine-1-carbonyl)phenyl)-6-(isopropylamino)nicotinamide

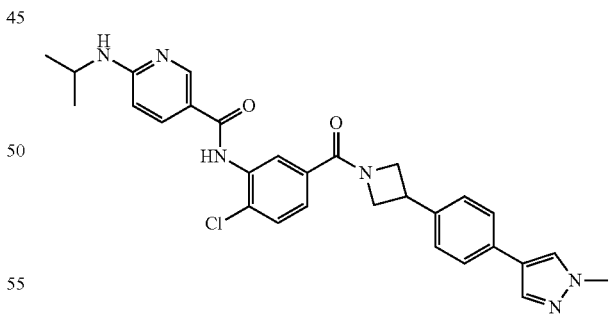

$^1$H NMR (300 MHz, DMSO-d$_6$) δ ppm 1.17 (d, J=6.5 Hz, 6H), 3.86 (s, 3H), 3.90-4.01 (m, 1H), 4.01-4.18 (m, 2H), 4.38 (t, J=7.1 Hz, 1H), 4.49 (t, J=9.3 Hz, 1H), 4.71 (t, J=8.7 Hz, 1H), 6.50 (d, J=8.9 Hz, 1H), 7.11 (d, J=7.6 Hz, 1H), 7.40 (d, J=8.1 Hz, 2H), 7.56 (d, J=8.2 Hz, 3H), 7.60-7.67 (m, 1H), 7.85 (s, 1H), 7.90 (dd, J=8.9, 2.3 Hz, 1H), 7.96 (d, J=1.8 Hz, 1H), 8.13 (s, 1H), 8.67 (d, J=2.2 Hz, 1H), 9.74 (s, 1H). MS m/z 529 (M+H)$^+$

Example 251

Compound #64

(1R,3S)—N-(2-methyl-5-(3-(4-(1-methyl-1H-pyrazol-5-yl)phenyl)azetidine-1-carbonyl)phenyl)-3-propionamidocyclopentanecarboxamide

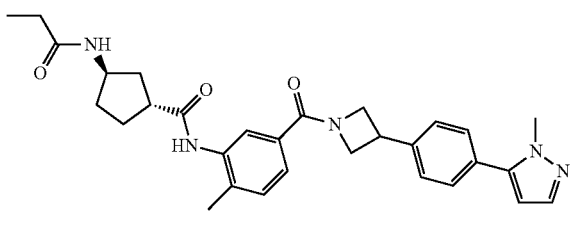 [SMILES: CCC(=O)N[C@@H]1CC[C@@H](C(=O)Nc2cc(C(=O)N3CC(c4ccc(-c5ccnn5C)cc4)C3)ccc2C)C1]

$^1$H NMR (300 MHz, DMSO-d$_6$) δ ppm 0.81 (t, J=7.6 Hz, 3H), 1.26-1.54 (m, 2H), 1.62-1.78 (m, 3H), 1.88 (q, J=7.6 Hz, 2H), 1.95-2.07 (m, 1H), 2.09 (s, 3H), 2.69-2.87 (m, 1H), 3.70 (s, 3H), 3.77-4.01 (m, 3H), 4.20 (t, J=6.5 Hz, 1H), 4.34 (t, J=8.9 Hz, 1H), 4.56 (t, J=8.3 Hz, 1H), 6.24 (d, J=1.8 Hz, 1H), 7.14 (d, J=8.0 Hz, 1H), 7.26 (dd, J=7.8, 1.4 Hz, 1H), 7.31 (d, J=1.9 Hz, 1H), 7.34-7.42 (m, 4H), 7.59-7.63 (m, 1H), 7.67 (d, J=7.3 Hz, 1H), 9.21 (s, 1H). MS m/z 514 (M+H)$^+$

Example 252

Compound #72

N-(2-chloro-5-(4-(4-(pyridin-4-yl)phenyl)piperidine-1-carbonyl)phenyl)-6-(isopropylamino)nicotinamide

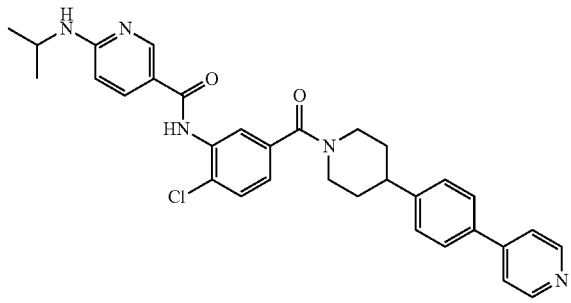 [SMILES: CC(C)Nc1ccc(C(=O)Nc2cc(C(=O)N3CCC(c4ccc(-c5ccncc5)cc4)CC3)ccc2Cl)cn1]

$^1$H NMR (300 MHz, DMSO-d$_6$) δ ppm 1.17 (d, J=6.5 Hz, 6H), 1.56-1.82 (m, 3H), 1.89 (br. s., 1H), 2.91 (t, J=11.5 Hz, 2H), 3.22 (br. s., 1H), 3.74 (br. s., 1H), 4.00-4.19 (m, 1H), 4.64 (br. s., 1H), 6.50 (d, J=8.9 Hz, 1H), 7.13 (d, J=7.7 Hz, 1H), 7.34 (dd, J=8.2, 1.9 Hz, 1H), 7.45 (d, J=8.2 Hz, 2H), 7.62 (d, J=8.2 Hz, 1H), 7.65-7.79 (m, 5H), 7.90 (dd, J=8.9, 2.4 Hz, 1H), 8.62 (d, J=5.6 Hz, 2H), 8.67 (d, J=2.3 Hz, 1H), 9.75 (s, 1H). MS m/z 554 (M+H)$^+$

Example 253

Compound #71

N-(2-chloro-5-(4-(4-(pyridin-3-yl)phenyl)piperidine-1-carbonyl)phenyl)-6-(isopropylamino)nicotinamide

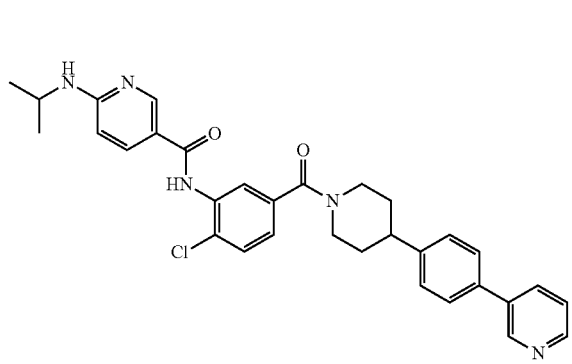 [SMILES: CC(C)Nc1ccc(C(=O)Nc2cc(C(=O)N3CCC(c4ccc(-c5cccnc5)cc4)CC3)ccc2Cl)cn1]

$^1$H NMR (300 MHz, DMSO-d$_6$) δ ppm 1.17 (d, J=6.5 Hz, 6H), 1.56-1.81 (m, 3H), 1.88 (br. s., 1H), 2.90 (t, J=11.6 Hz, 2H), 3.07-3.31 (m, 1H), 3.75 (br. s., 1H), 4.00-4.20 (m, 1H), 4.64 (br. s., 1H), 6.50 (d, J=8.8 Hz, 1H), 7.12 (d, J=7.6 Hz, 1H), 7.34 (dd, J=8.2, 1.9 Hz, 1H), 7.39-7.51 (m, 3H), 7.67 (d, J=8.1 Hz, 2H), 7.62 (d, J=8.2 Hz, 1H), 7.72 (d, J=1.9 Hz, 1H), 7.90 (dd, J=8.9, 2.4 Hz, 1H), 8.05 (dt, J=8.0, 1.8 Hz, 1H), 8.56 (dd, J=4.7, 1.4 Hz, 1H), 8.67 (d, J=2.3 Hz, 1H), 8.88 (d, J=1.9 Hz, 1H), 9.76 (s, 1H). MS m/z 554 (M+H)$^+$

Example 254

Compound #70

N-(2-chloro-5-(4-(4-(1-methyl-1H-pyrazol-5-yl)phenyl)piperidine-1-carbonyl)phenyl)-6-(isopropylamino)nicotinamide

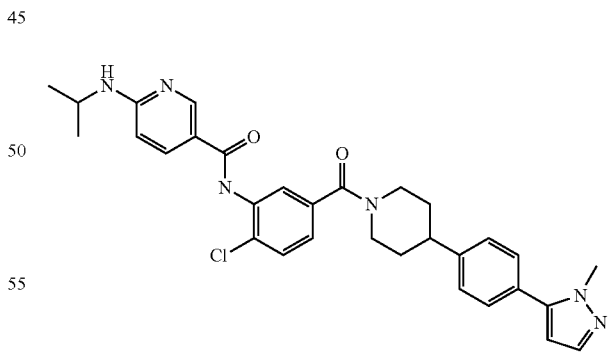

$^1$H NMR (300 MHz, DMSO-d$_6$) δ ppm 1.17 (d, J=6.6 Hz, 6H), 1.70 (dd, J=14.0, 11.9 Hz, 3H), 1.88 (br. s., 1H), 2.90 (t, J=11.9 Hz, 2H), 3.09-3.30 (m, 1H), 3.73 (br. s., 1H), 4.00-4.19 (m, 1H), 4.64 (br. s., 1H), 6.37 (d, J=1.8 Hz, 1H), 6.50 (d, J=8.9 Hz, 1H), 7.12 (d, J=7.6 Hz, 1H), 7.34 (dd, J=8.2, 1.9 Hz, 1H), 7.38-7.51 (m, 5H), 7.62 (d, J=8.2 Hz, 1H), 7.71 (d, J=1.9 Hz, 1H), 7.89 (dd, J=8.9, 2.4 Hz, 1H), 8.67 (d, J=2.3 Hz, 1H), 9.75 (s, 1H). MS m/z 557 (M+H)$^+$

Example 255

Compound #69

N-(2-chloro-5-(4-(4-(1-methyl-1H-pyrazol-4-yl)phenyl)piperidine-1-carbonyl)phenyl)-6-(isopropylamino)nicotinamide

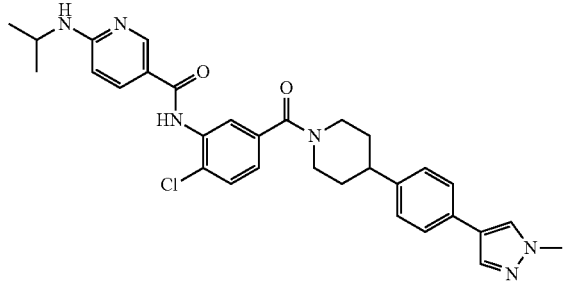 [SMILES: CC(C)Nc1ccc(C(=O)Nc2cc(C(=O)N3CCC(c4ccc(-c5cnn(C)c5)cc4)CC3)ccc2Cl)cn1]

¹H NMR (300 MHz, DMSO-d₆) δ ppm 1.17 (d, J=6.5 Hz, 6H), 1.53-1.77 (m, 3H), 1.84 (br. s., 1H), 2.70-2.99 (m, 2H), 3.05-3.29 (m, 1H), 3.70 (br. s., 1H), 3.99-4.20 (m, 1H), 4.62 (br. s., 1H), 6.50 (d, J=8.9 Hz, 1H), 7.12 (d, J=7.6 Hz, 1H), 7.26 (m, J=8.2 Hz, 2H), 7.33 (dd, J=8.2, 2.0 Hz, 1H), 7.48 (m, J=8.1 Hz, 2H), 7.62 (d, J=8.2 Hz, 1H), 7.71 (d, J=1.9 Hz, 1H), 7.81 (s, 1H), 7.90 (dd, J=8.9, 2.4 Hz, 1H), 8.08 (s, 1H), 8.67 (d, J=2.3 Hz, 1H), 9.75 (s, 1H). MS m/z 557 (M+H)⁺

Example 256

Compound #68

N-(2-chloro-5-(4-(4-(quinolin-4-yl)phenyl)piperidine-1-carbonyl)phenyl)-6-(isopropylamino)nicotinamide

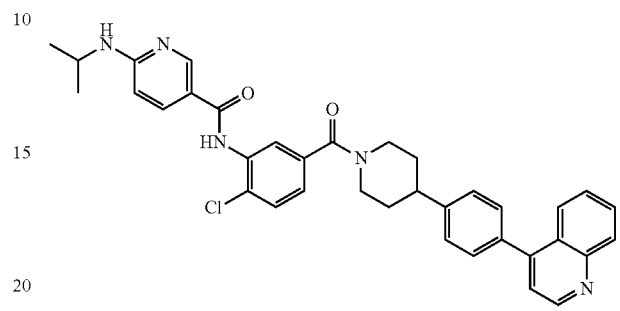

¹H NMR (300 MHz, DMSO-d₆) δ ppm 1.17 (d, J=6.5 Hz, 6H), 1.60-1.87 (m, 3H), 1.97 (d, J=15.3 Hz, 1H), 2.81-3.06 (m, 2H), 3.25 (br. s., 1H), 3.77 (br. s., 1H), 3.99-4.22 (m, 1H), 4.67 (br. s., 1H), 6.50 (d, J=8.9 Hz, 1H), 7.12 (d, J=7.6 Hz, 1H), 7.35 (dd, J=8.2, 2.0 Hz, 1H), 7.47 (d, J=4.5 Hz, 1H), 7.52 (s, 4H), 7.56-7.66 (m, 2H), 7.73 (d, J=1.9 Hz, 1H), 7.80 (t, J=7.1 Hz, 1H), 7.86-7.95 (m, 2H), 8.11 (d, J=8.4 Hz, 1H), 8.67 (d, J=2.3 Hz, 1H), 8.94 (d, J=4.4 Hz, 1H), 9.76 (s, 1H). MS m/z 604 (M+H)⁺

Example 257

Compound #67

N-(2-chloro-5-(4-(4-(isoquinolin-6-yl)phenyl)piperidine-1-carbonyl)phenyl)-6-(isopropylamino)nicotinamide

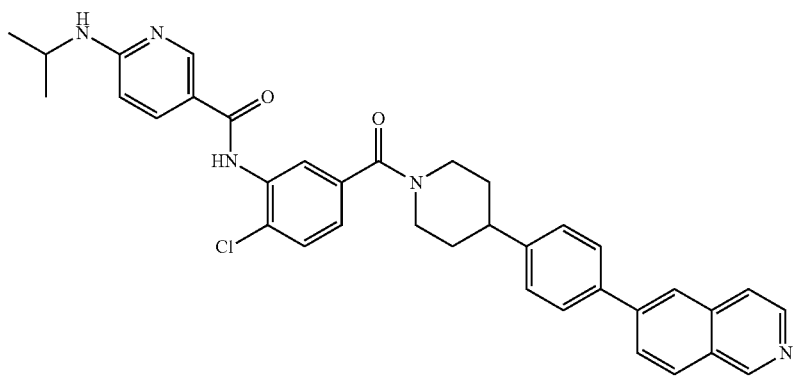 [SMILES: CC(C)Nc1ccc(C(=O)Nc2cc(C(=O)N3CCC(c4ccc(-c5ccc6cnccc6c5)cc4)CC3)ccc2Cl)cn1]

¹H NMR (300 MHz, DMSO-d₆) δ ppm 1.17 (d, J=6.5 Hz, 6H), 1.61-2.01 (m, 4H), 2.92 (t, J=11.5 Hz, 2H), 3.12-3.31 (m, 1H), 3.76 (br. s., 1H), 4.00-4.22 (m, 1H), 4.65 (br. s., 1H), 6.50 (d, J=8.9 Hz, 1H), 7.13 (d, J=7.6 Hz, 1H), 7.35 (dd, J=8.2, 2.0 Hz, 1H), 7.47 (m, J=8.2 Hz, 2H), 7.63 (d, J=8.1 Hz, 1H), 7.73 (d, J=1.9 Hz, 1H), 7.81 (m, J=8.4 Hz, 2H), 7.85-7.94 (m, 2H), 8.02 (dd, J=8.7, 1.6 Hz, 1H), 8.20 (d, J=8.7 Hz, 1H), 8.25 (s, 1H), 8.52 (d, J=5.6 Hz, 1H), 8.67 (d, J=2.3 Hz, 1H), 9.33 (s, 1H), 9.76 (s, 1H). MS m/z 604 (M+H)⁺

Example 258

Compound #108

N-(2-chloro-5-(3-(4-(1-methyl-1H-pyrazol-5-yl)phenyl)azetidine-1-carbonyl)phenyl)-6-(isopropylamino)nicotinamide

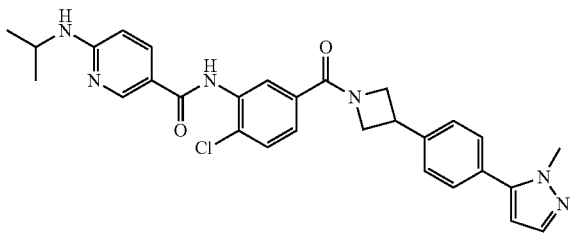 [SMILES: CC(C)Nc1ccc(C(=O)Nc2cc(C(=O)N3CC(c4ccc(-c5ccnn5C)cc4)C3)ccc2Cl)cn1]

¹H NMR (300 MHz, DMSO-d₆) δ ppm 1.17 (d, J=6.5 Hz, 6H), 3.86 (s, 3H), 3.96-4.18 (m, 3H), 4.35-4.47 (m, 1H), 4.53 (t, J=9.0 Hz, 1H), 4.75 (t, J=8.5 Hz, 1H), 6.40 (d, J=1.6 Hz, 1H), 6.50 (d, J=8.8 Hz, 1H), 7.12 (d, J=7.6 Hz, 1H), 7.47 (d, J=1.8 Hz, 1H), 7.48-7.60 (m, 5H), 7.60-7.68 (m, 1H), 7.90 (dd, J=8.8, 2.2 Hz, 1H), 7.97 (d, J=1.6 Hz, 1H), 8.67 (d, J=2.2 Hz, 1H), 9.75 (s, 1H). MS m/z 529 (M+H)⁺

Example 259

Compound #74

N-(2-chloro-5-(3-(4-(pyridin-4-yl)phenyl)azetidine-1-carbonyl)phenyl)-6-(isopropylamino)nicotinamide

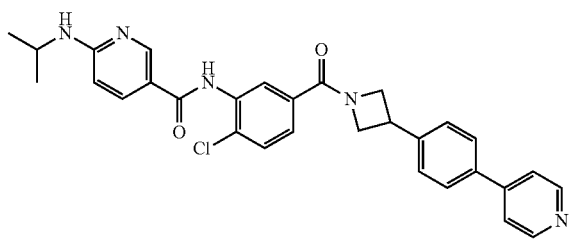 [SMILES: CC(C)Nc1ccc(C(=O)Nc2cc(C(=O)N3CC(c4ccc(-c5ccncc5)cc4)C3)ccc2Cl)cn1]

¹H NMR (300 MHz, DMSO-d₆) δ ppm 1.17 (d, J=6.5 Hz, 6H), 3.96-4.19 (m, 3H), 4.45 (br. s., 1H), 4.47-4.60 (m, 1H), 4.75 (t, J=8.4 Hz, 1H), 6.50 (d, J=8.8 Hz, 1H), 7.12 (d, J=7.6 Hz, 1H), 7.52-7.67 (m, 4H), 7.72 (d, J=6.0 Hz, 2H), 7.83 (d, J=8.2 Hz, 2H), 7.90 (dd, J=8.9, 2.4 Hz, 1H), 7.97 (d, J=1.9 Hz, 1H), 8.52-8.73 (m, 3H), 9.75 (s, 1H). MS m/z 526 (M+H)⁺

Example 260

Compound #73

N-(2-chloro-5-(3-(4-(pyridin-3-yl)phenyl)azetidine-1-carbonyl)phenyl)-6-(isopropylamino)nicotinamide

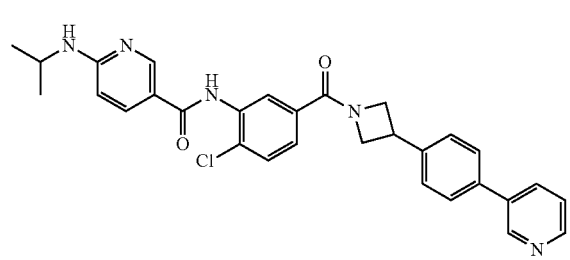 [SMILES: CC(C)Nc1ccc(C(=O)Nc2cc(C(=O)N3CC(c4ccc(-c5cccnc5)cc4)C3)ccc2Cl)cn1]

¹H NMR (300 MHz, DMSO-d₆) δ ppm 1.17 (d, J=6.3 Hz, 6H), 3.93-4.20 (m, 3H), 4.42 (t, J=7.4 Hz, 1H), 4.53 (t, J=9.1 Hz, 1H), 4.64-4.85 (m, 1H), 6.50 (d, J=8.9 Hz, 1H), 7.12 (d, J=7.6 Hz, 1H), 7.49 (dd, J=7.8, 4.8 Hz, 1H), 7.53-7.60 (m, 3H), 7.60-7.67 (m, 1H), 7.75 (d, J=8.2 Hz, 2H), 7.90 (dd, J=8.9, 2.4 Hz, 1H), 7.97 (d, J=1.8 Hz, 1H), 8.09 (dt, J=8.0, 1.9 Hz, 1H), 8.57 (dd, J=4.7, 1.4 Hz, 1H), 8.67 (d, J=2.2 Hz, 1H), 8.90 (d, J=2.1 Hz, 1H), 9.75 (s, 1H). MS m/z 526 (M+H)⁺

Example 261

Compound #86

N-(2-methyl-5-(4-(4-(1-methyl-1H-pyrazol-4-yl)phenyl)piperidine-1-carbonyl)phenyl)cyclohexanecarboxamide

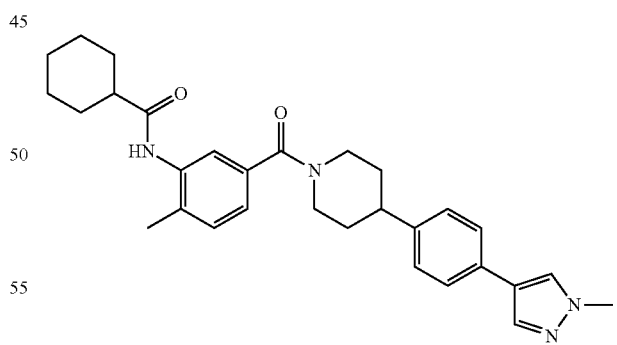

¹H NMR (300 MHz, DMSO-d₆) δ ppm 1.16-1.50 (m, 5H), 1.51-1.71 (m, 3H), 1.74 (br. s., 2H), 1.81 (br. s., 4H), 2.18-2.25 (m, 3H), 2.42 (d, J=3.2 Hz, 1H), 2.66-2.92 (m, 2H), 3.17 (br. s., 1H), 3.75 (br. s., 1H), 3.86 (s, 3H), 4.63 (br. s., 1H), 7.14 (dd, J=7.7, 1.5 Hz, 1H), 7.21-7.33 (m, 3H), 7.42-7.53 (m, 3H), 7.81 (s, 1H), 8.08 (s, 1H), 9.22 (s, 1H). MS m/z 485 (M+H)⁺

Example 262

Compound #87

N-(2-methyl-5-(4-(4-(1-methyl-1H-pyrazol-4-yl)phenyl)piperidine-1-carbonyl)phenyl)pivalamide

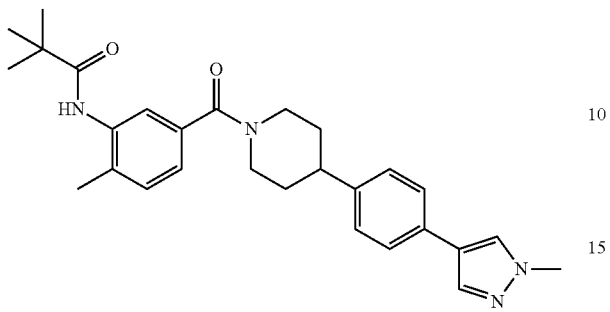

$^1$H NMR (300 MHz, DMSO-d$_6$) δ ppm 1.49-1.69 (m, 2H), 1.80 (br. s., 2H), 2.19 (s, 3H), 2.80 (t, J=12.0 Hz, 2H), 3.14 (br. s., 1H), 3.77 (br. s., 1H), 3.85 (s, 3H), 4.61 (br. s., 1H), 7.15-7.22 (m, 1H), 7.22-7.33 (m, 4H), 7.47 (s, 1H), 7.50 (s, 1H), 7.81 (s, 1H), 8.08 (s, 1H), 8.96 (s, 1H). MS m/z 459 (M+H)$^+$

Example 263

Compound #88

N-(2-methyl-5-(4-(4-(1-methyl-1H-pyrazol-4-yl)phenyl)piperidine-1-carbonyl)phenyl)cyclopentanecarboxamide

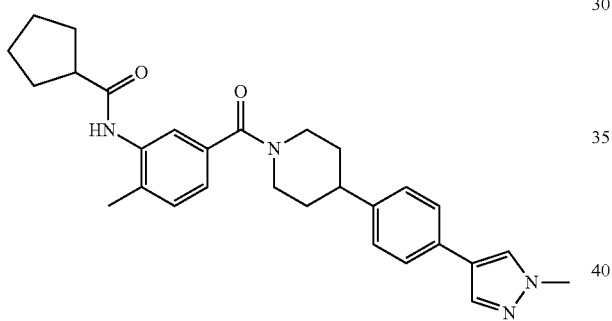

$^1$H NMR (300 MHz, DMSO-d$_6$) δ ppm 1.51-1.91 (m, 12H), 2.23 (s, 3H), 2.72-2.98 (m, 3H), 3.00-3.28 (m, 1H), 3.76 (br. s., 1H), 3.85 (s, 3H), 4.61 (br. s., 1H), 7.14 (dd, J=7.8, 1.4 Hz, 1H), 7.20-7.31 (m, 3H), 7.41-7.53 (m, 3H), 7.81 (s, 1H), 8.08 (s, 1H), 9.29 (s, 1H). MS m/z 471 (M+H)$^+$

Example 264

Compound #104

N-(2-methyl-5-(4-(4-(1-methyl-1H-pyrazol-4-yl)phenyl)piperidine-1-carbonyl)phenyl)tetrahydro-2H-pyran-4-carboxamide

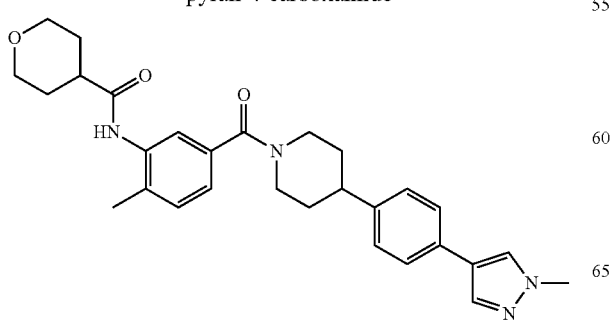

$^1$H NMR (300 MHz, DMSO-d$_6$) δ ppm 1.52-1.86 (m, 8H), 2.23 (s, 3H), 2.62-2.96 (m, 3H), 3.13 (br. s., 1H), 3.33 (d, J=3.2 Hz, 2H), 3.79 (br. s., 1H), 3.85 (s, 3H), 3.91 (dd, J=8.1, 2.9 Hz, 2H), 4.45-4.78 (m, 1H), 7.15 (dd, J=7.8, 1.4 Hz, 1H), 7.20-7.32 (m, 3H), 7.42-7.53 (m, 3H), 7.81 (s, 1H), 8.09 (s, 1H), 9.32 (s, 1H). MS m/z 487 (M+H)$^+$

Example 265

Compound #291

N-(2-(cyclopropanecarboxamido)-4-(4-(4-(1-methyl-1H-pyrazol-4-yl)phenyl)piperidine-1-carbonyl)phenyl)-N-(2-methoxyethyl)cyclopropanecarboxamide

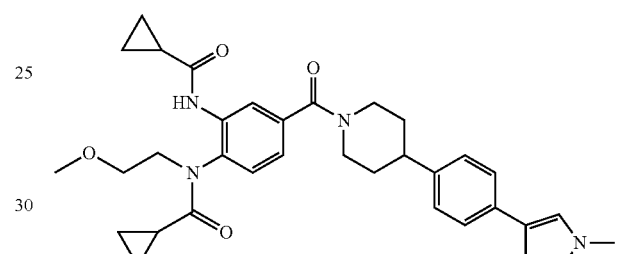

MS m/z 570 (M+H)$^+$

Example 266

Compound #292

N-(2-(isopropyl(methyl)amino)-5-(4-(4-(1-methyl-1H-pyrazol-4-yl)phenyl)piperidine-1-carbonyl)phenyl)cyclopropanecarboxamide

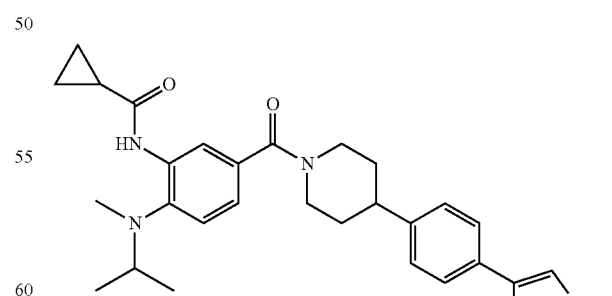

MS m/z 500 (M+H)$^+$

Example 267

Compound #293

1-cyclohexyl-N-(2-methyl-5-(4-(4-(1-methyl-1H-pyrazol-4-yl)phenyl)piperidine-1-carbonyl)phenyl)pyrrolidine-3-carboxamide

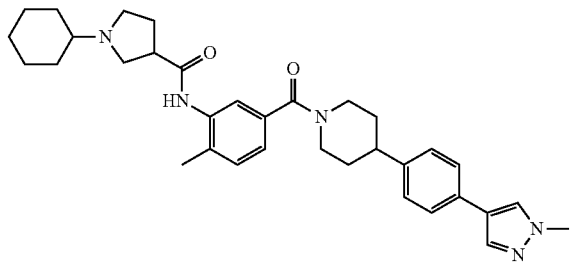 [SMILES: Cc1ccc(C(=O)N2CCC(c3ccc(-c4cnn(C)c4)cc3)CC2)cc1NC(=O)C1CCN(C2CCCCC2)C1]

MS m/z 554 (M+H)+

Example 268

Compound #294

N-(2-methyl-5-(4-(4-(1-methyl-1H-pyrazol-4-yl)phenyl)piperidine-1-carbonyl)phenyl)azetidine-3-carboxamide

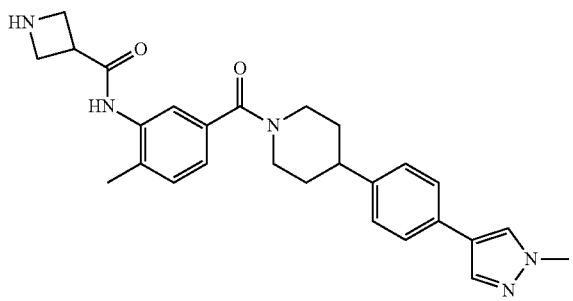 [SMILES: Cc1ccc(C(=O)N2CCC(c3ccc(-c4cnn(C)c4)cc3)CC2)cc1NC(=O)C1CNC1]

MS m/z 458 (M+H)+

Example 269

Compound #295

N-(2-methyl-5-(4-(4-(1-methyl-1H-pyrazol-4-yl)phenyl)piperidine-1-carbonyl)phenyl)-1-(3-methylcyclopentyl)piperidine-4-carboxamide

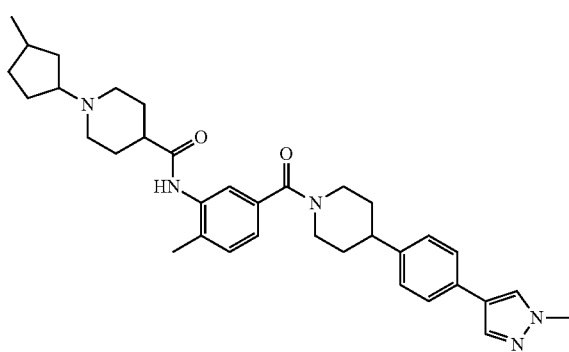 [SMILES: Cc1ccc(C(=O)N2CCC(c3ccc(-c4cnn(C)c4)cc3)CC2)cc1NC(=O)C1CCN(C2CCC(C)C2)CC1]

MS m/z 568 (M+H)+

Example 270

Compound #228

N-(cyclobutanecarbonyl)-N-(2-methyl-5-(3-(4-(1-methyl-1H-pyrazol-4-yl)phenyl)azetidine-1-carbonyl)phenyl)cyclobutanecarboxamide

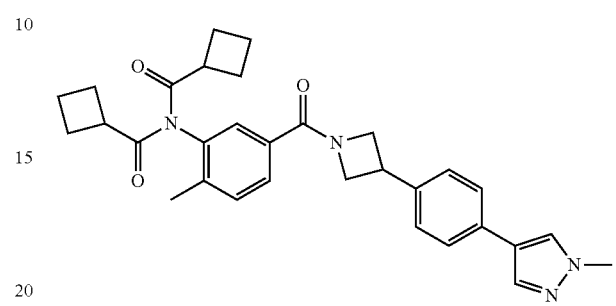

MS m/z 511.3 (M+H)+

Example 271

Compound #296

4-fluoro-2-methyl-N-(2-methyl-5-(4-(4-(1-methyl-1H-pyrazol-4-yl)phenyl)piperidine-1-carbonyl)phenyl)benzamide

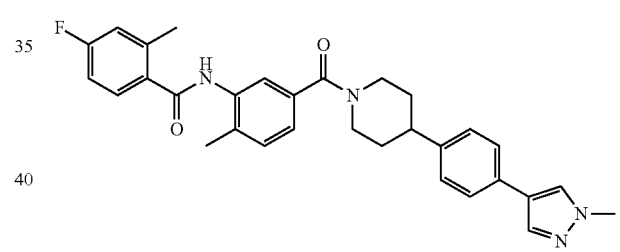

MS m/z 511 (M+H)+

Example 272

Compound #226

N-(2-methyl-5-(3-(4-(1-methyl-1H-pyrazol-4-yl)phenyl)azetidine-1-carbonyl)phenyl)cyclopentanecarboxamide

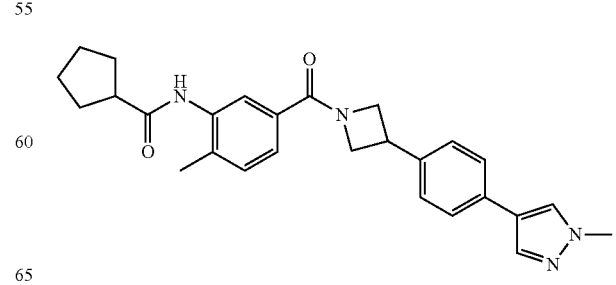

MS m/z 443.4 (M+H)+

Example 273

Compound #297

6-(dimethylamino)-N-(2-methyl-5-(4-(4-(1-methyl-1H-pyrazol-4-yl)phenyl)piperidine-1-carbonyl)phenyl)nicotinamide

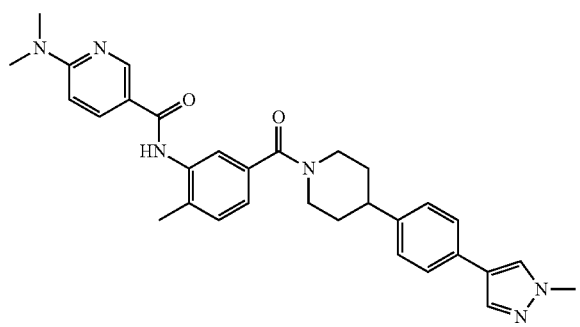

MS m/z 523 (M+H)+

Example 274

Compound #107

6-chloro-N-(5-(3-hydroxy-3-(4-(1-methyl-1H-pyrazol-5-yl)phenyl)azetidine-1-carbonyl)-2-methylphenyl)nicotinamide

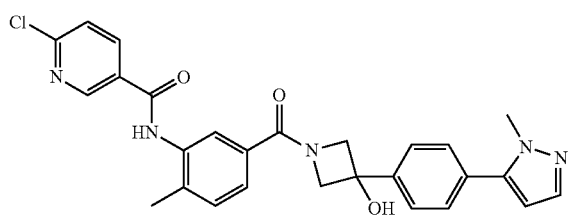 [SMILES: Cc1ccc(C(=O)N2CC(O)(c3ccc(-c4ccnn4C)cc3)C2)cc1NC(=O)c1ccc(Cl)nc1]

MS m/z 502 (M+H)+

Example 275

Compound #34

6-chloro-N-(2-methyl-5-(4-(4-(pyrimidin-2-ylcarbamoyl)phenyl)piperidine-1-carbonyl)phenyl)nicotinamide

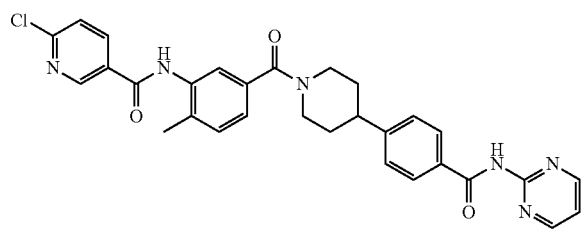 [SMILES: Cc1ccc(C(=O)N2CCC(c3ccc(C(=O)Nc4ncccn4)cc3)CC2)cc1NC(=O)c1ccc(Cl)nc1]

MS m/z 592 (M+H)+

Example 276

Compound #33

6-chloro-N-(2-methyl-5-(4-(4-((4-methylpyrimidin-2-yl)carbamoyl)phenyl)piperidine-1-carbonyl)phenyl)nicotinamide

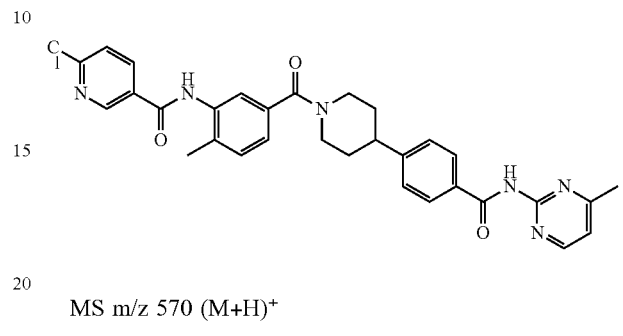

MS m/z 570 (M+H)+

Example 277

Compound #21

6-chloro-N-(5-(4-(2,3-dimethyl-1-oxoisoindolin-5-yl)piperidine-1-carbonyl)-2-methylphenyl)nicotinamide

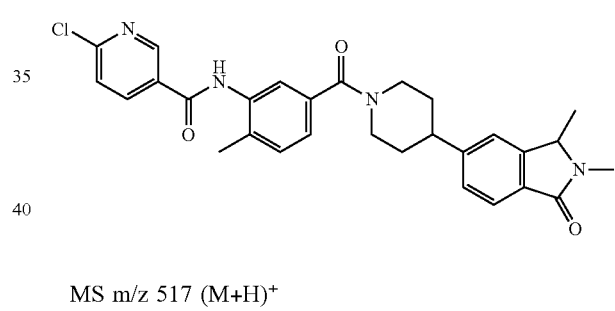

MS m/z 517 (M+H)+

Example 278

Compound #20

N-(5-(4-([1,2,4]triazolo[4,3-a]pyridin-6-yl)piperidine-1-carbonyl)-2-methylphenyl)-6-(isopropylamino)nicotinamide

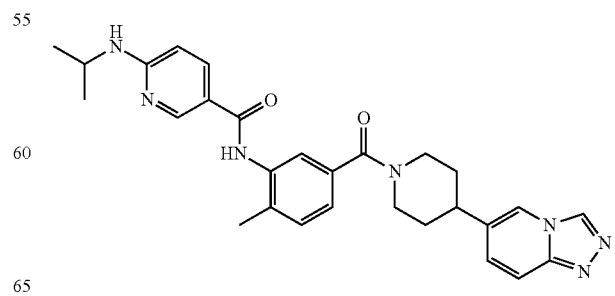

MS m/z 498 (M+H)+

Example 279

Compound #18

N-(5-(4-([1,2,4]triazolo[4,3-a]pyridin-6-yl)piperidine-1-carbonyl)-2-methylphenyl)-6-chloronicotinamide

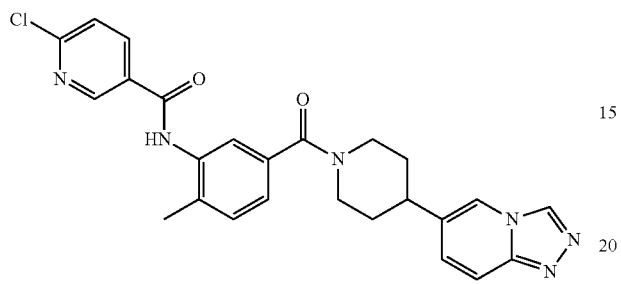

MS m/z 475 (M+H)+

Example 280

Compound #17

N-(5-(4-(imidazo[1,2-a]pyridin-6-yl)piperidine-1-carbonyl)-2-methylphenyl)-6-(isopropylamino)nicotinamide

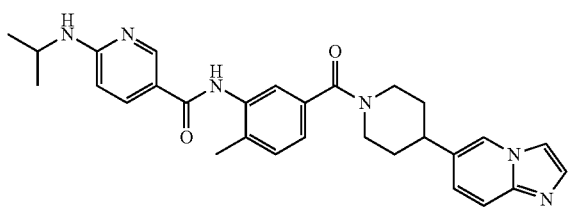 [SMILES: Cc1ccc(C(=O)N2CCC(c3ccc4nccn4c3)CC2)cc1NC(=O)c1ccc(NC(C)C)nc1]

MS m/z 497 (M+H)+

Example 281

Compound #14

6-chloro-N-(5-(4-(imidazo[1,2-a]pyridin-6-yl)piperidine-1-carbonyl)-2-methylphenyl)nicotinamide

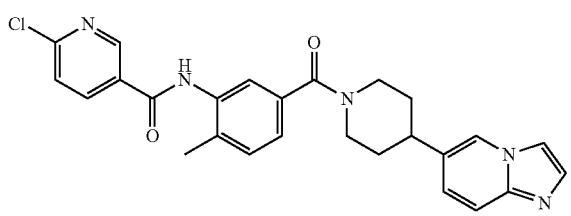 [SMILES: Cc1ccc(C(=O)N2CCC(c3ccc4nccn4c3)CC2)cc1NC(=O)c1ccc(Cl)nc1]

MS m/z 474 (M+H)+

Example 282

Compound #265

N-(5-(3-(4-(3-aminopyridin-4-yl)phenyl)azetidine-1-carbonyl)-2-methylphenyl)-6-morpholinonicotinamide

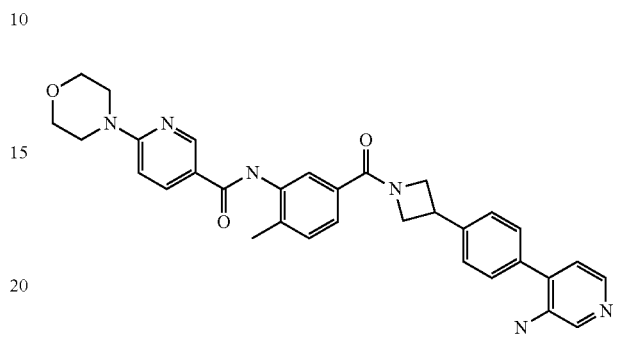

$^1$H NMR (400 MHz, CHLOROFORM-d) δ ppm 2.37 (s, 3H), 3.61-3.69 (m, 4H), 3.75-3.89 (m, 6H), 3.90-4.01 (m, 1H), 4.28-4.38 (m, 1H), 4.41-4.51 (m, 1H), 4.64 (t, J=9.6 Hz, 1H), 4.87 (t, J=8.6 Hz, 1H), 6.68 (d, J=9.1 Hz, 1H), 7.03 (d, J=5.1 Hz, 1H), 7.30 (d, J=8.1 Hz, 1H), 7.46 (s, 4H), 7.50-7.58 (m, 1H), 7.69 (s, 1H), 7.98-8.11 (m, 2H), 8.16 (s, 1H), 8.30 (d, J=1.5 Hz, 1H), 8.71 (d, J=2.5 Hz, 1H). MS m/z 550.3 (M+H)+

Biological Example 1

Fatty Acid Synthase (FASN) Inhibition Scintillation Proximity Assay

In this assay, inhibition of FASN activity is measured using $^3$H-acetyl-CoA and malonyl-CoA as substrates. $^3$H-Acetyl CoA is converted to $^3$H-palmitate through a series of reactions by the FASN protein, which contains 7 functional domains and carries out 7 enzymatic reactions to ultimately produce $^3$H-palmitate. The assay principle is based upon the fact that $^3$H-acetyl-CoA is hydrophilic and the end product, $^3$H-palmitate is hydrophobic. The hydrophobic $^3$H-palmitate binds to scintillation proximity assay (SPA) imaging beads (resulting in light emission from the imaging beads) whereas the hydrophilic $^3$H-acetyl-CoA does not bind to the imaging beads (and therefore does not result in light emission from the imaging beads).

10 μL assay buffer (100 mM $KH_2PO_4$ pH 7.5, 1 mM DTT) (20 μL in blanks) was added to a 384-well white Opti Plate plate (Perkin Elmer). 0.9 μL test compound (at concentrations of 30 μM, 10 μM, 3 μM, 1 μM, 0.30 μM, 0.10 μM, 0.03 μM and 0.01 μM)/DMSO and 10 μL hFASN enzyme (full length, 300 ng, purified in house) or 10 μL assay buffer was added to the wells. Then 10 μL 450 μM NADPH (Sigma N7505), 18.75 μM [$^3$H]-acetyl-CoA (Perkin Elmer NET-290L), 150 μM malonyl-CoA (Sigma M4263) were added, mixed and incubated at room temperature for 60 minutes. The reaction was stopped by adding 20 μL Streptavidin coupled imaging beads (25 mg/ml). After incubation for 30 minutes at room temperature in the dark, the 384 well plate was centrifuged at 1500 rpm for 3 minutes and was measured after at least 24 hrs by the LEADseeker™, measuring emission using a 610±20 nm pass filter. (Bays, N. W., et al., "A simplified scintillation proximity assay for fatty acid synthase activity: development and comparison with other FAS activity assays", *J. Biomol. Screen*, 2009, pp 636-642, Vol. 14(6).)

Raw data generated by the instrument were normalized to % Controlmin values, which were calculated as:

% Control$_{min}$=100*(x−mLC)/(mHC−mLC)

where mLC and mHC were the means of the low control wells and high control wells on the plate, after manual exclusion of outliers. A plot of Control$_{min}$ versus test compound concentration was fitted to a 4-parameter logistic curve using a non-linear least squares regression method. From the plot, an IC$_{50}$ (concentration at which 50% inhibition is achieved) was calculated. pIC$_{50}$ values were calculated as −log(IC$_{50}$), when IC$_{50}$ is expressed in molar units. Representative compounds of formula (I) the present invention were tested according to the procedure as described in Biological Example 1, with results as listed in Table BIO-1, below. Where a compound was tested more than once, the pIC$_{50}$ value listed below represents the mean of the measurements. Wherein the results listed below, the pIC$_{50}$ value is preceded with a "~", the "~" indicates that the standard error of the pIC$_{50}$ value, as estimated by the non-linear regression algorithm, is larger than 0.5. This corresponds to a factor of uncertainly on the pIC$_{50}$ that is larger than square root of 10 (>3.162).

TABLE BIO-1

Human FASN pIC$_{50}$

| ID No. | pIC$_{50}$ (µM) | FASN % Effect @1E−05M |
|---|---|---|
| 3 | 7.59 | 106 |
| 4 | 7.40 | 109 |
| 6 | 7.21 | 104 |
| 10 | 7.49 | 103 |
| 11 | 7.56 | 106 |
| 12 | 7.41 | 111 |
| 13 | 6.90 | 99 |
| 14 | <4.52 | 30 |
| 15 | 7.64 | 109 |
| 16 | 7.02 | 106 |
| 17 | ~4.89 | 51 |
| 18 | <4.52 | 2 |
| 19 | 5.18 | 50 |
| 20 | ~4.52 | 30 |
| 21 | 4.56 | 22 |
| 22 | 5.31 | 60 |
| 23 | 6.23 | 93 |
| 24 | 7.47 | 111 |
| 25 | 7.55 | 109 |
| 26 | 7.49 | 105 |
| 28 | 6.76 | 101 |
| 29 | 7.47 | 103 |
| 31 | ~7.75 | 104 |
| 32 | 7.57 | 104 |
| 35 | 6.36 | 99 |
| 36 | 7.36 | 106 |
| 37 | 6.27 | 94 |
| 39 | 7.52 | 111 |
| 42 | 7.67 | 106 |
| 43 | 7.35 | 106 |
| 44 | 7.21 | 102 |
| 46 | 5.64 | 74 |
| 47 | ~5.11 | 60 |
| 48 | 6.57 | 92 |
| 49 | 6.92 | 97 |
| 50 | 6.51 | 93 |
| 51 | 7.83 | 110 |
| 53 | 6.60 | 101 |
| 54 | 6.63 | 104 |
| 55 | 6.36 | 86 |
| 56 | 6.51 | 95 |
| 57 | 7.60 | 106 |
| 58 | 7.95 | 111 |
| 59 | 7.25 | 103 |
| 60 | 7.71 | 103 |
| 61 | 7.81 | 103 |
| 62 | 7.79 | 103 |
| 63 | 7.56 | 100 |
| 64 | 7.46 | 102 |
| 65 | 7.68 | 99 |
| 66 | 8.02 | 118 |
| 67 | 6.82 | 92 |
| 68 | 7.50 | 118 |
| 69 | 7.54 | 98 |
| 70 | 7.25 | 109 |
| 71 | 7.32 | 101 |
| 72 | 7.40 | 110 |
| 73 | 7.49 | 93 |
| 74 | 7.76 | 107 |
| 75 | 7.27 | 92 |
| 76 | 6.20 | 91 |
| 77 | 6.75 | 105 |
| 78 | ~7.99 | 120 |
| 79 | 7.03 | 108 |
| 80 | 7.29 | 110 |
| 81 | ~7.49 | 120 |
| 82 | 7.64 | 98 |
| 83 | 7.79 | 109 |
| 84 | 7.43 | 103 |
| 85 | 7.11 | 99 |
| 86 | 7.65 | 106 |
| 87 | 6.74 | 96 |
| 88 | 7.45 | 100 |
| 89 | 7.69 | 103 |
| 91 | 7.95 | 109 |
| 92 | 7.79 | 100 |
| 93 | 7.76 | 100 |
| 94 | 7.69 | 100 |
| 95 | 7.58 | 105 |
| 96 | 7.50 | 103 |
| 97 | 6.77 | 89 |
| 98 | 7.52 | 102 |
| 99 | 6.97 | 92 |
| 100 | 7.79 | 111 |
| 101 | 7.32 | 105 |
| 102 | 7.73 | 105 |
| 103 | 7.12 | 95 |
| 104 | 7.37 | 104 |
| 105 | 6.51 | 86 |
| 106 | 7.97 | 113 |
| 107 | <5 | 41 |
| 108 | 7.44 | 103 |
| 109 | 7.84 | 119 |
| 110 | 7.72 | 115 |
| 111 | 6.29 | 96 |
| 112 | 7.94 | 104 |
| 113 | 7.54 | 104 |
| 114 | 6.50 | 92 |
| 115 | 7.55 | 99 |
| 116 | 7.36 | 101 |
| 117 | 7.48 | 99 |
| 118 | 6.81 | 92 |
| 119 | 7.19 | 98 |
| 120 | 7.35 | 95 |
| 121 | 6.42 | 87 |
| 122 | 7.73 | 101 |
| 123 | 7.27 | 97 |
| 124 | 7.59 | 105 |
| 125 | 7.35 | 104 |
| 126 | 7.52 | 110 |
| 127 | 6.74 | 98 |
| 128 | 6.59 | 84 |
| 129 | 7.64 | 104 |
| 130 | 7.32 | 108 |
| 131 | 7.29 | 109 |
| 132 | 6.92 | 97 |
| 133 | 7.43 | 96 |
| 134 | 7.24 | 111 |

TABLE BIO-1-continued

Human FASN pIC$_{50}$

| ID No. | pIC$_{50}$ (μM) | FASN % Effect @1E−05M |
|---|---|---|
| 135 | 7.79 | 107 |
| 136 | 7.51 | 105 |
| 137 | 7.26 | 103 |
| 138 | 7.04 | 107 |
| 139 | 7.50 | 101 |
| 140 | 7.80 | 114 |
| 141 | 7.66 | 110 |
| 142 | 7.33 | 106 |
| 143 | 7.35 | 114 |
| 144 | 7.62 | 106 |
| 145 | 7.66 | 103 |
| 146 | 7.72 | 110 |
| 147 | 7.46 | 107 |
| 148 | 7.32 | 102 |
| 149 | 7.24 | 103 |
| 150 | 7.36 | 110 |
| 151 | 6.83 | 101 |
| 152 | 7.66 | 106 |
| 153 | 7.52 | 102 |
| 154 | 7.57 | 108 |
| 155 | 7.32 | 98 |
| 156 | 6.97 | 100 |
| 157 | 7.37 | 104 |
| 158 | 7.63 | 102 |
| 159 | 7.64 | 104 |
| 160 | 7.39 | 100 |
| 161 | 7.67 | 101 |
| 162 | 7.70 | 101 |
| 163 | 7.54 | 105 |
| 164 | 7.68 | 110 |
| 167 | 7.49 | 113 |
| 168 | 7.21 | 113 |
| 169 | 7.15 | 106 |
| 170 | 7.24 | 112 |
| 171 | 6.05 | 84 |
| 172 | 6.31 | 91 |
| 173 | 6.83 | 97 |
| 174 | 7.22 | 103 |
| 175 | 7.31 | 108 |
| 176 | 7.47 | 110 |
| 177 | 7.59 | 112 |
| 178 | 7.34 | 106 |
| 179 | 7.58 | 108 |
| 180 | 7.60 | 104 |
| 181 | 7.38 | 108 |
| 182 | 7.56 | 111 |
| 183 | 6.95 | 98 |
| 184 | 7.44 | 105 |
| 185 | 6.60 | 101 |
| 186 | 7.02 | 106 |
| 187 | 6.85 | 103 |
| 188 | 7.21 | 104 |
| 189 | 6.90 | 102 |
| 190 | 7.13 | 102 |
| 191 | 7.16 | 103 |
| 192 | 7.27 | 105 |
| 193 | 7.22 | 109 |
| 194 | 6.93 | 102 |
| 195 | 7.16 | 101 |
| 196 | 6.79 | 97 |
| 197 | 6.96 | 98 |
| 198 | 6.87 | 100 |
| 199 | ~6.17 | 59 |
| 200 | 6.19 | 86 |
| 201 | 6.67 | 86 |
| 202 | 7.28 | 113 |
| 203 | 6.55 | 97 |
| 204 | 6.89 | 107 |
| 205 | 6.57 | 95 |
| 206 | 6.80 | 99 |
| 207 | 6.88 | 105 |
| 208 | 6.57 | 101 |
| 209 | 7.50 | 105 |
| 210 | 7.07 | 108 |
| 211 | 7.50 | 113 |
| 212 | 6.92 | 108 |
| 213 | 7.34 | 111 |
| 214 | 6.78 | 107 |
| 215 | 6.98 | 107 |
| 216 | 7.44 | 113 |
| 217 | 6.76 | 105 |
| 218 | 6.84 | 105 |
| 219 | 7.19 | 116 |
| 220 | 7.17 | 110 |
| 221 | 7.12 | 109 |
| 222 | 7.65 | 113 |
| 223 | 7.16 | 102 |
| 224 | 6.77 | 92 |
| 225 | 6.47 | 79 |
| 226 | <5 | 17 |
| 227 | 5.61 | 63 |
| 229 | 5.39 | 61 |
| 230 | 6.44 | 79 |
| 231 | 7.47 | 114 |
| 232 | 6.49 | 85 |
| 233 | 6.24 | 72 |
| 234 | ~5.7 | 63 |
| 235 | 7.27 | 112 |
| 236 | ~6.51 | 74 |
| 237 | 6.89 | 101 |
| 238 | 6.32 | 100 |
| 239 | 6.91 | 110 |
| 240 | 7.08 | 106 |
| 241 | 6.84 | 101 |
| 242 | 7.14 | 105 |
| 243 | 6.89 | 105 |
| 244 | 7.35 | 106 |
| 245 | 7.47 | 108 |
| 246 | 7.27 | 110 |
| 247 | 7.47 | 112 |
| 248 | 7.36 | 108 |
| 249 | 7.27 | 109 |
| 250 | 6.64 | 65 |
| 251 | 7.54 | 112 |
| 252 | 6.78 | 106 |
| 253 | 6.50 | 104 |
| 254 | 7.37 | 103 |
| 255 | 7.62 | 113 |
| 256 | 7.59 | 116 |
| 257 | 6.21 | 95 |
| 258 | 6.61 | 99 |
| 259 | 7.25 | 103 |
| 260 | 7.60 | 112 |
| 261 | 7.22 | 107 |
| 262 | 6.58 | 89 |
| 263 | 7.04 | 111 |
| 264 | 7.23 | 109 |
| 265 | 7.66 | 110 |
| 266 | 7.42 | 112 |
| 267 | 7.59 | 112 |
| 268 | 6.78 | 104 |
| 269 | 7.16 | 107 |
| 270 | 6.23 | 93 |
| 271 | 7.00 | 101 |
| 272 | 7.53 | 112 |
| 273 | 6.95 | 98 |
| 274 | 6.36 | 88 |
| 275 | 7.25 | 99 |
| 276 | 6.43 | 93 |
| 277 | 5.35 | 62 |
| 278 | 6.09 | 85 |
| 279 | 7.38 | 98 |
| 280 | 7.15 | 99 |
| 281 | 6.34 | 93 |
| 282 | 7.15 | 99 |
| 283 | 6.96 | 98 |
| 284 | 6.90 | 95 |
| 285 | ~6.78 | 74 |
| 286 | 6.29 | 91 |
| 287 | 7.00 | 98 |

TABLE BIO-1-continued

Human FASN pIC$_{50}$

| ID No. | pIC$_{50}$ (μM) | FASN % Effect @1E−05M |
|---|---|---|
| 288 | 6.06 | 88 |
| 291 | <5 | |

Biological Example 2

Fatty Acid Synthase Keto-Reductase Domain (FASN KR) Inhibition

10 μL assay buffer (100 mM KH$_2$PO$_4$ pH 7.5) was added to a 384-well clear plate (costar 3702). 0.3 μL compound (at concentrations of 30 μM, 10 μM, 3 μM, 1 μM, 0.30 μM, 0.10 μM, 0.03 μM and 0.01 μM)/DMSO, 10 μL hFASN enzyme (full length, 300 ng, purified in house) and 360 μM NADPH (except in blank) were then added. Then, 10 μL 180 mM ethyl acetoacetate (Aldrich 688983) was added, mixed and immediately thereafter, the absorbance at 340 nm (T1) by Multiscan (Labsystems) was measured. After 20 minutes incubation at room temperature the plate was measured again (T2).

Enzymatic activity of FASN KR was measured as the oxidation of NADPH to NADP$^+$ (a decrease in NADPH signal was observed at OD 340 nm). The decrease in absorbance was calculated as (Absorbance before incubation T1)−(Absorbance following incubation T2).

Raw data generated by the instrument were normalized to % Control$_{min}$ values, which were calculated as:

% Control$_{min}$=100*(x−mLC)/(mHC−mLC)

where mLC and mHC were the means of the low control wells and high control wells on the plate, after manual exclusion of outliers. A plot of Control$_{min}$ versus test compound concentration was fitted to a 4-parameter logistic curve using a non-linear least squares regression method. From the plot, an IC$_{50}$ (concentration at which 50% inhibition is achieved) was calculated. pIC$_{50}$ values were calculated as −log(IC$_{50}$), when IC$_{50}$ is expressed in molar units.

Representative compounds of the present invention were tested according to the procedure as described in Biological Example 2 above, with results as listed in Table BIO-2, below. Where a compound was tested more than once, the pIC$_{50}$ value listed below represents the mean of the measurements.

TABLE BIO-2

FASN Keto-reductase Domain pIC$_{50}$

| ID No. | FASN K-R Domain pIC$_{50}$ (μM) |
|---|---|
| 3 | 7.19 |
| 4 | 7.01 |
| 6 | 7.05 |
| 10 | 7.35 |
| 11 | 7.31 |
| 12 | 7.64 |
| 13 | 6.64 |
| 14 | 4.77 |
| 15 | 7.43 |
| 16 | 7.02 |
| 17 | 5.09 |
| 18 | <4.52 |
| 19 | 5.26 |
| 21 | 4.88 |
| 22 | 5.10 |
| 23 | 5.93 |
| 24 | 7.41 |
| 25 | 7.34 |
| 26 | 7.39 |
| 28 | 6.55 |
| 29 | 7.53 |
| 31 | 7.28 |
| 32 | 7.43 |
| 35 | 6.10 |
| 36 | 7.56 |
| 37 | 6.25 |
| 39 | 7.78 |
| 42 | 7.46 |
| 43 | 7.16 |
| 44 | 7.05 |
| 48 | 6.34 |
| 49 | 6.64 |
| 50 | 6.22 |
| 51 | 7.60 |
| 53 | 6.25 |
| 54 | 6.54 |
| 55 | 6.29 |
| 56 | 6.34 |
| 57 | 7.59 |
| 58 | 7.55 |
| 59 | 6.94 |
| 60 | 7.54 |
| 61 | 7.16 |
| 62 | 7.29 |
| 63 | 7.61 |
| 64 | 7.07 |
| 65 | 7.54 |
| 66 | 7.50 |
| 67 | ~6.22 |
| 68 | 7.19 |
| 69 | 7.38 |
| 70 | 6.61 |
| 71 | 6.63 |
| 72 | 6.60 |
| 73 | 7.07 |
| 74 | 7.34 |
| 75 | 7.26 |
| 76 | 5.86 |
| 77 | 5.97 |
| 78 | 7.60 |
| 79 | 6.74 |
| 80 | 6.63 |
| 81 | 7.00 |
| 82 | 7.07 |
| 83 | 7.34 |
| 84 | 6.79 |
| 85 | 5.30 |
| 86 | 7.12 |
| 87 | 6.54 |
| 88 | 6.90 |
| 89 | 7.18 |
| 91 | 7.60 |
| 92 | 7.51 |
| 93 | 7.53 |
| 94 | 7.08 |
| 95 | 6.82 |
| 96 | 6.81 |
| 97 | 6.49 |
| 98 | 7.04 |
| 99 | 6.53 |
| 100 | 7.35 |
| 101 | 6.81 |
| 102 | 7.42 |
| 103 | 6.83 |
| 104 | 7.06 |
| 105 | 6.21 |
| 106 | 7.61 |
| 108 | 7.22 |
| 109 | 7.50 |
| 110 | 6.88 |

TABLE BIO-2-continued

FASN Keto-reductase Domain pIC$_{50}$

| ID No. | FASN K-R Domain pIC$_{50}$ (μM) |
|---|---|
| 111 | 5.75 |
| 112 | 7.18 |
| 113 | 7.32 |
| 114 | 6.20 |
| 115 | 6.93 |
| 116 | 7.03 |
| 117 | 7.08 |
| 118 | 6.54 |
| 119 | 6.85 |
| 120 | 7.01 |
| 121 | 6.10 |
| 122 | 7.12 |
| 123 | 7.11 |
| 124 | 7.09 |
| 125 | 7.10 |
| 126 | 7.49 |
| 127 | 6.41 |
| 128 | 6.54 |
| 129 | 7.46 |
| 130 | 6.90 |
| 131 | 6.97 |
| 132 | 6.69 |
| 133 | 7.13 |
| 134 | 7.28 |
| 135 | 7.26 |
| 136 | 7.16 |
| 137 | 6.62 |
| 138 | 6.71 |
| 139 | 7.02 |
| 140 | 7.40 |
| 141 | 7.14 |
| 142 | 6.96 |
| 143 | 6.77 |
| 144 | 7.45 |
| 145 | 7.47 |
| 146 | 7.49 |
| 147 | 6.86 |
| 148 | 7.27 |
| 149 | 6.67 |
| 150 | 6.81 |
| 151 | 6.15 |
| 152 | 7.76 |
| 153 | 7.21 |
| 154 | 6.98 |
| 155 | 7.03 |
| 156 | 6.58 |
| 157 | 6.92 |
| 158 | 7.43 |
| 159 | 7.47 |
| 160 | 7.04 |
| 161 | 7.41 |
| 162 | 7.49 |
| 163 | 7.33 |
| 164 | 7.38 |
| 167 | 7.33 |
| 168 | 6.90 |
| 169 | 6.72 |
| 170 | 6.47 |
| 171 | 6.00 |
| 172 | 6.13 |
| 173 | 6.36 |
| 174 | 6.87 |
| 175 | 7.11 |
| 176 | 6.98 |
| 177 | 7.30 |
| 178 | 7.23 |
| 179 | 7.43 |
| 180 | 7.39 |
| 181 | 6.96 |
| 182 | 6.95 |
| 183 | 6.53 |
| 184 | 6.91 |
| 185 | 6.30 |
| 186 | 6.48 |
| 187 | 6.52 |
| 188 | 6.77 |
| 189 | 6.51 |
| 190 | 6.60 |
| 191 | 6.72 |
| 192 | 6.77 |
| 193 | 6.75 |
| 194 | 6.67 |
| 195 | 6.72 |
| 196 | 6.55 |
| 197 | 6.51 |
| 198 | 6.43 |
| 199 | 6.14 |
| 200 | 6.19 |
| 201 | 6.42 |
| 202 | 6.82 |
| 203 | 6.01 |
| 204 | 6.40 |
| 205 | 6.23 |
| 206 | 6.34 |
| 207 | 6.32 |
| 208 | 6.20 |
| 209 | 7.13 |
| 210 | 6.51 |
| 211 | 7.13 |
| 212 | 6.49 |
| 213 | 6.71 |
| 214 | 6.55 |
| 215 | 6.51 |
| 216 | 7.04 |
| 217 | 6.30 |
| 218 | 6.41 |
| 219 | 6.70 |
| 220 | 6.76 |
| 221 | 6.61 |
| 222 | 7.22 |
| 223 | 6.85 |
| 224 | 6.55 |
| 225 | 6.34 |
| 230 | 6.28 |
| 231 | 6.97 |
| 232 | 6.31 |
| 233 | 6.11 |
| 235 | 6.99 |
| 236 | 6.45 |
| 237 | 6.42 |
| 238 | 5.99 |
| 239 | 6.34 |
| 240 | 6.39 |
| 241 | 6.33 |
| 242 | 6.80 |
| 243 | 6.73 |
| 244 | 6.72 |
| 245 | 7.12 |
| 246 | 6.61 |
| 247 | 7.04 |
| 248 | 7.03 |
| 249 | 7.00 |
| 250 | 6.68 |
| 251 | 6.94 |
| 252 | 6.36 |
| 253 | 5.91 |
| 254 | 7.27 |
| 255 | 7.14 |
| 256 | 7.22 |
| 257 | 5.69 |
| 258 | 5.91 |
| 259 | 6.45 |
| 260 | 6.99 |
| 261 | 6.90 |
| 262 | 5.98 |
| 263 | 6.32 |
| 264 | 6.66 |
| 265 | 7.22 |
| 266 | 6.97 |
| 267 | 7.23 |

TABLE BIO-2-continued

FASN Keto-reductase Domain pIC$_{50}$

| ID No. | FASN K-R Domain pIC$_{50}$ (μM) |
|---|---|
| 268 | 5.87 |
| 269 | 6.59 |
| 270 | 5.56 |
| 271 | 6.27 |
| 272 | 6.98 |
| 273 | 6.64 |
| 274 | ~5.66 |
| 275 | 6.90 |
| 276 | 6.32 |
| 278 | 5.96 |
| 279 | 7.03 |
| 280 | 6.83 |
| 281 | 6.03 |
| 282 | 6.34 |
| 283 | 6.20 |
| 284 | 6.39 |
| 285 | 6.67 |
| 286 | 6.07 |
| 287 | 6.69 |
| 288 | 5.60 |

Biological Example 3

A2780 Ovarian Cell Proliferation Assay in Lipid Reduced Medium, with and without Palmitate The biological assays described below correspond to comparative assays for ovarian cell proliferation. The assay procedure described below which includes addition of added palmitate correspond to the control relative to the assay procedure which does not include addition of the palmitate. Compounds active in the absence of palmitate would not be expected to be active in the control.

With Palmitate:

2500 cells were seeded in a 96-well clear well plate in 200 μL RPMI1640 with 10% Fetal Calf Serum (Hyclone), and incubated at 37° C., 5% $CO_2$. Blanks were wells without cells. The next day the culture medium was aspirated and replaced by 160 μL culture medium with 10% Lipid-Reduced Serum (LRS, Hyclone). 20 μL test compound (at concentrations of 30 μM, 10 μM, 3 μM, 1 μM, 0.30 μM, 0.10 μM, 0.03 μM and 0.01 μM)/DMSO dilution followed by 20 μL palmitate-BSA solution were added to a final concentrations of 0.2% DMSO, 25 μM palmitate (Sigma, P0500, 10 mM stock solution in ethanol) 0.2% fatty-acid-free BSA, 0.25% ethanol. After 96 h incubation, an MTT assay was performed. The absorbance was measured at 544 nm on a SPECTRAMAX.

A best fit curve was fitted by a minimum sum of squares method, plotting Control$_{min}$ versus test compound concentration. From the plot, an IC$_{50}$ (concentration at which 50% inhibition is achieved) was calculated. pIC$_{50}$ values, presented in the Table below, were calculated as $-\log(IC_{50})$.

Without Palmitate:

2500 cells were seeded in a 96-well clear well plate in 200 μL RPMI1640 with 10% Fetal Calf Serum (Hyclone), and incubated at 37° C., 5% $CO_2$. Blanks were wells without cells. The next day the culture medium was aspirated and replaced by 160 μL culture medium with 10% Lipid-Reduced Serum (LRS, Hyclone). 20 μL test compound (at concentrations of 30 μM, 10 μM, 3 μM, 1 μM, 0.30 μM, 0.10 μM, 0.03 μM and 0.01 μM)/DMSO dilution followed by 20 μL ethanol-BSA solution were added to a final concentrations of 0.2% DMSO, 0.2% fatty-acid-free BSA, 0.25% ethanol. After 96 h incubation an MTT assay was performed. The absorbance was measured at 544 nm on a SPECTRAMAX.

Raw data generated by the instrument were normalized to % Controlmin values, which were calculated as:

% Control$_{min}$ = 100*(x−mLC)/(mHC−mLC)

where mLC and mHC were the means of the low control wells and high control wells on the plate, after manual exclusion of outliers. A plot of Control$_{min}$ versus test compound concentration was fitted to a 4-parameter logistic curve using a non-linear least squares regression method. From the plot, an IC$_{50}$ (concentration at which 50% inhibition is achieved) was calculated. pIC$_{50}$ values were calculated as $-\log(IC_{50})$, when IC$_{50}$ is expressed in molar units.

Representative compounds of the present invention were tested according to the procedure as described in Biological Example 3 above, with results as listed in Table BIO-3, below. Where a compound was tested more than once, the pIC$_{50}$ value listed below represents the mean of the measurements. Wherein the results listed below, the pIC$_{50}$ value is preceded with a "~", the "~" the "~" indicates that the standard error of the pIC$_{50}$ value, as estimated by the non-linear regression algorithm, is larger than 0.5. This corresponds to a factor of uncertainly on the pIC$_{50}$ that is larger than square root of 10 (>3.162).

TABLE BIO-3 pIC50 Ovarian Cell, Reduced Medium With and Without Palmitate

| ID No. | Proliferation A2780 w/o Palmitate pIC$_{50}$ (μM) | Proliferation A2780 with Palmitate pIC$_{50}$ (μM) |
|---|---|---|
| 3 | 6.86 | 5.28 |
| 4 | 6.76 | <5 |
| 6 | 6.63 | <5 |
| 10 | ~7.24 | <4.82 |
| 11 | 7.25 | <5 |
| 12 | 7.31 | 5.65 |
| 13 | 6.22 | <5 |
| 15 | ~7.32 | <4.82 |
| 16 | 5.85 | <5 |
| 23 | 5.95 | ~5 |
| 24 | 7.07 | <5 |
| 25 | 7.46 | ~5.68 |
| 26 | ~5.64 | <5 |
| 28 | ~6.69 | 5.61 |
| 29 | 6.76 | <4.82 |
| 31 | 7.60 | 5.78 |
| 32 | 7.87 | 5.14 |
| 35 | 6.17 | ~5.05 |
| 36 | ~7.13 | 5.66 |
| 37 | 6.21 | 5.47 |
| 39 | 7.47 | 5.26 |
| 42 | 6.99 | <5 |
| 43 | 6.88 | <5 |
| 44 | 6.81 | <5 |
| 48 | 5.85 | <5 |
| 49 | 6.09 | <5 |
| 50 | 5.91 | <5 |
| 51 | ~7.47 | 5.77 |
| 53 | 6.22 | 5.07 |
| 54 | 6.69 | <5 |
| 55 | ~7.11 | ~7.07 |
| 56 | 6.36 | 6.04 |
| 57 | 7.34 | 5.20 |
| 58 | 7.74 | 5.43 |
| 59 | 7.03 | 5.14 |
| 60 | 7.29 | 5.56 |
| 61 | ~7.04 | 4.96 |
| 62 | 7.13 | 5.38 |
| 63 | 7.27 | 5.52 |
| 64 | ~6.52 | <5 |

TABLE BIO-3-continued pIC50 Ovarian Cell, Reduced Medium With and Without Palmitate

| ID No. | Proliferation A2780 w/o Palmitate pIC$_{50}$ (μM) | Proliferation A2780 with Palmitate pIC$_{50}$ (μM) |
|---|---|---|
| 65 | 7.25 | <5 |
| 66 | ~7.64 | <4.82 |
| 67 | 6.63 | 6.62 |
| 68 | 6.71 | 5.28 |
| 69 | 7.12 | 5.12 |
| 70 | 6.36 | 5.45 |
| 71 | 6.35 | 5.28 |
| 72 | 6.29 | 5.58 |
| 73 | 6.83 | 4.87 |
| 74 | 7.21 | 5.66 |
| 75 | 6.87 | <4.82 |
| 76 | 5.98 | 5.70 |
| 77 | 6.07 | 4.82 |
| 78 | ~7.53 | ~4.82 |
| 79 | 6.28 | ~5.02 |
| 80 | 6.16 | <4.82 |
| 81 | 6.96 | 5.37 |
| 82 | 7.02 | <5 |
| 83 | 7.13 | <5 |
| 84 | 6.63 | <5 |
| 85 | 6.98 | <5 |
| 86 | 6.74 | <5 |
| 87 | 6.24 | <5 |
| 88 | 6.68 | <5 |
| 89 | 6.82 | <5 |
| 91 | 7.80 | <5 |
| 92 | 8.04 | 5.22 |
| 93 | 7.02 | <5 |
| 94 | 6.83 | 5.12 |
| 95 | 6.58 | 5.46 |
| 96 | 6.84 | <5 |
| 97 | 6.30 | 5.22 |
| 98 | 7.33 | 5.92 |
| 99 | 6.41 | 5.20 |
| 100 | 7.03 | <5 |
| 101 | 7.04 | <5 |
| 102 | 7.44 | <5 |
| 103 | 6.85 | 5.34 |
| 104 | 7.15 | <5 |
| 105 | 6.02 | 5.52 |
| 106 | 7.10 | <4.82 |
| 108 | 7.03 | ~6.39 |
| 109 | ~7.63 | <4.82 |
| 110 | 6.76 | 5.20 |
| 111 | 5.79 | 5.35 |
| 112 | 7.52 | 5.57 |
| 113 | 7.17 | <5 |
| 114 | 6.27 | <5 |
| 115 | 6.79 | <5 |
| 116 | 6.90 | <5 |
| 117 | 6.86 | <5 |
| 118 | 6.41 | 5.56 |
| 119 | 6.72 | 5.19 |
| 120 | 6.84 | ~5 |
| 121 | 6.00 | 5.07 |
| 122 | 6.93 | <5 |
| 123 | 6.79 | 5.17 |
| 124 | 7.47 | 5.27 |
| 125 | 6.88 | 5.32 |
| 126 | 7.58 | <5 |
| 127 | 6.25 | 5.35 |
| 128 | ~6.38 | 5.21 |
| 129 | 7.67 | <5 |
| 130 | ~6.91 | <5 |
| 131 | 6.90 | <5.21 |
| 132 | 6.47 | <5 |
| 133 | 7.04 | <5 |
| 134 | ~7.42 | <5 |
| 135 | 7.06 | <5 |
| 136 | 5.91 | ~5.29 |
| 137 | 6.38 | <5 |
| 138 | 6.48 | <5 |
| 139 | 7.01 | <5 |
| 140 | ~7.63 | 5.11 |
| 141 | 7.44 | 5.18 |
| 142 | 6.97 | <5 |
| 143 | 6.52 | <5 |
| 144 | ~7.91 | 5.11 |
| 145 | 7.16 | 4.98 |
| 146 | ~7.69 | <5 |
| 147 | 6.63 | <5 |
| 148 | 7.05 | 5.08 |
| 149 | 6.34 | 5.02 |
| 150 | 6.32 | <5 |
| 151 | 5.93 | <5 |
| 152 | 7.91 | 5.14 |
| 153 | 7.42 | 5.33 |
| 154 | 5.87 | 5.39 |
| 155 | 7.07 | <5 |
| 156 | 6.56 | <5 |
| 157 | 6.94 | <5 |
| 158 | 8.00 | <5 |
| 159 | ~8.24 | <5 |
| 160 | 7.55 | 5.16 |
| 161 | 7.62 | 5.43 |
| 162 | 8.09 | ~5.12 |
| 163 | 7.88 | <5 |
| 167 | 7.89 | 5.13 |
| 168 | 7.14 | <5 |
| 169 | 7.11 | <5 |
| 170 | 6.52 | <5 |
| 171 | 5.92 | <5 |
| 172 | 6.10 | <5 |
| 173 | 6.06 | <5 |
| 174 | 6.85 | <5 |
| 175 | 7.41 | ~5 |
| 176 | 7.27 | ~5 |
| 177 | 7.86 | <5 |
| 178 | 7.57 | <5 |
| 179 | 7.24 | <5.21 |
| 180 | 7.78 | <5 |
| 181 | 7.49 | <5 |
| 182 | 7.34 | <5 |
| 183 | 6.39 | <5 |
| 184 | 7.23 | <5 |
| 185 | ~6.3 | <5 |
| 186 | ~6.71 | <5 |
| 187 | ~6.55 | <5 |
| 188 | 6.98 | <5 |
| 189 | 6.58 | <5 |
| 190 | 6.59 | <5 |
| 191 | 6.85 | 5.03 |
| 192 | 7.10 | <5 |
| 193 | 6.83 | 5.15 |
| 194 | 6.80 | ~5.06 |
| 195 | 6.96 | 5.04 |
| 196 | 6.39 | ~5.21 |
| 197 | 6.54 | <5 |
| 198 | 6.22 | <5 |
| 199 | 6.25 | 6.21 |
| 200 | 6.15 | 5.34 |
| 201 | 6.29 | 6.03 |
| 202 | 7.23 | <5 |
| 203 | 6.43 | <5 |
| 204 | 6.97 | <5 |
| 205 | 6.45 | <5 |
| 206 | 6.82 | <5 |
| 207 | 6.74 | <5 |
| 208 | 6.56 | <5 |
| 209 | 8.00 | <5 |
| 210 | 6.96 | <5 |
| 211 | 7.73 | <5 |
| 212 | 6.92 | <5 |
| 213 | 7.19 | <5 |
| 214 | 6.56 | 5.02 |
| 215 | 6.72 | 5.03 |
| 216 | 7.36 | 5.25 |
| 217 | 6.67 | <5 |

TABLE BIO-3-continued pIC50 Ovarian Cell, Reduced Medium With and Without Palmitate

| ID No. | Proliferation A2780 w/o Palmitate pIC$_{50}$ (µM) | Proliferation A2780 with Palmitate pIC$_{50}$ (µM) |
|---|---|---|
| 218 | 6.39 | 5.07 |
| 219 | 6.63 | <5 |
| 220 | 7.02 | <5 |
| 221 | 7.04 | 5.30 |
| 222 | 8.06 | <5 |
| 223 | 6.83 | 5.69 |
| 224 | 6.43 | 5.24 |
| 225 | 6.23 | 5.80 |
| 230 | 6.16 | 5.60 |
| 231 | 6.94 | <5 |
| 232 | 6.41 | 5.18 |
| 233 | 6.12 | 6.02 |
| 235 | 7.13 | 5.80 |
| 236 | 6.22 | 5.71 |
| 237 | 6.78 | <5 |
| 238 | 6.13 | <5 |
| 239 | 6.71 | <5 |
| 240 | 6.79 | <5 |
| 241 | 6.83 | <5 |
| 242 | 7.02 | <5 |
| 243 | 6.62 | 5.15 |
| 244 | 7.02 | 5.08 |
| 245 | ~7.5 | <5 |
| 246 | 6.95 | 5.08 |
| 247 | 7.41 | 5.21 |
| 248 | 7.45 | 5.45 |
| 249 | 7.14 | 5.28 |
| 250 | 6.31 | 5.79 |
| 251 | 7.38 | 5.62 |
| 252 | 6.46 | 5.84 |
| 253 | ~6.59 | ~5.73 |
| 254 | 7.74 | ~5 |
| 255 | 7.40 | <5 |
| 256 | 8.05 | 5.20 |
| 257 | 6.05 | <5 |
| 258 | 6.41 | <5 |
| 259 | ~7.07 | <5 |
| 260 | 7.46 | <5 |
| 261 | 6.95 | 5.48 |
| 262 | 6.21 | <5 |
| 263 | 6.77 | <5 |
| 264 | 7.06 | <5 |
| 265 | 7.68 | <5 |
| 266 | ~7.38 | <5 |
| 267 | ~7.65 | <5 |
| 268 | 6.27 | <5 |
| 269 | 6.50 | 5.14 |
| 270 | 5.83 | <5 |
| 271 | 6.31 | <5 |
| 272 | 7.36 | 5.86 |
| 273 | 6.74 | <5 |
| 274 | ~6.52 | <5 |
| 275 | 7.00 | <5 |
| 276 | ~6.59 | <5 |
| 278 | 5.75 | <5 |
| 279 | 7.38 | ~5 |
| 280 | 7.11 | 5.21 |
| 281 | 6.38 | ~5.2 |
| 282 | 6.68 | <5 |
| 283 | 6.44 | <5 |
| 284 | ~6.5 | <5 |
| 285 | 7.23 | 5.47 |
| 286 | 6.37 | <5 |
| 287 | 6.17 | <5 |
| 288 | 5.29 | <5 |

Biological Example 4

Example 4a

In Vitro LNCaP Vancouver Prostate Cell Proliferation Assay in Lipid Reduced Medium LNCaP_Vancouver prostate cells were obtained from the Vancouver Prostate Cancer Centre. Cells were maintained in RPMI-1640, 10% Fetal Calf Serum (FCS, Hyclone), 2 mM glutamine and 50 µg/ml Gentamicin.

For the proliferation experiment 1500 LNCaP_Vancouver cells per well were seeded in a 384-well black with clear bottom plate (costar 3712BC) in 40 µl RPMI-1640, 10% Lipid reduced serum (LRS, Hyclone), 50 µg/ml Gentamicin and 2 mM Glutamine and incubated at 37° C., 5% $CO_2$. The next day 10 µl of test compound/DMSO diluted in medium was added (3E-5M, 1E-5M, 3E-6M, 1E-6M, 3E-7M, 1E-7M, 3E-8M, 1E-8M final concentration). Compounds were tested in duplicate. After 96 h incubation at 37° C., 5% $CO_2$ 25 µl ATP-glow mix was added. The plate was incubated for 30 min at 37° C. and luminescence was measured with the Envision.

Example 4b

In Vitro PC-3M-Luc-C6 Prostate Cell Proliferation Assay in Lipid Reduced Medium

PC-3M-Luc-C6 prostate cells were obtained from Xenogen Corporation. Cells were maintained in MEM supplemented with 10% Fetal Calf Serum (FCS, Hyclone), 2 mM glutamine, 1 mM sodium pyruvate, 1% BME vitamins (available from for example, Sigma Aldrich), 0.1 mM non Essential Amino Acid and 50 µg/ml Gentamicin. The cells were passaged twice a week.

1000 PC-3M-Luc-C6 prostate cells (Xenogen) were seeded in a 384-well black with clear bottom plate (costar 3712BC) in 40 µl MEM, 10% LRS (Hyclo ne), 50 µg/ml Gentamicin, 2 mM Glutamine, 1 mM Sodium pyruvaat, 1% BME vitamins and 0.1 mM non Essential Amino Acid and incubated at 37° C., 5% $CO_2$. The next day 10 µl test compound/DMSO diluted in medium was added (3E-5M, 1E-5M, 3E-6M, 1E-6M, 3E-7M, 1E-7M, 3E-8M, 1E-8M final concentration). Compounds were tested in duplicate. After 96 h incubation at 37° C., 5% $CO_2$ 25 µl ATP-glow mix was added. The plate was incubated for 30 min at 37° C. and luminescence was measured with the Envision.

Analysis: Determination of pIC50 Values pIC$_{50}$ values were calculated as follows. Raw data generated by the instruments were normalized to % Control$_{min}$ values, which were calculated as:

% Control$_{min}$=100*(x−mLC)/(mHC−mLC), where mLC and mHC are the means of the low control wells and high control wells on the plate, after manual exclusion of outliers. The relation between the % Control$_{min}$ values and concentration was fitted to a 4-parameter logistic curve using a non-linear least squares regression method to determine the pIC$_{50}$ value. Outlying data points were excluded manually to get a correct fit. The pIC$_{50}$ corresponds to −log 10(IC$_{50}$), if the IC$_{50}$ is expressed in molar units (http://www.ncbi.nlm.nih.gov/books/NBK91994). The IC$_{50}$ parameter was always determined by non-linear regression, but one or more of the other parameters may have been held fixed on a relevant input value, such as 0 for the bottom values.

For dose response curves with FASN inhibitors in LNCaP_Vancouver or PC-3M-Luc_C6 cells the curves bottom out around 30 to 40% of the control value. A standard fit PL2, forcing the lower bound to this level was used. For those test compounds which did not exhibit FASN related toxicities (but other non-target related cellular toxicity), the % control value may go to 0, and curve fit was calculated using 0% as lower bound.

Representative compounds of the present invention were tested according to the procedure as described in Biological Example 4a and 4b above, with results as listed in Table BIO-4, below. Where a compound was tested more than once, the $pIC_{50}$ value listed below represents the mean of the measurements. Wherein the results listed below, the $pIC_{50}$ value is preceded with a "~", the "~" the "~" indicates that the standard error of the $pIC_{50}$ value, as estimated by the non-linear regression algorithm, is larger than 0.5. This corresponds to a factor of uncertainly on the $pIC_{50}$ that is larger than square root of 10 (>3.162).

TABLE BIO-4

$pIC_{50}$ Prostate Cell Proliferation, Liquid Reduced Medium

| ID No. | Vancouver Cells $pIC_{50}$ (μM) | PC-3M-Luc-C6 Cells $pIC_{50}$ (μM) |
| --- | --- | --- |
| 32 | 7.03 | 8.00 |
| 66 | 7.53 | ~8.09 |
| 78 | ~7.46 | ~8.06 |
| 273 | 5.66 | 6.57 |
| 274 | 5.71 | 6.11 |
| 275 | 6.16 | 6.92 |
| 276 | 5.86 | 6.31 |
| 278 | 5.21 | 5.67 |
| 279 | 6.58 | 7.45 |
| 280 | 6.43 | 7.14 |
| 281 | ~5.87 | ~6.11 |
| 282 | 5.99 | 6.77 |
| 283 | 5.98 | 6.61 |
| 284 | 5.99 | 6.71 |
| 285 | ~6.27 | 6.90 |
| 286 | 5.39 | 5.74 |
| 287 | 6.01 | 6.73 |
| 288 | ~5.01 | 5.51 |

Biological Example 5

Prophetic Example $^{14}C$-Acetate Incorporation in HEPG2 Liver Cells

HepG2 liver cells are obtained from the American Type Culture Collection. Cells are seeded in a 24-well plate at $7 \cdot 10^5$ cells/well in 400 μL MEM with 10% FCS (Hyclone). 100 μL of test compound dilution (25 μM to 5 μM final) is added and plates are incubated for 4 hours at 37° C. in 5% $CO_2$. 50 μL of $^{14}C$-acetic acid (Acetic acid, sodium salt (1,2-14C): Amersham CFA13; 50-62 mCi/mMol, 200 pCi/ml (7.4 mBq/ml)) diluted 1/50 in medium is added and plates are incubated for another 2 h at 37° C. in 5% $CO_2$. Medium is aspirated, and lipids are extracted from the cells by 3 rounds of chloroform:methanol:$MgSO_4$ mixture and centrifugation steps (2 min at 10000 rpm). Each time the upper layer is removed. Finally the remaining organic layer is evaporated under nitrogen gas, the pellet are dissolved in 500 μL heptanes and in 3 ml of scintillation fluid added to scintillation tubes. Incorporated $^{14}C$-labelled is counted in a Pachard, Tri-Carb Liquid scintillation counter. (2 minutes)

Biological Example 6

Prophetic Example

Analysis of Intact Phospholipid Species by Electrospray Ionization Tandem Mass Spectrometry PC-3 prostate and A2780 ovarian cells are obtained from the American Type Culture Collection. Cells are cultured in HamF12 or RPMI 1640 respectively, supplemented with 10% FCS (Invitrogen). Palmitic acid (Sigma) is complexed to fatty acid—free bovine serum albumin (Invitrogen). Cells are cultured for 72 hours in the presence or absence of test compound (10 μM to 0.1 μM). Xenografts are collected after 21 days treatment with or without compound (100-10 mg/kg).

Tissue or cells are homogenized in 1 N $HCl/CH_3OH$ (1:8, v/v). $CHCl_3$, 200 μg/mL of the antioxidant 2,6-di-tert-butyl-4-methylphenol (Sigma; ref. 29), and lipid standards are added. The organic fractions are evaporated and reconstituted in $CH_3OH/CHCl_3/NH_4OH$ (90:10:1.25, v/v/v). Phospholipids are analyzed by electrospray ionization tandem mass spectrometry (ESI-MS/MS) on a hybrid quadrupole linear ion trap mass spectrometer (4000 QTRAP system, Applied Biosystems) equipped with a robotic nanoflow/ion source (Advion Biosciences). The collision energy is varied as follows: precursor ion m/z 184, 50 eV; neutral loss of 141, 35 eV; neutral loss of 87, −40 eV; precursor ion m/z 241, −55 eV. The system is operated in the multiple reaction monitoring (MRM) mode for quantification of individual species. Typically, a 3-minute period of signal averaging is used for each spectrum. Data are corrected for $^{13}C$ isotope effects if the contribution is >10%. Corrected data were presented as heat maps using the HeatMap Builder software (Clifton Watt, Stanford University).

Biological Example 7

Prophetic Example

In Vivo Xenograft Tumor Growth Assay

Animals:
Male NMRI-nude mice (obtained from Janvier) are used for the study. Mice with an initial weight of approximately 20 to 25 g are obtained. The animals are habituated for one week prior to any experimental protocols/procedures being performed.

All animals are maintained under SPF (specific pathogen-free) "full barrier" conditions with free access to food and water. Mice are group housed under a 12-h light:dark cycle (lights on at 06:00 h) at a temperature of 19 to 22° C. and 35 to 40% humidity in Techniplast type-3 IVC cages. Mice are fed a standard Laboratory chow. All experiments are carried out in accordance with the European Communities Council Directives (86/609/EEC) and are approved by the local ethical committee.

Prostate Tumor Cells:
The human PC3 prostate tumor cells are cultured at 37° C. in a humidified atmosphere (5% $CO_2$, 95% air), in F12-Ham medium supplemented with 2 mM Sodium Pyruvate, 50 μg/ml Gentamycin, 1.5 g/l Sodium Bicarbonate, 0.1 mM Non Essential Amino Acids and 10% fetal bovine calf serum. Cells are maintained as cell monolayer cultures, passaged twice weekly at $3 \times 10^6$ cells per T175 flask, according to the following procedure. Cells are washed with PBS (w/o $Mg^{2+}$, $Ca^{2+}$), before addition of trypsin-EDTA to the culture flasks. After detachment of cells, the trypsin-EDTA is inactivated by addition of complete medium. The cell suspension is then transferred to 50 ml Falcon tube and centrifuged for 3 min at 1200 rpm. Medium is aspirated, with the cells being re-suspended in an appropriate volume of complete medium. The cells are counted in a haemocytometer and their viability is assessed by 0.25% trypan blue exclusion. An appropriate volume of cell suspension is then added to either a new T175 culture flask(s) or roller bottle containing fresh medium. For large scale-up growth of PC3 prostate tumor cells, an appropriate number of roller bottles are seeded with $1.2 \times 10^7$ cells 1 week prior to inoculation of the mice. The medium is changed twice during this period, with the last change being the day prior to cell injection. Cells are collected as described above, with the exception that after centrifugation, the cells are re-suspended in cold (4° C.) serum free medium at $5 \times 10^7$ cells/ml.

Experimental Design:

Human PC3 prostate tumor cells are injected directly into the inguinal region of the male NMRI Nude mice ($1 \times 10^7$ cells/200 µl/animal) on day 0. Approximately 35 days after inoculation, when tumor volumes reach an approximate average of 200 mm³, mice are randomized into test groups according to tumor volume, and treated for 21 days with either control (no test compound) or test compound at one of three dosage levels: 10 mg/kg, 30 mg/kg or 100 mg/kg.

Data Analysis:

For each individual animal, body weight and tumor size [using the commonly accepted formula: Tumor Volume (mm³)=(a×b²/2); where 'a' represents the length, and 'b' the width of the tumor as determined by caliper measurements], are monitored twice weekly throughout the study. A sustained body weight loss greater than 15% of the initial body weight is considered as clinical toxicity, with the animal removed from the study and sacrificed. Clinical signs of toxicity include, but are not limited to, persistent anorexia or dehydration, posture, moribund, lethargy, hypothermia and/or labored respiration (according to the UKCCCR guidelines for welfare of animals in preclinical in vivo tumor models)

A time-course of tumor growth is expressed as median values, or normalized to initial tumor volume on the day treatment started and expressed as mean±SEM (8 to 10 animals per group). For pre-established tumors, relative tumor volumes is calculated for each mouse (treated tumor volume/tumor volume on day 0) and expressed as mean±SEM for each treatment group. Twenty-four hours after the last treatment, animals are sacrificed, tumors excised and weighed. The anti-tumor effect of test compound versus control is determined and represented by a bar chart of median values±25/75 and 10/90 percentiles. Statistical significance is indicated by one-sided p-values from Wilcoxon-Mann-Whitney analysis (Wilcoxon rank sum test), with p<0.05 considered statistically significant. Treatment/control (T/C) ratios are calculated based on final relative tumor volumes, using the NCI criteria—"The effective criteria for T/C ratios is 42%".

Biological Example 8

In Vivo MaCoA Determination in NCI-H460 Xenografts

Test System

All experiments will be carried out in accordance with the European Communities Council Directives (86/609/EEC) and were approved by the local ethical committee.

Human NCI-H460 tumor cells (ATCC) were cultured at 37° C. in a humidified atmosphere (5% CO2, 95% air), in RPMI 1640 Medium supplemented with 10 mM HEPES, Glucose 4.5 g/l, 50 µg/ml Gentamycin, 1 mM Sodium Pyruvate, L-glutamine 2 mM and 10% fetal bovine calf serum (FBS). Cells were maintained as adherent epithelial cells being passaged once weekly at 10×10E6 cells per T300 using the following procedure. Briefly cells were washed with PBS (w/o Mg2+, Ca2+), before addition of trypsin-EDTA to the culture flasks. After detachment of cells the trypsin-EDTA was inactivated by addition of complete medium. Cell suspension was transferred to 50 ml Falcon tube and centrifuged for 3 min at 1200 rpm. Medium was aspirated, with the cells re-suspended in an appropriate volume of complete medium. The cells were counted in a cell counter (haemocytometer) and their viability assessed by 0.25% trypan blue exclusion. Last change of medium was performed 24 hours before cell collection. Cells were collected as described above except re-suspending after centrifugation in cold (4° C.) serum free medium at $5 \times 10^7$ cells/ml.

Male NMRI-nude mice (obtained from Janvier) were injected subcutaneously with $1 \times 10^7$ cells total in a 200 µl volume. Mice were dosed when tumors reach an average size of 300 mm³, with 3 and 30 mg/kg compound, orally, BID1.5× (n=3 per condition). 4 hours after the last dose tumors were excised and divided in two pieces of about 100 to 150 mg. One portion was used for MaCoA determination, the other portion was used for compound concentration. MaCoA induction was determined as fold induction versus the solvent treatment.

Analytical Procedure for the Quantification of Malonyl Coenzyme A in Tumor Tissue by LC/MS/MS (Calibration Range 5-5000 ng/mL in Tissue Homogenate)

The raw tissue samples were kept on dry ice at all times. Tumor tissue was weighed and homogenized with 2.0 mL of 5% trifluoroacetic acid (TFA) in water with an automated homogenizer (Bertin Precellys 24 tissue homogenizer). After centrifugation, a portion of the supernatant was combined with the internal standard (Malonyl CoA $^{13}C_3$ Lithium Salt).

The supernatant was subjected to solid-phase extraction (SPE). Samples were eluted with 0.1% TFA in methanol into a clean round-bottom plastic tubes. The eluent was evaporated under nitrogen, and the residue reconstituted and transferred in an HPLC vial. The standards were neat standards and the concentration applied was the final concentration for the standards in the HPLC vial.

The samples were analyzed by LC/MS/MS using a Zorbax Eclipse XDB-C8 column coupled with a triple quadrupole mass spectrometer (MDS Sciex API 5000 with TurboIonSpray™, Negative Polarity mode). Instrument was run in MRM mode choosing appropriate transitions for analyte and internal standard.

Chromatogram peaks were integrated using the Analyst version 1.4.2 software package. A weighted ($1/x^2$ where x equals concentration) linear regression analysis was used. The peak area ratio of malonyl CoA to the internal standard versus the nominal concentration was plotted. The slope, intercept and the correlation coefficient were calculated. The unknown concentration (x) was then calculated with the following formula:

$$x=(y-b)/m$$

where y is the peak area ratio of unknown malonyl CoA to internal standard, b is the y intercept and m is the slope.

Compound #32 and Compound #256 were dissolved in a 9:1 mixture of PEG400:ethanol to the desired concentration and tested according to the procedure as described above, with results as listed in Table BIO-8, below. Wherein a compound was tested multiple times, the value present below as MaCOa fold induction.

TABLE BIO-8

Human NCI-H460 tumor cells PD Assay

| ID No. | Dosage | MaCoA Fold Induction |
|---|---|---|
| 32 | 3 mg/kg | 5, 2, 3.37, 2.7 |
| 32 | 30 mg/kg | 39.7, 73.8, 24.7, 39.4 |
| 256 | 3 mg/kg | 1.9 |
| 256 | 30 mg/kg | 35.5 |

Biological Example 9

Antiviral Assays

Antiviral Activity Against RSV

Black 96-well clear-bottom microtiter plates (Corning, Amsterdam, The Netherlands) were filled in duplicate using a customized robot system with serial 4-fold dilutions of test compound in a final volume of 50 µl culture medium [RPMI medium without phenol red, 10% FBS, 0.04% gentamycin (50 mg/mL) and 0.5% DMSO]. Then, 100 µl of a HeLa cell suspension ($5 \times 10^4$ cells/mL) in culture medium was added to each well followed by the addition of 50 µl rgRSV224 (MOI=0.02) virus in culture medium using a multidrop dispenser (Thermo Scientific, Erembodegem, Belgium). rgRSV224 virus is an engineered virus that includes an additional GFP gene (HALLAK, L. K., et. al., "Glycosaminoglycan sulfation requirements for respiratory syncytial virus infection." *J. Virol.*, 2000, pp 10508-10513, Vol. 740). Medium, virus- and mock-infected controls were included in each test. Cells were incubated at 37° C. in a 5% $CO_2$ atmosphere. Three days post-virus exposure, viral replication was quantified by measuring GFP expression in the cells by a MSM laser microscope (Tibotec, Beerse, Belgium). The $EC_{50}$ was defined as the 50% inhibitory concentration for GFP expression. In parallel, test compounds were incubated for three days in a set of white 96-well microtiter plates (Corning) and the cytotoxicity of compounds in HeLa cells was determined by measuring the ATP content of the cells using the ATPlite kit (PerkinElmer, Zaventem, Belgium) according to the manufacturer's instructions. The $CC_{50}$ was defined as the 50% concentration for cytotoxicity.

Antiviral Activity Against HCV

The anti-HCV activity of compounds was tested in cell culture with replicon cells generated using reagents from the Bartenschlager laboratory (the HCV 1b bicistronic subgenomic luciferase reporter replicon clone ET). The protocol included a 3-day incubation of 2500 replicon cells in a 384-well format in a nine-point 1:4 dilution series of the compound. Dose response curves were generated based on the firefly luciferase read-out.

Antiviral Activity Against HBV Replication and HBsAg Secretion

The anti-HBV activity was measured using the HepG2.117 cell line, a stable, inducibly HBV producing cell line (SUN D., et al., "Stable HepG2- and Huh7-based human hepatoma cell lines for efficient regulated expression of infectious hepatitis B virus", *J. of Hepatology*, 2006, pp 636-645, Vol. 45) which replicates HBV in the absence of doxycycline (Tet-off system). For the antiviral assay, HBV replication was induced, followed by a treatment with serially diluted compound in 96-well plates in duplicate. After 3 days of treatment, the antiviral activity was determined by quantification of intracellular or extracellular HBV DNA using realtime PCR and an HBV specific primer set and probe. Cytotoxicity of the test compounds was tested using HepG2 cells, incubated for 4 days in the presence of test compounds. The viability of the cells was assessed using a Resazurin assay. The $CC_{50}$ was defined as the 50% concentration for cytotoxicity To determine the effect of test compounds on HBsAg secretion, HepG2.117 cells were treated in the presence of doxycycline with serially diluted compounds in 96-well plates in duplicate. After 3 days of treatment, sAg levels in the cell culture medium were determined with the Enzygnost HBsAg 6.0 ELISA, following the manufacturers recommendations.

Compound #32 was tested according to the procedures as describe above, with results as listed below.

| RSV Antiviral Activity | |
|---|---|
| $EC_{50}$ | 0.0177 |
| $CC_{50}$ (Toxicity HeLa Cells) | >25 |
| HCV Antiviral Activity | |
| $EC_{50}$ | 0.0146 |
| $CC_{50}$ (Toxicity Huh7-ATP) | >25 |
| HBV Antiviral Activity | |
| $IC_{50}$ (sAg secretion inhibition) | 0.0725 |
| $EC_{50}$ (HBV, HepG2.117) | >5 |
| $CC_{50}$ (Toxicity HepG2-4d) | >25 |

Formulation Example 1

Prophetic Example

Solid, Oral Dosage Form

As a specific embodiment of an oral composition, 100 mg of the Compound #1, prepared as in Example 1, above is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A compound of formula (I)

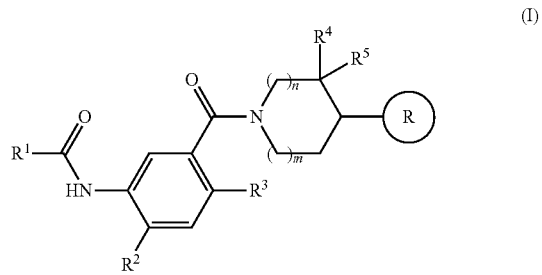

wherein $R^1$ is selected from the group consisting of $C_{1-6}$alkyl, fluorinated $C_{1-3}$alkyl, $C_{3-6}$cycloalkyl, —($C_{1-2}$alkyl)-$C_{3-6}$cycloalkyl, aryl, 5 to 6 membered heteroaryl, 9 to 10 membered heteroaryl, 4 to 6 membered saturated heterocyclyl and 9 to 10 membered saturated, partially unsaturated or benzo-fused heterocyclyl;

wherein the $C_{3-6}$cycloalkyl, aryl, 5 to 6 membered heteroaryl, 9 to 10 membered heteroaryl, 4 to 6 membered saturated heterocyclyl or 9 to 10 membered saturated, partially unsaturated or benzo-fused heterocyclyl is optionally substituted with one to three R⁰ substituents;

wherein each R⁰ is independently selected from the group consisting of halogen, hydroxy, cyano, $C_{1-6}$alkyl, fluorinated $C_{1-2}$alkyl, $C_{1-4}$alkoxy, —NR$^A$R$^B$, —C(O)—($C_{1-4}$alkyl), —S—($C_{1-4}$alkyl), —SO—($C_{1-4}$alkyl), —SO$_2$—($C_{1-4}$alkyl), —$C_{3-6}$cycloalkyl, —($C_{1-2}$alkyl)-$C_{3-6}$cycloalkyl, —C(O)—$C_{3-6}$cycloalkyl, —($C_{1-2}$alkyl)-phenyl and 5 to 6 membered saturated heterocyclyl;

wherein the $C_{3-6}$cycloalkyl or 5 to 6 membered saturated heterocyclyl is optionally substituted with one to two substituents independently selected from the group consisting of $C_{1-4}$alkyl and hydroxy substituted $C_{1-2}$alkyl;

wherein R$^A$ is selected from the group consisting of hydrogen and $C_{1-4}$alkyl; and wherein R$^B$ is selected from the group consisting of hydrogen, formyl, $C_{1-6}$alkyl, $C_{3-6}$cycloalkyl and 5 to 6 membered saturated heterocyclyl; wherein the R$^B$ 5 to 6 membered saturated heterocyclyl is optionally substituted with $C_{1-4}$alkyl;

R$^2$ is selected from the group consisting of halogen, hydroxy, cyano, $C_{1-4}$alkyl, fluorinated $C_{1-3}$alkyl, $C_{1-4}$alkoxy, benzyloxy and —NR$^X$R$^Y$;

wherein R$^X$ is selected from the group consisting of hydrogen, $C_{1-4}$alkyl and ($C_{2-4}$alkyl)-O—($C_{1-2}$alkyl); and wherein R$^Y$ is selected from the group consisting of hydrogen, $C_{1-4}$alkyl, —($C_{2-4}$alkyl)-O—($C_{1-2}$alkyl), $C_{3-6}$cycloalkyl and C(O)—$C_{3-6}$cycloalkyl;

R$^3$ is selected from the group consisting of hydrogen, halogen, methyl and trifluoromethyl;

n is 1; and m is 1; such that

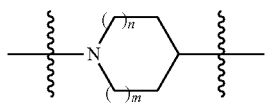

is piperidin-1,4-diyl;

R$^4$ is selected from the group consisting of hydrogen and $C_{1-3}$alkyl;

R$^5$ is selected from the group consisting of hydrogen, hydroxy and $C_{1-3}$alkyl;

is selected from the group consisting of,

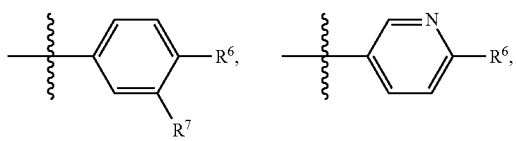

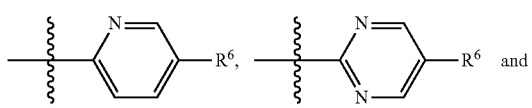

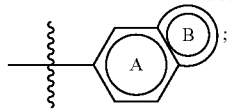

wherein R$^6$ is selected from the group consisting of aryl, 5 to 6 membered heteroaryl and 9 to 10 membered heteroaryl;

wherein the aryl, 5 to 6 membered heteroaryl or 9 to 10 membered heteroaryl is optionally substituted with one to three substituents independently selected from the group consisting of halogen, cyano, $C_{1-4}$alkyl, trifluoromethyl, hydroxy substituted $C_{1-3}$alkyl, $C_{1-4}$alkoxy, NR$^P$R$^Q$, —($C_{1-2}$alkyl)-NR$^P$R$^Q$, $C_{3-6}$cycloalkyl, —($C_{1-2}$ alkyl)-$C_{3-6}$cycloalkyl, 5 to 6 membered saturated heterocyclyl and 5 to 6 membered hereroaryl; wherein R$^P$ and R$^Q$ are each independently selected from the group consisting of hydrogen and $C_{1-4}$alkyl;

wherein R$^7$ is selected from the group consisting of hydrogen, halogen, cyano, $C_{1-4}$alkyl and trifluoromethyl;

wherein

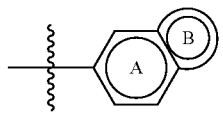

represents a 9 to 10 membered bicyclic, partially unsaturated or aromatic heterocyclyl; and wherein the

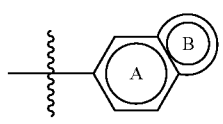

is optionally substituted with one to three substituents independently selected from the group consisting of halogen, oxo, cyano, $C_{1-4}$alkyl, trifluoromethyl, $C_{1-4}$alkoxy, NR$^S$R$^T$ and cyclopropyl; wherein R$^S$ and R$^T$ are each independently selected from the group consisting of hydrogen and $C_{1-4}$alkyl;

or a stereoisomer, tautomer or pharmaceutically acceptable salt thereof.

2. A compound as in claim 1, wherein

R$^1$ is selected from the group consisting of $C_{1-6}$alkyl, fluorinated $C_{1-3}$alkyl, $C_{3-6}$cycloalkyl, aryl, 5 to 6 membered heteroaryl, 9 to 10 membered heteroaryl, 4 to 6 membered saturated heterocyclyl and 9 to 10 membered benzo-fused heterocyclyl;

wherein the $C_{3-6}$cycloalkyl, aryl, 5 to 6 membered heteroaryl, 9 to 10 membered heteroaryl, 4 to 6 membered saturated heterocyclyl or 9 to 10 membered benzo-fused heterocyclyl is optionally substituted with one to three R⁰ substituents;

wherein each R⁰ is independently selected from the group consisting of halogen, hydroxy, cyano, $C_{1-6}$alkyl, fluorinated $C_{1-2}$alkyl, $C_{1-4}$alkoxy, —NR$^A$R$^B$, —C(O)—($C_{1-4}$alkyl), —S—($C_{1-4}$alkyl), —SO$_2$—($C_{1-4}$alkyl), —$C_{3-6}$cycloalkyl, —($C_{1-2}$alkyl)-$C_{3-6}$cycloalkyl, —C(O)—$C_{3-6}$cycloalkyl, —($C_{1-2}$alkyl)-phenyl and 5 to 6 membered saturated heterocyclyl;

wherein the $C_{3-6}$cycloalkyl or 5 to 6 membered saturated heterocyclyl is optionally substituted with one to two substituents independently selected from the group consisting of $C_{1-4}$alkyl and hydroxy substituted $C_{1-2}$alkyl;

wherein $R^A$ is selected from the group consisting of hydrogen and $C_{1-4}$alkyl; and wherein $R^B$ is selected from the group consisting of hydrogen, formyl, $C_{1-6}$alkyl, $C_{3-6}$cycloalkyl and 5 to 6 membered saturated, nitrogen containing heterocyclyl; wherein the $R^B$ 5 to 6 membered saturated, nitrogen containing heterocyclyl is optionally substituted with $C_{1-4}$alkyl;

$R^2$ is selected from the group consisting of halogen, hydroxy, cyano, $C_{1-4}$alkyl, fluorinated $C_{1-2}$alkyl, $C_{1-4}$alkoxy, benzyloxy and —$NR^XR^Y$;

wherein $R^X$ is selected from the group consisting of hydrogen, $C_{1-4}$alkyl and —$(C_{2-4}$alkyl$)$-O—$(C_{1-2}$alkyl$)$; and wherein $R^Y$ is selected from the group consisting of hydrogen, $C_{1-4}$alkyl, —$(C_{2-4}$alkyl$)$-O—$(C_{1-2}$alkyl$)$, $C_{3-6}$cycloalkyl and —C(O)—$C_{3-6}$cycloalkyl;

$R^3$ is selected from the group consisting of hydrogen, fluoro, chloro, bromo, methyl and trifluoromethyl;

$R^4$ is selected from the group consisting of hydrogen and $C_{1-3}$alkyl;

$R^5$ is selected from the group consisting of hydrogen, hydroxy and $C_{1-3}$alkyl;

is selected from the group consisting of,

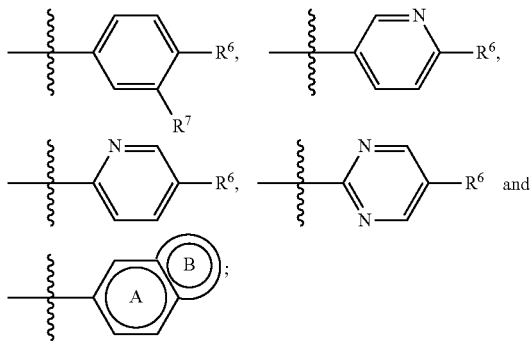

wherein $R^6$ is selected from the group consisting of aryl, 5 to 6 membered heteroaryl and 9 to 10 membered heteroaryl;

wherein the aryl, 5 to 6 membered heteroaryl or 9 to 10 membered heteroaryl is optionally substituted with one to two substituents independently selected from the group consisting of halogen, $C_{1-4}$alkyl, trifluoromethyl, hydroxy substituted $C_{1-2}$alkyl, $C_{1-4}$alkoxy, $NR^PR^Q$, —$(C_{1-2}$alkyl$)$-$NR^PR^Q$, $C_{3-6}$cycloalkyl, —$(C_{1-2}$alkyl$)$-$C_{3-6}$cycloalkyl, 5 to 6 membered saturated, nitrogen containing heterocyclyl and 5 to 6 membered nitrogen containing hereroaryl; wherein $R^P$ and $R^Q$ are each independently selected from the group consisting of hydrogen and $C_{1-4}$alkyl;

wherein $R^7$ is selected from the group consisting of hydrogen, fluoro, chloro, bromo, $C_{1-4}$alkyl and trifluoromethyl;

wherein

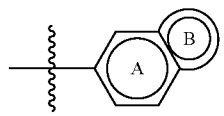

represents a 9 to 10 membered bicyclic, partially unsaturated or aromatic heterocyclyl; and wherein the

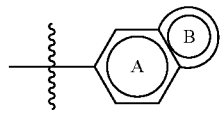

is optionally substituted with one to two substituents independently selected from the group consisting of halogen, oxo, cyano, $C_{1-4}$alkyl, trifluoromethyl, $C_{1-4}$alkoxy, $NR^SR^T$ and cyclopropyl; wherein $R^S$ and $R^T$ are each independently selected from the group consisting of hydrogen and $C_{1-4}$alkyl;

or a stereoisomer, tautomer or pharmaceutically acceptable salt thereof.

3. A compound as in claim 2, wherein $R^1$ is selected from the group consisting of $C_{2-5}$alkyl, fluorinated $C_{1-2}$alkyl, $C_{3-6}$cycloalkyl, phenyl, 4 to 6 membered saturated heterocyclyl, 5 to 6 membered heteroaryl, 9 to 10 membered heteroaryl and 1,3-benzodioxolyl;

wherein the $C_{3-6}$cycloalkyl, phenyl, 4 to 6 membered saturated heterocyclyl, 5 to 6 membered heteroaryl or 9 to 10 membered heteroaryl is optionally substituted with one to three $R^0$ substituents;

wherein each $R^0$ is independently selected from the group consisting of halogen, hydroxy, cyano, $C_{1-6}$alkyl, fluorinated $C_{1-2}$alkyl, $C_{1-2}$alkoxy, $NR^AR^B$, —C(O)—$(C_{1-2}$alkyl$)$, —S—$(C_{1-2}$alkyl$)$, $C_{5-6}$cycloalkyl, —C(O)—$C_3$cycloalkyl, —$(C_{1-2}$alkyl$)$-phenyl and 5 to 6 membered, saturated, nitrogen containing heterocyclyl wherein the $C_{5-6}$cycloalkyl or 5 to 6 membered saturated, nitrogen containing heterocyclyl is optionally substituted with a substituent selected from the group consisting of $C_{1-2}$alkyl and —$(C_{1-2}$alkyl$)$-OH;

wherein $R^A$ is selected from the group consisting of hydrogen and $C_{1-2}$alkyl; and wherein $R^B$ is selected from the group consisting of hydrogen, formyl, $C_{1-4}$alkyl, $C_{3-4}$cycloalkyl and 6 membered, saturated, nitrogen containing heterocyclyl; wherein the $R^B$ 6 membered saturated, nitrogen containing heterocyclyl is optionally substituted with $C_{1-2}$alkyl;

$R^2$ is selected from the group consisting of halogen, hydroxy, $C_{1-2}$alkyl, $C_{1-2}$alkoxy, benzyloxy and —$NR^XR^Y$;

wherein $R^X$ is selected from the group consisting of hydrogen, $C_{1-3}$alkyl and —$(C_2$alkyl$)$-O—$(C_{1-2}$alkyl$)$; and wherein $R^Y$ is selected from the group consisting of hydrogen, $C_{1-3}$alkyl, —$(C_2$alkyl$)$-O—$(C_{1-2}$alkyl$)$, $C_3$cycloalkyl and —C(O)—$C_3$cycloalkyl;

$R^3$ is hydrogen;

$R^4$ is selected from the group consisting of hydrogen and $C_{1-2}$alkyl;

$R^5$ is selected from the group consisting of hydrogen, hydroxy and $C_{1-2}$alkyl;

 is selected from the group consisting of

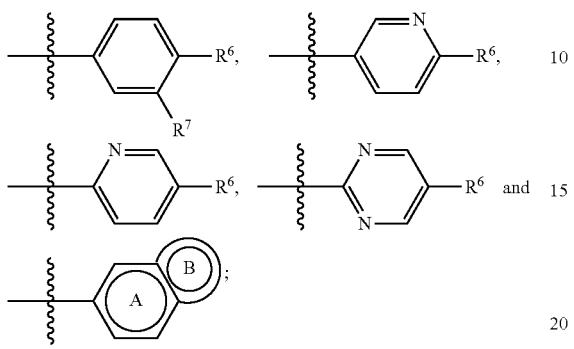

wherein $R^6$ is selected from the group consisting of phenyl, 5 to 6 membered heteroaryl and 9 to 10 membered, nitrogen containing heteroaryl;
wherein the phenyl, 5 to 6 membered heteroaryl or 9 to 10 membered, nitrogen containing heteroaryl is optionally substituted with a substituent selected from the group consisting of halogen, $C_{1-4}$alkyl, —($C_{1-2}$alkyl)-OH, $C_{1-2}$alkoxy, $NR^PR^Q$, —($C_{1-2}$alkyl)-$NR^PR^Q$, $C_{3-4}$cycloalkyl, —($C_{1-2}$alkyl)-$C_{3-4}$cycloalkyl, 6 membered saturated, nitrogen containing heterocyclyl and 6 membered, nitrogen containing heteroaryl; wherein $R^P$ and $R^Q$ are each independently selected from the group consisting of hydrogen and $C_{1-2}$alkyl;
$R^7$ is hydrogen;
and wherein

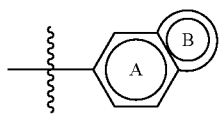

represents a 9 to 10 membered, bicyclic, partially unsaturated or aromatic, nitrogen containing heterocyclyl; wherein the

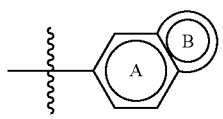

optionally substituted with one to two substituents independently selected from the group consisting of oxo and $C_{1-2}$alkyl;
or a stereoisomer, tautomer or pharmaceutically acceptable salt thereof.

4. A compound as in claim 3, wherein
$R^1$ is selected from the group consisting of t-butyl, n-pent-3-yl, isopropyl, 1-fluoro-ethyl, cyclopropyl, cyclobutyl, cyclopentyl, 4S-ethylcarbonyl-cyclopent-1S-yl, cyclohexyl, tetrahydropyran-4-yl, piperidin-4-yl, 1-methyl-piperidin-4-yl, 1-ethyl-piperidin-4-yl, 1-isopropyl-piperidin-4-yl, 1-(n-butyl)-piperidin-4-yl, 1-(1-methyl-n-pentyl)-piperidin-4-yl, 1-(n-pentyl)-piperidin-4-yl, 1-(2,2-dimethyl-propyl)-piperidin-4-yl, 1-isobutyl-piperidin-4-yl, 1-propyl-piperidin-4-yl, 1-isopentyl-piperidin-4-yl, 1-(n-hexyl)-piperidin-4-yl, 1-cyclobutyl-piperidin-4-yl, 1-cyclopentyl-piperidin-4-yl, 1-cyclohexyl-piperidin-4-yl, 1-(3-methyl-cyclopentyl)-piperidin-4-yl, 1-benzyl-piperidin-4-yl, tetrahydrofuran-2-yl, pyrrolidin-3-yl, pyrrolidin-2S-yl, pyrrolidin-2R-yl, 1-methyl-pyrrolidin-3R-yl, 1-methyl-pyrrolidin-3S-yl, 1-ethyl-pyrrolidin-3-yl, 1-propyl-pyrrolidin-3-yl, 1-isobutyl-pyrrolidin-3-yl, 1-(2,2-dimethyl-propyl)-pyrrolidin-3-yl, 1-isopropyl-pyrrolidin-3-yl, 1-(n-butyl)-pyrrolidin-3-yl, 1-(n-pentyl)-pyrrolidin-3-yl, 1-isopentyl-pyrrolidin-3-yl, 1-(1-methyl-n-pentyl)-pyrrolidin-3-yl, 1-(n-hexyl)-pyrrolidin-3-yl, 1-cyclobutyl-pyrrolidin-3-yl, 1-cyclopentyl-pyrrolidin-3-yl, 1-(3-methyl-cyclopentyl)-pyrrolidin-3-yl, 1-cyclohexyl-pyrrolidin-3-yl, 1-(cyclopropyl-carbonyl)-pyrrolidin-3-yl, azetidin-3-yl, 1-methyl-azetidin-3-yl, 1-ethyl-azetidin-3-yl, 1-isopropyl-azetidin-3-yl, 1-(n-propyl)-azetidin-3-yl, 1-(n-butyl)-azetidin-3-yl, 1-isobutyl-azetidin-3-yl, 1-isopentyl-azetidin-3-yl, 1-(n-pentyl)-azetidin-3-yl, 1-(2,2-dimethyl-propyl)-azetidin-3-yl, 1-(1-methyl-n-pentyl)-azetidin-3-yl, 1-(n-hexyl)-azetidin-3-yl, 1-cyclobutyl-azetidin-3-yl, 1-(3-methyl-cyclopentyl)-azetidin-3-yl, 1-cyclopentyl-azetidin-3-yl, 1-cyclohexyl-azetidin-3-yl, 1-(cyclopropyl-carbonyl)-azetidin-3-yl, phenyl, 2-chloro-phenyl, 3-chloro-phenyl, 4-chloro-phenyl, 2-fluoro-phenyl, 4-dichloro-phenyl, 2,4-dichloro-phenyl, 2,6-dichloro-phenyl, 3,4-dichloro-phenyl, 2,3,4-trifluoro-phenyl, 2,4-difluoro-phenyl, 2-fluoro-5-methyl-phenyl, 3-chloro-5-methoxy-phenyl, 2-fluoro-4-cyano-phenyl, 2-chloro-4-fluoro-phenyl, 4-isopropyl-phenyl, 2-methoxy-phenyl, 3-methoxy-phenyl, 2-methyl-4-fluoro-phenyl, 2-methyl-5-fluoro-phenyl, 3-hydroxy-4-methoxy-phenyl, 3-chloro-4-methoxy-phenyl, 4-methoxy-phenyl, 4-methylthio-phenyl, 2-trifluoromethyl-phenyl, 4-trifluoromethyl-phenyl, 4-cyano-phenyl, thiophen-2-yl, 3-chloro-thiophen-2-yl, 3-methyl-thiophen-2-yl, 5-methyl-thiophen-3-yl, 2-bromo-thiazol-2-yl, pyridin-2-yl, pyridin-4-yl, 2-chloro-pyridin-3-yl, 4-chloro-pyridin-3-yl, 6-chloro-pyridin-3-yl, 3-fluoro-pyridin-4-yl, 5-bromo-pyridin-3-yl, 2-chloro-6-methoxy-pyridin-4-yl, 6-methyl-pyridin-4-yl, 6-trifluoromethyl-pyridin-2-yl, 6-methoxy-pyridin-3-yl, 5-(dimethylamino)-pyridin-2-yl, 6-(isopropyl-amino)-pyridin-3-yl, 6-(cyclobutyl-amino)-pyridin-3-yl, 6-(piperidin-1-yl)-pyridin-3-yl, 6-(morpholin-4-yl)-pyridin-3-yl, 6-(4-methyl-piperazin-1-yl)-pyridin-3-yl, 6-(N-methyl-N-(1-methyl-piperidin-4-yl)-amino-)-pyridin-3-yl, 6-(N-methyl-N-isopropyl-amino)-pyridin-3-yl, 6-(pyrrolidin-1-yl)-pyridin-3-yl, 6-(3S-hydroxymethyl-piperazin-1-yl)-pyridin-3-yl, 6-(3R-hydroxymethyl-piperazin-4-yl)-pyridin-3-yl, 6-(N-isopropyl-N-formyl)-pyridin-3-yl, 6-(dimethylamino)-pyridin-3-yl, 2-chloro-pyrimidin-5-yl, 2-(isopropyl-amino)-pyrimidin-5-yl, 2-(N-methyl-N-isopropyl-amino)-pyrimidin-5-yl, 2-(morpholin-4-yl)-pyrimidin-5-yl, 6-(morpholin-4-yl)-pyrimidin-5-yl, 2-(cyclobutyl-amino)-pyrimidin-5-yl, 1-quinolin-2-yl, indol-5-yl and 1,3-benzodioxol-5-yl;
$R^2$ is selected from the group consisting of chloro, hydroxy, methyl, ethyl, methoxy, amino, methyl-amino, isopropyl-amino, (methoxyethyl)-amino, cyclopropyl-amino, (cyclopropylcarbonyl)-amino, N,N-dimethylamino, N-methyl-N-isopropyl-amino, N-methyl-N-(methoxyethyl)-amino, N-methyl-N-cyclopropyl-amino, N-(methoxyethyl)-N-(cyclopropyl-carbonyl)-amino and benzyloxy;

R³ is hydrogen;
R⁴ is selected from the group consisting of hydrogen and methyl;
R⁵ is selected from the group consisting of hydrogen, hydroxy, trans-hydroxy, methyl, trans-methyl and cis-methyl;

is selected from the group consisting of

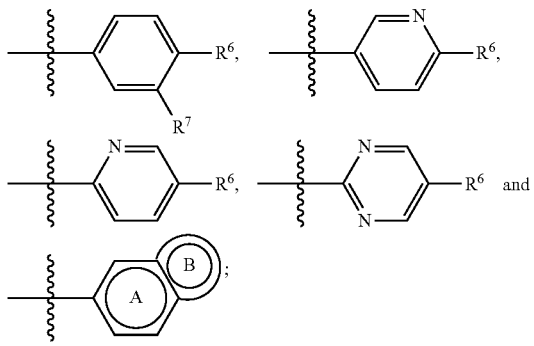

wherein R⁶ is selected from the group consisting of phenyl, 2-fluoro-phenyl, 3-fluoro-phenyl, 4-fluoro-phenyl, 2-methyl-phenyl, 3-methyl-phenyl, 4-methyl-phenyl, 2-methoxy-phenyl, 3-methoxy-phenyl, 4-methoxy-phenyl, thiophen-2-yl, thiophen-3-yl, furan-2-yl, furan-3-yl, isoxazol-4-yl, pyridin-3-yl, pyridin-4-yl, 2-amino-pyridin-3-yl, 3-amino-pyridin-4-yl, pyrazol-4-yl, 1-methyl-pyrazol-4-yl, 1-methyl-pyrazol-5-yl, 1-(tetrahydropyran-4-yl)-pyrazol-4-yl, 1-(cyclobutyl-methyl)-pyrazol-4-yl, 1,3-dimethyl-pyrazol-4-yl, 1-isopropyl-pyrazol-4-yl, 1-(2-hydroxyethyl)-pyrazol-4-yl, 1-cyclobutyl-pyrazol-4-yl, 1-(cyclopropyl)-pyrazol-4-yl, 1-(cyclopropyl-methyl)-pyrazol-4-yl, 1-(dimethylamino-ethyl)-pyrazol-4-yl, 1-(pyridin-3-yl)-pyrazol-4-yl, 1-(pyridin-4-yl)-pyrazol-4-yl, 1-methyl-indazol-6-yl, imidazol-1-yl, quinolin-4-yl, quinolin-5-yl and isoquinolin-6-yl;
R⁷ is hydrogen;
and wherein

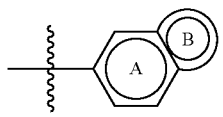

is selected from the group consisting of benzothiazol-6-yl, 2-oxo-benzothiazol-6-yl, 2-oxo-2,3,4-trihydroquinolin-7-yl, isoquinolin-6-y, isoquinolin-7-yl, 2-oxoindolin-5-yl, 1-methyl-2-oxo-isoindol-5-yl, 1,7-dimethyl-isoindol-5-yl, 1-methyl-indazol-6-yl, imidazo[1,2-a]pyridine-6-yl and [1,2,4]triazolo[4,3-a]pyridine-6-yl;
or a stereoisomer, tautomer or pharmaceutically acceptable salt thereof.
5. A compound as in claim 4, wherein
R¹ is selected from the group consisting of n-pent-3-yl, cyclopropyl, cyclobutyl, cyclopentyl, 4S-ethylcarbonyl-cyclopent-1S-yl, cyclohexyl, tetrahydropyran-4-yl, piperidin-4-yl, 1-methyl-piperidin-4-yl, 1-ethyl-piperidin-4-yl, 1-isopropyl-piperidin-4-yl, 1-(1-methyl-n-pentyl)-piperidin-4-yl, 1-(n-pentyl)-piperidin-4-yl, 1-(2,2-dimethyl-propyl)-piperidin-4-yl, 1-isobutyl-piperidin-4-yl, 1-propyl-piperidin-4-yl, 1-isopentyl-piperidin-4-yl, 1-(n-hexyl)-piperidin-4-yl, 1-cyclobutyl-piperidin-4-yl, 1-cyclopentyl-piperidin-4-yl, 1-cyclohexyl-piperidin-4-yl, 1-benzyl-piperidin-4-yl, pyrrolidin-3-yl, 1-propyl-pyrrolidin-3-yl, 1-isobutyl-pyrrolidin-3-yl, 1-isopentyl-pyrrolidin-3-yl, 1-(3-methyl-cyclopentyl)-pyrrolidin-3-yl, 1-(cyclopropyl-carbonyl)-pyrrolidin-3-yl, 1-methyl-azetidin-3-yl, 1-(n-butyl)-azetidin-3-yl, 1-isobutyl-azetidin-3-yl, 1-isopentyl-azetidin-3-yl, 1-(2,2-dimethyl-propyl)-azetidin-3-yl, 1-cyclobutyl-azetidin-3-yl, 1-cyclohexyl-azetidin-3-yl, 1-(cyclopropyl-carbonyl)-azetidin-3-yl, phenyl, 2-chloro-phenyl, 3-chloro-phenyl, 4-chloro-phenyl, 2-fluoro-phenyl, 4-dichloro-phenyl, 2,4-dichloro-phenyl, 3,4-dichloro-phenyl, 2,3,4-trifluoro-phenyl, 2,4-difluoro-phenyl, 2-fluoro-4-cyano-phenyl, 2-chloro-4-fluoro-phenyl, 4-isopropyl-phenyl, 3-methoxy-phenyl, 2-methyl-5-fluoro-phenyl, 3-hydroxy-4-methoxy-phenyl, 3-chloro-4-methoxy-phenyl, 4-methoxy-phenyl, 4-methylthio-phenyl, 4-trifluoromethyl-phenyl, 4-cyano-phenyl, thiophen-2-yl, 3-chloro-thiophen-2-yl, 3-methyl-thiophen-2-yl, 5-methyl-thiophen-3-yl, thiazol-5-yl, 2-bromo-thiazol-2-yl, pyridin-2-yl, pyridin-4-yl, 2-chloro-pyridin-3-yl, 6-chloro-pyridin-3-yl, 3-fluoro-pyridin-4-yl, 2-chloro-6-methoxy-pyridin-4-yl, 6-methyl-pyridin-4-yl, 6-methoxy-pyridin-3-yl, 5-(dimethylamino)-pyridin-2-yl, 6-(isopropyl-amino)-pyridin-3-yl, 6-(cyclobutyl-amino)-pyridin-3-yl, 6-(piperidin-1-yl)-pyridin-3-yl, 6-(morpholin-4-yl)-pyridin-3-yl, 6-(4-methyl-piperazin-1-yl)-pyridin-3-yl, 6-(N-methyl-N-(1-methyl-piperidin-4-yl)-amino)-pyridin-3-yl, 6-(N-methyl-N-isopropyl-amino)-pyridin-3-yl, 6-(pyrrolidin-1-yl)-pyridin-3-yl, 6-(3S-hydroxymethyl-piperazin-1-yl)-pyridin-3-yl, 6-(3R-hydroxymethyl-piperazin-4-yl)-pyridin-3-yl, 2-chloro-pyrimidin-5-yl, 2-(isopropyl-amino)-pyrimidin-5-yl, 2-(N-methyl-N-isopropyl-amino)-pyrimidin-5-yl, 2-(morpholin-4-yl)-pyrimidin-5-yl, 6-(morpholin-4-yl)-pyrimidin-5-yl, 2-(cyclobutyl-amino)-pyrimidin-5-yl, quinolin-2-yl, indol-5-yl and 1,3-benzodioxol-5-yl;
R² is selected from the group consisting of chloro, hydroxy, methyl, ethyl, methoxy, benzyloxy, methylamino, (methoxyethyl)amino, dimethylamino and N-methyl-N-cyclopropyl-amino;
R³ is hydrogen;
R⁴ is selected from the group consisting of hydrogen and methyl;
R⁵ is selected from the group consisting of hydrogen, methyl and trans-methyl;

is

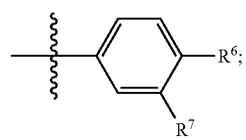

R[6] is selected from the group consisting of furan-3-yl, thiophen-3-yl, pyridin-3-yl, pyridin-4-yl, 2-amino-pyridin-3-yl, 3-amino-pyridin-4-yl, imidazol-1-yl, isoxazol-4-yl, pyrazol-4-yl, 1-methyl-pyrazol-4-yl, 1-isopropyl-pyrazol-4-yl, 1-(2-hydroxyethyl)-pyrazol-4-yl, 1-cyclopropyl-pyrazol-4-yl, 1-cyclobutyl-pyrazol-4-yl, 1-(cyclopropyl-methyl)-pyrazol-4-yl, 1,3-dimethyl-pyrazol-4-yl, 1-(pyridin-3-yl)-pyrazol-4-yl, 1-(pyridin-4-yl)-pyrazol-4-yl, quinolin-4-yl, quinolin-5-yl, isoquinolin-6-yl and 1-methyl-indazol-6-yl;
and R[7] is hydrogen;
or a stereoisomer, tautomer or pharmaceutically acceptable salt thereof.

6. A compound as in claim 4, wherein
R[1] is selected from the group consisting of n-pent-3-yl, cyclopropyl, cyclohexyl, 1-isopropyl-piperidin-4-yl, 1-isobutyl-piperidin-4-yl, 1-cyclopentyl-piperidin-4-yl, 1-cyclohexyl-piperidin-4-yl, 1-methyl-azetidin-3-yl, phenyl, 3-chloro-phenyl, 4-chloro-phenyl, 2-fluoro-phenyl, 2,4-dichloro-phenyl, 2-fluoro-4-cyano-phenyl, 3-methoxy-phenyl, 2-methyl-5-fluoro-phenyl, 3-hydroxy-4-methoxy-phenyl, 4-methoxy-phenyl, 4-methylthio-phenyl, 4-trifluoromethyl-phenyl, 3-chloro-thiophen-2-yl, pyridin-4-yl, 6-chloro-pyridin-3-yl, 3-fluoro-pyridin-4-yl, 6-methyl-pyridin-4-yl, 6-methoxy-pyridin-3-yl, 6-(isopropyl-amino)-pyridin-3-yl, 6-(cyclobutyl-amino)-pyridin-3-yl, 6-(piperidin-1-yl)-pyridin-3-yl, 6-(morpholin-4-yl)-pyridin-3-yl, 6-(4-methyl-piperazin-1-yl)-pyridin-3-yl, 6-(N-methyl-N-(1-methyl-piperidin-4-yl)-amino)-pyridin-3-yl, 6-(N-methyl-N-isopropyl-amino)-pyridin-3-yl, 6-(pyrrolidin-1-yl)-pyridin-3-yl, 6-(3S-hydroxymethyl-piperazin-1-yl)-pyridin-3-yl, 6-(3R-hydroxymethyl-piperazin-4-yl)-pyridin-3-yl, 2-chloro-pyrimidin-5-yl, 2-(isopropyl-amino)-pyrimidin-5-yl, 2-(N-methyl-N-isopropyl-amino)-pyrimidin-5-yl, 2-(morpholin-4-yl)-pyrimidin-5-yl, 6-(morpholin-4-yl)-pyrimidin-5-yl and 2-(cyclobutyl-amino)-pyrimidin-5-yl;
R[2] is selected from the group consisting of chloro, methyl, ethyl and methoxy;
R[3] is hydrogen;
R[4] is hydrogen;
R[5] is selected from the group consisting of hydrogen and trans-methyl;

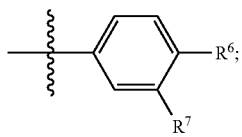

R[6] is selected from the group consisting of pyridin-4-yl, 2-amino-pyridin-3-yl, 3-amino-pyridin-4-yl, imidazol-1-yl, isoxazol-4-yl, pyrazol-4-yl, 1-methyl-pyrazol-4-yl, 1-(pyridin-4-yl)-pyrazol-4-yl, 1-methyl-pyrazol-5-yl and quinolin-4-yl;
and R[7] is hydrogen;
or a stereoisomer, tautomer or pharmaceutically acceptable salt thereof.

7. A compound as in claim 4, wherein
R[1] is selected from the group consisting of 1-methyl-azetidin-3-yl, 1-(n-butyl)-piperidin-4-yl, 1-(2,2-dimethyl-propyl)-piperidin-4-yl, 1-isopentyl-piperidin-4-yl, 1-cyclobutyl-piperidin-4-yl, 1-cyclopentyl-piperidin-4-yl, 1-cyclohexyl-piperidin-4-yl, 4-methylthio-phenyl, 2-fluoro-4-cyano-phenyl, 3-fluoro-pyridin-4-yl, 6-(3S-hydroxymethyl-piperidin-1-yl)-pyridin-3-yl, 6-(isopropyl-amino)-pyridin-3-yl, 6-(cyclobutyl-amino)-pyridin-3-yl, 6-(N-methyl-N-isopropyl-amino)-pyridin-3-yl, 6-(N-methyl-N-(1-methyl-piperidin-4-yl)-amino)-pyridin-3-yl, 6-(morpholin-4-yl)-pyridin-3-yl, 6-(4-methyl-piperazin-1-yl)-pyridin-3-yl, 2-(isopropyl-amino)-pyrimidin-5-yl, 2-(morpholin-4-yl)-pyrimidin-5-yl, 2-(cyclobutyl-amino)-pyrimidin-5-yl and indol-5-yl;
R[2] is methyl;
R[3] is hydrogen;
R[4] is hydrogen;
R[5] is hydrogen;

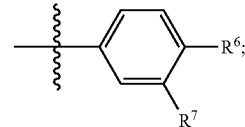

R[6] is selected from the group consisting of pyridin-4-yl, 3-amino-pyridin-4-yl, 1-methyl-pyrazol-4-yl, 1-(2-hydroxyethyl)-pyrazol-4-yl, 1-cyclopropyl-pyrazol-4-yl, 1-methyl-pyrazol-5-yl and quinolin-4-yl;
and R[7] is hydrogen;
or a stereoisomer, tautomer or pharmaceutically acceptable salt thereof.

8. A compound as in claim 4, wherein
R[1] is selected from the group consisting of cyclopropyl, 6-chloro-pyridin-3-yl, 6-(isopropyl-amino)-pyridin-3-yl, 6-(N-methyl-N-isopropyl-amino)-pyridin-3-yl and 6-(morpholin-4-yl)-pyridin-3-yl;
R[2] is selected from the group consisting of methyl, amino, methylamino, isopropylamino, (methoxyethyl)amino, cyclopropylamino, dimethylamino and N-methyl-N-cycloprpoyl-amino;
R[3] is hydrogen;
R[4] is hydrogen;
R[5] is hydrogen;

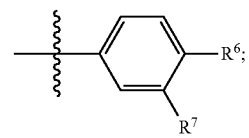

$R^6$ is 1-methyl-pyrazol-4-yl;
and $R^7$ is hydrogen;
or a stereoisomer, tautomer or pharmaceutically acceptable salt thereof.

9. A compound as in claim 4, wherein
$R^1$ is selected from the group consisting of t-butyl, n-pent-3-yl, isopropyl, 1-fluoro-ethyl, cyclopropyl, cyclobutyl, cyclopentyl, 4S-ethylcarbonyl-cyclopent-1S-yl, cyclohexyl, tetrahydropyran-4-yl, piperidin-4-yl, 1-methyl-piperidin-4-yl, 1-ethyl-piperidin-4-yl, 1-isopropyl-piperidin-4-yl, 1-(n-butyl)-piperidin-4-yl, 1-(1-methyl-n-pentyl)-piperidin-4-yl, 1-(n-pentyl)-piperidin-4-yl, 1-(2,2-dimethyl-propyl)-piperidin-4-yl, 1-isobutyl-piperidin-4-yl, 1-propyl-piperidin-4-yl, 1-isopentyl-piperidin-4-yl, 1-(n-hexyl)-piperidin-4-yl, 1-cyclobutyl-piperidin-4-yl, 1-cyclopentyl-piperidin-4-yl, 1-cyclohexyl-piperidin-4-yl, 1-(3-methyl-cyclopentyl)-piperidin-4-yl, 1-benzyl-piperidin-4-yl, tetrahydrofuran-2-yl, pyrrolidin-3-yl, pyrrolidin-2S-yl, pyrrolidin-2R-yl, 1-methyl-pyrrolidin-3R-yl, 1-methyl-pyrrolidin-3S-yl, 1-ethyl-pyrrolidin-3-yl, 1-propyl-pyrrolidin-3-yl, 1-isobutyl-pyrrolidin-3-yl, 1-(2,2-dimethyl-propyl)-pyrrolidin-3-yl, 1-isopropyl-pyrrolidin-3-yl, 1-(n-butyl)-pyrrolidin-3-yl, 1-(n-pentyl)-pyrrolidin-3-yl, 1-isopentyl-pyrrolidin-3-yl, 1-(1-methyl-n-pentyl)-pyrrolidin-3-yl, 1-(n-hexyl)-pyrrolidin-3-yl, 1-cyclobutyl-pyrrolidin-3-yl, 1-cyclopentyl-pyrrolidin-3-yl, 1-(3-methyl-cyclopentyl)-pyrrolidin-3-yl, 1-cyclohexyl-pyrrolidin-3-yl, 1-(cyclopropyl-carbonyl)-pyrrolidin-3-yl, azetidin-3-yl, 1-methyl-azetidin-3-yl, 1-ethyl-azetidin-3-yl, 1-isopropyl-azetidin-3-yl, 1-(n-propyl)-azetidin-3-yl, 1-(n-butyl)-azetidin-3-yl, 1-isobutyl-azetidin-3-yl, 1-isopentyl-azetidin-3-yl, 1-(n-pentyl)-azetidin-3-yl, 1-(2,2-dimethyl-propyl)-azetidin-3-yl, 1-(1-methyl-n-pentyl)-azetidin-3-yl, 1-(n-hexyl)-azetidin-3-yl, 1-cyclobutyl-azetidin-3-yl, 1-(3-methyl-cyclopentyl)-azetidin-3-yl, 1-cyclopentyl-azetidin-3-yl, 1-cyclohexyl-azetidin-3-yl, 1-(cyclopropyl-carbonyl)-azetidin-3-yl, phenyl, 2-chloro-phenyl, 3-chloro-phenyl, 4-chloro-phenyl, 2-fluoro-phenyl, 4-dichloro-phenyl, 2,4-dichloro-phenyl, 2,6-dichloro-phenyl, 3,4-dichloro-phenyl, 2,3,4-trifluoro-phenyl, 2,4-difluoro-phenyl, 2-fluoro-5-methyl-phenyl, 3-chloro-5-methoxy-phenyl, 2-fluoro-4-cyano-phenyl, 2-chloro-4-fluoro-phenyl, 4-isopropyl-phenyl, 2-methoxy-phenyl, 3-methoxy-phenyl, 2-methyl-4-fluoro-phenyl, 2-methyl-5-fluoro-phenyl, 3-hydroxy-4-methoxy-phenyl, 3-chloro-4-methoxy-phenyl, 4-methoxy-phenyl, 4-methylthio-phenyl, 2-trifluoromethyl-phenyl, 4-trifluoromethyl-phenyl, 4-cyano-phenyl, thiophen-2-yl, 3-chloro-thiophen-2-yl, 3-methyl-thiophen-2-yl, 5-methyl-thiophen-3-yl, thiazol-2-yl, thiazol-5-yl, 2-bromo-thiazol-2-yl, 4-t-butyl-thiazol-2-yl, pyridin-2-yl, pyridin-4-yl, 2-chloro-pyridin-3-yl, 4-chloro-pyridin-3-yl, 6-chloro-pyridin-3-yl, 3-fluoro-pyridin-4-yl, 5-bromo-pyridin-3-yl, 2-chloro-6-methoxy-pyridin-4-yl, 6-methyl-pyridin-4-yl, 6-trifluoromethyl-pyridin-2-yl, 6-methoxy-pyridin-3-yl, 5-(dimethylamino)-pyridin-2-yl, 6-(isopropyl-amino)-pyridin-3-yl, 6-(cyclobutyl-amino)-pyridin-3-yl, 6-(piperidin-1-yl)-pyridin-3-yl, 6-(morpholin-4-yl)-pyridin-3-yl, 6-(4-methyl-piperazin-1-yl)-pyridin-3-yl, 6-(N-methyl-N-(1-methyl-piperidin-4-yl)-amino-)-pyridin-3-yl, 6-(N-methyl-N-isopropyl-amino)-pyridin-3-yl, 6-(pyrrolidin-1-yl)-pyridin-3-yl, 6-(3S-hydroxymethyl-piperazin-1-yl)-pyridin-3-yl, 6-(3R-hydroxyethyl-piperazin-4-yl)-pyridin-3-yl, 6-(N-isopropyl-N-formyl)-pyridin-3-yl, 6-(dimethylamino)-pyridin-3-yl, 2-chloro-pyrimidin-5-yl, 2-(isopropyl-amino)-pyrimidin-5-yl, 2-(N-methyl-N-isopropyl-amino)-pyrimidin-5-yl, 2-(morpholin-4-yl)-pyrimidin-5-yl, 6-(morpholin-4-yl)-pyrimidin-5-yl, 2-(cyclobutyl-amino)-pyrimidin-5-yl, 1-methyl-imidazol-2-yl, quinolin-2-yl, indol-5-yl and 1,3-benzodioxol-5-yl;

$R^2$ is selected from the group consisting of chloro, hydroxy, methyl, ethyl, methoxy, amino, methyl-amino, isopropyl-amino, (methoxyethyl)-amino, cyclopropyl-amino, (cyclopropylcarbonyl)-amino, N,N-dimethylamino, N-methyl-N-isopropyl-amino, N-methyl-N-(methoxyethyl)-amino, N-methyl-N-cyclopropyl-amino, N-(methoxyethyl)-N-(cyclopropylcarbonyl)-amino and benzyloxy;

$R^3$ is hydrogen;
$R^4$ is selected from the group consisting of hydrogen and methyl;
$R^5$ is selected from the group consisting of hydrogen, hydroxy, methyl, trans-methyl and cis-methyl;

is

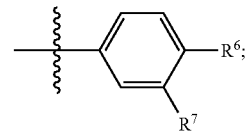

$R^6$ is selected from the group consisting of phenyl, 2-fluoro-phenyl, 3-fluoro-phenyl, 4-fluoro-phenyl, 2-methyl-phenyl, 3-methyl-phenyl, 4-methyl-phenyl, 2-methoxy-phenyl, 3-methoxy-phenyl, 4-methoxy-phenyl, thiophen-2-yl, thiophen-3-yl, furan-2-yl, furan-3-yl, isoxazol-4-yl, pyridin-3-yl, pyridin-4-yl, 2-amino-pyridin-3-yl, 3-amino-pyridin-4-yl, pyrazol-4-yl, 1-methyl-pyrazol-4-yl, 1-methyl-pyrazol-5-yl, 1-(tetrahydropyran-4-yl)-pyrazol-4-yl, 1-(cyclobutyl-methyl)-pyrazol-4-yl, 1,3-dimethyl-pyrazol-4-yl, 1-isopropyl-pyrazol-4-yl, 1-(2-hydroxyethyl)-pyrazol-4-yl, 1-cyclobutyl-pyrazol-4-yl, 1-(cyclopropyl)-pyrazol-4-yl, 1-(cyclopropyl-methyl)-pyrazol-4-yl, 1-(dimethylamino-ethyl)-pyrazol-4-yl, 1-(pyridin-3-yl)-pyrazol-4-yl, 1-(pyridin-4-yl)-pyrazol-4-yl, 1-methyl-indazol-6-yl, imidazol-1-yl, quinolin-4-yl, quinolin-5-yl and isoquinolin-6-yl;
and $R^7$ is hydrogen;
or a stereoisomer, tautomer or pharmaceutically acceptable salt thereof.

10. A compound as in claim 4, wherein
$R^1$ is selected from the group consisting of 6-chloro-pyridin-3-yl and 6-(isopropylamino)-pyridin-3-yl;
$R^2$ is methyl; $R^3$ is hydrogen;
$R^4$ is hydrogen; $R^5$ is hydrogen;

is

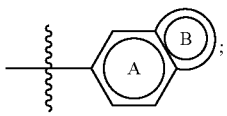

and

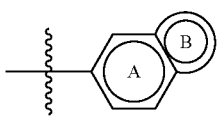

is selected from the group consisting of benzothiazol-6-yl, 2-oxo-benzothiazol-6-yl, 2-oxo-2,3,4-trihydroquinolin-7-yl, isoquinolin-6-y, isoquinolin-7-yl, 2-oxo-indolin-5-yl, 1-methyl-2-oxo-isoindol-5-yl, 1,7-dimethyl-isoindol-5-yl, 1-methyl-indazol-6-yl, imidazo[1,2-a]pyridine-6-yl and [1,2,4]triazolo[4,3-a]pyridine-6-yl;

or a stereoisomer, tautomer or pharmaceutically acceptable salt thereof.

11. A compound as in claim 4, wherein $R^1$ is selected from the group consisting of 6-chloropyridin-3-yl and 6-(isopropylamino)-pyridin-3-yl;
$R^2$ is methyl; $R^3$ is hydrogen;
$R^4$ is hydrogen; $R^5$ is hydrogen;

is selected from the group consisting of

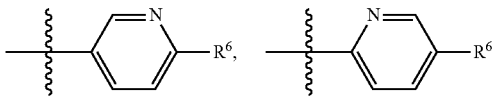

and

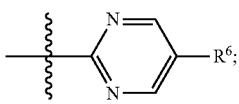

and $R^6$ is 1-methyl-pyrazol-4-yl;

or a stereoisomer, tautomer or pharmaceutically acceptable salt thereof.

12. A compound as in claim 4, selected from the group consisting of 6-(isopropylamino)-N-(2-methyl-5-(4-(4-(1-methyl-1H-pyrazol-4-yl)phenyl)piperidine-1-carbonyl)phenyl)nicotinamide;

N-(2-methyl-5-(4-(4-(1-methyl-1H-pyrazol-4-yl)phenyl)piperidine-1-carbonyl)phenyl)-6-morpholinonicotinamide;

4-chloro-N-(2-methyl-5-(4-(4-(1-methyl-1H-pyrazol-4-yl)phenyl)piperidine-1-carbonyl)phenyl)benzamide;

N-(2-Methyl-5-(4-(4-(1-methyl-1H-pyrazol-4-yl)phenyl)piperidine-1-carbonyl)phenyl)-6-(4-methylpiperazin-1-yl)nicotinamide;

6-(isopropylamino)-N-(2-methoxy-5-(4-(4-(1-methyl-1H-pyrazol-4-yl)phenyl)piperidine-1-carbonyl)phenyl)nicotinamide;

N-(2-ethyl-5-(4-(4-(1-methyl-1H-pyrazol-4-yl)phenyl)piperidine-1-carbonyl)phenyl)-6-(isopropylamino)nicotinamide;

6-(isopropylamino)-N-(5-(4-(4-(1-methyl-1H-pyrazol-4-yl)phenyl)piperidine-1-carbonyl)-2-(methylamino)phenyl)nicotinamide;

and stereoisomers, tautomers and pharmaceutically acceptable salts thereof.

13. A compound as in claim 4, selected from the group consisting of 6-(isopropylamino)-N-(2-methyl-5-(4-(4-(1-methyl-1H-pyrazol-4-yl)phenyl)piperidine-1-carbonyl)phenyl)nicotinamide;

N-(2-methyl-5-(4-(4-(1-methyl-1H-pyrazol-4-yl)phenyl)piperidine-1-carbonyl)phenyl)-6-morpholinonicotinamide;

N-(2-ethyl-5-(4-(4-(1-methyl-1H-pyrazol-4-yl)phenyl)piperidine-1-carbonyl)phenyl)-6-(isopropylamino)nicotinamide;

and stereoisomers, tautomers and pharmaceutically acceptable salts thereof.

14. A pharmaceutical composition comprising a pharmaceutically acceptable carrier and a compound as in claim 1.

15. A process for making a pharmaceutical composition comprising mixing a compound as in claim 1 and a pharmaceutically acceptable carrier.

16. A method of treating a disorder mediated by inhibition of fatty acid synthase (FASN) enzyme, wherein the disorder mediated by inhibition of fatty acid synthase (FASN) enzyme is selected from the group consisting of
    (a) cancer of the breast, prostate, head, neck, skin, lung, ovary, endometrium, thyroid, colon, rectum, esophagus, stomach, kidney, liver, bladder, pancreas, brain, spinal cord, blood or bone;
    (b) obesity or a related disorder selected from the group consisting of obesity, overweight, weight gain, Type II diabetes mellitus, Syndrome X, and appetite or satiety modulation;
    or (c) a liver related disorders selected from the group consisting of dyslipidemia, elevated cholesterol levels, elevated LDL, decreased HDL, elevated triglicerides, fatty liver, non-alcoholic steatohepatitis (NASH), fatty liver and non-alcoholic fatty liver disease (NAFLD);
comprising administering to a subject in need thereof a therapeutically effective amount of a compound as in claim 1.

17. The method of claim 16, wherein the disorder mediated by inhibition of fatty acid synthase (FASN) enzyme is cancer of the breast, prostate, head, neck, skin, lung, ovary, endometrium, thyroid, colon, rectum, esophagus, stomach, kidney, liver, bladder, pancreas, brain, spinal cord, blood or bone.

18. The method of claim 16, wherein the disorder mediated by inhibition of fatty acid synthase (FASN) enzyme is selected from the group consisting of obesity, overweight, weight gain, Type II diabetes mellitus, Syndrome X, and appetite or satiety modulation.

19. The method of claim 16, wherein the disorder mediated by inhibition of fatty acid synthase (FASN) enzyme is selected from the group consisting of dyslipidemia, elevated cholesterol levels, elevated LDL, decreased HDL, elevated triglicerides, fatty liver, non-alcoholic steatohepatitis (NASH), fatty liver and non-alcoholic fatty liver disease (NAFLD).

20. A method of treating
    (a) cancer of the breast, prostate, head, neck, skin, lung, ovary, endometrium, thyroid, colon, rectum, esophagus, stomach, kidney, liver, bladder, pancreas, brain, spinal cord, blood or bone;
(b) obesity or a related disorder selected from the group consisting of obesity, overweight, weight gain, Type II diabetes mellitus, Syndrome X, and appetite or satiety modulation;
or (c) a liver related disorders selected from the group consisting of dyslipidemia, elevated cholesterol levels, elevated LDL, decreased HDL, elevated triglicerides, fatty liver, non-alcoholic steatohepatitis (NASH), fatty liver and non-alcoholic fatty liver disease (NAFLD); comprising administering to a subject in need thereof a therapeutically effective amount of the composition of claim 14.

21. A method for the treatment of a viral infection selected from the group consisting of respiratory viruses, HBV and HCV, comprising administering to a subject in need thereof, a therapeutically effective amount of a compound as in claim 1.

22. A method of treating a viral infection selected from the group consisting of respiratory viruses, HBV and HCV, comprising administering to a subject in need thereof a therapeutically effective amount of the composition of claim 14.

23. The method of claim 16, wherein the disorder mediated by inhibition of fatty acid synthase (FASN) enzyme is cancer; and wherein the cancer is selected from the group consisting of glioma, glioblastoma, leukemia, Bannayan-Zonana syndrome, Cowden disease, Lhermitte-Duclos disease, breast cancer, inflammatory breast cancer, Wilm's tumor, Ewing's sarcoma, Rhabdomyosarcoma, ependymoma, medulloblastoma, sarcoma, osteosarcoma, melanoma, giant cell tumor of bone and giant cell tumor of thyroid.

* * * * *